(12) United States Patent
Wei et al.

(10) Patent No.: US 6,867,029 B2
(45) Date of Patent: Mar. 15, 2005

(54) ISOLATED HUMAN PHOSPHODIESTERASE PROTEINS, NUCLEIC ACID MOLECULES ENCODING HUMAN PHOSPHODIESTERASE PROTEINS, AND USES THEREOF

(75) Inventors: Ming-Hui Wei, Germantown, MD (US); Xin Wang, Bethesda, MD (US); Gennady V. Merkulov, Baltimore, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 138 days.

(21) Appl. No.: 10/094,989

(22) Filed: Mar. 12, 2002

(65) Prior Publication Data

US 2002/0115179 A1 Aug. 22, 2002

Related U.S. Application Data

(62) Division of application No. 09/754,250, filed on Jan. 5, 2001, now Pat. No. 6,376,225.

(51) Int. Cl.⁷ ............................................... C12N 9/22
(52) U.S. Cl. ...................................................... 435/196
(58) Field of Search ................................. 435/196, 199

(56) References Cited

FOREIGN PATENT DOCUMENTS

WO WO 92 18541 A 10/1992
WO WO 95 11995 A 5/1995

OTHER PUBLICATIONS

Hidaka, H., et al. (1976) Biochim. Biophys. Acta 485–497.*
Nagasaka, A., et al. (1976) Biochim. Biophys. Acta 438, 449–460.*
Suzuki, K., et al. (1980) Biochim. Biophys. Acta 602, 78–86.*
Singer, A.L., et al. (1976) Can. Res. 36, 60–66.*
Thompson, W.J., et al. (1980) Can. Res. 40, 1955–1960.*
Rosman G J et al. "Isolation and Characterization of Human CDNAs Encoding a CGMP–Stimulated 3+, 5+–Cyclic Nucleotide Phosphodieterase." Gene: An International Journal of Genes and Genomes, Elsevier Science Publishers, Barking, GB. vol. 191, 1997, pp. 89–95. XP002938026.

Database EBI Online! Database accession No. AC023176. XP002231139.

Database EBI Online! Database accession No. AC026173. XP002231140.

Graeme B Bolger et al. "Differential CNS Expression of Alternative Isoforms of the Mammalian Genes Encoding cAMP–Specific Phosphodieterases." Gene: An International Journal of Genes and Genomes, Elsevier Science Publishers, Barking, GB. vol. 149, No. 2, 1994. XP002150452.

International Search report dated Feb. 27, 2003, PCT/US02/00174.

* cited by examiner

*Primary Examiner*—Charles L. Patterson, Jr.
(74) *Attorney, Agent, or Firm*—Celera Genomics; Lin Sun-Hoffman

(57) ABSTRACT

The present invention provides amino acid sequences of peptides that are encoded by genes within the human genome, the phosphodiesterase peptides of the present invention. The present invention specifically provides isolated peptide and nucleic acid molecules, methods of identifying orthologs and paralogs of the phosphodiesterase peptides, and methods of identifying modulators of the phosphodiesterase peptides.

6 Claims, 101 Drawing Sheets

```
   1 GGGCCGGCGG GCGGGCGGGC GGCTGCGAGC ATGGTCCTGG TGCTGCACCA
  51 CATCCTCATC GCTGTTGTCC AATTCCTCAG GCGGGGCCAG CAGGTCTTCC
 101 TCAAGCCGGA CGAGCCGCCG CCGCCGCCGC AGCCATGCGC CGACAGCCTG
 151 CAGCCAGCCT GGACCCCCTT GCAAAGGAGC CAGGACCCCC AGGGAGTAGA
 201 GACGACCGAC TGGAGGACGC CTTGCTGAGT CTGGGCTCTG TCATCGACAT
 251 TTCAGGCCTG CAACGTGCTG TCAAGGAGGC CCTGTCAGCT GTGCTCCCCC
 301 GAGTGGAAAC TGTCTACACC TACCTACTGG ATGGTGAGTC CCAGCTGGTG
 351 TGTGAGGACC CCCCACATGA GCTGCCCCAG GAGGGGAAAG TCCGGGAGGC
 401 TATCATCTCC CAGAAGCGGC TGGGCTGCAA TGGGCTGGGC TTCTCAGACC
 451 TGCCAGGGAA GCCCTTGGCC AGGCTGGTGG CTCCACTGGC TCCTGATACC
 501 CAAGTGCTGG TCATGCCGCT AGCGGACAAG GAGGCTGGGG CCGTGGCAGC
 551 TGTCATCTTG GTGCACTGTG CCAGCTGAG TGATAATGAG GAATGGAGCC
 601 TGCAGGCGGT GGAGAAGCAT ACCCTGGTCG CCCTGCGGAG GGTGCAGGTC
 651 CTGCAGCAGC GCGGGCCCAG GGAGGCTCCC CGAGCCGTCC AGAACCCCCC
 701 GGAGGGGACG GCGGAAGACC AGAAGGGCGG GCGGCGTAC ATCGACCGCG
 751 ACCGCAAGAT CCTCCAACTG TGCGGGGAAC TCTACGACCT GGATGCCTCT
 801 TCCCTGCAGC TCAAAGTGCT CCAATACCTG CAGCAGGAGA CCCGGGCATC
 851 CCGCTGCTGC CTCCTGCTGG TGTCGGAGGA CAATCTCCAG CTTTCTTGCA
 901 AGGTCATCGG AGACAAAGTG CTCGGGGAAG AGGTCAGCTT TCCCTTGACA
 951 GGATGCCTGG GCCAGGTGGT GGAAGACAAG AAGTCCATCC AGCTGAAGGA
1001 CCTCACCTCC GAGGATGTAC AACAGCTGCA GAGCATGTTG GGCTGTGAGC
1051 TGCAGGCCAT GCTCTGTGTC CCTGTCATCA GCCGGGCCAC TGACCAGGTG
1101 GTGGCCTTGG CCTGCGCCTT CAACAAGCTA GAAGGAGACT TGTTCACCGA
1151 CGAGGACGAG CATGTGATCC AGCACTGCTT CCACTACACC AGCACCGTGC
1201 TCACCAGCAC CCTGGCCTTC CAGAAGGAAC AGAAACTCAA GTGTGAGTGC
1251 CAGGCTCTTC TCCAAGTGGC AAAGAACCTC TTCACCCACC TGGATGACGT
1301 CTCTGTCCTG CTCCAGGAGA TCATCACGGA GGCCAGAAAC CTCAGCAACG
1351 CAGAGATCTG CTCTGTGTTC CTGCTGGATC AGAATGAGCT GGTGGCCAAG
1401 GTGTTCGACG GGGGCGTGGT GGATGATGAG AGCTATGAGA TCCGCATCCC
1451 GGCCGATCAG GGCATCGCGG GACACGTGGC GACCACGGGC CAGATCCTGA
1501 ACATCCCTGA CGCATATGCC CATCCGCTTT TCTACCGCGG CGTGGACGAC
1551 AGCACCGGCT TCCGCACGCG CAACATCCTC TGCTTCCCCA TCAAGAACGA
1601 GAACCAGGAG GTCATCGGTG TGGCCGAGCT GGTGAACAAG ATCAATGGGC
1651 CATGGTTCAG CAAGTTCGAC GAGGACCTGG CGACGGCCTT CTCCATCTAC
1701 TGCGGCATCA GCATCGCCCA TTCTCTCCTA TACAAAAAAG TGAATGAGGC
1751 TCAGTATCGC AGCCACCTGG CCAATGAGAT GATGATGTAC CACATGAAGG
1801 TCTCCGACGA TGAGTATACC AAACTTCTCC ATGATGGGAT CCAGCCTGTG
1851 GCTGCCATTG ACTCCAATTT TGCAAGTTTC ACCTATACCC CTCGTTCCCT
1901 GCCCGAGGAT GACACGTCCA TGGCCATCCT GAGCATGCTG CAGGACATGA
1951 ATTTCATCAA CAACTACAAA ATTGACTGCC CGACCCTGGC CCGGTTCTGT
2001 TTGATGGTGA AGAAGGGCTA CCGGGATCCC CCTACCACA ACTGGATGCA
2051 CGCCTTTTCT GTCTCCCACT TCTGCTACCT GCTCTACAAG AACCTGGAGC
2101 TCACCAACTA CCTCGAGGAC ATCGAGATCT TTGCCTTGTT TATTTCCTGC
2151 ATGTGTCATG ACCTGGACCA CAGAGGCACA AACAACTCTT TCCAGGTGGC
2201 CTCGAAATCT GTGCTGGCTG CGCTCTACAG CTCTGAGGGC TCCGTCATGG
2251 AGAGGCACCA CTTTGCTCAG GCCATTGCCA TCCTCAACAC CCACGGCTGC
2301 AACATCTTTG ATCATTTCTC CCGGAAGGAC TATCAGCGCA TGCTGGATCT
2351 GATGCGGGAC ATCATCTTGG CCACAGACCT GGCCCACCAT CTCCGCATCT
2401 TCAAGGACCT CCAGAAGATG GCTGAGGTGG GCTACGACCG AAACAACAAG
2451 CAGCACCACA GACTTCTCCT CTGCCTCCTC ATGACCTCCT GTGACCTCTC
2501 TGACCAGACC AAGGGCTGGA AGACTACGAG AAAGATCGCG GAGCTGATCT
2551 ACAAAGAATT CTTCTCCCAG GGAGACCTGG AGAAGGCCAT GGGCAACAGG
2601 CCGATGGAGA TGATGGACCG GGAGAAGGCC TATATCCCTG AGCTGCAAAT
2651 CAGCTTCATG GAGCACATTG CAATGCCCAT CTACAAGCTG TTGCAGGACC
2701 TGTTCCCCAA AGCGGCAGAG CTGATGAGC GCGTGGCCTC CAACCGTGAG
2751 CACTGGACCA AGGTGTCCCA CAAGTTCACC ATCCGCGGCC TCCCAAGTAA
```

FIGURE 1A

```
2801 CAACTCGCTG GACTTCCTGG ATGAGGAGTA CGAGGTGCCT GATCTGGATG
2851 GCACTAGGGC CCCCATCAAT GGCTGCTGCA GCCTTGATGC TGAGTGATCC
2901 CCTCCAGGGA CACTTCCCTG CCCAGGCCAC CTCCCACAGC CCTCCACTGG
2951 TCTGGCCAGA TGCACTGGGA ACAGAGCCAC GGGTCCTGGG TCCTAGACCA
3001 GGACTTCCTG TGTGACCCTG GACAAGTACT ACCTTCCTGG GCCTCAGCTT
3051 TCTCGTCTGT ATAATGGAAG CAAGACTTCC AACCTCACGG AGACTTTGTA
3101 ATTTGTTCTC TGAGAGCACA GGGGTGACCA ATGAGCAGTG GGCCCTACTC
3151 TGCACCTCTG ACCACACCTT GGCAAGTCTT TCCCAAGCCA TTCTTTGTCT
3201 GAGCAGCTTG ATGGTTTCTC CTTGCCCCAT TTCTGCCCCA CCAGATCTTT
3251 GCTCCTTTCC CTTTGAGGAC TCCCACCCTT TGGGGTCTCC AGGATCCTCA
3301 TGGAAGGGGA AGGTGAGACA TCTGAGTGAG CAGAGTGTGG CATCTTGGAA
3351 ACAGTCCTTA GTTCTGTGGG AGGACTAGAA ACAGCCGCGG GGCGAAGGCC
3401 CCCTGAGGAC CACTACTATA CTGATGGTGG GATTGGGACC TGGGGATAC
3451 AGGGGCCCCA GGAAGAAGCT GCCAGAGGGG CAGCTCAGTG CTCTGCAGAG
3501 AGGGGCCCTG GGGAGAAGCA GGATGGGATT GATGGGCAGG AGGGATCCCC
3551 GCACTGGGAG ACAGGCCAG GTATGAATGA GCCAGCCATG CTTCCTCCTG
3601 CCTGTGTGAC GCTGGGCGAG TCTCTTCCCC TGTCTGGGCC AAACAGGGAG
3651 CGGGTAAGAC AATCCATGCT CTAAGATCCA TTTTAGATCA ATGTCTAAAA
3701 TAGCTCTATC GCTCTGCGGA GTCCCAGCAG AGGCTATGGA ATGTTTCTGC
3751 AACCCTAAGG CACAGAGAGC CCAACCCTGA GTGTCTCAGA GGCCCCCTGA
3801 GTGTTCCCCT TGGCCTGAGC CCCTTACCCA TTCCTGCAGC CAGTGAGAGA
3851 CCTGGCCTCA GCCCTGGCAG GGCTCTCTCT TCAAGGCCAT ATCCACCTGT
3901 GCCCTGGGGC TTGGGAGACC CCATAGGGCC GGGACTCTTG GGTCAGCCCG
3951 GCCACTGGCT TCTCTCTTTT TCTCCGTTTC ATTCTGTGTG CGTTGTGGGG
4001 TGGGGGAGGG GGTCCACCTG CCTTACCTTT CTGAGTTGCC TTTAGAGAGA
4051 TGCGTTTTTC TAGGACTCTG TGCAACTGTC GTATATGGTC CCGTGGGCTG
4101 ACCGCTTTGT ACATGAGAAT AAATCTATTT CTTTCTACCA GAAAAAAAAA
4151 AAAAAAAAAA AAAAAAAAAA A (SEQ ID NO:1)
```

FEATURES:
5' UTR: 1-134
Start: 135
Stop: 2734
3" UTR: 2735-4171

Homologous proteins:
Top BLAST Hits

```
                                                                          Score    E
gi|4505657|ref|NP_002590.1| phosphodiesterase 2A, cGMP-stimulat...         1821    0.0
gi|116569|sp|P14099|CN2A_BOVIN CGMP-DEPENDENT 3',5'-CYCLIC PHOS...         1769    0.0
gi|1184300|gb|AAA87353.1| (L49503) cGMP-stimulated cyclic nucle...         1746    0.0
gi|11439394|ref|XP_006369.1| phosphodiesterase 2A, cGMP-stimula...         1712    0.0
gi|1705944|sp|Q01062|CN2A_RAT CGMP-DEPENDENT 3',5'-CYCLIC PHOSP...         1677    0.0
gi|280898|pir||A60179 3',5'-cyclic-nucleotide phosphodiesterase...         1245    0.0
gi|3868997|dbj|BAA34308.1| (AB017022) EFPDE2 [Ephydatia fluviat...          628    e-179
gi|10716052|dbj|BAB16371.1| (AB036704) phosphodiesterase 11A [H...          368    e-100
gi|7298454|gb|AAF53675.1| (AE003659) CG10231 gene product [Dros...          362    8e-99
gi|732209|sp|P30645|YNE6_CAEEL PROBABLE 3',5'-CYCLIC PHOSPHODIE...          358    2e-97
gi|102513|pir||S24462 probable 3',5'-cyclic-nucleotide phosphod...          358    2e-97
gi|10716054|dbj|BAB16372.1| (AB038041) phosphodiesterase 11A2 [...          354    2e-96
gi|6683035|dbj|BAA88997.1| (AB027156) PDE10A3 [Rattus norvegicus]          336    6e-91
gi|6683033|dbj|BAA88996.1| (AB027155) PDE10A2 [Rattus norvegicus]          336    6e-91
gi|10716139|dbj|BAB16383.1| (AB041798) phosphodiesterase 10A1 (...          333    7e-90
gi|8218102|emb|CAB92797.1| (AL117345) dJ416F21.1 (phosphodieste...          333    7e-90
gi|5902442|dbj|BAA84467.1| (AB026816) 3',5'-cyclic nucleotide p...          333    7e-90
```

FIGURE 1B

BLAST to dbEST:

```
                                                                        Score    E
gb|AI333063|AI333063 qq17c03.x1 Soares_NhHMPu_S1 Homo sapiens c...       876    0.0
gb|AL119545|AL119545 DKFZp761B1623_r1 761 (synonym: hamy2) Homo...       763    0.0
gb|T33047|T33047 EST56468 Human Brain Homo sapiens cDNA 5' end ...       743    0.0
gb|AL046901|AL046901 DKFZp586G1217_r1 586 (synonym: hutel) Homo...       743    0.0
gb|T09162|T09162 EST07055 Infant Brain, Bento Soares Homo sapie...       692    0.0
gb|BE938766|BE938766 RC3-TN0093-280800-012-h11 TN0093 Homo sapi...       670    0.0
gb|BE543869|BE543869 601071557F1 NIH_MGC_12 Homo sapiens cDNA c...       658    0.0
gb|T66230|T66230 yc77d06.r1 Soares infant brain 1NIB Homo sapie...       620    e-175
gb|BE546407|BE546407 601070912F1 NIH_MGC_12 Homo sapiens cDNA c...       620    e-175
gb|BF346926|BF346926 602021761F1 NCI_CGAP_Brn67 Homo sapiens cD...       575    e-161
gb|AA188568|AA188568 zp78c04.s1 Stratagene HeLa cell s3 937216 ...       571    e-160
```

EXPRESSION INFORMATION FOR MODULATORY USE:
library source:
Expression information from BLAST dbEST hits:
gb|AI333063|AI333063  Pooled melanocyte, fetal heart, pregnant uterus
gb|AL119545|AL119545  Amygdala
gb|T33047|T33047   Brain
gb|AL046901|AL046901   Uterus
gb|T09162|T09162  Infant brain
gb|BE938766|BE938766  testis
gb|BE543869|BE543869  Placenta choriocarcinoma
gb|T66230|T66230  Infant brain
gb|BE546407|BE546407  Placenta choriocarcinoma
gb|BF346926|BF346926  Brain
gb|AA188568|AA188568  HeLa cells Expression information from PCR-based tissue screening panels:
whole brain

FIGURE 1C

```
  1 MRRQPAASLD PLAKEPGPPG SRDDRLEDAL LSLGSVIDIS GLQRAVKEAL
 51 SAVLPRVETV YTYLLDGESQ LVCEDPPHEL PQEGKVREAI ISQKRLGCNG
101 LGFSDLPGKP LARLVAPLAP DTQVLVMPLA DKEAGAVAAV ILVHCGQLSD
151 NEEWSLQAVE KHTLVALRRV QVLQQRGPRE APRAVQNPPE GTAEDQKGGA
201 AYIDRDRKIL QLCGELYDLD ASSLQLKVLQ YLQQETRASR CCLLLVSEDN
251 LQLSCKVIGD KVLGEEVSFP LTGCLGQWE DKKSIQLKDL TSEDVQQLQS
301 MLGCELQAML CVPVISRATD QWALACAFN KLEGDLFTDE DEHVIQHCFH
351 YTSTVLTSTL AFQKEQKLKC ECQALLQVAK NLFTHLDDVS VLLQEIITEA
401 RNLSNAEICS VFLLDQNELV AKVFDGGVVD DESYEIRIPA DQGIAGHVAT
451 TGQILNIPDA YAHPLFYRGV DDSTGFRTRN ILCFPIKNEN QEVIGVAELV
501 NKINGPWFSK FDEDLATAFS IYCGISIAHS LLYKKVNEAQ YRSHLANEMM
551 MYHMKVSDDE YTKLLHDGIQ PVAAIDSNFA SFTYTPRSLP EDDTSMAILS
601 MLQDMNFINN YKIDCPTLAR FCLMVKKGYR DPPYHNWMHA FSVSHFCYLL
651 YKNLELTNYL EDIEIFALFI SCMCHDLDHR GTNNSFQVAS KSVLAALYSS
701 EGSVMERHHF AQAIAILNTH GCNIFDHFSR KDYQRMLDLM RDIILATDLA
751 HHLRIFKDLQ KMAEVGYDRN NKQHHRLLLC LLMTSCDLSD QTKGWKTTRK
801 IAELIYKEFF SQGDLEKAMG NRPMEMMDRE KAYIPELQIS FMEHIAMPIY
851 KLLQDLFPKA AELYERVASN REHWTKVSHK FTIRGLPSNN SLDFLDEEYE
901 VPDLDGTRAP INGCCSLDAE  (SEQ ID NO:2)
```

FEATURES:
Functional domains and key regions:
[1] PDOC00001 PS00001 ASN_GLYCOSYLATION
N-glycosylation site Number of matches: 3
   1    402-405  NLSN
   2    683-686  NNSF
   3    889-892  NNSL

[2] PDOC00005 PS00005 PKC_PHOSPHO_SITE
Protein kinase C phosphorylation site

Number of matches: 9
   1     92-94   SQK
   2    254-256  SCK
   3    585-587  TPR
   4    729-731  SRK
   5    797-799  TTR
   6    798-800  TRK
   7    869-871  SNR
   8    878-880  SHK
   9    882-884  TIR

[3] PDOC00006 PS00006 CK2_PHOSPHO_SITE
Casein kinase II phosphorylation site

Number of matches: 17
   1     21-24   SRDD
   2     35-38   SVID
   3    149-152  SDNE
   4    192-195  TAED
   5    291-294  TSED
   6    338-341  TDED
   7    384-387  THLD
   8    404-407  SNAE
   9    509-512  SKFD
  10    557-560  SDDE

FIGURE 2A

| | | |
|---|---|---|
| 11 | 588-591 | SLPE |
| 12 | 703-706 | SVME |
| 13 | 729-732 | SRKD |
| 14 | 784-787 | TSCD |
| 15 | 811-814 | SQGD |
| 16 | 840-843 | SFME |
| 17 | 869-872 | SNRE |

[4] PDOC00007 PS00007 TYR_PHOSPHO_SITE
Tyrosine kinase phosphorylation site

Number of matches: 6

| | | |
|---|---|---|
| 1 | 534-541 | KKVNEAQY |
| 2 | 555-561 | KVSDDEY |
| 3 | 627-634 | KGYRDPPY |
| 4 | 652-659 | KNLELTNY |
| 5 | 761-767 | KMAEVGY |
| 6 | 799-806 | RKIAELIY |

[5] PDOC00008 PS00008 MYRISTYL
N-myristoylation site

Number of matches: 8

| | | |
|---|---|---|
| 1 | 41-46 | GLQRAV |
| 2 | 100-105 | GLGFSD |
| 3 | 135-140 | GAVAAV |
| 4 | 452-457 | GQILNI |
| 5 | 469-474 | GVDDST |
| 6 | 524-529 | GISIAH |
| 7 | 681-686 | GTNNSF |
| 8 | 885-890 | GLPSNN |

[6] PDOC00116 PS00126 PDEASE_I
3'5'-cyclic nucleotide phosphodiesterases signature 675-686 HDLDHRGTNNSF

Membrane spanning structure and domains:

| Helix | Begin | End | Score | Certainty |
|---|---|---|---|---|
| 1 | 297 | 317 | 0.713 | Putative |
| 2 | 343 | 363 | 0.863 | Putative |
| 3 | 514 | 534 | 1.277 | Certain |
| 4 | 632 | 652 | 0.613 | Putative |

BLAST Alignment to Top Hit:
Alignment to human cyclic nucleotide phosphodiesterase PDE2A3:
>gi|4505657|ref|NP_002590.1| phosphodiesterase 2A, cGMP-stimulated;
   Human cGMP-stimulated 3',5'-cyclic nucleotide
   phosphodiesterase PDE2A3 (PDE2A) mRNA, complete cds
   [Homo sapiens]
sp|O00408|CN2A_HUMAN CGMP-DEPENDENT 3',5'-CYCLIC PHOSPHODIESTERASE (CYCLIC GMP
   STIMULATED PHOSPHODIESTERASE) (CGS-PDE)
gb|AAC51320.1| (U67733) PDE2A3 [Homo sapiens]
   Length = 941

FIGURE 2B

```
Score = 1821 bits (4665), Expect = 0.0
Identities = 897/905 (99%), Positives = 898/905 (99%)

Query:  16 PGPPGSRDDRLEDALLSLGSVIDISGLQRAVKEALSAVLPRVETVYTYLLDGESQLVCED  75
            P  PP    D L+DALLSLGSVIDISGLQRAVKEALSAVLPRVETVYTYLLDGESQLVCED
Sbjct:  37 PPPPQPCADSLQDALLSLGSVIDISGLQRAVKEALSAVLPRVETVYTYLLDGESQLVCED  96

Query:  76 PPHELPQEGKVREAIISQKRLGCNGLGFSDLPGKPLARLVAPLAPDTQVLVMPLADKEAG 135
           PPHELPQEGKVREAIISQKRLGCNGLGFSDLPGKPLARLVAPLAPDTQVLVMPLADKEAG
Sbjct:  97 PPHELPQEGKVREAIISQKRLGCNGLGFSDLPGKPLARLVAPLAPDTQVLVMPLADKEAG 156

Query: 136 AVAAVILVHCGQLSDNEEWSLQAVEKHTLVALRRVQVLQQRGPREAPRAVQNPPEGTAED 195
           AVAAVILVHCGQLSDNEEWSLQAVEKHTLVALRRVQVLQQRGPREAPRAVQNPPEGTAED
Sbjct: 157 AVAAVILVHCGQLSDNEEWSLQAVEKHTLVALRRVQVLQQRGPREAPRAVQNPPEGTAED 216

Query: 196 QKGGAAYIDRDRKILQLCGELYDLDASSLQLKVLQYLQQETRASRCCLLLVSEDNLQLSC 255
           QKGGAAY DRDRKILQLCGELYDLDASSLQLKVLQYLQQETRASRCCLLLVSEDNLQLSC
Sbjct: 217 QKGGAAYTDRDRKILQLCGELYDLDASSLQLKVLQYLQQETRASRCCLLLVSEDNLQLSC 276

Query: 256 KVIGDKVLGEEVSFPLTGCLGQVVEDKKSIQLKDLTSEDVQQLQSMLGCELQAMLCVPVI 315
           KVIGDKVLGEEVSFPLTGCLGQVVEDKKSIQLKDLTSEDVQQLQSMLGCELQAMLCVPVI
Sbjct: 277 KVIGDKVLGEEVSFPLTGCLGQVVEDKKSIQLKDLTSEDVQQLQSMLGCELQAMLCVPVI 336

Query: 316 SRATDQVVALACAFNKLEGDLFTDEDEHVIQHCFHYTSTVLTSTLAFQKEQKLKCECQAL 375
           SRATDQVVALACAFNKLEGDLFTDEDEHVIQHCFHYTSTVLTSTLAFQKEQKLKCECQAL
Sbjct: 337 SRATDQVVALACAFNKLEGDLFTDEDEHVIQHCFHYTSTVLTSTLAFQKEQKLKCECQAL 396

Query: 376 LQVAKNLFTHLDDVSVLLQEIITEARNLSNAEICSVFLLDQNELVAKVFDGGVVDDESYE 435
           LQVAKNLFTHLDDVSVLLQEIITEARNLSNAEICSVFLLDQNELVAKVFDGGVVDDESYE
Sbjct: 397 LQVAKNLFTHLDDVSVLLQEIITEARNLSNAEICSVFLLDQNELVAKVFDGGVVDDESYE 456

Query: 436 IRIPADQGIAGHVATTGQILNIPDAYAHPLFYRGVDDSTGFRTRNILCFPIKNENQEVIG 495
           IRIPADQGIAGHVATTGQILNIPDAYAHPLFYRGVDDSTGFRTRNILCFPIKNENQEVIG
Sbjct: 457 IRIPADQGIAGHVATTGQILNIPDAYAHPLFYRGVDDSTGFRTRNILCFPIKNENQEVIG 516

Query: 496 VAELVNKINGPWFSKFDEDLATAFSIYCGISIAHSLLYKKVNEAQYRSHLANEMMMYHMK 555
           VAELVNKINGPWFSKFDEDLATAFSIYCGISIAHSLLYKKVNEAQYRSHLANEMMMYHMK
Sbjct: 517 VAELVNKINGPWFSKFDEDLATAFSIYCGISIAHSLLYKKVNEAQYRSHLANEMMMYHMK 576

Query: 556 VSDDEYTKLLHDGIQPVAAIDSNFASFTYTPRSLPEDDTSMAILSMLQDMNFINNYKIDC 615
           VSDDEYTKLLHDGIQPVAAIDSNFASFTYTPRSLPEDDTSMAILSMLQDMNFINNYKIDC
Sbjct: 577 VSDDEYTKLLHDGIQPVAAIDSNFASFTYTPRSLPEDDTSMAILSMLQDMNFINNYKIDC 636

Query: 616 PTLARFCLMVKKGYRDPPYHNWMHAFSVSHFCYLLYKNLELTNYLEDIEIFALFISCMCH 675
           PTLARFCLMVKKGYRDPPYHNWMHAFSVSHFCYLLYKNLELTNYLEDIEIFALFISCMCH
Sbjct: 637 PTLARFCLMVKKGYRDPPYHNWMHAFSVSHFCYLLYKNLELTNYLEDIEIFALFISCMCH 696

Query: 676 DLDHRGTNNSFQVASKSVLAALYSSEGSVMERHHFAQAIAILNTHGCNIFDHFSRKDYQR 735
           DLDHRGTNNSFQVASKSVLAALYSSEGSVMERHHFAQAIAILNTHGCNIFDHFSRKDYQR
Sbjct: 697 DLDHRGTNNSFQVASKSVLAALYSSEGSVMERHHFAQAIAILNTHGCNIFDHFSRKDYQR 756

Query: 736 MLDLMRDIILATDLAHHLRIFKDLQKMAEVGYDRNNKQHHRLLLCLLMTSCDLSDQTKGW 795
           MLDLMRDIILATDLAHHLRIFKDLQKMAEVGYDRNNKQHHRLLLCLLMTSCDLSDQTKGW
Sbjct: 757 MLDLMRDIILATDLAHHLRIFKDLQKMAEVGYDRNNKQHHRLLLCLLMTSCDLSDQTKGW 816
```

FIGURE 2C

```
Query: 796  KTTRKIAELIYKEFFSQGDLEKAMGNRPMEMVDREKAYIPELQISFMEHIAMPIYKLLQD 855
            KTTRKIAELIYKEFFSQGDLEKAMGNRPMEMVDREKAYIPELQISFMEHIAMPIYKLLQD
Sbjct: 817  KTTRKIAELIYKEFFSQGDLEKAMGNRPMEMVDREKAYIPELQISFMEHIAMPIYKLLQD 876

Query: 856  LFPKAAELYERVASNREHWTKVSHKFTIRGLPSNNSLDFLDEEYEVPDLDGTRAPINGCC 915
            LFPKAAELYERVASNREHWTKVSHKFTIRGLPSNNSLDFLDEEYEVPDLDGTRAPINGCC
Sbjct: 877  LFPKAAELYERVASNREHWTKVSHKFTIRGLPSNNSLDFLDEEYEVPDLDGTRAPINGCC 936

Query: 916  SLDAE 920
            SLDAE
Sbjct: 937  SLDAE 941 (SEQ ID NO:4)
```

Alignment to bovine cyclic nucleotide phosphodiesterase:
```
>gi|116569|sp|P14099|CN2A_BOVIN CGMP-DEPENDENT 3',5'-CYCLIC
          PHOSPHODIESTERASE (CYCLIC GMP STIMULATED
          PHOSPHODIESTERASE) (CGS-PDE)
 pir||A40981 3',5'-cyclic-nucleotide phosphodiesterase (EC 3.1.4.17),
          cGMP-stimulated - bovine
 gb|AAA74559.1| (M73512) cyclic nucleotide phosphodiesterase [Bos taurus]
          Length = 921

Score = 1769 bits (4532), Expect = 0.0
  Identities = 872/921 (94%), Positives = 893/921 (96%), Gaps = 1/921 (0%)

Query: 1    MRRQPAASLDPLAKEPGPPGSRDDRLEDALLSLGSVIDISGLQRAVKEALSAVLPRVETV 60
            MRRQPAAS D A+EP PPGS D  L+DALLSLGSVID++GLQ+AVKEALSAVLP+VETV
Sbjct: 1    MRRQPAASRDLFAQEPVPPGSGDGALQDALLSLGSVIDVAGLQQAVKEALSAVLPKVETV 60

Query: 61   YTYLLDGESQLVCEDPPHELPQEGKVREAIISQKRLGCNGLGFSDLPGKPLARLVAPLAP 120
            YTYLLDGES+LVCE+PPHELPQEGKVREA+IS+KRLGCNGLG SDLPGKPLARLVAPLAP
Sbjct: 61   YTYLLDGESRLVCEEPPHELPQEGKVREAVISRKRLGCNGLGPSDLPGKPLARLVAPLAP 120

Query: 121  DTQVLVMPLADKEAGAVAAVILVHCGQLSDNEEWSLQAVEKHTLVALRRVQVLQQRGPRE 180
            DTQVLV+PL DKEAGAVAAVILVHCGQLSDNEEWSLQAVEKHTLVAL+RVQ LQQR
Sbjct: 121  DTQVLVIPLVDKEAGAVAAVILVHCGQLSDNEEWSLQAVEKHTLVALKRVQALQQRESSV 180

Query: 181  APRAVQNPPEGTAEDQKGGAAYIDRDRKILQLCGELYDLDASSLQLKVLQYLQQETRASR 240
            AP A QNPPE A DQKGG AY ++DRKILQLCGELYDLDASSLQLKVLQYLQQET+ASR
Sbjct: 181  APEATQNPPEEAAGDQKGGVAYTNQDRKILQLCGELYDLDASSLQLKVLQYLQQETQASR 240

Query: 241  CCLLLVSEDNLQLSCKVIGDKVLGEEVSFPLT-GCLGQVVEDKKSIQLKDLTSEDVQQLQ 299
            CCLLLVSEDNLQLSCKVIGDKVL EE+SFPLT G LGQVVEDKKSIQLKDLTSED+QQLQ
Sbjct: 241  CCLLLVSEDNLQLSCKVIGDKVLEEEISFPLTTGRLGQVVEDKKSIQLKDLTSEDMQQLQ 300

Query: 300  SMLGCELQAMLCVPVISRATDQVVALACAFNKLEGDLFTDEDEHVIQHCFHYTSTVLTST 359
            SMLGCE+QAMLCVPVISRATDQVVALACAFNKL GDLFTD+DEHVIQHCFHYTSTVLTST
Sbjct: 301  SMLGCEVQAMLCVPVISRATDQVVALACAFNKLGGDLFTDQDEHVIQHCFHYTSTVLTST 360

Query: 360  LAFQKEQKLKCECQALLQVAKNLFTHLDDVSVLLQEIITEARNLSNAEICSVFLLDQNEL 419
            LAFQKEQKLKCECQALLQVAKNLFTHLDDVSVLLQEIITEARNLSNAEICSVFLLDQNEL
Sbjct: 361  LAFQKEQKLKCECQALLQVAKNLFTHLDDVSVLLQEIITEARNLSNAEICSVFLLDQNEL 420

Query: 420  VAKVFDGGVVDDESYEIRIPADQGIAGHVATTGQILNIPDAYAHPLFYRGVDDSTGFRTR 479
            VAKVFDGGVV+DESYEIRIPADQGIAGHVATTGQILNIPDAYAHPLFYRGVDDSTGFRTR
Sbjct: 421  VAKVFDGGVVEDESYEIRIPADQGIAGHVATTGQILNIPDAYAHPLFYRGVDDSTGFRTR 480
```

FIGURE 2D

```
Query: 480 NILCFPIKNENQEVIGVAELVNKINGPWFSKFDEDLATAFSIYCGISIAHSLLYKKVNEA 539
            NILCFPIKNENQEVIGVAELVNKINGPWFSKFDEDLATAFSIYCGISIAHSLLYKKVNEA
Sbjct: 481 NILCFPIKNENQEVIGVAELVNKINGPWFSKFDEDLATAFSIYCGISIAHSLLYKKVNEA 540

Query: 540 QYRSHLANEMMMYHMKVSDDEYTKLLHDGIQPVAAIDSNFASFTYTPRSLPEDDTSMAIL 599
            QYRSHLANEMMMYHMKVSDDEYTKLLHDGIQPVAAIDSNFASFTYTPRSLPEDDTSMAIL
Sbjct: 541 QYRSHLANEMMMYHMKVSDDEYTKLLHDGIQPVAAIDSNFASFTYTPRSLPEDDTSMAIL 600

Query: 600 SMLQDMNFINNYKIDCPTLARFCLMVKKGYRDPPYHNWMHAFSVSHFCYLLYKNLELTNY 659
            SMLQDMNFINNYKIDCPTLARFCLMVKKGYRDPPYHNWMHAFSVSHFCYLLYKNLELTNY
Sbjct: 601 SMLQDMNFINNYKIDCPTLARFCLMVKKGYRDPPYHNWMHAFSVSHFCYLLYKNLELTNY 660

Query: 660 LEDIEIFALFISCMCHDLDHRGTNNSFQVASKSVLAALYSSEGSVMERHHFAQAIAILNT 719
            LED+EIFALFISCMCHDLDHRGTNNSFQVASKSVLAALYSSEGSVMERHHFAQAIAILNT
Sbjct: 661 LEDMEIFALFISCMCHDLDHRGTNNSFQVASKSVLAALYSSEGSVMERHHFAQAIAILNT 720

Query: 720 HGCNIFDHFSRKDYQRMLDLMRDIILATDLAHHLRIFKDLQKMAEVGYDRNNKQHHRLLL 779
            HGCNIFDHFSRKDYQRMLDLMRDIILATDLAHHLRIFKDLQKMAEVGYDR NKQHH LLL
Sbjct: 721 HGCNIFDHFSRKDYQRMLDLMRDIILATDLAHHLRIFKDLQKMAEVGYDRTNKQHHSLLL 780

Query: 780 CLLMTSCDLSDQTKGWKTTRKIAELIYKEFFSQGDLEKAMGNRPMEMMDREKAYIPELQI 839
            CLLMTSCDLSDQTKGWKTTRKIAELIYKEFFSQGDLEKAMGNRPMEMMDREKAYIPELQI
Sbjct: 781 CLLMTSCDLSDQTKGWKTTRKIAELIYKEFFSQGDLEKAMGNRPMEMMDREKAYIPELQI 840

Query: 840 SFMEHIAMPIYKLLQDLFPKAAELYERVASNREHWTKVSHKFTIRGLPSNNSLDFLDEEY 899
            SFMEHIAMPIYKLLQDLFPKAAELYERVASNREHWTKVSHKFTIRGLPSNNSLDFLDEEY
Sbjct: 841 SFMEHIAMPIYKLLQDLFPKAAELYERVASNREHWTKVSHKFTIRGLPSNNSLDFLDEEY 900

Query: 900 EVPDLDGTRAPINGCCSLDAE 920
            EVPDLDG RAPINGCCSLDAE
Sbjct: 901 EVPDLDGARAPINGCCSLDAE 921 (SEQ ID NO:5)
```

Hmmer search results (Pfam):

| Model | Description | Score | E-value | N |
|---|---|---|---|---|
| PF00233 | 3'5'-cyclic nucleotide phosphodiesterase | 521.5 | 1.6e-181 | 1 |
| PF01590 | GAF domain | 197.1 | 2.8e-55 | 2 |
| PF00872 | Transposase, Mutator family | 2.4 | 9.5 | 1 |

Parsed for domains:

| Model | Domain | seq-f | seq-t | hmm-f | hmm-t | score | E-value |
|---|---|---|---|---|---|---|---|
| PF01590 | 1/2 | 220 | 361 .. | 1 | 142 [] | 65.2 | 1.9e-16 |
| PF01590 | 2/2 | 388 | 532 .. | 1 | 142 [] | 132.1 | 9.8e-36 |
| PF00872 | 1/1 | 723 | 751 .. | 280 | 308 .. | 2.4 | 9.5 |
| PF00233 | 1/1 | 634 | 871 .. | 1 | 279 [] | 521.5 | 1.6e-181 |

FIGURE 2E

```
   1 ACGTGGATGA ACACCCACCC ACACACAGCT CTCTAGGAAA ATTGCTCCCC
  51 TTCCCTCCTG CTCCTCCTCC ACCCTGTCCT CCCACCACCA CCCACTTCCA
 101 AATGCTGAGA CCAAAGAGAT GGGCTGGACG GTGCCTCTCA CCACTTGTCA
 151 GCCTGGGACG CCCTCCTCCC TTTGTGACTA GCATGCCCTC CTCCCCCTGC
 201 CCGTCTGCCT CCCCAGCTCT CTCTGCCTCC CTGTCGCCCT GCCACCTCCC
 251 TGCGTTCCTG TGTATCTGCC CTCCACACAA GTCACTCTGA GGCCTCTCTT
 301 TGTTACTCTT GACTCTGAAG TGGAAACTGC TCCTCCCAGC TCTCCTGAGA
 351 GGCTCAGGAT GGGGACCTGA CCTCATAGGG CTGATGGAGG CATAGGGACA
 401 AGTGAAAGGG ACCCCAGGTC CCGAATCTCC TCAGCTCCTG TCACCTTCAG
 451 TCCCTCCTAT TGGGTTAGGG GAGGGCTGTG TGCCTGGCAC CATGGAGACC
 501 AGTGTCATGG CAACACAGTT CGGGTGGGCA CAGCTTCCTC CTCCTGGGGT
 551 GTGGGGTCCA TAAGAGGAGG TGCCGAGGAG GTGGGCCTTG TGCTGGTGCC
 601 CACCATGGCT GCCTCCAGCT CACCATTCCC AGGACAGCCC ACCCCATCC
 651 CCCCAGCCAA CTTTGCTTGC CACTGCAGCT TCCAGTGCCA CAAGTCACTG
 701 ATCCCATTTG GGAAATCCTC TCTCAAACAC CAGCTCCAGA GCTGGGCGCC
 751 AGAGAGGGCA GGGGCTTGCC CAGGGTCACA CAGCAAGTCT GGCCAAGCTC
 801 CTGACTCTCA GACCTGTTTT CTCCTCCGGT CTCCCACCTT CCACCCAGAA
 851 AGGGGACTGG GGGCAGAGGG GTCAGTCCAA CCTCAGTTCC CACCACGATC
 901 TTCAGCCAGC CCTTAGAGTT GGCAGTGGGA GTGAAGATGC AAGTGATAGT
 951 GCCGAGAAAC CATCATGGGG CGCCACCAC CTGCTGTGCC AAGGCTTTGC
1001 ATGTGTCATC CCATTTTATT CCAAGACCCA GGAGGAAGAT GACTGGTAAG
1051 TGGAGTAGCT GGGACAGGAA CACAGGTCCC TCTCAGATGG GGCAGGTGAG
1101 TCAAGGCTCG TGTGTATTGC TGTCTCCATC AGGCGCTCTT TTAAAAGAAT
1151 GGCAAAGCTT TTAATCCCAT CTTTATTACC GGTAAGAGTG TAGGGGGAGG
1201 ATCTGGGCA TAGCCTGGGT CTGGCCTTAG GGTTTCTAGA AACCAGGGGA
1251 TATTTTTCTA AGAAGATAGA GAATAGAGCT TTCCTAGTGT GGTTAGACCT
1301 AGGGAAGACC TTTCTTGCAG TGCAGCAATG CAGACCGACT TCCAATCCCT
1351 AGGTCAAGCT GGAGTCTAGG GACAGAGGGG AGGAGACCCC TGCCTCCTGT
1401 GCCCAGCCTC AACTTGTCTC CTGACCTTCA TGGAGTCACG TTGCAGCTGC
1451 CTCCCTCCTG GCTTATGTAA TAATTCAAAT ATAGCAGCTG CCTTTATCCC
1501 ACTGAGTCAC ACCCCCTGCA TCCCCCCTCA GGTGCGGGGA GTTATGGGG
1551 AAGAGGTGGT TCAGGGCTGA GTGGGAGGTT CGGGGCCTCC TGGCAAGGAA
1601 GATCCCTAGT GTGCTGGATT GGAGGGTGGT GGTGGTGAGG GGGCTGGTGC
1651 TGAGGCCCCA AGAAGAGCAG AGCCTTCGCC AGAATATGAA GCCACAGGGG
1701 CCACTTCTGC CCTGACCCAT CCCTGCTGGA ATTCCACATT CCTGGGGGCC
1751 CTCCCCAGAG TCACAAGCTA TATGTACAGC CTTCTCTTGT GGGCTGCTGT
1801 CTCAGTTGGA GGAGGAAGGA GAGGTGGAAG AGTATGAAGA GGGGGAAGTA
1851 GTCCGGTGGG GCAATGGCCA CCGTCTTTGG TCCTAGGCTC AGCCTCGCCC
1901 TTCACTCACT GGGTTACCTG GCACCCCTC TGACCTCAGT TTTCCCATCT
1951 GCACAGTGAA GGATTAGATT AACTGGCTCT AGCGTCTCAT TCTCTCCGAT
2001 TTATAACCCT GGAGATGATC TCAACCTGAG GCTGAAGGCA CTTCCGAGTG
2051 TCTGGCCCAG CCGCGTTCCA GGCTGACTTC CCTCCCTCTT TTCTCTGCCA
2101 TCCCTCCTAG ACCAATGCAG CCACCCCAC CCACAAGACA AAAGAGGCAG
2151 GAGAGGGCCC TGGACTCAGC TGGGGCTGGG CGGCTTCTCC CTTCCCTGAA
2201 CTCGCCATCT GTTCCAGCCC CCAGCCCCC TGCCTAGCAG CCATGGGTAG
2251 GTCACTGCCC TCACCTGGGG TCACCCCTTC CTCCCCGGAG AGCTCTGACA
2301 GATATCCTGG AACCTGAAGT GGATCCTTCA TGCCCCATCC TGAATCCCAA
2351 AGCCACCTTC CTGAGGTGTT GAAGAAGCTG CTCCACCTTG GAACTACTAT
2401 AGGGGCTGTG GTGGCCTTTC ATTCCTTTAT CAGCAAAAGC TTTTGTCACT
2451 TGTGTGGTGG GGGACATGCT TAGTGTGAGA ATGCAGAGAC CCATGCCAGG
2501 CCCTACCCAA GGACATGGTG CTCCTTCAGC CATTGTCATC AGAGCCACAG
2551 AGGGGAGCTT CCTGGCAGAG GAGGAGTGGG GAGAAGCTGT GGAATGGCTC
2601 CTTGAGCTCC CCACTCCACC CCTTCCCCAT GCCTGGGCTC CCATTGCAAA
2651 GACCCAGATG TGGGCTTATC CTGTCCCCCA GCCAGAGGGA GTCACCCAGG
2701 GGTGTTCAGG CCAACCCTTT GTGAAATCCA TGTTCCACCA GTTACCAGCC
2751 TTTCTCCGGA GAGCTGAGGG CTGTCTCACA CTGGGTAGTC TCAGCCTGCC
2801 CTGGGGTTGG GGGGTGCTC ACAGAGCAGT AAGCGTCACT GCCTGCATCC
2851 CCACACACCT GCATTATCTT GTCTGCAAGA CACGTGTGCC CCTGAGCTGA
```

FIGURE 3-1

```
2901  GCTCTGTTGT GCACCACCCG ATTTCCGTCG GCCTCCTTTC TGACTTTTCT
2951  CCATCAACAT TTCCTGCTTG GGCCTGTTGC GGGCTGCCCA AAGGCTGTGG
3001  ACTGGGGCCG AGGTACATAG GACTTTGGCT TGTCTTTTGA GCTAACAGGA
3051  TCCTGTAGAA GAAATGAGAT GAGCCTGAGA GGGGGTCGGG GGGTGAGACA
3101  TTAGGGAAGG GAGAGGCCAC CAAGGGTCTC TAGCCCAGAA TCCAATGCCC
3151  CTTCCTGCCT ACCTGTCCTT GTGGGTGGGA GGCAGGGTGT GTGCTGACTG
3201  GCCCAGCAAT GGTGGGCTAG GATTTGGGAT AGGCAGAGAA AAGGAAGAGG
3251  AGGGGGAAGT CGGCCTGGGA GGAGAAACAC TGTACAAAGT CGAGGAGGAG
3301  AGAACCAGAG TGTGCTTAGG GACCAGACCT GGCCCCACCT GGAGCAGAGG
3351  ATGGTGAGGT CAGTCAGGGC TGGATCACAA GGGACCTCAA ATGCCAGGCT
3401  GAGGAGCTTG GCCTTTATCC TGAGGGCACT GGGGAGCCCT GCAAAGGTTT
3451  TGAGAGGGAA TTCCATTACC AGATAGATGT CTTTGGAAGC CGCCTCTAGG
3501  TGCAAGGAGG AGGTGGAGTA GAGAGGTTGA CCTGGGGTAA GGGTTGGAGC
3551  ATGACCAGGG GAGGGGGAAG GAAGCAGGGG GTGGGGATGG AGGGAGTGGA
3601  TGGATCTAAG AGAATCTACT GTCCTTTGGA ACAAACGATA CAGGAAGTGT
3651  AGGAGAGGGA TGGGCAAGG CGACTTTGAA GTGTCCAGCT CAGAGATTGG
3701  AGGTTTGCTG ATGCCTTTGG GAGGCCAAGG CAGGCAGATC ACGAGGTCAG
3751  GAGTTGAAGA CCAGCCTGGC CAATATGGTG AAACCCCGTC TCTACTAAAA
3801  ATACAAAAAT TAGCCGGGCG TGGTGCGGGT GCCTGTAGTC CCAGCTACTT
3851  AGGAGGCTGA GGCAGGAGAA TTGCTTGAAC CCGGGAGGCA GAGGTTGCAG
3901  TGAGCCCAGA TCGCACCACT GCACTCCCCA CTCCACCCCT TCCCCATGCC
3951  TGGGTGACAG AGCGAGACTC CGTCTCAAAA ACAAAACAAA AACCCAAAAA
4001  ACAAAAAACT AAGAAGTTTG CTGATGCCTT TAATAGTAAC AAAAGGTGTA
4051  TTGGATGTTC AATATTTGAG GGACCTACGG GTTGTTCCCA GAGGAGATGT
4101  CCAAGAGACA GCCTGGACAC CTGGAGCTCC AGGGAGAGGG ATGGGCAGCA
4151  GGGGACACCC GGAGTTGTTG GTATGCTGGG AGAAGGCTGC ATGCTCCGTG
4201  GGAGTAGGGT GGAGAATGAG GAGAGACAGG GCCGCCGTCC TGCAAGGAGC
4251  ATCCATATTG AGGGGGCGAA GATAGGGTGC ACCAGTGAGG GAGACAGAGG
4301  AGGGGCCGTC TGGAAGGTGG GAGGGAAACA GCCGCGCAGG ACGGGGCGGG
4351  GGCGGGCGCT GAGAAGAAGC CGCCTTCTTC GGCAAAGAGG TAGCTGAAGC
4401  CTGTGGAGCC TGCAGTCCTC TCAAGGCTAT GGGGCAGCG CGGAGGCCGG
4451  ATTCCAGAAC TGAATCTTCC CATCGCTTTG GGCAGCCACC CTACCTCCCA
4501  GGAGCATCCT TCCTGCCATC CCACCTCCAG TTCCCCAGCT AACAAAAAAC
4551  GGTGTTTCTT GACTCCCGGC AGGGCGGCGG GGCGGGCAGG TCTTGTGAAC
4601  ACGGCTCGCA GGGTTCAGCA CCCTGGAGAG AGGCCTGTGG CCGGGGCGGG
4651  GCCTGCGGCG GGGGTAGGGG CGCGCAGTCA GAGCAGTCGG GCCTTTGGCT
4701  CCGTCTGGGA GCGGTCTTGC AGGCAGGCAA TTGGTGGAGG AGGGAAAAAC
4751  AATCTTGGAT TTTCTCCAGC TCTCTCCCCT TTATGCACCT CCCCCATCCC
4801  GGCACTGGCC TACAGGAGCC CCTATCCCAG CATTTGGGGC TATTACTCTC
4851  CTGACGACTT CAGGAAATGA GATGGGAGGA GAGGGGCAAC TATTTACTGG
4901  GAACTTTTCA GACATTCCCA AAACCTCACA ACCTTTTGAG CTTGGAATTC
4951  GTGACCCCAT ATTTCAGATG AGGAAACTAA ATTGAAGTTC AGGAAGGTGA
5001  AATACCTTGC CTAGGCACTT GGCAGAGCTG GGATTTGAAT TCCACCTGCC
5051  GGGCTCTAAG TCCTGAGTGC CCATTAGCCC TTCTGAGTCC TGAATCTTGC
5101  AGTTTGTTCC TGCAGACTCT CCACTTCTGG GTGGCTGTGG AGTCTGGTGT
5151  GGCAGTGGGA TGGGGAGGAG ACCTTCCCTT CCACCTGCTT GCTTGAGTGT
5201  ATTCCCAGGA GATTTCTGAA GATGAGGCCA CCACCATTGT TTCTGAAGTG
5251  GGAGGGCAGA AAGGAGGCTG AGGGCCAGGT GAGACCTCGT CACACCTGCA
5301  CCCATGCATG CCCAGGAGGA ACCCTCCTTT GAACTCTTCT GACTCAGCTT
5351  CTTGCTGCCA GGTTCCTCCG ACCAGTGAGC AGGTTCCCAG GACATGAAGG
5401  GGAGCTGTGA GGGAGCAGGA CGCCATGGTC CAGGGCTGCA GCTTCCTGAG
5451  CCCAGAGAAT GCCTTCCTAG CTGTCAGGAA TGGAGCAGCG AGGCCCCAGT
5501  GATAGGTGAG GTGGAGAAGC AAGACATGAG TTCTGGGCTG GCTCAGCTGC
5551  TTTACAACCA GCCTGGGCCT CGTTCCCTTT GAGAAAATGG TTTGCCCAGA
5601  GTTCAGAGAT CTAAAATTCT ATGATGCCTT CTGGGGCCAC AGTGGGAAAC
5651  AAAGACTCCT CATATTTTCT TTCCTGACAC TTCCCAGGCC ACAAGACAAC
5701  TGCTTTCTGC AGCACCCAGC CTGGGCAGGC CATCTACACA AGCTCAGTCA
5751  TTTCTGACCT TGCCCCCTCC ACCGTGCACC CCCATGTTCT TCAACATGGG
```

FIGURE 3-2

```
5801  TCAGGTTTCT ATTCAGCCTC AGGGACTTCT CTGCTTGAAG CCTGTTGTGT
5851  GGCGGGGAGG TATTCTCCCC ACAGCTCAGA GAGATGGGGT TGCTGTGGAG
5901  GGTTTGCTGT AGCTCCTCTA CCCTGGAATA TACCCTCTTC TGCCTTAAAA
5951  GACCCAACTT GGACCCTCTC TTCCAGAAAT GCTTGCTAAC CGCCCCCCCA
6001  CCACCCAAAC TAGGTCAGGG GTCCCTCTGG GCTTCACAGA CCCTGTGCTT
6051  CTTTCTGTCA CAGCCTGCAA GTCTCCCCTC CCCACTCCCC AGCCCGAGTG
6101  CTTCTCTGAG ACAAGGGATA GTGTGAGCCA TGAGCTCAGC CACTGGTAGG
6151  CCAATGAATA AGTAAGTTAA TGGTGAAGCC AGGATCCAAA TCCCCATTTC
6201  CTGCCTCAAG GTGTGGAGCT GTTTCTCCTG CATACAATAG TAGCTCTGCT
6251  GTGACAACTC TCTATCTGTC CTAGGGCCTA AAATGCCTCT ATTTCACTAG
6301  GTTATAGCTT TATCCTAGGG AGTCCTCTTT GGAAGCAGGG TGGGGGTGCA
6351  ACAGGCCTTC CCCCATGCCT GTAGTCTGTG AGCAGCGAAG GCCATGTGGG
6401  GCAGGCTGTG GCCTAGGTCT CCACAGATCC TGGTAGAAGT CCATGCTCAC
6451  GCATCAGCTC CAAGTCCCAG CTAAACCAAG CCACCAAGAG GTGGGCCCTG
6501  TGACAAGGCT CTGAGTCCAA AGGCCATCAG TAAAGCCCCC TAAGTCTTCC
6551  GTGGACCCAG CTCCAGGCTG GGATGCACGC TAGGAGATGA TACACACCGG
6601  GTGAGGGAGC CCAGAGGAGA GGGCAGCTAG CTGTGCATGG AGGCCTGATC
6651  TCTCAGACTT GAGGGCACAA GCGTGTCCCC TCATCCTGAA GGCTTCTGCG
6701  ATGGGCAGC AGAGGGTCTG GGTCTGCTGC CCCTCAAGTC CCCAGCCCCA
6751  TCCTAGCCCA TGAGGATTGT AAATCCCTCG TCCTCTCCCC TCTCTCCTCT
6801  GTCAGCCACT CCCCTTTCCC CCTACCCCAC TCTCTTTCTA TTTCTGCCTC
6851  TGATTTTTTT TCCTTTTCTG CCTTTGTTCC TCTGTGTGTG TGTTTCTCTA
6901  TGCCTCTCTG ATCTCTTTGT ACTTCCATCT TGATCTCGCT AAGGCTCTGA
6951  TCCCTCTCTC CTCTCCCTCT TCATGTGTTA CTGTCCCCCT TCCTGTCTCT
7001  GTTTATCTCT CAGTCTCTCT GTCTGTGAGT CTTTTTTCCT CTCTCCCAGT
7051  CAGACTCTCT CTCTACCCCT CCCTCTCTCC CTCTCTCCCT CTCTGTCTGG
7101  GCCTCTCTCT GTTCCTCCTC CCTCCTCCCT CCCCCTTCTG CATTATCAGA
7151  CCTGCTCCAA CCTCCTCCCA GAGCCAGCCG AGCAGCAGAG GCAGTGGCAG
7201  CGGGAGAGGC GGGAGCAGCG GGGCAGCAGA GCTGGATTGG GGTGTTGAGT
7251  CCAGGCTGAG TAGGGGGCAG CCCACTGCTC TTGGTCCCTG TGCCTGCTGG
7301  GGGTGCCCTG CCCTGAACTC CAGGCAGCGG GGACAGGGCG AGGTGCCACC
7351  TTAGTCTGGC TGGGGAGGCG GACGATGAGG AGTGATGGGG CAGGCATGCG
7401  GCCACTCCAT CCTCTGCAGG AGCCAGCAGT ACCCGGCAGC GCGACCGGCT
7451  GAGCCGTGAG TATAGTGAGG GGCTGGGGTG GTGAGCGGCT GTGAGAGGTG
7501  CCACAGACAG GGTCCTGGGA GTCCCTCCAA GGAGCTGGGG CTGGCATGGA
7551  GCTGAGCCAC GTGGAAGGAT CGATCCTGTT CCTGGGCACC CCTCCTCCCC
7601  GCGTTGCCAG ACTGCAGCCT GGGGTGGGGG CAGGTTACCT CTGAGCAGAA
7651  TGAGGGTGTC TAACGTCAAC CTAGTAGGTG ATGAGGCTGG GGTCCCATGG
7701  AAGGGGCTGC TGGTTGGAGG AGGGGCTGAT AATGAACCTG AACCGCTTCT
7751  TCAAGGGCTG AGGGTGTATG TGGGGAGGGG GAGGTCTGCC AAGTAGTTGG
7801  GAGGAGCTCT CGGGGCTGCA ATAGGCTGGT TCAGGACCCT GGAGAGGGAG
7851  AGTGTCTTGG CCCACCAAGG CTATGTGTGT GTGAAGGAGG TGGGGAGGGG
7901  GAAAGATGGA GAAAATATGA ATAAGAGTGG CCCTGGAGCA AGAGAGGGTT
7951  AGAGGTAACC ACCTTCCATG GAATTGGGAA TTGGGGTTCA GGGACACCAC
8001  TTTATGAAAC TTTACCCCAA AGCGTCTGTC CCAGGATAGG GTTCTACGGA
8051  GCCAGATGGA ATATGGTGCC AGCCTCGTGT GTGTCCACGT GCAGGGGGGT
8101  GCATGTGCAA GTGAGTGGGG GGCGCCGTGG CGACACCCCT CTACTAAGGG
8151  CTGCCGAGGT GGTAGGCAGG GTGTGTGTGT GTGTGTGTGT GTGTGTGTGT
8201  ATACATGTGG AATGTAAGGG ACATGTTGGG TGTAGAGGGG CCTGTAGAGC
8251  TCTAGGGTCC TTGGTGGTTG GATGTAAAGC AGCCTGTCAG AGTTTGTGAT
8301  CATCCCTGTG TGAGTGAGAG TTTATTCGCA TGTGTCTGAG TGTGAGTGCA
8351  GGTTGGTCTG CATATGTATG TAGGTGTGTC TATTAGGTTG AGTTTGTATA
8401  TTATGTGTGT TGTGTCTGCA AAATAGAGTG AATCAGTGTG CATTTTTTAT
8451  CTGTTCCATG TGCATTTATG TGTGTGTATT TGTTAGTGTG TGAATAATAG
8501  CATTGCTGTG TGTGGAGGTG GATGTGGCTG TGTGCGTATA AGTATTCTGG
8551  TGTGGGTGTG TGATCATGGT GCTAGTGTGT ATATCGGTGC TTCTGTGGCT
8601  GGTGTGTGTG TGTATCTATA TGTGTGTATT CATCTGAGTG TGTGTGGGTG
8651  GCTGTTTCCT TCCCCTGGCA ATTGAGGATA CAGCTGGGAC ACCATGGCCC
```

FIGURE 3-3

```
8701  ACTGATGCAG GGCAGGGAGG GGCTGAATGT ATGACCGCCT CTTTGAACTC
8751  AGGACAATTC ATTCTACACC CTGTGGGAAA GATGCAGAAA AGAAATAGGC
8801  AATAATGACT CTGCCCTCTG GGGCTTCCTA AGCTTCTTAG ACATAAAATA
8851  GCTTGAGAAT AATTAAGCAG TAGAGATCAA CGTCATGCTA ACAGGTGGGG
8901  GTGGGGTGGG AACTGCATAA GCAAAGGCCC TGGGCTGGGC ATGTCCTGGA
8951  GCAGTGAAGA CACTGTATAG AGTGGGGGGC AGGCAGGACC CACATTCAAT
9001  AGAACTTTAA GATCCAGGAC TCTTAGGCTT TATCCAGAGA GCCCTGGGGA
9051  GCCCAGAAAG GTTTTATATA GCGGAGAGAC ATGATCAGAT TTGGGTTCTA
9101  GAAACCTGCC CTGGGCCAGG CATGGTGGCT CATGCCTGTA ATCCCATCAC
9151  TTTGGGAGGC AGAAGCAGGT GGATCACTTG AGGCCAGGAG TTTGAGACGA
9201  GACTGGCCAA CATGGTGAAA CCCAGTGTCT ATTAGAAATA CAATAAAATT
9251  AGCTGGGTGT GGTGGCACAC GCCTGTAGTC CCAGCTACTT AGAAGGCTGA
9301  GGCATGAGAA TATGAGAATC GCTTGAACTT GGGAGGTGGA GGTTGCAGTG
9351  AGCTGAGATT GCCTTACTGC ACTTTAGCCT GGGGGTGACA AAGTGAGACT
9401  CTGTCTCAAA AAAAGAAAAA AAAAAGAAGA AGAAAAATAA AGAAACCTGC
9451  CTCGGTGGCA TTGTCTGGGT TGAACTGGAA GAGAGAGGTG GGGCCAGGAG
9501  GCTAGAGTGG AGGCCAAGCC AATACAGGGG TCAGTGAGTT CTGGAGCTTT
9551  TTGAGAACTT GGGAAAGGCT GGATAGATGA GAACAGGGAA GGGAATGTCT
9601  AGGTGGCTCA GGCTTGGACT GGGGTCAGGG GTGTAGTGCA GACATCTCAG
9651  TAAGTCAGGA TCTCATGAGG GAAAAGGCTC ATGGAAGGCT CAGGAAAGCT
9701  GGGCGTGGGT GGGCTGAGGT AGTGGGAGAG ATCTTTGTAG TGTTTCTAGC
9751  TAGGATGCAG AGGGTCAGAG ATCATGGAGC CATCTCTTGC CAGACAGGGA
9801  AACTGAGACT ATGGCTTCAT CACTATCCTT TGGCTGCAAG GCTGGGGCTC
9851  AACCTCTTCA TCAGACCTGA CCCTCAATAT CATTCTCCTT CAGGCCCTGC
9901  CCGGAACCTC TTGGTTGCTG AGCTTGGTCA GCTCAGTGAG GGTTAATTGT
9951  CTTTATGCTC CCTGCACCCC CACCCCCCGC AGTCATTCCC CCTGCCCACC
10001 AAGCAGCTCC TGCCACTCTT CCTGCTTCCC ACTCCAGCCT CCTGTCCCCA
10051 GGGACTGCTG ATGGCTTGGC TGGGATCTAG CCAAATGGTG GGGGGTGGGG
10101 GCGGGGGTGG GGGGAAGAGC TCCCAGCAGT CCTTTACCCC TTGGTCTTAA
10151 TGGACTGGGA GTCTCACCCT CAGCCATGCT GCTGTCAGGC CAGGCCTGCG
10201 CTCCCCGGGC TTCTGCTGCT TGGGCCTATG AAATCTCCCG ACTCAGCATG
10251 ATTCCATTGC TGCATTCATT CATTCAACCA CTCAACAGGA ACTTCTCAGT
10301 AGCTGCTTGG TGCCCACTTG GCTTGTCACC GGGGACACAG AGCAGACACT
10351 GACTGAGTCC CTGTTCTCAG GGAGTGCCCA GTCTGATGAA GGAGAAAGAA
10401 ATGGAAAGCT GCAACCCTAC AGGGTGAGCA GTGCTGTGTA GGAGGTGGGG
10451 GGCCCACAGC AAGCCTGGGC TTCAGAGGAA GAGACATTTG AGCCGGACCT
10501 TGAAGGATGG GTAGGAATCA CCCAGGCAGG GAAGAGCAGA GGGAACAGTT
10551 TGTGAAGGTG GGTAGGAAAG GCACAGGGCT AGGCACCTGA CTCAGTGCAG
10601 CCTCTGGGTG GGAGAAGACA GTAAGGGCGT TTGGGTCATT TTCTAGCAGT
10651 TGTTTTAGTA CTCTCTACAA CTTGCCCTGC AGATCTATCC AGCCTGCTGT
10701 TTGCATACCC CCGGACATAG GATGTTCATC TCTTCCCTCC TGGGCAGCCC
10751 TTCCCTTGTG GTGGTTATAT CTGTCCTGGG TCTTCTCCGC AGGGCCCAGC
10801 AACTCCAGGC TACCCAGCCT GGCCTTATGT CCTTTCTCCG TCCTGTGTCA
10851 CTGTCCCCTG AAGTAGGGCC AGGCTGGGGC ACAATGATCC AGGAGTGGCA
10901 AGAACACATC TAGGCAGAGA GTGGGAGAAA TGCGCAGCCT TTATTAACAA
10951 AAATCTGAGA TGGGTGCAGG CCCTGACTCC TCTCCAAAAA TAATGATAAA
11001 GAAGCAGGCA TGGCCAAATA AGGGAGTGAG GACAGACAGC AGGAAGAACT
11051 TCCTACCAAT GCAGAAGGGC TGTGAGTCTC TTGGTTTTAT GAGAGTGGGC
11101 TGTACGTGTG AAAGGGAGGG TCTCAGAGGA CAAGAGGGGG AATTGGAGGC
11151 AGAGGCACTG TCAGCCTCTG ACTCTCCCAT AGGTGAGTGA GTGAAGTCAT
11201 CCAGGGAGAG GGAACAGAGG AGGGAGATCA GGACTCATCA TTCATTCATT
11251 CAGCAGCCGT TCACTGGCCC TACCAAACAT GACACCCCTG GGGGCAGATG
11301 GACAGAGCCA GTGACCACGT GGATGGAAGC TCCGAGTCTT TCCTACCTGT
11351 GTTAATGTCG CAGGAAGGTA TTTAGGAGGA GGGGCCATTG GGGCTGGCCT
11401 TATAAGGAAG AGCCACTTCA GGCTGAGTTG AGGGACAGCA CTAGGAAGAT
11451 GGAAGAGCAT TTGCAAAGGC CTCAAGGTAA GGGCAAGCAG GATTTTGTTC
11501 ACTTAGCACT ATAGGAGTTC AGAGTGGCCT AGGCATGAAG TGCCAGGCTG
11551 GGGGGAAGCC CTGGGCCGTG GTGGAGCAGG AGAGGAGTGG GGAATTGAGC
```

FIGURE 3-4

```
11601 CTAGACTGTA GGAAGCACTT TCTTCCGTGA AGGTGTCTCC AACAGGCTTG
11651 ATGTGTAGGC ATTATTGTAA GTTTGCAACT TCTTGGTCTC TCCTGGTGCT
11701 CGTGACCAGA GCTTGCTGAG GGACCCAGCC TTGCTTGAGA AAGGGGTGTT
11751 CAGTGAACAA AAGAGACCCT GGAAATGAGA GAGAAGCAGT GGCTGAAGAA
11801 TGTGGGCCCC TTCCAGAAAG TGGCGTGCAA ACAAATACAA AGCAATATGC
11851 AAATCAGCTG GCTAGGGCTT GGCAGCTTTG GTTGGAAGAA ATGAGCCATC
11901 ACCCCTTATT ATGCCGGCCT CCTACCCCCT CTGCCCCAGC CTCCAGGACA
11951 GCCGGAACAG CCTTGTCTGC TCCTTGGAGC GCCCCAGCTT TTCTGAGACA
12001 CAGGATTGTG GCCTCCAGGG TGGTGGCCGT GGGCTCCCTG TCAGCACCCT
12051 CGTCCTCCTG GGAAGTCGAT ATATTTAGTA ACAGAAATGT TTTCACACAT
12101 TTATCTCCTA TTGTTCAGCT GCTTGCTCCC TGGGAAAGGC CAGGTCCCCA
12151 GTGATGTGAC CCACTTCTTG AAGTCCCTGA AGTCACCCTT CTCACTGCCC
12201 CCCCACCCCG AAAAACAGGA GGCAACTGGG GCTTGGTGCA GCAGAACAGA
12251 TTTGAGTCAA ATATCTGGGA GGACTTCCCA ACAGTGTGGT TGCTGAGATG
12301 TGTGGACCCT GGATTTCTGG GCTTTCATTC TTTGGATGGT TGCCTTGGGC
12351 GCAGAGGAGG CTTTGAAGAT AGAGCAGAGA AGGTGGCAGG CAGGCTTATG
12401 CTCAAATTTC AGCATACTGA AAGATGTACT GTTACTCTGT AGCTGTGTGG
12451 TCCTGGGCAA GTTACTTAAC TTCTCTGAAC CTTGTGTGAA TAGTGGGGTG
12501 GAGATAATTA TCCTTTCTTG GCAGGATGAT TCTGAAGAAT CTGGAAGTGC
12551 AGAGCTTAGC CCCTGGCATG CGGCAGGTGC TCACAAAGGT TAGCTACTGT
12601 CATTATGAAC CACCCACGAT CAGCCACACT TTCAGAAAGA TTTAGCGGGG
12651 CCTGGAGAGG GAGAGACCAG AGCTAGGAGC TCAGGGCTGT CATCGTGTGG
12701 GAGGGACCAG GAGGCCTGAA ACAGAGCTGT GGTTGTGGCT ACGGTGAGAA
12751 GCACAAAGCT CTGTGGGAGG GACCGAGGTT TCTCAGAGAA GTGTGGCCAC
12801 CTCATTAAGT TGTTCTGACT GGTCTGAGAC CAATCCCCAG ATAATACAAT
12851 GGAAGAAAGG GCTTGGTGAA GAAGGGGTTA AGTCTGTGGC CACACCCATG
12901 CAGTCTGTGA GCCATTCTGG GAGCTGTAGT CTGTTGTGAA TTTGCAGTAA
12951 GCATAGTTTG TACTGCCTCT TTTGATCCAA ATCCACACCC TGCTGCCAAG
13001 GCTGGCCGAG GGCCGGCCCT GGTGGGTGCT GGGCTGTGTG GAGCCCAAAG
13051 GTGAAGCAGC ATCGACCTCT TCCCTCAGGG ACCCCCTGGC TTGCTATGTG
13101 TTGGGGGGTG CAGGTAGGAG CAGGGATAGA AGTATTAAGC CATAATTACG
13151 ACTTCTCACA TGTTCACACA GAAGTTTACA GCTTCCTGAG CACTGTTTCC
13201 ACACCTGTGA TCTCATTTAA TCCTCACCAC AAACCCAAGA GACTGCTGTT
13251 TTCTGGATGA AGAAACAGAG GATCCAGGAG GGGAAATCGC TTGCCCACAG
13301 GTATTCAGCC AGTGGAGCCA GACCTGGGGC ACAAATCTGT CTGCTTCCAG
13351 AGCTCCTGCT CTTTCCATAC ATTACTGTTC CAGATGGCAG ACAGGCAAGA
13401 TGTGGACAAC TAAAGTTGGA TGTGAGACAT CTCGGCAGAG GAACAGCTGA
13451 GCAGAGAGCT GCTGATTCCA GGCTGAGAGT TTGGACTTTG TGTTGTGGCC
13501 CACCAGGATC CACCCAAGGG TTTTCTGATT AGAGCTGAGC TTTGAGAGAA
13551 TTGGTCTTGC AGCTTAGGCT GAATGGATTG AACTGGAGAA ACCAAAGTCA
13601 GACTGAGGCT TCTAAATCCC ATCCTTGGTG CACCCAGCAC TTTGCTGCTG
13651 TCCCTCCTCC ATGCTTCTTC TCAGTTTCTT CCTTCTCCTC TCCTTCATCT
13701 TCTTCCCTCA CCCTTTTTTT TTTTTTTTTT AATAGAGACA GTGTCTTGCT
13751 GGCTGGAGTA CAGTGGTGCC ATAATAGCTC ACTGCAGCCT CAAATTCCTG
13801 GGCTGAAGCT ATCCTCCTGC CTGGGCCTCC CAAAGTGCTG GGATTACAGG
13851 TGTGAGCCAC TGCACCCAGC TCATCTTCCT CTTTCTCTCC TACTCCTCTC
13901 TGCCTCAGGC TGAGGAGTGA TGACTTTTAT ACCATAGAGC TGTGCTGTAA
13951 TATCACATGT CTCCAGAAGG GGGTGCTGTC ACATACAGTC CATTCCAGCC
14001 TGAATCTTCG TTGTGTTTGA AGGGCCAGTA GAAGTGTTGG ACAAGTGGCA
14051 GAGATGAAGG ATGGAGAGAA GGATAGCCCA TTGTTCTCCA CCTCCATTGA
14101 GCCCAGGACA TGAGGGCCCT GCTGAAATGG CACTGGGAGG AATGAAGGCT
14151 GAGGAGAGGT TGGACCCCAA CCAGAAGGGA CAGACATACT GAGTTAAGCC
14201 AGAGGAAATT TTCTCCTCAT GGTTCTGGGA CAGGCTAAGA TTTGGAAATG
14251 CATCTAGAAT GACATTGCAG TTGGGGTCTG GGTTTCTTTT GGGTCATGAC
14301 TTGCTTGATA CTGAGGTGCT GGGGATATTG CTTGTGTCTC AGTGTGTGTA
14351 TGTGTACCTG AATGTGAGCT TCCAGTTGTG CATATGTGTA TGCTGATCTG
14401 AGAGGGTGAG AATGTGTGGG TCAGTGTTCG TATAAAAGTG TGAACATACT
14451 CACATGTGTG AGCATGTGAG TGTCCTTTTT TTTAGTTTAG TTTTGAGACA
```

FIGURE 3-5

```
14501 GGGTCTCACA CTCTCACCCA GACTGGAGTG CAGTGGCGTG ATCTCGGCTC
14551 ACCGCAACCT CCGCATCCCA GGCTCAAGCT ATTCTCCTGC CTCAGCCTCC
14601 TGAGTAGCTG GGACTACAGG CATGCACCAC CACACCTGCA TAATTTTTGT
14651 ATTTTTAGTA GAGATGGGGT TTCACCATGT TGGCCAGGCT GGTCTTGAAC
14701 TCCTGACCTC AAATGATCCA CCCACCTTGG CCTCCCAAAG TACTGGGATT
14751 ACAGGCATGA GCCACTGCAC CCGGCTGTGA CTGTCCATCT TTATGTCTGA
14801 TTTTGGTAAA CAGTTATATG CATGTGACTG TGGCTTGTGT GTGTGTACAT
14851 GTATGTAGAG TGCCATATAC ATATGTTCTA GTGAAACCGT ATGTGTGTTC
14901 CCTGTGTATA CAGATGCCTG TGTCTCAATG TGAGCACAGG GATGAGGGGA
14951 TATGTGTGTG TGAAGGCCCA GACACCTGCT GTGCTAACCT TTAAGGCCGC
15001 GCCTAATGTC TGGCTATTCA ATACTTTTTC TCCTGGGTCG CGCTTTCCTG
15051 TAGGTAGAGA CCCTTGAAGG GCTGGGCTTC CTTCAGGGGA CTCTGGGCCA
15101 GAGTCAGGCT TTGTGTTCAG TCTCAGGTTG GGCCAGCCAG GGTCCTAGTC
15151 TATCGGATTG GGCAGCTAGA CATGGCTGGG AAGTGTCTAG GTTCCATTCT
15201 CCCCAGGAAC TCTTAATGGT CACACTTAAA GAGTTTCAGG GACTCCCAGC
15251 ACGGTCCTCT TGTACTGATG CAACTACTGA AGTTCAGAGA GGTGCAGTGA
15301 TTAACCCAAG GTCACCCAGC AGGACCCAGG ATGAGATGAT AGGGCTTGCA
15351 GCAGAGAGGG GAGTGTCTGA CCTGGAAGGC TGCCCTCCCT CCAGCCCCTA
15401 GAGCAGGTGG GGAGCTCAGA GGAGAGCCAA GTCTGTGGTG TGAAGCCACC
15451 TCCTGCACCT GGCTATTTCC ATGCCTCCTG GGCCTCAGAG GCTGCCTTTG
15501 AAGTTTTTAC CAGAGCTTCT GCATGCTGTG AGATTCCTCC TGGGGACGTG
15551 TGAAGTCGAC TGTTCCATGG AGCATGGAGA CTCGATGGAG AGGAGCCCAG
15601 TGGTGAAGTG AGGCCAGAGG AGGGGCTTCC TCTGGAAGCC TCAATTTCTT
15651 CTTTGCAGTA GTTGCTTTTT TTTTCGTGTT TTTTTTTGTT GTTGTTTTTT
15701 AGGTTTTCAC CGTTCTAACA TTCAAGGCTT TCTCTGTTAT CTCTCTTTGA
15751 GCTCTTAGTA CTGAGACAGT GCTGGGGTTT GGGGCAGTCC TGGAGGCCTA
15801 TCTGGGCTCA AAGTGAGGGT GGCAGGGCAG TCCCTTAGGG AAAGGGCTGC
15851 GTGGGAGACA GGGATGAGCT TCCTGCCCAT AGTGGGGAGG CATGAGCAGG
15901 GGCTGGACAG CCTGGTTAGC AAGGCTGTAT ACAAGGTACC TACCCTAGTG
15951 AGGAAGTTGG TTGCAGATTA TCTTGAGTCC CTTCAAGCTG TAGCTGCCAT
16001 GGGGGGCCAG AGAAGAACGT GCCTCAGCTC TCTTGGGCCT GGGGAGGATT
16051 GAGTCCACAG AGTGCTCCTG GTGTCCTGGG CAGTGGAAGG TGCAAGGTTA
16101 GACTGTGCAC CTGGAAGCAG AGAGATCCCA TTCCCTGGAG AACTGAAGGG
16151 AAATTTGTCT TCCTGGAGGT TTGGGGCTGG AGGCAGGGGC TGGATGGGAG
16201 GACACTCTGG GGTGGAGTGG GGGTGGGATG GGGAGGACTG GGCAAGTCCG
16251 AGGCGGCTCT GCTGTTCAGC ACCCGCAGGA AGGAGCAGGG AGGCATATCC
16301 TGAATCATGC AGGGCTCTAG GGTGGGAGGC CCATGGTTGT GGGGCTCAAA
16351 CATGGGCTCT GGTTGGGGCA GAGGAGAGGC TTCCTGGGGT TGGGGTCTGG
16401 GCAGGAATTG GGGTAGAAAA GGAGAGAAGC AGCAATTGGG TACCACCTCC
16451 TTCCCAGGTC AGGTAATTCG GAGTTGTCTT AAAACTCTCA GTGGGCCAGG
16501 CATAGTGGCT CGCGCCTGTA ACCCAAGCAC TTTGGGAGGC TGAGGTGGGT
16551 GGATCACCTG AGGTTGGGAG TTCAAGACCA GCCTGGCCAA CCTGGAGAAA
16601 CTCTGTCTTT ACTAAAAATA CAGAATTAGC TGGGCGTGGT GGTGGATGCC
16651 TGTAATCCCA GCTACTCGGG GGGCTGAGGC AGGAGAATTG CTTGAACCCA
16701 GGAGGCGGAG GTTGCAGTGA GCCTAGATTG TGCCATTGCA TTCCAGCCTA
16751 GGCAACAAGA GCAAAACTCT GCCTCAAACA AGAAACAAA CAAAACCTCT
16801 CAGTGAGGGG GGATCTGGGG TCCAGATGGA GAGAACTAAT GTTTACAGAG
16851 TGACCTTTAA GTTTTAAAAA TGATTATTTA AGGAGGCGAT TAAACAAATC
16901 GCCTCCTTAA ATAATCCTTC CAGGGAGGCC GGGCACGGTG GCTCACACCT
16951 GTAATCCCAG TACTTTGGGA GGCTGAGGTG GCGGATCAC GAGGTCNNNN
17001 NNNNNNNNNN NNNNNNNNNN NNNNNNNNNN NNNNNNNNNN NNNNNGGAA
17051 AAGAGATATT AGNTGAGTA TTAGTAAGAG ATAAAAGAGA AAAACAACGA
17101 AAAAAAAGCA GAGTGATAGA AGGGAAATAG AATAAGGAAG AATAGATTGA
17151 TAGTAGCGGC GGACGAAGAA AAAGACGAAA AACAGCGAGT ACGGAGGCGG
17201 GGGCGGTATA ATGAGAAAAT AGAAGATGAA CGCGATACGA AGGATGAGGG
17251 CGGAGGGAAA GTACAATGGT GGTGGGGTAT GGAGGCGAGA GTGAAAGGGA
17301 GGTAAATGAC GCACAAAAAC AAAAGACGGA AGGGAACAG GAGGAGGGGG
17351 TGGTAGGGGG GNATCGCCTC CTTAAATAAT CCTTCCAGGG AGGCCGGGCA
```

FIGURE 3-6

```
17401  CGGTGGCTCA CACCTGTAAT CCCAGTACTT TGGGAGGCTG AGGTGGGCGG
17451  ATCACGAGGT CAGGAGATCG AGACCATCCT GGCTAACACG GTGAAACCCC
17501  GTCTCTACTA AAAATACAAA AAATTAACCG GGCGTGGTGG GGGGCGCCTG
17551  TAGTCCCAGC TACTCGGGAG GCTGAGGCAG GATAATGGCA TGAACTCAGG
17601  AGGCGGAGCT TGCAGTGAGC CGAGATTGTG CCACTGCACT CCAAGCCTGA
17651  GGGACAGAGC AAGACTCCGT CTCAAAAAAA AAAAAAAAAA AAAAAAAAAT
17701  CCTTCAAGGG GCTAGCCCTA TTTTGTAGAG GGGAAACAGA TGACAAACTT
17751  AAATGGTTTA ACTGAAGACA GTTAGTGAAG CAAGTATTAT GGAGATGGGG
17801  AAGGCTTAAG GGAACCAGCA GGACATGTCA AGTTACTCAG GACTGGCATC
17851  CAAGGGGCCA GGGGCGTTGG CAGAGGGGGG CCGAGGAGAG TGCCCCAGCT
17901  CCATGAGCCA GAGCCCTGGA GATGGGGCTG CCCTGCAGGA GCTGTGGCTG
17951  CAGCCACTGC TTGTCGAAGG AGGCAGGTGG GTGAGGGGGT GAATACCCAC
18001  CATGAGCCTG CATGCTTCTC ACCCTTTGCT CTCCTGCCAG TACCCTGACC
18051  CTCACTGGCA GAATTTCTCT GGATGCCAGG GGGCAAGGGA GCCCTGGATG
18101  AAGCTGCCAC TTAGAAGTCG GCCTCTGGGG CACACAACCC AGCAGCAAAA
18151  GTTAGAGATT GGATGTGGAG GGACAAAGAG ATGATGGGAA ACCGAAGAAC
18201  AGAGAGGGCA TGGACTTGCC CAAGGTCACA CAGCCTGTTG ATATCAGAAT
18251  TGGAGTCAGA AGCCAGGCTC TGCCTCTGAA CACTCACTTT TTTGTTTGTT
18301  TGGTTTTCTT TTTTTTCTTT CTTTTTTTTT TTTTTTGAGA CAGTCTTGCT
18351  CTGTCGCCCA GGCTGGAGTG CAGTGGTGCG ATCTTGTCTC ACTGCAACCT
18401  CCACCTCCTG GGTTCAAGTG ATTGTCCTGC CTCAGCCTCC CAAGTAGCTG
18451  GGATCACAGG CACCTGCCAG CATGCCGGC TAATTTTTGT ACTTTTGGTA
18501  GAGACGGGGT TTCACCATAT TGGCCAGGCT GGTCTCGAAC TCCTGCCCTC
18551  AGGTGATCTG CCCGCCTTGA CCTCCCAAAG TGCTGGGATT ACAGGCGTGA
18601  GCCACTGCAC CTGGCCTGAA CACTCACTTT GTCACATTCA CTGAGGTCTC
18651  CTGAGTGGAC TCATATGCGC ATTATCTACT CTCTGGCTGA GAGCTGCTTC
18701  CTGCCGTGAT CACCGCGCTC TGTATCTGGG CAGCACAGGG GCTGCTGAAG
18751  AATGTCATTC TCAGAACGCA GTGTGCCCTG GAGCCCCCCA AGCCACCTGT
18801  TCATTCATCC CAACTGGCCT TGAGGGTGCC CTGGTGTGCC CTGCCTGTGC
18851  TTGTCACCCT GGCCATGGAG ATGGACCCAA AAGCCCTTGC TCTCCGCTTC
18901  ATTAGAGACA GGCACACCCA GACGCAGGCA ATCAATTTTG TCGGGTGAGT
18951  GCTGGGACCG CTGATGAGGA CCCTTCCTGA GGAGGCGATG CTGGGTCTTA
19001  GCCTTAAAGA ACAACTGAGA GTTTTCCAGG TGGAGGAGAA AAGGAAGGGT
19051  ATTCCAGGCA AAAATCCCCA TAAGAGCAAA GGTGTGAGCA GCAAGAAATC
19101  AAGGGTGGCA GGTTCAGGGC TCCTGGGCTG GAGGAAGGGC CTGGCGGTGG
19151  AGAGGAAGGG AGTGAAGGCC CAGCTCACAA AGGGAAGCAG AGGAAAGTTT
19201  AAGCAGGGTC AGGCCATGGT TAGCTTTGGG GTTAGGAAGC TCCAAATGAT
19251  GGGTGAAGTA GGGGGGCTAG ACCCAGGTGA GAGGCAGTAT TGCGGTTGGC
19301  CAAGGACACG TGAGTTGCAT AAATGGGCCA GAGGAGGGGT GACAGCCGCT
19351  ACTTCCCGGC TCACCTGCCT GAGCTAAGGC CCTAGTTCCT CAGTGTCTGC
19401  CCACCAATGC AGGTGTGTGG CAGCTCTAGA CCCTCCTCTA GGGACATCCC
19451  TCCCTGCCTC ATGCTGCCTA TGGCTTTCAC TCTCTGGAGC ACTCATCCAT
19501  GGCACCCATA AGCCACCCCC TCAGACAATG GCCCCCTCCA CAAAACTGTG
19551  TCACCGTTGC ATATCTCTTG ATAACACTCT GACCCCTCCA CTGCCAAATC
19601  TGATAAAAGA CCTCCCTTTG AAGACCTTCC TCCTGGAGTC GGATCTCAGT
19651  CCTTCTTGCT GTCCAGAGCC TGGGCCTTGG GCCTCCCTGG GAGGCGAGTC
19701  AGTGAGGGCA GCCCCCTTAT GGTGCTGGGA GTTGAGGGAC CTTGGCCCAG
19751  CCAACTCATC CCTGTTGTGT CAGCCTCTCT GGGCCTGGGC AGCCAACTCA
19801  TTTTCAGTGC TAATTAGCAT CTCCCCTGCA GCTTTCTGCC CCACTCTAAG
19851  TGCTTGACAA TCATTAGGTG TTACTGTGTG CAACTGGATC CCAGCTCCGG
19901  CACCTCCCTG CCCCAGCTTC TCCTCCAGAC CCCAGCTGCC TGAGATAAGG
19951  GACCTGGCCA CAAACATACA ACACACCGAA ACCCGGACAC AATCTAGGCA
20001  TAGGGACTTG AACACCAACA TAAATATACA AAGAGGAAAA ACCCAATAAC
20051  ACAGAAGAAC TCCCCATACC AGGAAGCAGA CCATAGCACA GACAGAGACC
20101  CACAGTACAC ACACAACACA GACACCAACA GATGCTGAAA AGCAGACACA
20151  GGATCATTCC AAAAAGTGAC CCAGAAACGA AAACAGAACA AATGGGAACA
20201  TCAATGCACA TGACACAGGT ATACACATCT AGATATGCAA CACAGGTACG
20251  ATTCAGCACA TGTGTGGCGC ATCGCAGGGA AGCACTTGCA CTTGAAGTAT
```

FIGURE 3-7

```
20301  ACACAGATGC CAAGATAGTC AGAGGGAGCC GCCTGTGGTT CCCCACCTGT
20351  GCAGCGTCTC TCGCCTCTGG GCTGCCGCAC ATGCTGTTGC CCGGAATTCC
20401  CTTCCCCAAG GCCCTCCTCT TTTTACCTGG CTAATTCCTG TCATTCTTCA
20451  GATCTTCTAG GAAGACTTCT GCCTCCTTGA TAGGGGCCTT TCCATACTCC
20501  CCAGCCTTGG AGTGCTTCCT GCCACATGGC ATCACTGACT GTTTTCCAAT
20551  GAGTTTCTGT CAAGTTTTGG GATGAAGGAT TTTGCCTGTG CTCGTTGAGG
20601  TGGTGACTGT GGGTGTGAGT GGGTGATTAG GGCCAAAAAA ACCCCCCAAA
20651  AAACTGGACA GAGGCAAATT TGGGGGGAAA TGAGTTAGGA ATAGCTGTGA
20701  GGAGCCCCAG CTACTCAGGG CCTCAGAAGA TATTTATTTC TGTATTTATT
20751  TATTTATTGA GACAGAGTCT TGCTCTGTCA CCCAGGCTGG AGGGCAGTGG
20801  CGCTATCCTG GCCCACTGCA ACCTCCACCT CCCAGGTTCA GGCGATTCTC
20851  CTTCCTCAGC CTCCCGAGTA GCTGGGATTA CAGGTGCGCA CCACCATGCC
20901  TGGCTAATTT TTCTATTTTT AGCAGAGACG GGGTTTCACC ATGTTGGCCA
20951  GGCTGGTCTT CAACTTCTGA GCTCAGGTGA TCCTCCTGCC TCGGCCTCCC
21001  AAAGTGCTGA GATTACAGGT GTGAGCCACT GCACCCGACC TCAGAAGACA
21051  TTGAAACCCA CAGAGAGGAC ACAGCCAGAT GCCCTCTGCC TCATTTTCTC
21101  AGACCCTGCC TGATTTCTCT TATGTTTCTT CTAGGCTTGC TCCCTGACCC
21151  AGTTCCCTCC TTCCCAGAGC TGGCCTTGCC CCTTGCCACC TCTCGGAGCT
21201  CACACATACT CACTCACCTT CTCTGCTTGG CTGTGCCCTA CCCCTACTTC
21251  TACGTGCAGT GAAATCCTTG TTATTCAAGG CCTGAGGTCA GTGGGCACAT
21301  CATCCATGCC TGGCGTCCTA ACCCGTGCCA CTGAGTATCG TGAAGGGAGG
21351  TAGTGGAGGG ACGTGCTTGG GAGCACAAGC CTTGAGGACT GTCTCTTGGT
21401  TCAGATCTCT GCTCCTCTAC TTCTTAGCTG CAGGATTGTG CAAGTTCTGC
21451  CACCTTTGTT CCCTCATCTG TAGAAAGGAG AGGATAATAG AGCCCACCTC
21501  ATTAGGGCAG CCATGAGGAT TAAATGAGAC ACAGTGTGTA ATGTACCTGG
21551  CTCCCTCTCC AGGTTGCGTG AGAGCAGGGA GAAAGCTAAT GAGATCAAGG
21601  ATGTGCAAAT GCACTCAGAA GGTGCCTAGT GAGTCCTTGC TAACTGGCAC
21651  TTAGTGAAAC AAACACCTCC TGTGTGAGCA CCTAATATGT GCCTCTGTAG
21701  TGGGCTCTGT GACCCGCCCC TCCTTAGTTT CTGCATGGCT GCCAGTTCTG
21751  CACAGCTGTT ACTGCTGTGG GGGCTTAGAA GGTGGGGGTA TGACTACTTT
21801  TTCTGAATTT ATTTTTAATT TTTTACATCT GTTTTATGGA GGCATAATTT
21851  ACATACAGTA AAATCACCAA TTTAAAGTGT ATAATGAGTT TTGATAAATA
21901  TATATGGTCA TAACCACCAT GACAATTAAG AAAAGAATAT TTTTATCCTG
21951  GCAAACTTCC CTTGTGCCCT TTGTAGTCAG TCCCTTTGAG GGGGACTTCT
22001  TATAGGAGTG TGAGAAGTAC TGGGTTTTCC TTGGGCTGCA AACCTGGGCA
22051  CATGGAGTGG GGGTGCCTCC AACATGCTGG AAGTTGCCAG GGAACTGCTG
22101  ACCCTCTCTG GGCCTTGGTT CCTGGCAGAG GCAGTGCAGC CAGGCAGGGG
22151  AAGGGATGCT TAGGCCTTGG TCTCCTGAGG GCAAGCCTTG GATGTGAGGG
22201  TTGGATCAGC TGGAAGTGGT GGCTTCAGAA ACCCATAGAG TGGGTGACAG
22251  GGTAGGGACT TGGTGTTTCC ACAAACCCGC CCCTCCTTTG ACCAGGTGTG
22301  CCCTGTGGTC CTGGTGGAAA TGGCTATATA TTGTCCAGAC TGTAGCAGGG
22351  GCTGGCCAAG ATGGTCCACT CCTCTCCCCA TCCTCCTCCA ACCAGAGGCC
22401  ATAAACCCCA CTCTATAGAT TAACAATTCC CTGAAAAGAA GGGGGTCACT
22451  TTTGTTCCCC AGTTCTAGAA CTAAATATTA AAGCAATTAT GTAACTAGCA
22501  ATAAATTACT TAAAGTAGTG ACTCACTCAG CTTAATTAGA GCGCAAGCAA
22551  GGAGGGATTA AGGTATTTTT AGAGCACACA CCTCACTCTC TCCTGTGGGG
22601  GAGGCCTCTG TGCAAGGTGG GGGTGGAAAA AAGGCTGGGA ACTCATGGGA
22651  GCACCCCAGG TGTCTGCAAG GAGATGAAAG CTGATCCTCC GCCCCACTGA
22701  GGTCCTAAGG AAGAAAGGCC GAGTCAGAGC TGCAGCAGGA GGGATTCGGA
22751  TCAGACTCAA GAACACTTCC CAGTGGTGCT TATTTGAGAA CTGGGACGGC
22801  AACACTAGAT TGTAAACTCT GTGAGGGCAG GGATTAGGTC TGTGACCGCC
22851  TCCTCACCCA GCGGGAGACC AAGAATGAGA CTTGGGAGTC AGACACAACT
22901  GGGTGTGACT CCTGCCTTTG CGGGTTGCCA GCACGTGGGC TTGGGCAGGT
22951  TCCTTTATCA CCAGAAGCTT TGCCGTCTCC TCCACTATAA AGTGGGCACA
23001  ATAACATCCA CCTGCATGCA TATTATAAGG ATTGAGTGGG TTAAAATGTG
23051  CAAAGCAAGA CTTTGTGCTC AGCTGGGCAC AGCGGCTCAC ACCTGTAATC
23101  CCAGTACTTT GGGAGGCTGA GACAGAGTGC TTCAGCCCAG TAGTTTTGAG
23151  ACCAGCCTGG GAAACATAGG GAGACCCTGT CTCTTAAAAG AAAAAAAAAA
```

FIGURE 3-8

```
23201  TTAGAAGACT CGGTGCTGAC TCTGCTAGAC CAAAAGCCCA CAAAGGCAGG
23251  GATTAGGTTT GGTTTGTGTT GTTCATTGTT GTATCTCAAG CTTCATTCAT
23301  AGGACTGCAC AAAGTAGGTG TTCAGTAAAT GCTTTGTTGT GTGACTGCGT
23351  GTTAATTTTG TTCCCATTCT CCTGCTCCAA AAAAAAGTTC ATTTTCCTGA
23401  GGTTGTGAGT GAAGAAAATA GGCAGTGTGG GCTGGGTGTG GTGTCTCATG
23451  CCTGTAATCC CCAGCACTTT GGGAAGCTGA GGCGGGAGGA TCACTTGAGG
23501  CCAGGAGTTC AAGACCAGCC TGGGTAACTT AGCGAGATCC CATCTCTACT
23551  TCAAAAAAAT TTAAAACAGA AAAAATCTAG GGTGTGTGGG GGGGCAGGTG
23601  GGGAGGTTGC AGGGGTGCCT CACAGGTGGG AGTCTGGCAT TTCTCCTCCA
23651  GGCTGAGGAG GTGGTGACTT CCAGGGAAAG TCCTGGGAGG GATCAGAACC
23701  ACAGCTCCAG CCTGCTTGGA TAAGGGTGGT CTTCTGGCTG CCAGGAGGGT
23751  AGCTAGGTGG GAAGATCTGC CCTTGTTTCC TCCATAACCT GGGGTGGGAG
23801  GAGGAGGAGC TCCCAGCCCA ATCTGATGGG GGAGACCAGA ACCCTCACCC
23851  ACCATTGCTG GCAGTTCAGA GAAGGCAGCG ATAAGTCGGG GTGGGGCATC
23901  CTGAAAGGCT TCCCAGAGGA TTGGATGGGA GGATTAGCTG AGAAGACATC
23951  CGGCATCCGT AAAATGGAGT AATGATTCTG ACCCTGCAGG TTTTCTGGGA
24001  GGATTAAATG AGTTACATTT TAAAGATGCC TGGTACATGC CTGCCAGGAG
24051  AAGGCACAAC ATATGAACTC CCTCCCTCTT CCCTCCACAC CTCCTCAGCT
24101  CCTGTGACAT CAGGAGGGAC ATGCCCTGCC CTGCTCACAG AGGCTGGGTG
24151  GGAGGCTCCC ATCATGGCCT TCACTGAGGC TGCCTCTGCA GTTGGACCAA
24201  GCTGGACACA CAGTAGGTGC ACATAACAGA TGGGGGCAGG TCTGTGCTTG
24251  TTTTACCAGG GTGTTGGGAG GCTGAGGGAA GGGCACAGCT GGATTGGGGT
24301  GATGGAGTTC AATCCCTGCT CCTCCCCCAG ATCCAAGATC CTAAGACGCC
24351  TATGTCCAGT GGCTGCTCTG ATCAGCTCTG ACCAGCTCTC CTCACACCTC
24401  ATAGGCCTTC CAGGGTTCAG GTGATGAATT AGTGATGACA GCATCCAGCA
24451  TCGCTATGAC AACCACATGG CACTCTTAGC CTCCAGTCAG GGCTCAGCCG
24501  CAGAGGCCAG AGACCCCTTT GGCTCTGGGC CTTTGTACTG GCGTGTGTGA
24551  GCGGGGCTGG GGCCTGAGGG AGATGGAGGA GTGGGAGGGG CAGGGGCCGG
24601  GGCATGGGGC TGCATCTGGC ATGGACTGGA GTTCATTCAG ATTGTTCCAT
24651  CCAGAGGGAC CTTGGGGACA GTTGTTTCTC TCCTTCCTTC CCCCTTTCTT
24701  TTCATTCCTC CATCCCTCCT CTTTCCCCTC CTCCCACTTC TTCTGAGCCT
24751  TGTTCCTGTT TGAGGCCCTG GGCTGCCAAC CCTTTTCCCC TCCTCTGGGA
24801  ATAAAGCCAG GCTCAGCCCT CACCCCGGGG AGCTGAGTGA GGTGGGGGAC
24851  AGCCACCTTC TGGTCTAGGC CTCAGGGAAG GTGTGTGGGG ACCACTGATG
24901  GCTTGGTGAG AGGGCCTGAC CCAGCTGGGC CAGGGGCTGT GCAAGTGGCT
24951  GCTGACCCTG ATGAGTGGGG AGGAGGTTTT CAGTAGAGAG GCAGGGTCAG
25001  AGATGAAGCA GCGTGGGATG GGGGAGCGAC AGATGTTCAG AGTGGCCTAA
25051  GTGTGAGATG CGGAGCAGAG AACGTGGGAG GAATCGAGGC TCGAGAAGGA
25101  CTGGGAGAGA GTGGATGCAG TGAGGAGTTT GAAGTTTGTC CCTGGGGGAA
25151  GAGGAGCCCT GAAGATTTTT GTTGTTGCTT CTTTGATTTT TAAATGGGAG
25201  GGTTCATTTT AGAGATGGGG AAACAGGCCC AGGGTGGGAA AGTGACTTGC
25251  TCAAGCTTAA GTCACTAGAG ACAGACTGAG AGTACAGGCT CTGCTTGGGT
25301  CCTGCTGGAC TCTAGCTGGG ACCTCTTGCC CCAGACTTGC TGGCCAGGAT
25351  TTTCCCAGGT AATCACTACC TCCGAGAAAG GCGAGGAGAG CCCATGGGTG
25401  ACTTTGCCCT CAGTTTGAAT GAAATTTGCA TCAGCAAGGG CTATGCCGAT
25451  AGTCCTTTCT GCTCGTGTCT GGCCTGTTTG GGGGTGGGAG TGGGGTGGAG
25501  GTGAGCATCC AGGGAAGGAT CTGGGAAGTC AGGGGCTTGC CAGGGCCAGC
25551  AAGGCATTAG GGTCAGAGAT GGATTCAAAC TTGGGTCTTT GGAGACCCAG
25601  CCCAGACTCT GTGCTCCATC TCCTTCCTCC GTCTCTCAGG AGCCTTTGGC
25651  TGAGTTAGGC ACCTACAGGA GGCAAGGGCC CCCCGAGCC CCTCACATTC
25701  TCCTCAGGGC TCCTTCTGGC CCTGGGGCCT GATATTGGGC CTGCTGTGCT
25751  GGAACTTATC CAGGCAGAAT AAACCTTTAG CCCCATTGTC CTGATGAAGA
25801  AACTGAGGTC CCGAGGTAAC AGTGACTCAT TCAGGGTTAC AACAGGTCAG
25851  TGGCTGGGCT GGGCCTAGCG TCTGGCCCTC AGCTTGTCTA CATGGCCCCC
25901  CTCGTGGCTC TCCCCTTGCC TCTCGCACCC CACTGTGCAG CATGGTTGGG
25951  CCTGCCAGCC TTGATGGATG GCTCTGCAGC TCAACCTCCC TCCCATTCCT
26001  CTCCAGATGC CGGGCCGTGA GCCTCCTAAT CACCAGTCCT GCCTGGTGGC
26051  CGCCAAGCCA TCCATCTCCC CACACAGCCT TGCCCAGCAC AGGTGATTTT
```

FIGURE 3-9

```
26101  GTTTGGGGAG AAGGGGGGCA CAGCAGGTCT TCCTCTGAGG CTGAGCCAAG
26151  AGTTTGGCTG CAGCCCCCAC TCTGGGGTGC CCGAGGGTTA GGGAATAGCC
26201  TGCACTCCCT TGCTGGAGTG TCAGAAATCC CTCCTGAATC TCCCTAGGGC
26251  ACGTGCACAT GCACACACAG GCACACACAC TCACAGTAAC ACTAATAAAA
26301  GCTCTCGTGT AGCAAAAGAA TATTGTATGG CAAGTATTGT TGCAGAGCCA
26351  TATGTATCAT CTCATTCATC ACTCCACTGT AGAGATACAG AAACTCAGGC
26401  TCAGAGAGGT TAAGTGACTT GCATAGGCTC CATATCCAGG AAATGGAGGA
26451  GCTGGGATTT GAACCCACAT CCTTATGGCT CACATCTTGC ATTCACAACT
26501  CCTGCTCTAC TGACTCACCT GTGCACACAC ACACACATGC ACACACACAC
26551  ACGTGCGTGC ACACACACAC ACAGGCACTC ACTTGCATGC ATGAGCACGA
26601  GCCACCATTT TGGCTCTTGT ACCATCCATC TACCTGGGCC AGGTTCTTGA
26651  GGAGTGAGGA GAATGCTGGG CTGCAGAGGG CATGAGGGGT CACTGCTCAT
26701  TGTCCCCAGG CTGCCCCAAG CTGGCTGTGG CACTGGCTGG CTGGGGAGCT
26751  GCAGGGAGGC AGCAGCCTCC AGGCAGTGGA AAGGGGAGGC TGGGAGACAG
26801  TCGATCGATC ATCCCTGCAG TGCCTCCTTC CAGGAACTGG GGCCCAGGGG
26851  AGTGTGGCGC CACGGGTCGA TGTTCTGGGC AGCAGCACAG TCTCTGAGTG
26901  CGTACAGGGT GTGTGTGGGG CGAGGCTGGT GTGCAGCTGC CCGCCTTCCC
26951  CTGGCTCCCT TCCCCTGCTC CTGCCTTCCT CCTGCCATTC ACCTGCCAGC
27001  CCCACACCTT CCCCTGATTC CCCCACTGTC CCCAACCTGG GCACTACAGA
27051  GGCTGAGAAT CAAACTCCCA GTTCCCAGGC ACCTGTGTGC CTGCTGCTAC
27101  CATCCCGCCC TGCCCTAGAG GCAGGTCTCG GGTGGGTGCT GCAAGAGTCA
27151  CCCTATGGTG GTTGGGGATG GGTGGGTAGG GGGACCGGGG GCTGGAGCTG
27201  TGGGGATGTG AGGCAAGCCC ACCTCAGAGC CTTTGGAGAC CTCGACAGAC
27251  AATACGATGA GTTAAGAAAT GTAAAGGGGC ACATAGTGGG TGCTGAATTC
27301  ATCTTGTCTC GTTCCTCCAG TAAGAGTCTG GAGAAACCAA GAGCAGCTGG
27351  GTGCCTCTGA GGGCACAGGA GCTCCCAGGG CTGGCTGGCA GGTGCAGCTA
27401  ACAGTGTTAG CAATCCCAAG GACAGGTAGC TTGGGGCGGA GGACAGCATG
27451  CTGTCACCCA TCCTGATGAG GGGAGAGATG TCTGGTGCTA GGAGCAGTGG
27501  TGGCCGGAGG AGGGCTGGGG ACCCTCCCCA GGCCACCCCA CACTCTCCCT
27551  CTGGGAGGGG CTCCTGAGCA GGCCTGGTCA CCTTGCTTCT TGGCTGCTTC
27601  TTCCCCGGCG GAGGAGCCTC CCCCAGGCTC TCCCACCTGC ACTGGCCTCA
27651  AGAGAGCTGG GATTGAGCCC CAGTTCAGGC ACCTGCTGGC TGGCGGAGGT
27701  TAGGGCAAAT CACTTTCCTC AGCCCTCTCA TCCGTGACAG GCTCTGGTGA
27751  GGGTTAAATG AGATGTTGCC CGTCAAGTGC CTGCCACTTC CCTGACGCCG
27801  AGCAGCTAGG CTGCTCTGGG TTCTCTAGCA CCTGCCTCCC CTGGTCCCAG
27851  CACTGGGTGG GCGGCTGTGT TCTACCGGTC ACTGGTGGGT CCTCAGGGCC
27901  CCGACACAGG GCCTGCTATT GGGAAAGAGG GAAGTAAACA TCCCAGGGCT
27951  GGAGCTCTGC CCACTATGGA GGTGTTCCAT CTTAGGCTCT GTAATCTCCT
28001  CATTCACTCT GGTATGGGGA CAAATGTGCC TCTCTGCACT AACTGAGCCC
28051  CCATGGGCAA CTAGGAGTGG TGTCACTTGG GGTGGAGGTG GGCAAGGATC
28101  TCTGGACTGG GATTTCCAAG CCCTGACTTC CTGTTATTTC AGGCACTACC
28151  TCATTGTTCC ATCTTGGGCA AGACCTGTCC CCTTGAGGGT AAGAGACACA
28201  TGTGACCTCT GACCTCCAGA GTCTCTCTTC TGAGCTTCTG TGCCCAGATG
28251  ATTCTGTGTT CTAGGGGACA GGCGAGGCTG GGGGGTGACC CCCATGCCAC
28301  TGATGGGCAG ACTAAGGAGC AGGGGCCCAG GACTGGGCC AGCTCAGGAC
28351  TCTGGTGGCC TCGGTGCCCT TGACCTGGTA TTGCTGCCGT TTTGCCCCAC
28401  TGCTGTCTGT CTCCGCGTCC GAGTCACCAC CTGTCCCTCT CCAGTCCTCT
28451  CCTCTCTTCC TTTATTACTA TCTCTATATT GCCTCCTGCC TCAGGCTTAT
28501  CTCCTCCTGT CATGCCTCTA TCCACCTCTG TCACTCCCCT GCGACTCTGC
28551  CTCACTCCCT GGCACACCCT CTCCCTCCCT GGGAGTCGGG AGTGGAGCCT
28601  CGCTGGGAAT CAGGACCCCC CTGCCTCTGG TCTCTGTCTA AGCAGTCTCT
28651  GCGATTCTGG CCAGCTCTTA TCTTTTTCCA CCTTCCCGAA TCTCTCTTGC
28701  TGTCTGATGG TGTCTCTGCC TTTCACTGTC TCTGAACTCC CTTTGTTTTT
28751  CTCTATATGC TTCTCTCTGC TCTTATCTCT GGGCCTCTGT CTCTCAGGGC
28801  CTGACTGGTC TTGACCTCTT TGCCTCCTTC TTCCCCTCGA GAGCCCAGCC
28851  AGGCAGCAGG TCCAGCCCTC CAGCCCAGAG AACAGATGGA GTCCACCCTC
28901  CCTCTCTCTT GCTGGCTGCC TCGGAAGCCC AAACAATGG CCTCCGCCCT
28951  GCACCGTGCC TTGTTGCTAG GCCTTGGGCT GGCAGCACCT GGCTTCCATA
```

FIGURE 3-10

```
29001  GCGACGGGTG CTTAGAAACA GAATGCCACA TCTCCCAGTC CCACCACAGG
29051  AGCCTTTGCC GATTGAGCGA GTGCCTTTTG ATCAATCAGG AAGTGTGGCC
29101  AGGCTCTAGG TTGCCTCCAA CTTGAGGAGG CAAGAGAGGA GGGGACTGTG
29151  GTCTCTGCCT TCTGGAGCTG GGGGACTGC  TGGGCTGGGA GGAGTTGCTC
29201  AAGTACAGCC CTGAAGCCAA GGAAGGACTG GGGGAGGCCC TGGGCTCTTT
29251  TCCCCAAGTC AGCCTGCTGC AAGAGGCACA AGCTTGGGAG CTGGAAGGGG
29301  CTGTGTTGAA ATTGCTGTTC CATCATTTCT AGCTGCATGA CTTTGGATGA
29351  ATGACCTCAG GTCCCAGGGC CTCAGTTTCA TCAACTGTAA AATTGGGCTA
29401  ATAATATCAT GAAGATTAAA TGAGAGAATA GATCTGGCAC TTAGTAGGTG
29451  GTCATCAATG GCCATTCCCC TCCCTTCCCC TTTAAAGTTG TTTAAAATTT
29501  AATTGACAGA GAGGAGAAGG AGGGTTCTTC AGGCCTGTGG AATGGTGTAA
29551  GCAAAGGGGT GGAGGCTGGC ATGCACCTCA CATATGCTGG AGTATTTAGG
29601  GAGGACCAGG GGCCATATCT GGAAATGGTT CTGCCAGAAG CAGCCAGGCC
29651  AAGCTGGGTG CCATGTCATG CACCTGTAAT TCCAGCTACT AGGGAGGCTG
29701  AGGCAGGAGG ATCACTTGAG CCCTGGAGTT CCAGATCAGC CTGGGCAACA
29751  TAGTGAGACC CCATCTCAAA AAAACAAAAC ACAACAGGCA GGCTGATGGG
29801  CCCATGGAGA AGGGACTCTG TCTCCTGGGA GGTATATTCT TGCCAGGTGC
29851  AAAGGGATGG GCTTGACTAA TTTCTCCTCT AGCATTTGGG GCTGCTGGGT
29901  AGGGAGCTAC ATTGGGGTCC CCTTGCTTAT TCTCATGCTG CTCCCTACTT
29951  CTGCCCTGTC ACTTGGTCCC AGGAGAGGGG CTCCCACTGG TTCCTTTTCC
30001  CTGCCAGGCC TGCCCACCAA GGCCACCATG GCCACACAGC CTGAATCCTG
30051  GGCCAGCAA  GTGTCCATGG AAGGCCCCAC TCTGTCATCG TAGAGATCAG
30101  GAAACAGGCT CAGAAGTAGG AGGGCTTCCT GGTCCTAGGG CCCAGCTCTT
30151  CCCTCTTTTC AGGCCTGTCT TCTGCACTAA GGACTTCAGG CCACCAGGGA
30201  AGGTGGGGAG GGAGGAAAGG AGATGAGATA GACTTGGGCG GGGGCCTGAG
30251  GACAGAGTTT CATGTCACTT GGGCAGCCAG GAAAGGGTTA AAGATCCCTT
30301  ATCCCAAGCC ATGGGCACTG GCACTGCCAG AGGATGCTGA GGCCTGCTGG
30351  GGCATAAGGA CAACAAGCAA CATCCTTTTC TGAGCTGTTG GGAGTGCCAA
30401  GCTCTCTGTT AAATACTTTT GAGCCTCTTC TCATGTATTC ACAGCCACCT
30451  TTCAAGGAAG GCCAGTTGAT CCCCAGTTTA GAAGTGAGAA AACGGGGTCT
30501  CCAGGAGGCA CTTGTCTAAG GTGACACAGC TGGAGAGTTG GAGATGGTGG
30551  TTAGACCGAG TCACCCCCCC AGACCCTGGC CTCTCCCTGC GTGCCCCTTC
30601  CAGGACACCC ATCACTCCCT TGACACCCCT TGGGAGTGGG TGTTCATTTC
30651  CTTGGGCTCT CCCAATCCCA GTCCTTGGTA TCCCCAACTG CAGGCAGACA
30701  CAGGTGCTTG CTGCTGTGCC CTCCCCTTTA CCTGGCATCA CAGAGACTCA
30751  AGCCCACTGA CCATTAGGCC CTCAGGGGCA TAGAAACCAG GTGCTGGAGT
30801  CTTAGAGTCC TGCAATCAGG CATCTCAGGC AGTCAGGACA TTAGAATGTT
30851  AGAATCTTGG GCTTCTACAT TCTCAAGACC CCAGGTTCTC GCATTCACAG
30901  AATGTAAGAA AAACAGACTT TTTGAATGAT GGGGTGTTAT AACAGAAGCT
30951  TTGATTTTCT AAGAACATGA AGCTCTGGGA GTTCTTGGAG CCTTGAAGCC
31001  ATAGACTGGG GCCTCCCTGT GTGATGGTTT CTGAGTTAGC AGGGAGTGTT
31051  CAGAGTATGG GGCCTTGGTC CCTGTTGCTT AGACCTTCTT GCCTTGGTAT
31101  CTCTGATGGG CTCAGCTCTT AGTAGCCTTT GTGTATGTGT GTGTGTATGT
31151  GTGTGTGTGT GTGTGTGTGT GTGTGTGTGT GTGTGTGTGT AGTGGGGACT
31201  GGGGTCAGGG GTCAGGGACT GACTCTAACC TGAGGCACCC CTGGAGTGGG
31251  GCCAGCCCAG GAATAGCAGG TGGAGGAAAG CCGGGCAGCC TCAGGGCTGC
31301  AGCTGTCTGG TGGTACAGGG CAGGGCTCTG GGTGGCTGCC TTTGGCAGAG
31351  GACCAGCCTG CCTCCTTCGT CCCCTACCCA GCCTGCTACC AGGATCAGGA
31401  GGAGGCATCT CCATGGGACT CCTAGGGCTG GAGTCAGAGC AGCCCCTCCA
31451  GGTTCTGCAG CCTGGACGGT AGGAGGTGCC ACTAAGGGGA GGAGATTGGG
31501  GAAGGATTGG GACCTTTATC TGCGGTGAGG TGGGCACGG  GGGGATGAGA
31551  GATATAGTGG GAGTCTTTGA AGGGTGTGGG ATCAGTGAAG GGGCTGGGGA
31601  TTTAGTGATG GGCTGGGGCT TAGGATGGAG CCAAGGGCTC TGTGGGTGGG
31651  AGACCTTTTG AGAGGGTGGA GACTCAGAGA GAAGGATGGG GGCTCAGCAA
31701  GGGGATGTGG CTCAGTGGAG GTTGCTGAAG AGTTTCTTGG GGTTGGCTAC
31751  ACGCGGTGGC TCACGCCTGT AATCCCAGCA CTTTGGGAGG CCAAGGCGGA
31801  TGGATCACTT GAGGTCAGGA CTTCAAGACC AGCCTGGCCA ACATGGTGAA
31851  ACCCTGCCTC TACCAAAAAA TACAAATATT AGCCGGGCGT AATGGCAGGC
```

FIGURE 3-11

```
31901  GCCTGTAATC TCAGCTACTC GGGAGGCTGA GGCAGGAGAA TTGCTTGAAC
31951  CTGAGAGGCG GAGGTTGCAG TGAGTCGAGA TTGTACCACT GCATTCCAGC
32001  CCTGGGCGAC AGAGCAAGAC TCCATCTAAA AAAAAAAAAA AAAAAAAGTC
32051  TCAGGGCTGT CTCTGCACTG CTCCAGGTTC CTGAGGACGG CGGTTGGGGC
32101  TGGGGGAGTC TTCTGTCCCT GGGGTAGGCT GAGAAGCAAG AGCTCCTTTT
32151  CCCAACTCTG CCCAAAGCTG GAAAGGTTGT TAGAGCTGCT AAGAAAGCTG
32201  GCATCTGCCT CTCCTTTTGC TCATCTTCCT TTCTGGTTTC CATGGGAATC
32251  TGTGGCTCAG GATGATCAGG GGTTGACAGG ATGGCGCTGT GGAAGGAGTC
32301  TGTGTCAGGC ACAGCCATCC CACATGGGAA GGAGCCGGCT GGTAAGAAAG
32351  TGAGTTCCCT GTCCCTGGGA GTGTGCAAGC AGGGTAGGGG CTGAATGGCT
32401  AGAGTGACTC CAGAAAGGGG TTCAGATGGG GCAGAGGAAG CAGTCTGGAG
32451  GCCACTTCCC TGAGACAATC ATGTTTTGTG TGATTGGCTC TGGGGGCCCC
32501  ACCAGCCCCA CCTTCCAGAC GTCCCTGGGC CTCACAAAGG GGGTTGCTGC
32551  ACCCTAGGCA CTGCCTCTGA TCCAGCCCCA ACTCCTGTGC TCTGTGCCTG
32601  GCCTATGCTG AACACGGACA TGTGCAGCTG AATCAGATTC AGTCTCTGCC
32651  TAGAGGAGCC CCAGTCTGAT GGGGGAGGCA CACAGGGACA CAAATATAGC
32701  TGGGTAAGTC CTACAAAAGG GGGCATACCT GGCTGGGAGG CAGTTCCATC
32751  ACTGATTCCT GTAGTCTGTA GATGTCTTTT TGAGCAATTC TTCTGGGTCA
32801  AGACTTGTTC TTATTTGCTG GGATAAAACA GCAGTGAGCA AAACAGAGCT
32851  GACAGCATGG TGGGAAGGTT GAGCTCTTCC AGACCGTGAT GAGAAGTATT
32901  GGTGAGTGGT GGGGAGAGTG GCCAGAAGGC AGAGTGTGGG CGCAGCATGA
32951  GAGGAGGCTT TGTCCAGACT TAAGGACCTG GAAGGCCTTG AAGGCCAGGA
33001  CCAGGGCTCC AATTGTCCTG CTGGCAATAG GAAGCCATAT GGGTGGGGGT
33051  GAGGCAGAAT CAGATTTAGG TGTGGAAAAG ATGACTCCAG CCAGTGTGGG
33101  CATCGAAGAG GAGGCACAGA AGCAGGCGTG GCCACCTGTG CCTCTGTGTA
33151  GGAGCTGTGT GAGCATGTGC TTGAGGATGT GTGTCTGTGT AGAGGACTGG
33201  GGTGTAGGCG TGATAGGAAC ATGGACGTGT ATCTATGGAA AGACTCCAAT
33251  TGTGCATAGG GGTGTATGTG TGTAAGATTC TGTGGCCCAG GGCAGCCTGT
33301  GAAAAGGAAG GATCTTGGGG TCTCTGGATG ATGGGGAGCA GAGACTAAGG
33351  CCTAAGGTAT GCTGGGCTC  GAGCCCCCTG GACTTTATCC CCTGTGAGCT
33401  GGCAGGTCTT AGACTAGTCC TGGACTAGAA TCCTATGGGT TCCCTTCCCC
33451  CAGAGGGTCA TGGGGCCAGC CATCTGCTGC AGACAAGACA AACATGCATG
33501  CAAATCACAT GAAAATGGAT GAGGCCTGTG GCTGACCCAC CCTACAGCCC
33551  CCATCCCCTG GGCCTGAGTT CACTCAGCCT GTACCCTTCC TGACCCAGAG
33601  CTGCTGCCAG GGCTCTGGGA ACAGGCCTTG CCCACTAGGA GCTGAAATTC
33651  ACATTGTCCC CAGCACCTGC CCGTGGCCAC ATCCTCTCTC TGTGAGGGCT
33701  ACCCCCACAT CTGGAGCCAT AGCCAGCGGA CACAGAGCTG GATCTGGACT
33751  GGTGGCCATG GGCAGCACCT CTGGCAGGTG CTGAGGTGGA GGAGGCAGTA
33801  TCCAGGCAGG CATCCCTGGG CAGAAGGTAC CTCTCCTGAG CAGACAGGCC
33851  TACCCAGGCA CCAGGCCCAA AGATAGGGGC AAGGGCTAGA TCCTGGTATT
33901  GGAGGACCCT CAGGAGAGGC TGTGTGTGAC TTGCTCTCTC TCTGACCTGG
33951  GCTAGAGCAT AAAACACGTGT CACATACTTG CACACACATT CACACGTGAA
34001  AGCACGCACA TGCTATTCCT GGACACTTGT GTACACACAC CACTGCACAC
34051  ATATACCTGC ATGTGTGAAT ATACACTCAC TTCTGCACAC AGACACATGC
34101  CTATCTGCAT AGACACACCC GTGCCAACCC CTATAGATAC ACAGACATAT
34151  CTGTGTATAC ACATATAAGT TCAGCTATAC CACTGCAGTA TCACACACCC
34201  TCACAAGGAT ACAAACCTGT GCTCACACTC TCTTCCACCC TCACACACAT
34251  CATGCTTACA AGCCTGTGTG CAGCCTTACA CACATGCACA CACGTACAGA
34301  GCAGCCTAAG GGTGGCTCAC CCCTGCCCAG GTGAACACCT GTGCCCACTC
34351  CAGGGCTGGA GTGTTGAGGA AAGGGTCTGG ATGGAGGCAG AACCTGCAGA
34401  GATGTCAGTT TCTTCCAGGA AGCATCTTGG ATTGTCCCTT CACAGAGCCC
34451  TTGGAAGTGG GGCCCTCTTT TAGTCCATGG GCTCTAGCCC AGGTCACAGA
34501  GAGAGCAAGT CACACACAGC CTCTCCTGAG GGTCCTCCAA TACCAGGATC
34551  CAGCCCTTGT CCATATCTTT GGGCCTGGTG CCTGCGTAGG ACCATCTGCT
34601  CAGGAGAGGT ACCTTCTGCC CAGGGAGGCC TGCCTGGATA CTGCCTCCTC
34651  CACCTCAGCT TCCTGAGCAC TCAAAGAGAA GCAGGCCAAG CTTCACGGCT
34701  GCTGAGAAGT CTGAGACCAG GGAGGGCCAA AGCCTTGCCT GAGGTCACCC
34751  AGCATGTCAG GGAAGGGCTA GGGTTTGAAC CTGGGCTTCC AGGTGGGGGT
```

FIGURE 3-12

```
34801  GTAACCATGG TCCATGGCAA CAGGATAGAT GCATGTCAGG CAGCAGACAG
34851  GCCCTTGGAA GCAAGACATG TGGTCATGGG GGATAGGAAA AGACTTACAG
34901  TCTATGGAGA TCTGCCAGGA CCAAGTGTGT GAGATGGAGA GATGGTGCTT
34951  CTTCACCAGA GCTCACTGGG CACCACAGGG CTCCCAGCTT GGCTGGACCA
35001  TGGGGACTCA GGGAAGAATC AGACAGGCCC TGCTCTTGAG GGAGGGCTGG
35051  GGATAGGTGA AGAAGGAAGA GGGCATTATA GACTGGGGAG ATGGTGGGGG
35101  CTACTTCTCG TTGGATGGCA GTTTTCTTCC TGCATCTTGA AAGATCTAAC
35151  TTTCAAATTT CTTTACCCTC AAAACTCGGC ATGGAGTACA TTCTCAGTAA
35201  ATATTTATGG CATGAATGAA TTAATGAAAG TATGATATTG GCAGGCAGAT
35251  ATGCCTTTGG AAGGGTATTC AAAATGGGAG GGCAACAGGT TGGGCAAAGG
35301  CAAAGAGGTG GAAGAAAAGC CAGAGGTTCA GGGTACAGCT GAGTCAGGCA
35351  TGGCTGGACG GGAAGTGGTA GGAGAAGCAG CAGGAAAAAG TCACGTGGGG
35401  ATGAGCCTTG CATCTTATAC TGAGTTTGGA TGTTGCCTTG GAGGCCATGG
35451  GGAGCCCAGT GAAGATTATG AGCAGAGGGT GAACATGGTC AGAGTGAACC
35501  TGCCCTGGCT TTGGGGGGTC CTGGGCTACA TAGTAGCTGC TTATCCTTGG
35551  TGCAAAGAGC ACTGGGTTTG GAGTCTATAG GCCAGGGTTC ACATTCCTAT
35601  AGTAACCAGC TGTGCCATCT CAGGTAAGCA TCTACATTTC TCTGAGCCTC
35651  ACTTTCCTTA TTTGTAAAAT GGGGCTAATG CCGTGCCTCC TGAGGCTGTT
35701  GGATCTGGCC TGGGTGAGGA AATGCTTTGC CAGCACAAGG CCCTACCAAT
35751  GAGAGGTGTC ATTTTTATTA GGAACAAGGC AGGGCTGGTT CCTAGACAGG
35801  GCCTGAGGTT GAGTGGGCCC AGGACCCAGG CTGACAGCTG AGTCACCTTT
35851  TCCAGGCCAA GTGGCCTCTA AGGTGGGAAG ACAAAAAGAG TTGGCTAGAG
35901  GGGCTGGGCT ATGCATTCCT AAGCTGGAGC TGGGAGGAAA GCTGGGGCTG
35951  GGACTGGGCT TCCTGGTGTC CGAGATGGGC AGAGGGTGCA GACACCGGGA
36001  TAGTAGGACC CTCAGCCACT GCATTCTTGG GGACAAAAGA GGAGCTGGGA
36051  AATCTGATTT CCTTACCTGG CTTTGCTCAA GAAGCAAGGA ATGTATTTAA
36101  GGCACAGACT GGAGTGAGAT GGCCTGGGTT TGAATTTTGA CTACTTACAA
36151  GCTATGTGAC TGTGGGCAGT TTACTTTGTG CCTGAGTTTT CCTTATCTGT
36201  GAAGTGTGAC TAATAATAGA TCCCACCCTA TAACATTGTT GAGAAGATGA
36251  AATGTGAGGC ACACAGTATG TGCTCAATAA ATGCGAAAGC CTCCCAGCCC
36301  CAGATGTATA CACTCGGCCA GTAGGGGCCA GCCCTGGCCC TCACCTCCAT
36351  GGGACAGAGG TCAGCCAGGG AGGAGATGCA TCTACTCCAG GGTTCTCTGA
36401  CCTGGCAGCA AATTAGAATC ACCGGGGGAC ATTCACAAAC ATCTGGGATG
36451  GGGGTTCCAG ATATCAGTAT TTAAAATGCT CCCAGGCAAT TCTAACATGA
36501  GTCAGGGTGA GAACCCAGAA CAGGATCACA GATTGTGCAG TTGGAGTGAG
36551  GTAGGGATCT GCGTGTGAGT GGAGGAGTCC TTGGAGTGGG GTCACTCCTA
36601  GCTATAAGAG CTCGGCAAGG CCTTTAAATG TGCCAACTCA AGGAGCCTTG
36651  GTTGCCCCCT CAGGAAGGGT GCTGGTTGGG GAATTTCAAG GATTGTGTGA
36701  GAGGGTTTTT CTGAAAGGGC TCTGCACTCT ACCAAGCACT GGAAGAAAGC
36751  AGTGCACTTG TTTATTGAGT CTAGTGTAAT AACATTTCAC AGATGGGAA
36801  ATAGAGGCCT AGAGAGGTGC TGTGGCCTGC TCAGAATCCC ACAGCAAGTC
36851  TATGGCACAG TTAGGACTCA AACCCTCTGA GGAATGCTTG GATCTGAAAG
36901  GTTGACACAG AAAGACTCTT TGAGCTGAGG GACACATAGA GCACACACCA
36951  GGGACCCCAG TCATTGAGCT GTAGTTTGAG AGATTCAAGT AAGACTGAAG
37001  AAATAACTTC TTGGCTGGGT GCAGTGGCTC ACACCTGTAA TCCCAACACT
37051  TTGGGAGGCT GAGGTGGGTG GATCATGAGG TCAAGAGATC GAGACCATCC
37101  TGGCCAACAT GGCGAAATCC CATCTGTACT AAAAATATAA AAATTAGCTG
37151  GGCATGGTGG TGCATGCCTG TAGTCCCATC TACTCGGGAG GCTGAGGCAG
37201  GAGAATTGCT TGAACCCGGG AGGCGGAGGT TGCAGTGAGC TGAGATCGCG
37251  CCACTGCGCT CCAGCCTGGT GACAGAGCGA GACTCCGTCT CAAAAAAATA
37301  AAATAAAATA AAATAAAATA AAATAAAATA AAATAAAATA AAATAAATAA
37351  AATAACTTCT CAAGAGGTGA GTGCCATGGA GGTGGTGCCT GGAGTTGGGA
37401  GCCCAAGAGA TGGTGGCGGT GCCAGGCCAG GGTCGGCTGT TGACCATGGT
37451  CTGAGGTGGC CTCCCCTGAA GAACAAGTAA CTCTGGCCAG TGGCTGTAAC
37501  AGATACCTCC CGGGCACCTG TATCTCACCC AGCCTTGTCC AGAGCCCAGG
37551  ACTGAGCCAG TGACACATGC TCAGAATTTA CCAAGAGACT TGTGCACTGA
37601  GCTCAGACTC AGACCTAGTC CTTCCAACAG CCCTTACATG GGTCATCCCC
37651  TTTTACGGAA GAGAAAACTG AGGCCAAAAA TAGGAAGGGA GGCCCTGTGG
```

FIGURE 3-13

| | | | | |
|---|---|---|---|---|
| 37701 | GGGCCAGAAC | CTTTACACAT | CTTAGCCCAG | GTAATTTTTT | CTACAGTGTT |
| 37751 | AATAAGTAGG | ATGAATTGCC | CCTGTTTGGA | AGATTCAGTA | AAATACATTG |
| 37801 | ACTTGGCCCA | GATCACTTAC | TCTACACCTC | TCCTAAGTCC | CCAGATGTGA |
| 37851 | CTCCCAGGAA | AGACACAAAA | AAGGGCTACC | CAGAGGGATA | AGATAGTAAC |
| 37901 | CAGGGAAGCC | CTCCCAGAGG | AGGTGGGCCT | TCAAATGGCC | CCTAAATGAC |
| 37951 | AGGCAGGAGG | GAAGGATCTG | GGAGGGTATT | GGGGGTGGGG | TGGCATGGGC |
| 38001 | AAAGGCCTGG | AGGTGAGAGT | CAGTCAGTCA | TTGATGTGAG | AAGAGCAAGA |
| 38051 | AGTAGAAATG | TAAGGAATGG | TGGGGAGGGG | AGTCAGAGCT | GGATGACCAA |
| 38101 | GCAAGGGTTC | AGCTGTAGAG | GGTCTGGCCC | GCCAGGCTCA | GGGCTCGGGC |
| 38151 | TTTATTGTGC | TGGTGGTAGG | GAGCCACTGA | GGGTGAGTGG | GGGAGAGCAT |
| 38201 | GCCAGAGCAT | GCCTCAGAAA | GAAAGGTGGG | AGAAACGCTG | GCATGGAGGG |
| 38251 | CCGCCCCCTG | AGTTGGTGGG | GTGGCCGGGC | TCTGCCAAGG | CTATGTGCCA |
| 38301 | GCTGCCTGGA | CTGTGTCCAG | GAATGGGCAC | AATGACTCAA | CATTGAGAAA |
| 38351 | ATCACTCCCC | AGGGAGAAAG | GGCCCTGATG | AATCACCCAG | CTGAGGTGGG |
| 38401 | GAGGCTGGGA | GGCTGGGAGG | CTGGGAGGCT | GGGAGCTCAC | TGAGTCACCG |
| 38451 | TCCAAGAGTT | GGTGAGGAGG | GGAGCTGCAG | AGAGAGGGGC | CGGCAGTGCA |
| 38501 | GTTGACGGGG | GGATTCAGGT | CAGACCACAT | TGAGGGCTGT | CGGGGGACTC |
| 38551 | TACCTTCCCG | CCATTCCCGG | GTTTGGTCCT | CCTGGCCGTC | CTGTGAGGGA |
| 38601 | GATGAGAAAA | CTGAGGCCCA | GGAAGTGGGG | GGAGGGGATC | CGAGCAAGGT |
| 38651 | CATGCGGCAA | GTCGCTGGCA | AAGGCCTAGC | GAGACCCAAG | CGCACCCTCC |
| 38701 | AGTCCAGACA | CGTCCTGCCG | CCCCAGCCGC | TTTCATGCCA | AGCAGAGGCC |
| 38751 | TAAGAACCGG | GTCGGTCCGG | GCAGGGAGCT | GACCCCGGTG | ACCCGCTGAA |
| 38801 | TCCCCGGACG | CGGCCCCTCC | GGGCAGCCGG | CAACTGAGGC | CGGATTGCGC |
| 38851 | CGCCGCGATG | GGACGGCAGG | GGGCGCAGGA | GCGTCGCGGC | TGCCGCAGGC |
| 38901 | TCCTGAACCC | AGAAGCCGCT | CTGCGGAGAA | ACGCGCTCCC | GGAGCGCGGG |
| 38951 | TCCCACCGCG | GAACTGCGGA | CCGTGTGGCC | CTGGGGCCTG | CACCCTCTCC |
| 39001 | GGCTCCGGGG | ACGGCGACAG | AGACCTGCCC | ACCCAGGCCT | GGGGGCCCCA |
| 39051 | GTCAGTGGCG | GCCGCCGTGT | GTGCGCTCGG | TGTCTGTTCG | CACGTGTCTC |
| 39101 | CCTCGCAGAT | GGGCGACTGC | TCCAGGGCCT | GTCCGTCTCA | CAGCGACCTC |
| 39151 | CAACATTCTC | CCGACTTCCC | CCTGCCTCCT | AGGCTGAGGG | AGAGGAGCAA |
| 39201 | GCCCGAGGCT | CCTGCGGTGT | CCGCGGCCCC | TGCCCCCCTT | CCCCTTCCCT |
| 39251 | CCCCACCCCA | CCCCACTGCG | CCGGTCTCTG | CCTGGGGCTC | TGGCCGGGCC |
| 39301 | CCGGACCCCA | GAGTGGTGGC | GGGGAAACAG | GGTGCGATCA | GACAGGGTGG |
| 39351 | AGGCTCTGAG | AGCGGCCCCT | GCGAGATGCG | AGAGAAGTGG | CGACGGGGCG |
| 39401 | AGGGGCAGCG | AGCGCAGGCT | GACAGCAGGC | CAGCTGGAAG | GGCCGAGGGA |
| 39451 | ACCCAGGGCG | AGACAGAAGC | GGGGTGACAG | CGGCCGGGTG | TCCGGTGGGG |
| 39501 | TCGGAGGATC | CGACGGGCCG | AGAGGTGCGG | TCCGCGGTGG | CGGGGACATA |
| 39551 | GGCGGGGCCG | GGGCGGGCCG | GGGGCGGGCG | GGGGCGGGC | CGGGGCGGGG |
| 39601 | CCGGGGCGGA | CACTCGGGCG | GACCAGGCGA | AGCTGTCGCG | GACGCGCTGA |
| 39651 | CCGAGCGCAG | CGGCCGGGCC | GGCGGGCGGG | CGGGCGGCTG | CGAGCATGGT |
| 39701 | CCTGGTGCTG | CACCACATCC | TCATCGCTGT | TGTCCAATTC | CTCAGGCGGG |
| 39751 | GCCAGCAGGT | CTTCCTCAAG | CCGGACGAGC | CGCCGCCGCC | GCCGCAGCCA |
| 39801 | TGCGCCGACA | GCCTGCAGGT | AGGGGGCCC | CCGCGCTGGG | CACCAGGAGA |
| 39851 | ACGGGGTGTC | CGGCGAGCGC | CGGGCCGGGT | CTGCCCGCCC | CCGTAACCCT |
| 39901 | TCTCAGGGTA | GGAGACCCCT | CCTCTAGTTC | TGAATTCTAC | TCCTGTGCTG |
| 39951 | GGACGGCAGC | GCAGACCAAG | AGCCCTTGAA | GCCCCAGCTC | TCAGTCCACA |
| 40001 | CGTCACCCCA | GACTCTGAAC | TCCTTTCGGA | TCCGGGGCTC | CACCCCAAGC |
| 40051 | ACTGAGCTTC | CAGTCCACGG | TGGACCGGCA | GTGCACACTG | AGAGCTGTGC |
| 40101 | CCAAGCCTCG | AATTCCCTTT | CCTTAGATTA | GTGGGACCC | TGCCCACGCC |
| 40151 | TCGGAACCTT | CACCATATAT | GTGGGGCTCC | CGGCACACCT | GGAGCACCTG |
| 40201 | AACCCCCAGC | TGTCATCCAG | GACTCCACCT | CAGAGCCGGC | CTCACCCAAA |
| 40251 | GCCCCAAACC | TCCATTCCAA | GCCTCAACTG | GACACCCGCT | CAGATTCCCA |
| 40301 | CCCAAACATC | TGGACTTCAG | TCCTCAGCCT | GGAACCTACC | CCAGAGTCCA |
| 40351 | AATCTCTCCT | TCCATCAGGG | CTTCACTGGC | TTTCTCTGTG | GGACCCACTC |
| 40401 | CCCGATCCCT | TCCCTCCCTC | CTGTGTTGGA | GATCTCCGAG | TCTTTCCTCG |
| 40451 | TGGGGGGCCC | CTCCTCTTGT | TCCTCTCCAG | GTACAGTGGT | CCCACTTTAT |
| 40501 | TCTCTGGGCT | TCTCCTCTGG | TTTCTCTTCA | AGTATTTCTG | GGCTCTCTAA |
| 40551 | TTTGGTCTGT | TGCCCCATGT | GCCCACCTCT | CTTGGTCTAT | CTTGGTCTCT |

FIGURE 3-14

```
40601 CTCCTGTTTC TCTAGGTCTC CATCTTCGTT TTGGGGTCTC TTTCTGCAGC
40651 CACCCCTTCC TCTTGTATCT ACCTCTGCTT TGTGGTGAGG AGGGGGCAGG
40701 CTCAGAGAGC AGGGCTAGTG TCCCTGGGAC ACCCCCGCCC CCCATGTTCT
40751 CAGGCATGGC ATGGTGTGGG CTCAGGTGGA AGGGCCTAAA TGTGGAGTGT
40801 GCTGCCCTCA GGCGATGCCC AGGGATCTGA GGTGGTGGGG GGATGATGTG
40851 GTGGGCACTG GCTTTTGTAA CTTATAAAGC CCCTCATCCC AGCTGCCCTG
40901 GTCTTGACGG GGGCGGCTAG GGCTTGAGAT AGGGAAGAGT AAACTGCAAT
40951 CTGGTGTCAA CCTGCGGTGG GATGTGTCCA GGCTGGGTGG GTCTATAGTG
41001 TATGTGTTTG TGTGAGTGTT CCTGTCTGTG TGTAGCACGG GCTGGGTTGC
41051 ATGTGTTGGG TGTGTCTTGT GTGTAATCAT GTGTGTTGTG CCGTGTATGA
41101 ATGTGTCATC GAGAGTGGGA TTATTTGTGG GGAGATTATG GGAATTATGG
41151 GTCTATGGCA TTGTGTGCTA TGTGTGGCTG GGGAGGCAGT GTTGTGGCTG
41201 TGGAGTGGTA GCTGGGTGTG TGGCTGTTGT GTGTGTAGAG AACTTGTGTG
41251 TATGTGGCTG TATGTCTGTT ATTGTACAGT GGAGTTGTTG TAGGGACAGC
41301 TTGCATACAG GATTCTATAT GTAGTTGTGT GTGTTACTGG CTGTTGTGTG
41351 TGGCCAGGAA GGGCCACTGC AGGGGCCTGA TGGTTTCCAC TGGGTGTCTT
41401 GTCAGAGAGG AGTTGGGGCA GGGGGTGCCG TGTGTGCCAA TGTGTTTGCA
41451 GCCTAGGTGG CTGGCTTAGA GTCACTATGG CACATCCTGG GATTGCTTGG
41501 GTAATATATC TATTAGGACC TGAGTGCTGG TGTTTGAATG TCATGTGTCT
41551 GTGTGGTGGC TGCTCCGCGC ATTCTGGACA GGAAAGGGTT GCAGCCAGGG
41601 CTGAGGGGTC TGAGGTGAGG AGCCAGTTGA CAAGTGTGTG AGTGTGTGAG
41651 TGTGTGTGTG TGCGTGCATG TACACGTGCA TATGGGAATG GGGTGGGGTG
41701 GGAGGAGGCA GTGGGCCAGC AGCGCTGTCT ATGCTGAGGG GCTGTGTGTG
41751 CCCACAAACG TGTGACATTA GGTGTGCACA TTATCTATGC AGGTTGTGTC
41801 TGCATGTGTC TCTGTGTCTA GGTGGCGTGC GTATTGAATT TAATTGGATG
41851 CATACACCTG TGGCTGGGGA GGTGAGAGGT GTGTGAGGTG CGTGGTGGGA
41901 GACGGTGTGA GTGTGGTGTG AAGTGAGGGT GTGTGAGCTG GGTGACTTTT
41951 TGGTGTGACG TGTGAATTAT GTGATCTTTT CTCCCCATGA GCTGTGTGTG
42001 CCTGTGGTGA GGAGTGAGTG GAGGATGGCC AGTGAGCTGG CGGTGTGTGT
42051 GTTGGGGGTG TTGAGGACTG TAGAATGTGC TGCGGTGGCA GTGTGTGCAT
42101 GAGGTGTGTG TGAGGAATGA GGTCTGTAAC ATTTGGGGCG TGTGGAATAT
42151 AGTGGGTGTC CCCATAAATG TCTGTGGAGT GACGCATGTG TGCAAAAGGG
42201 CTTGGCTGCC ATCCTGTTCT TGCTCCCCTC CTGATCAGGT CCCTAGAGAT
42251 GCCCTGGAAT GTTCTCCATG CCCCCCCAAC CCCAGCTGCC CCTACCCTTT
42301 GCCCTTCATC CTCCTTGCCT TGACCAAGCC CTTTGTTTTG GGTTTCCGGC
42351 GGAGCAGGCG CTGGACAGGC GGGCGGCAGG CAATGTCGTG GTCTGAGAAC
42401 CTTTGTTCTC TTAGTTTGAC TGGTGTTTGG GGCCTTGGTT TGGAGGAGGG
42451 TGTGGAGAGG ATGCACGTGG CAGCAAGGTC ACTGTGTTTA CTACACCACT
42501 TCGTGCTCCG CAGAGGGGAG GCGTACGGCG CAGGCAGTGA GGCCTGGGTG
42551 GTGTCTTTGG TGGCGCCTGT TGGTGTAAGA ACAGCTTAGG CTGGGCTTGG
42601 AGTTTGCCAG CCATGCAGTC TTAGTCCATA GTGGCCCAGC GCCCTTCCTG
42651 GCTCATGTCA GCGGGGCTGA GCAGCCGAGC AGCCAAGCAC TCACTTCTCC
42701 AAGTTCACCT GCCCTCGCCC CTTCTCTGTG TGGCTGCAGC CCCTGGAGAC
42751 AACCAGGAAG ACCTCGATTT AGTTCTATTT GTGTTCACTC CAGGTCAGAT
42801 GGAGGAGAAA GAGTCCCCAT CCTCACAGAG ACACTTATCT GAAAGGAGAG
42851 AGCTGGTCAC ACCTTTGGGG ACCCTCTAGA CTGACGCAGT CTGTAGGGGG
42901 ATCGAGGTCA TACCTTCCAG AGAGAGCTGT GGGAAAACCC TACTGGGCTG
42951 CCTCCCAGCA GGTGCTTGAG AGAAGAAACA TCCAAGGTTC CTTGAGATTG
43001 GAAGGCTTAG AGAAGTCTGA GTCAGTCAGG GAAGGGGCTG GGGTCGATGC
43051 CGCAGTGTCA CATACCAGAA GGTTCTCTGA AATGAATAGG CTTGAACTGG
43101 ACCTTGAAGG GGGTGTTGGG GTGGGCAGAG AAATGCAGCC TGGGGCTGAG
43151 GAAGGTTCTG GCCTGACTGG CAAAAGGGAT CTTGCTGGCC ATTCCCCAGG
43201 CAACACTGTC TGGCTTTGGG TAGCCATCCC TGGGCCTCCA GCCTTCTCAA
43251 GCTTTCACGG TACCTTTTTT ATCCCATTGT CTCTGGCTGG AATTATCTTC
43301 ATTGTCGTTG ACATTGTCAT CTTCATCATC TTTAGGCAG TTATTTCCAA
43351 ATTCCAGGGT CCTTTCACAA ATGTCTCATT TAGCAGGTTA ACTCATGCAA
43401 TTGTCCAAAA GTCTTTATGG AACACTGCTG TGTACCAGGC AGGCACAGTT
43451 TTAAGTGCCG GGGTCATGGT GGTGGCCAAA CTGGCCTCAT GGAGCTCCTA
```

FIGURE 3-15

```
43501  CCTTCTGTGT CCAGCCATGC TGTCAGTTGC CCACCCTTCT GTGTTTCCCC
43551  CAGTCTGGGG CGCCTGGTTC TGTGGGGCTC CGCATGTGCA CCCTCTGGTG
43601  CTGGGGTCTG GCTCCTACCA GAATGTGAGC TCTGCAGAGG CTGGGCCCGG
43651  GTCTCTCCTC TACCCACCGT GTGTGTCCTG AGCTGGGTCT GGCAGAGTCC
43701  AGATGCTCAC ACCTATCATC AAGTGACTGG AACTGCCATG TAGGGTTGGC
43751  AGTCCAGCTC TGTCTAGGGA AACTGGGGTC CATCGGATGA GGGGACTCTC
43801  ATCTCATCAG GCAGCATCTC ATCAGGCCCT TCTTTTACCA GTAGCTCCAG
43851  AGACCAAGAA GGGTCAGGTG ACTGGTGCAG GTCTCACAGC AGGGTGGCGC
43901  GGCTGGTGTC AGAAGACAGC ACTTCTTGCT GCCAGGTTGG GCTCTGGTCC
43951  TAGCACCATG CTGCTCTCTG GCTGGCCTCT GTGCTGCCTG CGGCGGGTAA
44001  ACGATTATTA ATGACCCCCC TGGCAAGGAG ACAGGAAATG TTTCCCAGCC
44051  ACAGCTGGGG ACCTGCTCCC TGCCAGCCCC AGCTATCCAT ACCCGTCCTG
44101  ACCATGGCAT CGGTGCTGAT GTTATCTTCA TTCTGCCTCA GTCTTCTTTA
44151  CTCCTTCTGC CCATCCCCCG ACCTCCCTGA TCTTGACATC CTAAGGGTAA
44201  ATGACGAGAA GCTACAGAGC TTTCTTTTCC ATATCCCTGT CCCTCACCAC
44251  TTTCTCCAAC CTGACTCATC TCTACCTTCT TCCTTGTCCC ATGCCAGCCA
44301  GAAGTAGCTC TTCCTCCAAG AAGGCTTCTC TGAATGCACA GCCAGCTCCT
44351  CCAGTGTCCA CTACCCTGAG CCCGAGGCAC TGAGTCCCCC TCATTGCAGA
44401  CTCTAGTCCT CCACTGATGG TTTGCTCTGA CAGCCCTAGG GCTGGCCTGG
44451  GCACTTCCCG CAGACTGTCC CTAATTGCTG CCTTAGGACT GACATATGAA
44501  GGGTCCTCCC AGATGCTACC TCCAGGAAGT CTCCAGTTCT ACTCAGCCCA
44551  GGGATTCTTA CCTCCTTTGA GCACAGTGCC CTTCCTGTCT GAGTCACACA
44601  TGTGTACTTC CAGGACTTCC TAGGTGGACA TTAGTGAACA CCTGCTATGT
44651  GCCCAGCACA GAGGGTGGGA AGAGATGAGC AGGATGCAGG CCTTAAAATC
44701  CCCACACCTT CCTCCAAGCC TGAGCAATGT TGCATCAGCC CCTTGGCAGG
44751  TGGCACAGAC CTAGGTACTA GGGCTGGGGG AGGGGAGGCG GAGAAACAGG
44801  GAGTGATGTT GGTAGAGTGT GTGGGGAGGG CAACGAGGGA GATAAACTCA
44851  GGGGCCATGG TGATATAAAG CAGGGACCCC TATTTCAGCC CAGAGTGGGA
44901  GGGAGGGGCA TGTTGGGGAG CTTCCAGGAG GAAACAAATC TGAACTGAGA
44951  GCTAAGGTCA AGCCAGGAGA AAGTTCTGGA CAGAGGGGAG AGAATGGTTA
45001  CTGTGAAGGT TCGCTGGTGG CAGACAGAGG GAGGAGAGCC TGTGGCAGCA
45051  CCACTCCATG GAGCAGGCCC CTGGGTGCCA GCCGGCTGGG TCCGGGGGGA
45101  TGGGGACTGG TAAAGCTGGC CCAGCCAGAT GGTGCAGGAC TTGTAAGCCA
45151  TGTTAAGGAC TGCGGACTTA TTCTGGAGGG AAATTGACCC TGGGGAAGAG
45201  TTGAGAGAAC GGATATGACA GATCAGATCT GCATGTTCAA TAGCTCCCTG
45251  GACCATGGTG TGGAGACTGA AGGGGAGGCT GGTGTGGTCC AGGTAAGCGG
45301  GGGTGATGAG GCCTGGACAG GGAAATGGCT GAAGAATGGA GGGGAGGGGA
45351  CGGAGTGGCC AGGGCTGGTG GAGGGAGCTG GACAGCTGTA GACGTGAAGG
45401  GCAAGGGAGG AGAATGCTGC CCACCCAGG TGTCTGGATG GGTTTTTGTGC
45451  AGTCTCTGAG ATGTATAGGA GGGAAGACAG GGGTTAGTGG CAGATGCCTG
45501  GGCCTGTGTC AGGGCCCTTT AAGGACCAAA AGGTCTTGGA AAAGCCTCAG
45551  AGGAGATCAT GAGCTTTGAG ATTAAAGGGA GACCTGAAGC CGGCCCAGGG
45601  CTGCTACAGC CTCACCTGTA ACATGGGAAC TTGAGATCTG CCCTGGGCAA
45651  AGGGTGTTCA GAATTCAATA ATCAAAACAA TCTGTGAAAT GTAATACTTA
45701  ATAAAATTCA AATCCAAAAA TGTCTGAGTA CATTCCAAAA TGAGTAAAAA
45751  TGTAAATTTA TGAAAATGCT AAACATGCGT GATTGTTCTA ATGTAAATTG
45801  TAAGCCTCAG CTGCTTCCCA GAACTTTGGA TCTGGCTCCC TTGAAGCTGC
45851  TGCCTCTGAT GTGGCTGCCC CCTGCAGCTC CAGGACCTTC CTGTTCAGCT
45901  CCCTTGAGAG TAGCCGGCAG GGCCCCTCCT CTGCAGAGCC TGTACTCTGG
45951  CTGGTGGCTT CAGGGGGCAG GCATTCTGCC TTTCCTGTCT CCCACCCTAA
46001  GGGAGTTGGC CTTGCATGCC TCCCATCCAC GGTTGCCTCT ACTGGGGGCT
46051  GCCACTGGGA GACAGGAAGG GCATGGGAGT TTCGGGAGCT CAGGGTAAGA
46101  GGGGCTGAGA TCTCGTGGTG TGGAGGGGGA GCGGGAAGGT CGGGTGGCCG
46151  AAAGAATGGA GAGGGCCGGG AGTGAGAGCA AAGGGAGACA GGCAGAGCTG
46201  AAGAGCAGTA TCGCCCCAAC ATCAATACTG GTATTTCAGA ATGGGAAAGC
46251  TGTTCCATTT CCCGAAATAT CAGAATGCTG AGGTCCGATC TTGCAGTCTC
46301  TGAGCTGGGC ATTCCTTGGC CCCACTCTC GGGTATTCTT GCACAAGACC
46351  ATTTTTCTGG GCTGCATTTT CTCACTTGTA AAAGGAGGAA GTTGGGGGTC
```

FIGURE 3-16

```
46401  AATATCTCCA AGCGATATAT GAGCTCTAGC TCTAGGAGTA TAGGATTTTG
46451  AGAATCTGGA ATTGTTAGTC TGTGGGGTTC TAACTGGGAC AATTCTAGCA
46501  TTCCTTGACT CTCAGCTCCC AGCCAGGGCT GTGTGGATGC GTGGTTGTGT
46551  GATTCCGACA TTCTGAGACT TTAAGATGCT GAGGCTCTAG GAGCTAGAGA
46601  TACGGACATT CTGTGAATCT AGGATTCTAG GATTTGATGG TTTGATGATT
46651  CAATGATTCT AAATGGGGCT GCTGGGAAGA GCTGCAACCA CCTGCCTTGT
46701  TAATGTCAAT GTTCAGTTAT TAAAAACATA ACAAGAAGCA ATGGAGACAG
46751  ATAGCTCAGA ATGGTGGGCG CTCCCTCCAC TCCCAGTGAG GGAGGACAGA
46801  AGAGGCTGGG CTGGCCTTAG AGAATAGAGA CCTTTTCAAC CTGGGTCACA
46851  CAGGTTGTTT CTCCTGTCAC AACAGAACTG GTGTGTGTAC ATTCGAGAGA
46901  GCTTCCACTC CCAAAGCTTG CAGGGTAAGG GGCTCATTTC CTTCAGCACT
46951  GGCCTCTATT CCTTAACCAT TTCAGACTGG GCAGAGAGAG GGGTAACTAC
47001  CCTTTCCTCC CAGCCCTCGA AGTCTCTGGG CAGAAATGGC AGCAGTGGAG
47051  GAAGGAGAGG TCTGCTCACC CCCGCCCCTT CCCTGACAGC CTGAGGGGGA
47101  AAACAGGACA TGAATACTTC CTGGACACAG ACATGGAAAT GCATGAACCC
47151  CTGCCTTCGA GGGCCCCGCG TCCAAAGGCT CAGACAAGGG CAGAGGCCAG
47201  GACAGCCAGT GGGGTCCCAT CAGCACCCTC TCAGTATAGG CTGAGGAGGG
47251  AAGACCCTGT TCTTGCCCCA AGGGTGACAG TGAGAAGGGG TCAAGGAAAG
47301  GAGTCCCAGG TCAGGGACTG GAAGTGCTGA CAGGTCCTCC CCTGTGTGCA
47351  AGGCCACAGT CCAGCCTGGC AGAAGGCCAG CCCAATTGTC CAGTGTTTCA
47401  CTGCCTCCTG AGTCCTTCTT ATGCCTTGGC ACCCAGGCCA GAGTTGGGGA
47451  GGGGTCCAGG CTGCAGGGGA GGGTTTCCTT CCAGAGTGCC CATCCCTGAT
47501  GGATCCTTAG AAGCCCAGTA CAGCTGCACA GTTCCAAGGG CTTCCGCTGC
47551  CTGGTAGGTT CACAGACCAA AGCTGGCCCT GGTCACACAG CACAACGGGG
47601  CCTGAAATCA GGCTTCCTGA TTCCCAGTCC TGGGTGTTCC TTTTTGCCCA
47651  CAGCCTCCCC CACTTCCCCT GGGACACCTG AGGGGCAGGA GTGGAGGTGG
47701  GGCTCAGGTT AGGGAGCAGA GCCTCTGTCC ATCATCCCTC CGTCTTCCTC
47751  TTCCCACAGG CCAGAAGCAG GTGTGGTGGT GACAGCTGCC CCCAGTCCTC
47801  CACAAGGCTC CATTGTCCCC GGCAGGGAGC CCCTCCCCAG CTGCAGGCCA
47851  GAAGTGTGCC TCCCCGGGCC CTCCTGTCGT GACTCTGCCA CCCGCTTCCT
47901  CCTGCTGCCC CTTCCCTCTT CTCATCTCCG CTTGGGTTTAA GCCTCTCTCC
47951  ATCCCCGTGA GGTCTCGTCT CTGGCGCTCT CTGGGTTTAA GCCTCTCTCC
48001  AGTGAAAGTT AGATTTGGAA GGGCCCTGGG AGATCACCAA GTCCAACCCT
48051  TTTATTCTTC GGATAAGGAG GCCAGGTCAG AGAGGGGAAG GTCCTGTCCA
48101  AAGCTGCACA GTAGGCTGAG GCAGAGCCCA GTGCTGTGCT CCCTTCAGCG
48151  CTGGGTCATG GGTGCACACT GCCCTTGGCA TCAGGCGTCC AGGGTTTGAG
48201  AACTGACTGT GATGATCAGC GCTAAGCACA CAGGCACCTA CAGAAATGCG
48251  GTAGGGGGCT TCTCTCCTCA GCCCTTCTTC ACAGCCCTGA GCTGCCCTCC
48301  CTTCCTCTTC TTTGCCCAGC TCCTCTCTCC TTCACTATCC CTGCTGTCTG
48351  CTGACTCCTG CCTCTGGCAG ACACTGTCCT TGGGACACAG ACTAGAGCTC
48401  AGGCCTCCAG GACTGGGATG CACACCCATG CACCCAGACA CAGACACATA
48451  AACATGTGCA AGCGTGTCAC GGGGTCCATA AATCCCAGCT GAAAACTGGT
48501  CAGACCATCA GGAGGCCACC CTGGAACCCA GTGTCCTCCT CTTCCTGTCA
48551  GGCCTCACAC ACCTCCTCCA GGAAGCCCCT TAGGACCCCT GAAGACCATC
48601  TTCATCCAAC TAGCCCCTTT GTGACAACTG AACTCTGTGA GCCTAGGTTC
48651  CTCCTGTGAC TCGAAGGGCA AGGCTGAGTC CCCCCTTCAG TCCTGGGGCC
48701  ACTCCTTCAG TGTCTTCAGG AGGGGCTCAG CTTCCTGTTG CTGGGTGGGG
48751  AGAGCCCTGA GGTCCCCACA GGACGTGGGA CAATGGGGAG GCGGTGACAG
48801  ATGAGAGGCT GAGTCTTCCC TAAAGCAGAC TCCACCCTCC CCTGACCTCC
48851  CTGGCTGGTG GCTTGGACAC AGCCCTGGCC TGGACTAGGG TCCTGGTCTG
48901  ACCCCACAAT GCAGAGGTCT GGGAATCAGA AGCCCTGGTT CTCCAGCAGC
48951  AGTTCTCTAA CTGGCGGCTA TGGAGTCCAG GCCTCCAGGG CACTGGTAGG
49001  TTATTGGCGG GTTGGTGCAG ATTCCAGTGT CCAGGAGGGG TGAGCTGGCC
49051  TGGGGGGCCT ATGTACAGGA GATAGGAGGG TGATAAACAC AGGCTAGGTG
49101  GGATTACAGG GAGCTGGGAA TACCTAGCTA AGAATCCCCT CATCCTAGGC
49151  ACTTTCCCCA CACTTGAAAT TGGCTGGAGG GGGAACCAGA AGTTAGGTGG
49201  GGTTGGGGAG GGACAGGAGC CAGCACCCTG CCTCCACCTC CGGGCAGTGC
49251  CTCTGCTGGG GGGAGGGAAC CTGTCCTGGG GGTGGTGGGA GGTGTGAGGG
```

FIGURE 3-17

```
49301  GGGAGCTGGA TTCTCCAGTG AAACTGGCCC TCCCTCCTCT CAGGGGAGGG
49351  GAGGGGGCTG TCCCTGGCTG CTCAGCAGGT AGCCCATCTG GCTGTGGGTG
49401  GAAAAGAAGA CTCAGGCTTT GTGGATAAAA GGGACAGCCC TGGGTCAGGC
49451  ACTTATCTCA ACCCTCGTCA TTTCCTCTGC CGGACATGAC TGGGTGAGTG
49501  GGGTCATTGC ACAGAGGGAA GGAACAGGCC AGGGCCAGTG CATACCAGGC
49551  CCTACAGGAG AGTCAGGCAC ATGGGTGACC CTGCCACACC CTGGGCTGCA
49601  GTCAGCCCCT CATAGAGGCC CAGACACACA CCACAGTCAC TGCCGGAGAT
49651  GGCCACACCT AGACCATCAC ACCACACACA GACCCAGTCT CTCCAGGTGA
49701  CACTCAGGCC CAGCTGCAGG CGCAGCTAAG AGGGAAGACC CTGCAGGGCA
49751  CAGGGACACG TGGGACAAAC AGACGCCCTG CTTCGGCCAC ACCACAAGCC
49801  TCCACACACC AGGTGCAGCT CCTGTCACCC CTACGGTCAA CCCAAGGAGA
49851  GCCAGAGATT CCAGTAGTCG TGGGCAGGTA TCCAGTGCCC AGGCGAGAAG
49901  AGGGGGACAC CAGCAGGGAA CCCAGAACCT CCTCCATGCC AGACTGTGCC
49951  CTCCCCCCAG CTCACAGAAG GAGTGCCTCA GGCTGTTTAT TTCCTAGCAG
50001  GGACTAGCAG GGATGGGTGT CTCATCCCCC TCCCCCTCCC AGTCCCCACC
50051  ACACGATTCT GAAGCTGCCA AATCAAATCA GCCCCTGCAC CCGCGCCAGG
50101  CTGGCATGGC GGCCAGCAGC TGACGGGAAC GAAGCCAGGC TCAGAATATC
50151  CCACCGCCTG TCCGATGCCT GAGTAGGCTT GTTGGGTGGG GGTGGGGAGG
50201  GGCAGGAGCC TGGCAGCCAG GCCCTGGGCA GTGCCCCTCA GAGAGGCTGG
50251  GGGTTTGGAA TGCTGCAGGG TGGTGGGCTT CTGGAGAATG AGTGAGCAGG
50301  TCTCTGTTGT GTCTCCAGGC TGCTGTGGCA GTGTCTCCAC CGCTAGCATT
50351  CCGGGAACTG TGGAAGTGGT GCTGGTAGGA TACAGGTCGG GGGTCTGATC
50401  CCAGTCCAGA TGACTGGGCG CCAGGCTGGG GTAGGGGGGC TCCCACATGG
50451  TCTCACATTC ATTTGAGACT CACAGCACCC AGGTTGGAAG CCCCTTGGTT
50501  GTCTGTCAGT AAAGGCCCAA CTCACTGTGG AGGCCCAGTG ACTGTGTGAG
50551  GTGGACATTA CGGATCCCAT TTTACAGACA GAGAAACTGA GGCTTAGAGA
50601  GGGCTAGTAG AGCTCCCTGG AGAGAAGCAG AAGTGGAGGA GGCCTCAGAA
50651  AGAGTAAAGA GGTGGTCATT TCCACTCCTT AGGAGCCCTA GGTGGAAAGA
50701  AGGAATATGG CTCTGTTCTC AGAGTCAAGG AACAGAGAAT ATGGCAGAGC
50751  CAGAGGTGCC CATGGGAAGC AGAGAACAAG GAGGGAGTCT TGGGAGAGAG
50801  CAGGGTGCAA GCAGGCAAGG CTCCCTGGAG GAGGGGGCCA TCCGTGGGCT
50851  TGCTGGGGGC TAATGGGAGG ACAGTCTGGG GAGAAGGGGA GAAGGCCTGG
50901  CCGGCCTCAG CCCCTGACCT TCTTGTCTCT GCAGCCAGCC TGGACCCCCT
50951  TGCAAAGGAG CCAGGACCCC CAGGGAGTAG AGACGACCGA CTGGAGGTGA
51001  GAGCTCAGTG GAGGGAGAAG TGGGTGGGCT TGAGGGGGTG GGGCGCAGAC
51051  TGAAGATCAG TCTGAGTGGT GCCCTCCCCC TTGGGAGGAC GGGGAGGCTG
51101  GAGTCACATC CCAGCCCCAG CCCTCCAGAC TAGGACCACC CCTATATCAA
51151  GACCATCTCC CCTCACCCTA TATATCCCCA GCCTGGAAGT CCTCCCATGA
51201  GGATTCCTCC TCCCAACTCA CCTGGGGAGT CACTACAGAC TCCTCCCTTG
51251  TCCTCCCCAC CCTCACCCAA CAATTCCCGT TGATTCTCTG CCCTGAGTAT
51301  TTCCCGAGTT CCTCTCCTCT CCATTCTGCC GCCTGCTTGG GTCCAGGCTC
51351  CCTCAACTCT CCCCTGGGCC ACTCACTGGC TGCTTGCTTT CAGTTTCCCC
51401  CATCATCCAC GTGGCCACCA GGAGGATCTT TCTAATGCAC AGACCTGAAC
51451  TTGTCACTCT CTTGCCCCAG AATCCTCCAT GCTCCCCACC CCCATGCCCC
51501  CTCCACAACC CCAGCCTGGC AATCGTTCCC CTTCATCCAT TCCTGCCTCC
51551  CCCAAACTGC TCCTGCTGGC CTCTTCCCCA CTCAGCTTCC TAAATCCTTC
51601  GGGGATCAGC TCTAGCCTCC TTTCCTCTGG GAAGTCCTCT CTACCCCTTG
51651  ACCATGGGAC CAAGCTCACT CCTGCTCCCT CCTCTGAGCT CTCCTGCCCT
51701  GGCAGTCAGA TGCCAGGGCG CTCTGCTGTC TGTCGCCCAC TGTGCTGTGC
51751  CACGAGCACC CTGTTTTCTC CATCATGTGA CTCTGTATGT GTGTCTGCCT
51801  TGTCTTCTCT GCACTGTGAG CTCTTTGAGC CTCGGGACTG TGCTTTCTTC
51851  ATTCCTGAAC CTTCTACCAC CCTTGGATGG GTACCGGTGC AGGGCTCAGC
51901  CAGCGCATTT CCTGCCCTGC GAGGGGTGCC ATCCCCACCC CCGACCATG
51951  CCTTCCTTCC CTGTGAGGGG TGCCTCATAG GACTCTTCAG TGCTCAAAGG
52001  GGCCTTGACG AGCAAACAAG GTGGGCTGCT GATGTTGAAG ATCGGCACAG
52051  AGGAGGGTGT GTGTGTGTGT GAGAGAGAGA GAGAGAACTG GACCCACAGC
52101  CAGAACAGAG TCTGCCCAGG CCTGGCTGAG AGGGAGAGGA AGATGATGCT
52151  TGTATCAGCC CTCCTGTGTG CCAGGAGCCT TTGACACCCA CCTTGTTTAA
```

FIGURE 3-18

```
52201  TTATTACAGC ACCCCCATGA GGTAGGGGCT GCTATTATTC CTATTTCACA
52251  TTTGGGGAAG CTGAGGCCCA GAGGGATCAT TCAGCAAGTG AGTTGGGACA
52301  GAGCTAAGAT TGGAGCCTAG ATGTGTCTCA GGCTCGAGGC TCACTCTTTC
52351  CCGGCCCCTG AGTAAGATGG GAAAGAAGGT GCCCACACAG GGCCTGGTGC
52401  ACAGGAGGGG CTCAGCACAG GTTCCCTGCT GGGACACAGG GCCAAGACCT
52451  GAGAATGTGC CTCCAAGTGG GGCTGGGCCC TGCTGCTGGG AGCTGGCAAA
52501  GGGAGCTGGG AGGGGAGGGC CTGGAAAGCC ACATTATTAA TTTATTTACT
52551  GCCATGGCAT TCCCCATGGG GCGGGGCTCC CCCCAGAGCT GGGACAGATG
52601  GTGTTCCTGG GAGCCTGCAG TGTCTCAGCA GCCTCGGCCA CCCGCCAGGA
52651  AAGACTGGAT TTGTCATCCA CCCAGGGAGC CACAAGAAGA GGGGGCTTTG
52701  GCAAAGCTGA GACCCTCCTG GGCAACGGGG ACTGTGCCCT GAGGGAAGGA
52751  GTATGGCTCC AGGCACCCTG CTATGCCTCT GGGGCAGCCC CCGCTGCCTA
52801  GGCCATCTGC CTGCCCTCTG CAGGTTCAAG TTCTGCTCTT TGTCCAGCTC
52851  CACCGGCCTC GTCCTTCCCA TGAGGCTTCC CTGGGTCGGC CCCACCTGCT
52901  CCTATCCCTG TATTTTCTCT GCCTTTCCTT GAGCTGGGTC CTGCTGCCTC
52951  TTCCCTCTGA CCGAGGATCT GGAGCCATGA GCTCCTCAGC CCTCAGCTCT
53001  GTCCTGACCC CATCCCCACA CTCATCCCCA AAACAGTTAG TGTCTGCCTG
53051  GACTCTTGGC AGGGCCTGCT GGATTTCTGG GTCCTGCCAG CACCCCACCC
53101  GAGTGCCCAG GCCTATACTC AGCACTGCTG GGAAGAGATG GGCTGCCTGA
53151  GGGGACGCTG CCAACATGGA GAGGGCAAGA CTGGAGAGAG TGGGGACCCG
53201  AGGGCATTGC TCAGACCACA GGGGCAGCTG GAGGGAAAAG GGACTGGGAG
53251  CCTGAGGGGC CCTCCTGTCA GGGTGGATCT GGGAAGCCAA GATGGCCTCA
53301  TATAGTGGAC AAGCCACAGG GTCAGATGAG CACGGGTTCA AGTCCCAACT
53351  CCCTTGCTTC CTAGGTGTGT GGCCTTGTGC CTGTCACTTA ACCAGCCTGA
53401  GCATCAGTCT CCTCACCTGC CAGGCGGGAT AAGAACGTCT ATCACTGCCG
53451  GGAGCGGTGG CTCACGCTTG TAATCTCAGC ACTTTGGGAG GCCAAGGCAG
53501  GTGGATCACA AGGTCAGGAG ATCGAGACCA TTCTGGTTAA CAGGGTGAAA
53551  CCTGTCTCTA CTAAAAATAC AAAAAATTAG CCGGTTGTGG TGGTGGGCGC
53601  CTGTAGTCCC AGCTACTTGG GAGGCTGAGG CAGGAGAATG GTGTGAACCC
53651  GGGAGGCAGA GCTTGCAGTG AGCCGAGATC GCGCCACTGC ACTTCAGCCT
53701  GGGTGACAGA GTGAGACTCC ATCTCAAAAA AAAAAAAAAA GAACCTCTAT
53751  CATTCTTGGA TGTAATCACT GTTATTCAAC ATTACCACAA TAGAGCTGTT
53801  GGGAGAAGTT ACAAAGACTG TATGTGTGGG GTGCCCGGCG CAGGCCTGGC
53851  ACATGGCAGA TCCTTGGGGA GAGTTAGCCT CCTCTCTGTT TCCCTCAAGG
53901  ATGACATCCT TAGAGCCAGG ACTAGGCTGT ACCCCTGTGA GACAGGATGC
53951  TCTGCAGAGC TGGGCTGAGG CTTATGGAAG TTCTATGGGC ATGGCACACT
54001  CTCCTGGCAC TGGCTGGGCA GCAGCCAAGA AAGCAGAGCT GCCAGCACCC
54051  ATCCCCACCC AGCAGGCGTG TGTTCAGCAC ACCCTCCTGG GATGGTTACC
54101  TAGCCCCTGT GCCAGCAGCT GACTTGGAGG AGGGGCTCTT CCAGCTCAGC
54151  CTGGCATCCT CCTTCAGGGC CAGGCCTCTG CATCATTACT GTCTCTCTGA
54201  AAGTCAGGTC TGGGGCAGTT CAAGTTGGTG AATTGAGCAT GCTGAGTCAA
54251  TGCCCTCTTT GTGATGGCTC TCAGGGCCCA GATGCGGCT TGGGAGCCTT
54301  AGCTGGGATG GGGGCATGGG GAGAGGCGGA CGTGGATGAG GGCACTGACA
54351  TCCACAATAA GTACTGAAAT GCACTGCCCA ACACCGGCTC CTCTATTGCT
54401  GCCCCTTGGA CAAAGACCAC ACCCCTTGGC AGGGCATTGC TGGCCTTGCC
54451  TGCTGGGTCC CCTCATGTCC CCTTGTGTCC CCTTATGCCC TGAGACAGCC
54501  AGCGCTACAG CCACATTGTT GTGTTCACTC CCAGCACACA GCAGCTCCCC
54551  CTGCCTCCCT GCCTTTGCTC ACACTGACCA CCTGTCTGGA ATACCTTTCC
54601  TTTCTTTCTC CACCTACTCT CTTTTCAAGG CCCAGATGAA ATGTCACCTC
54651  CTTTGTGACG TTCCTCAGAC TGGTCCCTCT ACCTCAGGCC GAGCCAGTCT
54701  CCTCCCTTCC CTGGGCACTC ACAGTCCCCA TTTCCCTGAG CCCACAGTTG
54751  GGAAACCTGT TACCCCACGG GGTGCTGTGG GTAGTGTATC CTTCCCCATG
54801  GGGTTGTAAA CACCCAGGAG GCAGAGGCTG AGACTGAGTC TCCTTTGTCT
54851  CTCTTGGGCC CATGTGGTGC TTGGTATAGG CCTGGTATAT GGTAGGTGCT
54901  CAATAAATAC TTCTTGAATG AACAAGAGTG GCTGTGAGTA GGGCTGGAGT
54951  AGTTCCAAGA AGGGGCACAG TTGGGTTGGG CGGTCTTGGA GACTTGGAGG
55001  AGGCAACCTT AGAACTTTGA AGGATGGAGA GGGTCAAGGG CACCAACCGA
55051  AGAAGCCAGG GACCAGCTAG GCAGTCAGAG AGGTCCATGA GGTCAGCTTC
```

FIGURE 3-19

```
55101  TGACAGCAGC AGCTAAGGAC AACCAGGACC AGAACAGGAC TGGGAAAAAG
55151  CAGATAGAGG AGGCTGGAGC AAGGACTCAG CCCCAGAGGA GGCTGCAGGA
55201  GGTTGGCTCA TGCTCAGAAC CCGGCTCCAA AACACTCTGC CCATGAGTGC
55251  TGGGCTGAGG AAGGCTTGGT GCCAGAGTCA GGGTGAGGCT GAGGCCACCA
55301  GTGAATATGT GGGCCCAGCT GCGGGGGTAG CACTAGGCAG GGGCGGGAGC
55351  CAGGTTGGAG GGGGTATTGC CATTGCCGCT GCAGGTGGAG TAGGGCTTCG
55401  CTGGGGAAGG AGCAGCTTGT GCGAGAGTGT GGGCAGGAGT GGGAGGGGAG
55451  AAGGCTCCGA GTATACGAGC ATAGCTTACC AGCAAGTCCT GGGGTGAGGC
55501  TGGAGGGGCC GCGCTGTAGG CAGCACTTTT CAGGCCCTTA TCTAACATTC
55551  TCAAGTGAGT GCTCCTAGCT GCCAGATGTG CTACTTCCTC CTGGATTCTG
55601  CACATCAGGA GCCAGTGGCC TCTACAATGC CCCATGGCCC CAAGGGAGTG
55651  GCTGCCAACA AGTTGGCCTT AGCATCTGGC ATCCATGGGG GTCCTGAGGC
55701  CCTGCCATCT GTCTGTGCCC CTGTTGGGCT GCACAGGCCC GGGGCGTGCA
55751  GGGACCTGGG ACCAGGGAGG CGGTCTCAGC TGCCACTCTA GCCTGTCTCT
55801  CTGCCTGCCC ATCCACTGTC CACACCCCTG GCTGACTGAG TAAAGAGAGA
55851  GATGGGCATC GCAGGTCCTG CCATCAAAGA AGCCTAGTCT AAAGGAGGAG
55901  GCATAAAGCA CCGGGGACTT ATACCCAGAG AAGACACATG CTGAGACCAC
55951  GCCAGGCTCG CGGGCAAGGC CTAGGCCCAG GGAGGGCCAG CCTCGTCAAG
56001  GGCCTGGAGT TGAGACTCAG GGAAAGGCAG GAGCTGGCTT AGAGGCGCAG
56051  GCAGGTCCAA GGCAGTGCCC AGGCCAGATG CGGCGGCCCC GGGCTGAGGT
56101  TGCTCCAGCC GGCCCCACCC CCCACCGTCC TGCCTGGCCT TTGGCTGTAA
56151  ACACTGAGAG AACAAGTTCC GTTTCCCGGG AAATATTTAT CTCAGGCTGT
56201  GTGAAGAGCG TGTGCACTGG CCTCCGTGTG TCCTTCCTGC AGACCGGCTG
56251  GGGCAGGAGG AGAGGGAGCT TGGCAGCGCC CTTGCTGGGG GGAGTCTGTG
56301  GGGCTAGGAG GGAAGGGTGT GCCAGAGGCC CCTGCCTAGA GCCTGAATTT
56351  GAGTGCTGGC TGAGGGAGAG GTGGGAGCAG ATGGGAGAGA AGCCTGTTTT
56401  CTCCAAACCC CACAAATGCC CTCCGCCTCT CTCATGTTCC TTTCTTCTTC
56451  CTGGTCCATC CTGTCTCCTC CAGGTTCCGG CCTCCAGCCT GGTGTCCCCT
56501  CCTCAGGCTG CCTTTTCCTC CTCCTCCTCC CTGTTTCCTG GCTCTTAGCC
56551  GCTCCATCTG GGAAGTCTTC CTCAACTTTA AACCCTCGAA CCCTTGTCCT
56601  CTGCCCCTCCA TCTCCCACTC CTCAGGCTTT CAGCAGCTTC ACGTGGAGCA
56651  TTGGGCTGGT CCTGTCCACA GTTGTTCAGT TGCTGTAACA GCTTGTGCAG
56701  GCTGCCCTGG AGCCCTGTTC TGGGAAGCAC AGGTCTGGGC ACCCTGGGGC
56751  TGGGGCGAGG CCCGGAGCTG ATCTCCTCTG TCCATCCCAG TAGAGCCAGC
56801  ACCAGTGCAG ACACATGGGG GATCCAGGTT GGTGGACCAG GGGAGGATGG
56851  AAAGTCCCAT GGATCCAGCC GGAATGTTGG AGTGGGGAGG CAGAGGGCCC
56901  AGGGTTCCTG CTGGCCAGCC TCTGGGCTTA GGGGTGTGTA TCCCAGACAG
56951  GCCAGGCCTG CCAGGGGCCC TGACAACAGG AAATCCTTGA AGGAACAAGC
57001  AGAGGCTGAG GACTCTGAGC ACAACAACAG GAAACAGCCG TGACATGGGG
57051  CAAACAGCCCT GGCGACTGTG CCCAGTTGGG GTGGGGACGA GGGGCCAAGC
57101  TTGTGGGACC CAGGGTGATG CCAAGAGGGA CACTGAGACA CTGTGGGACA
57151  GGGGGCGTTC TGCACATGTG ACACGGAGCT TATGACGTGT AATATCAAGT
57201  ACGTGACCAT GATCATAGGG TACTGTGTGG AGTGTGGGTG AGTCACTGAG
57251  TATGTGACAC TGGCTGTGAG GCACTCCATG ATAGCAGATG TGTACAGTGG
57301  CTGTGCCACC AAGTGTGTAA CACTGTGTGA TATTGATTGT GTGATGCTGA
57351  CACCGAGTGT GTGACATTGC ACATTGCATG CTACCACGTG TGTGACACTG
57401  AAAGTGACAG TGAGCACATG GAGGGTGTGT CTCCATGAGA ATCAAATACA
57451  GAAACGTGAG CAAATGACGC TGCAGTAGCA GGTATGGTCC TGAGTCTGTG
57501  GCTCGAGTGT CTGACACTGA ATTGTGACAT TGAGTGTGTC CCAAGCATAT
57551  GATCTAGTGA GGCTGAGTGT GTAAACAAAG GCATGACATG GAGTGATAGC
57601  AAGTGTGTGG AAGTGGGTGT GTGATGCTGT GTGATCTTGG GCCTGACATT
57651  ACATGTGTGA TGCTCTGTAA TGGTTGTAAC AGTATGCAAT GTGCACATAC
57701  AGTGCTGTGT AGGACACTGT CATGGGAAGG CACCGATGGG TTCAGGCGGG
57751  AAAGTAACAC CGTCCAAAGG ATGGTTTTAA AAGATTGCTC TGGCCGGATG
57801  CAGTGGCTCA CACCTATAAT CCCAGCACTT TGGGAGGCTG AGCTGGGTGG
57851  ATCACCTGAG GTCAGGAGTT CAAGACCAGT CTGGTGAAAC CCCATCTCTA
57901  CTAAAAATAC AAAAATTAGC CAGGCATGGT GACAGGCGCC TGTAATCTCA
57951  GCTGCTCGGG AGGTTGAGAC AGGAGAATCA CTTGAACCCA GGGGCAGAG
```

FIGURE 3-20

```
58001  GTTGCAGTGA GCCAAGATTG AGCCATTGCA CTCCAGCCTG GGTGACGAGT
58051  GAAATACCAT CTCAAAAAAA AAAAAAAGAA AAAGATTGCT CAGGTTGCAG
58101  AATATGTATG TGTGCGAGTG TGCATGGTGC GTGGCAGGGG AGGGGAGATA
58151  AGTTAGGGGG AGGCAGAGAG AAGGTGGGTA GAGCAACTGG AGGCTCCTGC
58201  AGCTGCCCAG GCAGGAGATG GTGGTGCCTG TGTTAATGGA ATGGCAGAAG
58251  AGTTAGAGAT ATGGAGCAAC TTTGGAGATA TTTGAAAACA GAAATGACAG
58301  AACTTGCTGA TAAATGAGAA GATGAGCAAG AGGGAAAACC AGAGAACAAT
58351  TTCCAGGGTT CTGGCTTGAA GAACCAAGCG ATGGATGGTG AAGATGTTTC
58401  TGAGATGGGC AAAGGCAAGG GGGAGGGTCA GCACTAGTGG GGTGGGAGGA
58451  CAAGGAGGCA GAAACCGAGT GAGCTGTTTT GGATGTGTTA AGGGAAGCAT
58501  CCAGGTGAAG GTGTGCAGTG GGCAGCGGGG CCAGGCTAGG GATACATCTG
58551  GGAGTCGACA GGCATGGGGG GTTTGTTAAG GTCGTGGACC TGGCTGGGAT
58601  AATGGAGAGA GGGAGCTTGG CAACAGAAGA GGTGGGGACT GAGGACCGAG
58651  CCTTAAACTC TGAATATTCC ATTGTCTAGA GGCCGGGGAG GTGAGAAGGA
58701  GCAGCAACGA GACAGAGGAG GAGGGCCAGG GAGGCAGAGG AGACCAGGAG
58751  TGTGAAGCCA GAAGCCAAGG GAGGAAAGAG GCTCAAGTGG GAGGGAGGGT
58801  CGGTGTGTGG ATGGTGCTGG CCCACAGGTA AGATGGGAAC CGGAAGATTG
58851  TGCTGTGCTG GGCACTGTGG GTGAGTCAGG CTAATGGGAG CCATTTCAGT
58901  GATGGGCTGG AGCCAGAAGT CAGACTGGCC TGTGTAGGAT GGTGAGGGAG
58951  GTGAAGACGT TAGCCTGGAG AGCCCTTTGG AGACGTTGGG CTGTGAGGGC
59001  TGCAGAGAAG GACATGATCG CTGGAAAGGG AGATTACATT TTTTTATTAT
59051  GGGTGATTCT AAGCAGACAC AATACCAGAG AGAAGCATAT AAGAAACTGC
59101  CATATACTCA TCACCCCAGT TCAACAGTTG CTGGGATTTG GCCTCATTTC
59151  TTCCTCTCTT GCCCCCTATC TGTTCTTTCA TTTTCCTTTG CTTAAGCTTA
59201  AAATTTTTTA AATTGTGGTA AAATATACAT AACTTAAACT TTACCATCAT
59251  AACCATTTCT AAGTGTACAG TTCAGTTGTG GTAGGTACAT TCACACTGTT
59301  TTGCAACCAA TCTCTGGAAC TCTTTCATCT TCTCAAACTG AAACTCTGCA
59351  CCTATTAAAC GACAGCCCCC ATCCTCCTCT GTCTCCAGCT CCTGGCACCC
59401  ACCATTCTAC TTTCTGTCTC TATGACTTGG ACTACTCTAG ATACCTCAAG
59451  TAATTGGAAT AATGTAGTAT CTGTCTTTTT GTGACTGGTT TTTAAGTTTA
59501  CTTAGCATAA CGTCTTCAAG TTTTACCCAT GTTGTAGCAT GTGACAGGAT
59551  TTCCTTCCTT TTTATGGCCA CATAATATTC CAGTGTATGG ACAGACCACA
59601  TCCATCCAAC ACCAGACACT TGGGTTGCTT TCACATTTTA GCTATTGTGA
59651  GTAATGCTGC TATGAACATA AGTGTACAAA TATCTCTTCA AGATCCTGCT
59701  TCCAATTCTT TCAGATGTAT ACCTAGAAGT ACGCTTGCTG GATCACACAG
59751  TCATTCTATT TTTTGGTTTT TGAGGAACTG CCATACTGTT TTCTGTATCT
59801  TTTTACATTC CCACGGACAG TGTACAGGGG TTTCAGTTTC TCCACATCCT
59851  TGCCAACATG TGTTATTTTC TGTTCTTTTT TTTCTTTTAT TTTTTTAATG
59901  GTAGCCATCC TAATGGGTGT GGGGTGACAT TTCATTGTGG TTTTGATTTG
59951  CATTTCCCTA ATGATTAGTG AAGTTGAGCA TCTTTTCATG TGCTGGTTGG
60001  CCACTTGTAT ATCTTCTTTG GGAAAATGTT GATTCAAGTC CTTTGCCCAT
60051  TTAAAACATT GGGTTGTTTG CTTTTTTGTT GTTATTGAAT TGCAGGGGTT
60101  CTTTATATAT TCCAGATATT ACCTCTTTAT CAGATAAAAG CTTTGCAAAT
60151  ATTTTTCTCC CATTTCATAG GTTGCTTCGC TGAAATATTT TAAAGCAAAT
60201  CCCAGACATG ATGTCATTTC ACCAAAGGTA GACTTTTTTT TTGGTGGGGG
60251  GAGCTTTCCG GTGAAGACTG AAAAACCTGC TAGACAAATT CTAAAATAGA
60301  TGTGACTTTG GATTTTTGTT TTTTAAGGCT AGGAGGTCCT GGATGATGCT
60351  GAAATGTAAC AGTGACACAG AGCCAGTGTG GAACTGTGTC TGATGCTGTG
60401  TGAGGGTGAC ATGGTGGCTT TGGGAACATG GGTGCAACAC TGAAGATATG
60451  GGAGACTCCA AGTGAGGGTG ACAGTGAGAG ATCACTGTGT GTGTGGCCCT
60501  GTGACACCCA GTGACATGGG ACAGTGGGAC GCTGTGGACC CTGAAATGAC
60551  TGTGTGTCAC CGAGCAGGTG GGACCTGCTG TGTGAAGGCC ACAGGTGTCA
60601  TGTCTTCTTG TGTCATCCTG GTTGATGAGT GTGACACAGT GCAGGACTCT
60651  GCATGGGAGT AAGAGGGACT GAAGCTGTGC TATAGGTGAC CGGGCTGCAT
60701  GTGATTCAAG TGGGCTCAGC CCCAGCTTCA GCTGCTGAGT ATGGGAGGGA
60751  GCATGGACAT TGTAGGGTAG ATGAGGAGAA ACACTGAATG GGAACAGAAA
60801  TGGTGTCTGT GCCCAGATGC GAGCTCCTCC CTTCTCTGAA TACCCAGGAA
60851  GGCTTCCTGG AGGCAGGATG TGGGCACTTC AGCAGGATGT TGTAGGTGCT
```

FIGURE 3-21

```
60901  GATTAAGAGC AGGGCCTGTG GTGTCAGACA GCCCTGTCTA GGCTCTGACA
60951  TTCAGCAGGT CATTTTATCT CTTGAGCCTC AATTTCCTCA AGTATAAAAT
61001  GGGAGCTCTT AGGAGGATTG CATGAAGCAG TGCTCCAATG CATGCAGTCT
61051  CTGGCACTTG GTAAATACTC TATGGTCTCT TGGGGAGCAG CAACCTCAAC
61101  ACCTGCACCC CAGGTCCCCA AATAACAGGA GCACCAGTAG GAGCACAGTG
61151  AAGGTGCGCT GAGTGAGGTG TCCTCTTACA CCCACAGCCC TCCTCTCTCC
61201  CTCTCCCCCA ACTTCTGTCC CCTGCTTGGT GTTGTCAGCG ATACCCCCTC
61251  CTGCCCACTC ACTCCTGCCC CCTCCTCTCC CCTGCCGTCC TTACCACTGT
61301  CAGCCTCCAG CCCAGGCTCC TGCAGCCTCA TCCAATTAGG CCAATGCAAT
61351  TTGCTCAAGA AAAAGCCCCA TAATTTGGTT AATCACACCA GTAGGGGATC
61401  TGGTCCCGGT CGGGAGGGTG GGGGTGGATA GGAGTCCATA CCCGCAGCTG
61451  AGGCACAGGT GTCAAAGTGC CTGTCTTTTG GGACCTTTAC CCACTTCCTT
61501  GGGCTCCTTT CAGGAGCCAA CAGAGTCCCA AAGCTTGGGT CTTCTCAAAC
61551  CCCAACTACA GAGGCCTTGA AACAGGAGTC TGGACTTCCT GGGTTCGCTT
61601  GTGTTCCTGG GAGGGTCCCT GCTACTCTCT GGGCCTCAGT CTCCCTTTCC
61651  AAAAATGGGA GTGGAACTGG GGAGTCTCAG AGGCCCCAGT TGGCCTAGCT
61701  CTGCATCCCA GCTCTGGTCA GTCCCCCTTG TGGCTTCTGA GGGGCCTTCT
61751  CCTGGGCCTT GGGGAGGGAG CACTGAGGGG TAGGTGGAGA GCACAGGGCC
61801  CCAGGGAAGT GAGGAGGGGT AAGTGTCCTC TGAGTCTCAT CTGGAATGTG
61851  TCTACCCCAG TCCTATAATC AGAGACCCTC TAGTTCCAGG CTGCACACCT
61901  GAAGGTGGGG CAGGAAGAAA GGAAGCTGCC CTTTCTTGGT CACCTGCAAG
61951  GCCAAAGTCT CTTAACCGTG CAGGCTATAC CTTGCACAGG AGCTCCAGCA
62001  GAGGTGGGGT GGTGCTGAAA CTGAGCCCAC TCTCCCTCAC CAAGCCTTTC
62051  CCCTCAGGCC CGCATCTGCC CAGAGAATTG GGGTCCCTCC TTTCTAATGT
62101  GCACACAGGT GGCCCCAGCC CCCTGCTGGG AGTCAGCTTA GGCAAGGTTT
62151  GATGGCTCAG CTTAATCTTC TCAGCAGCTC TGGGGGAAGA GACCATTTTA
62201  CGGATGAGGA ACTGAGCCCA GGAAGGTCCA AAGACTTGTC CAGTACATGT
62251  GGTGTGTGGC AGGGCAGGCA GATGAGCCCG CATCTGAGGG AGGCGATGGG
62301  AGAAGTGACA GGGGTGCGCA GAGGAGGAGA ATTAGACCCT CTCAGATTCC
62351  ACCACTCTCA GCCACACGTT CACTCACTCA TTTGGAGACA AGACTAACCA
62401  CCAGCGCATT CACAGCCCCC CAGACAGCCA CATACTGACT ATACCACTGT
62451  CACATGGACA TCAATGACCT GAATCACATA TGCATAGATG CAGGCCCACA
62501  TGGTCACTCC CACGTGCAGA TGCCAGTGC ACACACATAG ACACAGGGTA
62551  CTCACACATG TTTACACTCT CACGACCCAT GTGGGTTACA GATTCCTACA
62601  GAGACACAGA CCTACATACT TTCACAAGGA AATTCTCCCA GTGACCCAGG
62651  GAACATAGTC TGCCATGATG ATGTGATGGT CCGTAGGGGC TCGCCACTAT
62701  GGACCATTAA TGGGCAGGCT GCACACATGC TTAGGTCCCC AGCAAAGCGG
62751  GAGTTCTGCA CAGAGTGAGA GGAGAGGTCA GTTCTGATGA GTGTATCCAG
62801  AATTTTGCAA TCAGAAAAAC CACACAAAAA CTATTTTAAT TTTCATTTCC
62851  AAGATAAAAT TTAGTTTGAA TTGTATAGAG GGTCCGAGGG TCTGGTGGGA
62901  GGGCATCATC ATCTTTTCAA GGCTTTGGGG TTCTAAGGCA CCCACAGATT
62951  CACAACAGTC CCACAAGATA TCCCAGGCTG ACATATTTAC CCAGCCCAGT
63001  GTGTGCGTGT GTGTGTGTGT GTGTGCGCAC GCTGTGTGCA TGCTCATGCT
63051  GGCTCCCAGA TCCTCGGGAT GTGAGGAAGG AAAGTAGGAG AGATTCCAGA
63101  GACTCCGGAT GTTTGTTCTC TGGCTTCCTG GGCCCTTCAA AGGAAAATAA
63151  CTCTGGATGT CAGCCTGCCT GCCTGGCGGG CTGGGTGGAG AGGTGGGCTG
63201  TTTTGGGAGG TGGGCTGTAT GACAGCCTGC CTCAGCCCCT GTGGCCCCAC
63251  TGACCGGGAC CCTGTGTAAT GAGGCAGAGT GACCAAGGCC CATGGCCAGC
63301  GTCCCATGGG CTCGTAGGCC CATCGCCTCC CCTCTCTGGG GCTTGGCTCT
63351  CTCATCTGAA AAATGGAGGT GGGAAGGAGA TGAGACTGGA TGGGCTTTCT
63401  CCTGGAGACT GATTAGAGAG ACAGAGACTC AGGCCCGGGG TCCAGAAAAG
63451  ACAACCAAAG CTGGGGAGGG CACATGAAGG GGGGCAAAGA AGGTCTGGGT
63501  TCAGGGGAGT GCGTGGGGCC CCAGAGCCTG CCATGTCTCC GCCAACTCTC
63551  TCCCTCACTG GAGGAGGGCT CTGTGCCTTG GTGCCCCACC TGCCCAGGGC
63601  CCTGTGGCTC AGCCCCTTGC TTGCTCTGTG AGGGGGACGG GAGAAGGATG
63651  AGAGTCCCAG TGATAGGGGG AGGACAAGAC CAGGGGAGAG GGCTGGGGGT
63701  TTCTGGAGGG CCAGAGCAGG AAGAGCAGGA GAGAAGAGAG GACACCACAG
63751  TGCAGGAAAC GGAGGAGCAA AGGCTGGGAG TGGGGAGGCT GGAGGGGTGC
```

FIGURE 3-22

```
63801  AGGGAATCAG ACTGGGGCGC TGCGAAGAGG CCTGAGGCCA GAGCAGGCAG
63851  TGCCTGGATG GAGGGAGCGA GCAGCTCCTC ACCCTCAGCT CCTTGATGAG
63901  GTAAGGTGAC CACGAGCCCT GCTCCAGGCT GTGTGCTGAG CACTTTGCTC
63951  GGAGCCTGTC ACTCTGGAGG AGGGGAGGGG GTGTTCCCAG GAGCTATGAC
64001  AGTCTTGTGC AAGGGAGGGA CAGGGTCACA TTTATGTTTA ACAAAGCACT
64051  GCGCTGGGAG AGAGGAGCTG AGAGACCCCG GCCCTGGGGA GCATGGTGGC
64101  TGGGACCCCG GAGGGCAGGC GTGCCCCAGA CGGACCCCAC TCAGAAGATT
64151  GCTTATCCCA ACCCCCCAAA GAGAAAGGCT ATTTTTAGGA ACAATAAAAG
64201  TGCTCACACA TTCCTGCAGG GGCAGAGAGA GGGAAAGGGG GCAGGAGTCA
64251  GTGCAGAGGA AGAGGGTGGA CCCCGCTCTT CTCCCAACTC TGCCTTGGTC
64301  TTCAGGGACT TCTCCTCAGG GGCTTCCCCA GCCAGCCCTG CCTCTCCAGC
64351  CTCCGCCTGT CCCTGGGGTT CCCTACCGGC TCTTATGTCT ATCCCTCTGC
64401  TTCTGAATTG GTACTTGTTC TGTCCCTGTC TCTCTTTCTC ATACTTCCAC
64451  TTTCCCCCTC CCCCTGGGGT TTGGGGAACA GCTGGGATGG GCCAAGCTCT
64501  GTTGAGAGAG CCAAATACAG TCATAGGACA AAGCAGCGGG AGGCTGTGGG
64551  ATACACACAT GCCGCAGAGC ACAGACAGAG AGAGGTGGCC AGGCACAGAG
64601  AGAGCGCCCA GGGAGGCTGA GAGGCAGGGA GAAAACACGC TGGGACAGTC
64651  AGGGAGAGCC CCAGGGCAGG CATCACCGGG CAGCCAGCCT CTGTGCCCTG
64701  CTCTCTATCT TGTCCCTAAG AAGACCAGCA TGGCTGGGCT TGCCTCCCGC
64751  CATCCACCCC ACCAGCCCTA CCCCAGGCTG GCCCTTCCTC CCCGCCCTCT
64801  GCAGGCCCAC ACTAACCCTA GGCCAGGCCG CCTCCTTCAG CATTTACCTC
64851  CCACACACAA TGGGCACAGT GAGGACATAA GAGACCCAGT CTCTGGCCTG
64901  GAGGCAGATA CTCAGCCTTA CCCGACATCT GAGAGGGCTC AGCCCATCCC
64951  CTGGCCAAGG CAGGTATTAG AGGGGCCCCA AAGACAAGCA GGACTCTGGG
65001  ACAAGGTGTC CTAGTGTGGC CCAAAGGGCT GGGCTGAAGC ATGGGTCTCC
65051  TGGCTCCAGA TGAGAGCCTG GGTGAATCCT TCCCTGCCTC CTCTGGCCTT
65101  AGTCTACCCC ATCAAGCTTG GGATTGGACT ACATGAGGCC TGAGGCCCTG
65151  TAGCCCCTGG TCCCTGGGAA TTCTCAGAAG GCCTGGGAGG GGACAGGTG
65201  ACCACGCAGG AAGGCTTCCT GGAGGAGGTG TCCTCACTCA TGAAAGAAGG
65251  TGATAGTGAC AGTGCTCCTC TTGGGGAAGA GCCCTCCATC CTGACCTGCT
65301  GCCCCCACCC GGTCTGCACG TGGAGATGAT CCTGAAGCAC AAAGGGCCTC
65351  CCGGCCTGCA GAGGTGCCTG GGAGAGGTTG CCAAAGGCTC TCAGTAGGAG
65401  ACACCCCATT CCTCAGGCTC CTTCTCTGAG ACTGTAACTG TGCCAGACTG
65451  GGGAGGCTTT GAGAGGTCTC AGCTATCTCC CCTGCCTAGA TCCTTCCTCC
65501  ACACCCCTCT TCTCCCTGAT GGCATGTAGC CCTCACAGTA CAGTAGTCCT
65551  GGGCACACAG GAGTTTACCC AGTCATTTAC AGCTCAGCAA ACACCTACCA
65601  ACACCTATGA GGGGCTGGGT AATGCTGGAG ACCCGGAGAG GGGCAGGACA
65651  CAATCTCTGC CCTCCAAAAG CTCCCAGTCT GTTGTGGGAG CCAGACGGGA
65701  AAGGGTGGCA CTGCATTGAT GCACACAGTG CATGCCATGG TGGGGGAAAG
65751  GGGGGCAGTG GGAGCCCCAG GTGGGAGGGT CAGACTTGCC TGGAGAGAGA
65801  ACAACAACAG ACTCTCCCTG GAGGGGATCC AGAGAAGGGA GATCACTTCA
65851  TTCATTCATT CGTCATTCAT CCATCCACCC ATTCAATTAT TCCTTTGGCC
65901  ATCATTTCCT GAGGGATGTA AACTCTCTTC TGACACTGAC CCAGCGGGAC
65951  ACTCAGCGTC CTCCTCCTCT CCTGCTTGAG CCACCATGCC TGCCTCTTGG
66001  AGGCTCCTGG ACTTGCTTTG CTCAGCTCCC AACCCAAACTC GAGGGGGTGA
66051  GGCTGAGGAG GGTGTACAGA CATTCAGGGT CACCACAGGC CCCTGGTGGC
66101  GCCTGCCACC TCACCAGGGG CCTTTCTCAG GGCACAGGCT CCCCCCTCAT
66151  AGGGCCTTGG CCCTTGCTTG CACACCCTTG GGGACTAGGA GCCCCCTCAT
66201  CCATCCTGCT CAGGCTCTCT TTTGTGGCGC GACTCTGATT CACAGTGTGC
66251  CCAAATCTGC CTCCTTGTGA CTGCCGCGAG CTGCCTCGTG GGCCCCAGGC
66301  CAGAGGACAA GGATAGCTAG AATGCCAGGT GACCAGGATG ACTGTGATGG
66351  CATGGAGAGG GGGATGCTGT GATGTGTTTG GGAGGAAGTT TGTGGTGTCC
66401  AGGAGAATGT GGGCAGCAGA AATGGGACCA CTCTCGGTTC TTCCCTGTAG
66451  ATGAAGCAGC TGAAGGTGGG AGGGGGTGGG AGGAGACCTG AGCTGGCTCT
66501  GCCCCGCTTG ATCTGATGTC TGCCTTGCAG GGCCATCCTC CCCCTCCCCA
66551  CACTCAGCTC CTGCCTCCCT CCCTCTACCC ACTCTGACTG TTCCCTCCTT
66601  TCCTGACTCC AGACTCTGGG TGAGGGACTG AGGTGATTCC AGTGAGTCAG
66651  GCCCTCAGGG AACTGATCGT GCAGGCAACT CTTGCCTGCC TTCTCCTGCT
```

FIGURE 3-23

```
66701  CTTTCCCTCT TCCCATTCCT TCATCCACCC CCAAACCTAG CTCCTGATGG
66751  ATCCAAGGGT GCGGGGGACA ACCGGGAGGT CATTTTGGAG GAGGCAGGAG
66801  CTGGAATAGA AGCTGGGACT GGCTTGGGAA GGGCGAGAGG CCGGGGCGGA
66851  GCTGGTTGTG GGCGCTGGAA GGGAGGAGCC AACAGTGTGG GGTCAGGCTC
66901  CTGTGGACGG GGACACCCTT GGGAGGCACT GGGACTGGCT CAGGTGTATT
66951  CTACAGTGCA CGTGTCTCCA GTGTGGCTCG GAGGCTGGAG ACGCGGCCCT
67001  GTTGGAGTAA CAACTGAAGC CGGAGTCTGC GAAGGGTGGG CAGGAGGGTG
67051  GAGGGATGGG GGCATGGAGC GGGAGGGGGT AAGTAGAGGA GGGAGGGGAG
67101  GAAGAGAAAG AGGGAGGAGG AAAGGTCTCT GGCAGGTCCC TCCTTTAAGA
67151  CTGGGCTCCT GCGCTGCGAG TGGCCCCGTC CATACTGCCT TGTTATCCAT
67201  ATCTCCCCAC CACTAGTCTC CCTCTGTCCT TCCACCCCCA GCCTCTCCCC
67251  TCCATTGGGA CCTTCCCTGG GGCGTCCCCT CATTGGCTGT TCTCACCTGA
67301  GCAAGGCCCC TCCCCTCCAG TCCTTAGCCT CTTCACCTGT ACAATGGGAT
67351  GACCCAAACA GGCACCTCTT GGGCTTGTAG GAGGATCCAA GATAGTGTCA
67401  GTGGGTCTCG AGGTGTGGTC CCCCGACCAG CAGCATCAGT GTCATCTAGG
67451  AATGTTTGGA AACGCAAGTT CTTGGACCTC GTCCCAGACC TACTGTATCA
67501  GAAACCCTGG GGGTGGGGCC AGCAATCTGC ACTTTAACAA GCACTCTGGG
67551  TGGGTTCTGG TGCACATGAA AATTGGGGAA CGGCTGGTGG AAACCTCTAG
67601  CCACAGGAGG TGCTTGGGAA AGGTACCTTC CCCTCCCAA AGCCTGATGC
67651  CTCACTCAAG CATGACACTG ACAGTTGGGC TAGTTCAGCT GCGTTCTGGG
67701  TCTCTGTCTT GCCTCCTCCT TCAGACTAAG CCTCCCAAGG GTTGCCAAGC
67751  CTCTTTCCTC TATTCTCCTC ACCCTGATCC AGCTCAGCCT CATTGAGAGA
67801  AGTCTGGGGC TGCAAGATCT TCGCACTCAC AGGCAGTTCC TCTTTGCACA
67851  TCCAAGGCAC CAGTGTCTTT GAGAGGCGTC TCCTTGGCCA GGTGGCAGGC
67901  GTGGGTGTGT GGGGAGGAAG GAGGAGGAAC CGCCTTGTTC TGCTTTCTTG
67951  TCTCTGACTC TGCAGGCTGG GGGTGCTGTA AGGCTGCGAG GAGGCATAGA
68001  GTCAGCTTGG GTGCTGGGCT GAGGCCAGGG GCCGAGGCTC AGCTGAAGCG
68051  GGCTTCTCTG GTCTGAGCCT ACAGGATGCC TCCTTTGGGG CAGTTCTGCC
68101  AGTCACCCTG ACTGGGCGGC TGTGCTTGCT AGTGCCAGAC CCATGCTAGG
68151  CACAGAGGTC GATACGTTCT CCTGTGCTCT TGAAGGGCCC TGTCCTCTGG
68201  GAAGATAAGA GGCTGTGTAT ATTGCCCACC GGAACAGGAG GCAGGAAGCA
68251  AAAGAGGCGT AGATGACACT TGCCTGGCAC CCCCTGTTTC CCCTCTAGCT
68301  GCCTTCCTGG GTTTCCCATT CTGTGGGCGC TTCTGTTGAG TTAGGTGCTT
68351  TCTCCCAGTG TTCTCAAGGT GACTATTTGG AGGTTTGTGG GAGGAGTGGG
68401  CTGGAGACAC AGGAGTAGGT GGGGGCAGGA AGTATGCAGG AGAGAGATGG
68451  AGAGTGGGAG GAGAAGCTAT GAGAGGAAGA GAGGACGCGG AGGTGGGAAA
68501  AGACGTCAAG ACTCCTGGAG AGGAACAGGA GTGCAGCCTG GGACAGAGGT
68551  GGACGTCGGC CGGGGGAGGC AGGGAGGAAG GCAGGGAGGT CCACCCGAAA
68601  GGAAGGGAAG GGATGATGGA CAGAGAATGA GAGGGCTCCG AGGTCCTGGG
68651  GGATCTAGAA GGACCCTTCC CTTTACAGAA GGGGACACCA AGGCCCAGAG
68701  AGAGAGGAGG GCCTCACAGA GGACCTAACA CAAGCAGAGT TGCATGAATC
68751  AGTGTGAACG GACAGTCCCA AGAGCACAGC CGGACCTTGG GAGGTACTTG
68801  ACTCTTGAGT TTGATGTTAT TGCCTTCCTG TAGGCCAGTG TGAGGGGCAC
68851  TGTGAGGCTT CCTTCCAGAG AAGGAGGCAT GGAGCCAGTG CCAGGCAGTG
68901  GGGTGAGCCA TAGGAGGACC TGTGGAGATG GGGAAAGGCA TAGAGACTCA
68951  TGAAGATGAA ACAGGAAAGA TCTTATGGCA GCGACCCCAA CCCTCAGGAA
69001  GGGCGTTGGT CTTGTGCTTG TGGCTCCAAA GGGGATAAGA CCAAGGTCTC
69051  TGGTTTCATA GAATCTTAGG CTTTAAGAAC GAGTTAGAAG TAATTTAGTC
69101  CAGACCCTCT CCTCTCCCCA GATAAGTGCA GAAATGCAGA TCTAGCCCAC
69151  GGCTGAGCCC CAACCCTGGC TTCAGAGGAG GCCTGACTCA GAACAGGCTC
69201  CCCTTTCTTG GTACCTGGGG TGAATGAAAG ATAAGTCTGT GGTAATGGTG
69251  CTGTCTGTGG TGCTGACTGG CCTTACCTTG GACTACAGAG CTGCAGGTGG
69301  AGCTGGAGAG AGCAGAAAGG CTCCATCTAT CCATCTACCC ACCCACCCAG
69351  CCACCCATCT ACCTATCCAC CCACCATCCA CCCACCCATC CATCCACCAT
69401  CCCTCCCCCA ACCCATCCTG CACCCATTCA TCTATCCACC TACCCACTCA
69451  TCCATCCAGC CTCATTGAAT TAAACCATAG AACTATATGC TGCAGAGCTA
69501  GAAAGATCCA TTTTTTAGTA ATGACAAAAC TGAGGCTCAG AAGAGGAAAG
69551  GTGTTGCGTA AGGCCACACA GAACTTCTGT AGTCAGTCTG GTACAGGATT
```

FIGURE 3-24

```
69601  GGAAATTGCG GCTCTTTTCT ACACACCACA AGTTCTCCTC TGTGGTCTGG
69651  GAAATTGCCT GGTTTTTATG CTGATATCTA TACTGATATT TGTTCCAAAA
69701  AGCTGTGAAG GCAGGAAATG TGACCTCCTT CACCCCATCC CGAGCCTGAG
69751  TTCTGTGTGT GTGTGTGTGT GTGTGTGTGT GTGTGTGTGT GTATGTGATG
69801  TGCATGTCTA AGTGCAACCT TGTATATGCA TTGAATATAT GATTGCCTTT
69851  TGATCTGTCT GTGTGCGTGT TTGTGTGAGA GCCTGTGCAT ATACGTATGA
69901  GTAGAGGAGT GCGTAGCAAT ATGTATTTGT GTGGCATGTG TAGATGGGCA
69951  TGTGAGCAGG TAAAGCTGTG TCTGTATTTT TCCTTTCCTC TTCCTTTTAA
70001  GATCGAAGCC CCCTGACTTG AGCCTTGCTC CCCATCTGTG CCTCCAATTC
70051  AGGAATCTCC CTGCTTCCCA TTAGCAGCTG CTCCCCACTG ATTCTCTCCT
70101  TCCTTCACTG AAGCAGCAAC TCTTCCCTCT GAGCCCACAC CTCATGGGCT
70151  TTGCAATTTG AGCTATTTCC TCCCCTGAGT TGGTGCAATG GGGGTGAAGT
70201  TGCTTTGAGA TCTGAGGAAG ATTCATGGAG GAGATGGCAT TTGAGCAAGC
70251  CTTGAAGGCC CCTTTGAGTG CCAGATCTGA AGTGGCCCTT CCCAGCTGCA
70301  GTTCCTGCAC CCAACACCCT CCATTCCTGG GGCATGCTGG GCAGGACCAG
70351  GAGGTGGATT GACAGAAGGA TGCCCACAAA GAGCCCTGGG CTTCATCAGT
70401  CACATTACCA TCCAGTCCGC TCTAGCACAG ATGGGAAGCC CTTCCCTGCT
70451  GCTGCCCCAA CTCTCCCCAA CTTTCCTTTC CTGCTCTCCT TATTGCTACT
70501  ATCCTGCACT TGGCCTGAAA AGTCACAGAA AACTGAACAA TCAGAGCAAA
70551  GGTCAGGCAG GCACCCACCA ATTCCAGTAA AGGACAGTTG AGGGCATTCC
70601  CCAATTGAAG CAAAGGGCAG GTTGAGGAGT CCACCAATCA GAATAAAGGA
70651  CAGACTGTTC TTTCTGAGCA CCCTAGGGTG GGAGCTGGGG ATCGGGTGCT
70701  GAGCAGGAAC CAGACAGGGC TAGAGATCCA GAGGTTTGGG TTCTGGACCT
70751  GGCTCTGCTC TGACTGGCTG TCTGACCACA GGTTGATCAT TGCTTCTCAT
70801  TGAACCTCAG CTTCCTCATC GGTCAAATGG GGAGACTTAG CTCTCTGAAG
70851  GCTGTGGCTT TGAAGAATTT CTCCCCCTGT ATCAGGCTCA CTCCGTCACC
70901  TGGGTCTCTC TTCCCCAAGT CCACATCACA TACATCAGAC TCCACCAAGG
70951  GCAGGGCCTC TCAGGAGTCA GCTTGTGGGC TCCTCTGCCT CCAAGAAGGA
71001  ATAGACACAA ACCAACACCA CCTTCTGTGC TGTCTTTAGA GCCCCCGTCT
71051  GGGGAGCGTG CATCTGGAAG ACTTTATCTT GGGAGTACTG GGGGCATCAG
71101  CTCTTCCTCC CCTTTTTAGT CTTCAGAATT GACCTTGGAA GGCCATAATA
71151  GCCTGCGTGT ATTGTGCACA GGTATCACTC GAGCTCTTGC CCTGTGAATC
71201  TTTAAGGAAC TGTACCAGTG AGAACGTGTG TGTGTGTGCG CACATGGATG
71251  GTGTCTGAAG GCCTGCTGGG ATGTCTGCGA GGACGTGGGA TCTGTGGCTG
71301  TGTGGTGCTG AAGTTGTCTG TGCTGTGATG AGGAGTGCCT AAGGGTCAAA
71351  AGACAAGTGA TCCAATTTGG GTATTGTGTT GTCTGGAATC AGTAGCTTCT
71401  GATGTCTGAG GGTAGACATC TTCCCATGAC CAAGATATGT GTCTTCATCC
71451  TTGAGCAGTG GGAGGGACCA AGGAAGCCTG GGGGTTGGGG AAAGCGATGC
71501  TGAGTAAGCA TCTGGGGAGA AGGCCCACTA CTGCCCTCCT CCTGGGAACA
71551  CTGGATTGGG TGGGGAAGG GGAGGAAACT GCAGCCAAGA AGACCCAGGA
71601  GTGAAATTTG GAGCTGAAGC CTGGATGCAA GTCTTCATTG AGAGCCCAGC
71651  GTGGAACTTT CTGGCAAATA GGCATTCAGC CCACTCTTGT GCACCCTTGA
71701  GGATGGGAAG CTCACTTCCT CCCTCTCTCC TGGTGACCTG TGGCATGCCT
71751  TTGTAGCATG GCCCTACCTG GAAGAAGGTC CTTCAGCCCA CTAGACCAAG
71801  GCCAGCCTCC TGTGAAATCC TATGGGTCCC CAGGCTGTCC ATGGGGCCAC
71851  AGAGTTCAGA TCCCCATCT AGGAGGGTCT GAGAGATTGG AGTTGGAGAC
71901  TGATAACCCT GGGTCTCCTC TGCTTTAGAT GAGGCATCCC TGGGTTATCC
71951  AGTCTTAGTC ACATGCAAAA CTTGGTTTCC AATTCCCTCG TTTCATAGGT
72001  CGCCTCCTCT GGATGAGTGT CATCTTGTCA GCCCCTGGGA CACAATGAAC
72051  AGGGGATGGT CTAACTAGAC TATAAAAGTG GGGGAACTGT CATCTTCCCA
72101  ATTGGGTTAA CAGACCTCTA TTAATATGGC CTGCAGTTTG AGCATTTTTA
72151  TTTCTTGCCA GTCATGCTTA CACTGTGGGC TCATGCTGAA CTGTGGTCTT
72201  TTAAGACCCT CAACCTCATA TCATGTTCAC ATGAATGGGG ACCCAGCCAT
72251  GTCTCCTTCA TCTTGCAGTT AATCACTTTG CTTTCTGAAC ACAGACCCAA
72301  CCTTCCACTG GGAAGACATC TGAAAGGACT TCCAAGGGCT TGCGGGAGGG
72351  CATGGCTGGT GGCTGGTATG AGTCACGATC TTGCCTTGGC CCTCGTTTCC
72401  TTTGTTCTGT TACCTTTCTC TTTGATCCCC ATGGCTCTGG CCAAGTTAAT
72451  AGAGCGAGAA GCAGGGACTT TTGTCTCCGT TCCGGCTCTG CAAGGACGAG
```

FIGURE 3-25

```
72501  TTCTGTTCCT GGGATGGGAA GGCTGTGAGA CAGTCAAGGC TGACGTCTCC
72551  TTCTCCTCCT ATAGTTGCCA GGGGTGGCCC AGCTGTTCTC CCACCTTATG
72601  GGTTATGCAC CCCATAGGCT CTTGCTACTC TCAACCCAGC CCCTCACTAG
72651  GCTGGAAAAT GAGACTAGGT GAGACCACCT TCCTTCTGGG GAAAGTGAGC
72701  GGGACCCAGC TTCAGCGAAT ATTCAGCTGA GCATCTACTC TGTGTTGGGC
72751  ATTCTGTGAG GCACTTTTAG GACTCTGATT TTTATTTTCA TTTTTAAGGG
72801  CTCAATTTCA TTTTATCTTC ATGTCAGCCT GTAGGGGGCA ATAGCCCCAG
72851  CTGCTTCCAA CTTACAGATA GGAGACTGAG GCTCAGTGAC TGAACCAAGA
72901  CACTCACTGC TCATACACAG CGGAGCTAGG ATTCAAATTT GGGTGTTTTT
72951  TTGTTTGCTT GTTTTGTTTT AATTTGGAGC CTTGTGGTTT CCCTACTGTG
73001  CCAGAATTGT CCTCGACTAG AGAACAAGAG ACCTGGGGTC TAGGCCAGGC
73051  TTGACCTGTT GACTCACTAT GAGGCCTTTG CTAAGTCCCT GGCCCTTCTC
73101  TGCGCCTCAG TTTCCCCACC TGTAAGATGA GGGTACTTGG ACATTCTGTG
73151  GCCTTAAGAC TGTTTGATTT TGAGATCCTA AGATCCTGGG ATTCCTGTGC
73201  CTGAAAGACT CGGGCTCTGG ACTAAGCTGG GGGGTTTTGC TCACAGTCCT
73251  TTGGGCAGAT GGGGCTGCCC TGGCCTGCCT GGCAAAGCCT CTCACTGCCC
73301  TCTCCTCTCT TCCAGGACGC CTTGCTGAGT CTGGGCTCTG TCATCGACAT
73351  TTCAGGCCTG CAACGTGCTG TCAAGGAGGC CCTGTCAGCT GTGCTCCCCC
73401  GAGTGGTAGG TGCCCGCCCT TGCCCCACGC TTCCCACCCC ACCCCCAAAT
73451  CCTTTGACCA GCTCTATGCT GTACCTCACT CAGGGCCAAG GAGGAAGGAA
73501  GAGGCAGGGT CCCTGCCCAG AGGACTTTCA TGGGGAAGTG AAGGGTCTGG
73551  ATGGGTGTTC TGAGACAGCT TTCTGGAGGA GGAAGCCTTA GGCTAAGCAT
73601  CAAGGAATGA ACTTGCATAG GAATCCTGCA ATGGCTGAGC CAGAAGGGGC
73651  CTTAGAGGTT AAGTGGAAAA GCTGTGTCTC AGATAATGAA AGGGATTCAC
73701  CTAGGATAAC AGGACGTGGT GGAGCCAGCT GAGTTTTGGA ATACATGCAG
73751  CAGGAGAAGT TGAGGGTAGA CATGTAGAAG AACTTCCTGG AAGCCAGGTC
73801  TGGGAGGTAC TAGAATAGGG CTCAGCTTTG ATGAATAGAC ATGCATTGGG
73851  TTAAAGTGCC CTGCCTGGAG ATGGGAGGCT GGAAAAATGG CCTCTAGCAG
73901  CCTTTTAGCA GCTTTCTTTC TGTCCCATCC CAATACCATG GATGAGTTGC
73951  AGGTTTGGGG CAGGTTTGGG GTGATCATGG TTGCCTGAGC CAGAGTGCC
74001  TTACTGGGGA GATTGTGCCC CTCATCATCT GTTCCAGGCC ACTCCCCTAC
74051  CTGGCTTCAA TGGCCACTGT TCATCCCTTA GGCAGGAGGA TGGGTAAACC
74101  AGCCCTTGAG GCCCAAAGTA GCAGGGTGTT AGTTGCACCA GAAAGAGGGA
74151  AGCAGGGGAC GTTTGAAGCC TGGAGAAGGG AGTCTGATCC AGCCTAAGGG
74201  GCATGGAAGA CTTCCTGGAG GAGGAGATTC CCTAACTGAG TCCTGATAGC
74251  CTTGAATGTC CTCTTCCCTA CTCTAAACCC GGCCAAGGGC AGCCTCTGCT
74301  CCAGGAAATA TGGCCAACTC AGAATGTGAC CTTCCCATCC CTCCAGAGCC
74351  CATTGTCCCT GAATCTGCTT GATGGATGAA CCACCGGAGG CCCAGAGAGA
74401  GAGGGCACTT GTCCCAAGGT CACACAGCAT GACAGGGATA AATGGGACTT
74451  GGTATCTAAG CAGCCCCATT CCCTCTCTTC AGCTCTGCCT TCCCCAAACC
74501  TCCTAGAAGT TCAGAGCCCA GGAGGAGGGC TAATGAGTGA GCTTTATTGA
74551  GTGTGAAATT GGTAGGAAGT GGGTGGTGTG TTGGCGCCCA AAAATAAATC
74601  CTCCTGGAGA AGGACGGGAC TAAGGCAACA TCTGGCCTGG GGTGAAGGCA
74651  CATCTGGAAA GGGAGGGTGG TGGAAACTGG CAGGTCGGTT TCTGTAGGGC
74701  TGCCCCGAGA GCCTCTGTGG CCACTGAGGC TGCCGTAGGG TGGGAGGAGG
74751  AAGTGACTGG CTCTGTTTCA CAGGCAGGGT GCCCTGGCGG CTGTGCCAGC
74801  CTAGATGCTC TGCAACAGAT TAATTGTCTC CCCAAAGCTG GGGGCTGGGA
74851  TGACAGCTGT GGTCCAGGTT CCTGGGACAG TGGGAAATGT CAGCCCTGGC
74901  CCACCCAAGA GCCCTATAGG AGCTAGGGAA GCCCTGACTT TCGGGAGTCC
74951  TGGCTTGATT GCACGGAGGG GCTCAGCCCC CAGTGAGGTA AGGGAGCTGA
75001  GGTCTGCTCT GCTGCCCCCA GGGAGGGAAG CAGAGATGGG GAGGGGACCC
75051  CCGCCCAGGG AGGAGAGCTG CTGGCACCTG GCTTCCTCAT CAGCACCCAT
75101  TGTGGCAGGC AGCCCCGAAT GCAGATGGTG CTGATGTGTC TGAAATGGTT
75151  CCCTCCTTCT CTCCAATAGA CTCAGCTAAT TTTAACCCAG AGGGCTGAGA
75201  GTAAGGGGGT GGGAGACATA CGGACATGCG GAAGTGAAGC GAGAATCTGT
75251  CCCCCTCTGC CCCCATGGAC TACCCACCCC TCCCTCTGCC TGGGCAGGAC
75301  TTTCTGTATA ACCCCGGCTG GTCTCTTAAC CTCTTTGGGC CAAATAACTC
75351  AGGCCCCTCC CAGGCTGCTG GAAGAGATGG ATGACAAGGA GGCTAGATAT
```

FIGURE 3-26

```
75401  AGCCGAAGAG TGGGCGGCCT CCTTCCCACT GAATTCTTTA TCCCTGAACA
75451  TCCCACTTAG GTTTCCTTCC AGCCAAACAA GAGGGTGTCT GCCCCTCTCA
75501  CTCCCTTCAG GCCTTATCAT TCCCACCCCA TGCCACACCC ACCACGGAAC
75551  CTGGCTCAGT GTCTCTGGAA GTAGTGGCCA GGCATCTCCT GTGGTGGGGG
75601  CTGGCTGGCG ACAGCTGATG ACAAGAAGAG TGGCTGGCAG GATTGTGGAC
75651  GCTCTCAGAG TCATGGAAGG CAACTGCTTC TTCTGGGAAG GATTCCACAC
75701  TTACTGAGGG TGGGCCTTCA ACACGTAGCT CCACTGTCAG CTCCTCCCAA
75751  AGCCCTCCAG GATACCCTCA GCTGGGAGGC AAGCCCTTCT CCATCCTCCT
75801  GCGGAGAAAA CAGCAGAGTT GTGGACAAGG CTGCGTTGCA TGGGGGTTGG
75851  TCAGGGATCC CGAAGGGTTG CCAGTTCTGC TTGAAGGAA TGTGGATTTT
75901  TGCCTGTAGG TCAGTGAGGG CAACTACTTC TGCCAAGACA TGGCCTGGAA
75951  CTGAGGCCAG AGCTGCTCTG GGCCCTTGGG GAGGGAGGAT TAAAGAGCAA
76001  GAGCTTTGAT CTCCCTCTGA GGAGTAATCG GTCCAAAATA CAAATCTGCT
76051  CACGTCTCCC TGTGCACGTC CTGCCCTGCC CCAGTTCTGT TCGTAAGCCC
76101  ATCCCACTCA GCCCTACTGA CCTTGGGCCC AGCCCCTGTG CCCCTTCCCT
76151  CACTGTCTGT TCCTAAATGC TCCATGCTTT ATACGCCTCT GGACCTACCT
76201  GTGTACCTGC TATAAGGCCT GGGAGCCCAT TCTGCACCCT GCCCACTCCC
76251  TGAATGTGTC TAATTCCCAC TCAGTGACAG CTGAAAGGTC ACTTCCTCCA
76301  GGAAGCCCTC TCCAGCCCCA CCGGAGGATG GCGCAGTGCC CTGCTCTGTG
76351  TTCCTCCCCT GGCTGGGGTT ATGGGTGTGT GGTTTCTTGT AGAGGTGAAG
76401  GAGGGATGCT TCCTAGAACA TTCTGAGCCC CATCCCTGGT ACAGCTCAGA
76451  GTGGATGCTC AGTTATTGTT TGCTGAATGC CTGAGGCTGG AGTCAGGCAG
76501  GGAAATATCC CAGGTGGGAG GTGATTTGTC TGCACCCTCA GTCCTTGAAA
76551  CTCTTTACCT GGCACATTGG GTTTTGGGTG GTAAAAAAGG TCATAGGTTC
76601  ATGAATCATT GCCTGCTTAG AATTCCTTCC AAGAGGAGAG GACGAGGTGC
76651  TTAGTTCACC GGGTGTTTTG CTGCCCTGGC TGCATCTTAG AATCACCTGG
76701  AGAGAAAAAC AAACAGATCA TTGCCAGAGC TCCACTCCCA CAGGTTCCAT
76751  GACCTTGCCC CACAGACCCC TGTGTACAGG CTGGGACTGG GCAGCTGGGA
76801  GGGCCTCTCC ACAGGGTCTC ATAAGTGCCT TCTGTCCTAG GAAACTGTCT
76851  ACACCTACCT ACTGGATGGT GAGTCCCAGC TGGTGTGTGA GGACCCCCCA
76901  CATGAGCTGC CCCAGGAGGG GAAAGTCCGG TGAGCCATTC TCTGCACCCC
76951  CATTGCCCTC TTGCATGGCC AAGGATTCTC AGGGCTGAGG CACCATCCAA
77001  GGTCATCTGG TCTGACCCTC CCCTTCCAAC ATTGATCCCC GCCTCCCTGC
77051  CAGGTGGGAT TCCTTGGCCA GGTTGCTGAC TCCAGCACAG AAGGGCAGAA
77101  GCAATGTCTT CTCTTCCTTG GGGAAATGGA TAGGCACAGA GAAAATACCA
77151  ATTGATGGTA AATTTTCTCC TTCTAATTGC TTCTAAATGG CTGCAGCCTC
77201  CTCAGAGCAG AGTCTCAGAA CATTGGGGCT ATGGGGTGTA TCAGTTAGAA
77251  CACCGGCATG CTGTGAGAAC TACTGCGAGG CTGGACCTGG AATCCCAGCA
77301  TGCTGGGCCT GCAGGAGCTC ACAGTGCCAA CTCCTTGCAT CTGAGAACAG
77351  GGAGATCACA GGCAGCGTCC TGCTGAGGGT TCTGGAGCCC CACTGCCTGG
77401  GTTCAAATCT CAGCTCCCTG TTTACTAGCT GTGTAACCTT GGGCAAATGA
77451  CACAACCTCT CTGTGCCTCA GTTTTGTTTA TGAAATGGTG ATAATAATGG
77501  TGCTTATAGG ATTGTGGGGA GGATTAAATG TGTCACACAT GTAAAGCATT
77551  TAAATCAGGC CTGATCCATG GTGAGGGCTG TCTGTTGGGG ATTACCATTG
77601  TGAGAGAATG CTGGAATCAC TGACTTCAGG ATCATGGGAT CAGGGCACTT
77651  GGCCCCCTGA TACCTTGATG CCCATTTAAT TCAGCCTCCT CATCTTCCAG
77701  ATGGGTGGAT ATCATGAGAC ATGACCAAGG CCACATGCCA GGTATGAGGC
77751  AGAGCCAGGC CTAGGACTCG GGTCTTCTGA CTCCTGGCTG TTTAGGGGAA
77801  AGTGAGAGGA AGTGGAACTC ATCAGATGAG AAAACCTTGG GGGCAGGCAT
77851  GCTGCTGGGA GGAGGCAGGC TCTGAAGGAT GTGGCCATTG CCTGCTAAGC
77901  ACTGAATGCA GGGCCATTGT GGGGCCCAGG GAGCACTGGG CAGGAGCTGA
77951  GGGCAGAGTG GGCACCAGTG GGGATGTCCC AAGAAGGCAG CTCTCTACCC
78001  CTGTGAGGAG GGCTTTTCCA GCAGGCCAGG TGGTCCAGGG ATGTGGCTTT
78051  TTCAGGTAGC AGCTGAGCCT GGCAAGCCAC TCACCTTTCA CAGGGACCAT
78101  GGAAAGAATT CCTGTTTGAG GATGCTGGAC TCATGGTCCT GAGGCCCCTC
78151  CTTGTGCTGG AAACCCTGGT TTCTAGGATG CTGGTCTCTC CTCAGCCCTT
78201  TCCCGTGGAA GGAGTTGGTT CTGCTCTGAT AGCCACCTTC CCATTTCCTA
78251  TTCTCCCACT GAGCTCCTTT CACCTTCCCC TAACAACTTC TCCGTCAAGG
```

FIGURE 3-27

```
78301  AGCATGGGAA CAAAGCCATT ACCACCTCTC TCTAGCCTTT GTGTCCCGTC
78351  TGTAAGAGGA TGGTCTGAAA GGTCTTTAGA ACCTTAAGGG GAAAAATGTG
78401  GTCATGTCCC CCTTTCTCCT CTAATTCCAA AGAACTTCGC TCTCCTCCAG
78451  CATCCCCCAC CTCTAATTCT AAAGAACTTT GCTTCATATA AGCTCCACTC
78501  CTCCAGGAAG GCTCCTCGGA GCAGCCTGGG AGGCCTTCCT GGGAGGGATG
78551  CAGGAAAACA GGCTCAGGAG GCAGCGGGGA GCAGCCTGCA GGTTTGCTTC
78601  ACTCCCTAGG ACCCACACAT GCTCCCCTCA GCTGTCTGGG CATGTAGAGT
78651  GGGTGCGTAT CTGCGGTCCA GGCATTTTTG AGAGGGCTCA GATCCTTGGC
78701  ATCAGCTGCC CTTTCAACAT CCTCCTTCCA ACCACTTCAG ACTCAGTAAG
78751  GCCTTTGGAA AAAATACCAA AAAAAAAGCA ATTAAAAGTG AATATTCAAA
78801  TCCAATTATC CCAGAGCTCA GTGGAGATGG GGAGGTGAGT GCCTGCTGGT
78851  AGACAGGGGC TGAAGATTCC AGGAGGAGGG CCAGGGGATG AGAAGGCAAG
78901  AGAGTGAGGA CAGCAAGGAC CTCCCAGGGG ACATACCCAT CATCAGGACA
78951  CACCCGTCAT CATCCCCAAA CAGGAATTCT TTCCATGGCC CCTGTGAAAG
79001  GTGAGTGGCT TGCCAGGCTC AGCTGCTACC TGAAAAAGGA TTGGGGGAAG
79051  GCCCAGGCCC AGTGCTCTCT CTGGTATCTG AGCTCTGCTT GCCCACCTTT
79101  GTGCCTGGTG TCTGGTGGTG AGCCCATCTC CACAATTAGG GCGGAGAGGC
79151  CCCAGGGTTG GCTGGGCCCT GCTCTCAGGA GCTCCCAGCA GGATGGGGAC
79201  TTGAGACCCA GGTGTATGGA CGAGGGAAGA GCACTGGAAT GGGATTCAGA
79251  CAGGTCTGGA TTCTAGCTCA GCCCCCTCCC TGTCTCTCTG CTTTCCTACC
79301  TGAGGCCCGG TCTATTGGCT TAATGGGGTA ACAGGGGCCA AGTGCTTGGC
79351  ACAGTGCCCA GCACACAGTA GGAGCTCAGT GATTGCTACT TGCACTCCCA
79401  AGTCCCAACC AATGATTAGC CTTGAGTGAC CTTGAGAAAA CGACTTCTCT
79451  TCTGGCCTTT TTTCTGTGAA ATGGGTGGGG TTGGGTACAG GGTCCTTCCG
79501  ATGGTGACCT TTGTGGCTCT GGTCCCCCCA GGAGGGAGAG GGACTGACCT
79551  ACAGGCTGCC GTGGAGCCTG AGGCTCTAGC AGTGCCCGAG GAGGTGGGGG
79601  TGTGGGGAGG GTGCTACTCC AGGAAACCCT GGACTGTGGG CAAACAGCAG
79651  CAGGTGTGGC GTGGAGGCTG GATCATAGAG ACAGATAAGG AGGCCCGAGG
79701  CAATGGGCAG GGAATGGGAT CAGGGCAGTG TGGGGAGAGA CAGGGTGGAA
79751  AAGGGTCAAG GCGGGAGTGA GGAGGCCCCC GCCAGCTCCC AGCCCCACCT
79801  GTCCCTGTTC CTGCCGCTGT TTGGGCTCTC AGATGCCCAG CTGCATCCCC
79851  CCAGTGTGTT TGGCTTTCCT GTCTTCTTGT GCTTGTAAGG GCTGCTTGCT
79901  CCCTTGCAAA GACCGTCCCT GCTCCACTTT CATCTCAGCC AATCCCATTG
79951  TAATTATCTT TCATGGCCTG ACCAGAAGCT GTCTTGGGGA AGCCTGCTCC
80001  ACAGTTCCCT GACACTGAGA AGGAACCAAG TTTCAGAAAA GGGGTCTGGG
80051  CCATATTGGC CTCCCTTAGG GTTCTTCCAC AGGAAGAACC TTGGGCTGGG
80101  AGTCAGAGAC CTGGGATCCA GGACAACATG GCTGCAATCA CAATCCGATG
80151  CCCTCTTCCT GGGCCTCCAT ATGCCCTTCT GTAAAATGAT ACGCTGAACA
80201  TTCTGATATT GAGGGCTGGT GAGGCTCTGA ATTGTAAGGG CTGCAAACGA
80251  CCTTGGGGCT GGAGAGGAGA GAATCCTGGA AGGCTGCCTG GGCCAGGGTC
80301  TTCCTGAAAG GAGGCTTCAC TTCCCTCTTG TTGGTGCCCC ACCTCCATCT
80351  CCCAGACTGT TTCAGGCCCC AGCTCTGCCG CCTTCCTCTT CTTGTGTCTC
80401  CTGCTATCTT AAAGCCTCTG ATTACCTGAT GCTGAGTGCA GCAAAAATCT
80451  CAGGCCTTTC AGCTGCAACT GAAGCACCCA CCGCCCACCT CGGCCCAGGC
80501  TGGCTGTCTC CCTCTGCTAC CATTTTGGGG TCCCCAGGGC CCATCCCTAA
80551  GAAATTTCTT CCCCTAAGCT GACCAGGTCT TCTTTCATTG CAGAATCTGA
80601  CCATCCCTAG GGGTTGTCTC AGAGGACACC GGGAACGGTC TGCTCCCATC
80651  TCGGGATCCT CACATGCTGG GGGAAGGAGG GCAAGAAGAG GGTCCAGGTC
80701  CTGGGGCTC AGTGAGAGTG GGGGCTTAG TGAGGGGATG GGGGCCCAGT
80751  GACAGTGGGC AGCCTCAGTG AGGTGATGGG GGCCCAGTGA GGATATGAGG
80801  GCTCAGTGAG AGTGGGGTGG CCCAGTGAGG GGATTGGGGC ACAGTGAGAG
80851  TGAGGGCTC TGTGAGGGGG TAGGGACTTA AGTGAGGGGA TGGAGGCTGA
80901  GTGAGTGTGT GGGGGCTCAT TGAGAGGGTG GGGGCTAAGT GGGGAATGGG
80951  GGCTCAGTGA GGGGATGGAG GCTCAGTGAG AGGATGAGGG CTCAGTGAGG
81001  GGATGGGGGC TCGGTGAGGG GATGGGGGTT CAATGAGGGG ATGGGGGCTG
81051  AGTGAGGGGA TGGGGCTGA GTGAGGGGAT GGGGGCTGAG TGAGAGGATG
81101  GGGCTGAGT GAGGGGATGG GGCTCAATGA GAGGATGAGG GCTAGGTGAG
81151  AGGATGAGGG TTCAGTGAGG GGATGGGGCT CAGTGAGGGG ATAGGGGCTC
```

FIGURE 3-28

```
81201  AGTGAGAGGT TGGGGGCTCA GAGAGGGGAT GGGGACTCAG TGGGGGATGA
81251  GGGCTCAATA AGGGGATGGG GGCTGAGTGA GAGGATGGGG GCTGAGTGAG
81301  GGGATGGGGG CTGAGTGAGA AGATGGGGGC TGAGTGAGAG GATGGGGGCT
81351  GAGTGAGGGG ATGGGGGCTC AGTGGGGGAT GAGGGTTCAG TGAGAGGATG
81401  GGGGCTCACT CGAGGGGATG GGGGCTCAGT GAGGGGATGG GGGCTCAGTG
81451  AGAAGTTGGG GGCTCAGTGA GGGGATGGGG GCTCAGTGAG AGGAAGAGGG
81501  CTAAGTAAGA GGATGAGGGC TCAATGAGGG GATGGGGGCT GAGTGAGGGG
81551  ATGGGGCTCA GTGAGAGGAT GAGGGCTAGG TGAGAGGATG AGGGTTTGGT
81601  GATGGGATGG GGGTTAGTGA GGGGATAGGG GTTCAGTGAG AGGATGGGGG
81651  CTCAGTGAGG TGATGGGGGC TCAGTGGGGG ATTAGGGCTC AGTGAGAGGA
81701  TGGGGGCTCA GTGAGAGGAT GAGGGTTAGT GAGGGGATGG GGCTCAGTGA
81751  GAGGATGGGG GCTTAGTGAA ATGATGGGAG CTCAGTGAGA GGATGGGGGC
81801  TCAGTGAGGG GATGAGGCCG AGTGAGAGGT TGCGGCTCAG TGAGGGGATG
81851  GGGACTTAGT GAGAGGATAG GGGCTCAGTG AGGGAATGGG GGCTCAGTGA
81901  GAAGGTGGGG GCTCAGTGCG GGATTGGGTC TCAGTGAGAA GGTGGGGGCT
81951  CAGTGAGAGG GTGAGGGCTT AGTGAGGGTA TTCGGGCTCA GTGAGGGGAT
82001  GGGGGCTCAG TGAGGATG GGGGCTTGGT GAGGAGATGG GGGCTCAGTG
82051  GGGGATGGGG GCTGAGTGAG GGGATGGGGG CTCAGTGAGA GGATGAGACC
82101  TCGGTGAGGG GATGGGGGCT CAGTGGGGGA TGAGGGCTAA GTGGTAGATG
82151  GGGGCTGAGT GGGGGGATGG GGGCTCAGTG ACAGGGTGGG GCTCAGTGAG
82201  AGGATGGGGG CTCAGTGAGG TGATGGGGCT CAGTGAGAGG GTGAGGGCTT
82251  AGTGAGGGGA TTGGGTCTCA GTGAGGGGAT GGGGGCTCAG TGGGGGATGG
82301  GGGCTCAGTG GTAGATAGGG GCTGAGTGGG GGGATGGGGG CTCAGTGAGA
82351  GGGTGAGGGC CTGGCGAAGG GATTGGGGCT CAGTGAGGGG GTGGGGAGTC
82401  AGCGGGGGAT AGGAGCTCAG TGGGGGATGG AGGGTCAGTG GGGGATGGGG
82451  GCTGAGTGGT AGATGGGGGC TGAGTGGGGG GATGGAGGCT CAGTGAGAGG
82501  ATGGGGGCTC AGTGAGGGGA TGGGGCTCAG TGAAAGGGTG AGGGCTTAGT
82551  GAGGGGATTG GGGCTCAGTG GTAGATGGGG GCTCAATTGG GGGATGGGGG
82601  CTCAGTGAGG GGGTGGAGAC TTAGTGAGAG TCGGGGGGCT CAGTGAGGGT
82651  GGGGGTTCCC CTGGGGGGAT GGGGTTCCGT GGGAGGATGG GCTCAGCAAC
82701  AGGCTTGGCT GCTTAATGAT GCCTGGGACC TAGTGGGTGT TGGAGGGGGG
82751  CTTCTCCAAA GTAGAGAACG CGAGAAGGAC ACACACAGGG GCTCAGAGAA
82801  GTGCAGGGGA CCCAGCTCTT TCCAGGCTGT TGGCCCTACC AGCAGAGAAC
82851  CTTTCCCTCG ATTCTTTTTC CATTAAACAA ATAGTTGTTA AAGGGACGGA
82901  ACTGCCATAA AGTCCACGCC TGTTCCTCTC TCCACTCTGT GCCCATCTGT
82951  CCTTATCTTC AGTGGGGCAG GCCATGACCA CCCAGGCACC CAGTGCTGTC
83001  ATTAGCCTTC GCCTGGGCAG CTGGCCCTGG GTTGTGGAGT TCCCCACAAC
83051  CCCCAGCATG AGCCTGGAAG GCAGGGTGGG GGTGGGGTAG TAGTAAGGGA
83101  GGAACTGGAG AGGAGCAGGG AGCGGCTCTG AGTTGAGCAA GGAGCTATCG
83151  GGGGTCTGAG CAGTGGACGA AGCTCCCGCT CCCATGTGGG TGGGGGAGAC
83201  TCAGCCTTGG CACATTCCCC CTCGCAGTCT GTGGGCATCT TTGGAGACTT
83251  CAGGAGGACA GCAGTTCTGG GAGGGCTATG GCAGAGGAAA GGGGCTCCCA
83301  TGGGGGTAGG TTGAGGTGAG TGTGGGCTAT GGGGTCCCGC AAAGCCGGGG
83351  GAGGGCAGGC TGCAGAGCAA GGTGCCGAGG CTGCCTAAGA ATTGAGGGTC
83401  CTTGGAAGCC CCAGTGCTTG GGGGCATCTC GGCTTATCAA GATTGGTCTA
83451  TCCCAGCTCA GCCTCTGTCT TGTCCAGGGC CACTAAGATG ATAGGACCCT
83501  CACTGAGACC AGGTTTCCAG TGTCACAGTC TCCTTATGTG GAGAGTTTTA
83551  CCCAGGCAGC ATGATCGTTC TGAAATCATA CCTGACCATT ACCGTCCCTG
83601  CTCAAATCCC TCCCAGGGCA CCCCCTGCCC TCAGGCTCAA GCCCAGCTCC
83651  ATAGGGCCCT GGCCCCTGTC TAGCCTTGCT CTCGGCTGTC CAGTCACACC
83701  AACCTCCTTG TGGCCATACC TTTCAGCAGG CACACAATCT TCTCGCCTCC
83751  AAGCCTTCAC AATTGCAATT CCCTGGACAT CCTTTCCTGT CTGCCTCGAT
83801  AACCTCTGCC TGTCCTTTAG GACTCAACTC AGGTGTCTCC CTCTACAGGA
83851  AGCCTTCTCT GACTCCATCA CACCCTGCAC CTGAGTGGGC TGGGGCCTGC
83901  TCTTCCTGCC TTTGGCAGAG CTCTCATCTC CCGACTGAAG CGTGGGTCTG
83951  TACGTTGATC TCTGCGTGTT CTTGGCCTCC TCAAGTGAGG CATATGTCTG
84001  ACCCCTCTGC TCATCTCAGC CCTCAGCACT GAACCTGACC CAGAAGGACC
84051  CAGTGAAATG AGAGACTTTA AGTAGAATGC TCCCCGAGGT TTTTCATCTA
```

FIGURE 3-29

```
84101  GAACACTTAT TCTTGCTCTG CCATGGAGAA TGGATTGAAG AGACCCAGCT
84151  AGGAGGCTAG AGGCTTGGGG AGAGGCTGCT TCAGGGTTCA GGGAAAAGGT
84201  GTCTCCATGT GAGCTGGGCA GTGGCTTGGG CATAGAGAGC AGAGGACAGT
84251  TGTGAGAGAC AACTGGGAGG TGACTCACTG ATCGGATGGG GGAGGTGAGG
84301  AAAGAAGGCA GGTTTTTGGA CAAGCCGTGA AGGACCTGGT GGATGGTTGT
84351  GCTGCTTTGT TGTGAGGTGG AGGGAGTGGA GATAATAATT CAGATGGTAT
84401  GGGGGTCCCT GGGCCACCTC AGGGACGTGG TGGGGAGGCT CCAGGTGGCC
84451  TTTGGGTATC TGGGGTCTGG AGCTCATGAG TGAGGGCTGG AGAGTCATGA
84501  GGCCGTGAGC ACAGAGGAGG GGTTTTGTGC AAAAGAGAAG AAAGGCTGAG
84551  GACAGATTCC TTCATCAGGG TCCTGGGAAA GAGAGGCCAA GCAGCTCCAG
84601  TCCAGGGGTG GGAGGGGAAA TAGTTGGGAG TCGGCAGGAT GAGGCTGCAG
84651  TGCGCACTGA CCAGCAACGC AAGGACCAGT GCCACCTTGT GGCCTCCGGT
84701  TAACCAGATT GTCTGAGGCC AAGGAGCTGG GCAGGGTTTG GCCAGGGGTC
84751  ACCCCCTGCC TCCGTGAAGC CTCAGCCTTC ATCAGTTTAA TCATCAGGAA
84801  ACGTGGCTCC CGTTGCCCTC CTGCCACCCT ACGTCCCTCT CCTTCCCGGG
84851  GTGACTGGCA ATGTGGACAG CCGGGAACTG GAGCCCAGCA CTTCAGGAAC
84901  CTTAAAGGTC CTGGGTGTAG GGGCTGGAAG GTGGGAGACA CCACCGGTTC
84951  CTGTAGATCC TGGATTACTT AAAGTGGCCA GGAAGGAATG GGTTTGGTTC
85001  AGAATGCTGC GTGAGCTTGA ACGAGATGCT CAACCTCTTT GGTCCTCGAT
85051  TTGTCTAGAG TCTCTGACCT AGTGATCTCG TGACTTGCAG GCCACCCCCT
85101  CCTTTTCCTC ATGTGACCTT TGCTGGGCTT CCCTTAGTGA CCCTGTATGC
85151  ACACAGTTCC CCAAGTTTCT CTTCTGTCCA GGCCAGGCAG TTCCTACAAG
85201  CACAATTAAG TGGAGGCAGC ATGAGGGATG AAGAACCCAG GACAATTAAT
85251  CATCAAGGAG TGACATTTGG TGCAAACNTC AGGTGCTTAA TTAAGCGGGA
85301  TGAGCCAGAG GCTGGGGGGT AGAGGAGGTG GGTTGTGTGG TGGGACAGAG
85351  AGAAACTCAT TCTTCCCATA CCAACCTCCC CTGCCTTGGT TCCCACCACC
85401  CCTCTGCCAC TGTCATACCC TGCCACTCAC ACCTGCCCCC TGTTCAAAGC
85451  TCACACCTCC ACAGGTATTT GGGAAGGTTC CAGCATAGTG GTTAGACCTA
85501  GCCCTGGTGC CACCTACCTG GGTTCAAATC CTGGCTCTAC CGCTTATTCA
85551  CTGTGTAACC CTGGGCAAGT GAATTAGCCT CTTGGTGCCA TAGCTTCTCC
85601  ATCTGAAAAT GAAGATATCT AATTCATAGA ATTGCTGGGA ATTCTGAGTT
85651  CATCTATGTG AGTTGCTTGG GCTGTGCACG GGACATAGGA AATGGCCAAT
85701  AAACTTTAGT TATGATGATT ACCTCCTGTG CTTAGCACTA AAAGCTGATC
85751  AACAATTGTT TTCTGAGGAT GGTGACAGGG AGGGTTCTTC TCTCTCCACC
85801  CTAGTTCTCC TTGGGAAGAT CAGAGAGGTC AGGTCATGTG CCTAAGGTCA
85851  GATTGTAGCA GGCAGCCTAG CTTTGAGCCC CTGCATTCAC TTCCTCTGCT
85901  CTCCCACTGC CTGGAAGATC TGCACTGGGC CCCACCCGAG CCTTTACCAG
85951  CAAGGGGCAC CAGAGGCCAA ACTGTGGCTG CCTGTTTCTC CACATAGGGT
86001  CCAGGGTCCC CTACTTTTTT ACTTGTGCTG TCATCGTGTC CAACCTGAGG
86051  CAGGTCAGCT TGCCCAGATC CTTGCACATG TGCAGGGTCC AAACTGTCCT
86101  GTGTTCCCAG GCCAGGCCTC GTTCCTCCCT GAGTCGGGGG CTCTCAAGGT
86151  GGCATCATGT CCTCTTTTCA GGGAGGCTAT CATCTCCCAG AAGCGGCTGG
86201  GCTGCAATGG GCTGGGCTTC TCAGACCTGC CAGGGGAAGC CCTTGGCCAG
86251  GCTGGTGGCT CCACTGGCTC CTGATACCCA AGGTAAGGGC TAGGGGCTGG
86301  GCAGGGGCAG GGGCAGGGAG GGACTGTGGC CCCTGCACTC CAGGTCATGT
86351  GTGTCTTCTA TTCCTCTTCA TCTCTGGCTC CTTNNNNNNN NNNNNNNNNN
86401  NNNNNNNNNN NNNNNNNNNN NNNNNNNNNN NNNNNNNNNN NNNNNNNNNN
86451  NNNNNNNNNN NNNNNNNNNN NNNNNNNNNN NNNNNNNNNN NNNNNNNNNN
86501  NNNNNNNNNN NNNNNNNNNN NNNNNNNNNN NNNNNNNNNN NNNNNNNNNN
86551  NNNNNNNNNN NNNNNNNNNN NNNNNNNNNN NNNNNNNNNN NNNNNNNNNN
86601  NNNNNNNNNN NNNNNNNNNN NNNNNNNNNN NNNNNNNNNN NNNNNNNNNN
86651  NNNNNNNNNN NNNNNNNNNN NNNNNNNNNN NNNNNNNNNN NNNNNNNNNN
86701  NNNNNNNNNN NNNNNNNNNN NNNNNNNNNN NNNNNNNNNN NNNNNNNNNN
86751  NNNNNNNNNN NNNNNNNNNN NNNNNNNNNN NNNNNNNNNN NNNNNNNNNN
86801  NNNNNNNNNN NNNNNNNNNN NNNNNNNNNN NNNNNNNNNN NNNNNNNNNN
86851  NNNNNNNNNN NNNNNNNNNN NNNNNNNNNN NNNNNNNNNN NNNNNNNNNN
86901  NNNNNNNNNN NNNNNNNNNN NNNNNNNNNN NNNNNNNNNN NNNNNNNNNN
86951  NNNNNNNNNN NNNNNNNNNN NNNNNNNNNN NNNNNNNNNN NNNNNNNNNN
```

FIGURE 3-30

```
87001  NNNNNNNNNN NNNNNNNNNN NNNNNNNNNN NNNNNNNNNN NNNNNNNNNN
87051  NNNNNNNNNN NNNNNNNNNN NNNNNNNNNN NNNNNNNNNN NNNNNNNNNN
87101  NNNNNNNNNN NNNNNNNNNN NNNNNNNNNN NNNNNNNNNN NNNNNNNNNN
87151  NNNNNNNNNN NNNNNNNNNN NNNNNNNNNN NNNNNNNNNN NNNNNNNNNN
87201  NNNNNNNNNN NNNNNNNNNN NNNNNNNNNN NNNNNNNNNN NNNNNNNNNN
87251  NNNNNNNNNN NNNNNNNNNN NNNNNNNNNN NNNNNNNNNN NNNNNNNNNN
87301  NNNNNNNNNN NNNNNNNNNN NNNNNNNNNN NNNNNNNNNN NNNNNNNNNN
87351  NNNNNNNNNN NNNNNNNNNN NNNNNNNNNN NNNNNNNNNN NNNNNNNNNN
87401  NNNNNNNNNN NNNNNNNNNN NNNNNNNNNN NNNNNNNNNN NNNNNNNNNN
87451  NNNNNNNNNN NNNNNNNNNN NNNNNNNNNN NNNNNNNNNN NNNNNNNNNN
87501  NNNNNNNNNN NNNNNNNNNN NNNNNNNNNN NNNNNNNNNN NNNNNNNNNN
87551  NNNNNNNNNN NNNNNNNNNN NNNNNNNNNN NNNNNNNNNN NNNNNNNNNN
87601  NNNNNNNNNN NNNNNNNNNN NNNNNNNNNN NNNNNNNNNN NNNNNNNNNN
87651  NNNNNNNNNN NNNNNNNNNN NNNNNNNNNN NNNNNNNNNN NNNNNNNNNN
87701  NNNNNNNNNN NNNNNNNNNN NNNNNNNNNN NNNNNNNNNN NNNNNNNNNN
87751  NNNNNNNNNN NNNNNNNNNN NNNNNNNNNN NNNNNNNNNN NNNNNNNNNN
87801  NNNNNNNNNN NNNNNNNNNN NNNNNNNNNN NNNNNNNNNN NNNNNNNNNN
87851  NNNNNNNNNN NNNNNNNNNN NNNNNNNNNN NNNNNNNNNN NNNNNNTCTG
87901  CCCCACCTCG AATAGGTAGG ATGAAGCCAT TGCCCAGTC AGCAGCTTTC
87951  TGAGGGGTGT GCAAGCCCCT GCTGGACTCT CAGCCCCCAT AAGGTTAGAA
88001  GGCCCAGCCT TTGGCGTACG CAGCACTAAC CTTGGTTTCT CTTTGGGATC
88051  CTCCAGATGG GGTGGGGATA ATGTCCAGGA GGGCATGAAC CAAGTGAGGT
88101  GTGAAGAGAG ATGCTGCGGA GGGACAGATG GACATAAGGG CCTGACCAAT
88151  AGAGATAGTG TGGAAAACTA GCCAGAGATT TGGAGTGGCT GGAGCTGGGG
88201  GCCTTGAGGA GAGAAAGGCC ATGGTCAGGC CAGCCAGACC CAGGGCTGAG
88251  GCTGGGCGGA AGACAGGCAG CTAGGGGGGC TTTCTGGAGT GGCTGAGGAA
88301  GGAGTGTTAG TGGGAAGTGG TGGATGCTCT GCCAGAGCCC CAGAACCCAG
88351  ACAAGCCTCC CTCTGCAGCC CCTCGAGGAG TTCCCAGGGT TTCTGCTCCG
88401  TGGAGGGGAT TGTGGAAGTG CAGAGCCTGT GGGGACGGGA TTCTGCCGCT
88451  CTTTCCGTTT CTTCTCCTGT ATGGAGGTGG GGGTTCAAAC TCGTTCTATC
88501  CTAGTAACCA AAGGATGAGT TCCCCAAATT GCTATTATTG GGGGTCTGCT
88551  TCTGTCGAGG GGGCTGCCAT TCCAGTAAAG GGCAGGCTTG GGGGCATGGA
88601  CAGATAAATG AGCAGGTGTT GGTTCCCCGG GGACTCCTCT CCAGCTCATT
88651  AAAAATGGAAT TAAACGCTTC CCAGGCGCCT GACCTTTCTG AGCTGCTGGC
88701  AGGAGAGGGC AGTGGGAGTC AGGGATGGCT GAGAGGGGAG GAGAGGGGGG
88751  AGGGGAGGGA GGGGTACTTG GCTGGGTCTC CTCTGCACCC ATCTTCCTGA
88801  CTGAGGGAGC CAAGGCCGCT GCTTGGTTTC TCCGCAAGCT GCTCCCCCCA
88851  CCCCCGGTTT CTGGAACGGA GCTGCTGTTG CACGGAGTTC TCAGGGGGTC
88901  GCCTCCCCCT ATTCTTTGCT CTTGGTCTGC CCCAGGGCTG GTCAGCTTTG
88951  AGGGGCACTG AGGTGAGGGG CTGTGTGCAG AGGTGGGGAT TGGGAGGTGG
89001  TGGCTGGGTC ACGCACCTCC TTCTCTGCTG AGGGCAAAGG GCCTGGGGTG
89051  CCAGGTGCCT GAGAAGGACT TCCTTAGATT GAGGCTATGA GGACTGGGTC
89101  AGGAGGGAAG TAAGGGGAAG ACATTTGGAA GGTTGCTTCC CTTGTGGGCG
89151  GAATGCTTGC CATGGCCGCT GCTCACCTTG GCTCAGGCTG GGCCAGAGGC
89201  CAATGTGTGT GTGTGTGTGT GTGTGTGTGT GTCTCAGGGA CGCTGGTGGG
89251  ATCAGATCAC TTACACTTAA CTCACCCAGT AGAACTCTGG TCTGGTCCTG
89301  CGGCAGGCTG GGTGCTGGAG CCGACTCTGC CTTCAGGGAG CTCTCAGTCT
89351  GGGGGAAGGC AGGGACACCC TCCCCACCAC AGGCCAGATG AAATACTGTT
89401  GCCAGCAGGT GTTCTGGTGG CAAAGCCTGG AGCAGCAAGT GGTACCTCAT
89451  CACAGAGAAA GCATTTGTGT GGGGCCTTGG GGCACAGGTA GGAGGTCCAC
89501  AGGCAGGGAA GAAGGGAAAG GGGATTCTAG GCAGAGGAGG AATGTGAGCA
89551  AGGCAGGAAG GAGGCCGGGG GAAGGGGTGG TGTGCTGAGG GGAGAGTGTG
89601  GTCCTGGGGA AGCTGAAGTA GGGGTGCATG CTGTTGAGCA GGATGCTAGC
89651  CAGCTGGGCT CTGGCTGCCA GGAGTTTTCA ACAACCGTCC CTTCACCTCC
89701  TCAAATACCC TGGGCAGGGA AGAACTCTTG AAAGGTGTTT AGATTATTCA
89751  CATCTGCCTC TCCTCTAAGC CTGCACCTTC CCACTCATGT GTAAATGCAC
89801  TTCCCTAGGA TGCCCCCTCC CCAAGGCATA CATGTCTGAC AGATGCACCC
89851  TGGCTCACAG GATCTCACTG CCTCCCAGAG GTAGCACAGG CAGCCCCAGA
```

FIGURE 3-31

```
89901  CTTCCCAGCT GCTGCCAGAT CCTGAGGGCA GAGGGTGCAG AAGGAAGATG
89951  GAGAGCCACA GGGTCGGTTG ATCTTTTGGG AAGGCCGAGT CACCAGCTCC
90001  TTCCTGGACA AGCCCCATTC CCCTCTCTCA GTCTCTGCTC TTAGTATTCA
90051  TCCACTGATC CACCTACCCA TCCACCCCCT CATCCATCAG TTGAACAACT
90101  ATTTCTTGAG TACCCACTGT ATGTCAGGCA TGGAGTGCTA GGTGCTGGGA
90151  ACACAGAAGT GACCAAGACA GATTAGACAG GCCCTGCCTT CACAGACCAT
90201  ATGGTCTGGA GGGTTGGTGG TGAGAAGCAC TAAAGTGAGC ATAACCCCAG
90251  CTACTTGGGA GTATTCCTTG AGCTCAGGAG TTTGAATCTG GCCTGGAGAA
90301  TAGAGTGCGA CTCCATCTCT AAAGACAATA AAAATAACAA AATACTGCA
90351  AAACAAGTGA GCAAAATAAG GATAGGATCA CACGTGATGG CAAGTGCTAG
90401  CAAGGAAACC CCTCGAGGGA GTCCTGCAAA GGAATGCTGG GGTCCAGTGG
90451  CGACGCCATC AGCGAGGGCT CTCTGAGGAA TATGCTGGCC AGGTGCAGGG
90501  CTGTGTGGCT GACTTCTGGG CCTTTACAGC TCACTGCTCA AAGCACCTTG
90551  ATTGCAAATT TTTTGTGTGG AAAGTCTTTG GCTCTGTTCC TTAATCCTGG
90601  GATAATAAGT CCCTTTGAGG AGTGGCAGCC CTTGGTCTCT GGCATTTGAT
90651  GCCTGATTTG TGCCCACTCT TCCCCAGCT GCACCAGCCA CACCAGCTCC
90701  CTGCACGGGG ATGGGGTGTT CATGCCATTA ACCATTTTGA ACTTGGTTAG
90751  GGTGGGGACC TGGGGGCTGT GCTGGGTTTT AACCCTCTCT TACAGCCACA
90801  GTGCCCAATG TTGAGTGTTC CCACTGGGTC CCAGACACTT GCCCTGATTA
90851  GCAAGAGCAG GTGTAAGTGT GTGTTCCTGT TGGCGAACAA AAAGCCATGA
90901  GTGTGTGGGG GTGATTGTGT GTGTTTGTGT ATGGGGCGC CAGGTGCATG
90951  TGCATGGCTT TTGGGTAAGT GAACTATTTC CTGTGTACAG GCATGAATGT
91001  GCCTGTGGGG ATGCTGTGGA CACTGTAAGG GTGGGTGTGT GGATGTCTTT
91051  GTGTCTGTGA CTGCACCGTG TGTGTGTGTG TGTGTGTGTG TGTACCACCT
91101  CCATGGGAGA TTGAGTGTAA GTGCATGTGT GTGAGGGCCT GACGTTCTTC
91151  ATGAGAGTGT AGGTGTGTGT GTTTGTGCAC ATGCTGGGTG CAAGTAGGCC
91201  AAGGCAGCCC GAGAACTGGT TGCCCCCACA GCCTTAGAGG GGTCCCAGCC
91251  TTCTCTATTC TTGAGAGATG GGACCAGGTG GAAGGAACAA GAACCACGTC
91301  CTCCTCCATG TGCTAACAGT AAAATGCCAA CATATTTATA TAAGCCATAT
91351  GCAAATGAAC CATAGCCCCA GCTTCTCCTC CCTCCCGCCC CCGCTGTCCT
91401  GTAGGAGTCA CAGATTGAGC CTCATCCAGA GCTTAAGTTT AAACACCATC
91451  CTTGACAGCC CAGGTCTCTT CCAGGTCTTC CTGCCTCCAA TCTCCCTCCC
91501  TCAAATTCAC CCTACACCCC ACAGACAGTG GCCCTCAGAT GCTAAAGTCT
91551  GCCATGGCTC CCCAGTACTC TCAGGCTAAA GTCTAACTTC TTAGCCTGGC
91601  ACTCAAGGCC CTTCCTTCTG TGGTACCATG GACCACACCC CTACCTGGAT
91651  CCTCATCTCC CCGCACCACC TACCGCCAGT GTCCTGGTCT CTTCAAGGTC
91701  TACTTGTCCT CCCCATGCCA ATTCAGGAAG CCTTCCAAAT GTCCTCCCCT
91751  CTGAGCTACC CACCTAGTTT TCTCTCTCCT TCCTCAGGTA TGAGGCTCCA
91801  CACCTCCTCC CAGTCATGTC TCCCCACTCG TCCCACCCCA GACAGACTGT
91851  GAGCTTCCCG AGAACCTGCT GGTCTCCTCC TCCCCATCTG CTCCTGGCAG
91901  GAGACCCAGA GCTGAGGCAG GCATTGGCTG CTGACTGGGG AGGGAGGAGG
91951  AAGGAGGAGC CCCCAGTGCA GGCGCTGTGG GGAGCTCTGC AGGTGGTGAG
92001  CAGCTTTGAG TAAGCTCCGG AAGCTAGTGA CGCAGGTGGG GAGCCTTGCT
92051  GGCAGGGCCT GTAGTGGGTC CCTAGGCTGC CACCCTCCCT CCCCACCGTC
92101  TCTCATTTTC CTCGACAAGC ACCCAAGTAG GAGTGGGGGA AGGGACTTCA
92151  CAGAGTATGA AAGATGGGCT GAGTTCCCTG GTGACTGGCA CAGGGAGCTT
92201  GGAGAGGGAC AGGATGATGG GGGTGGTGGA GAGAGTGGAT CTAGAGGGGG
92251  GAAGGTGTGG GCAGAGAACG GGAGGGAGTG GGTGGTGCTG TCTTCACTCT
92301  GCCACTTTCT GCTATGTGAT TTTGGGCAAG TCACTCCACT TTTCTGGCCA
92351  TGGCTTGCCT GCCAGGTGGA GGCTTGCATC ACAGTGGTGA GAATCACATG
92401  TAAGGCAAAG CACTTCACGA ACCCATTTAT CCATTTATTC ATTCACCCGT
92451  CCATCCTCAC CATGGCAGGT GCATCATACT GAGCCCATTC CTTTATCCAA
92501  GACTTAGGGG CAGCTCAAAC CCTAACTCAG ACAGGATAGA GCCGGGAGGC
92551  TGAGGCTAAT ACCACCAATT CTAAAATCAG GACCTGCAGC GCTCCATAAT
92601  CTGTGAGCTA AAAGGGGTC TAAGGTCCCT CCATCCCCTG AACCATACAC
92651  CCGGACTGTG CTCTTGATGA GACAGTGATT GAAAGGCAG AGACAAAAAA
92701  GTTTCACGTC CTTAGGTTAG TCCTAGGAGA CTTCCTACAG GAGGGATTTT
92751  CCTGGAGCTG TCTGAGTGGT CAGAAAGATG GGGTTATCAC TGAGGCCCAC
```

FIGURE 3-32

```
92801  AGACTGGAGT GTGTATGTGT TGGTGGGGAC CAGTGTGTGC TGCGCATGGG
92851  GAGGGCACTC TGGCAGAGAC AGACACTGAG AGAGGTCACA GCTAGTTCCC
92901  TTCTCCCATC CCTCCAGGTG CACTGTGGCC AGCTGAGTGA TAATGAGGAA
92951  TGGAGCCTGC AGGCGGTGGA GAAGCATGTG AGTGGGAGTG GGGCCATGTG
93001  CAATGAGGCT GAAGACCCTT ATCACAGCTG GTGGGAAGAT GGCCTGGCCA
93051  GGGAGCTGGA CAGACCTGGG TTTCAGCTTC GGCTTTGCTG CTTTTGAGCT
93101  GTGTGACCTT GAGCAAGTCA CTAAACCTCT CTGGGCCTCA GTTTCACACC
93151  TGAAAATGGG GATAATGATA GCACCGACTG ACCTAGGGCA GTGGTGAAAC
93201  AAAACTGGTC AAATATCTTG TAAATACACA CGGTTGCCAA CTTACAATTT
93251  TCGACTTTTT GATGGATTTA TGGGGAAGCA ACCCTATCCT AAGTCCAGGA
93301  GCATCTGTAC TTAGAAAGAA CCCTCCACAT AATGATACTG AGGCTCTTTC
93351  ATGCCTGAGA CTTTATGATT TTGTGACTTT AACAAGGACT TACGACTTCC
93401  TGAGGGGGCT GGAGACAGAA ATCTGACATC TTGTCTTGGA AGAATCTAGG
93451  GGCTAGGGAT GGAGATAGAC CCTGTACCCT CCTGTTCCTG GACCGCCGGA
93501  CGCTCCAGGG GCTGTGGGAG CCCCCGGGGG AGCCCTCAGG AAGGTAGAGT
93551  CCAGGGATGA GGTGTTTGGG ACGGCGGCGG GGTCCCTGGG CCCGGCAGGC
93601  AGAGGGAACG GCGGGAGCAA AGGCAGGAAT CCCGCTGCAG CAAGCGCAGC
93651  GAGCTTGGGG CGAGCGGCGC GCTAACCGCT CGGCCTGCCC CAGACCCTGG
93701  TCGCCCTGCG GAGGGTGCAG GTCCTGCAGC AGCGCGGGCC CAGGGAGGCT
93751  CCCCGAGCCG TCCAGAACCC CCGGAGGGG ACGGCGGAAG ACCAGAAGGG
93801  CGGGGCGGCG TACACCGACC GCGACCGCAA GATCCTCCAA CTGTGCGGTG
93851  AGGGCCCGGC CTGGACAGGT CACGAGGGCG GGGCCGGGCA GAACTTGGAG
93901  GGGAGGTGGG CGGGTTAGGC GATCCCGGGA GCCGGCGGCG GGCCCGGCGC
93951  GGAGCTGAGC GGCGCCTGAG GGACCCGGAC ACGGAGGTGC GGAGGGGCCC
94001  TCTCTCTGAC CGGCGCCTGG CCCTTGCAGG GGAACTCTAC GACCTGGATG
94051  CCTCTTCCCT GCAGCTCAAA GTGCTCCAAT ACGTGAGTCC CTGCGCCCCT
94101  GCCGGCCACC TCCCCGTCCT GTCTCCCTCC GGGGACCAAC TTCCCCTTGA
94151  GCCCTCCATC TCAGTTCCAA TTACGATGTC CTTCCTTCCT CTCTCCTCCA
94201  CCCGCCTGAA GAGCCCCGGA GAGGGGAGCA GGTGGGGAGT GGGGTGACCC
94251  GGATCCGCGG TCACCCCCTC GCCCTGCCTG TCCCTCTCTC AGCTGCAGCA
94301  GGAGACCCGG GCATCCCGCT GCTGCCTCCT GCTGGTGTCG GAGGACAATC
94351  TCCAGCTTTC TTGCAAGGTG AGGGCCCAGG TCCACTGTAG AGCGGGGGCG
94401  GGGCTGGGCG AGGAACTCGG GTCTCCGAGG GGGAAATCCA TTGCCTTTCC
94451  TTTAACCAGC CCCCTGCACT CCGTTCCTCA GGTCATCGGA GACAAAGTGC
94501  TCGGGGAAGA GGTCAGCTTT CCCGTGAGTC CCGCGTCTGT CTTCTCGTTG
94551  GAGTCTGCAG GGGCGGTTGA GGCCGGGTAG ACACTCCTGG GATCTGCCTG
94601  GAGTATTTGG ATCTTCTAGA CTCTTGGAAT CCGATGAAT TATCTGGATC
94651  TTGGGACTAC TTAGAAATGC TGCAGGGATC ACAACCTGTG ATCAGCAGGC
94701  TCTATTAGGA AGAATCTCTT AGCATCTACA GAAAGGCTTA CCTGGGACCT
94751  GTTCACTTCT GTTGGAGTAT TTCTGGATAT GGATCTGCTA GAATCTGTTG
94801  ACGAGAATCC TTGGAGTCTG CTTATCTCTC TCGTAGTTAG GGAAGACTCT
94851  AGAGTCCTTT ATAGCGAATT CTGCCAGACT CCCCTCCATC TCTGCTCATC
94901  AATGCTGACC CTGTCCACCA TTTGGACTGA CTGAAGGGTT CTTTGAAACT
94951  TCCAGATTTG AGGGTGGGGA CAGGTTGAGA TCCCCTGACC TGGGGAGTAC
95001  TGGGCCCTGA CTCAGTCTCT CCTCACCCCC TAGTTGACAG GATGCCTGGG
95051  CCAGGTGGTG GAAGACAAGA AGTCCATCCA GCTGAAGGAC CTCACCTCCG
95101  TAAGTCATGG CCTGGCTGAC CCAGAGGGGA AAGAGGAGAC CCCACTGCCA
95151  GCCCCTAGAG CCAGGGTCTC TGTTACAGAG CAGCCTAGGA ATGGGGCAGA
95201  TAAGACCTGG GGACTTTCTA CTGTCCCATC TCCATGACAC AGAGCTTCCA
95251  GCCTTGCATG AGTCCCTTAG AACTGCCTGT TGCAAAATGT GATGGAGGGC
95301  TGGAGGAGGG AAGCATACTG CGCCCTGCTT CCCTGCCCTG ACTTGCCTCG
95351  CCTTTGCAGG AGGATGTACA ACAGCTGCAG AGCATGTTGG GCTGTGAGCT
95401  GCAGGCCATG CTCTGTGTCC CTGTCATCAG CCGGGCCACT GACCAGGTGG
95451  TGGCCTTGGC CTGCGCCTTC AACAAGCTAG AAGGAGACTT GTGAGTCTTT
95501  GTGGGATGAT GCAGATCAGG AGATGTCACT GAGAGGCTGG CTAGGGCTCC
95551  ACGAGGGTAA CAATGTGGGA TGGGTACTGG GCAGGGGCTA CTGTCTCAGC
95601  AGCAGTGGGT TGAACAGTGT GTTAGTGCAA GAGAATGAAA GTCATGTTGA
95651  GGTCCAAGCT AGTTCCTCTT CTCTTCTCCT GCTTCCTGAA GTTTGGGTAA
```

FIGURE 3-33

```
95701  TCTGCTCTTG GGGTATTGGG TTCCCTCCCT TGCCATCCCT GTTTTTGCAT
95751  TACTGCTATA AACTGCTAGA TGGAGGGGTG GGTGTGCTCT GGGTTGGATG
95801  AACCCTCTGG GACCCACAAA GCATCATCAA CACAGTGGAC AGTGGCTAAA
95851  GGGAATATGC TTGGGGACTG GGAAAAGCTG TGGATCTTTT GAGCCCCTGA
95901  CAGGGCAGCT ATAAAAATGA TACACAAAAA TCTCTTTTTT TGTGGGCAGG
95951  GCACAGTGGA CAGGAAAGCA GGCTTGGAGG CTTAGTTGGA AAGGATATCT
96001  CGAGAACTGA GGACAAACCT GGGGTCTAGA AATGGTGTCA TAAATAAATT
96051  TCATATCCTA CACCAACTCA TAAACAGGCA GTAGGTGCCT GAATTTTATT
96101  GCAAATGGAT CTTAGTTCAG GGAGAAACAG TGCTGCGTCT GATGAGCCAT
96151  TTCTGTCCTG GGTGCAGGTT CACACTTGGG CTGGCAGGAT GAGCAGTTTG
96201  TGCTGTGTCA CATAGGTGGG GAGAAGTAGA CAGATGAGGG GCTGAGTCCT
96251  GATGCAAAGA GATGCTGATA GGATGCTGGT CTCTGGAGTC CAAGCAAACA
96301  GGCTGGGTTT CAGGGCCTGG AGCTCCTGCA GGAGGTGGAC ACTAGAGAGC
96351  CTGGGACTAG GTAGGTGTCA GAGCCCGGGC CTGAGGTCTG CTGGGGTAGG
96401  GTGGAGATCC AGGAGTCCTA GGTCTGAGCT GCAGAACCTA CCAGCATGGA
96451  ACTGTGTTGA CAGTTGGGTG GGCCTGGAGA AACAAAGATA GGGGCAAGGC
96501  AGAATCAGCT GAGGCAGGGA GAATGTGGGA TTGGTGGCAT TTGGAACTTG
96551  TGGGCATCCT AATGGTGGGA GAATTTATGC CATTCAGCAA ACAAATATTG
96601  AGCACTTAAT GTTGCCATCC CAGTGCTGAC CAGATGGCCT TGGGAAGGCC
96651  TTTGGGGAAG GGAAGGTAGA GTGAATGGGG GTCCAGCAGG GGCCATGACT
96701  TCTTGCTGCT GGCTGTGAGA TTGGGTTCTA GGATGGCCCC AGAGCTGGAG
96751  AAGAGGTGGT ATCAGCAGGA AATAAGGATG GGGCCTTGGT GGCAGCTTTG
96801  AGGCCCAGGG CAGGGGCAGG GCTATCTCTG GGTCCCACGC ATTTCAGGGA
96851  GTGAGTGTTG AATGACTGCA TGAGCCAGGG TGGGGCTCAG CTCAGTGCAG
96901  TGACTACAGA GAAGCTTCCT GAAACACAGC TAAGTAGCCA GAGAACAGGG
96951  GCTCCAGAAG CCCTTCAGCT GTGAGTGGGA TGGGGCTGGT GGCAAGGCCA
97001  GGGATAGGAT ACACTGACGA CATTAGCAAA GACCTCCGAA GTGTTTCCTC
97051  TGTACCAGGC TCTGCACTGG GCATGGGTGA TATAGTCATG GCCCCATTTC
97101  ATAAGACTCA AAGCTCATTT TCAGGGCATA GAGGGAAGAG AGTGAGAAGG
97151  GTATTCTAGG CCGAGGGAAC AGTGTAGAAA AAAAAGCATG AAGGTGTGAA
97201  AGAGCCCAAG GTTTTCTCAG AATGATGAGG ATCTTTGTGT GGCTGAAGCT
97251  GAGAGATGTT CTGGGTTGAG GGGTGACAGG TGGGTGGGGC TAGCTGAGGG
97301  ACCACAAATG TAAGAAAGGT GTGCAGACAG ACCCAGGATG GTGGGGATGG
97351  GATCTAGATC CGAATCACTG GATGGCAAGC ATGAATGGGG GATGCCCCAC
97401  CAGGGTGGAG CACCAAGGCC AGCCAAAAAG TGGGGAAGGG CTTAGGCAGG
97451  GACACCTCAG GGCAGCGTGA TGTGGGCTAA GGCAGGCTCT TCCCATGACC
97501  CACACCATTG GTCCACCCAG CCCCATGCAG CTCCCCAGTG ACAAATCATT
97551  TGGTGGCCAG ATTGAATGAC GTGAGCAGGA TTTGGGGCTT ATCTTGTCTC
97601  ACCAGAGCTA GCTCCATGAG CAGGGCAAGC AGTCCTCTCC ACACCACCAC
97651  CCTAAGATTT CTGGAGGCAC CGAATCAGGG CCAGCGGAGT CCAGGGAGAG
97701  TGGGGTAGTG ACAGGAGCTG CACAAGATAG GGCAGTGCCA CCGCCCCTCC
97751  CCAAGGCTGG AGGTGTGCCT GGGGAAGAGC AGAACACCAG CTTGAGCCCA
97801  GGCAATCTCT AGTCTGAGGG AGGAGACCCA GCTTTGGGCT GGGTAAATCC
97851  CAAATCAGAG ACGGGAGGTA TGGCTCTGGT TTCAAGCATC TAAGGAGGAC
97901  TGGAGCCCTC CCCTTGGGCA GCCCCAGTC TGCAGGGTCA TGGGGGTGGG
97951  AAGCTGTTCC AAGGGCCTGT GCAGTGGTTA TATAGTTGGC AGGTGGGTAC
98001  CCCTGTGGGC TTCTGATGGA ACAGAAGTAA GGAGAGTGGG GAGAGAAGCC
98051  AGTCTTCCCT TCCCTCCTGA GTGAGCCCAC CCCCTCCTCC AGGTTCACCG
98101  ACGAGGACGA GCATGTGATC CAGCACTGCT TCCACTACAC CAGCACCGTG
98151  CTCACCAGCA CCCTGGCCTT CCAGAAGGAA CAGAAACTCA AGTGTGAGTG
98201  CCAGGTGAGT GACCTGCCTT CAGCCTCTCT CGGGCACCGA CTCGCTCAGT
98251  TTTCAGCCCC GAGAGCCATT CAGAAGGGAA ATGCCCATGT CTTTCTGGAC
98301  TGGTGGCAGC CCTTCCCCAG GTGGCTCCAT AACCTCATAA CTTGAAGGCT
98351  TGCAGTTGTT CAGGACCCGC GCCACTGCCC GCAGGCACTG TATGTGATCG
98401  CCCTCTAGTG TTCAATATGT GCACTACAGC AACACCTAGG CAGCTAGAGC
98451  TGGCGTGAAG GCGGCTGAGA CACTCAGGAG ACTCCTCACC TGCACCGGGG
98501  CTATTCCCTC ACTCCTTCAC TTAGTAGCCA AATGATATAA TTAGACACTG
98551  ACAGTTTCTG GCTTGTCCAG TGAGCCCTAG GGAAGGAAGG AGAAGACCCG
```

FIGURE 3-34

```
98601  GGTGCTGTTG GAGGCAGAAG GTTGGATAGG GTGACCCCTA CACCCCGACC
98651  CCCCTATGAT CTCCATTTCC TTCATTCCAG GCTCTTCTCC AAGTGGCAAA
98701  GAACCTCTTC ACCCACCTGG GTGAGTGCAC TGTTCTCTCT GCCTGGCTGT
98751  GTGTGGGCAT GGGGGCTGGC ATTTGCAGAG GAGAGGCGGG AGGTCTTGGC
98801  AGCCTGGTCT CACCCTGCCT GGTCTTCTCC CTTCCCCAGA TGACGTCTCT
98851  GTCCTGCTCC AGGAGATCAT CACGGAGGCC AGAAACCTCA GCAACGCAGA
98901  GATGTGAGTG ACTCTACCCA GGGGACAGGG CGAGAGAGGC TGTGGCCTTC
98951  AGTCCCCATC ATCTCCTTTC CTGCCCCACC CACTTCCCTT TCTCTGCCTT
99001  CTGCGGGACT TCATCACCTT TTGAGGGATC CTTTATTTCA TGCCTGTCTC
99051  CCTCGCTAGA CTGTAGGCTC CAATACAGCA GGGACAGGGC TGGCTTTGGA
99101  TCCTCAGCTC CTATCACAGT GCCTGGCACA TAGTAGGTGC TTCCAAAAAA
99151  AAAAAAAACA AAACACTTGA ATGGACACGT TTCTGGAGCC AGCCAGCCCT
99201  GAGCAGAGTG TCTTACCTTG GAGCACTCCT CCCAGGCCTC GGAAATCCGG
99251  CCTTTGCCTC CTTATGGGAC GTGAGGGCGA TCAGAGGGGG TTGTCAGGCC
99301  CCAGAGGACC AAACCCCTCC CTCCACAGCT GCTCTGTGTT CCTGCTGGAT
99351  CAGAATGAGC TGGTGGCCAA GGTGTTCGAC GGGGGCGTGG TGGATGATGA
99401  GGTGAGAGGG CGTGGAGGGA GTATGTGGCC CTAGGGGTGT CCGGGAGTCC
99451  GCCGGCGGCG CTGGGGAGCG GCCCGAGGTT TAACAGTCCC CTCTGTGGCC
99501  GGGTCACTAA CTTCTTCCTC TCGACTCCAT CTCTGCTCCG GCAGAGCTAT
99551  GAGATCCGCA TCCCGGCCGA TCAGGGCATC GCGGGACACG TGGCGACCAC
99601  GGGCCAGATC CTGAACATCC CTGACGCATA TGCCCATCCG CTTTTCTACC
99651  GCGGCGTGGA CGACAGCACC GGCTTCCGCA CGCGCAACAT CCTCTGCTTC
99701  CCCATCAAGA ACGAGAACCA GGGTGCGCGT GGCGGCCCGG GCGGAGGGGC
99751  GGGGCCTGCG CCGGGCGGGG CGGGTCCGAG CGAGCGGGGG TGGCAACACT
99801  TCCCCACCGC CTCCGGCGTC CCGGAGCATA AGGGAGTCGG GTTCCATGCC
99851  TGGGACGTAC GTAACCTGCG GAAACTGCGA GGGCAGGTCC CGGCCGGATC
99901  CCTCCCTCCA ACCGATCCCT CCCTCCACCG GTGGTTCCTT GCCCCTCTCC
99951  CTTCCCCAGA GGTCATCGGT GTGGCCGAGC TGGTGAACAA GATCAATGGG
100001 CCATGGTTCA GCAAGTTCGA CGAGGACCTG GCGACGGCCT TCTCCATCTA
100051 CTGCGGCATC AGCATCGCCC ATGTGAGGGC GGGGTTGGGA GTGGGGTGTG
100101 GGGTGATAGG GGGCGGGGCC CACGAAGGAC CCTCGGTTCT CCTCCTCCGA
100151 CTGACTCTCC TTGTGGATTG ATCCCTTGGT CTGGCACTCA GAGTCCCGCC
100201 GCTGGGGTGC AGCCTTCAGG ACACGCTGGC CACCTCTGGG CTCAGTTTCC
100251 CATCTAAAAA TTGGGCATAC GATTTCCTGC CCTGTCCACT CAGCCTCCTG
100301 GGACCATGAG AAACTCCCGT TGTCAAAACC TCCTCTCTTC CCTGGAAGCA
100351 GTCTCAACCC AAGCCGAGTG CTTTTTTGGA AGTGCTGGGT CTCGGTGTCC
100401 AGGCCTACTG GCGCTCTGGC CTGGGAATCC AGCCCCAAGG TCCCTGACAT
100451 GATCCCCTCC TTGCTTCTCC TTCCCTGCCA TGGGCCTTGG GCTCCATCAC
100501 TGAAGCCTGG ATCAGGTGTG GGGGAGTGCA AAGGGCCAGA CCAAATGCTG
100551 GGAGAACTTG ATGAGGAGGA ACCGGCGCGG GGGTCTGGAT GAAAGTGGGG
100601 GTGAGGTCTT TACTGTGGAC TGGAGCTTGA AGGTTTTGAC TGGGGCCAGA
100651 ATGGGACAGG AAGTGGGGTG TCTTTTTGAC CCCTTCATCC CAGTCCTGGG
100701 CATTGCTAAA TTTTCACAGC CACCTTCCTT GAGCCCTCTT TTTCCCTCTT
100751 TCCCCTAGTC TCTCCTATAC AAAAAAGTGA ATGAGGCTCA GTATCGCAGC
100801 CACCTGGCCA ATGAGATGAT GATGTACCAC ATGAAGGTGA GGCTTGCAGA
100851 GACCTCTGGT CCTCCTCCCA GATTCCCCGG GGACCCAGGG CCAGGCAGGG
100901 CTTCCTGATC AATCTCTACT GAGGATGAGA GGATAGGCCC AGAGCCACAG
100951 CAGGCCTCCT GCCCTCCTTA GGGGCAGCTC CCACCCCTGC TTAGAGACCT
101001 CTCCTCCAAG CTGCTTCTGA GCTCAGTCCC AAGGCTGGAA GTAGCCAGAG
101051 GAACCAGCCC AGGGAGTAAT TGGTTCAGCC AGGTATTCCC CATGTTCAGG
101101 GAATAATTCC CATCTTGGGA ATTACTGAGG GCTAGGAAGC TCACCCAGGA
101151 CCCGTCCCCA TGGCTTCCCT AGGTACAATG CCCATGCAGC CCTGGGCAGT
101201 CTTAATTGCT GATAATCTAT CCCATTCCCT ACCCTGGGTC ACAAAAGCTG
101251 GCTTAGTTCC ATGTATATGG TAGTCGCTGT TCATTTGGAC ATTTCCTCTC
101301 ACCTGTGTCC AAACCAGAGA GGCCCAGACC TTGTGAGTTG GATCAAAACT
101351 GTAGTAGGAA GAGTTAAGGT TAGAGAGTAG AAAGGTCTCC ACAAAAGGAG
101401 GACTGCTACA GTTACTGTGT ATGAAATGCT GCCATGGTTT GGGGGTGTCA
101451 TGAAGGGGTG TTGTCGATCT TTGCCAAGGT TATGCTGTTA CAGATAAAGG
```

FIGURE 3-35

```
101501  GTGGTCACCT GCAGGAAGGC GCGCGGGGTG GGCTGCAGGG CTGTGAGGGG
101551  AGGGTGGTGA TTTCCTGCCC AGTTACAGTC CACAGCGTGG TGGCCCAACT
101601  GTGGTACATT CTGGGTGACG GATCCCCCAC CTGCCATGGG AATTTGAGGG
101651  TGAAGACACC AGATGGGGTG AAGGCTGTCT TCTAATGCTC TGGCTGGTCT
101701  CCTCTAGGTC TCCGACGATG AGTATACCAA ACTTCTCCAT GATGGGATCC
101751  AGCCTGTGGC TGCCATTGAC TCCAATTTTG CAAGTTTCAC CTATACCCCT
101801  CGTTCCCTGC CCGAGGATGA CACGTCCATG GTGAGTTGCT CTCCTCCACT
101851  TGACTGGCCA GGCCGAAGGT ATGTAGCCAG AGGCTTAAGT TAAATGCGCA
101901  TCAAGAACTT CCTGGGAAGA CAGAGTCATC AAGGAAGGCT GTGGAGGGTC
101951  CCTCAGAGAT GGAGGGGCTT GTAGTCTGCC ATCAGGAAGC CATGGGGCCT
102001  GCCCAGGGGC TAGAGGCTGG ACTGGATGAT CCCAAGGGCT GCTCTTGGAC
102051  CAACCATGCC CAGGGCATGT GACCTCAGGG TTTGCATCCC TCCCAACCCT
102101  GTTTTTCTAA CATTTTGTGT GGGCTTGGTT TCAAGAGTTC TTAGTTCTTA
102151  GATCTCTAAA AATGCATAGC TCTGAGAACG GTTGCTTCAA CTATTTTGTG
102201  GTTCTCTAGT TTAGATGTAA GTTTCTAAGA CTCCAGATCT TGAGTGTGGA
102251  GCTTGAAGAA GGACCCAGGC AAGGGCCCTG TCTTGATACT GGCAGCCCCT
102301  CTGATACCTC CCTCTGCCCT CTCCAGGCCA TCCTGAGCAT GCTGCAGGAC
102351  ATGAATTTCA TCAACAACTA CAAAATTGAC TGCCCGACCC TGGCCCGGTT
102401  CGTGCGCCCA CAGACAGCCC CAGTCTTCGC CTCCCTCTTT CCTCTACTGT
102451  CACATCCATT GCCCCGGCA TTCTGGAGAG GATCTCTCTA AGGATGACTG
102501  GGGAGACCCA GTCTTATGGG GGTGGGGAGG ATCCATGAAT GAGAAGCAAT
102551  TCCTAGACAC TGAACTGTCA ATAAAGGCAA GAAATGAGGC AAGGCAAAGC
102601  CTGGAGGCAA GGCCGAGAGT GTGTAGCCAG AGGTTTAAGT TAGATGTGCA
102651  TAGGAACTTC CTGCTAAGAC AGAGTCATCA AGGAAGGCTG TGGAGGGTCC
102701  CTCAGGGATG GAGGGGACAT GTAGTTTGCC ATCATGGGGC CGTGATGGAG
102751  GAGGAGAGGC TGAGGCCCCT CTTCTGCCCT CTTCCCTCCC CCAGGTTCTG
102801  TTTGATGGTG AAGAAGGGCT ACCGGGATCC CCCCTACCAC AACTGGATGC
102851  ACGCCTTTTC TGTCTCCCAC TTCTGCTACC TGCTCTACAA GAACCTGGAG
102901  CTCACCAACT ACCTCGAGTG AGTGGCTGCA TCTCCCCCAC ATCTGGCAGC
102951  CACTGGGGTC CCCTTCCCTG GGACAGGGAA GCACCCCCTG TGTGTCAGGC
103001  ACTTTACACG CACTGCCTCA TGGGATCTTC TTAGCCCCAG GGGACTAGAG
103051  GGGAAGGCTG TGAGCCCCAT CTTCCAGGAG GGGCTTGCTC ACAGCCAAGC
103101  AGCTAGTGAA GACTGAGCCT GATTTAAACC CGGGTCTGCT GGACTCCAAA
103151  CCAGTGCTTC TTTCCAGGAA GGGAACCCAG GTGTTCCAAC CTCCTGTCCC
103201  AGTGGCTCCT GGGCATGTCA TCTCCTGTCT GTCCTCTTCTGC GGATTTAGGG
103251  AGGGAACTGT GGGCTGACCT CTTTTTTTTC TCCTTTCTGC CTCTCAACCA
103301  GGGACATCGA GATCTTTGCC TTGTTTATTT CCTGCATGTG TCATGACCTG
103351  GACCACAGAG GCACAAACAA CTCTTTCCAG GTGGCCTCGG TGAGACCCTG
103401  CCCTGCTCAC AGTGGGGACC CTCCATGGGG TGTCTTGGAT CTCATCCTCT
103451  CCCAGCCTGA ATAGGGTGGG AGCGAGTGAG ACCAGGAGCC AGGTTTAGAC
103501  ACAGGAGGAG GTTCCCCCAG GGTTTGCCCC TGGCTCTGAG ATAGGGAGGA
103551  GGGGAGAAAG GTGGAAGGGC AGGACACTGC TCAGCCTAAA GCAGTGGCAC
103601  TTGGATCCGG ATGTGAGGAG TGACCACAGT TTTCCTGGGC TTTTCCAGAA
103651  ATCTGTGCTG GCTGCGCTCT ACAGCTCTGA GGGCTCCGTC ATGGAGGTAT
103701  CACTCTTCTG TCCCACCCCG TCCTTCTTCC CCTTTAAGGC CAGTGACTTG
103751  CAAAGTTATG ACCCAGCTCC TCCTATTCCC AAACCATGCT CTCCAGACAG
103801  GCTGCGAGAG CTGCAGCCAC ACCTAGGACA TGTCTGGCTC ATTTTCCTGG
103851  AGTGGGCTTG GAAGGGTGCA GGTGCGGATG ATAGCAAGGA TTTGTGTTCA
103901  GCGTGTTTCC CTTTGGCTGC CTGGGAACAC CCCATTCAGC CCCCTCCTGC
103951  CAAACTTGGG ATGGGCTCCA CTCCCATCAC TTAGCGTCAC CTTAGATTGT
104001  TTGGTTTGGG TCTGCCTACC TCCTCGTGCA CAAGGTCTGA GCCATTTCTG
104051  AGTTCCCTGC ACTTGGCACA GGGCTTGGCA CAGAGTAGGA GACACATTTC
104101  CAAGGTCACC TTGCCTCATG CTACTTCCCA CAACACCTCT CCAGAGGCTG
104151  CCCCTGCTTG CACACCCCCA GAGACGAGGT TCTCTGTCTC TCTCCCAGGA
104201  GGCCTGGTGG CAGTGCTGGT TCTGCCCTCT GCCCCCCTGA GATAAGCTGC
104251  TCCTTTTCTG AGTGACAGCC CTTCAGCATC CGGAAATGGG GGCCTTGCCC
104301  TTGCCTCATC ACTGCCTCTC CTTGTCAGCA AACAAATGTG TTCTGCATGA
104351  TTTGGTGTCT AGGACTCCAA AGGATCATTT CAAAAATGTT CCAGCTTTCA
```

FIGURE 3-36

```
104401  GGGACCCCAG AGCTTACCTT GTTGGGTCCC TGCATGTGAC AGCTGAGGAG
104451  TCTGAGGCTC AGAGTGGTCT AGGGACTCAC CCTGGGTCAC ACAGAGGGTT
104501  GAAACAGAGC TCAGAAAGGG AACTGGGGCC CCTGACTCCC CCTTTCTGAC
104551  TGCTCTGCTT ACCTGGGGGC TGGAGCTGGA CGAGGCCCCT GCTTCCTCTC
104601  TTGGGGTCAA TGGTAAGGGA GCCCATCTGC CCCAGCTGGG CCCCCATCAC
104651  TCCTCTCCCC CCAGAGGCAC CACTTTGCTC AGGCCATCGC CATCCTCAAC
104701  ACCCACGGCT GCAACATCTT TGATCATTTC TCCCGGAAGG TGATGGGGTT
104751  GGGGTGGGG TGGGGATTGA GGGGGAGCTG GGAGCTGGCT GGAGGTGGGA
104801  TAAGGAGCCA AGGAGTGGAG GCTCACTGGG ATGGGCAAAT GGGTGGGGGT
104851  GTCCAGTAGG AGGGCATGAC ACCCCTGCCC TCGCCTCAGG ACTATCAGCG
104901  CATGCTGGAT CTGATGCGGG ACATCATCTT GGCCACAGAC CTGGCCCACC
104951  ATCTCCGCAT CTTCAAGGAC CTCCAGAAGA TGGCTGAGGG TGACTGCTGT
105001  TAGCCCCAGT CCTTGGGGCT GGGGAGGAAC AACCAGGGGA AGGATTTGCC
105051  AGGGGAGCAT TCCCAGGGTG CAGACCCATC CCCTGCAACA TCAACCCTTC
105101  TCTGGCTGCA CGGCCCCCCC CAGGCAGACC CAGCACTGGC CCCTTGGCTC
105151  CCATCAAGGG TGCCCAATTC CCTGGACCGC TCTGGGTTGG GCCCTGGGAG
105201  CCTTGTCCTC AGAAGGGCAA AGAGGCTGGG CCCCGCTCCT TGACCCCATC
105251  CTCCCCTCAA CAGTGGGCTA CGACCGAAAC AACAAGCAGC ACCACAGACT
105301  TCTCCTCTGC CTCCTCATGA CCTCCTGTGA CCTCTCTGAC CAGACCAAGG
105351  GCTGGAAGAC TACGAGAAAG ATCGCGGTAG GTGTAGTCCT CCCTGGGAAG
105401  GCACAGGCTG CCCACCCTGC CCAGCTTTGG GTGCCCCCTG TGCCTGAATA
105451  CCCTCTCTCT GCTCAGCTCA GCCTGGCTGT GTTCTGGGGA GACAGAAACC
105501  TAGACCATCT CAGGGTGACA AATGGAGACT CAGAGAGGGG AACAGACCTA
105551  GCAAGTCAGT GGCTGGTGGA AGGTGGGCCC CAACCCAGCC ACTCCCTGCC
105601  TCAGGCCATC CCACTGCCAA GCTGGGGCTG GTGGGACGG CTCCTGAGCT
105651  GGGACTGAAT CCCTGGGCCT CAGTTTTCTC TCCTGGGAAC GGGCTGTCAG
105701  AGGAGCTTGG GTGGATGTAT CCTACATAGA GGATGTGATG AGAGTGTTGG
105751  CCTTTCAGGA GCTGATCTAC AAAGAATTCT TCTCCCAGGG AGACCTGGTA
105801  TGTGTGGAGT GACCCCAGGA TGTCCAGGAT GGGGGAGGGT TCCTGGCCTG
105851  GGACAGGGAG GGCTTGAACT AGCCTGACCC TGGTACCCGA TGGAGGAATG
105901  AGAGGGACAG GCCTGACGAC TCGATGCCTG CAGGAGAAGG CCATGGGCAA
105951  CAGGCCGATG GAGATGATGG ACCGGGAGAA GGCCTATATC CCTGAGCTGC
106001  AAATCAGCTT CATGGAGCAC ATTGCAATGC CCATCTACAA GTGAGTGAGC
106051  TCATGGGGAC AAGCTGCACC CTGCACAGAG AGGGTAGGCT GGAGTGGGGA
106101  CATCACAGGA AACACAGGTG CTGAGATTGG CCTGGCCCAG CTCCAACTGA
106151  TTCATCCCCT TGCCTCTGGG CATAACTGTC TCCCGCTGTG CCCCTCAGTG
106201  GGTCCTTCAC TTCATCCTTG GTCCTCAGTG GAAAGAGACC ATCATGCTTT
106251  CCTAGGTGTC CTCCTCTGTC TCACATTCTT GTGGAAGTTC TTGTTTTTTT
106301  TGAGATGGAG TCTCACTCTG TTGCCCAGGC TGGAGTGCAA TGGCACGATC
106351  TTGGCTCACT GCAACCTCCC CCTCCTGGGT TCAAGCGATT CTCCTGCCTC
106401  AGCCTCCCAA GTAGCTGGGA TTACAGGCAT GCACCACCAC GCCCAGCTAA
106451  TTTTGTATTT TTAGTAGAGA TGGGGCTTCA CCATTTTGGT CAGGCTGGTC
106501  TTGAACTCCT GACTTCAGGT GATCCACACA CCTCGGCATC TCTGAGTGTT
106551  GGGATTACAG GCGTGAGCTA CCGTACCTGG CCCTTGTGGA AATTCTATTT
106601  GTTGTGTAGC CCTAGTCTTT CTTGCTGCCC ATGGTCTGAT TTCTGGCCTC
106651  TCACCCTCTG CCCCCATGCA CCCGCAGGCT GTTGCAGGAC CTGTTCCCCA
106701  AAGCGGCAGA GCTGTACGAG CGCGTGGCCT CCAACCGTGA GCACTGGACC
106751  AAGGTGTCCC ACAAGTTCAC CATCCGCGGC CTCCCAAGTA ACAACTCGCT
106801  GGACTTCCTG GATGAGGAGT ACGAGGTGCC TGATCTGGAT GGCACTAGGG
106851  CCCCCATCAA TGGCTGCTGC AGCCTTGATG CTGAGTGATC CCCTCCAGGG
106901  ACACTTCCCT GCCCAGGCCA CCTCCCACAG CCCTCCACTG GTCTGGCCAG
106951  ATGCACTGGG AACAGAGCCA CGGGTCCTGG GTCCTCAGCT TTCTCGTCTG
107001  GTGTGACCCT GGACAAGTAC TACCTTCCTG GGCCTCAGCT TTCTCGTCTG
107051  TATAATGGAA GCAAGACTTC CAACCTCACG GAGACTTTGT AATTTGTTCT
107101  CTGAGAGCAC AGGGGTGACC AATGAGCAGT GGGCCCTACT CTGCACCTCT
107151  GACCACACCT TGGCAAGTCT TTCCCAAGCC ATTCTTTGTC TGAGCAGCTT
107201  GATGGTTTCT CCTTGCCCCA TTTCTGCCCC ACCAGATCTT TGCTCCTTTC
107251  CCTTTGAGGA CTCCCACCCT TTGGGGTCTC CAGGATCCTC ATGGAAGGGG
```

FIGURE 3-37

```
107301  AAGGTGAGAC ATCTGAGTGA GCAGAGTGTG GCATCTTGGA AACAGTCCTT
107351  AGTTCTGTGG GAGGACTAGA AACAGCCGCG GGGCGAAGGC CCCCTGAGGA
107401  CCACTACTAT ACTGATGGTG GGATTGGGAC CTGGGGGATA CAGGGGCCCC
107451  AGGAAGAAGC TGCCAGAGGG GCAGCTCAGT GCTCTGCAGA GAGGGGCCCT
107501  GGGGAGAAGC AGGATGGGAT TGATGGGCAG GAGGGATCCC CGCACTGGGA
107551  GACAGGCCCA GGTATGAATG AGCCAGCCAT GCTTCCTCCT GCCTGTGTGA
107601  CGCTGGGCGA GTCTCTTCCC CTGTCTGGGC CAAACAGGGA GCGGGTAAGA
107651  CAATCCATGC TCTAAGATCC ATTTTAGATC AATGTCTAAA ATAGCTCTAT
107701  CGCTCTGCGG AGTCCCAGCA GAGGCTATGG AATGTTTCTG CAACCCTAAG
107751  GCACAGAGAG CCCAACCCTG AGTGTCTCAG AGGCCCCCTG AGTGTTCCCC
107801  TTGGCCTGAG CCCCTTACCC ATTCCTGCAG CCAGTGAGAG ACCTGGCCTC
107851  AGCCCTGGCA GGGCTCTCTC TTCAAGGCCA TATCCACCTG TGCCCTGGGG
107901  CTTGGGAGAC CCCATAGGGC CGGGACTCTT GGGTCAGCCC GGCCACTGGC
107951  TTCTCTCTTT TTCTCCGTTT CATTCTGTGT GCGTTGTGGG GTGGGGGAGG
108001  GGGTCCACCT GCCTTACCTT TCTGAGTTGC CTTTAGAGAG ATGCGTTTTT
108051  CTAGGACTCT GTGCAACTGT CGTATATGGT CCCGTGGGCT GACCGCTTTG
108101  TACATGAGAA TAAATCTATT TCTTTCTACC AGTCCTCCCC CATGGGGCTG
108151  TTTGCAGACT TTGTGCTTGG GGTGGGTGGA GGGGGGGAAT AGAACTGGGA
108201  GAGGCAAACG CCCTTTGGAA CTCCATGGCT TCCAGGGTCC TCCACCCTTG
108251  GTGCCTAGCC CCCCTTCTGG GGAAGTCATA GACCTGTTGG GGTACTCCCT
108301  AGGCCAGATC GTGGAGGCTA AGGGGTGGGT GGCAGATGAG AAGGCCTGGC
108351  CATGGAGCAG TGATGGGACA TGTTGGCTGG CAGAGATTGT AGAATAGAGG
108401  AAAAACAAAG GTTGAGGCAA GCAGGCAGGC TGCCTGGAGG AGGTAGCCTG
108451  GAGCTTGTCC TAGACCCTCC CAGCGCTGGC CTGCCCTGGT CATGAGTGCC
108501  CATACGGCGA GGGCCTAGGC CTCTGAACTC TGTTTCTAGC TGCAGTGATG
108551  CCTGGCTGTG TCCCAGGAAG TCCCACATCC CAGTTACTCT GAGTCCTGCC
108601  GAAGGTGCAC GCCTGAGTCA GACTCCACAC CAGATCCAGC CCCGGGTTGT
108651  GTCTGAGGAG TTGCGTCTGT TCCTCTGCAT GAGAGTGTTT ACTTCCGCCC
108701  AGTCCAAGAT GGGCAGACTG CAGGTTGGGG CTACGCGGAG GCTCTGCCTG
108751  GCACAGTCTC CAGACCCTGT CCCCGACTTG CCTACCCCCC TCTGAGCTCC
108801  TCTCCGTGTT CATCTCTTCC TGGTCAGTAA AGGTTGATGT GTTAAGAGGG
108851  TGGGCACTGG GGTCTCCTTT CTTGGTGGGA GCAGGAAGGA GATGGACAGG
108901  GCCATCCTGT GACCATCAGC CATTGCCAGC TTTGCCTTTG GGACCACAGA
108951  GCCCATCTGC TTCCTCTGCA GCTCCCCCTG CCCCACTAGC CTGTCTGGGT
109001  TTGGAATCTG CTCCTCTGGC TGAATGGTCT CCAGGTTTCC AGCTTCCCTT
109051  AGCGTCATGG GGCTCCAGGC TCCTCCCATT CCCAGCTCCT GCTGTGGGCT
109101  CCCCAAGTCC GTCTCTATCC TCTCACAGCA CAGGACCCAG GCTTGGCCAG
109151  TGGGTCCCCG GGTGGGGGTG GGAGTGGTCA GTTTGTGGCC CACGGCCAAT
109201  AAGAGATGGC TATTCTAATG GTGCCTGGCT GACCCCAGGG TCACTGTGGG
109251  CTGATGTAGC TGCTCTTCTG CCTGACCCCT GACCCTGAGT GTGTGTGCGT
109301  GTTCCTCTTC CACAACTCTT CAGGCAAAGA GAACCTTGAC CCTGCATCTG
109351  TCTGTCCCCA GCCCAGCCCT CCTTTGAGGC TCATGCTGTG ACACATCCCT
109401  GTTTTTCACC AAATGGAGGG AACAACCACA GATATTTCCT TGTGCACGCA
109451  GGACCCTGTG CTAGGGCTGA GGGCTTTGTC TTTGTCCTGC TCTGGAAAGT
109501  CTCACAGTTT GATTGGAGAG CTAGATCTAA ACTCAGATGC AGGCCATGAC
109551  AACGCTGTGG GGTGCCCGGC CATGGGCTC CAGGCAGGAT CATAACCCTG
109601  AGAACAACAA TGAGGTTTGA AAGATGAGCA GATGTTGTTT ATAGGCAAAA
109651  GGGGACAGGC ACTCCTGGTA GAAGAAACTG CTTTTGCAAA GGCCTCGAGA
109701  ACAGAAGGGA CTGGCAGGTG GAGGAGCCGA GAGATGGAGG AGGAGGCAAG
109751  GCCAGATCCT GAAGGGCCTT AAATGCCAGG TTGTGGAGTT TGGCTTTATT
109801  CTGTGGGCAG TGGAGAACCA GAGAAAGGTT TTCAGTAGGA GAGTGACTCA
109851  GAAGTGCATT TTAGAAAGAT CCCCCTGGAG AGCAGGGAAG TGACTGCAAG
109901  GGGAGAGGGT GGGCAGGGAT TATTCTATGG GTGATGTGCT GTGCCCTGGG
109951  CTGGGCGAGG AGAGGAATTC GGAGATGCTA GGTTGGCAGA ACATGGTGAC
110001  CAGTGGGTCG GGGGATGCAG AGGGAGGACT TGGAGGGGCC CTGGGAGGTG
110051  GGGTCTATGC CACTCCATGA AGAGCTGTGG GGCTCTGTT CAGCATCACC
110101  CTCACCCACA ACAGGTATTG GGTGGAGCCT CTGGCAGGGG TGAGCTCCCT
110151  GCAAAGGTGA GCAAAACAGC TATCTGAGGA TGCCCAGGGA GGAGAGGTGG
```

FIGURE 3-38

```
110201  GAGGAAGGGA GAGAGGACAG ATGGGAGGAG GCTCTGCACA GAGCCTGAGG
110251  ACAGCCCTCA CCAGGTTACA GAACACAAGG CTTGACCCCA TTGGCTTCCT
110301  GTAGCTGTCC TGCTCTCCCA ACTTAATGGT TTCATTTTGC ATTTTATTTA
110351  AATTTCACAA TGATTCTAGC AGATACCATT AGTCTATTCT GCAGCCAAGT
110401  TGTCTAAGGT TTGGAGAGGT TAAGTAATGC ACCAAGGTTA GGATTTGAGC
110451  CCTACCTGTC TGATTCCCCT CCGAGAGCTG TCTGATTCCT TTCTCCTCCT
110501  CTGGGATAGG GGAAGGAGAC TCAGAAGGAC GGGGTCTCCA TCTTCAGTCT
110551  TTGCAAGACT ATTGTAGGGC ATTGGGATGG TGAGCACAAA GTGGGTTGAA
110601  GCCCCAGAGA AAGAGCTGAG AGCTGGGATC AACTGTGTGT GTGCATGTGT
110651  GTGTCTGTGT GTGTGTGAGT TGGAGTAGGG GGCAGGGAGA AAAGAGTGGG
110701  GTGGTGGTGG CTTGTAGTGC AGCTCAGGGC CACCAGGTGG TGTCCAGCCC
110751  TCGCTGTCCT CACCTCCCCA GAGGTCAGAG AAGGATATGG GAGGGGGTGG
110801  GGTGGGGTGA GGGGGACGCG GCGGGGACGG GGGGGACGGT GGTTGGTAGT
110851  CTCACTCCTG TCCATTCACC TACAGGTTGA GTATCCCTTA TCCAAAATGC
110901  TTGGGGCCAG AAGTGTCTCA GATTTAAGAT TTTTTTCGGA TTTTGGAATA
110951  TTTGCATATA CATAATGAGA TATCTTGGGA ATGAGACCCC AGGCTAAACA
111001  GGAAATTCAT TTATGTTTTA TATACACACA GCCTGAAGCA GTTTTATATA
111051  ATATTTTGAA TAATTTTATG CATGAAACAA AGTTTGTGCA CATTGAAGCA
111101  AGTGTGGAAT TTTCCACTTG TGGCATTATG TCGGTGCTAA AAAATGTTTT
111151  AGATTTTGGA GCATTTTGGA TCTCAGAACT TTGCATTAGG AATTGAGGAC
111201  TAAGTCTGAT ATTCTGTCTT ACCCAGATTC CTACCTAAGA GGTCTAGGAA
111251  GTCATGCCCT ACAAACCATA CATTCTCATC AG (SEQ ID NO:3)
```

CHROMOSOME MAP POSITION:
Chromosome 11

ALLELIC VARIANTS (SNPs):

DNA

| Position | Major | Minor |
|---|---|---|
| 254 | G | A |
| 1997 | C | T |
| 2653 | C | A |
| 2986 | G | A |
| 3702 | G | A |
| 3710 | A | G |
| 4661 | G | T |
| 4734 | G | A |
| 5649 | A | G |
| 5957 | A | G |
| 6060 | A | C |
| 6133 | A | G |
| 6692 | A | G C T |
| 6911 | A | G |
| 7541 | C | T |
| 8173 | G | T C A |
| 8694 | A | G T C |
| 9072 | C | G |
| 9426 | – | A G |
| 9426 | A | G C T |
| 9573 | A | G |
| 9826 | C | T |
| 10134 | C | T A G |
| 11014 | C | T |
| 12390 | G | A |
| 13720 | T | – |
| 14701 | C | T A G |
| 15679 | – | T |

FIGURE 3-39

| | | | | |
|---|---|---|---|---|
| 15687 | – | T | | |
| 18322 | – | T | | |
| 18606 | C | T | | |
| 19070 | A | G | | |
| 19470 | A | G | | |
| 19611 | C | A | | |
| 20641 | A | C | | |
| 20642 | A | C | | |
| 21036 | C | T | | |
| 21871 | T | C | | |
| 22907 | G | A | | |
| 23722 | A | G | | |
| 24121 | A | C | | |
| 24553 | G | C | | |
| 25917 | T | C | | |
| 26573 | – | A | | |
| 27525 | T | A | | |
| 27625 | T | C | A | |
| 27833 | C | T | | |
| 27852 | A | G | | |
| 28478 | C | A | | |
| 28514 | T | C | G | |
| 28702 | G | C | | |
| 28859 | A | C | G | T |
| 28960 | C | G | | |
| 29030 | A | G | | |
| 29348 | T | C | | |
| 29973 | T | C | G | A |
| 30153 | C | T | | |
| 30389 | T | C | | |
| 30581 | C | G | | |
| 31147 | G | A | | |
| 31224 | C | T | | |
| 31735 | G | A | T | C |
| 31739 | G | – | | |
| 31742 | G | – | | |
| 31798 | G | C | A | T |
| 31994 | A | G | T | |
| 32324 | A | T | | |
| 32891 | G | A | | |
| 33104 | C | T | | |
| 33296 | C | T | | |
| 33324 | C | G | | |
| 33533 | T | C | | |
| 33852 | A | T | | |
| 33907 | A | C | | |
| 34294 | A | G | | |
| 37090 | C | T | | |
| 37248 | C | T | G | |
| 37355 | A | – | | |
| 37893 | A | G | | |
| 38252 | A | G | C | |
| 38726 | G | T | C | A |
| 40472 | G | C | | |
| 40965 | C | T | | |
| 41664 | G | A | | |
| 41760 | G | T | C | A |
| 42523 | G | A | | |

FIGURE 3-40

| | | |
|---|---|---|
| 42904 | G | A |
| 43382 | - | C A |
| 43386 | - | C G |
| 43387 | - | G |
| 43728 | G | A T |
| 45012 | C | T |
| 45079 | C | T |
| 45247 | A | G C |
| 46267 | T | A |
| 46268 | T | C |
| 46414 | G | A |
| 46822 | G | A C T |
| 47169 | C | T |
| 47214 | G | C A T |
| 47431 | A | G |
| 47773 | G | T G T |
| 47821 | G | A |
| 48186 | C | T |
| 48544 | G | A C |
| 48577 | G | C |
| 48705 | G | A C |
| 48873 | - | C |
| 48874 | - | G C |
| 48876 | - | T |
| 48879 | - | C |
| 48880 | - | T C |
| 48881 | - | A T |
| 49008 | C | T |
| 49259 | G | C |
| 49821 | C | T |
| 52352 | C | T |
| 55378 | G | A |
| 55440 | T | G |
| 55532 | A | G |
| 56039 | T | A |
| 56082 | T | G |
| 56113 | G | C |
| 56425 | G | A |
| 56554 | C | T |
| 57097 | A | G |
| 57284 | G | A |
| 57618 | T | C |
| 57795 | C | T |
| 57796 | A | G |
| 57957 | C | T |
| 58064 | - | A |
| 58069 | - | A |
| 58108 | A | G |
| 58125 | T | C |
| 58171 | G | A |
| 58246 | A | G |
| 59173 | T | A |
| 60931 | G | C |
| 62318 | G | A |
| 62417 | C | T G A |
| 62655 | A | G |
| 62676 | A | G |
| 63504 | G | A |

FIGURE 3-41

| | | |
|---|---|---|
| 63823 | C | T |
| 64793 | T | C |
| 64829 | C | T |
| 65593 | G | C A T |
| 65634 | A | G C |
| 65848 | A | G T |
| 66187 | A | G |
| 66843 | T | C G |
| 66908 | A | G C |
| 67481 | G | A |
| 67637 | C | T |
| 69231 | A | C |
| 69238 | T | C |
| 70821 | G | A |
| 72136 | T | C G |
| 72285 | C | T |
| 72611 | C | A |
| 73103 | C | T |
| 73589 | G | T |
| 73591 | G | C A T |
| 74229 | T | A G C |
| 74478 | T | C |
| 74636 | C | G |
| 75308 | A | C T G |
| 75554 | G | C A T |
| 76209 | G | A |
| 76627 | T | C T C |
| 76767 | C | A |
| 77530 | G | A |
| 78642 | A | G |
| 78774 | A | - |
| 79135 | A | G |
| 79648 | C | T |
| 80969 | C | T A |
| 82103 | G | A |
| 83833 | G | A |
| 84945 | T | C |
| 84985 | A | G |
| 85295 | G | A |
| 89241 | C | T |
| 91827 | A | G C |
| 93127 | C | G |
| 93815 | C | T |
| 96136 | C | T |
| 96831 | T | G |
| 97038 | G | A T C |
| 97110 | G | A T C |
| 98446 | A | G |
| 98618 | G | A |
| 99145 | - | A |
| 99158 | A | - |
| 99278 | C | A |
| 99411 | G | A C |
| 99744 | G | C |
| 99815 | A | G |
| 100604 | G | A |
| 100878 | C | A G T |
| 101440 | A | T |

FIGURE 3-42

| | | | |
|---|---|---|---|
| 101516 | A | T C G | |
| 101994 | A | G | |
| 102173 | T | C | |
| 102239 | G | A C | |
| 102279 | A | G T | |
| 102458 | A | T C G | |
| 102522 | G | T C A | |
| 102687 | A | C G | |
| 103134 | G | T | |
| 103152 | C | A | |
| 103392 | G | A | |
| 103436 | G | T | |
| 104138 | T | C | |
| 104175 | C | T | |
| 104560 | T | G | |
| 104688 | T | C | |
| 105118 | C | T | |
| 105179 | G | A | |
| 106026 | A | G | |
| 106141 | C | G | |
| 106474 | G | A | |
| 106717 | T | C | |
| 107099 | C | T | |
| 107322 | C | G | |
| 108611 | G | C | |
| 108664 | A | G | C |
| 109160 | T | C | G |
| 110512 | G | A | |
| 110746 | A | G | |
| 110781 | A | T | |

Context:

DNA
Position
254   ACGTGGATGAACACCCACCCACACACAGCTCTCTAGGAAAATTGCTCCCCTTCCCTCCTG
CTCCTCCTCCACCCTGTCCTCCCACCACCACCCACTTCCAAATGCTGAGACCAAAGAGAT
GGGCTGGACGGTGCCTCTCACCACTTGTCAGCCTGGGACGCCCTCCTCCCTTTGTGACTA
GCATGCCCTCCTCCCCCTGCCCGTCTGCCTCCCCAGCTCTCTCTGCCTCCCTGTCGCCCT
GCCACCTCCCTGC
[G,A]
TTCCTGTGTATCTGCCCTCCACACAAGTCACTCTGAGGCCTCTCTTTGTTACTCTTGACT
CTGAAGTGGAAACTGCTCCTCCCAGCTCTCCTGAGAGGCTCAGGATGGGGACCTGACCTC
ATAGGGCTGATGGAGGCATAGGGACAAGTGAAAGGGACCCCAGGTCCCGAATCTCCTCAG
CTCCTGTCACCTTCAGTCCCTCCTATTGGGTTAGGGGAGGGCTGTGTGCCTGGCACCATG
GAGACCAGTGTCATGGCAACACAGTTCGGGTGGGCACAGCTTCCTCCTCCTGGGGTGTGG 1997   GGGGCCACTTCTGCCCTGACCCATCCCTGCTGGAATTCCACATTCCTGGGGGCCCTCCCC
AGAGTCACAAGCTATATGTACAGCCTTCTCTTGTGGGCTGCTGTCTCAGTTGGAGGAGGA
AGGAGAGGTGGAAGAGTATGAAGAGGGGGAAGTAGTCCGGTGGGGCAATGGCCACCGTCT
TTGGTCCTAGGCTCAGCCTCGCCCTTCACTCACTGGGTTACCTGGGCACCCCTCTGACCT
CAGTTTTCCCATCTGCACAGTGAAGGATTAGATTAACTGGCTCTAGCGTCTCATTCTCTC
[C,T]
GATTTATAACCCTGGAGATGATCTCAACCTGAGGCTGAAGGCACTTCCGAGTGTCTGGCC
CAGCCGCGTTCCAGGCTGACTTCCCTCCCTCTTTTCTCTGCCATCCCTCCTAGACCAATG
CAGCCACCCCCACCCACAAGACAAAAGAGGCAGGAGAGGGCCCTGGACTCAGCTGGGGCT
GGGCGGCTTCTCCCTTCCCTGAACTCGCCATCTGTTCCAGCCCCCCAGCCCCCTGCCTAG
CAGCCATGGGTAGGTCACTGCCCTCACCTGGGGTCACCCCTTCCTCCCCGGAGAGCTCTG

FIGURE 3-43

2653
CCACCTTCCTGAGGTGTTGAAGAAGCTGCTCCACCTTGGAACTACTATAGGGGCTGTGGT
GGCCTTTCATTCCTTTATCAGCAAAAGCTTTTGTCACTTGTGTGGTGGGGGACATGCTTA
GTGTGAGAATGCAGAGACCCATGCCAGGCCCTACCCAAGGACATGGTGCTCCTTCAGCCA
TTGTCATCAGAGCCACAGAGGGGAGCTTCCTGGCAGAGGAGGAGTGGGGAGAAGCTGTGG
AATGGCTCCTTGAGCTCCCCACTCCACCCCTTCCCCATGCCTGGGCTCCCATTGCAAAGA
[C,A]
CCAGATGTGGGCTTATCCTGTCCCCCAGCCAGAGGGAGTCACCCAGGGGTGTTCAGGCCA
ACCCTTTGTGAAATCCATGTTCCACCAGTTACCAGCCTTTCTCCGGAGAGCTGAGGGCTG
TCTCACACTGGGTAGTCTCAGCCTGCCCTGGGGTTGGGGGGGTGCTCACAGAGCAGTAAG
CGTCACTGCCTGCATCCCCACACACCTGCATTATCTTGTCTGCAAGACACGTGTGCCCCT
GAGCTGAGCTCTGTTGTGCACCACCCGATTTCCGTCGGCCTCCTTTCTGACTTTTCTCCA

2986
AGGGAGTCACCCAGGGGTGTTCAGGCCAACCCTTTGTGAAATCCATGTTCCACCAGTTAC
CAGCCTTTCTCCGGAGAGCTGAGGGCTGTCTCACACTGGGTAGTCTCAGCCTGCCCTGGG
GTTGGGGGGGTGCTCACAGAGCAGTAAGCGTCACTGCCTGCATCCCCACACACCTGCATT
ATCTTGTCTGCAAGACACGTGTGCCCCTGAGCTGAGCTCTGTTGTGCACCACCCGATTTC
CGTCGGCCTCCTTTCTGACTTTTCTCCATCAACATTTCCTGCTTGGGCCTGTTGCGGGCT
[G,A]
CCCAAAGGCTGTGGACTGGGGCCGAGGTACATAGGACTTTGGCTTGTCTTTTGAGCTAAC
AGGATCCTGTAGAAGAAATGAGATGAGCCTGAGAGGGGGTCGGGGGGTGAGACATTAGGG
AAGGGAGAGGCCACCAAGGGTCTCTAGCCCAGAATCCAATGCCCCTTCCTGCCTACCTGT
CCTTGTGGGTGGGAGGCAGGGTGTGTGCTGACTGCCCAGCAATGGTGGGCTAGGATTTG
GGATAGGCAGAGAAAAGGAAGAGGAGGGGGAAGTCGGCCTGGGAGGAGAAACACTGTACA

3702
AGGAGCTTTGGCCTTTATCCTGAGGGCACTGGGGAGCCCTGCAAAGGTTTTGAGAGGGAAT
TCCATTACCAGATAGATGTCTTTGGAAGCCGCCTCTAGGTGCAAGGAGGAGGTGGAGTAG
AGAGGTTGACCTGGGGTAAGGGTTGGAGCATGACCAGGGGAGGGGGAAGGAAGCAGGGGG
TGGGGATGGAGGGAGTGGATGGATCTAAGAGAATCTACTGTCCTTTGGAACAAACGATAC
AGGAAGTGTAGGAGAGGGATGGGGCAAGGCGACTTTGAAGTGTCCAGCTCAGAGATTGGA
[G,A]
GTTTGCTGATGCCTTTGGGAGGCCAAGGCAGGCAGATCACGAGGTCAGGAGTTGAAGACC
AGCCTGGCCAATATGGTGAAACCCCGTCTCTACTAAAAATACAAAAATTAGCCGGGCGTG
GTGCGGGTGCCTGTAGTCCCAGCTACTTAGGAGGCTGAGGCAGGAGAATTGCTTGAACCC
GGGAGGCAGAGGTTGCAGTGAGCCCAGATCGCACCACTGCACTCCCCACTCCACCCCTTC
CCCATGCCTGGGTGACAGAGCGAGACTCCGTCTCAAAAACAAAAACAAAAACCCAAAAAAC

3710
GGCCTTTATCCTGAGGGCACTGGGGAGCCCTGCAAAGGTTTTGAGAGGGAATTCCATTAC
CAGATAGATGTCTTTGGAAGCCGCCTCTAGGTGCAAGGAGGAGGTGGAGTAGAGAGGTTG
ACCTGGGGTAAGGGTTGGAGCATGACCAGGGGAGGGGGAAGGAAGCAGGGGGTGGGGATG
GAGGGAGTGGATGGATCTAAGAGAATCTACTGTCCTTTGGAACAAACGATACAGGAAGTG
TAGGAGAGGGATGGGGCAAGGCGACTTTGAAGTGTCCAGCTCAGAGATTGGAGGTTTGCT
[A,G]
ATGCCTTTGGGAGGCCAAGGCAGGCAGATCACGAGGTCAGGAGTTGAAGACCAGCCTGGC
CAATATGGTGAAACCCCGTCTCTACTAAAAATACAAAAATTAGCCGGGCGTGGTGCGGGT
GCCTGTAGTCCCAGCTACTTAGGAGGCTGAGGCAGGAGAATTGCTTGAACCCGGGAGGCA
GAGGTTGCAGTGAGCCCAGATCGCACCACTGCACTCCCCACTCCACCCCTTCCCCATGCC
TGGGTGACAGAGCGAGACTCCGTCTCAAAAACAAAAACAAAAACCCAAAAAACAAAAAACT

4661
GAGAAGAAGCCGCCTTCTTCGGCAAAGAGGTAGCTGAAGCCTGTGGAGCCTGCAGTCCTC
TCAAGGCTATGGGGCAGCGCGGAGGCCGGATTCCAGAACTGAATCTTCCCATCGCTTTG
GGCAGCCACCCTACCTCCCAGGAGCATCCTTCCTGCCATCCCACCTCCAGTTCCCCAGCT
AACAAAAAACGGTGTTTCTTGACTCCCGGCAGGGCGGCGGGGCGGGCAGGTCTTGTGAAC
ACGGCTCGCAGGGTTCAGCACCCTGGAGAGAGGCCTGTGGCCGGGGCGGGGCCTGCGGCG
[G,T]
GGGTAGGGGCGCGCAGTCAGAGCAGTCGGGCCTTTGGCTCCGTCTGGGAGCGGTCTTGCA
GGCAGGCAATTGGTGGAGGAGGGAAAAACAATCTTGGATTTTCTCCAGCTCTCTCCCCTT
TATGCACCTCCCCCATCCCGGCACTGGCCTACAGGAGCCCCTATCCCAGCATTTGGGGCT

FIGURE 3-44

```
           ATTACTCTCCTGACGACTTCAGGAAATGAGATGGGAGGAGAGGGGCAACTATTTACTGGG
           AACTTTTCAGACATTCCCAAAACCTCACAACCTTTTGAGCTTGGAATTCGTGACCCCATA

4734       GGCAGCGCGGAGGCCGGATTCCAGAACTGAATCTTCCCATCGCTTTGGGCAGCCACCCTA
           CCTCCCAGGAGCATCCTTCCTGCCATCCCACCTCCAGTTCCCCAGCTAACAAAAAACGGT
           GTTTCTTGACTCCCGGCAGGGCGGCGGGGCGGGCAGGTCTTGTGAACACGGCTCGCAGGG
           TTCAGCACCCTGGAGAGAGGCCTGTGGCCGGGGCGGGGCCTGCGGCGGGGGTAGGGGCGC
           GCAGTCAGAGCAGTCGGGCCTTTGGCTCCGTCTGGGAGCGGTCTTGCAGGCAGGCAATTG
           [G,A]
           TGGAGGAGGGAAAAACAATCTTGGATTTTTCTCCAGCTCTCTCCCCTTTATGCACCTCCCC
           CATCCCGGCACTGGCCTACAGGAGCCCCTATCCCAGCATTTGGGGCTATTACTCTCCTGA
           CGACTTCAGGAAATGAGATGGGAGGAGAGGGGCAACTATTTACTGGGAACTTTTCAGACA
           TTCCCAAAACCTCACAACCTTTTGAGCTTGGAATTCGTGACCCCATATTTCAGATGAGGA
           AACTAAATTGAAGTTCAGGAAGGTGAAATACCTTGCCTAGGCACTTGGCAGAGCTGGGAT

5649       TTCTTGCTGCCAGGTTCCTCCGACCAGTGAGCAGGTTCCCAGGACATGAAGGGGAGCTGT
           GAGGGAGCAGGACGCCATGGTCCAGGGCTGCAGCTTCCTGAGCCCAGAGAATGCCTTCCT
           AGCTGTCAGGAATGGAGCAGCGAGGCCCCAGTGATAGGTGAGGTGGAGAAGCAAGACATG
           AGTTCTGGGCTGGCTCAGCTGCTTTACAACCAGCCTGGGCCTCGTTCCCTTTGAGAAAAT
           GGTTTGCCCAGAGTTCAGAGATCTAAAATTCTATGATGCCTTCTGGGGCCACAGTGGGAA
           [A,G]
           CAAAGACTCCTCATATTTTCTTTCCTGACACTTCCCAGGCCACAAGACAACTGCTTTCTG
           CAGCACCCAGCCTGGGCAGGCCATCTACACAAGCTCAGTCATTTCTGACCTTGCCCCCTC
           CACCGTGCACCCCCATGTTCTTCAACATGGGTCAGGTTTCTATTCAGCCTCAGGGACTTC
           TCTGCTTGAAGCCTGTTGTGTGGCGGGGAGGTATTCTCCCCACAGCTCAGAGAGATGGGG
           TTGCTGTGGAGGGTTTGCTGTAGCTCCTCTACCCTGGAATATACCCTCTTCTGCCTTAAA

5957       TCCTCATATTTTCTTTCCTGACACTTCCCAGGCCACAAGACAACTGCTTTCTGCAGCACC
           CAGCCTGGGCAGGCCATCTACACAAGCTCAGTCATTTCTGACCTTGCCCCCTCCACCGTG
           CACCCCCATGTTCTTCAACATGGGTCAGGTTTCTATTCAGCCTCAGGGACTTCTCTGCTT
           GAAGCCTGTTGTGTGGCGGGGAGGTATTCTCCCCACAGCTCAGAGAGATGGGGTTGCTGT
           GGAGGGTTTGCTGTAGCTCCTCTACCCTGGAATATACCCTCTTCTGCCTTAAAAGACCCA
           [A,G]
           CTTGGACCCTCTCTTCCAGAAATGCTTGCTAACCGCCCCCCCACCACCCAAACTAGGTCA
           GGGGTCCCTCTGGGCTTCACAGACCCTGTGCTTCTTTCTGTCACAGCCTGCAAGTCTCCC
           CTCCCCACTCCCCAGCCCGAGTGCTTCTCTGAGACAAGGGATAGTGTGAGCCATGAGCTC
           AGCCACTGGTAGGCCAATGAATAAGTAAGTTAATGGTGAAGCCAGGATCCAAATCCCCAT
           TTCCTGCCTCAAGGTGTGGAGCTGTTTCTCCTGCATACAATAGTAGCTCTGCTGTGACAA

6060       TTGCCCCCTCCACCGTGCACCCCCATGTTCTTCAACATGGGTCAGGTTTCTATTCAGCCT
           CAGGGACTTCTCTGCTTGAAGCCTGTTGTGTGGCGGGGAGGTATTCTCCCCACAGCTCAG
           AGAGATGGGGTTGCTGTGGAGGGTTTGCTGTAGCTCCTCTACCCTGGAATATACCCTCTT
           CTGCCTTAAAAGACCCAACTTGGACCCTCTCTTCCAGAAATGCTTGCTAACCGCCCCCCC
           ACCACCCAAACTAGGTCAGGGGTCCCTCTGGGCTTCACAGACCCTGTGCTTCTTTCTGTC
           [A,C]
           CAGCCTGCAAGTCTCCCCTCCCCACTCCCCAGCCCGAGTGCTTCTCTGAGACAAGGGATA
           GTGTGAGCCATGAGCTCAGCCACTGGTAGGCCAATGAATAAGTAAGTTAATGGTGAAGCC
           AGGATCCAAATCCCCATTTCCTGCCTCAAGGTGTGGAGCTGTTTCTCCTGCATACAATAG
           TAGCTCTGCTGTGACAACTCTCTATCTGTCCTAGGGCCTAAAATGCCTCTATTTCACTAG
           GTTATAGCTTTATCCTAGGGAGTCCTCTTTGGAAGCAGGGTGGGGGTGCAACAGGCCTTC

6133       GCTTGAAGCCTGTTGTGTGGCGGGGAGGTATTCTCCCCACAGCTCAGAGAGATGGGGTTG
           CTGTGGAGGGTTTGCTGTAGCTCCTCTACCCTGGAATATACCCTCTTCTGCCTTAAAAGA
           CCCAACTTGGACCCTCTCTTCCAGAAATGCTTGCTAACCGCCCCCCCACCACCCAAACTA
           GGTCAGGGGTCCCTCTGGGCTTCACAGACCCTGTGCTTCTTTCTGTCACAGCCTGCAAGT
           CTCCCCTCCCCACTCCCCAGCCCGAGTGCTTCTCTGAGACAAGGGATAGTGTGAGCCATG
           [A,G]
           GCTCAGCCACTGGTAGGCCAATGAATAAGTAAGTTAATGGTGAAGCCAGGATCCAAATCC
```

FIGURE 3-45

```
CCATTTCCTGCCCTCAAGGTGTGGAGCTGTTTCTCCTGCATACAATAGTAGCTCTGCTGTG
ACAAACTCTCTATCTGTCCTAGGGCCTAAAATGCCTCTATTTCACTAGGTTATAGCTTTAT
CCTAGGGAGTCCTCTTTGGAAGCAGGGTGGGGGTGCAACAGGCCTTCCCCCATGCCTGTA
GTCTGTGAGCAGCGAAGGCCATGTGGGCAGGCTGTGGCCTAGGTCTCCACAGATCCTGG
```

6692
```
CCATGTGGGGCAGGCTGTGGCCTAGGTCTCCACAGATCCTGGTAGAAGTCCATGCTCACG
CATCAGCTCCAAGTCCCAGCTAAACCAAGCCACCAAGAGGTGGGCCCTGTGACAAGGCTC
TGAGTCCAAAGGCCATCAGTAAAGCCCCCTAAGTCTTCCGTGGACCCAGCTCCAGGCTGG
GATGCACGCTAGGAGATGATACACACCGGGTGAGGGAGCCCAGAGGAGAGGGCAGCTAGC
TGTGCATGGAGGCCTGATCTCTCAGACTTGAGGGCACAAGCGTGTCCCCTCATCCTGAAG
[A,G,C,T]
CTTCTGCGATGGGGCAGCAGAGGGTCTGGGTCTGCTGCCCCTCAAGTCCCCAGCCCCATC
CTAGCCCATGAGGATTGTAAATCCCTCGTCCTCTCCCCTCTCTCCTCTGTCAGCCACTCC
CCTTTCCCCCCTACCCCACTCTCTTTCTATTTCTGCCTCTGATTTTTTTTCCTTTTCTGCC
TTTGTTCCTCTGTGTGTGTGTTTCTCTATGCCTCTCTGATCTCTTTGTACTTCCATCTTG
ATCTCGCTAAGGCTCTGATCCCTCTCTCCTCTCCCTCTTCATGTGTTACTGTCCCCCTTC
```

6911
```
CCAGAGGAGAGGGCAGCTAGCTGTGCATGGAGGCCTGATCTCTCAGACTTGAGGGCACAA
GCGTGTCCCCTCATCCTGAAGGCTTCTGCGATGGGGCAGCAGAGGGTCTGGGTCTGCTGC
CCCTCAAGTCCCCAGCCCCATCCTAGCCCATGAGGATTGTAAATCCCTCGTCCTCTCCCC
TCTCTCCTCTGTCAGCCACTCCCCTTTCCCCCTACCCCACTCTCTTTCTATTTCTGCCTC
TGATTTTTTTTCCTTTTCTGCCTTTGTTCCTCTGTGTGTGTGTTTCTCTATGCCTCTCTG
[A,G]
TCTCTTTGTACTTCCATCTTGATCTCGCTAAGGCTCTGATCCCTCTCTCCTCTCCCTCTT
CATGTGTTACTGTCCCCCTTCCTGTCTCTGTTTATCTCTCAGTCTCTCTGTCTGTGAGTC
TTTTTTCCTCTCTCCCAGTCAGACTCTCTCTCTACCCCTCCCTCTCTCCCTCTCTCCCTC
TCTGTCTGGGCCTCTCTCTGTTCCTCCTCCCTCCTCCCTCCCCCTTCTGCATTATCAGAC
CTGCTCCAACCTCCTCCCAGAGCCAGCCGAGCAGCAGAGGCAGTGGCAGCGGGAGAGGCG
```

7541
```
GGTGTTGAGTCCAGGCTGAGTAGGGGGCAGCCCACTGCTCTTGGTCCCTGTGCCTGCTGG
GGGTGCCCTGCCCTGAACTCCAGGCAGCGGGGACAGGGCGAGGTGCCACCTTAGTCTGGC
TGGGGAGGCGGACGATGAGGAGTGATGGGGCAGGCATGCGGCCACTCCATCCTCTGCAGG
AGCCAGCAGTACCCGGCAGCGCGACCGGCTGAGCCGTGAGTATAGTGAGGGGCTGGGGTG
GTGAGCGGCTGTGAGAGGTGCCACAGACAGGGTCCTGGGAGTCCCTCCAAGGAGCTGGGG
[C,T]
TGGCATGGAGCTGAGCCACGTGGAAGGATCGATCCTGTTCCTGGGCACCCCTCCTCCCCG
CGTTGCCAGACTGCAGCCTGGGGTGGGGGCAGGTTACCTCTGAGCAGAATGAGGGTGTCT
AACGTCAACCTAGTAGGTGATGAGGCTGGGGTCCCATGGAAGGGGCTGCTGGTTGGAGGA
GGGGCTGATAATGAACCTGAACCGCTTCTTCAAGGGCTGAGGGTGTATGTGGGGAGGGGG
AGGTCTGCCAAGTAGTTGGGAGGAGCTCTCGGGGCTGCAATAGGCTGGTTCAGGACCCTG
```

8173
```
ATGTGTGTGTGAAGGAGGTGGGGAGGGGGAAAGATGGAGAAAATATGAATAAGAGTGGCC
CTGGAGCAAGAGAGGGTTAGAGGTAACCACCTTCCATGGAATTGGGAATTGGGGTTCAGG
GACACCACTTTATGAAACTTTACCCCAAAGCGTCTGTCCCAGGATAGGGTTCTACGGAGC
CAGATGGAATATGGTGCCAGCCTCGTGTGTGTCCACGTGCAGGGGGGTGCATGTGCAAGT
GAGTGGGGGCGCCGTGGCGACACCCCTCTACTAAGGGCTGCCGAGGTGGTAGGCAGGGT
[G,T,C,A]
TGTGTGTGTGTGTGTGTGTGTGTGTATACATGTGGAATGTAAGGGACATGTTGGGTGT
AGAGGGGCCTGTAGAGCTCTAGGGTCCTTGGTGGTTGGATGTAAAGCAGCCTGTCAGAGT
TTGTGATCATCCCTGTGTGAGTGAGAGTTTATTCGCATGTGTCTGAGTGTGAGTGCAGGT
TGGTCTGCATATGTATGTAGGTGTGTCTATTAGGTTGAGTTTGTATATTATGTGTGTTGT
GTCTGCAAAATAGAGTGAATCAGTGTGCATTTTTTATCTGTTCCATGTGCATTTATGTGT
```

8694
```
TTGTATATTATGTGTGTTGTGTCTGCAAAATAGAGTGAATCAGTGTGCATTTTTTATCTG
TTCCATGTGCATTTATGTGTGTGTATTTGTTAGTGTGTGAATAATAGCATTGCTGTGTGT
GGAGGTGGATGTGGCTGTGTGCGTATAAGTATTCTGGTGTGGGTGTGTGATCATGGTGCT
AGTGTGTATATCGGTGCTTCTGTGGCTGGTGTGTGTGTGTATCTATATGTGTGTATTCAT
CTGAGTGTGTGTGGGTGGCTGTTTCCTTCCCCTGGCAATTGAGGATACAGCTGGGACACC
```

FIGURE 3-46

```
                [A,G,T,C]
                TGGCCCACTGATGCAGGGCAGGGAGGGGCTGAATGTATGACCGCCTCTTTGAACTCAGGA
                CAATTCATTCTACACCCTGTGGGAAAGATGCAGAAAAGAAATAGGCAATAATGACTCTGC
                CCTCTGGGGCTTCCTAAGCTTCTTAGACATAAAATAGCTTGAGAATAATTAAGCAGTAGA
                GATCAACGTCATGCTAACAGGTGGGGGTGGGGTGGGAACTGCATAAGCAAAGGCCCTGGG
                CTGGGCATGTCCTGGAGCAGTGAAGACACTGTATAGAGTGGGGGGCAGGCAGGACCCACA

9072            TGTGGGAAAGATGCAGAAAAGAAATAGGCAATAATGACTCTGCCCTCTGGGGCTTCCTAA
                GCTTCTTAGACATAAAATAGCTTGAGAATAATTAAGCAGTAGAGATCAACGTCATGCTAA
                CAGGTGGGGGTGGGGTGGGAACTGCATAAGCAAAGGCCCTGGGCTGGGCATGTCCTGGAG
                CAGTGAAGACACTGTATAGAGTGGGGGGCAGGCAGGACCCACATTCAATAGAACTTTAAG
                ATCCAGGACTCTTAGGCTTTATCCAGAGAGCCCTGGGGAGCCCAGAAAGGTTTTATATAG
                [C,G]
                GGAGAGACATGATCAGATTTGGGTTCTAGAAACCTGCCCTGGGCCAGGCATGGTGGCTCA
                TGCCTGTAATCCCATCACTTTGGGAGGCAGAAGCAGGTGGATCACTTGAGGCCAGGAGTT
                TGAGACGAGACTGGCCAACATGGTGAAACCCAGTGTCTATTAGAAATACAATAAAATTAG
                CTGGGTGTGGTGGCACACGCCTGTAGTCCCAGCTACTTAGAAGGCTGAGGCATGAGAATA
                TGAGAATCGCTTGAACTTGGGAGGTGGAGGTTGCAGTGAGCTGAGATTGCCTTACTGCAC

9426            TGGCTCATGCCTGTAATCCCATCACTTTGGGAGGCAGAAGCAGGTGGATCACTTGAGGCC
                AGGAGTTTGAGACGAGACTGGCCAACATGGTGAAACCCAGTGTCTATTAGAAATACAATA
                AAATTAGCTGGGTGTGGTGGCACACGCCTGTAGTCCCAGCTACTTAGAAGGCTGAGGCAT
                GAGAATATGAGAATCGCTTGAACTTGGGAGGTGGAGGTTGCAGTGAGCTGAGATTGCCTT
                ACTGCACTTTAGCCTGGGGGTGACAAAGTGAGACTCTGTCTCAAAAAAAGAAAAAAAAAA
                [-,A,G]
                AAGAAGAAAAATAAAGAAACCTGCCTCGGTGGCATTGTCTGGGTTGAACTGGAAGAGAGA
                GGTGGGGCCAGGAGGCTAGAGTGGAGGCCAAGCCAATACAGGGGTCAGTGAGTTCTGGAG
                CTTTTTGAGAACTTGGGAAAGGCTGGATAGATGAGAACAGGGAAGGGAATGTCTAGGTGG
                CTCAGGCTTGGACTGGGGTCAGGGGTGTAGTGCAGACATCTCAGTAAGTCAGGATCTCAT
                GAGGGAAAAGGCTCATGGAAGGCTCAGGAAAGCTGGGCGTGGGTGGGCTGAGGTAGTGGG

9426            TGGCTCATGCCTGTAATCCCATCACTTTGGGAGGCAGAAGCAGGTGGATCACTTGAGGCC
                AGGAGTTTGAGACGAGACTGGCCAACATGGTGAAACCCAGTGTCTATTAGAAATACAATA
                AAATTAGCTGGGTGTGGTGGCACACGCCTGTAGTCCCAGCTACTTAGAAGGCTGAGGCAT
                GAGAATATGAGAATCGCTTGAACTTGGGAGGTGGAGGTTGCAGTGAGCTGAGATTGCCTT
                ACTGCACTTTAGCCTGGGGGTGACAAAGTGAGACTCTGTCTCAAAAAAAGAAAAAAAAAA
                [-,A,G]
                AAGAAGAAAAATAAAGAAACCTGCCTCGGTGGCATTGTCTGGGTTGAACTGGAAGAGAGA
                GGTGGGGCCAGGAGGCTAGAGTGGAGGCCAAGCCAATACAGGGGTCAGTGAGTTCTGGAG
                CTTTTTGAGAACTTGGGAAAGGCTGGATAGATGAGAACAGGGAAGGGAATGTCTAGGTGG
                CTCAGGCTTGGACTGGGGTCAGGGGTGTAGTGCAGACATCTCAGTAAGTCAGGATCTCAT
                GAGGGAAAAGGCTCATGGAAGGCTCAGGAAAGCTGGGCGTGGGTGGGCTGAGGTAGTGGG

9426            TGGCTCATGCCTGTAATCCCATCACTTTGGGAGGCAGAAGCAGGTGGATCACTTGAGGCC
                AGGAGTTTGAGACGAGACTGGCCAACATGGTGAAACCCAGTGTCTATTAGAAATACAATA
                AAATTAGCTGGGTGTGGTGGCACACGCCTGTAGTCCCAGCTACTTAGAAGGCTGAGGCAT
                GAGAATATGAGAATCGCTTGAACTTGGGAGGTGGAGGTTGCAGTGAGCTGAGATTGCCTT
                ACTGCACTTTAGCCTGGGGGTGACAAAGTGAGACTCTGTCTCAAAAAAAGAAAAAAAAAA
                [-,A,G]
                AAGAAGAAAAATAAAGAAACCTGCCTCGGTGGCATTGTCTGGGTTGAACTGGAAGAGAGA
                GGTGGGGCCAGGAGGCTAGAGTGGAGGCCAAGCCAATACAGGGGTCAGTGAGTTCTGGAG
                CTTTTTGAGAACTTGGGAAAGGCTGGATAGATGAGAACAGGGAAGGGAATGTCTAGGTGG
                CTCAGGCTTGGACTGGGTCAGGGGTGTAGTGCAGACATCTCAGTAAGTCAGGATCTCAT
                GAGGGAAAAGGCTCATGGAAGGCTCAGGAAAGCTGGGCGTGGGTGGGCTGAGGTAGTGGG

9426            TGGCTCATGCCTGTAATCCCATCACTTTGGGAGGCAGAAGCAGGTGGATCACTTGAGGCC
                AGGAGTTTGAGACGAGACTGGCCAACATGGTGAAACCCAGTGTCTATTAGAAATACAATA
                AAATTAGCTGGGTGTGGTGGCACACGCCTGTAGTCCCAGCTACTTAGAAGGCTGAGGCAT
```

FIGURE 3-47

```
        GAGAATATGAGAATCGCTTGAACTTGGGAGGTGGAGGTTGCAGTGAGCTGAGATTGCCTTT
        ACTGCACTTTAGCCTGGGGGTGACAAAGTGAGACTCTGTCTCAAAAAAAGAAAAAAAAAA
        [A,GsC,T]
        AAGAAGAAAAATAAAGAAACCTGCCTCGGTGGCATTGTCTGGGTTGAACTGGAAGAGAGA
        GGTGGGGCCAGGAGGCTAGAGTGGAGGCCAAGCCAATACAGGGGTCAGTGAGTTCTGGAG
        CTTTTTGAGAACTTGGGAAAGGCTGGATAGATGAGAACAGGGAAGGGAATGTCTAGGTGG
        CTCAGGCTTGGACTGGGGTCAGGGGTGTAGTGCAGACATCTCAGTAAGTCAGGATCTCAT
        GAGGGAAAAGGCTCATGGAAGGCTCAGGAAAGCTGGGCGTGGGTGGGCTGAGGTAGTGGG

9573    CTGTAGTCCCAGCTACTTAGAAGGCTGAGGCATGAGAATATGAGAATCGCTTGAACTTGG
        GAGGTGGAGGTTGCAGTGAGCTGAGATTGCCTTACTGCACTTTAGCCTGGGGGTGACAAA
        GTGAGACTCTGTCTCAAAAAAAGAAAAAAAAAAGAAGAAGAAAATAAAGAAACCTGCCT
        CGGTGGCATTGTCTGGGTTGAACTGGAAGAGAGAGGTGGGGCCAGGAGGCTAGAGTGGAG
        GCCAAGCCAATACAGGGGTCAGTGAGTTCTGGAGCTTTTTGAGAACTTGGGAAAGGCTGG
        [A,G]
        TAGATGAGAACAGGGAAGGGAATGTCTAGGTGGCTCAGGCTTGGACTGGGGTCAGGGGTG
        TAGTGCAGACATCTCAGTAAGTCAGGATCTCATGAGGGAAAAGGCTCATGGAAGGCTCAG
        GAAAGCTGGGCGTGGGTGGGCTGAGGTAGTGGGAGAGATCTTTGTAGTGTTTCTAGCTAG
        GATGCAGAGGGTCAGAGATCATGGAGCCATCTCTTGCCAGACAGGGAAACTGAGACTATG
        GCTTCATCACTATCCTTTGGCTGCAAGGCTGGGGCTCAACCTCTTCATCAGACCTGACCC

9826    AGGGGTCAGTGAGTTCTGGAGCTTTTTGAGAACTTGGGAAAGGCTGGATAGATGAGAACA
        GGGAAGGGAATGTCTAGGTGGCTCAGGCTTGGACTGGGGTCAGGGGTGTAGTGCAGACAT
        CTCAGTAAGTCAGGATCTCATGAGGGAAAAGGCTCATGGAAGGCTCAGGAAAGCTGGGCG
        TGGGTGGGCTGAGGTAGTGGGAGAGATCTTTGTAGTGTTTCTAGCTAGGATGCAGAGGGT
        CAGAGATCATGGAGCCATCTCTTGCCAGACAGGGAAACTGAGACTATGGCTTCATCACTA
        [C,T]
        CCTTTGGCTGCAAGGCTGGGGCTCAACCTCTTCATCAGACCTGACCCTCAATATCATTCT
        CCTTCAGGCCCTGCCCGGAACCTCTTGGTTGCTGAGCTTGGTCAGCTCAGTGAGGGTTAA
        TTGTCTTTATGCTCCCTGCACCCCCACCCCCCGCAGTCATTCCCCCTGCCCACCAAGCAG
        CTCCTGCCACTCTTCCTGCTTCCCACTCCAGCCTCCTGTCCCCAGGGACTGCTGATGGCT
        TGGCTGGGATCTAGCCAAATGGTGGGGGGTGGGGCGGGGGTGGGGGGAAGAGCTCCCAG

10134   CTGCAAGGCTGGGGCTCAACCTCTTCATCAGACCTGACCCTCAATATCATTCTCCTTCAG
        GCCCTGCCCGGAACCTCTTGGTTGCTGAGCTTGGTCAGCTCAGTGAGGGTTAATTGTCTT
        TATGCTCCCTGCACCCCCACCCCCCGCAGTCATTCCCCCTGCCCACCAAGCAGCTCCTGC
        CACTCTTCCTGCTTCCCACTCCAGCCTCCTGTCCCCAGGGACTGCTGATGGCTTGGCTGG
        GATCTAGCCAAATGGTGGGGGGTGGGGCGGGGGTGGGGGGAAGAGCTCCCAGCAGTCCT
        [C,T,A,G]
        TACCCCTTGGTCTTAATGGACTGGGAGTCTCACCCTCAGCCATGCTGCTGTCAGGCCAGG
        CCTGCGCTCCCCGGGCTTCTGCTGCTTGGGCCTATGAAATCTCCCGACTCAGCATGATTC
        CATTGCTGCATTCATTCATTCAACCACTCAACAGGAACTTCTCAGTAGCTGCTTGGTGCC
        CACTTGGCTTGTCACCGGGGACACAGAGCAGACACTGACTGAGTCCCTGTTCTCAGGGAG
        TGCCCAGTCTGATGAAGGAGAAAGAAATGGAAAGCTGCAACCCTACAGGGTGAGCAGTGC

11014   GACATAGGATGTTCATCTCTTCCCTCCTGGGCAGCCCTTCCCTTGTGGTGGTTATATCTG
        TCCTGGGTCTTCTCCGCAGGGCCCAGCAACTCCAGGCTACCCAGCCTGGCCTTATGTCCT
        TTCTCCGTCCTGTGTCACTGTCCCCTGAAGTAGGGCCAGGCTGGGGCACAATGATCCAGG
        AGTGGCAAGAACACATCTAGGCAGAGAGTGGGAGAAATGCGCAGCCTTTATTAACAAAAA
        TCTGAGATGGGTGCAGGCCCTGACTCCTCTCCAAAAATAATGATAAAGAAGCAGGCATGG
        [C,T]
        CAAATAAGGGAGTGAGGACAGACAGCAGGAAGAACTTCCTACCAATGCAGAAGGGCTGTG
        AGTCTCTTGGTTTTATGAGAGTGGGCTGTACGTGTGAAAGGGAGGGTCTCAGAGGACAAG
        AGGGGGAATTGGAGGCAGAGGCACTGTCAGCCTCTGACTCTCCCATAGGTGAGTGAGTGA
        AGTCATCCAGGGAGAGGGAACAGAGGAGGGAGATCAGGACTCATCATTCATTCATTCAGC
        AGCCGTTCACTGGCCCTACCAAACATGACACCCCTGGGGGCAGATGGACAGAGCCAGTGA

12390   TTTTCACACATTTATCTCCTATTGTTCAGCTGCTTGCTCCCTGGGAAAGGCCAGGTCCCC
```

FIGURE 3-48

```
      AGTGATGTGACCCACTTCTTGAAGTCCCTGAAGTCACCCTTCTCACTGCCCCCCCACCCC
      GAAAAACAGGAGGCAACTGGGGCTTGGTGCAGCAGAACAGATTTGAGTCAAATATCTGGG
      AGGACTTCCCAACAGTGTGGTTGCTGAGATGTGTGGACCCTGGATTTCTGGGCTTTCATT
      CTTTGGATGGTTGCCTTGGGCGCAGAGGAGGCTTTGAAGATAGAGCAGAGAAGGTGGCAG
      [G,A]
      CAGGCTTATGCTCAAATTTCAGCATACTGAAAGATGTACTGTTACTCTGTAGCTGTGTGG
      TCCTGGGCAAGTTACTTAACTTCTCTGAACCTTGTGTGAATAGTGGGGTGGAGATAATTA
      TCCTTTCTTGGCAGGATGATTCTGAAGAATCTGGAAGTGCAGAGCTTAGCCCCTGGCATG
      CGGCAGGTGCTCACAAAGGTTAGCTACTGTCATTATGAACCACCCACGATCAGCCACACT
      TTCAGAAAGATTTAGCGGGGCCTGGAGAGGGAGAGACCAGAGCTAGGAGCTCAGGGCTGT

13720 ATGTGAGACATCTCGGCAGAGGAACAGCTGAGCAGAGAGCTGCTGATTCCAGGCTGAGAG
      TTTGGACTTTGTGTTGTGGCCCACCAGGATCCACCCAAGGGTTTTCTGATTAGAGCTGAG
      CTTTGAGAGAATTGGTCTTGCAGCTTAGGCTGAATGGATTGAACTGGAGAAACCAAAGTC
      AGACTGAGGCTTCTAAATCCCATCCTTGGTGCACCCAGCACTTTGCTGCTGTCCCTCCTC
      CATGCTTCTTCTCAGTTTCTTCCTTCTCCTCTCCTTCATCTTCTTCCCTCACCCTTTTTT
      [T,-]
      TTTTTTTTTTAATAGAGACAGTGTCTTGCTGGCTGGAGTACAGTGGTGCCATAATAGCTC
      ACTGCAGCCTCAAATTCCTGGGCTGAAGCTATCCTCCTGCCTGGGCCTCCCAAAGTGCTG
      GGATTACAGGTGTGAGCCACTGCACCCAGCTCATCTTCCTCTTTCTCTCCTACTCCTCTC
      TGCCTCAGGCTGAGGAGTGATGACTTTTATACCATAGAGCTGTGCTGTAATATCACATGT
      CTCCAGAAGGGGGTGCTGTCACATACAGTCCATTCCAGCCTGAATCTTCGTTGTGTTTGA

14701 AGAGGGTGAGAATGTGTGGGTCAGTGTTCGTATAAAAGTGTGAACATACTCACATGTGTG
      AGCATGTGAGTGTCCTTTTTTTTAGTTTAGTTTTGAGACAGGGTCTCACACTCTCACCCA
      GACTGGAGTGCAGTGGCCGTGATCTCGGCTCACCGCAACCTCCGCATCCCAGGCTCAAGCT
      ATTCTCCTGCCTCAGCCTCCTGAGTAGCTGGGACTACAGGCATGCACCACCACACCTGCA
      TAATTTTTGTATTTTTAGTAGAGATGGGGTTTTCACCATGTTGGCCAGGCTGGTCTTGAAC
      [C,T,A,G]
      CCTGACCTCAAATGATCCACCCACCTTGGCCTCCCAAAGTACTGGGATTACAGGCATGAG
      CCACTGCACCCGGCTGTGACTGTCCATCTTTATGTCTGATTTTGGTAAACAGTTATATGC
      ATGTGACTGTGGCTTGTGTGTGTGTACATGTATGTAGAGTGCCATATACATATGTTCTAG
      TGAAACCGTATGTGTGTTCCCTGTGTATACAGATGCCTGTGTCTCAATGTGAGCACAGGG
      ATGAGGGGATATGTGTGTGTGAAGGCCCAGACACCTGCTGTGCTAACCTTTAAGGCCGCG

15679 GCTGCCCTCCCTCCAGCCCCTAGAGCAGGTGGGGAGCTCAGAGGAGAGCCAAGTCTGTGG
      TGTGAAGCCACCTCCTGCACCTGGCTATTTCCATGCCTCCTGGGCCTCAGAGGCTGCCTT
      TGAAGTTTTTACCAGAGCTTCTGCATGCTGTGAGATTCCTCCTGGGGACGTGTGAAGTCG
      ACTGTTCCATGGAGCATGGAGACTCGATGGAGAGGAGCCCAGTGGTGAAGTGAGGCCAGA
      GGAGGGGCTTCCTCTGGAAGCCTCAATTTCTTCTTTGCAGTAGTTGCTTTTTTTTTCGTG
      [-,T]
      TTTTTTTGTTGTTGTTTTTTAGGTTTTCACCGTTCTAACATTCAAGGCTTTCTCTGTTA
      TCTCTCTTTGAGCTCTTAGTACTGAGACAGTGCTGGGGTTTGGGGCAGTCCTGGAGGCCT
      ATCTGGGCTCAAAGTGAGGGTGGCAGGGCAGTCCCTTAGGGAAAGGGCTGCGTGGGAGAC
      AGGGATGAGCTTCCTGCCCATAGTGGGGAGGCATGAGCAGGGGCTGGACAGCCTGGTTAG
      CAAGGCTGTATACAAGGTACCTACCCTAGTGAGGAAGTTGGTTGCAGATTATCTTGAGTC

15687 CCCTCCAGCCCCTAGAGCAGGTGGGGAGCTCAGAGGAGAGCCAAGTCTGTGGTGTGAAGC
      CACCTCCTGCACCTGGCTATTTCCATGCCTCCTGGGCCTCAGAGGCTGCCTTTGAAGTTT
      TTACCAGAGCTTCTGCATGCTGTGAGATTCCTCCTGGGGACGTGTGAAGTCGACTGTTCC
      ATGGAGCATGGAGACTCGATGGAGAGGAGCCCAGTGGTGAAGTGAGGCCAGAGGAGGGGC
      TTCCTCTGGAAGCCTCAATTTCTTCTTTGCAGTAGTTGCTTTTTTTTTCGTGTTTTTTTT
      [-,T]
      GTTGTTGTTTTTTAGGTTTTCACCGTTCTAACATTCAAGGCTTTCTCTGTTATCTCTCTT
      TGAGCTCTTAGTACTGAGACAGTGCTGGGGTTTGGGGCAGTCCTGGAGGCCTATCTGGGC
      TCAAAGTGAGGGTGGCAGGGCAGTCCCTTAGGGAAAGGGCTGCGTGGGAGACAGGGATGA
      GCTTCCTGCCCATAGTGGGGAGGCATGAGCAGGGGCTGGACAGCCTGGTTAGCAAGGCTG
      TATACAAGGTACCTACCCTAGTGAGGAAGTTGGTTGCAGATTATCTTGAGTCCCTTCAAG
```

FIGURE 3-49

| | |
|---|---|
| 18322 | CCCTTTGCTCTCCTGCCAGTACCCTGACCCTCACTGGCAGAATTTCTCTGGATGCCAGGG<br>GGCAAGGGAGCCCTGGATGAAGCTGCCACTTAGAAGTCGGCCTCTGGGGCACACAACCCA<br>GCAGCAAAAGTTAGAGATTGGATGTGGAGGGACAAAGAGATGATGGGAAACCGAAGAACA<br>GAGAGGGCATGGACTTGCCCAAGGTCACACAGCCTGTTGATATCAGAATTGGAGTCAGAA<br>GCCAGGCTCTGCCTCTGAACACTCACTTTTTTGTTTGTTTGGTTTCTTTTTTTTCTTTC<br>[-,T]<br>TTTTTTTTTTTTTGAGACAGTCTTGCTCTGTCGCCCAGGCTGGAGTGCAGTGGTGCGAT<br>CTTGTCTCACTGCAACCTCCACCTCCTGGGTTCAAGTGATTGTCCTGCCTCAGCCTCCCA<br>AGTAGCTGGGATCACAGGCACCTGCCAGCATGCCCGGCTAATTTTTTGTACTTTTGGTAGA<br>GACGGGGTTTCACCATATTGGCCAGGCTGGTCTCGAACTCCTGCCCCTCAGGTGATCTGCC<br>CGCCTTGACCTCCCAAAGTGCTGGGATTACAGGCGTGAGCCACTGCACCTGGCCTGAACA |
| 18606 | TTCTTTTTTTTTCTTTCTTTTTTTTTTTTTTGAGACAGTCTTGCTCTGTCGCCCAGGCTG<br>GAGTGCAGTGGTGCGATCTTGTCTCACTGCAACCTCCACCTCCTGGGTTCAAGTGATTGT<br>CCTGCCTCAGCCTCCCAAGTAGCTGGGATCACAGGCACCTGCCAGCATGCCCGGCTAATT<br>TTTGTACTTTTGGTAGAGACGGGGTTTCACCATATTGGCCAGGCTGGTCTCGAACTCCTG<br>CCCTCAGGTGATCTGCCCGCCTTGACCTCCCAAAGTGCTGGGATTACAGGCGTGAGCCAC<br>[C,T]<br>GCACCTGGCCTGAACACTCACTTTGTCACATTCACTGAGGTCTCCTGAGTGGACTCATAT<br>GCGCATTATCTACTCTCTGGCTGAGAGCTGCTTCCTGCCGTGATCACCGCGCTCTGTATC<br>TGGGCAGCACAGGGGCTGCTGAAGAATGTCATTCTCAGAACGCAGTGTGCCCTGGAGCCC<br>CCCAAGCCACCTGTTCATTCATCCCAACTGGCCTTGAGGGTGCCCTGGTGTGCCCTGCCT<br>GTGCTTGTCACCCTGGCCATGGAGATGGACCCAAAAGCCCTTGCTCTCCGCTTCATTAGA |
| 19070 | AGTGTGCCCTGGAGCCCCCCAAGCCACCTGTTCATTCATCCCAACTGGCCTTGAGGGTGC<br>CCTGGTGTGCCCTGCCTGTGCTTGTCACCCTGGCCATGGAGATGGACCCAAAAGCCCTTG<br>CTCTCCGCTTCATTAGAGACAGGCACACCCAGACGCAGGCAATCAATTTTGTCGGGTGAG<br>TGCTGGGACCGCTGATGAGGACCCTTCCTGAGGAGGCGATGCTGGGTCTTAGCCTTAAAG<br>AACAACTGAGAGTTTTCCAGGTGGAGGAGAAAAGGAAGGGTATTCCAGGCAAAAATCCCC<br>[A,G]<br>TAAGAGCAAAGGTGTGAGCAGCAAGAAATCAAGGGTGGCAGGTTCAGGGCTCCTGGGCTG<br>GAGGAAGGGCCTGGCGGTGGAGAGGAAGGGAGTGAAGGCCCAGCTCACAAAGGGAAGCAG<br>AGGAAAGTTTAAGCAGGGTCAGGCCATGGTTAGCTTTGGGGTTAGGAAGCTCCAAATGAT<br>GGGTGAAGTAGGGGGGCTAGACCCAGGTGAGAGGCAGTATTGCGGTTGGCCAAGGACACG<br>TGAGTTGCATAAATGGGCCAGAGGAGGGGTGACAGCCGCTACTTCCCGGCTCACCTGCCT |
| 19470 | CCAGCTCACAAAGGGAAGCAGAGGAAAGTTTAAGCAGGGTCAGGCCATGGTTAGCTTTGG<br>GGTTAGGAAGCTCCAAATGATGGGTGAAGTAGGGGGGCTAGACCCAGGTGAGAGGCAGTA<br>TTGCGGTTGGCCAAGGACACGTGAGTTGCATAAATGGGCCAGAGGAGGGGTGACAGCCGC<br>TACTTCCCGGCTCACCTGCCTGAGCTAAGGCCCTAGTTCCTCAGTGTCTGCCCACCAATG<br>CAGGTGTGTGGCAGCTCTAGACCCTCCTCTAGGGACATCCCTCCCTGCCTCATGCTGCCT<br>[A,G]<br>TGGCTTTCACTCTCTGGAGCACTCATCCATGGCACCCATAAGCCACCCCCTCAGACAATG<br>GCCCCTAAAGCAAAACTGTGTCACCGTTGCATATCTCTTGATAACACTCTGACCCCTCCA<br>CTGCCAAATCTGATAAAAGACCTCCCTTTGAAGACCTTCCTCCTGGAGTCGGATCTCAGT<br>CCTTCTTGCTGTCCAGAGCCTGGGCCTTGGGCCTCCCTGGGAGGCGAGTCAGTGAGGGCA<br>GCCCCCTTATGGTGCTGGGAGTTGAGGGACCTTGGCCCAGCCAACTCATCCCTGTTGTGT |
| 19611 | TGAGTTGCATAAATGGGCCAGAGGAGGGGTGACAGCCGCTACTTCCCGGCTCACCTGCCT<br>GAGCTAAGGCCCTAGTTCCTCAGTGTCTGCCCACCAATGCAGGTGTGTGGCAGCTCTAGA<br>CCCTCCTCTAGGGACATCCCTCCCTGCCTCATGCTGCCTATGGCTTTCACTCTCTGGAGC<br>ACTCATCCATGGCACCCATAAGCCACCCCCTCAGACAATGGCCCCTAAAGCAAAACTGTG<br>TCACCGTTGCATATCTCTTGATAACACTCTGACCCCTCCACTGCCAAATCTGATAAAAGA<br>[C,A]<br>CTCCCTTTGAAGACCTTCCTCCTGGAGTCGGATCTCAGTCCTTCTTGCTGTCCAGAGCCT<br>GGGCCTTGGGCCTCCCTGGGAGGCGAGTCAGTGAGGGCAGCCCCCTTATGGTGCTGGGAG<br>TTGAGGGACCTTGGCCCAGCCAACTCATCCCTGTTGTGTCAGCCTCTCTGGGCCTGGGCA |

FIGURE 3-50

```
             GCCAACTCATTTTTCAGTGCTAATTAGCATCTCCCCTGCAGCTTTCTGCCCCACTCTAAGT
             GCTTGACAATCATTAGGTGTTACTGTGTGCAACTGGATCCCAGCTCCGGCACCTCCCTGC

20641  CCCCACCTGTGCAGCGTCTCTCGCCTCTGGGCTGCCGCACATGCTGTTGCCCGGAATTCC
             CTTCCCCAAGGCCCTCCTCTTTTTACCTGGCTAATTCCTGTCATTCTTCAGATCTTCTAG
             GAAGACTTCTGCCTCCTTGATAGGGGCCTTTCCATACTCCCCAGCCTTGGAGTGCTTCCT
             GCCACATGGCATCACTGACTGTTTTCCAATGAGTTTCTGTCAAGTTTTGGGATGAAGGAT
             TTTGCCTGTGCTCGTTGAGGTGGTGACTGTGGGTGTGAGTGGGTGATTAGGGCCAAAAAA
             [A,C]
             CCCCCCAAAAAACTGGACAGAGGCAAATTTGGGGGGAAATGAGTTAGGAATAGCTGTGAG
             GAGCCCCAGCTACTCAGGGCCTCAGAAGATATTTATTTCTGTATTTATTTATTTATTGAG
             ACAGAGTCTTGCTCTGTCACCCAGGCTGGAGGGCAGTGGCGCTATCCTGGCCCACTGCAA
             CCTCCACCTCCCAGGTTCAGGCGATTCTCCTTCCTCAGCCTCCCGAGTAGCTGGGATTAC
             AGGTGCGCACCACCATGCCTGGCTAATTTTTCTATTTTTAGCAGAGACGGGGTTTCACCA

20642  CCCACCTGTGCAGCGTCTCTCGCCTCTGGGCTGCCGCACATGCTGTTGCCCGGAATTCCC
             TTCCCCAAGGCCCTCCTCTTTTTACCTGGCTAATTCCTGTCATTCTTCAGATCTTCTAGG
             AAGACTTCTGCCTCCTTGATAGGGGCCTTTCCATACTCCCCAGCCTTGGAGTGCTTCCTG
             CCACATGGCATCACTGACTGTTTTCCAATGAGTTTCTGTCAAGTTTTGGGATGAAGGATT
             TTGCCTGTGCTCGTTGAGGTGGTGACTGTGGGTGTGAGTGGGTGATTAGGGCCAAAAAAA
             [A,C]
             CCCCCAAAAAACTGGACAGAGGCAAATTTGGGGGGAAATGAGTTAGGAATAGCTGTGAGG
             AGCCCCAGCTACTCAGGGCCTCAGAAGATATTTATTTCTGTATTTATTTATTTATTGAGA
             CAGAGTCTTGCTCTGTCACCCAGGCTGGAGGGCAGTGGCGCTATCCTGGCCCACTGCAAC
             CTCCACCTCCCAGGTTCAGGCGATTCTCCTTCCTCAGCCTCCCGAGTAGCTGGGATTACA
             GGTGCGCACCACCATGCCTGGCTAATTTTTCTATTTTTAGCAGAGACGGGGTTTCACCAT

21036  ATTTCTGTATTTATTTATTTATTGAGACAGAGTCTTGCTCTGTCACCCAGGCTGGAGGGC
             AGTGGCGCTATCCTGGCCCACTGCAACCTCCACCTCCCAGGTTCAGGCGATTCTCCTTCC
             TCAGCCTCCCGAGTAGCTGGGATTACAGGTGCGCACCACCATGCCTGGCTAATTTTTCTA
             TTTTTAGCAGAGACGGGGTTTCACCATGTTGGCCAGGCTGGTCTTCAACTTCTGAGCTCA
             GGTGATCCTCCTGCCTCGGCCTCCCAAAGTGCTGAGATTACAGGTGTGAGCCACTGCACC
             [C,T]
             GACCCTCAGAAGACATTGAAACCCACAGAGAGGACACAGCCAGATGCCCTCTGCCTCATTT
             TCTCAGACCCTGCCTGATTTCTCTTATGTTTCTTCTAGGCTTGCTCCCTGACCCAGTTCC
             CTCCTTCCCAGAGCTGGCCTTGCCCCTTGCCACCTCTCGGAGCTCACACATACTCACTCA
             CCTTCTCTGCTTGGCTGTGCCCTACCCCTACTTCTACGTGCAGTGAAATCCTTGTTATTC
             AAGGCCTGAGGTCAGTGGGCACATCATCCATGCCTGGCGTCCTAACCCGTGCCACTGAGT

21871  AGAGCAGGGAGAAAGCTAATGAGATCAAGGATGTGCAAATGCACTCAGAAGGTGCCTAGT
             GAGTCCTTGCTAACTGGCACTTAGTGAAACAAACACCTCCTGTGTGAGCACCTAATATGT
             GCCTCTGTAGTGGGCTCTGTGACCCGCCCCTCCTTAGTTTCTGCATGGCTGCCAGTTCTG
             CACAGCTGTTACTGCTGTGGGGGCTTAGAAGGTGGGGGTATGACTACTTTTTCTGAATTT
             ATTTTTTAATTTTTTTACATCTGTTTTATGGAGGCATAATTTACATACAGTAAAATCACCAA
             [T,C]
             TTAAAGTGTATAATGAGTTTTGATAAATATATATATGGTCATAACCACCATGACAATTAAGA
             AAAGAATATTTTTATCCTGGCAAACTTCCCTTGTGCCCTTTGTAGTCAGTCCCTTTGAGG
             GGGACTTCTTATAGGAGTGTGAGAAGTACTGGGTTTTCCTTGGGCTGCAAACCTGGGCAC
             ATGGAGTGGGGGTGCCTCCAACATGCTGGAAGTTGCCAGGGAACTGCTGACCCTCTCTGG
             GCCTTGGTTCCTGGCAGAGGCAGTGCAGCCAGGCAGGGGAAGGGATGCTTAGGCCTTGGT

22907  TCTGTGCAAGGTGGGGGTGGAAAAAAGGCTGGGAACTCATGGGAGCACCCCAGGTGTCTG
             CAAGGAGATGAAAGCTGATCCTCCGCCCCACTGAGGTCCTAAGGAAGAAAGGCCGAGTCA
             GAGCTGCAGCAGGAGGGATTCGGATCAGACTCAAGAACACTTCCCAGTGGTGCTTATTTG
             AGAACTGGGACGGCAACACTAGATTGTAAACTCTGTGAGGGCAGGGATTAGGTCTGTGAC
             CGCCTCCTCACCCAGCGGGAGACCAAGAATGAGACTTGGGAGTCAGACACAACTGGGTGT
             [G,A]
             ACTCCTGCCTTTGCGGGTTGCCAGCACGTGGGCTTGGGCAGGTTCCTTTATCACCAGAAG
```

FIGURE 3-51

CTTTGCCGTCTCCTCCACTATAAAGTGGGCACAATAACATCCACCTGCATGCATATTATA
AGGATTGAGTGGGTTAAAATGTGCAAAGCAAGACTTTGTGCTCAGCTGGGCACAGCGGCT
CACACCTGTAATCCCAGTACTTTGGGAGGCTGAGACAGAGTGCTTCAGCCCAGTAGTTTT
GAGACCAGCCTGGGAAACATAGGGAGACCCTGTCTCTTAAAAGAAAAAAAAAATTAGAAG

23722  GCAGTGTGGGCTGGGTGTGGTGTCTCATGCCTGTAATCCCCAGCACTTTGGGAAGCTGAG
GCGGGAGGATCACTTGAGGCCAGGAGTTCAAGACCAGCCTGGGTAACTTAGCGAGATCCC
ATCTCTACTTCAAAAAAAATTTAAAACAGAAAAAATCTAGGGTGTGTGGGGGGCAGGTGG
GGAGGTTGCAGGGGTGCCTCACAGGTGGGAGTCTGGCATTTCTCCTCCAGGCTGAGGAGG
TGGTGACTTCCAGGGAAAGTCCTGGGAGGGATCAGAACCACAGCTCCAGCCTGCTTGGAT
[A,G]
AGGGTGGTCTTCTGGCTGCCAGGAGGGTAGCTAGGTGGGAAGATCTGCCCTTGTTTCCTC
CATAACCTGGGGTGGGAGGAGGAGGAGCTCCCAGCCCAATCTGATGGGGGAGACCAGAAC
CCTCACCCACCATTGCTGGCAGTTCAGAGAAGGCAGCGATAAGTCGGGGTGGGGCATCCT
GAAAGGCTTCCCAGAGGATTGGATGGGAGGATTAGCTGAGAAGACATCCGGCATCCGTAA
AATGGAGTAATGATTCTGACCCTGCAGGTTTTCTGGGAGGATTAAATGAGTTACATTTTA

24121  ATCTGATGGGGGAGACCAGAACCCTCACCCACCATTGCTGGCAGTTCAGAGAAGGCAGCG
ATAAGTCGGGGTGGGGCATCCTGAAAGGCTTCCCAGAGGATTGGATGGGAGGATTAGCTG
AGAAGACATCCGGCATCCGTAAAATGGAGTAATGATTCTGACCCTGCAGGTTTTCTGGGA
GGATTAAATGAGTTACATTTTAAAGATGCCTGGTACATGCCTGCCAGGAGAAGGCACAAC
ATATGAACTCCCTCCCTCTTCCCTCCACCCCTCCTCAGCTCCTGTGACATCAGGAGGGAC
[A,C]
TGCCCTGCCCTGCTCACAGAGGCTGGGTGGGAGGCTCCCATCATGGCCTTCACTGAGGCT
GCCTCTGCAGTTGGACCAAGCTGGACACACAGTAGGTGCACATAACAGATGGGGGCAGGT
CTGTGCTTGTTTTACCAGGGTGTTGGGAGGCTGAGGGAAGGGCACAGCTGGATTGGGGTG
ATGGAGTTCAATCCCTGCTCCTCCCCCAGATCCAAGATCCTAAGACGCCTATGTCCAGTG
GCTGCTCTGATCAGCTCTGACCAGCTCTCCTCACACCTCATAGGCCTTCCAGGGTTCAGG

24553  TTACCAGGGTGTTGGGAGGCTGAGGGAAGGGCACAGCTGGATTGGGGTGATGGAGTTCAA
TCCCTGCTCCTCCCCCAGATCCAAGATCCTAAGACGCCTATGTCCAGTGGCTGCTCTGAT
CAGCTCTGACCAGCTCTCCTCACACCTCATAGGCCTTCCAGGGTTCAGGTGATGAATTAG
TGATGACAGCATCCAGCATCGCTATGACAACCACATGGCACTCTTAGCCTCCAGTCAGGG
CTCAGCCGCAGAGGCCAGAGACCCCTTTGGCTCTGGGCCTTTGTACTGGCGTGTGTGAGC
[G,C]
GGGCTGGGGCCTGAGGGAGATGGAGGAGTGGGAGGGGCAGGGGCCGGGGCATGGGGCTGC
ATCTGGCATGGACTGGAGTTCATTCAGATTGTTCCATCCAGAGGGACCTTGGGGACAGTT
GTTTCTCTCCTTCCTTCCCCCTTTCTTTTCATTCCTCCATCCCTCCTCTTTCCCCTCCTC
CCACTTCTTCTGAGCCTTGTTCCTGTTTGAGGCCCTGGGCTGCCAACCCTTTTCCCCTCC
TCTGGGAATAAAGCCAGGCTCAGCCCTCACCCCGGGGAGCTGAGTGAGGTGGGGGACAGC

25917  CATCTCCTTCCTCCGTCTCTCAGGAGCCTTTGGCTGAGTTAGGCACCTACAGGAGGCAAG
GGCCCCCCCGAGCCCCTCACATTCTCCTCAGGGCTCCTTCTGGCCCTGGGGCCTGATATT
GGGCCTGCTGTGCTGGAACTTATCCAGGCAGAATAAACCTTTAGCCCCATTGTCCTGATG
AAGAAACTGAGGTCCCGAGGTAACAGTGACTCATTCAGGGTTACAACAGGTCAGTGGCTG
GGCTGGGCCTAGCGTCTGGCCCTCAGCTTGTCTACATGGCCCCCCTCGTGGCTCTCCCCT
[T,C]
GCCTCTCGCACCCCACTGTGCAGCATGGTTGGGCCTGCCAGCCTTGATGGATGGCTCTGC
AGCTCAACCTCCCTCCCATTCCTCTCCAGATGCCGGGCCGTGAGCCTCCTAATCACCAGT
CCTGCCTGGTGGCCGCCAAGCCATCCATCTCCCCACACAGCCTTGCCCAGCACAGGTGAT
TTTGTTTGGGGAGAAGGGGGGCACAGCAGGTCTTCCTCTGAGGCTGAGCCAAGAGTTTGG
CTGCAGCCCCCACTCTGGGGTGCCCGAGGGTTAGGGAATAGCCTGCACTCCCTTGCTGGA

26573  ACACACACTCACAGTAACACTAATAAAAGCTCTCGTGTAGCAAAAGAATATTGTATGGCA
AGTATTGTTGCAGAGCCATATGTATCATCTCATTCATCACTCCACTGTAGAGATACAGAA
ACTCAGGCTCAGAGAGGTTAAGTGACTTGCATAGGCTCCATATCCAGGAAATGGAGGAGC
TGGGATTTGAACCCACATCCTTATGGCTCACATCTTGCATTCACAACTCCTGCTCTACTG
ACTCACCTGTGCACACACACACACATGCACACACACACACGTGCGTGCACACACACACAC

FIGURE 3-52

[-,A]
GGCACTCACTTGCATGCATGAGCACGAGCCACCATTTTGGCTCTTGTACCATCCATCTAC
CTGGGCCAGGTTCTTGAGGAGTGAGGAGAATGCTGGGCTGCAGAGGGCATGAGGGGTCAC
TGCTCATTGTCCCCAGGCTGCCCCAAGCTGGCTGTGGCACTGGCTGGCTGGGGAGCTGCA
GGGAGGCAGCAGCCTCCAGGCAGTGGAAAGGGGAGGCTGGGAGACAGTCGATCGATCATC
CCTGCAGTGCCTCCTTCCAGGAACTGGGGCCCAGGGGAGTGTGGCGCCACGGGTCGATGT

27525  CAGAGCCTTTGGAGACCTCGACAGACAATACGATGAGTTAAGAAATGTAAAGGGGCACAT
AGTGGGTGCTGAATTCATCTTGTCTCGTTCCTCCAGTAAGAGTCTGGAGAAACCAAGAGC
AGCTGGGTGCCTCTGAGGGCACAGGAGCTCCCAGGGCTGGCTGGCAGGTGCAGCTAACAG
TGTTAGCAATCCCAAGGACAGGTAGCTTGGGGCGGAGGACAGCATGCTGTCACCCATCCT
GATGAGGGGAGAGATGTCTGGTGCTAGGAGCAGTGGTGGCCGGAGGAGGGCTGGGGACCC
[T,A]
CCCCAGGCCACCCCACACTCTCCCTCTGGGAGGGGCTCCTGAGCAGGCCTGGTCACCTTG
CTTCTTGGCTGCTTCTTCCCCGGCGGAGGAGCCTCCCCCAGGCTCTCCCACCTGCACTGG
CCTCAAGAGAGCTGGGATTGAGCCCCAGTTCAGGCACCTGCTGGCTGGCGGAGGTTAGGG
CAAATCACTTTCCTCAGCCCTCTCATCCGTGACAGGCTCTGGTGAGGGTTAAATGAGATG
TTGCCCGTCAAGTGCCTGCCACTTCCCTGACGCCGAGCAGCTAGGCTGCTCTGGGTTCTC

27625  AGTCTGGAGAAACCAAGAGCAGCTGGGTGCCTCTGAGGGCACAGGAGCTCCCAGGGCTGG
CTGGCAGGTGCAGCTAACAGTGTTAGCAATCCCAAGGACAGGTAGCTTGGGGCGGAGGAC
AGCATGCTGTCACCCATCCTGATGAGGGGAGAGATGTCTGGTGCTAGGAGCAGTGGTGGC
CGGAGGAGGGCTGGGGACCCTCCCCAGGCCACCCCACACTCTCCCTCTGGGAGGGGCTCC
TGAGCAGGCCTGGTCACCTTGCTTCTTGGCTGCTTCTTCCCCGGCGGAGGAGCCTCCCCC
[T,C,A]
GGCTCTCCCACCTGCACTGGCCTCAAGAGAGCTGGGATTGAGCCCCAGTTCAGGCACCTG
CTGGCTGGCGGAGGTTAGGGCAAATCACTTTCCTCAGCCCTCTCATCCGTGACAGGCTCT
GGTGAGGGTTAAATGAGATGTTGCCCGTCAAGTGCCTGCCACTTCCCTGACGCCGAGCAG
CTAGGCTGCTCTGGGTTCTCTAGCACCTGCCTCCCCTGGTCCCAGCACTGGGTGGGCGGC
TGTGTTCTACCGGTCACTGGTGGGTCCTCAGGGCCCCGACACAGGGCCTGCTATTGGGAA

27833  CCACCCCACACTCTCCCTCTGGGAGGGGCTCCTGAGCAGGCCTGGTCACCTTGCTTCTTG
GCTGCTTCTTCCCCGGCGGAGGAGCCTCCCCCAGGCTCTCCCACCTGCACTGGCCTCAAG
AGAGCTGGGATTGAGCCCCAGTTCAGGCACCTGCTGGCTGGCGGAGGTTAGGGCAAATCA
CTTTCCTCAGCCCTCTCATCCGTGACAGGCTCTGGTGAGGGTTAAATGAGATGTTGCCCG
TCAAGTGCCTGCCACTTCCCTGACGCCGAGCAGCTAGGCTGCTCTGGGTTCTCTAGCACC
[C,T]
GCCTCCCCTGGTCCCAGCACTGGGTGGGCGGCTGTGTTCTACCGGTCACTGGTGGGTCCT
CAGGGCCCCGACACAGGGCCTGCTATTGGGAAAGAGGGAAGTAAACATCCCAGGGCTGGA
GCTCTGCCCACTATGGAGGTGTTCCATCTTAGGCTCTGTAATCTCCTCATTCACTCTGGT
ATGGGGACAAATGTGCCTCTCTGCACTAACTGAGCCCCCATGGGCAACTAGGAGTGGTGT
CACTTGGGGTGGAGGTGGGCAAGGATCTCTGGACTGGGATTTCCAAGCCCTGACTTCCTG

27852  TGGGAGGGGCTCCTGAGCAGGCCTGGTCACCTTGCTTCTTGGCTGCTTCTTCCCCGGCGG
AGGAGCCTCCCCCAGGCTCTCCCACCTGCACTGGCCTCAAGAGAGCTGGGATTGAGCCCC
AGTTCAGGCACCTGCTGGCTGGCGGAGGTTAGGGCAAATCACTTTCCTCAGCCCTCTCAT
CCGTGACAGGCTCTGGTGAGGGTTAAATGAGATGTTGCCCGTCAAGTGCCTGCCACTTCC
CTGACGCCGAGCAGCTAGGCTGCTCTGGGTTCTCTAGCACCTGCCTCCCCTGGTCCCAGC
[A,G]
CTGGGTGGGCGGCTGTGTTCTACCGGTCACTGGTGGGTCCTCAGGGCCCCGACACAGGGC
CTGCTATTGGGAAAGAGGGAAGTAAACATCCCAGGGCTGGAGCTCTGCCCACTATGGAGG
TGTTCCATCTTAGGCTCTGTAATCTCCTCATTCACTCTGGTATGGGGACAAATGTGCCTC
TCTGCACTAACTGAGCCCCCATGGGCAACTAGGAGTGGTGTCACTTGGGGTGGAGGTGGG
CAAGGATCTCTGGACTGGGATTTCCAAGCCCTGACTTCCTGTTATTTCAGGCACTACCTC

28478  TCCCCTTGAGGGTAAGAGACACATGTGACCTCTGACCTCCAGAGTCTCTCTTCTGAGCTT
CTGTGCCCAGATGATTCTGTGTTCTAGGGGACAGGCGAGGCTGGGGGGTGACCCCCATGC
CACTGATGGGCAGACTAAGGAGCAGGGGCCCAGGACTGGGGCCAGCTCAGGACTCTGGTG

FIGURE 3-53

```
       GCCTCGGTGCCCTTGACCTGGTATTGCTGCCGTTTTGCCCCACTGCTGTCTGTCTCCGCG
       TCCGAGTCACCACCTGTCCCTCTCCAGTCCTCTCCTCTCTTCCTTTATTACTATCTCTAT
       [C,A]
       TTGCCTCCTGCCTCAGGCTTATCTCCTCCTGTCATGCCTCTATCCACCTCTGTCACTCCC
       CTGCGACTCTGCCTCACTCCCTGGCACACCCTCTCCCTCCCTGGGAGTCGGGAGTGGAGC
       CTCGCTGGGAATCAGGACCCCCCTGCCTCTGGTCTCTGTCTAAGCAGTCTCTGCGATTCT
       GGCCAGCTCTTATCTTTTTCCACCTTCCCGAATCTCTCTTGCTGTCTGATGGTGTCTCTG
       CCTTTCACTGTCTCTGAACTCCCTTTGTTTTTCTCTATATGCTTCTCTCTGCTCTTATCT

28514  CTCCAGAGTCTCTCTTCTGAGCTTCTGTGCCCAGATGATTCTGTGTTCTAGGGGACAGGC
       GAGGCTGGGGGGTGACCCCCATGCCACTGATGGGCAGACTAAGGAGCAGGGGCCCAGGAC
       TGGGGCCAGCTCAGGACTCTGGTGGCCTCGGTGCCCTTGACCTGGTATTGCTGCCGTTTT
       GCCCCACTGCTGTCTGTCTCCGCGTCCGAGTCACCACCTGTCCCTCTCCAGTCCTCTCCT
       CTCTTCCTTTATTACTATCTCTATATTGCCTCCTGCCTCAGGCTTATCTCCTCCTGTCAT
       [T,C,G]
       CCTCTATCCACCTCTGTCACTCCCCTGCGACTCTGCCTCACTCCCTGGCACACCCTCTCC
       CTCCCTGGGAGTCGGGAGTGGAGCCTCGCTGGGAATCAGGACCCCCCTGCCTCTGGTCTC
       TGTCTAAGCAGTCTCTGCGATTCTGGCCAGCTCTTATCTTTTTCCACCTTCCCGAATCTC
       TCTTGCTGTCTGATGGTGTCTCTGCCTTTCACTGTCTCTGAACTCCCTTTGTTTTTCTCT
       ATATGCTTCTCTCTGCTCTTATCTCTGGGCCTCTGTCTCTCAGGGCCTGACTGGTCTTGA

28702  GCTGTCTGTCTCCGCGTCCGAGTCACCACCTGTCCCTCTCCAGTCCTCTCCTCTCTTCCT
       TTATTACTATCTCTATATTGCCTCCTGCCTCAGGCTTATCTCCTCCTGTCATGCCTCTAT
       CCACCTCTGTCACTCCCCTGCGACTCTGCCTCACTCCCTGGCACACCCTCTCCCTCCCTG
       GGAGTCGGGAGTGGAGCCTCGCTGGGAATCAGGACCCCCCTGCCTCTGGTCTCTGTCTAA
       GCAGTCTCTGCGATTCTGGCCAGCTCTTATCTTTTTCCACCTTCCCGAATCTCTCTTGCT
       [G,C]
       TCTGATGGTGTCTCTGCCTTTCACTGTCTCTGAACTCCCTTTGTTTTTCTCTATATGCTT
       CTCTCTGCTCTTATCTCTGGGCCTCTGTCTCTCAGGGCCTGACTGGTCTTGACCTCTTTG
       CCTCCTTCTTCCCCTCGAGAGCCCAGCCAGGCAGCAGGTCCAGCCCTCCAGCCCAGAGAA
       CAGATGGAGTCCACCCTCCCTCTCTCTTGCTGGCTGCCTCGGAAGCCCCAAACAATGGCC
       TCCGCCCTGCACCGTGCCTTGTTGCTAGGCCTTGGGCTGGCAGCACCTGGCTTCCATAGC

28859  CTGGCACACCCTCTCCCTCCCTGGGAGTCGGGAGTGGAGCCTCGCTGGGAATCAGGACCC
       CCCTGCCTCTGGTCTCTGTCTAAGCAGTCTCTGCGATTCTGGCCAGCTCTTATCTTTTTC
       CACCTTCCCGAATCTCTCTTGCTGTCTGATGGTGTCTCTGCCTTTCACTGTCTCTGAACT
       CCCTTTGTTTTTCTCTATATGCTTCTCTCTGCTCTTATCTCTGGGCCTCTGTCTCTCAGG
       GCCTGACTGGTCTTGACCTCTTTGCCTCCTTCTTCCCCTCGAGAGCCCAGCCAGGCAGCA
       [A,C,G,T]
       GTCCAGCCCTCCAGCCCAGAGAACAGATGGAGTCCACCCTCCCTCTCTCTTGCTGGCTGC
       CTCGGAAGCCCCAAACAATGGCCTCCGCCCTGCACCGTGCCTTGTTGCTAGGCCTTGGGC
       TGGCAGCACCTGGCTTCCATAGCGACGGGTGCTTAGAAACAGAATGCCACATCTCCCAGT
       CCCACCACAGGAGCCTTTGCCGATTGAGCGAGTGCCTTTTGATCAATCAGGAAGTGTGGC
       CAGGCTCTAGGTTGCCTCCAACTTGAGGAGGCAAGAGAGGAGGGGACTGTGGTCTCTGCC

28960  GCCAGCTCTTATCTTTTTCCACCTTCCCGAATCTCTCTTGCTGTCTGATGGTGTCTCTGC
       CTTTCACTGTCTCTGAACTCCCTTTGTTTTTCTCTATATGCTTCTCTCTGCTCTTATCTC
       TGGGCCTCTGTCTCTCAGGGCCTGACTGGTCTTGACCTCTTTGCCTCCTTCTTCCCCTCG
       AGAGCCCAGCCAGGCAGCAGGTCCAGCCCTCCAGCCCAGAGAACAGATGGAGTCCACCCT
       CCCTCTCTCTTGCTGGCTGCCTCGGAAGCCCCAAACAATGGCCTCCGCCCTGCACCGTGC
       [C,G]
       TTGTTGCTAGGCCTTGGGCTGGCAGCACCTGGCTTCCATAGCGACGGGTGCTTAGAAACA
       GAATGCCACATCTCCCAGTCCCACCACAGGAGCCTTTGCCGATTGAGCGAGTGCCTTTTG
       ATCAATCAGGAAGTGTGGCCAGGCTCTAGGTTGCCTCCAACTTGAGGAGGCAAGAGAGGA
       GGGGACTGTGGTCTCTGCCTTCTGGAGCTGGGGGGACTGCTGGGCTGGGAGGAGTTGCTC
       AAGTACAGCCCTGAAGCCAAGGAAGGACTGGGGGAGGCCCTGGGCTCTTTTCCCCAAGTC

29030  CTCTGAACTCCCTTTGTTTTTCTCTATATGCTTCTCTCTGCTCTTATCTCTGGGCCTCTG
```

FIGURE 3-54

```
            TCTCTCAGGGCCTGACTGGTCTTGACCTCTTTGCCTCCTTCTTCCCCTCGAGAGCCCAGC
            CAGGCAGCAGGTCCAGCCCTCCAGCCCAGAGAACAGATGGAGTCCACCCTCCCTCTCTCT
            TGCTGGCTGCCTCGGAAGCCCCAAACAATGGCCTCCGCCCTGCACCGTGCCTTGTTGCTA
            GGCCTTGGGCTGGCAGCACCTGGCTTCCATAGCGACGGGTGCTTAGAAACAGAATGCCAC
            [A,G]
            TCTCCCAGTCCCACCACAGGAGCCTTTGCCGATTGAGCGAGTGCCTTTTGATCAATCAGG
            AAGTGTGGCCAGGCTCTAGGTTGCCTCCAACTTGAGGAGGCAAGAGAGGAGGGGACTGTG
            GTCTCTGCCTTCTGGAGCTGGGGGGACTGCTGGGCTGGGAGGAGTTGCTCAAGTACAGCC
            CTGAAGCCAAGGAAGGACTGGGGGAGGCCCTGGGCTCTTTTCCCCAAGTCAGCCTGCTGC
            AAGAGGCACAAGCTTGGGAGCTGGAAGGGGCTGTGTTGAAATTGCTGTTCCATCATTTCT
    29348   AGGAGCCTTTGCCGATTGAGCGAGTGCCTTTTGATCAATCAGGAAGTGTGGCCAGGCTCT
            AGGTTGCCTCCAACTTGAGGAGGCAAGAGAGGAGGGGACTGTGGTCTCTGCCTTCTGGAG
            CTGGGGGGACTGCTGGGCTGGGAGGAGTTGCTCAAGTACAGCCCTGAAGCCAAGGAAGGA
            CTGGGGGAGGCCCTGGGCTCTTTTCCCCAAGTCAGCCTGCTGCAAGAGGCACAAGCTTGG
            GAGCTGGAAGGGGCTGTGTTGAAATTGCTGTTCCATCATTTCTAGCTGCATGACTTTGGA
            [T,C]
            GAATGACCTCAGGTCCCAGGGCCTCAGTTTCATCAACTGTAAAATTGGGCTAATAATATC
            ATGAAGATTAAATGAGAGAATAGATCTGGCACTTAGTAGGTGGTCATCAATGGCCATTCC
            CCTCCCTTCCCCTTTAAAGTTGTTTAAAATTTAATTGACAGAGAGGAGAAGGAGGGTTCT
            TCAGGCCTGTGGAATGGTGTAAGCAAAGGGGTGGAGGCTGGCATGCACCTCACATATGCT
            GGAGTATTTAGGGAGGACCAGGGGCCATATCTGGAAATGGTTCTGCCAGAAGCAGCCAGG
    29973   CCTGTAATTCCAGCTACTAGGGAGGCTGAGGCAGGAGGATCACTTGAGCCCTGGAGTTCC
            AGATCAGCCTGGGCAACATAGTGAGACCCCATCTCAAAAAAACAAAACACAACAGGCAGG
            CTGATGGGCCCATGGAGAAGGGACTCTGTCTCCTGGGAGGTATATTCTTGCCAGGTGCAA
            AGGGATGGGCTTGACTAATTTCTCCTCTAGCATTTGGGGCTGCTGGGTAGGGAGCTACAT
            TGGGGTCCCCTTGCTTATTCTCATGCTGCTCCCTACTTCTGCCCTGTCACTTGGTCCCAG
            [T,C,G,A]
            AGAGGGGCTCCCACTGGTTCCTTTTCCCTGCCAGGCCTGCCCACCAAGGCCACCATGGCC
            ACACAGCCTGAATCCTGGGGCCAGCAAGTGTCCATGGAAGGCCCCACTCTGTCATCGTAG
            AGATCAGGAAACAGGCTCAGAAGTAGGAGGGCTTCCTGGTCCTAGGGCCCAGCTCTTCCC
            TCTTTTCAGGCCTGTCTTCTGCACTAAGGACTTCAGGCCACCAGGGAAGGTGGGGAGGGA
            GGAAAGGAGATGAGATAGACTTGGGCGGGGGCCTGAGGACAGAGTTTCATGTCACTTGGG
    30153   AGGGATGGGCTTGACTAATTTCTCCTCTAGCATTTGGGGCTGCTGGGTAGGGAGCTACAT
            TGGGGTCCCCTTGCTTATTCTCATGCTGCTCCCTACTTCTGCCCTGTCACTTGGTCCCAG
            GAGAGGGGCTCCCACTGGTTCCTTTTCCCTGCCAGGCCTGCCCACCAAGGCCACCATGGC
            CACACAGCCTGAATCCTGGGGCCAGCAAGTGTCCATGGAAGGCCCCACTCTGTCATCGTA
            GAGATCAGGAAACAGGCTCAGAAGTAGGAGGGCTTCCTGGTCCTAGGGCCCAGCTCTTCC
            [C,T]
            TCTTTTCAGGCCTGTCTTCTGCACTAAGGACTTCAGGCCACCAGGGAAGGTGGGGAGGGA
            GGAAAGGAGATGAGATAGACTTGGGCGGGGGCCTGAGGACAGAGTTTCATGTCACTTGGG
            CAGCCAGGAAAGGGTTAAAGATCCCTTATCCCAAGCCATGGGCACTGGCACTGCCAGAGG
            ATGCTGAGGCCTGCTGGGGCATAAGGACAACAAGCAACATCCTTTTCTGAGCTGTTGGGA
            GTGCCAAGCTCTCTGTTAAATACTTTTGAGCCTCTTCTCATGTATTCACAGCCACCTTTC
    30389   CGTAGAGATCAGGAAACAGGCTCAGAAGTAGGAGGGCTTCCTGGTCCTAGGGCCCAGCTC
            TTCCCTCTTTTCAGGCCTGTCTTCTGCACTAAGGACTTCAGGCCACCAGGGAAGGTGGGG
            AGGGAGGAAAGGAGATGAGATAGACTTGGGCGGGGGCCTGAGGACAGAGTTTCATGTCAC
            TTGGGCAGCCAGGAAAGGGTTAAAGATCCCTTATCCCAAGCCATGGGCACTGGCACTGCC
            AGAGGATGCTGAGGCCTGCTGGGGCATAAGGACAACAAGCAACATCCTTTTCTGAGCTGT
            [T,C]
            GGGAGTGCCAAGCTCTCTGTTAAATACTTTTGAGCCTCTTCTCATGTATTCACAGCCACC
            TTTCAAGGAAGGCCAGTTGATCCCCAGTTTAGAAGTGAGAAAACGGGGTCTCCAGGAGGC
            ACTTGTCTAAGGTGACACAGCTGGAGAGTTGGAGATGGTGGTTAGACCGAGTCACCCCCC
            CAGACCCTGGCCTCTCCCTGCGTGCCCCTTCCAGGACACCCATCACTCCCTTGACACCCC
            TTGGGAGTGGGTGTTCATTTCCTTGGGCTCTCCCAATCCCAGTCCTTGGTATCCCCAACT
```

FIGURE 3-55

30581    GAAAGGGTTAAAGATCCCTTATCCCAAGCCATGGGCACTGGCACTGCCAGAGGATGCTGA
         GGCCTGCTGGGGCATAAGGACAACAAGCAACATCCTTTTCTGAGCTGTTGGGAGTGCCAA
         GCTCTCTGTTAAATACTTTTTGAGCCTCTTCTCATGTATTCACAGCCACCTTTCAAGGAAG
         GCCAGTTGATCCCCAGTTTAGAAGTGAGAAAACGGGGTCTCCAGGAGGCACTTGTCTAAG
         GTGACACAGCTGGAGAGTTGGAGATGGTGGTTAGACCGAGTCACCCCCCCAGACCCTGGC
         [C,G]
         TCTCCCTGCGTGCCCCTTCCAGGACACCCATCACTCCCTTGACACCCCTTGGGAGTGGGT
         GTTCATTTCCTTGGGCTCTCCCAATCCCAGTCCTTGGTATCCCCAACTGCAGGCAGACAC
         AGGTGCTTGCTGCTGTGCCCTCCCCTTTACCTGGCATCACAGAGACTCAAGCCCACTGAC
         CATTAGGCTCTCAGGGGCATAGAAACCAGGTGCTGGAGTCTTAGAGTCCTGCAATCAGGC
         ATCTCAGGCAGTCAGGACATTAGAATGTTAGAATCTTGGGCTTCTACATTCTCAAGACCC

31147    TGTTAGAATCTTGGGCTTCTACATTCTCAAGACCCCAGGTTCTCGCATTCACAGAATGTA
         AGAAAAACAGACTTTTTGAATGATGGGGTGTTATAACAGAAGCTTTGATTTTCTAAGAAC
         ATGAAGCTCTGGGAGTTCTTGGAGCCTTGAAGCCATAGACTGGGGCCTCCCTGTGTGATG
         GTTTCTGAGTTAGCAGGGAGTGTTCAGAGTATGGGGCCTTGGTCCCTGTTGCTTAGACCT
         TCTTGCCTTGGTATCTCTGATGGGCTCAGCTCTTAGTAGCCTTTGTGTATGTGTGTGTGT
         [G,A]
         TGTGTGTGTGTGTGTGTGTGTGTGTGTGTGTGTGTGTGTGTAGTGGGGACTGGGGTCA
         GGGGTCAGGGACTGACTCTAACCTGAGGCACCCCTGGAGTGGGGCCAGCCCAGGAATAGC
         AGGTGGAGGAAAGCCGGGCAGCCTCAGGGCTGCAGCTGTCTGGTGGTACAGGGCAGGGCT
         CTGGGTGGCTGCCTTTGGCAGAGGACCAGCCTGCCTCCTTCGTCCCCTACCCAGCCTGCT
         ACCAGGATCAGGAGGAGGCATCTCCATGGGACTCCTAGGGCTGGAGTCAGAGCAGCCCCT

31224    GAATGATGGGGTGTTATAACAGAAGCTTTGATTTTCTAAGAACATGAAGCTCTGGGAGTT
         CTTGGAGCCTTGAAGCCATAGACTGGGGCCTCCCTGTGTGATGGTTTCTGAGTTAGCAGG
         GAGTGTTCAGAGTATGGGGCCTTGGTCCCTGTTGCTTAGACCTTCTTGCCTTGGTATCTC
         TGATGGGCTCAGCTCTTAGTAGCCTTTGTGTATGTGTGTGTGTATGTGTGTGTGTGTGT
         TGTGTGTGTGTGTGTGTGTGTGTGTGTAGTGGGGACTGGGGTCAGGGGTCAGGGACTGAC
         [C,T]
         CTAACCTGAGGCACCCCTGGAGTGGGGCCAGCCCAGGAATAGCAGGTGGAGGAAAGCCGG
         GCAGCCTCAGGGCTGCAGCTGTCTGGTGGTACAGGGCAGGGCTCTGGGTGGCTGCCTTTG
         GCAGAGGACCAGCCTGCCTCCTTCGTCCCCTACCCAGCCTGCTACCAGGATCAGGAGGAG
         GCATCTCCATGGGACTCCTAGGGCTGGAGTCAGAGCAGCCCCTCCAGGTTCTGCAGCCTG
         GACGGTAGGAGGTGCCACTAAGGGGAGGAGATTGGGGAAGGATTGGGACCTTTATCTGCG

31735    CAGAGCAGCCCCTCCAGGTTCTGCAGCCTGGACGGTAGGAGGTGCCACTAAGGGGAGGAG
         ATTGGGGAAGGATTGGGACCTTTATCTGCGGTGAGGTGGGGCACGGGGGGATGAGAGATA
         TAGTGGGAGTCTTTGAAGGGTGTGGGATCAGTGAAGGGGCTGGGGATTTAGTGATGGGCT
         GGGGCTTAGGATGGAGCCAAGGGCTCTGTGGGTGGGAGACCTTTTGAGAGGGTGGAGACT
         CAGAGAGAAGGATGGGGGCTCAGCAAGGGGATGTGGCTCAGTGGAGGTTGCTGAAGAGTT
         [G,A,T,C]
         CTTGGGGTTGGCTACACGCGGTGGCTCACGCCTGTAATCCCAGCACTTTGGGAGGCCAAG
         GCGGATGGATCACTTGAGGTCAGGACTTCAAGACCAGCCTGGCCAACATGGTGAAACCCT
         GCCTCTACCAAAAAATACAAATATTAGCCGGGCGTAATGGCAGGCGCCTGTAATCTCAGC
         TACTCGGGAGGCTGAGGCAGGAGAATTGCTTGAACCTGAGAGGCGGAGGTTGCAGTGAGT
         CGAGATTGTACCACTGCATTCCAGCCCTGGGCGACAGAGCAAGACTCCATCTAAAAAAAA

31739    GCAGCCCCTCCAGGTTCTGCAGCCTGGACGGTAGGAGGTGCCACTAAGGGGAGGAGATTG
         GGGAAGGATTGGGACCTTTATCTGCGGTGAGGTGGGGCACGGGGGGATGAGAGATATAGT
         GGGAGTCTTTGAAGGGTGTGGGATCAGTGAAGGGGCTGGGGATTTAGTGATGGGCTGGGG
         CTTAGGATGGAGCCAAGGGCTCTGTGGGTGGGAGACCTTTTGAGAGGGTGGAGACTCAGA
         GAGAAGGATGGGGGCTCAGCAAGGGGATGTGGCTCAGTGGAGGTTGCTGAAGAGTTTCTT
         [G,-]
         GGGTTGGCTACACGCGGTGGCTCACGCCTGTAATCCCAGCACTTTGGGAGGCCAAGGCGG
         ATGGATCACTTGAGGTCAGGACTTCAAGACCAGCCTGGCCAACATGGTGAAACCCTGCCT
         CTACCAAAAAATACAAATATTAGCCGGGCGTAATGGCAGGCGCCTGTAATCTCAGCTACT

FIGURE 3-56

```
        CGGGAGGCTGAGGCAGGAGAATTGCTTGAACCTGAGAGGCGGAGGTTGCAGTGAGTCGAG
        ATTGTACCACTGCATTCCAGCCCTGGGCGACAGAGCAAGACTCCATCTAAAAAAAAAAAA

31742   GCCCCTCCAGGTTCTGCAGCCTGGACGGTAGGAGGTGCCACTAAGGGGAGGAGATTGGGG
        AAGGATTGGGACCTTTATCTGCGGTGAGGTGGGGCACGGGGGGATGAGAGATATAGTGGG
        AGTCTTTGAAGGGTGTGGGATCAGTGAAGGGGCTGGGGATTTAGTGATGGGCTGGGGCTT
        AGGATGGAGCCAAGGGCTCTGTGGGTGGGAGACCTTTTGAGAGGGTGGAGACTCAGAGAG
        AAGGATGGGGGCTCAGCAAGGGGATGTGGCTCAGTGGAGGTTGCTGAAGAGTTTCTTGGG
        [G,-]
        TTGGCTACACGCGGTGGCTCACGCCTGTAATCCCAGCACTTTGGGAGGCCAAGGCGGATG
        GATCACTTGAGGTCAGGACTTCAAGACCAGCCTGGCCAACATGGTGAAACCCTGCCTCTA
        CCAAAAAATACAAATATTAGCCGGGCGTAATGGCAGGCGCCTGTAATCTCAGCTACTCGG
        GAGGCTGAGGCAGGAGAATTGCTTGAACCTGAGAGGCGGAGGTTGCAGTGAGTCGAGATT
        GTACCACTGCATTCCAGCCCTGGGCGACAGAGCAAGACTCCATCTAAAAAAAAAAAAAAA

31798   GGGGAAGGATTGGGACCTTTATCTGCGGTGAGGTGGGGCACGGGGGGATGAGAGATATAG
        TGGGAGTCTTTGAAGGGTGTGGGATCAGTGAAGGGGCTGGGGATTTAGTGATGGGCTGGG
        GCTTAGGATGGAGCCAAGGGCTCTGTGGGTGGGAGACCTTTTGAGAGGGTGGAGACTCAG
        AGAGAAGGATGGGGGCTCAGCAAGGGGATGTGGCTCAGTGGAGGTTGCTGAAGAGTTTCT
        TGGGGTTGGCTACACGCGGTGGCTCACGCCTGTAATCCCAGCACTTTGGGAGGCCAAGGC
        [G,C,AsT]
        GATGGATCACTTGAGGTCAGGACTTCAAGACCAGCCTGGCCAACATGGTGAAACCCTGCC
        TCTACCAAAAAATACAAATATTAGCCGGGCGTAATGGCAGGCGCCTGTAATCTCAGCTAC
        TCGGGAGGCTGAGGCAGGAGAATTGCTTGAACCTGAGAGGCGGAGGTTGCAGTGAGTCGA
        GATTGTACCACTGCATTCCAGCCCTGGGCGACAGAGCAAGACTCCATCTAAAAAAAAAAA
        AAAAAAAAAGTCTCAGGGCTGTCTCTGCACTGCTCCAGGTTCCTGAGGACGGCGGTTGGG

31994   TCAGCAAGGGGATGTGGCTCAGTGGAGGTTGCTGAAGAGTTTCTTGGGGTTGGCTACACG
        CGGTGGCTCACGCCTGTAATCCCAGCACTTTGGGAGGCCAAGGCGGATGGATCACTTGAG
        GTCAGGACTTCAAGACCAGCCTGGCCAACATGGTGAAACCCTGCCTCTACCAAAAAATAC
        AAATATTAGCCGGGCGTAATGGCAGGCGCCTGTAATCTCAGCTACTCGGGAGGCTGAGGC
        AGGAGAATTGCTTGAACCTGAGAGGCGGAGGTTGCAGTGAGTCGAGATTGTACCACTGCA
        [A,G,T]
        TCCAGCCCTGGGCGACAGAGCAAGACTCCATCTAAAAAAAAAAAAAAAAAAAAAGTCTCAG
        GGCTGTCTCTGCACTGCTCCAGGTTCCTGAGGACGGCGGTTGGGGCTGGGGGAGTCTTCT
        GTCCCTGGGGTAGGCTGAGAAGCAAGAGCTCCTTTTCCCAACTCTGCCCAAAGCTGGAAA
        GGTTGTTAGAGCTGCTAAGAAAGCTGGCATCTGCCTCTCCTTTTGCTCATCTTCCTTTCT
        GGTTTCCATGGGAATCTGTGGCTCAGGATGATCAGGGGTTGACAGGATGGCGCTGTGGAA

32324   ATCTAAAAAAAAAAAAAAAAAAAAAGTCTCAGGGCTGTCTCTGCACTGCTCCAGGTTCCTG
        AGGACGGCGGTTGGGGCTGGGGGAGTCTTCTGTCCCTGGGGTAGGCTGAGAAGCAAGAGC
        TCCTTTTCCCAACTCTGCCCAAAGCTGGAAAGGTTGTTAGAGCTGCTAAGAAAGCTGGCA
        TCTGCCTCTCCTTTTGCTCATCTTCCTTTCTGGTTTCCATGGGAATCTGTGGCTCAGGAT
        GATCAGGGGTTGACAGGATGGCGCTGTGGAAGGAGTCTGTGTCAGGCACAGCCATCCCAC
        [A,T]
        TGGGAAGGAGCCGGCTGGTAAGAAAGTGAGTTCCCTGTCCCTGGGAGTGTGCAAGCAGGG
        TAGGGGCTGAATGGCTAGAGTGACTCCAGAAAGGGGTTCAGATGGGGCAGAGGAAGCAGT
        CTGGAGGCCACTTCCCTGAGACAATCATGTTTTGTGTGATTGGCTCTGGGGGCCCCACCA
        GCCCCACCTTCCAGACGTCCCTGGGCCTCACAAAGGGGGTTGCTGCACCCTAGGCACTGC
        CTCTGATCCAGCCCCAACTCCTGTGCTCTGTGCCTGGCCTATGCTGAACACGGACATGTG

32891   TCTGTGCCTGGCCTATGCTGAACACGGACATGTGCAGCTGAATCAGATTCAGTCTCTGCC
        TAGAGGAGCCCCAGTCTGATGGGGGAGGCACACAGGGACACAAATATAGCTGGGTAAGTC
        CTACAAAAGGGGGCATACCTGGCTGGGAGGCAGTTCCATCACTGATTCCTGTAGTCTGTA
        GATGTCTTTTTGAGCAATTCTTCTGGGTCAAGACTTGTTCTTATTTGCTGGGATAAAACA
        GCAGTGAGCAAAACAGAGCTGACAGCATGGTGGGAAGGTTGAGCTCTTCCAGACCGTGAT
        [G,A]
        AGAAGTATTGGTGAGTGGTGGGGAGAGTGGCCAGAAGGCAGAGTGTGGGCGCAGCATGAG
```

FIGURE 3-57

```
        AGGAGGCTTTGTCCAGACTTAAGGACCTGGAAGGCCTTGAAGGCCAGGACCAGGGCTCCA
        ATTGTCCTGCTGGCAATAGGAAGCCATATGGGTGGGGGTGAGGCAGAATCAGATTTAGGT
        GTGGAAAAGATGACTCCAGCCAGTGTGGGCATCGAAGAGGAGGCACAGAAGCAGGCGTGG
        CCACCTGTGCCTCTGTGTAGGAGCTGTGTGAGCATGTGCTTGAGGATGTGTGTCTGTGTA

33104   CTTGTTCTTATTTGCTGGGATAAAACAGCAGTGAGCAAAACAGAGCTGACAGCATGGTGG
        GAAGGTTGAGCTCTTCCAGACCGTGATGAGAAGTATTGGTGAGTGGTGGGGAGAGTGGCC
        AGAAGGCAGAGTGTGGGCGCAGCATGAGAGGAGGCTTTGTCCAGACTTAAGGACCTGGAA
        GGCCTTGAAGGCCAGGACCAGGGCTCCAATTGTCCTGCTGGCAATAGGAAGCCATATGGG
        TGGGGGTGAGGCAGAATCAGATTTAGGTGTGGAAAAGATGACTCCAGCCAGTGTGGGCAT
        [C,T]
        GAAGAGGAGGCACAGAAGCAGGCGTGGCCACCTGTGCCTCTGTGTAGGAGCTGTGTGAGC
        ATGTGCTTGAGGATGTGTGTCTGTGTAGAGGACTGGGGTGTAGGCGTGATAGGAACATGG
        ACGTGTATCTATGGAAAGACTCCAATTGTGCATAGGGGTGTATGTGTGTAAGATTCTGTG
        GCCCAGGGCAGCCTGTGAAAAGGAAGGATCTTGGGGTCTCTGGATGATGGGGAGCAGAGA
        CTAAGGCCTAAGGTATGCTGGGGCTCGAGCCCCCTGGACTTTATCCCCTGTGAGCTGGCA

33296   CAGGACCAGGGCTCCAATTGTCCTGCTGGCAATAGGAAGCCATATGGGTGGGGGTGAGGC
        AGAATCAGATTTAGGTGTGGAAAAGATGACTCCAGCCAGTGTGGGCATCGAAGAGGAGGC
        ACAGAAGCAGGCGTGGCCACCTGTGCCTCTGTGTAGGAGCTGTGTGAGCATGTGCTTGAG
        GATGTGTGTCTGTGTAGAGGACTGGGGTGTAGGCGTGATAGGAACATGGACGTGTATCTA
        TGGAAAGACTCCAATTGTGCATAGGGGTGTATGTGTGTAAGATTCTGTGGCCCAGGGCAG
        [C,T]
        CTGTGAAAAGGAAGGATCTTGGGGTCTCTGGATGATGGGGAGCAGAGACTAAGGCCTAAG
        GTATGCTGGGGCTCGAGCCCCCTGGACTTTATCCCCTGTGAGCTGGCAGGTCTTAGACTA
        GTCCTGGACTAGAATCCTATGGGTTCCCTTCCCCCAGAGGGTCATGGGGCCAGCCATCTG
        CTGCAGACAAGACAAACATGCATGCAAATCACATGAAAATGGATGAGGCCTGTGGCTGAC
        CCACCCTACAGCCCCCATCCCCTGGGCCTGAGTTCACTCAGCCTGTACCCTTCCTGACCC

33324   GCAATAGGAAGCCATATGGGTGGGGGTGAGGCAGAATCAGATTTAGGTGTGGAAAAGATG
        ACTCCAGCCAGTGTGGGCATCGAAGAGGAGGCACAGAAGCAGGCGTGGCCACCTGTGCCT
        CTGTGTAGGAGCTGTGTGAGCATGTGCTTGAGGATGTGTGTCTGTGTAGAGGACTGGGGT
        GTAGGCGTGATAGGAACATGGACGTGTATCTATGGAAAGACTCCAATTGTGCATAGGGGT
        GTATGTGTGTAAGATTCTGTGGCCCAGGGCAGCCTGTGAAAAGGAAGGATCTTGGGGTCT
        [C,G]
        TGGATGATGGGGAGCAGAGACTAAGGCCTAAGGTATGCTGGGGCTCGAGCCCCCTGGACT
        TTATCCCCTGTGAGCTGGCAGGTCTTAGACTAGTCCTGGACTAGAATCCTATGGGTTCCC
        TTCCCCCAGAGGGTCATGGGGCCAGCCATCTGCTGCAGACAAGACAAACATGCATGCAAA
        TCACATGAAAATGGATGAGGCCTGTGGCTGACCCACCCTACAGCCCCCATCCCCTGGGCC
        TGAGTTCACTCAGCCTGTACCCTTCCTGACCCAGAGCTGCTGCCAGGGCTCTGGGAACAG

33533   CTATGGAAAGACTCCAATTGTGCATAGGGGTGTATGTGTGTAAGATTCTGTGGCCCAGGG
        CAGCCTGTGAAAAGGAAGGATCTTGGGGTCTCTGGATGATGGGGAGCAGAGACTAAGGCC
        TAAGGTATGCTGGGGCTCGAGCCCCCTGGACTTTATCCCCTGTGAGCTGGCAGGTCTTAG
        ACTAGTCCTGGACTAGAATCCTATGGGTTCCCTTCCCCCAGAGGGTCATGGGGCCAGCCA
        TCTGCTGCAGACAAGACAAACATGCATGCAAATCACATGAAAATGGATGAGGCCTGTGGC
        [T,C]
        GACCCACCCTACAGCCCCCATCCCCTGGGCCTGAGTTCACTCAGCCTGTACCCTTCCTGA
        CCCAGAGCTGCTGCCAGGGCTCTGGGAACAGGCCTTGCCCACTAGGAGCTGAAATTCACA
        TTGTCCCCAGCACCTGCCCGTGGCCACATCCTCTCTCTGTGAGGGCTACCCCCACATCTG
        GAGCCATAGCCAGCGGACACAGAGCTGGATCTGGACTGGTGGCCATGGGCAGCACCTCTG
        GCAGGTGCTGAGGTGGAGGAGGCAGTATCCAGGCAGGCATCCCTGGGCAGAAGGTACCTC

33852   CATCCCCTGGGCCTGAGTTCACTCAGCCTGTACCCTTCCTGACCCAGAGCTGCTGCCAGG
        GCTCTGGGAACAGGCCTTGCCCACTAGGAGCTGAAATTCACATTGTCCCCAGCACCTGCC
        CGTGGCCACATCCTCTCTCTGTGAGGGCTACCCCCACATCTGGAGCCATAGCCAGCGGAC
        ACAGAGCTGGATCTGGACTGGTGGCCATGGGCAGCACCTCTGGCAGGTGCTGAGGTGGAG
        GAGGCAGTATCCAGGCAGGCATCCCTGGGCAGAAGGTACCTCTCCTGAGCAGACAGGCCT
```

FIGURE 3-58

[A,T]
CCCAGGCACCAGGCCCAAAGATAGGGGCAAGGGCTAGATCCTGGTATTGGAGGACCCTCA
GGAGAGGCTGTGTGTGACTTGCTCTCTCTCTGACCTGGGCTAGAGCATAAACACGTGTCA
CATACTTGCACACACATTCACACGTGAAAGCACGCACATGCTATTCCTGGACACTTGTGT
ACACACACCACTGCACACATATACCTGCATGTGTGAATATACACTCACTTCTGCACACAG
ACACATGCCTATCTGCATAGACACACCCGTGCCAACCCCTATAGATACACAGACATATCT

33907 CCAGGGCTCTGGGAACAGGCCTTGCCCACTAGGAGCTGAAATTCACATTGTCCCCAGCAC
CTGCCCGTGGCCACATCCTCTCTCTGTGAGGGCTACCCCCACATCTGGAGCCATAGCCAG
CGGACACAGAGCTGGATCTGGACTGGTGGCCATGGGCAGCACCTCTGGCAGGTGCTGAGG
TGGAGGAGGCAGTATCCAGGCAGGCATCCCTGGGCAGAAGGTACCTCTCCTGAGCAGACA
GGCCTACCCAGGCACCAGGCCCAAAGATAGGGGCAAGGGCTAGATCCTGGTATTGGAGGA
[A,C]
CCTCAGGAGAGGCTGTGTGTGACTTGCTCTCTCTCTGACCTGGGCTAGAGCATAAACACG
TGTCACATACTTGCACACACATTCACACGTGAAAGCACGCACATGCTATTCCTGGACACT
TGTGTACACACACCACTGCACACATATACCTGCATGTGTGAATATACACTCACTTCTGCA
CACAGACACATGCCTATCTGCATAGACACACCCGTGCCAACCCCTATAGATACACAGACA
TATCTGTGTATACACATATAAGTTCAGCTATACCACTGCAGTATCACACACCCTCACAAG

34294 ACGTGAAAGCACGCACATGCTATTCCTGGACACTTGTGTACACACACCACTGCACACATA
TACCTGCATGTGTGAATATACACTCACTTCTGCACACAGACACATGCCTATCTGCATAGA
CACACCCGTGCCAACCCCTATAGATACACAGACATATCTGTGTATACACATATAAGTTCA
GCTATACCACTGCAGTATCACACACCCTCACAAGGATACAAACCTGTGCTCACACTCTCT
TCCACCCTCACACACATCATGCTTACAAGCCTGTGTGCAGCCTTACACACATGCACACAC
[A,G]
TACAGAGCAGCCTAAGGGTGGCTCACCCCTGCCCAGGTGAACACCTGTGCCCACTCCAGG
GCTGGAGTGTTGAGGAAAGGGTCTGGATGGAGGCAGAACCTGCAGAGATGTCAGTTTCTT
CCAGGAAGCATCTTGGATTGTCCCTTCACAGAGCCCTTGGAAGTGGGGCCCTCTTTTAGT
CCATGGGCTCTAGCCCAGGTCACAGAGAGAGCAAGTCACACACAGCCTCTCCTGAGGGTC
CTCCAATACCAGGATCCAGCCCTTGTCCATATCTTTGGGCCTGGTGCCTGCGTAGGACCA

37090 CAGATGGGGAAATAGAGGCCTAGAGAGGTGCTGTGGCCTGCTCAGAATCCCACAGCAAGT
CTATGGCACAGTTAGGACTCAAACCCTCTGAGGAATGCTTGGATCTGAAAGGTTGACACA
GAAAGACTCTTTGAGCTGAGGGACACATAGAGCACACACCAGGGACCCCAGTCATTGAGC
TGTAGTTTGAGAGATTCAAGTAAGACTGAAGAAATAACTTCTTGGCTGGGTGCAGTGGCT
CACACCTGTAATCCCAACACTTTGGGAGGCTGAGGTGGGTGGATCATGAGGTCAAGAGAT
[C,T]
GAGACCATCCTGGCCAACATGGCGAAATCCCATCTGTACTAAAAATATAAAAATTAGCTG
GGCATGGTGGTGCATGCCTGTAGTCCCATCTACTCGGGAGGCTGAGGCAGGAGAATTGCT
TGAACCCGGGAGGCGGAGGTTGCAGTGAGCTGAGATCGCGCCACTGCGCTCCAGCCTGGT
GACAGAGCGAGACTCCGTCTCAAAAAAATAAAATAAAATAAAATAAAATAAAATAAAATA
AAATAAAATAAAATAAATAAAATAACTTCTCAAGAGGTGAGTGCCATGGAGGTGGTGCCT

37248 CCAGGGACCCCAGTCATTGAGCTGTAGTTTGAGAGATTCAAGTAAGACTGAAGAAATAAC
TTCTTGGCTGGGTGCAGTGGCTCACACCTGTAATCCCAACACTTTGGGAGGCTGAGGTGG
GTGGATCATGAGGTCAAGAGATCGAGACCATCCTGGCCAACATGGCGAAATCCCATCTGT
ACTAAAAATATAAAAATTAGCTGGGCATGGTGGTGCATGCCTGTAGTCCCATCTACTCGG
GAGGCTGAGGCAGGAGAATTGCTTGAACCCGGGAGGCGGAGGTTGCAGTGAGCTGAGATC
[C,T,G]
CGCCACTGCGCTCCAGCCTGGTGACAGAGCGAGACTCCGTCTCAAAAAAATAAAATAAAA
TAAAATAAAATAAAATAAAATAAAATAAAATAAAATAAAATAACTTCTCAAGAGGT
GAGTGCCATGGAGGTGGTGCCTGGAGTTGGGAGCCCAAGAGATGGTGGCGGTGCCAGGCC
AGGGTCGGCTGTTGACCATGGTCTGAGGTGGCCTCCCCTGAAGAACAAGTAACTCTGGCC
AGTGGCTGTAACAGATACCTCCCGGGCACCTGTATCTCACCCAGCCTTGTCCAGAGCCCA

37355 GAGGCTGAGGTGGGTGGATCATGAGGTCAAGAGATCGAGACCATCCTGGCCAACATGGCG
AAATCCCATCTGTACTAAAAATATAAAAATTAGCTGGGCATGGTGGTGCATGCCTGTAGT
CCCATCTACTCGGGAGGCTGAGGCAGGAGAATTGCTTGAACCCGGGAGGCGGAGGTTGCA

FIGURE 3-59

```
           GTGAGCTGAGATCGCGCCACTGCGCTCCAGCCTGGTGACAGAGCGAGACTCCGTCTCAAA
           AAAATAAAATAAAATAAAATAAAATAAAATAAAATAAAATAAAATAAAATAAAATAAAATA
           [A,-]
           CTTCTCAAGAGGTGAGTGCCATGGAGGTGGTGCCTGGAGTTGGGAGCCCAAGAGATGGTG
           GCGGTGCCAGGCCAGGGTCGGCTGTTGACCATGGTCTGAGGTGGCCTCCCCTGAAGAACA
           AGTAACTCTGGCCAGTGGCTGTAACAGATACCTCCCGGGCACCTGTATCTCACCCAGCCT
           TGTCCAGAGCCCAGGACTGAGCCAGTGACACATGCTCAGAATTTACCAAGAGACTTGTGC
           ACTGAGCTCAGACTCAGACCTAGTCCTTCCAACAGCCCTTACATGGGTCATCCCCTTTTA

37893      TGCACTGAGCTCAGACTCAGACCTAGTCCTTCCAACAGCCCTTACATGGGTCATCCCCTT
           TTACGGAAGAGAAAACTGAGGCCAAAAATAGGAAGGGAGGCCCTGTGGGGGCCAGAACCT
           TTACACATCTTAGCCCAGGTAATTTTTTTCTACAGTGTTAATAAGTAGGATGAATTGCCCC
           TGTTTGGAAGATTCAGTAAAATACATTGACTTGGCCCAGATCACTTACTCTACACCTCTC
           CTAAGTCCCCAGATGTGACTCCCAGGAAAGACACAAAAAAGGGCTACCCAGAGGGATAAG
           [A,G]
           TAGTAACCAGGGAAGCCCTCCCAGAGGAGGTGGGCCTTCAAATGGCCCCTAAATGACAGG
           CAGGAGGGAAGGATCTGGGAGGGTATTGGGGGTGGGGTGGCATGGGCAAAGGCCTGGAGG
           TGAGAGTCAGTCAGTCATTGATGTGAGAAGAGCAAGAAGTAGAAATGTAAGGAATGGTGG
           GGAGGGGAGTCAGAGCTGGATGACCAAGCAAGGGTTCAGCTGTAGAGGGTCTGGCCCGCC
           AGGCTCAGGGCTCGGGCTTTATTGTGCTGGTGGTAGGGAGCCACTGAGGGTGAGTGGGGG

38252      GGCAGGAGGGAAGGATCTGGGAGGGTATTGGGGGTGGGGTGGCATGGGCAAAGGCCTGGA
           GGTGAGAGTCAGTCAGTCATTGATGTGAGAAGAGCAAGAAGTAGAAATGTAAGGAATGGT
           GGGGAGGGGAGTCAGAGCTGGATGACCAAGCAAGGGTTCAGCTGTAGAGGGTCTGGCCCG
           CCAGGCTCAGGGCTCGGGCTTTATTGTGCTGGTGGTAGGGAGCCACTGAGGGTGAGTGGG
           GGAGAGCATGCCAGAGCATGCCTCAGAAAGAAAGGTGGGAGAAACGCTGGCATGGAGGGC
           [A,G,C]
           GCCCCCTGAGTTGGTGGGGTGGCCGGGCTCTGCCAAGGCTATGTGCCAGCTGCCTGGACT
           GTGTCCAGGAATGGGCACAATGACTCAACATTGAGAAAATCACTCCCCAGGGAGAAAGGG
           CCCTGATGAATCACCCAGCTGAGGTGGGGAGGCTGGGAGGCTGGGAGGCTGGGAGGCTGG
           GAGCTCACTGAGTCACCGTCCAAGAGTTGGTGAGGAGGGGAGCTGCAGAGAGAGGGCCG
           GCAGTGCAGTTGACGGGGGGATTCAGGTCAGACCACATTGAGGGCTGTCGGGGGACTCTA

38726      AGGCTGGGAGCTCACTGAGTCACCGTCCAAGAGTTGGTGAGGAGGGGAGCTGCAGAGAGA
           GGGGCCGGCAGTGCAGTTGACGGGGGGATTCAGGTCAGACCACATTGAGGGCTGTCGGGG
           GACTCTACCTTCCCGCCATTCCCGGGTTTGGTCCTCCTGGCCGTCCTGTGAGGGAGATGA
           GAAAACTGAGGCCCAGGAAGTGGGGGGAGGGGATCCGAGCAAGGTCATGCGGCAAGTCGC
           TGGCAAAGGCCTAGCGAGACCCAAGCGCACCCTCCAGTCCAGACACGTCCTGCCGCCCCA
           [G,T,C,A]
           CCGCTTTCATGCCAAGCAGAGGCCTAAGAACCGGGTCGGTCCGGGCAGGGAGCTGACCCC
           GGTGACCCGCTGAATCCCCGGACGCGGCCCCTCCGGGCAGCCGGCAACTGAGGCCGGATT
           GCGCCGCCGCGATGGGACGGCAGGGGCGCAGGAGCGTCGCGGCTGCCGCAGGCTCCTGA
           ACCCAGAAGCCGCTCTGCGGAGAAACGCGCTCCCGGAGCGCGGGTCCCACCGCGGAACTG
           CGGACCGTGTGGCCCTGGGGCCTGCACCCTCTCCGGCTCCGGGGACGGCGACAGAGACCT

40472      TGGGGCTCCCGGCACACCTGGAGCACCTGAACCCCCAGCTGTCATCCAGGACTCCACCTC
           AGAGCCGGCCTCACCCAAAGCCCCAAACCTCCATTCCAAGCCTCAACTGGACACCCGCTC
           AGATTCCCACCCAAACATCTGGACTTCAGTCCTCAGCCTGGAACCTACCCCAGAGTCCAA
           ATCTCTCCTTCCATCAGGGCTTCACTGGCTTTCTCTGTGGGACCCACTCCCCGATCCCTT
           CCCTCCCTCCTGTGTTGGAGATCTCCGAGTCTTTCCTCGTGGGGGGCCCCTCCTCTTGTT
           [G,C]
           CTCTCCAGGTACAGTGGTCCCACTTTATTCTCTGGGCTTCTCCTCTGGTTTCTCTTCAAG
           TATTTCTGGGCTCTCTAATTTGGTCTGTTGCCCCATGTGCCCACCTCTCTTGGTCTATCT
           TGGTCTCTCTCCTGTTTCTCTAGGTCTCCATCTTCGTTTTGGGGTCTCTTTCTGCAGCCA
           CCCCTTCCTCTTGTATCTACCTCTGCTTTGTGGTGAGGAGGGGGCAGGCTCAGAGAGCAG
           GGCTAGTGTCCCTGGGACACCCCCGCCCCCCATGTTCTCAGGCATGGCATGGTGTGGGCT

40965      GTATCTACCTCTGCTTTGTGGTGAGGAGGGGGCAGGCTCAGAGAGCAGGGCTAGTGTCCC
```

FIGURE 3-60

```
         TGGGACACCCCCGCCCCCCATGTTCTCAGGCATGGCATGGTGTGGGCTCAGGTGGAAGGG
         CCTAAATGTGGAGTGTGCTGCCCTCAGGCGATGCCCAGGGATCTGAGGTGGTGGGGGGAT
         GATGTGGTGGGCACTGGCTTTTGTAACTTATAAAGCCCCTCATCCCAGCTGCCCTGGTCT
         TGACGGGGGCGGCTAGGGCTTGAGATAGGGAAGAGTAAACTGCAATCTGGTGTCAACCTG
         [C,T]
         GGTGGGATGTGTCCAGGCTGGGTGGGTCTATAGTGTATGTGTTTGTGTGAGTGTTCCTGT
         CTGTGTGTAGCACGGGCTGGGTTGCATGTGTTGGGTGTGTCTTGTGTGTAATCATGTGTG
         TTGTGCCGTGTATGAATGTGTCATCGAGAGTGGGATTATTTGTGGGGAGATTATGGGAAT
         TATGGGTCTATGGCATTGTGTGCTATGTGTGGCTGGGGAGGCAGTGTTGTGGCTGTGGAG
         TGGTAGCTGGGTGTGTGGCTGTTGTGTGTGTAGAGAACTTGTGTGTATGTGGCTGTATGT

41664    CCACTGCAGGGGCCTGATGGTTTTCCACTGGGTGTCTTGTCAGAGAGGAGTTGGGGCAGGG
         GGTGCCGTGTGTGCCAATGTGTTTGCAGCCTAGGTGGCTGGCTTAGAGTCACTATGGCAC
         ATCCTGGGATTGCTTGGGTAATATATCTATTAGGACCTGAGTGCTGGTGTTTGAATGTCA
         TGTGTCTGTGTGGTGGCTGCTCCCGCGATTCTGGACAGGAAAGGGTTGCAGCCAGGGCTG
         AGGGGTCTGAGGTGAGGAGCCAGTTGACAAGTGTGTGAGTGTGTGAGTGTGTGTGTGTGC
         [G,A]
         TGCATGTACACGTGCATATGGGAATGGGGTGGGGTGGGAGGGAGGCAGTGGGCCAGCAGCG
         CTGTCTATGCTGAGGGGCTGTGTGTGCCCACAAACGTGTGACATTAGGTGTGCACATTAT
         CTATGCAGGTTGTGTCTGCATGTGTCTCTGTGTCTAGGTGGCGTGCGTATTGAATTTAAT
         TGGATGCATACACCTGTGGCTGGGGAGGTGAGAGGTGTGTGAGGTGCGTGGTGGGAGACG
         GTGTGAGTGTGGTGTGAAGTGAGGGTGTGTGAGCTGGGTGACTTTTTGGTGTGACGTGTG

41760    GCTGGCTTAGAGTCACTATGGCACATCCTGGGATTGCTTGGGTAATATATCTATTAGGAC
         CTGAGTGCTGGTGTTTGAATGTCATGTGTCTGTGTGGTGGCTGCTCCCGCGATTCTGGAC
         AGGAAAGGGTTGCAGCCAGGGCTGAGGGGTCTGAGGTGAGGAGCCAGTTGACAAGTGTGT
         GAGTGTGTGAGTGTGTGTGTGTGCGTGCATGTACACGTGCATATGGGAATGGGGTGGGGT
         GGGAGGGAGGCAGTGGGCCAGCAGCGCTGTCTATGCTGAGGGGCTGTGTGTGCCCACAAAC
         [G,T,C,A]
         TGTGACATTAGGTGTGCACATTATCTATGCAGGTTGTGTCTGCATGTGTCTCTGTGTCTA
         GGTGGCGTGCGTATTGAATTTAATTGGATGCATACACCTGTGGCTGGGGAGGTGAGAGGT
         GTGTGAGGTGCGTGGTGGGAGACGGTGTGAGTGTGGTGTGAAGTGAGGGTGTGTGAGCTG
         GGTGACTTTTTGGTGTGACGTGTGAATTATGTGATCTTTTCTCCCCATGAGCTGTGTGTG
         CCTGTGGTGAGGAGTGAGTGGAGGATGGCCAGTGAGCTGGCGGTGTGTGTGTTGGGGGTG

42523    CTCCCCTCCTGATCAGGTCCCTAGAGATGCCCTGGAATGTTCTCCATGCCCCCCCAACCC
         CAGCTGCCCCTACCCTTTGCCCTTCATCCTCCTTGCCTTGACCAAGCCCTTTGTTTTGGG
         TTTCCGGCGGAGCAGGCGCTGGACAGGCGGGCGGCAGGCAATGTCGTGGTCTGAGAACCT
         TTGTTCTCTTAGTTTGACTGGTGTTTGGGGCCTTGGTTTGGAGGAGGGTGTGGAGAGGAT
         GCACGTGGCAGCAAGGTCACTGTGTTTACTACACCACTTCGTGCTCCGCAGAGGGGAGGC
         [G,A]
         TACGGCGCAGGCAGTGAGGCCTGGGTGGTGTCTTTGGTGGCGCCTGTTGGTGTAAGAACA
         GCTTAGGCTGGGCTTGGAGTTTGCCAGCCATGCAGTCTTAGTCCATAGTGGCCCAGCGCC
         CTTCCTGGCTCATGTCAGCGGGGCTGAGCAGCCGAGCAGCCAAGCACTCACTTCTCCAAG
         TTCACCTGCCCTCGCCCCTTCTCTGTGTGGCTGCAGCCCCTGGAGACAACCAGGAAGACC
         TCGATTTAGTTCTATTTGTGTTCACTCCAGGTCAGATGGAGGAGAAAGAGTCCCCATCCT

42904    TTGCCAGCCATGCAGTCTTAGTCCATAGTGGCCCAGCGCCCTTCCTGGCTCATGTCAGCG
         GGGCTGAGCAGCCGAGCAGCCAAGCACTCACTTCTCCAAGTTCACCTGCCCTCGCCCCTT
         CTCTGTGTGGCTGCAGCCCCTGGAGACAACCAGGAAGACCTCGATTTAGTTCTATTTGTG
         TTCACTCCAGGTCAGATGGAGGAGAAAGAGTCCCCATCCTCACAGAGACACTTATCTGAA
         AGGAGAGAGCTGGTCACACCTTTGGGGACCCTCTAGACTGACGCAGTCTGTAGGGGGATC
         [G,A]
         AGGTCATACCTTCCAGAGAGAGCTGTGGGAAAACCCTACTGGGCTGCCTCCCAGCAGGTG
         CTTGAGAGAAGAAACATCCAAGGTTCCTTGAGATTGGAAGGCTTAGAGAAGTCTGAGTCA
         GTCAGGGAAGGGGCTGGGGTCGATGCCGCAGTGTCACATACCAGAAGGTTCTCTGAAATG
         AATAGGCTTGAACTGGACCTTGAAGGGGGTGTTGGGGTGGGCAGAGAAATGCAGCCTGGG
         GCTGAGGAAGGTTCTGGCCTGACTGGCAAAAGGGATCTTGCTGGCCATTCCCCAGGCAAC
```

FIGURE 3-61

| | |
|---|---|
| 43382 | ATGAATAGGCTTGAACTGGACCTTGAAGGGGGTGTTGGGGTGGGCAGAGAAATGCAGCCT
GGGGCTGAGGAAGGTTCTGGCCTGACTGGCAAAAGGGATCTTGCTGGCCATTCCCCAGGC
AACACTGTCTGGCTTTGGGTAGCCATCCCTGGGCCTCCAGCCTTCTCAAGCTTTCACGGT
ACCTTTTTTATCCCATTGTCTCTGGCTGGAATTATCTTCATTGTCGTTGACATTGTCATC
TTCATCATCTTTTAGGCAGTTATTTCCAAATTCCAGGGTCCTTTCACAAATGTCTCATTT
[-,C,A]
GCAGGTTAACTCATGCAATTGTCCAAAAGTCTTTATGGAACACTGCTGTGTACCAGGCAG
GCACAGTTTTAAGTGCCGGGGTCATGGTGGTGGCCAAACTGGCCTCATGGAGCTCCTACC
TTCTGTGTCCAGCCATGCTGTCAGTTGCCCACCCTTCTGTGTTTCCCCCAGTCTGGGGCG
CCTGGTTCTGTGGGGCTCCGCATGTGCACCCTCTGGTGCTGGGGTCTGGCTCCTACCAGA
ATGTGAGCTCTGCAGAGGCTGGGCCCGGGTCTCTCCTCTACCCACCGTGTGTGTCCTGAG |
| 43386 | ATAGGCTTGAACTGGACCTTGAAGGGGGTGTTGGGGTGGGCAGAGAAATGCAGCCTGGGG
CTGAGGAAGGTTCTGGCCTGACTGGCAAAAGGGATCTTGCTGGCCATTCCCCAGGCAACA
CTGTCTGGCTTTGGGTAGCCATCCCTGGGCCTCCAGCCTTCTCAAGCTTTCACGGTACCT
TTTTTATCCCATTGTCTCTGGCTGGAATTATCTTCATTGTCGTTGACATTGTCATCTTCA
TCATCTTTTAGGCAGTTATTTCCAAATTCCAGGGTCCTTTCACAAATGTCTCATTTAGCA
[-,C,G]
GTTAACTCATGCAATTGTCCAAAAGTCTTTATGGAACACTGCTGTGTACCAGGCAGGCAC
AGTTTTAAGTGCCGGGGTCATGGTGGTGGCCAAACTGGCCTCATGGAGCTCCTACCTTCT
GTGTCCAGCCATGCTGTCAGTTGCCCACCCTTCTGTGTTTCCCCCAGTCTGGGGCGCCTG
GTTCTGTGGGGCTCCGCATGTGCACCCTCTGGTGCTGGGGTCTGGCTCCTACCAGAATGT
GAGCTCTGCAGAGGCTGGGCCCGGGTCTCTCCTCTACCCACCGTGTGTGTCCTGAGCTGG |
| 43387 | TAGGCTTGAACTGGACCTTGAAGGGGGTGTTGGGGTGGGCAGAGAAATGCAGCCTGGGGC
TGAGGAAGGTTCTGGCCTGACTGGCAAAAGGGATCTTGCTGGCCATTCCCCAGGCAACAC
TGTCTGGCTTTGGGTAGCCATCCCTGGGCCTCCAGCCTTCTCAAGCTTTCACGGTACCTT
TTTTATCCCATTGTCTCTGGCTGGAATTATCTTCATTGTCGTTGACATTGTCATCTTCAT
CATCTTTTAGGCAGTTATTTCCAAATTCCAGGGTCCTTTCACAAATGTCTCATTTAGCAG
[-,G]
TTAACTCATGCAATTGTCCAAAAGTCTTTATGGAACACTGCTGTGTACCAGGCAGGCACA
GTTTTAAGTGCCGGGGTCATGGTGGTGGCCAAACTGGCCTCATGGAGCTCCTACCTTCTG
TGTCCAGCCATGCTGTCAGTTGCCCACCCTTCTGTGTTTCCCCCAGTCTGGGGCGCCTGG
TTCTGTGGGGCTCCGCATGTGCACCCTCTGGTGCTGGGGTCTGGCTCCTACCAGAATGTG
AGCTCTGCAGAGGCTGGGCCCGGGTCTCTCCTCTACCCACCGTGTGTGTCCTGAGCTGGG |
| 43728 | CTGTGTACCAGGCAGGCACAGTTTTAAGTGCCGGGGTCATGGTGGTGGCCAAACTGGCCT
CATGGAGCTCCTACCTTCTGTGTCCAGCCATGCTGTCAGTTGCCCACCCTTCTGTGTTTC
CCCCAGTCTGGGGCGCCTGGTTCTGTGGGGCTCCGCATGTGCACCCTCTGGTGCTGGGGT
CTGGCTCCTACCAGAATGTGAGCTCTGCAGAGGCTGGGCCCGGGTCTCTCCTCTACCCAC
CGTGTGTGTCCTGAGCTGGGTCTGGCAGAGTCCAGATGCTCACACCTATCATCAAGTGAC
[G,A,T]
GGAACTGCCATGTAGGGTTGGCAGTCCAGCTCTGTCTAGGGAAACTGGGGTCCATCGGAT
GAGGGGACTCTCATCTCATCAGGCAGCATCTCATCAGGCCCTTCTTTTACCAGTAGCTCC
AGAGACCAAGAAGGGTCAGGTGACTGGTGCAGGTCTCACAGCAGGGTGGCGCGGCTGGTG
TCAGAAGACAGCACTTCTTGCTGCCAGGTTGGGCTCTGGTCCTAGCACCATGCTGCTCTC
TGGCTGGCCTCTGTGCTGCCTGCGGCGGGTAAACGATTATTAATGACCCCCCTGGCAAGG |
| 45012 | CTCCAAGCCTGAGCAATGTTGCATCAGCCCCTTGGCAGGTGGCACAGACCTAGGTACTAG
GGCTGGGGGAGGGGAGGCGGAGAAACAGGGAGTGATGTTGGTAGAGTGTGTGGGGAGGGC
AACGAGGGAGATAAACTCAGGGGCCATGGTGATATAAAGCAGGGACCCCTATTTCAGCCC
AGAGTGGGAGGGAGGGGCATGTTGGGGAGCTTCCAGGAGGAAACAAATCTGAACTGAGAG
CTAAGGTCAAGCCAGGAGAAAGTTCTGGACAGAGGGGAGAGAATGGTTACTGTGAAGGTT
[C,T]
GCTGGTGGCAGACAGAGGGAGGAGAGCCTGTGGCAGCACCACTCCATGGAGCAGGCCCCT
GGGTGCCAGCCGGCTGGGTCCGGGGGGATGGGGACTGGTAAAGCTGGCCCAGCCAGATGG
TGCAGGACTTGTAAGCCATGTTAAGGACTGCGGACTTATTCTGGAGGGAAATTGACCCTG |

FIGURE 3-62

GGGAAGAGTTGAGAGAACGGATATGACAGATCAGATCTGCATGTTCAATAGCTCCCTGGA
CCATGGTGTGGAGACTGAAGGGGAGGCTGGTGTGGTCCAGGTAAGCGGGGGTGATGAGGC

45079  GGAGGGGAGGCGGAGAAACAGGGAGTGATGTTGGTAGAGTGTGTGGGGAGGGCAACGAGG
GAGATAAACTCAGGGGCCATGGTGATATAAAGCAGGGACCCCTATTTCAGCCCAGAGTGG
GAGGGAGGGGCATGTTGGGGAGCTTCCAGGAGGAAACAAATCTGAACTGAGAGCTAAGGT
CAAGCCAGGAGAAAGTTCTGGACAGAGGGGAGAGAATGGTTACTGTGAAGGTTCGCTGGT
GGCAGACAGAGGGAGGAGAGCCTGTGGCAGCACCACTCCATGGAGCAGGCCCCTGGGTGC
[C,T]
AGCCGGCTGGGTCCGGGGGGATGGGGACTGGTAAAGCTGGCCCAGCCAGATGGTGCAGGA
CTTGTAAGCCATGTTAAGGACTGCGGACTTATTCTGGAGGGAAATTGACCCTGGGGAAGA
GTTGAGAGAACGGATATGACAGATCAGATCTGCATGTTCAATAGCTCCCTGGACCATGGT
GTGGAGACTGAAGGGGAGGCTGGTGTGGTCCAGGTAAGCGGGGGTGATGAGGCCTGGACA
GGGAAATGGCTGAAGAATGGAGGGGAGGGGACGGAGTGGCCAGGGCTGGTGGAGGGAGCT

45247  GAGAGCTAAGGTCAAGCCAGGAGAAAGTTCTGGACAGAGGGGAGAGAATGGTTACTGTGA
AGGTTCGCTGGTGGCAGACAGAGGGAGGAGAGCCTGTGGCAGCACCACTCCATGGAGCAG
GCCCCTGGGTGCCAGCCGGCTGGGTCCGGGGGGATGGGGACTGGTAAAGCTGGCCCAGCC
AGATGGTGCAGGACTTGTAAGCCATGTTAAGGACTGCGGACTTATTCTGGAGGGAAATTG
ACCCTGGGGAAGAGTTGAGAGAACGGATATGACAGATCAGATCTGCATGTTCAATAGCTC
[A,G,C]
CTGGACCATGGTGTGGAGACTGAAGGGGAGGCTGGTGTGGTCCAGGTAAGCGGGGGTGAT
GAGGCCTGGACAGGGAAATGGCTGAAGAATGGAGGGGAGGGGACGGAGTGGCCAGGGCTG
GTGGAGGGAGCTGGACAGCTGTAGACGTGAAGGGCAAGGGAGGAGAATGCTGCCCCACCC
AGGTGTCTGGATGGGTTTTGTGCAGTCTCTGAGATGTATAGGAGGGAAGACAGGGGTTAG
TGGCAGATGCCTGGGCCTGTGTCAGGGCCCTTTAAGGACCAAAAGGTCTTGGAAAAGCCT

46267  GCAGGCATTCTGCCTTTCCTGTCTCCCACCCTAAGGGAGTTGGCCTTGCATGCCTCCCAT
CCACGGTTGCCTCTACTGGGGGCTGCCACTGGGAGACAGGAAGGGCATGGGAGTTTCGGG
AGCTCAGGGTAAGAGGGGCTGAGATCTCGTGGTGTGGAGGGGGAGCGGGAAGGTCGGGTG
GCCGAAAGAATGGAGAGGGCCGGGAGTGAGAGCAAAGGGAGACAGGCAGAGCTGAAGAGC
AGTATCGCCCCAACATCAATACTGGTATTTCAGAATGGGAAAGCTGTTCCATTTCCCGAA
[T,A]
TATCAGAATGCTGAGGTCCGATCTTGCAGTCTCTGAGCTGGGCATTCCTTGGCCCCCACT
CTCGGGTATTCTTGCACAAGACCATTTTTTCTGGGCTGCATTTTCTCACTTGTAAAAGGAG
GAAGTTGGGGGTCAATATCTCCAAGCGATATATGAGCTCTAGCTCTAGGAGTATAGGATT
TTGAGAATCTGGAATTGTTAGTCTGTGGGGTTCTAACTGGGACAATTCTAGCATTCCTTG
ACTCTCAGCTCCCAGCCAGGGCTGTGTGGATGCGTGGTTGTGTGATTCCGACATTCTGAG

46268  CAGGCATTCTGCCTTTCCTGTCTCCCACCCTAAGGGAGTTGGCCTTGCATGCCTCCCATC
CACGGTTGCCTCTACTGGGGGCTGCCACTGGGAGACAGGAAGGGCATGGGAGTTTCGGGA
GCTCAGGGTAAGAGGGGCTGAGATCTCGTGGTGTGGAGGGGGAGCGGGAAGGTCGGGTGG
CCGAAAGAATGGAGAGGGCCGGGAGTGAGAGCAAAGGGAGACAGGCAGAGCTGAAGAGCA
GTATCGCCCCAACATCAATACTGGTATTTCAGAATGGGAAAGCTGTTCCATTTCCCGAAA
[T,C]
ATCAGAATGCTGAGGTCCGATCTTGCAGTCTCTGAGCTGGGCATTCCTTGGCCCCCACTC
TCGGGTATTCTTGCACAAGACCATTTTTTCTGGGCTGCATTTTCTCACTTGTAAAAGGAGG
AAGTTGGGGGTCAATATCTCCAAGCGATATATGAGCTCTAGCTCTAGGAGTATAGGATTT
TGAGAATCTGGAATTGTTAGTCTGTGGGGTTCTAACTGGGACAATTCTAGCATTCCTTGA
CTCTCAGCTCCCAGCCAGGGCTGTGTGGATGCGTGGTTGTGTGATTCCGACATTCTGAGA

46414  CGTGGTGTGGAGGGGGAGCGGGAAGGTCGGGTGGCCGAAAGAATGGAGAGGGCCGGGAGT
GAGAGCAAAGGGAGACAGGCAGAGCTGAAGAGCAGTATCGCCCCAACATCAATACTGGTA
TTTCAGAATGGGAAAGCTGTTCCATTTCCCGAAATATCAGAATGCTGAGGTCCGATCTTG
CAGTCTCTGAGCTGGGCATTCCTTGGCCCCCACTCTCGGGTATTCTTGCACAAGACCATT
TTTCTGGGCTGCATTTTCTCACTTGTAAAAGGAGGAAGTTGGGGGTCAATATCTCCAAGC
[G,A]
ATATATGAGCTCTAGCTCTAGGAGTATAGGATTTTGAGAATCTGGAATTGTTAGTCTGTG

FIGURE 3-63

```
       GGGTTCTAACTGGGACAATTCTAGCATTCCTTGACTCTCAGCTCCCAGCCAGGGCTGTGT
       GGATGCGTGGTTGTGTGATTCCGACATTCTGAGACTTTAAGATGCTGAGGCTCTAGGAGC
       TAGAGATACGGACATTCTGTGAATCTAGGATTCTAGGATTTGATGGTTTTGATGATTCAAT
       GATTCTAAATGGGGCTGCTGGGAAGAGCTGCAACCACCTGCCTTGTTAATGTCAATGTTC
```

46822
```
       GCCAGGGCTGTGTGGATGCGTGGTTGTGTGATTCCGACATTCTGAGACTTTAAGATGCTG
       AGGCTCTAGGAGCTAGAGATACGGACATTCTGTGAATCTAGGATTCTAGGATTTGATGGT
       TTGATGATTCAATGATTCTAAATGGGGCTGCTGGGAAGAGCTGCAACCACCTGCCTTGTT
       AATGTCAATGTTCAGTTATTAAAAACATAACAAGAAGCAATGGAGACAGATAGCTCAGAA
       TGGTGGGCGCTCCCTCCACTCCCAGTGAGGGAGGACAGAAGAGGCTGGGCTGGCCTTAGA
       [G,A,C,T]
       AATAGAGACCTTTTCAACCTGGGTCACACAGGTTGTTTCTCCTGTCACAACAGAACTGGT
       GTGTGTACATTCGAGAGAGCTTCCACTCCCAAAGCTTGCAGGGTAAGGGGCTCATTTCCT
       TCAGCACTGGCCTCTATTCCTTAACCATTTCAGACTGGGCAGAGAGAGGGGTAACTACCC
       TTTCCTCCCAGCCCTCGAAGTCTCTGGGCAGAAATGGCAGCAGTGGAGGAAGGAGAGGTC
       TGCTCACCCCCGCCCCTTCCCTGACAGCCTGAGGGGGAAAACAGGACATGAATACTTCCT
```

47169
```
       ACAACAGAACTGGTGTGTGTACATTCGAGAGAGCTTCCACTCCCAAAGCTTGCAGGGTAA
       GGGGCTCATTTCCTTCAGCACTGGCCTCTATTCCTTAACCATTTCAGACTGGGCAGAGAG
       AGGGGTAACTACCCTTTCCTCCCAGCCCTCGAAGTCTCTGGGCAGAAATGGCAGCAGTGG
       AGGAAGGAGAGGTCTGCTCACCCCCGCCCCTTCCCTGACAGCCTGAGGGGGAAAACAGGA
       CATGAATACTTCCTGGACACAGACATGGAAATGCATGAACCCCTGCCTTCGAGGGCCCCG
       [C,T]
       GTCCAAAGGCTCAGACAAGGGCAGAGGCCAGGACAGCCAGTGGGGTCCCATCAGCACCCT
       CTCAGTATAGGCTGAGGAGGGAAGACCCTGTTCTTGCCCCAAGGGTGACAGTGAGAAGGG
       GTCAAGGAAAGGAGTCCCAGGTCAGGGACTGGAAGTGCTGACAGGTCCTCCCCTGTGTGC
       AAGGCCACAGTCCAGCCTGGCAGAAGGCCAGCCCAATTGTCCAGTGTTTCACTGCCTCCT
       GAGTCCTTCTTATGCCTTGGCACCCAGGCCAGAGTTGGGGAGGGGTCCAGGCTGCAGGGG
```

47214
```
       AAGCTTGCAGGGTAAGGGGCTCATTTCCTTCAGCACTGGCCTCTATTCCTTAACCATTTC
       AGACTGGGCAGAGAGAGGGGTAACTACCCTTTCCTCCCAGCCCTCGAAGTCTCTGGGCAG
       AAATGGCAGCAGTGGAGGAAGGAGAGGTCTGCTCACCCCCGCCCCTTCCCTGACAGCCTG
       AGGGGGAAAACAGGACATGAATACTTCCTGGACACAGACATGGAAATGCATGAACCCCTG
       CCTTCGAGGGCCCCGCGTCCAAAGGCTCAGACAAGGGCAGAGGCCAGGACAGCCAGTGGG
       [G,C,AsT]
       TCCCATCAGCACCCTCTCAGTATAGGCTGAGGAGGGAAGACCCTGTTCTTGCCCCAAGGG
       TGACAGTGAGAAGGGGTCAAGGAAAGGAGTCCCAGGTCAGGGACTGGAAGTGCTGACAGG
       TCCTCCCCTGTGTGCAAGGCCACAGTCCAGCCTGGCAGAAGGCCAGCCCAATTGTCCAGT
       GTTTCACTGCCTCCTGAGTCCTTCTTATGCCTTGGCACCCAGGCCAGAGTTGGGGAGGGG
       TCCAGGCTGCAGGGGAGGGTTTCCTTCCAGAGTGCCCATCCCTGATGGATCCTTAGAAGC
```

47431
```
       ACATGGAAATGCATGAACCCCTGCCTTCGAGGGCCCCGCGTCCAAAGGCTCAGACAAGGG
       CAGAGGCCAGGACAGCCAGTGGGGTCCCATCAGCACCCTCTCAGTATAGGCTGAGGAGGG
       AAGACCCTGTTCTTGCCCCAAGGGTGACAGTGAGAAGGGGTCAAGGAAAGGAGTCCCAGG
       TCAGGGACTGGAAGTGCTGACAGGTCCTCCCCTGTGTGCAAGGCCACAGTCCAGCCTGGC
       AGAAGGCCAGCCCAATTGTCCAGTGTTTCACTGCCTCCTGAGTCCTTCTTATGCCTTGGC
       [A,G]
       CCCAGGCCAGAGTTGGGGAGGGGTCCAGGCTGCAGGGGAGGGTTTCCTTCCAGAGTGCCC
       ATCCCTGATGGATCCTTAGAAGCCAGTACAGCTGCACAGTTCCAAGGGCTTCCGCTGCC
       TGGTAGGTTCACAGACCAAAGCTGGCCCTGGTCACACAGCACAACGGGGCCTGAAATCAG
       GCTTCCTGATTCCCAGTCCTGGGTGTTCCTTTTTGCCCACAGCCTCCCCCACTTCCCCTG
       GGACACCTGAGGGGCAGGAGTGGAGGTGGGGCTCAGGTTAGGGAGCAGAGCCTCTGTCCA
```

47773
```
       GTTTCCTTCCAGAGTGCCCATCCCTGATGGATCCTTAGAAGCCCAGTACAGCTGCACAGT
       TCCAAGGGCTTCCGCTGCCTGGTAGGTTCACAGACCAAAGCTGGCCCTGGTCACACAGCA
       CAACGGGGCCTGAAATCAGGCTTCCTGATTCCCAGTCCTGGGTGTTCCTTTTTGCCCACA
       GCCTCCCCCACTTCCCCTGGGACACCTGAGGGGCAGGAGTGGAGGTGGGGCTCAGGTTAG
       GGAGCAGAGCCTCTGTCCATCATCCCTCCGTCTTCCTCTTCCCACAGGCCAGAAGCAGGT
```

FIGURE 3-64

```
        [G,T,GsT]
        TGGTGGTGACAGCTGCCCCCAGTCCTCCACAAGGCTCCATTGTCCCCGGCAGGGAGCCCC
        TCCCCAGCTGCAGGCCAGAAGTGTGCCTCCCCGGGCCCTCCTGTCGTGACTCTGCCACCC
        GCTTCCTCCTGCTGCCCCTTCCCTCTTCTCATCTCCGCTTGCCCTCAGGCCCTCCCCATC
        CCCGTGAGGTCTCGTCTCTGGCGCTCTCTGGGTTTAAGCCTCTCTCCAGTGAAAGTTAGA
        TTTGGAAGGGCCCTGGGAGATCACCAAGTCCAACCCTTTTATTCTTCGGATAAGGAGGCC
```

47821   CAGCTGCACAGTTCCAAGGGCTTCCGCTGCCTGGTAGGTTCACAGACCAAAGCTGGCCCT
        GGTCACACAGCACAACGGGGCCTGAAATCAGGCTTCCTGATTCCCAGTCCTGGGTGTTCC
        TTTTTGCCCACAGCCTCCCCCACTTCCCCTGGGACACCTGAGGGGCAGGAGTGGAGGTGG
        GGCTCAGGTTAGGGAGCAGAGCCTCTGTCCATCATCCCTCCGTCTTCCTCTTCCCACAGG
        CCAGAAGCAGGTGTGGTGGTGACAGCTGCCCCCAGTCCTCCACAAGGCTCCATTGTCCCC
        [G,A]
        GCAGGGAGCCCCTCCCCAGCTGCAGGCCAGAAGTGTGCCTCCCCGGGCCCTCCTGTCGTG
        ACTCTGCCACCCGCTTCCTCCTGCTGCCCCTTCCCTCTTCTCATCTCCGCTTGCCCTCAG
        GCCCTCCCCATCCCCGTGAGGTCTCGTCTCTGGCGCTCTCTGGGTTTAAGCCTCTCTCCA
        GTGAAAGTTAGATTTGGAAGGGCCCTGGGAGATCACCAAGTCCAACCCTTTTATTCTTCG
        GATAAGGAGGCCAGGTCAGAGAGGGGAAGGTCCTGTCCAAAGCTGCACAGTAGGCTGAGG

48186   TGCCACCCGCTTCCTCCTGCTGCCCCTTCCCTCTTCTCATCTCCGCTTGCCCTCAGGCCC
        TCCCCATCCCCGTGAGGTCTCGTCTCTGGCGCTCTCTGGGTTTAAGCCTCTCTCCAGTGA
        AAGTTAGATTTGGAAGGGCCCTGGGAGATCACCAAGTCCAACCCTTTTATTCTTCGGATA
        AGGAGGCCAGGTCAGAGAGGGGAAGGTCCTGTCCAAAGCTGCACAGTAGGCTGAGGCAGA
        GCCCAGTGCTGTGCTCCCTTCAGCGCTGGGTCATGGGTGCACACTGCCCTTGGCATCAGG
        [C,T]
        GTCCAGGGTTTGAGAACTGACTGTGATGATCAGCGCTAAGCACACAGGCACCTACAGAAA
        TGCGGTAGGGGGCTTCTCTCCTCAGCCCTTCTTCACAGCCCTGAGCTGCCCTCCCTTCCT
        CTTCTTTGCCCAGCTCCTCTCTCCTTCACTATCCCTGCTGTCTGCTGACTCCTGCCTCTG
        GCAGACACTGTCCTTGGGACACAGACTAGAGCTCAGGCCTCCAGGACTGGGATGCACACC
        CATGCACCCAGACACAGACACATAAACATGTGCAAGCGTGTCACGGGGTCCATAAATCCC

48544   AAATGCGGTAGGGGGCTTCTCTCCTCAGCCCTTCTTCACAGCCCTGAGCTGCCCTCCCTT
        CCTCTTCTTTGCCCAGCTCCTCTCTCCTTCACTATCCCTGCTGTCTGCTGACTCCTGCCT
        CTGGCAGACACTGTCCTTGGGACACAGACTAGAGCTCAGGCCTCCAGGACTGGGATGCAC
        ACCCATGCACCCAGACACAGACACATAAACATGTGCAAGCGTGTCACGGGGTCCATAAAT
        CCCAGCTGAAAACTGGTCAGACCATCAGGAGGCCACCCTGGAACCCAGTGTCCTCCTCTT
        [G,A,C]
        CTGTCAGGCCTCACACACCTCCTCCAGGAAGCCCCTTAGGACCCCTGAAGACCATCTTCA
        TCCAACTAGCCCCTTTGTGACAACTGAACTCTGTGAGCCTAGGTTCCTCCTGTGACTCGA
        AGGGCAAGGCTGAGTCCCCCCTTCAGTCCTGGGGCCACTCCTTCAGTGTCTTCAGGAGGG
        GCTCAGCTTCCTGTTGCTGGGTGGGGAGAGCCCTGAGGTCCCCACAGGACGTGGGACAAT
        GGGGAGGCGGTGACAGATGAGAGGCTGAGTCTTCCCTAAAGCAGACTCCACCCTCCCCTG

48577   CTTCACAGCCCTGAGCTGCCCTCCCTTCCTCTTCTTTGCCCAGCTCCTCTCTCCTTCACT
        ATCCCTGCTGTCTGCTGACTCCTGCCTCTGGCAGACACTGTCCTTGGGACACAGACTAGA
        GCTCAGGCCTCCAGGACTGGGATGCACACCCATGCACCCAGACACAGACACATAAACATG
        TGCAAGCGTGTCACGGGGTCCATAAATCCCAGCTGAAAACTGGTCAGACCATCAGGAGGC
        CACCCTGGAACCCAGTGTCCTCCTCTTCCTGTCAGGCCTCACACACCTCCTCCAGGAAGC
        [G,C]
        CCTTAGGACCCCTGAAGACCATCTTCATCCAACTAGCCCCTTTGTGACAACTGAACTCTG
        TGAGCCTAGGTTCCTCCTGTGACTCGAAGGGCAAGGCTGAGTCCCCCCTTCAGTCCTGGG
        GCCACTCCTTCAGTGTCTTCAGGAGGGGCTCAGCTTCCTGTTGCTGGGTGGGGAGAGCCC
        TGAGGTCCCCACAGGACGTGGGACAATGGGGAGGCGGTGACAGATGAGAGGCTGAGTCTT
        CCCTAAAGCAGACTCCACCCTCCCCTGACCTCCCTGGCTGGTGGCTTGGACACAGCCCTG

48705   CTCCAGGACTGGGATGCACACCCATGCACCCAGACACAGACACATAAACATGTGCAAGCG
        TGTCACGGGGTCCATAAATCCCAGCTGAAAACTGGTCAGACCATCAGGAGGCCACCCTGG
        AACCCAGTGTCCTCCTCTTCCTGTCAGGCCTCACACACCTCCTCCAGGAAGCCCCTTAGG

FIGURE 3-65

```
         ACCCCTGAAGACCATCTTCATCCAACTAGCCCCTTTGTGACAACTGAACTCTGTGAGCCT
         AGGTTCCTCCTGTGACTCGAAGGGCAAGGCTGAGTCCCCCCTTCAGTCCTGGGGCCACTC
         [G,A,C]
         TTCAGTGTCTTCAGGAGGGGCTCAGCTTCCTGTTGCTGGGTGGGGAGAGCCCTGAGGTCC
         CCACAGGACGTGGGACAATGGGGAGGCGGTGACAGATGAGAGGCTGAGTCTTCCCTAAAG
         CAGACTCCACCCTCCCCTGACCTCCCTGGCTGGTGGCTTGGACACAGCCCTGGCCTGGAC
         TAGGGTCCTGGTCTGACCCCACAATGCAGAGGTCTGGGAATCAGAAGCCCTGGTTCTCCA
         GCAGCAGTTCTCTAACTGGCGGCTATGGAGTCCAGGCCTCCAGGGCACTGGTAGGTTATT

48873    AAGCCCCTTAGGACCCCTGAAGACCATCTTCATCCAACTAGCCCCTTTGTGACAACTGAA
         CTCTGTGAGCCTAGGTTCCTCCTGTGACTCGAAGGGCAAGGCTGAGTCCCCCCTTCAGTC
         CTGGGGCCACTCCTTCAGTGTCTTCAGGAGGGGCTCAGCTTCCTGTTGCTGGGTGGGGAG
         AGCCCTGAGGTCCCCACAGGACGTGGGACAATGGGGAGGCGGTGACAGATGAGAGGCTGA
         GTCTTCCCTAAAGCAGACTCCACCCTCCCCTGACCTCCCTGGCTGGTGGCTTGGACACAG
         [-,C]
         CCTGGCCTGGACTAGGGTCCTGGTCTGACCCCACAATGCAGAGGTCTGGGAATCAGAAGC
         CCTGGTTCTCCAGCAGCAGTTCTCTAACTGGCGGCTATGGAGTCCAGGCCTCCAGGGCAC
         TGGTAGGTTATTGGCGGGTTGGTGCAGATTCCAGTGTCCAGGAGGGGTGAGCTGGCCTGG
         GGGGCCTATGTACAGGAGATAGGAGGGTGATAAACACAGGCTAGGTGGGATTACAGGGAG
         CTGGGAATACCTAGCTAAGAATCCCCTCATCCTAGGCACTTTCCCCACACTTGAAATTGG

48874    AGCCCCTTAGGACCCCTGAAGACCATCTTCATCCAACTAGCCCCTTTGTGACAACTGAAC
         TCTGTGAGCCTAGGTTCCTCCTGTGACTCGAAGGGCAAGGCTGAGTCCCCCCTTCAGTCC
         TGGGGCCACTCCTTCAGTGTCTTCAGGAGGGGCTCAGCTTCCTGTTGCTGGGTGGGGAGA
         GCCCTGAGGTCCCCACAGGACGTGGGACAATGGGGAGGCGGTGACAGATGAGAGGCTGAG
         TCTTCCCTAAAGCAGACTCCACCCTCCCCTGACCTCCCTGGCTGGTGGCTTGGACACAGC
         [-,G,C]
         CTGGCCTGGACTAGGGTCCTGGTCTGACCCCACAATGCAGAGGTCTGGGAATCAGAAGCC
         CTGGTTCTCCAGCAGCAGTTCTCTAACTGGCGGCTATGGAGTCCAGGCCTCCAGGGCACT
         GGTAGGTTATTGGCGGGTTGGTGCAGATTCCAGTGTCCAGGAGGGGTGAGCTGGCCTGGG
         GGGCCTATGTACAGGAGATAGGAGGGTGATAAACACAGGCTAGGTGGGATTACAGGGAGC
         TGGGAATACCTAGCTAAGAATCCCCTCATCCTAGGCACTTTCCCCACACTTGAAATTGGC

48876    CCCCTTAGGACCCCTGAAGACCATCTTCATCCAACTAGCCCCTTTGTGACAACTGAACTC
         TGTGAGCCTAGGTTCCTCCTGTGACTCGAAGGGCAAGGCTGAGTCCCCCCTTCAGTCCTG
         GGGCCACTCCTTCAGTGTCTTCAGGAGGGGCTCAGCTTCCTGTTGCTGGGTGGGGAGAGC
         CCTGAGGTCCCCACAGGACGTGGGACAATGGGGAGGCGGTGACAGATGAGAGGCTGAGTC
         TTCCCTAAAGCAGACTCCACCCTCCCCTGACCTCCCTGGCTGGTGGCTTGGACACAGCCC
         [-,T]
         GGCCTGGACTAGGGTCCTGGTCTGACCCCACAATGCAGAGGTCTGGGAATCAGAAGCCCT
         GGTTCTCCAGCAGCAGTTCTCTAACTGGCGGCTATGGAGTCCAGGCCTCCAGGGCACTGG
         TAGGTTATTGGCGGGTTGGTGCAGATTCCAGTGTCCAGGAGGGGTGAGCTGGCCTGGGGG
         GCCTATGTACAGGAGATAGGAGGGTGATAAACACAGGCTAGGTGGGATTACAGGGAGCTG
         GGAATACCTAGCTAAGAATCCCCTCATCCTAGGCACTTTCCCCACACTTGAAATTGGCTG

48879    CTTAGGACCCCTGAAGACCATCTTCATCCAACTAGCCCCTTTGTGACAACTGAACTCTGT
         GAGCCTAGGTTCCTCCTGTGACTCGAAGGGCAAGGCTGAGTCCCCCCTTCAGTCCTGGGG
         CCACTCCTTCAGTGTCTTCAGGAGGGGCTCAGCTTCCTGTTGCTGGGTGGGGAGAGCCCT
         GAGGTCCCCACAGGACGTGGGACAATGGGGAGGCGGTGACAGATGAGAGGCTGAGTCTTC
         CCTAAAGCAGACTCCACCCTCCCCTGACCTCCCTGGCTGGTGGCTTGGACACAGCCCTGG
         [-,C]
         CTGGACTAGGGTCCTGGTCTGACCCCACAATGCAGAGGTCTGGGAATCAGAAGCCCTGGT
         TCTCCAGCAGCAGTTCTCTAACTGGCGGCTATGGAGTCCAGGCCTCCAGGGCACTGGTAG
         GTTATTGGCGGGTTGGTGCAGATTCCAGTGTCCAGGAGGGGTGAGCTGGCCTGGGGGGCC
         TATGTACAGGAGATAGGAGGGTGATAAACACAGGCTAGGTGGGATTACAGGGAGCTGGGA
         ATACCTAGCTAAGAATCCCCTCATCCTAGGCACTTTCCCCACACTTGAAATTGGCTGGAG

48880    TTAGGACCCCTGAAGACCATCTTCATCCAACTAGCCCCTTTGTGACAACTGAACTCTGTG
```

FIGURE 3-66

```
         AGCCTAGGTTCCTCCTGTGACTCGAAGGGCAAGGCTGAGTCCCCCCTTCAGTCCTGGGGC
         CACTCCTTCAGTGTCTTCAGGAGGGGCTCAGCTTCCTGTTGCTGGGTGGGGAGAGCCCTG
         AGGTCCCCACAGGACGTGGGACAATGGGGAGGCGGTGACAGATGAGAGGCTGAGTCTTCC
         CTAAAGCAGACTCCACCCTCCCCTGACCTCCCTGGCTGGTGGCTTGGACACAGCCCTGGC
         [-,T,C]
         TGGACTAGGGTCCTGGTCTGACCCCACAATGCAGAGGTCTGGGAATCAGAAGCCCTGGTT
         CTCCAGCAGCAGTTCTCTAACTGGCGGCTATGGAGTCCAGGCCTCCAGGGCACTGGTAGG
         TTATTGGCGGGTTGGTGCAGATTCCAGTGTCCAGGAGGGGTGAGCTGGCCTGGGGGGCCT
         ATGTACAGGAGATAGGAGGGTGATAAACACAGGCTAGGTGGGATTACAGGGAGCTGGGAA
         TACCTAGCTAAGAATCCCCTCATCCTAGGCACTTTCCCCACACTTGAAATTGGCTGGAGG

48881    TAGGACCCCTGAAGACCATCTTCATCCAACTAGCCCCTTTGTGACAACTGAACTCTGTGA
         GCCTAGGTTCCTCCTGTGACTCGAAGGGCAAGGCTGAGTCCCCCCTTCAGTCCTGGGGCC
         ACTCCTTCAGTGTCTTCAGGAGGGGCTCAGCTTCCTGTTGCTGGGTGGGGAGAGCCCTGA
         GGTCCCCACAGGACGTGGGACAATGGGGAGGCGGTGACAGATGAGAGGCTGAGTCTTCCC
         TAAAGCAGACTCCACCCTCCCCTGACCTCCCTGGCTGGTGGCTTGGACACAGCCCTGGCC
         [-,A,T]
         GGACTAGGGTCCTGGTCTGACCCCACAATGCAGAGGTCTGGGAATCAGAAGCCCTGGTTC
         TCCAGCAGCAGTTCTCTAACTGGCGGCTATGGAGTCCAGGCCTCCAGGGCACTGGTAGGT
         TATTGGCGGGTTGGTGCAGATTCCAGTGTCCAGGAGGGGTGAGCTGGCCTGGGGGGCCTA
         TGTACAGGAGATAGGAGGGTGATAAACACAGGCTAGGTGGGATTACAGGGAGCTGGGAAT
         ACCTAGCTAAGAATCCCCTCATCCTAGGCACTTTCCCCACACTTGAAATTGGCTGGAGGG

49008    CAGTGTCTTCAGGAGGGGCTCAGCTTCCTGTTGCTGGGTGGGGAGAGCCCTGAGGTCCCC
         ACAGGACGTGGGACAATGGGGAGGCGGTGACAGATGAGAGGCTGAGTCTTCCCTAAAGCA
         GACTCCACCCTCCCCTGACCTCCCTGGCTGGTGGCTTGGACACAGCCCTGGCCTGGACTA
         GGGTCCTGGTCTGACCCCACAATGCAGAGGTCTGGGAATCAGAAGCCCTGGTTCTCCAGC
         AGCAGTTCTCTAACTGGCGGCTATGGAGTCCAGGCCTCCAGGGCACTGGTAGGTTATTGG
         [C,T]
         GGGTTGGTGCAGATTCCAGTGTCCAGGAGGGGTGAGCTGGCCTGGGGGGCCTATGTACAG
         GAGATAGGAGGGTGATAAACACAGGCTAGGTGGGATTACAGGGAGCTGGGAATACCTAGC
         TAAGAATCCCCTCATCCTAGGCACTTTCCCCACACTTGAAATTGGCTGGAGGGGGGAACCA
         GAAGTTAGGTGGGGTTGGGGAGGGACAGGAGCCAGCACCCTGCCTCCACCTCCGGGCAGT
         GCCTCTGCTGGGGGGAGGGAACCTGTCCTGGGGGTGGTGGGAGGTGTGAGGGGGGAGCTG

49259    AACTGGCGGCTATGGAGTCCAGGCCTCCAGGGCACTGGTAGGTTATTGGCGGGTTGGTGC
         AGATTCCAGTGTCCAGGAGGGGTGAGCTGGCCTGGGGGGCCTATGTACAGGAGATAGGAG
         GGTGATAAACACAGGCTAGGTGGGATTACAGGGAGCTGGGAATACCTAGCTAAGAATCCC
         CTCATCCTAGGCACTTTCCCCACACTTGAAATTGGCTGGAGGGGGGAACCAGAAGTTAGGT
         GGGGTTGGGGAGGGACAGGAGCCAGCACCCTGCCTCCACCTCCGGGCAGTGCCTCTGCTG
         [G,C]
         GGGGAGGGAACCTGTCCTGGGGGTGGTGGGAGGTGTGAGGGGGGAGCTGGATTCTCCAGT
         GAAACTGGCCCTCCCTCCTCTCAGGGGAGGGGAGGGGGCTGTCCCTGGCTGCTCAGCAGG
         TAGCCCATCTGGCTGTGGGTGGAAAAGAAGACTCAGGCTTTGTGGATAAAAGGGACAGCC
         CTGGGTCAGGCACTTATCTCAACCCTCGTCATTTCCTCTGCCGGACATGACTGGGTGAGT
         GGGGTCATTGCACAGAGGGAAGGAACAGGCCAGGGCCAGTGCATACCAGGCCCTACAGGA

49821    GGAACAGGCCAGGGCCAGTGCATACCAGGCCCTACAGGAGAGTCAGGCACATGGGTGACC
         CTGCCACACCCTGGGCTGCAGTCAGCCCCTCATAGAGGCCCAGACACACACCACAGTCAC
         TGCCGGAGATGGCCACACCTAGACCATCACACCACACACAGACCCAGTCTCTCCAGGTGA
         CACTCAGGCCCAGCTGCAGGCGCAGCTAAGAGGGAAGACCCTGCAGGGCACAGGGACACG
         TGGGACAACCAGACGCCCTGCTTCGGCCACACCACAAGCCTCCACACACCAGGTGCAGCT
         [C,T]
         CTGTCACCCCTACGGTCAACCCAAGGAGAGCCAGAGATTCCAGTAGTCGTGGGCAGGTAT
         CCAGTGCCCAGGCGAGAAGAGGGGGACACCAGCAGGGAACCCAGAACCTCCTCCATGCCA
         GACTGTGCCCTCCCCCCAGCTCACAGAAGGAGTGCCTCAGGCTGTTTATTTCCTAGCAGG
         GACTAGCAGGGATGGGTGTCTCATCCCCCTCCCCCTCCCAGTCCCCACCACACGATTCTG
         AAGCTGCCAAATCAAATCAGCCCCTGCACCCGCGCCAGGCTGGCATGGCGGCCAGCAGCT
```

FIGURE 3-67

52352    GGAGGGTGTGTGTGTGTGTGAGAGAGAGAGAGAGAACTGGACCCACAGCCAGAACAGAGT
CTGCCCAGGCCTGGCTGAGAGGGAGAGGAAGATGATGCTTGTATCAGCCCTCCTGTGTGC
CAGGAGCCTTTGACACCCACCTTGTTTAATTATTACAGCACCCCCATGAGGTAGGGGCTG
CTATTATTCCTATTTCACATTTGGGGAAGCTGAGGCCCAGAGGGATCATTCAGCAAGTGA
GTTGGGACAGAGCTAAGATTGGAGCCTAGATGTGTCTCAGGCTCGAGGCTCACTCTTTCC
[C,T]
GGCCCCTGAGTAAGATGGGAAAGAAGGTGCCCACACAGGGCCTGGTGCACAGGAGGGGCT
CAGCACAGGTTCCCTGCTGGGACACAGGGCCAAGACCTGAGAATGTGCCTCCAAGTGGGG
CTGGGCCCTGCTGCTGGGAGCTGGCAAAGGGAGCTGGGAGGGGAGGGCCTGGAAAGCCAC
ATTATTAATTTATTTACTGCCATGGCATTCCCCATGGGCGGGGCTCCCCCCAGAGCTGG
GACAGATGGTGTTCCTGGGAGCCTGCAGTGTCTCAGCAGCCTCGGCCACCCGCCAGGAAA

55378    GAGAGGTCCATGAGGTCAGCTTCTGACAGCAGCAGCTAAGGACAACCAGGACCAGAACAG
GACTGGGAAAAAGCAGATAGAGGAGGCTGGAGCAAGGACTCAGCCCCAGAGGAGGCTGCA
GGAGGTTGGCTCATGCTCAGAACCCGGCTCCAAAACACTCTGCCCATGAGTGCTGGGCTG
AGGAAGGCTTGGTGCCAGAGTCAGGGTGAGGCTGAGGCCACCAGTGAATATGTGGGCCCA
GCTGCGGGGGTAGCACTAGGCAGGGGCGGGAGCCAGGTTGGAGGGGGTATTGCCATTGCC
[G,A]
CTGCAGGTGGAGTAGGGCTTCGCTGGGGAAGGAGCAGCTTGTGCGAGAGTGTGGGCAGGA
GTGGGAGGGGAGAAGGCTCCGAGTATACGAGCATAGCTTACCAGCAAGTCCTGGGGTGAG
GCTGGAGGGGCCGCGCTGTAGGCAGCACTTTTCAGGCCCTTATCTAACATTCTCAAGTGA
GTGCTCCTAGCTGCCAGATGTGCTACTTCCTCCTGGATTCTGCACATCAGGAGCCAGTGG
CCTCTACAATGCCCCATGGCCCCAAGGGAGTGGCTGCCAACAAGTTGGCCTTAGCATCTG

55440    CTGGGAAAAAGCAGATAGAGGAGGCTGGAGCAAGGACTCAGCCCCAGAGGAGGCTGCAGG
AGGTTGGCTCATGCTCAGAACCCGGCTCCAAAACACTCTGCCCATGAGTGCTGGGCTGAG
GAAGGCTTGGTGCCAGAGTCAGGGTGAGGCTGAGGCCACCAGTGAATATGTGGGCCCAGC
TGCGGGGGTAGCACTAGGCAGGGGCGGGAGCCAGGTTGGAGGGGGTATTGCCATTGCCGC
TGCAGGTGGAGTAGGGCTTCGCTGGGGAAGGAGCAGCTTGTGCGAGAGTGTGGGCAGGAG
[T,G]
GGGAGGGGAGAAGGCTCCGAGTATACGAGCATAGCTTACCAGCAAGTCCTGGGGTGAGGC
TGGAGGGGCCGCGCTGTAGGCAGCACTTTTCAGGCCCTTATCTAACATTCTCAAGTGAGT
GCTCCTAGCTGCCAGATGTGCTACTTCCTCCTGGATTCTGCACATCAGGAGCCAGTGGCC
TCTACAATGCCCCATGGCCCCAAGGGAGTGGCTGCCAACAAGTTGGCCTTAGCATCTGGC
ATCCATGGGGGTCCTGAGGCCCTGCCATCTGTCTGTGCCCCTGTTGGGCTGCACAGGCCC

55532    ACACTCTGCCCATGAGTGCTGGGCTGAGGAAGGCTTGGTGCCAGAGTCAGGGTGAGGCTG
AGGCCACCAGTGAATATGTGGGCCCAGCTGCGGGGGTAGCACTAGGCAGGGGCGGGAGCC
AGGTTGGAGGGGGTATTGCCATTGCCGCTGCAGGTGGAGTAGGGCTTCGCTGGGGAAGGA
GCAGCTTGTGCGAGAGTGTGGGCAGGAGTGGGAGGGGAGAAGGCTCCGAGTATACGAGCA
TAGCTTACCAGCAAGTCCTGGGGTGAGGCTGGAGGGGCCGCGCTGTAGGCAGCACTTTTC
[A,G]
GGCCCTTATCTAACATTCTCAAGTGAGTGCTCCTAGCTGCCAGATGTGCTACTTCCTCCT
GGATTCTGCACATCAGGAGCCAGTGGCCTCTACAATGCCCCATGGCCCCAAGGGAGTGGC
TGCCAACAAGTTGGCCTTAGCATCTGGCATCCATGGGGGTCCTGAGGCCCTGCCATCTGT
CTGTGCCCCTGTTGGGCTGCACAGGCCCGGGGCGTGCAGGGACCTGGGACCAGGGAGGCG
GTCTCAGCTGCCACTCTAGCCTGTCTCTCTGCCTGCCCATCCACTGTCCACACCCCTGGC

56039    CCGGGGCGTGCAGGGACCTGGGACCAGGGAGGCGGTCTCAGCTGCCACTCTAGCCTGTCT
CTCTGCCTGCCCATCCACTGTCCACACCCCTGGCTGACTGAGTAAAGAGAGAGATGGGCA
TCGCAGGTCCTGCCATCAAAGAAGCCTAGTCTAAAGGAGGAGGCATAAAGCACCGGGGAC
TTATACCCAGAGAAGACACATGCTGAGACCACGCCAGGCTCGCGGGCAAGGCCTAGGCCC
AGGGAGGGCCAGCCTCGTCAAGGGCCTGGAGTTGAGACTCAGGGAAAGGCAGGAGCTGGC
[T,A]
TAGAGGCGCAGGCAGGTCCAAGGCAGTGCCCAGGCCAGATGCGGCGGCCCCGGGCTGAGG
TTGCTCCAGCCGGCCCCACCCCCCACCGTCCTGCCTGGCCTTTGGCTGTAAACACTGAGA
GAACAAGTTCCGTTTCCCGGGAAATATTTATCTCAGGCTGTGTGAAGAGCGTGTGCACTG

FIGURE 3-68

```
       GCCTCCGTGTGTCCTTCCTGCAGACCGGCTGGGGCAGGAGGAGAGGGAGCTTGGCAGCGC
       CCTTGCTGGGGGGAGTCTGTGGGGCTAGGAGGGAAGGGTGTGCCAGAGGCCCCTGCCTAG

56082  GCCACTCTAGCCTGTCTCTCTGCCTGCCCATCCACTGTCCACACCCCTGGCTGACTGAGT
       AAAGAGAGAGATGGGCATCGCAGGTCCTGCCATCAAAGAAGCCTAGTCTAAAGGAGGAGG
       CATAAAGCACCGGGGACTTATACCCAGAGAAGACACATGCTGAGACCACGCCAGGCTCGC
       GGGCAAGGCCTAGGCCCAGGGAGGGCCAGCCTCGTCAAGGGCCTGGAGTTGAGACTCAGG
       GAAAGGCAGGAGCTGGCTTAGAGGCGCAGGCAGGTCCAAGGCAGTGCCCAGGCCAGATGC
       [T,G]
       GCGGCCCCGGGCTGAGGTTGCTCCAGCCGGCCCCACCCCCCACCGTCCTGCCTGGCCTTT
       GGCTGTAAACACTGAGAGAACAAGTTCCGTTTCCCGGGAAATATTTATCTCAGGCTGTGT
       GAAGAGCGTGTGCACTGGCCTCCGTGTGTCCTTCCTGCAGACCGGCTGGGGCAGGAGGAG
       AGGGAGCTTGGCAGCGCCCTTGCTGGGGGGAGTCTGTGGGGCTAGGAGGGAAGGGTGTGC
       CAGAGGCCCCTGCCTAGAGCCTGAATTTGAGTGCTGGCTGAGGGAGAGGTGGGAGCAGAT

56113  CCACTGTCCACACCCCTGGCTGACTGAGTAAAGAGAGAGATGGGCATCGCAGGTCCTGCC
       ATCAAAGAAGCCTAGTCTAAAGGAGGAGGCATAAAGCACCGGGGACTTATACCCAGAGAA
       GACACATGCTGAGACCACGCCAGGCTCGCGGGCAAGGCCTAGGCCCAGGGAGGGCCAGCC
       TCGTCAAGGGCCTGGAGTTGAGACTCAGGGAAAGGCAGGAGCTGGCTTAGAGGCGCAGGC
       AGGTCCAAGGCAGTGCCCAGGCCAGATGCGGCGGCCCCGGGCTGAGGTTGCTCCAGCCGG
       [G,C]
       CCCACCCCCCACCGTCCTGCCTGGCCTTTGGCTGTAAACACTGAGAGAACAAGTTCCGTT
       TCCCGGGAAATATTTATCTCAGGCTGTGTGAAGAGCGTGTGCACTGGCCTCCGTGTGTCC
       TTCCTGCAGACCGGCTGGGGCAGGAGGAGAGGGAGCTTGGCAGCGCCCTTGCTGGGGGGA
       GTCTGTGGGGCTAGGAGGGAAGGGTGTGCCAGAGGCCCCTGCCTAGAGCCTGAATTTGAG
       TGCTGGCTGAGGGAGAGGTGGGAGCAGATGGGAGAGAAGCCTGTTTTCTCCAAACCCCAC

56425  CCGTCCTGCCTGGCCTTTGGCTGTAAACACTGAGAGAACAAGTTCCGTTTCCCGGGAAAT
       ATTTATCTCAGGCTGTGTGAAGAGCGTGTGCACTGGCCTCCGTGTGTCCTTCCTGCAGAC
       CGGCTGGGGCAGGAGGAGAGGGAGCTTGGCAGCGCCCTTGCTGGGGGGAGTCTGTGGGGC
       TAGGAGGGAAGGGTGTGCCAGAGGCCCCTGCCTAGAGCCTGAATTTGAGTGCTGGCTGAG
       GGAGAGGTGGGAGCAGATGGGAGAGAAGCCTGTTTTCTCCAAACCCCACAAATGCCCTCC
       [G,A]
       CCTCTCTCATGTTCCTTTCTTCTTCCTGGTCCATCCTGTCTCCTCCAGGTTCCGGCCTCC
       AGCCTGGTGTCCCCTCCTCAGGCTGCCTTTTCCTCCTCCTCCTCCCTGTTTCCTGGCTCT
       TAGCCGCTCCATCTGGGAAGTCTTCCTCAACTTTAAACCCTCGAACCCTTGTCCTCTGCC
       CTCCATCTCCCACTCCTCAGGCTTTCAGCAGCTTCACGTGGAGCATTGGGCTGGTCCTGT
       CCACAGTTGTTCAGTTGCTGTAACAGCTTGTGCAGGCTGCCCTGGAGCCCTGTTCTGGGA

56554  CAGGAGGAGAGGGAGCTTGGCAGCGCCCTTGCTGGGGGGAGTCTGTGGGGCTAGGAGGGA
       AGGGTGTGCCAGAGGCCCCTGCCTAGAGCCTGAATTTGAGTGCTGGCTGAGGGAGAGGTG
       GGAGCAGATGGGAGAGAAGCCTGTTTTCTCCAAACCCCACAAATGCCCTCCGCCTCTCTC
       ATGTTCCTTTCTTCTTCCTGGTCCATCCTGTCTCCTCCAGGTTCCGGCCTCCAGCCTGGT
       GTCCCCTCCTCAGGCTGCCTTTTCCTCCTCCTCCTCCCTGTTTCCTGGCTCTTAGCCGCT
       [C,T]
       CATCTGGGAAGTCTTCCTCAACTTTAAACCCTCGAACCCTTGTCCTCTGCCCTCCATCTC
       CCACTCCTCAGGCTTTCAGCAGCTTCACGTGGAGCATTGGGCTGGTCCTGTCCACAGTTG
       TTCAGTTGCTGTAACAGCTTGTGCAGGCTGCCCTGGAGCCCTGTTCTGGGAAGCACAGGT
       CTGGGCACCCTGGGGCTGGGGCGAGGCCCGGAGCTGATCTCCTCTGTCCATCCCAGTAGA
       GCCAGCACCAGTGCAGACACATGGGGGATCCAGGTTGGTGGACCAGGGGAGGATGGAAAG

57097  CAGCACCAGTGCAGACACATGGGGGATCCAGGTTGGTGGACCAGGGGAGGATGGAAAGTC
       CCATGGATCCAGCCGGAATGTTGGAGTGGGGAGGCAGAGGGCCCAGGGTTCCTGCTGGCC
       AGCCTCTGGGCTTAGGGGTGTGTATCCCAGACAGGCCAGGCCTGCCAGGGGCCCTGACAA
       CAGGAAATCCTTGAAGGAACAAGCAGAGGCTGAGGACTCTGAGCACAACAACAGGAAACA
       GCCGTGACATGGGCAACAGCCCTGGCGACTGTGCCCAGTTGGGGTGGGGACGAGGGGCC
       [A,G]
       AGCTTGTGGGACCCAGGGTGATGCCAAGAGGGACACTGAGACACTGTGGGACAGGGGGCG
```

FIGURE 3-69

TTCTGCACATGTGACACGGAGCTTATGACGTGTAATATCAAGTACGTGACCATGATCATA
GGGTACTGTGTGGAGTGTGGGTGAGTCACTGAGTATGTGACACTGGCTGTGAGGCACTCC
ATGATAGCAGATGTGTACAGTGGCTGTGCCACCAAGTGTGTAACACTGTGTGATATTGAT
TGTGTGATGCTGACACCGAGTGTGTGACATTGCACATTGCATGCTACCACGTGTGTGACA

57284   TCCTTGAAGGAACAAGCAGAGGCTGAGGACTCTGAGCACAACAACAGGAAACAGCCGTGA
CATGGGGCAACAGCCCTGGCGACTGTGCCCAGTTGGGGTGGGGACGAGGGGCCAAGCTTG
TGGGACCCAGGGTGATGCCAAGAGGGACACTGAGACACTGTGGGACAGGGGGCGTTCTGC
ACATGTGACACGGAGCTTATGACGTGTAATATCAAGTACGTGACCATGATCATAGGGTAC
TGTGTGGAGTGTGGGTGAGTCACTGAGTATGTGACACTGGCTGTGAGGCACTCCATGATA
[G,A]
CAGATGTGTACAGTGGCTGTGCCACCAAGTGTGTAACACTGTGTGATATTGATTGTGTGA
TGCTGACACCGAGTGTGTGACATTGCACATTGCATGCTACCACGTGTGTGACACTGAAAG
TGACAGTGAGCACATGGAGGGTGTGTCTCCATGAGAATCAAATACAGAAACGTGAGCAAA
TGACGCTGCAGTAGCAGGTATGGTCCTGAGTCTGTGGCTCGAGTGTCTGACACTGAATTG
TGACATTGAGTGTGTCCCAAGCATATGATCTAGTGAGGCTGAGTGTGTAAACAAAGGCAT

57618   TAACACTGTGTGATATTGATTGTGTGATGCTGACACCGAGTGTGTGACATTGCACATTGC
ATGCTACCACGTGTGTGACACTGAAAGTGACAGTGAGCACATGGAGGGTGTGTCTCCATG
AGAATCAAATACAGAAACGTGAGCAAATGACGCTGCAGTAGCAGGTATGGTCCTGAGTCT
GTGGCTCGAGTGTCTGACACTGAATTGTGACATTGAGTGTGTCCCAAGCATATGATCTAG
TGAGGCTGAGTGTGTAAACAAAGGCATGACATGGAGTGATAGCAAGTGTGTGGAAGTGGG
[T,C]
GTGTGATGCTGTGTGATCTTGGGCCTGACATTACATGTGTGATGCTCTGTAATGGTTGTA
ACAGTATGCAATGTGCACATACAGTGCTGTGTAGGACACTGTCATGGGAAGGCACCGATG
GGTTCAGGCGGGAAAGTAACACCGTCCAAAGGATGGTTTTAAAAGATTGCTCTGGCCGGA
TGCAGTGGCTCACACCTATAATCCCAGCACTTTGGGAGGCTGAGCTGGGTGGATCACCTG
AGGTCAGGAGTTCAAGACCAGTCTGGTGAAACCCCATCTCTACTAAAAATACAAAAATTA

57795   TCTGTGGCTCGAGTGTCTGACACTGAATTGTGACATTGAGTGTGTCCCAAGCATATGATC
TAGTGAGGCTGAGTGTGTAAACAAAGGCATGACATGGAGTGATAGCAAGTGTGTGGAAGT
GGGTGTGTGATGCTGTGTGATCTTGGGCCTGACATTACATGTGTGATGCTCTGTAATGGT
TGTAACAGTATGCAATGTGCACATACAGTGCTGTGTAGGACACTGTCATGGGAAGGCACC
GATGGGTTCAGGCGGGAAAGTAACACCGTCCAAAGGATGGTTTTAAAAGATTGCTCTGGC
[C,T]
GGATGCAGTGGCTCACACCTATAATCCCAGCACTTTGGGAGGCTGAGCTGGGTGGATCAC
CTGAGGTCAGGAGTTCAAGACCAGTCTGGTGAAACCCCATCTCTACTAAAAATACAAAAA
TTAGCCAGGCATGGTGACAGGCGCCTGTAATCTCAGCTGCTCGGGAGGTTGAGACAGGAG
AATCACTTGAACCCAGGGGGCAGAGGTTGCAGTGAGCCAAGATTGAGCCATTGCACTCCA
GCCTGGGTGACGAGTGAAATACCATCTCAAAAAAAAAAAAAAGAAAAAGATTGCTCAGGT

57796   CTGTGGCTCGAGTGTCTGACACTGAATTGTGACATTGAGTGTGTCCCAAGCATATGATCT
AGTGAGGCTGAGTGTGTAAACAAAGGCATGACATGGAGTGATAGCAAGTGTGTGGAAGTG
GGTGTGTGATGCTGTGTGATCTTGGGCCTGACATTACATGTGTGATGCTCTGTAATGGTT
GTAACAGTATGCAATGTGCACATACAGTGCTGTGTAGGACACTGTCATGGGAAGGCACCG
ATGGGTTCAGGCGGGAAAGTAACACCGTCCAAAGGATGGTTTTAAAAGATTGCTCTGGCC
[A,G]
GATGCAGTGGCTCACACCTATAATCCCAGCACTTTGGGAGGCTGAGCTGGGTGGATCACC
TGAGGTCAGGAGTTCAAGACCAGTCTGGTGAAACCCCATCTCTACTAAAAATACAAAAAT
TAGCCAGGCATGGTGACAGGCGCCTGTAATCTCAGCTGCTCGGGAGGTTGAGACAGGAGA
ATCACTTGAACCCAGGGGGCAGAGGTTGCAGTGAGCCAAGATTGAGCCATTGCACTCCAG
CCTGGGTGACGAGTGAAATACCATCTCAAAAAAAAAAAAAAGAAAAAGATTGCTCAGGTT

57957   GTGATGCTCTGTAATGGTTGTAACAGTATGCAATGTGCACATACAGTGCTGTGTAGGACA
CTGTCATGGGAAGGCACCGATGGGTTCAGGCGGGAAAGTAACACCGTCCAAAGGATGGTT
TTAAAAGATTGCTCTGGCCGGATGCAGTGGCTCACACCTATAATCCCAGCACTTTGGGAG
GCTGAGCTGGGTGGATCACCTGAGGTCAGGAGTTCAAGACCAGTCTGGTGAAACCCCATC
TCTACTAAAAATACAAAAATTAGCCAGGCATGGTGACAGGCGCCTGTAATCTCAGCTGCT

FIGURE 3-70

[C,T]
GGGAGGTTGAGACAGGAGAATCACTTGAACCCAGGGGGCAGAGGTTGCAGTGAGCCAAGA
TTGAGCCATTGCACTCCAGCCTGGGTGACGAGTGAAATACCATCTCAAAAAAAAAAAAAA
GAAAAAGATTGCTCAGGTTGCAGAATATGTATGTGTGCGAGTGTGCATGGTGCGTGGCAG
GGGAGGGGAGATAAGTTAGGGGGAGGCAGAGAGAAGGTGGGTAGAGCAACTGGAGGCTCC
TGCAGCTGCCCAGGCAGGAGATGGTGGTGCCTGTGTTAATGGAATGGCAGAAGAGTTAGA

58064  CCAAAGGATGGTTTTAAAAGATTGCTCTGGCCGGATGCAGTGGCTCACACCTATAATCCC
AGCACTTTGGGAGGCTGAGCTGGGTGGATCACCTGAGGTCAGGAGTTCAAGACCAGTCTG
GTGAAACCCCATCTCTACTAAAAATACAAAAATTAGCCAGGCATGGTGACAGGCGCCTGT
AATCTCAGCTGCTCGGGAGGTTGAGACAGGAGAATCACTTGAACCCAGGGGGCAGAGGTT
GCAGTGAGCCAAGATTGAGCCATTGCACTCCAGCCTGGGTGACGAGTGAAATACCATCTC
[-,A]
AAAAAAAAAAAAAAGAAAAAGATTGCTCAGGTTGCAGAATATGTATGTGTGCGAGTGTGCA
TGGTGCGTGGCAGGGGAGGGGAGATAAGTTAGGGGGAGGCAGAGAGAAGGTGGGTAGAGC
AACTGGAGGCTCCTGCAGCTGCCCAGGCAGGAGATGGTGGTGCCTGTGTTAATGGAATGG
CAGAAGAGTTAGAGATATGGAGCAACTTTGGAGATATTTGAAAACAGAAATGACAGAACT
TGCTGATAAATGAGAAGATGAGCAAGAGGGAAAACCAGAGAACAATTTCCAGGGTTCTGG

58069  GGATGGTTTTAAAAGATTGCTCTGGCCGGATGCAGTGGCTCACACCTATAATCCCAGCAC
TTTGGGAGGCTGAGCTGGGTGGATCACCTGAGGTCAGGAGTTCAAGACCAGTCTGGTGAA
ACCCCATCTCTACTAAAAATACAAAAATTAGCCAGGCATGGTGACAGGCGCCTGTAATCT
CAGCTGCTCGGGAGGTTGAGACAGGAGAATCACTTGAACCCAGGGGGCAGAGGTTGCAGT
GAGCCAAGATTGAGCCATTGCACTCCAGCCTGGGTGACGAGTGAAATACCATCTCAAAAA
[-,A]
AAAAAAAAGAAAAAGATTGCTCAGGTTGCAGAATATGTATGTGTGCGAGTGTGCATGGTG
CGTGGCAGGGGAGGGGAGATAAGTTAGGGGGAGGCAGAGAGAAGGTGGGTAGAGCAACTG
GAGGCTCCTGCAGCTGCCCAGGCAGGAGATGGTGGTGCCTGTGTTAATGGAATGGCAGAA
GAGTTAGAGATATGGAGCAACTTTGGAGATATTTGAAAACAGAAATGACAGAACTTGCTG
ATAAATGAGAAGATGAGCAAGAGGGAAAACCAGAGAACAATTTCCAGGGTTCTGGCTTGA

58108  TCACACCTATAATCCCAGCACTTTGGGAGGCTGAGCTGGGTGGATCACCTGAGGTCAGGA
GTTCAAGACCAGTCTGGTGAAACCCCATCTCTACTAAAAATACAAAAATTAGCCAGGCAT
GGTGACAGGCGCCTGTAATCTCAGCTGCTCGGGAGGTTGAGACAGGAGAATCACTTGAAC
CCAGGGGGCAGAGGTTGCAGTGAGCCAAGATTGAGCCATTGCACTCCAGCCTGGGTGACG
AGTGAAATACCATCTCAAAAAAAAAAAAAAGAAAAAGATTGCTCAGGTTGCAGAATATGT
[A,G]
TGTGTGCGAGTGTGCATGGTGCGTGGCAGGGGAGGGGAGATAAGTTAGGGGGAGGCAGAG
AGAAGGTGGGTAGAGCAACTGGAGGCTCCTGCAGCTGCCCAGGCAGGAGATGGTGGTGCC
TGTGTTAATGGAATGGCAGAAGAGTTAGAGATATGGAGCAACTTTGGAGATATTTGAAAA
CAGAAATGACAGAACTTGCTGATAAATGAGAAGATGAGCAAGAGGGAAAACCAGAGAACA
ATTTCCAGGGTTCTGGCTTGAAGAACCAAGCGATGGATGGTGAAGATGTTTCTGAGATGG

58125  GCACTTTGGGAGGCTGAGCTGGGTGGATCACCTGAGGTCAGGAGTTCAAGACCAGTCTGG
TGAAACCCCATCTCTACTAAAAATACAAAAATTAGCCAGGCATGGTGACAGGCGCCTGTA
ATCTCAGCTGCTCGGGAGGTTGAGACAGGAGAATCACTTGAACCCAGGGGGCAGAGGTTG
CAGTGAGCCAAGATTGAGCCATTGCACTCCAGCCTGGGTGACGAGTGAAATACCATCTCA
AAAAAAAAAAAAGAAAAAGATTGCTCAGGTTGCAGAATATGTATGTGTGCGAGTGTGCA
[T,C]
GGTGCGTGGCAGGGGAGGGGAGATAAGTTAGGGGGAGGCAGAGAGAAGGTGGGTAGAGCA
ACTGGAGGCTCCTGCAGCTGCCCAGGCAGGAGATGGTGGTGCCTGTGTTAATGGAATGGC
AGAAGAGTTAGAGATATGGAGCAACTTTGGAGATATTTGAAAACAGAAATGACAGAACTT
GCTGATAAATGAGAAGATGAGCAAGAGGGAAAACCAGAGAACAATTTCCAGGGTTCTGGC
TTGAAGAACCAAGCGATGGATGGTGAAGATGTTTCTGAGATGGGCAAAGGCAAGGGGGAG

58171  CAAGACCAGTCTGGTGAAACCCCATCTCTACTAAAAATACAAAAATTAGCCAGGCATGGT
GACAGGCGCCTGTAATCTCAGCTGCTCGGGAGGTTGAGACAGGAGAATCACTTGAACCCA
GGGGGCAGAGGTTGCAGTGAGCCAAGATTGAGCCATTGCACTCCAGCCTGGGTGACGAGT

FIGURE 3-71

```
              GAAATACCATCTCAAAAAAAAAAAAAAGAAAAAGATTGCTCAGGTTGCAGAATATGTATG
              TGTGCGAGTGTGCATGGTGCGTGGCAGGGGAGGGGAGATAAGTTAGGGGGAGGCAGAGAG
              [G,A]
              AGGTGGGTAGAGCAACTGGAGGCTCCTGCAGCTGCCCAGGCAGGAGATGGTGGTGCCTGT
              GTTAATGGAATGGCAGAAGAGTTAGAGATATGGAGCAACTTTGGAGATATTTGAAAACAG
              AAATGACAGAACTTGCTGATAAATGAGAAGATGAGCAAGAGGGAAAACCAGAGAACAATT
              TCCAGGGTTCTGGCTTGAAGAACCAAGCGATGGATGGTGAAGATGTTTCTGAGATGGGCA
              AAGGCAAGGGGGAGGGTCAGCACTAGTGGGGTGGGAGGACAAGGAGGCAGAAACCGAGTG

58246    TCTCAGCTGCTCGGGAGGTTGAGACAGGAGAATCACTTGAACCCAGGGGGCAGAGGTTGC
              AGTGAGCCAAGATTGAGCCATTGCACTCCAGCCTGGGTGACGAGTGAAATACCATCTCAA
              AAAAAAAAAAAAGAAAAAGATTGCTCAGGTTGCAGAATATGTATGTGTGCGAGTGTGCAT
              GGTGCGTGGCAGGGGAGGGGAGATAAGTTAGGGGGAGGCAGAGAGAAGGTGGGTAGAGCA
              ACTGGAGGCTCCTGCAGCTGCCCAGGCAGGAGATGGTGGTGCCTGTGTTAATGGAATGGC
              [A,G]
              GAAGAGTTAGAGATATGGAGCAACTTTGGAGATATTTGAAAACAGAAATGACAGAACTTG
              CTGATAAATGAGAAGATGAGCAAGAGGGAAAACCAGAGAACAATTTCCAGGGTTCTGGCT
              TGAAGAACCAAGCGATGGATGGTGAAGATGTTTCTGAGATGGGCAAAGGCAAGGGGGAGG
              GTCAGCACTAGTGGGGTGGGAGGACAAGGAGGCAGAAACCGAGTGAGCTGTTTTGGATGT
              GTTAAGGGAAGCATCCAGGTGAAGGTGTGCAGTGGGCAGCGGGGCCAGGCTAGGGATACA

59173    GAGTCAGGCTAATGGGAGCCATTTCAGTGATGGGCTGGAGCCAGAAGTCAGACTGGCCTG
              TGTAGGATGGTGAGGGAGGTGAAGACGTTAGCCTGGAGAGCCCTTTGGAGACGTTGGGCT
              GTGAGGGCTGCAGAGAAGGACATGATCGCTGGAAAGGGAGATTACATTTTTTTATTATGG
              GTGATTCTAAGCAGACACAATACCAGAGAGAAGCATATAAGAAACTGCCATATACTCATC
              ACCCCAGTTCAACAGTTGCTGGGATTTGGCCTCATTTCTTCCTCTCTTGCCCCCTATCTG
              [T,A]
              TCTTTCATTTTTCCTTTGCTTAAGCTTAAAATTTTTTAAATTGTGGTAAAATATACATAAC
              TTAAACTTTACCATCATAACCATTTCTAAGTGTACAGTTCAGTTGTGGTAGGTACATTCA
              CACTGTTTTGCAACCAATCTCTGGAACTCTTTCATCTTCTCAAACTGAAACTCTGCACCT
              ATTAAACGACAGCCCCCATCCTCCTCTGTCTCCAGCTCCTGGCACCCACCATTCTACTTT
              CTGTCTCTATGACTTGGACTACTCTAGATACCTCAAGTAATTGGAATAATGTAGTATCTG

60931    GTGACACAGTGCAGGACTCTGCATGGGAGTAAGAGGGACTGAAGCTGTGCTATAGGTGAC
              CGGGCTGCATGTGATTCAAGTGGGCTCAGCCCCAGCTTCAGCTGCTGAGTATGGGAGGGA
              GCATGGACATTGTAGGGTAGATGAGGAGAAACACTGAATGGGAACAGAAATGGTGTCTGT
              GCCCAGATGCGAGCTCCTCCCTTCTCTGAATACCCAGGAAGGCTTCCTGGAGGCAGGATG
              TGGGCACTTCAGCAGGATGTTGTAGGTGCTGATTAAGAGCAGGGCCTGTGGTGTCAGACA
              [G,C]
              CCCTGTCTAGGCTCTGACATTCAGCAGGTCATTTTATCTCTTGAGCCTCAATTTCCTCAA
              GTATAAAATGGGAGCTCTTAGGAGGATTGCATGAAGCAGTGCTCCAATGCATGCAGTCTC
              TGGCACTTGGTAAATACTCTATGGTCTCTTGGGGAGCAGCAACCTCAACACCTGCACCCC
              AGGTCCCCAAATAACAGGAGCACCAGTAGGAGCACAGTGAAGGTGCGCTGAGTGAGGTGT
              CCTCTTACACCCACAGCCCTCCTCTCTCCCTCTCCCCCAACTTCTGTCCCCTGCTTGGTG

62318    AAACTGAGCCCACTCTCCCTCACCAAGCCTTTCCCCTCAGGCCCGCATCTGCCCAGAGAA
              TTGGGGTCCCTCCTTTCTAATGTGCACACAGGTGGCCCCAGCCCCCTGCTGGGAGTCAGC
              TTAGGCAAGGTTTGATGGCTCAGCTTAATCTTCTCAGCAGCTCTGGGGGAAGAGACCATT
              TTACGGATGAGGAACTGAGCCCAGGAAGGTCCAAAGACTTGTCCAGTACATGTGGTGTGT
              GGCAGGGCAGGCAGATGAGCCCGCATCTGAGGGAGGCGATGGGAGAAGTGACAGGGGTGC
              [G,A]
              CAGAGGAGGAGAATTAGACCCTCTCAGATTCCACCACTCTCAGCCACACGTTCACTCACT
              CATTTGGAGACAAGACTAACCACCAGCGCATTCACAGCCCCCCAGACAGCCACATACTGA
              CTATACCACTGTCACATGGACATCAATGACCTGAATCACATATGCATAGATGCAGGCCCA
              CATGGTCACTCCCACGTGCAGATGGCCAGTGCACACACATAGACACAGGGTACTCACACA
              TGTTTACACTCTCACGACCCATGTGGGTTACAGATTCCTACAGAGACACAGACCTACATA

62417    AGCCCCCTGCTGGGAGTCAGCTTAGGCAAGGTTTGATGGCTCAGCTTAATCTTCTCAGCA
```

FIGURE 3-72

```
         GCTCTGGGGGAAGAGACCATTTTTACGGATGAGGAACTGAGCCCAGGAAGGTCCAAAGACT
         TGTCCAGTACATGTGGTGTGTGGCAGGGCAGGCAGATGAGCCCGCATCTGAGGGAGGCGA
         TGGGAGAAGTGACAGGGGTGCGCAGAGGAGGAGAATTAGACCCTCTCAGATTCCACCACT
         CTCAGCCACACGTTCACTCACTCATTTGGAGACAAGACTAACCACCAGCGCATTCACAGC
         [C,T,G,A]
         CCCCAGACAGCCACATACTGACTATACCACTGTCACATGGACATCAATGACCTGAATCAC
         ATATGCATAGATGCAGGCCCACATGGTCACTCCCACGTGCAGATGGCCAGTGCACACACA
         TAGACACAGGGTACTCACACATGTTTACACTCTCACGACCCATGTGGGTTACAGATTCCT
         ACAGAGACACAGACCTACATACTTTCACAAGGAAATTCTCCCAGTGACCCAGGGAACATA
         GTCTGCCATGATGATGTGATGGTCCGTAGGGGCTCGCCACTATGGACCATTAATGGGCAG

62655    CTCTCAGCCACACGTTCACTCACTCATTTGGAGACAAGACTAACCACCAGCGCATTCACA
         GCCCCCCAGACAGCCACATACTGACTATACCACTGTCACATGGACATCAATGACCTGAAT
         CACATATGCATAGATGCAGGCCCACATGGTCACTCCCACGTGCAGATGGCCAGTGCACAC
         ACATAGACACAGGGTACTCACACATGTTTACACTCTCACGACCCATGTGGGTTACAGATT
         CCTACAGAGACACAGACCTACATACTTTCACAAGGAAATTCTCCCAGTGACCCAGGGAAC
         [A,G]
         TAGTCTGCCATGATGATGTGATGGTCCGTAGGGGCTCGCCACTATGGACCATTAATGGGC
         AGGCTGCACACATGCTTAGGTCCCCAGCAAAGCGGGAGTTCTGCACAGAGTGAGAGGAGA
         GGTCAGTTCTGATGAGTGTATCCAGAATTTTTGCAATCAGAAAAACCACACAAAAACTATT
         TTAATTTTCATTTCCAAGATAAAATTTAGTTTGAATTGTATAGAGGGTCCGAGGGTCTGG
         TGGGAGGGCATCATCATCTTTTCAAGGCTTTGGGGTTCTAAGGCACCCACAGATTCACAA

62676    ACTCATTTGGAGACAAGACTAACCACCAGCGCATTCACAGCCCCCCAGACAGCCACATAC
         TGACTATACCACTGTCACATGGACATCAATGACCTGAATCACATATGCATAGATGCAGGC
         CCACATGGTCACTCCCACGTGCAGATGGCCAGTGCACACACATAGACACAGGGTACTCAC
         ACATGTTTACACTCTCACGACCCATGTGGGTTACAGATTCCTACAGAGACACAGACCTAC
         ATACTTTCACAAGGAAATTCTCCCAGTGACCCAGGGAACATAGTCTGCCATGATGATGTG
         [A,G]
         TGGTCCGTAGGGGCTCGCCACTATGGACCATTAATGGGCAGGCTGCACACATGCTTAGGT
         CCCCAGCAAAGCGGGAGTTCTGCACAGAGTGAGAGGAGAGGTCAGTTCTGATGAGTGTAT
         CCAGAATTTTGCAATCAGAAAAACCACACAAAAACTATTTTAATTTTCATTTCCAAGATA
         AAATTTAGTTTGAATTGTATAGAGGGTCCGAGGGTCTGGTGGGAGGGCATCATCATCTTT
         TCAAGGCTTTGGGGTTCTAAGGCACCCACAGATTCACAACAGTCCCACAAGATATCCCAG

63504    TGGGAGGTGGGCTGTATGACAGCCTGCCTCAGCCCCTGTGGCCCCACTGACCGGGACCCT
         GTGTAATGAGGCAGAGTGACCAAGGCCCATGGCCAGCGTCCCATGGGCTCGTAGGCCCAT
         CGCCTCCCCTCTCTGGGGCTTGGCTCTCTCATCTGAAAAATGGAGGTGGGAAGGAGATGA
         GACTGGATGGGCTTTCTCCTGGAGACTGATTAGAGAGACAGAGACTCAGGCCCGGGGTCC
         AGAAAAGACAACCAAAGCTGGGGAGGGCACATGAAGGGGGGCAAAGAAGGTCTGGGTTCA
         [G,A]
         GGGAGTGCGTGGGGCCCCAGAGCCTGCCATGTCTCCGCCAACTCTCTCCCTCACTGGAGG
         AGGGCTCTGTGCCTTGGTGCCCCACCTGCCCAGGGCCCTGTGGCTCAGCCCCTTGCTTGC
         TCTGTGAGGGGACGGGAGAAGGATGAGAGTCCCAGTGATAGGGGGAGGACAAGACCAGG
         GGAGAGGGCTGGGGGTTTCTGGAGGGCCAGAGCAGGAAGAGCAGGAGAGAAGAGAGGACA
         CCACAGTGCAGGAAACGGAGGAGCAAAGGCTGGGAGTGGGGAGGCTGGAGGGGTGCAGGG

63823    AGAGCCTGCCATGTCTCCGCCAACTCTCTCCCTCACTGGAGGAGGGCTCTGTGCCTTGGT
         GCCCCACCTGCCCAGGGCCCTGTGGCTCAGCCCCTTGCTTGCTCTGTGAGGGGACGGGA
         GAAGGATGAGAGTCCCAGTGATAGGGGGAGGACAAGACCAGGGGAGAGGGCTGGGGGTTT
         CTGGAGGGCCAGAGCAGGAAGAGCAGGAGAGAAGAGAGGACACCACAGTGCAGGAAACGG
         AGGAGCAAAGGCTGGGAGTGGGGAGGCTGGAGGGGTGCAGGGAATCAGACTGGGGCGCTG
         [C,T]
         GAAGAGGCCTGAGGCCAGAGCAGGCAGTGCCTGGATGGAGGGAGCGAGCAGCTCCTCACC
         CTCAGCTCCTTGATGAGGTAAGGTGACCACGAGCCCTGCTCCAGGCTGTGTGCTGAGCAC
         TTTGCTCGGAGCCTGTCACTCTGGAGGAGGGGAGGGGTGTTCCCAGGAGCTATGACAGT
         CTTGTGCAAGGGAGGGACAGGGTCACATTTATGTTTAACAAAGCACTGCGCTGGGAGAGA
         GGAGCTGAGAGACCCCGGCCCTGGGGAGCATGGTGGCTGGGACCCCGGAGGGCAGGCGTG
```

FIGURE 3-73

64793  CAAGCTCTGTTGAGAGAGCCAAATACAGTCATAGGACAAAGCAGCGGGAGGCTGTGGGAT
ACACACATGCCGCAGAGCACAGACAGAGAGAGGTGGCCAGGCACAGAGAGAGCGCCCAGG
GAGGCTGAGAGGCAGGGAGAAAACACGCTGGGACAGTCAGGGAGAGCCCCAGGGCAGGCA
TCACCGGGCAGCCAGCCTCTGTGCCCTGCTCTCTATCTTGTCCCTAAGAAGACCAGCATG
GCTGGGCTTGCCTCCCGCCATCCACCCCACCAGCCCTACCCCAGGCTGGCCCTTCCTCCC
[T,C]
GCCCTCTGCAGGCCCACACTAACCCTAGGCCAGGCCGCCTCCTTCAGCATTTACCTCCCA
CACACAATGGGCACAGTGAGGACATAAGAGACCCAGTCTCTGGCCTGGAGGCAGATACTC
AGCCTTACCCGACATCTGAGAGGGCTCAGCCCATCCCCTGGCCAAGGCAGGTATTAGAGG
GGCCCCAAAGACAAGCAGGACTCTGGGACAAGGTGTCCTAGTGTGGCCCAAAGGGCTGGG
CTGAAGCATGGGTCTCCTGGCTCCAGATGAGAGCCTGGGTGAATCCTTCCCTGCCTCCTC

64829  CAAAGCAGCGGGAGGCTGTGGGATACACACATGCCGCAGAGCACAGACAGAGAGAGGTGG
CCAGGCACAGAGAGAGCGCCCAGGGAGGCTGAGAGGCAGGGAGAAAACACGCTGGGACAG
TCAGGGAGAGCCCCAGGGCAGGCATCACCGGGCAGCCAGCCTCTGTGCCCTGCTCTCTAT
CTTGTCCCTAAGAAGACCAGCATGGCTGGGCTTGCCTCCCGCCATCCACCCCACCAGCCC
TACCCCAGGCTGGCCCTTCCTCCCCGCCCTCTGCAGGCCCACACTAACCCTAGGCCAGGC
[C,T]
GCCTCCTTCAGCATTTACCTCCCACACACAATGGGCACAGTGAGGACATAAGAGACCCAG
TCTCTGGCCTGGAGGCAGATACTCAGCCTTACCCGACATCTGAGAGGGCTCAGCCCATCC
CCTGGCCAAGGCAGGTATTAGAGGGGCCCCAAAGACAAGCAGGACTCTGGGACAAGGTGT
CCTAGTGTGGCCCAAAGGGCTGGGCTGAAGCATGGGTCTCCTGGCTCCAGATGAGAGCCT
GGGTGAATCCTTCCCTGCCTCCTCTGGCCTTAGTCTACCCCATCAAGCTTGGGATTGGAC

65593  GACCTGCTGCCCCCACCCGGTCTGCACGTGGAGATGATCCTGAAGCACAAAGGGCCTCCC
GGCCTGCAGAGGTGCCTGGGAGAGGTTGCCAAAGGCTCTCAGTAGGAGACACCCCATTCC
TCAGGCTCCTTCTCTGAGACTGTAACTGTGCCAGACTGGGGAGGCTTTGAGAGGTCTCAG
CTATCTCCCCTGCCTAGATCCTTCCTCCACACCCCTCTTCTCCCTGATGGCATGTAGCCC
TCACAGTACAGTAGTCCTGGGCACACAGGAGTTTACCCAGTCATTTACAGCTCAGCAAAC
[G,C,AsT]
CCTACCAACACCTATGAGGGGCTGGGTAATGCTGGAGACCCGGAGAGGGGCAGGACACAA
TCTCTGCCCTCCAAAAGCTCCCAGTCTGTTGTGGGAGCCAGACGGGAAAGGGTGGCACTG
CATTGATGCACACAGTGCATGCCATGGTGGGGGAAAGGGGGGCAGTGGGAGCCCCAGGTG
GGAGGGTCAGACTTGCCTGGAGAGAGAACAACAACAGACTCTCCCTGGAGGGGATCCAGA
GAAGGGAGATCACTTCATTCATTCATTCGTCATTCATCCATCCACCCATTCAATTATTCC

65634  GAAGCACAAAGGGCCTCCCGGCCTGCAGAGGTGCCTGGGAGAGGTTGCCAAAGGCTCTCA
GTAGGAGACACCCCATTCCTCAGGCTCCTTCTCTGAGACTGTAACTGTGCCAGACTGGGG
AGGCTTTGAGAGGTCTCAGCTATCTCCCCTGCCTAGATCCTTCCTCCACACCCCTCTTCT
CCCTGATGGCATGTAGCCCTCACAGTACAGTAGTCCTGGGCACACAGGAGTTTACCCAGT
CATTTACAGCTCAGCAAACACCTACCAACACCTATGAGGGGCTGGGTAATGCTGGAGACC
[A,G,C]
GGAGAGGGGCAGGACACAATCTCTGCCCTCCAAAAGCTCCCAGTCTGTTGTGGGAGCCAG
ACGGGAAAGGGTGGCACTGCATTGATGCACACAGTGCATGCCATGGTGGGGGAAAGGGGG
GCAGTGGGAGCCCCAGGTGGGAGGGTCAGACTTGCCTGGAGAGAGAACAACAACAGACTC
TCCCTGGAGGGGATCCAGAGAAGGGAGATCACTTCATTCATTCATTCGTCATTCATCCAT
CCACCCATTCAATTATTCCTTTGGCCATCATTTCCTGAGGGATGTAAACTCTCTTCTGAC

65848  CCTGGGCACACAGGAGTTTACCCAGTCATTTACAGCTCAGCAAACACCTACCAACACCTA
TGAGGGGCTGGGTAATGCTGGAGACCCGGAGAGGGGCAGGACACAATCTCTGCCCTCCAA
AAGCTCCCAGTCTGTTGTGGGAGCCAGACGGGAAAGGGTGGCACTGCATTGATGCACACA
GTGCATGCCATGGTGGGGGAAAGGGGGGCAGTGGGAGCCCCAGGTGGGAGGGTCAGACTT
GCCTGGAGAGAGAACAACAACAGACTCTCCCTGGAGGGGATCCAGAGAAGGGAGATCACT
[A,G,T]
CATTCATTCATTCGTCATTCATCCATCCACCCATTCAATTATTCCTTTGGCCATCATTTC
CTGAGGGATGTAAACTCTCTTCTGACACTGACCCAGCGGGACACTCAGCGTCCTCCTCCT
CTCCTGCTTGAGCCACCATGCCTGCCTCTTGGAGGCTCCTGGACTTGCTTTGCTCAGCTC

FIGURE 3-74

```
           CCAACCCACCCTGAGGGGGTGAGGCTGAGGAGGGTGTACAGACATTCAGGGTCACCAAAC
           TCAGAGCTGGAGGCCTGCCACCTCACCAGGGGCCTTTCTCAGGGCACAGGCTCCCTGGTG

66187  TTATTCCTTTGGCCATCATTTCCTGAGGGATGTAAACTCTCTTCTGACACTGACCCAGCG
           GGACACTCAGCGTCCTCCTCCTCTCCTGCTTGAGCCACCATGCCTGCCTCTTGGAGGCTC
           CTGGACTTGCTTTGCTCAGCTCCCAACCCACCCTGAGGGGGTGAGGCTGAGGAGGGTGTA
           CAGACATTCAGGGTCACCAAACTCAGAGCTGGAGGCCTGCCACCTCACCAGGGGCCTTTC
           TCAGGGCACAGGCTCCCTGGTGGCAGGGCCTTGGCCCTTGCTTGCACACCCTTGGGGACT
           [A,G]
           GGAGCCCCCTCATCCATCCTGCTCAGGCTCTCTTTTGTGGCGCGACTCTGATTCACAGTG
           TGCCCAAATCTGCCTCCTTGTGACTGCCGCGAGCTGCCTCGTGGGCCCCAGGCCAGAGGA
           CAAGGATAGCTAGAATGCCAGGTGACCAGGATGACTGTGATGGCATGGAGAGGGGGATGC
           TGTGATGTGTTTGGGAGGAAGTTTGTGGTGTCCAGGAGAATGTGGGCAGCAGAAATGGGA
           CCACTCTCGGTTCTTCCCTGTAGATGAAGCAGCTGAAGGTGGGAGGGGGTGGGAGGAGAC

66843  CCTCCCCACACTCAGCTCCTGCCTCCCTCCCTCTACCCACTCTGACTGTTCCCTCCTTTC
           CTGACTCCAGACTCTGGGTGAGGGACTGAGGTGATTCCAGTGAGTCAGGCCCTCAGGGAA
           CTGATCGTGCAGGCAACTCTTGCCTGCCTTCTCCTGCTCTTTCCCTCTTCCCATTCCTTC
           ATCCACCCCCAAACCTAGCTCCTGATGGATCCAAGGGTGCGGGGGACAACCGGGAGGTCA
           TTTTGGAGGAGGCAGGAGCTGGAATAGAAGCTGGGACTGGCTTGGGAAGGGCGAGAGGCC
           [T,C,G]
           GGGCGGAGCTGGTTGTGGGCGCTGGAAGGGAGGAGCCAACAGTGTGGGGTCAGGCTCCTG
           TGGACGGGGACACCCTTGGGAGGCACTGGGACTGGCTCAGGTGTATTCTACAGTGCACGT
           GTCTCCAGTGTGGCTCGGAGGCTGGAGACGCGGCCCTGTTGGAGTAACAACTGAAGCCGG
           AGTCTGCGAAGGGTGGGCAGGAGGGTGGAGGGATGGGGGCATGGAGCGGGAGGGGGTAAG
           TAGAGGAGGGAGGGGAGGAAGAGAAAGAGGGAGGAGGAAAGGTCTCTGGCAGGTCCCTCC

66908  TCCAGACTCTGGGTGAGGGACTGAGGTGATTCCAGTGAGTCAGGCCCTCAGGGAACTGAT
           CGTGCAGGCAACTCTTGCCTGCCTTCTCCTGCTCTTTCCCTCTTCCCATTCCTTCATCCA
           CCCCCAAACCTAGCTCCTGATGGATCCAAGGGTGCGGGGGACAACCGGGAGGTCATTTTG
           GAGGAGGCAGGAGCTGGAATAGAAGCTGGGACTGGCTTGGGAAGGGCGAGAGGCCGGGGC
           GGAGCTGGTTGTGGGCGCTGGAAGGGAGGAGCCAACAGTGTGGGGTCAGGCTCCTGTGGA
           [A,G,C]
           GGGGACACCCTTGGGAGGCACTGGGACTGGCTCAGGTGTATTCTACAGTGCACGTGTCTC
           CAGTGTGGCTCGGAGGCTGGAGACGCGGCCCTGTTGGAGTAACAACTGAAGCCGGAGTCT
           GCGAAGGGTGGGCAGGAGGGTGGAGGGATGGGGGCATGGAGCGGGAGGGGGTAAGTAGAG
           GAGGGAGGGGAGGAAGAGAAAGAGGGAGGAGGAAAGGTCTCTGGCAGGTCCCTCCTTTAA
           GACTGGGCTCCTGCGCTGCGAGTGGCCCCGTCCATACTGCCTTGTTATCCATATCTCCCC

67481  CATACTGCCTTGTTATCCATATCTCCCCACCACTAGTCTCCCTCTGTCCTTCCACCCCCA
           GCCTCTCCCCTCCATTGGGACCTTCCCTGGGGCGTCCCCTCATTGGCTGTTCTCACCTGA
           GCAAGGCCCCTCCCCTCCAGTCCTTAGCCTCTTCACCTGTACAATGGGATGACCCAAACA
           GGCACCTCTTGGGCTTGTAGGAGGATCCAAGATAGTGTCAGTGGGTCTCGAGGTGTGGTC
           CCCCGACCAGCAGCATCAGTGTCATCTAGGAATGTTTGGAAACGCAAGTTCTTGGACCTC
           [G,A]
           TCCCAGACCTACTGTATCAGAAACCCTGGGGGTGGGGCCAGCAATCTGCACTTTAACAAG
           CACTCTGGGTGGGTTCTGGTGCACATGAAAATTGGGGAACGGCTGGTGGAAACCTCTAGC
           CACAGGAGGTGCTTGGGAAAGGTACCTTCCCCTCCCCAAAGCCTGATGCCTCACTCAAGC
           ATGACACTGACAGTTGGGCTAGTTCAGCTGCGTTCTGGGTCTCTGTCTTGCCTCCTCCTT
           CAGACTAAGCCTCCCAAGGGTTGCCAAGCCTCTTTCCTCTATTCTCCTCACCCTGATCCA

67637  CTGTACAATGGGATGACCCAAACAGGCACCTCTTGGGCTTGTAGGAGGATCCAAGATAGT
           GTCAGTGGGTCTCGAGGTGTGGTCCCCCGACCAGCAGCATCAGTGTCATCTAGGAATGTT
           TGGAAACGCAAGTTCTTGGACCTCGTCCCAGACCTACTGTATCAGAAACCCTGGGGGTGG
           GGCCAGCAATCTGCACTTTAACAAGCACTCTGGGTGGGTTCTGGTGCACATGAAAATTGG
           GGAACGGCTGGTGGAAACCTCTAGCCACAGGAGGTGCTTGGGAAAGGTACCTTCCCCTCC
           [C,T]
           CAAAGCCTGATGCCTCACTCAAGCATGACACTGACAGTTGGGCTAGTTCAGCTGCGTTCT
```

FIGURE 3-75

```
       GGGTCTCTGTCTTGCCTCCTCCTTCAGACTAAGCCTCCCAAGGGTTGCCAAGCCTCTTTC
       CTCTATTCTCCTCACCCTGATCCAGCTCAGCCTCATTGAGAGAAGTCTGGGGCTGCAAGA
       TCTTCGCACTCACAGGCAGTTCCTCTTTGCACATCCAAGGCACCAGTGTCTTTGAGAGGC
       GTCTCCTTGGCCAGGTGGCAGGCGTGGGTGTGTGGGGAGGAAGGAGGAGGAACCGCCTTG

69231  GGGAAAGGCATAGAGACTCATGAAGATGAAACAGGAAAGATCTTATGGCAGCGACCCCAA
       CCCTCAGGAAGGGCGTTGGTCTTGTGCTTGTGGCTCCAAAGGGGATAAGACCAAGGTCTC
       TGGTTTCATAGAATCTTAGGCTTTAAGAACGAGTTAGAAGTAATTTAGTCCAGACCCTCT
       CCTCTCCCCAGATAAGTGCAGAAATGCAGATCTAGCCCACGGCTGAGCCCCAACCCTGGC
       TTCAGAGGAGGCCTGACTCAGAACAGGCTCCCCTTTCTTGGTACCTGGGGTGAATGAAAG
       [A,C]
       TAAGTCTGTGGTAATGGTGCTGTCTGTGGTGCTGACTGGCCTTACCTTGGACTACAGAGC
       TGCAGGTGGAGCTGGAGAGAGCAGAAAGGCTCCATCTATCCATCTACCCACCCACCCAGC
       CACCCATCTACCTATCCACCCACCATCCACCCACCCATCCATCCACCATCCCTCCCCCAA
       CCCATCCTGCACCCATTCATCTATCCACCTACCCACTCATCCATCCAGCCTCATTGAATT
       AAACCATAGAACTATATGCTGCAGAGCTAGAAAGATCCATTTTTTAGTAATGACAAAACT

69238  GCATAGAGACTCATGAAGATGAAACAGGAAAGATCTTATGGCAGCGACCCCAACCCTCAG
       GAAGGGCGTTGGTCTTGTGCTTGTGGCTCCAAAGGGGATAAGACCAAGGTCTCTGGTTTC
       ATAGAATCTTAGGCTTTAAGAACGAGTTAGAAGTAATTTAGTCCAGACCCTCTCCTCTCC
       CCAGATAAGTGCAGAAATGCAGATCTAGCCCACGGCTGAGCCCCAACCCTGGCTTCAGAG
       GAGGCCTGACTCAGAACAGGCTCCCCTTTCTTGGTACCTGGGGTGAATGAAAGATAAGTC
       [T,C]
       GTGGTAATGGTGCTGTCTGTGGTGCTGACTGGCCTTACCTTGGACTACAGAGCTGCAGGT
       GGAGCTGGAGAGAGCAGAAAGGCTCCATCTATCCATCTACCCACCCACCCAGCCACCCAT
       CTACCTATCCACCCACCATCCACCCACCCATCCATCCACCATCCCTCCCCCAACCCATCC
       TGCACCCATTCATCTATCCACCTACCCACTCATCCATCCAGCCTCATTGAATTAAACCAT
       AGAACTATATGCTGCAGAGCTAGAAAGATCCATTTTTTAGTAATGACAAAACTGAGGCTC

70821  AGTCACAGAAAACTGAACAATCAGAGCAAAGGTCAGGCAGGCACCCACCAATTCCAGTAA
       AGGACAGTTGAGGGCATTCCCCAATTGAAGCAAAGGGCAGGTTGAGGAGTCCACCAATCA
       GAATAAAGGACAGACTGTTCTTTCTGAGCACCCTAGGGTGGGAGCTGGGGATCGGGTGCT
       GAGCAGGAACCAGACAGGGCTAGAGATCCAGAGGTTTGGGTTCTGGACCTGGCTCTGCTC
       TGACTGGCTGTCTGACCACAGGTTGATCATTGCTTCTCATTGAACCTCAGCTTCCTCATC
       [G,A]
       GTCAAATGGGGAGACTTAGCTCTCTGAAGGCTGTGGCTTTGAAGAATTTCTCCCCCTGTA
       TCAGGCTCACTCCGTCACCTGGGTCTCTCTTCCCAAGTCCACATCACATACATCAGACT
       CCACCAAGGGCAGGGCCTCTCAGGAGTCAGCTTGTGGGCTCCTCTGCCTCCAAGAAGGAA
       TAGACACAAACCAACACCACCTTCTGTGCTGTCTTTAGAGCCCCCGTCTGGGGAGCGTGC
       ATCTGGAAGACTTTATCTTGGGAGTACTGGGGGCATCAGCTCTTCCTCCCCTTTTTAGTC

72136  TGTCCATGGGGCCACAGAGTTCAGATCCCCCATCTAGGAGGGTCTGAGAGATTGGAGTTG
       GAGACTGATAACCCTGGGTCTCCTCTGCTTTAGATGAGGCATCCCTGGGTTATCCAGTCT
       TAGTCACATGCAAAACTTGGTTTCCAATTCCCTCGTTTCATAGGTCGCCTCCTCTGGATG
       AGTGTCATCTTGTCAGCCCCTGGGACACAATGAACAGGGGATGGTCTAACTAGACTATAA
       AAGTGGGGGAACTGTCATCTTCCCAATTGGGTTAACAGACCTCTATTAATATGGCCTGCA
       [T,C,G]
       TTTGAGCATTTTTATTTCTTGCCAGTCATGCTTACACTGTGGGCTCATGCTGAACTGTGG
       TCTTTTAAGACCCTCAACCTCATATCATGTTCACATGAATGGGGACCCAGCCATGTCTCC
       TTCATCTTGCAGTTAATCACTTTGCTTTCTGAACACAGACCCAACCTTCCACTGGGAAGA
       CATCTGAAAGGACTTCCAAGGGCTTGCGGGAGGGCATGGCTGGTGGCTGGTATGAGTCAC
       GATCTTGCCTTGGCCCTCGTTTCCTTTGTTCTGTTACCTTTCTCTTTGATCCCCATGGCT

72285  CCCTCGTTTCATAGGTCGCCTCCTCTGGATGAGTGTCATCTTGTCAGCCCCTGGGACACA
       ATGAACAGGGGATGGTCTAACTAGACTATAAAAGTGGGGGAACTGTCATCTTCCCAATTG
       GGTTAACAGACCTCTATTAATATGGCCTGCAGTTTGAGCATTTTTATTTCTTGCCAGTCA
       TGCTTACACTGTGGGCTCATGCTGAACTGTGGTCTTTTAAGACCCTCAACCTCATATCAT
       GTTCACATGAATGGGGACCCAGCCATGTCTCCTTCATCTTGCAGTTAATCACTTTGCTTT
```

FIGURE 3-76

```
       [C,T]
       TGAACACAGACCCAACCTTCCACTGGGAAGACATCTGAAAGGACTTCCAAGGGCTTGCGG
       GAGGGCATGGCTGGTGGCTGGTATGAGTCACGATCTTGCCTTGGCCCTCGTTTCCTTTGT
       TCTGTTACCTTTCTCTTTGATCCCCATGGCTCTGGCCAAGTTAATAGAGCGAGAAGCAGG
       GACTTTTGTCTCCGTTCCGGCTCTGCAAGGACGAGTTCTGTTCCTGGGATGGGAAGGCTG
       TGAGACAGTCAAGGCTGACGTCTCCTTCTCCTCCTATAGTTGCCAGGGGTGGCCCAGCTG

72611  GGAAGACATCTGAAAGGACTTCCAAGGGCTTGCGGGAGGGCATGGCTGGTGGCTGGTATG
       AGTCACGATCTTGCCTTGGCCCTCGTTTCCTTTGTTCTGTTACCTTTCTCTTTGATCCCC
       ATGGCTCTGGCCAAGTTAATAGAGCGAGAAGCAGGGACTTTTGTCTCCGTTCCGGCTCTG
       CAAGGACGAGTTCTGTTCCTGGGATGGGAAGGCTGTGAGACAGTCAAGGCTGACGTCTCC
       TTCTCCTCCTATAGTTGCCAGGGGTGGCCCAGCTGTTCTCCCACCTTATGGGTTATGCAC
       [C,A]
       CCATAGGCTCTTGCTACTCTCAACCCCAGCCCCTCACTAGGCTGGAAAATGAGACTAGGTG
       AGACCACCTTCCTTCTGGGGAAAGTGAGCGGGACCCAGCTTCAGCGAATATTCAGCTGAG
       CATCTACTCTGTGTTGGGCATTCTGTGAGGCACTTTTAGGACTCTGATTTTTATTTTCAT
       TTTTAAGGGCTCAATTTCATTTTATCTTCATGTCAGCCTGTAGGGGGCAATAGCCCCAGC
       TGCTTCCAACTTACAGATAGGAGACTGAGGCTCAGTGACTGAACCAAGACACTCACTGCT

73103  CAATTTCATTTTATCTTCATGTCAGCCTGTAGGGGGCAATAGCCCCAGCTGCTTCCAACT
       TACAGATAGGAGACTGAGGCTCAGTGACTGAACCAAGACACTCACTGCTCATACACAGCG
       GAGCTAGGATTCAAATTTGGGTGTTTTTTTGTTTGCTTGTTTTGTTTTAATTTGGAGCCT
       TGTGGTTTCCCTACTGTGCCAGAATTGTCCTCGACTAGAGAACAAGAGACCTGGGGTCTA
       GGCCAGGCTTGACCTGTTGACTCACTATGAGGCCTTTGCTAAGTCCCTGGCCCTTCTCTG
       [C,T]
       GCCTCAGTTTCCCCACCTGTAAGATGAGGGTACTTGGACATTCTGTGGCCTTAAGACTGT
       TTGATTTTGAGATCCTAAGATCCTGGGATTCCTGTGCCTGAAAGACTCGGGCTCTGGACT
       AAGCTGGGGGGTTTTGCTCACAGTCCTTTGGGCAGATGGGGCTGCCCTGGCCTGCCTGGC
       AAAGCCTCTCACTGCCCTCTCCTCTCTTCCAGGACGCCTTGCTGAGTCTGGGCTCTGTCA
       TCGACATTTCAGGCCTGCAACGTGCTGTCAAGGAGGCCCTGTCAGCTGTGCTCCCCCGAG

73589  CTCTCACTGCCCTCTCCTCTCTTCCAGGACGCCTTGCTGAGTCTGGGCTCTGTCATCGAC
       ATTTCAGGCCTGCAACGTGCTGTCAAGGAGGCCCTGTCAGCTGTGCTCCCCCGAGTGGTA
       GGTGCCCGCCCTTGCCCCACGCTTCCCACCCCACCCCCAAATCCTTTGACCAGCTCTATG
       CTGTACCTCACTCAGGGCCAAGGAGGAAGGAAGAGGCAGGGTCCCTGCCCAGAGGACTTT
       CATGGGGAAGTGAAGGGTCTGGATGGGTGTTCTGAGACAGCTTTCTGGAGGAGGAAGCCT
       [G,T]
       AGGCTAAGCATCAAGGAATGAACTTGCATAGGAATCCTGCAATGGCTGAGCCAGAAGGGG
       CCTTAGAGGTTAAGTGGAAAAGCTGTGTCTCAGATAATGAAAGGGATTCACCTAGGATAA
       CAGGACGTGGTGGAGCCAGCTGAGTTTTGGAATACATGCAGCAGGAGAAGTTGAGGGTAG
       ACATGTAGAAGAACTTCCTGGAAGCCAGGTCTGGGAGGTACTAGAATAGGGCTCAGCTTT
       GATGAATAGACATGCATTGGGTTAAAGTGCCCTGCCTGGAGATGGGAGGCTGGAAAAATG

73591  CTCACTGCCCTCTCCTCTCTTCCAGGACGCCTTGCTGAGTCTGGGCTCTGTCATCGACAT
       TTCAGGCCTGCAACGTGCTGTCAAGGAGGCCCTGTCAGCTGTGCTCCCCCGAGTGGTAGG
       TGCCCGCCCTTGCCCCACGCTTCCCACCCCACCCCCAAATCCTTTGACCAGCTCTATGCT
       GTACCTCACTCAGGGCCAAGGAGGAAGGAAGAGGCAGGGTCCCTGCCCAGAGGACTTTCA
       TGGGGAAGTGAAGGGTCTGGATGGGTGTTCTGAGACAGCTTTCTGGAGGAGGAAGCCTTA
       [G,C,AsT]
       GCTAAGCATCAAGGAATGAACTTGCATAGGAATCCTGCAATGGCTGAGCCAGAAGGGGCC
       TTAGAGGTTAAGTGGAAAAGCTGTGTCTCAGATAATGAAAGGGATTCACCTAGGATAACA
       GGACGTGGTGGAGCCAGCTGAGTTTTGGAATACATGCAGCAGGAGAAGTTGAGGGTAGAC
       ATGTAGAAGAACTTCCTGGAAGCCAGGTCTGGGAGGTACTAGAATAGGGCTCAGCTTTGA
       TGAATAGACATGCATTGGGTTAAAGTGCCCTGCCTGGAGATGGGAGGCTGGAAAAATGGC

74229  CCCAATACCATGGATGAGTTGCAGGTTTGGGGCAGGTTTGGGGTGATCATGGTTGCCTGA
       GCCCAGAGTGCCTTACTGGGGAGATTGTGCCCCTCATCATCTGTTCCAGGCCACTCCCCT
       ACCTGGCTTCAATGGCCACTGTTCATCCCTTAGGCAGGAGGATGGGTAAACCAGCCCTTG
```

FIGURE 3-77

```
          AGGCCCAAAGTAGCAGGGTGTTAGTTGCACCAGAAAGAGGGAAGCAGGGGACGTTTGAAG
          CCTGGAGAAGGGAGTCTGATCCAGCCTAAGGGGCATGGAAGACTTCCTGGAGGAGGAGAT
          [T,A,GsC]
          CCCTAACTGAGTCCTGATAGCCTTGAATGTCCTCTTCCCTACTCTAAACCCGGCCAAGGG
          CAGCCTCTGCTCCAGGAAATATGGCCAACTCAGAATGTGACCTTCCCATCCCTCCAGAGC
          CCATTGTCCCTGAATCTGCTTGATGGATGAACCACCGGAGGCCCAGAGAGAGAGGGCACT
          TGTCCCAAGGTCACACAGCATGACAGGGATAAATGGGACTTGGTATCTAAGCAGCCCCAT
          TCCCTCTCTTCAGCTCTGCCTTCCCCAAACCTCCTAGAAGTTCAGAGCCCAGGAGGAGGG

74478     GGGAGTCTGATCCAGCCTAAGGGGCATGGAAGACTTCCTGGAGGAGGAGATTCCCTAACT
          GAGTCCTGATAGCCTTGAATGTCCTCTTCCCTACTCTAAACCCGGCCAAGGGCAGCCTCT
          GCTCCAGGAAATATGGCCAACTCAGAATGTGACCTTCCCATCCCTCCAGAGCCCATTGTC
          CCTGAATCTGCTTGATGGATGAACCACCGGAGGCCCAGAGAGAGAGGGCACTTGTCCCAA
          GGTCACACAGCATGACAGGGATAAATGGGACTTGGTATCTAAGCAGCCCCATTCCCTCTC
          [T,C]
          TCAGCTCTGCCTTCCCCAAACCTCCTAGAAGTTCAGAGCCCAGGAGGAGGGCTAATGAGT
          GAGCTTTATTGAGTGTGAAATTGGTAGGAAGTGGGTGGTGTGTTGGCGCCCAAAAATAAA
          TCCTCCTGGAGAAGGACGGGACTAAGGCAACATCTGGCCTGGGGTGAAGGCACATCTGGA
          AAGGGAGGGTGGTGGAAACTGGCAGGTCGGTTTCTGTAGGGCTGCCCCGAGAGCCTCTGT
          GGCCACTGAGGCTGCCGTAGGGTGGGAGGAGGAAGTGACTGGCTCTGTTTCACAGGCAGG

74636     CATCCCTCCAGAGCCCATTGTCCCTGAATCTGCTTGATGGATGAACCACCGGAGGCCCAG
          AGAGAGAGGGCACTTGTCCCAAGGTCACACAGCATGACAGGGATAAATGGGACTTGGTAT
          CTAAGCAGCCCCATTCCCTCTCTTCAGCTCTGCCTTCCCCAAACCTCCTAGAAGTTCAGA
          GCCCAGGAGGAGGGCTAATGAGTGAGCTTTATTGAGTGTGAAATTGGTAGGAAGTGGGTG
          GTGTGTTGGCGCCCAAAAATAAATCCTCCTGGAGAAGGACGGGACTAAGGCAACATCTGG
          [C,G]
          CTGGGGTGAAGGCACATCTGGAAAGGGAGGGTGGTGGAAACTGGCAGGTCGGTTTCTGTA
          GGGCTGCCCCGAGAGCCTCTGTGGCCACTGAGGCTGCCGTAGGGTGGGAGGAGGAAGTGA
          CTGGCTCTGTTTCACAGGCAGGGTGCCCTGGCGGCTGTGCCAGCCTAGATGCTCTGCAAC
          AGATTAATTGTCTCCCCAAAGCTGGGGGCTGGGATGACAGCTGTGGTCCAGGTTCCTGGG
          ACAGTGGGAAATGTCAGCCCTGGCCCACCCAAGAGCCCTATAGGAGCTAGGGAAGCCCTG

75308     TCTGCTGCCCCCAGGGAGGGAAGCAGAGATGGGGAGGGGACCCCCGCCCAGGGAGGAGAG
          CTGCTGGCACCTGGCTTCCTCATCAGCACCCATTGTGGCAGGCAGCCCCGAATGCAGATG
          GTGCTGATGTGTCTGAAATGGTTCCCTCCTTCTCTCCAATAGACTCAGCTAATTTTTAACC
          CAGAGGGCTGAGAGTAAGGGGGTGGGAGACATACGGACATGCGGAAGTGAAGCGAGAATC
          TGTCCCCCTCTGCCCCATGGACTACCCACCCCTCCCTCTGCCTGGGCAGGACTTTCTGT
          [A,C,T,G]
          TAACCCCGGCTGGTCTCTTAACCTCTTTGGGCCAAATAACTCAGGCCCCTCCCAGGCTGC
          TGGAAGAGATGGATGACAAGGAGGCTAGATATAGCCGAAGAGTGGGCGGCCTCCTTCCCA
          CTGAATTCTTTATCCCTGAACATCCCACTTAGGTTTCCTTCCAGCCAAACAAGAGGGTGT
          CTGCCCCTCTCACTCCCTTCAGGCCTTATCATTCCCACCCCATGCCACACCCACCACGGA
          ACCTGGCTCAGTGTCTCTGGAAGTAGTGGCCAGGCATCTCCTGTGGTGGGGGCTGGCTGG

75554     CCTCTGCCCCCATGGACTACCCACCCCTCCCTCTGCCTGGGCAGGACTTTCTGTATAACC
          CCGGCTGGTCTCTTAACCTCTTTGGGCCAAATAACTCAGGCCCCTCCCAGGCTGCTGGAA
          GAGATGGATGACAAGGAGGCTAGATATAGCCGAAGAGTGGGCGGCCTCCTTCCCACTGAA
          TTCTTTATCCCTGAACATCCCACTTAGGTTTCCTTCCAGCCAAACAAGAGGGTGTCTGCC
          CCTCTCACTCCCTTCAGGCCTTATCATTCCCACCCCATGCCACACCCACCACGGAACCTG
          [G,C,AsT]
          CTCAGTGTCTCTGGAAGTAGTGGCCAGGCATCTCCTGTGGTGGGGGCTGGCTGGCGACAG
          CTGATGACAAGAAGAGTGGCTGGCAGGATTGTGGACGCTCTCAGAGTCATGGAAGGCAAC
          TGCTTCTTCTGGGAAGGATTCCACACTTACTGAGGGTGGGCCTTCAACACGTAGCTCCAC
          TGTCAGCTCCTCCCAAAGCCCTCCAGGATACCCTCAGCTGGGAGGCAAGCCCTTCTCCAT
          CCTCCTGCGGAGAAAACAGCAGAGTTGTGGACAAGGCTGCGTTGCATGGGGGTTGGTCAG

76209     GGTCAGTGAGGGCAACTACTTCTGCCAAGACATGGCCTGGAACTGAGGCCAGAGCTGCTC
```

FIGURE 3-78

```
         TGGGCCCTTGGGGAGGGAGGATTAAAGAGCAAGAGCTTTGATCTCCCTCTGAGGAGTAAT
         CGGTCCAAAATACAAATCTGCTCACGTCTCCCTGTGCACGTCCTGCCCTGCCCCAGTTCT
         GTTCGTAAGCCCATCCCACTCAGCCCTACTGACCTTGGGCCCAGCCCCTGTGCCCCTTCC
         CTCACTGTCTGTTCCTAAATGCTCCATGCTTTATACGCCTCTGGACCTACCTGTGTACCT
         [G,A]
         CTATAAGGCCTGGGAGCCCATTCTGCACCCTGCCCACTCCCTGAATGTGTCTAATTCCCA
         CTCAGTGACAGCTGAAAGGTCACTTCCTCCAGGAAGCCCTCTCCAGCCCCACCGGAGGAT
         GGCGCAGTGCCCTGCTCTGTGTTCCTCCCCTGGCTGGGGTTATGGGTGTGTGGTTTCTTG
         TAGAGGTGAAGGAGGGATGCTTCCTAGAACATTCTGAGCCCCATCCCTGGTACAGCTCAG
         AGTGGATGCTCAGTTATTGTTTGCTGAATGCCTGAGGCTGGAGTCAGGCAGGGAAATATC

76627    GATGGCGCAGTGCCCTGCTCTGTGTTCCTCCCCTGGCTGGGGTTATGGGTGTGTGGTTTC
         TTGTAGAGGTGAAGGAGGGATGCTTCCTAGAACATTCTGAGCCCCATCCCTGGTACAGCT
         CAGAGTGGATGCTCAGTTATTGTTTGCTGAATGCCTGAGGCTGGAGTCAGGCAGGGAAAT
         ATCCCAGGTGGGAGGTGATTTGTCTGCACCCTCAGTCCTTGAAACTCTTTACCTGGCACA
         TTGGGTTTTGGGTGGTAAAAAAGGTCATAGGTTCATGAATCATTGCCTGCTTAGAATTCC
         [T,C,TsC]
         TCCAAGAGGAGAGGACGAGGTGCTTAGTTCACCGGGTGTTTTGCTGCCCTGGCTGCATCT
         TAGAATCACCTGGAGAGAAAAACAAACAGATCATTGCCAGAGCTCCACTCCCACAGGTTC
         CATGACCTTGCCCCACAGACCCCTGTGTACAGGCTGGGACTGGGCAGCTGGGAGGGCCTC
         TCCACAGGGTCTCATAAGTGCCTTCTGTCCTAGGAAACTGTCTACACCTACCTACTGGAT
         GGTGAGTCCCAGCTGGTGTGTGAGGACCCCCCACATGAGCTGCCCCAGGAGGGGAAAGTC

76767    TGTTTGCTGAATGCCTGAGGCTGGAGTCAGGCAGGGAAATATCCCAGGTGGGAGGTGATT
         TGTCTGCACCCTCAGTCCTTGAAACTCTTTACCTGGCACATTGGGTTTTGGGTGGTAAAA
         AAGGTCATAGGTTCATGAATCATTGCCTGCTTAGAATTCCTTCCAAGAGGAGAGGACGAG
         GTGCTTAGTTCACCGGGTGTTTTGCTGCCCTGGCTGCATCTTAGAATCACCTGGAGAGAA
         AAACAAACAGATCATTGCCAGAGCTCCACTCCCACAGGTTCCATGACCTTGCCCCACAGA
         [C,A]
         CCCTGTGTACAGGCTGGGACTGGGCAGCTGGGAGGGCCTCTCCACAGGGTCTCATAAGTG
         CCTTCTGTCCTAGGAAACTGTCTACACCTACCTACTGGATGGTGAGTCCCAGCTGGTGTG
         TGAGGACCCCCCACATGAGCTGCCCCAGGAGGGGAAAGTCCGGTGAGCCATTCTCTGCAC
         CCCCATTGCCCTCTTGCATGGCCAAGGATTCTCAGGGCTGAGGCACCATCCAAGGTCATC
         TGGTCTGACCCTCCCCTTCCAACATTGATCCCCGCCTCCCTGCCAGGTGGGATTCCTTGG

77530    TATGGGGTGTATCAGTTAGAACACCGGCATGCTGTGAGAACTACTGCGAGGCTGGACCTG
         GAATCCCAGCATGCTGGGCCTGCAGGAGCTCACAGTGCCAACTCCTTGCATCTGAGAACA
         GGGAGATCACAGGCAGCGTCCTGCTGAGGGTTCTGGAGCCCCACTGCCTGGGTTCAAATC
         TCAGCTCCCTGTTTACTAGCTGTGTAACCTTGGGCAAATGACACAACCTCTCTGTGCCTC
         AGTTTTGTTTATGAAATGGTGATAATAATGGTGCTTATAGGATTGTGGGGAGGATTAAAT
         [G,A]
         TGTCACACATGTAAAGCATTTAAAATCAGGCCTGATCCATGGTGAGGGCTGTCTGTTGGGG
         ATTACCATTGTGAGAGAATGCTGGAATCACTGACTTCAGGATCATGGGATCAGGGCACTT
         GGCCCCCTGATACCTTGATGCCCATTTAATTCAGCCTCCTCATCTTCCAGATGGGTGGAT
         ATCATGAGACATGACCAAGGCCACATGCCAGGTATGAGGCAGAGCCAGGCCTAGGACTCG
         GGTCTTCTGACTCCTGGCTGTTTAGGGGAAAGTGAGAGGAAGTGGAACTCATCAGATGAG

78642    TGTCCCGTCTGTAAGAGGATGGTCTGAAAGGTCTTTAGAACCTTAAGGGGAAAAATGTGG
         TCATGTCCCCCTTTCTCCTCTAATTCCAAAGAACTTCGCTCTCCTCCAGCATCCCCCACC
         TCTAATTCTAAAGAACTTTGCTTCATATAAGCTCCACTCCTCCAGGAAGGCTCCTCGGAG
         CAGCCTGGGAGGCCTTCCTGGGAGGGATGCAGGAAAACAGGCTCAGGAGGCAGCGGGGAG
         CAGCCTGCAGGTTTGCTTCACTCCCTAGGACCCACACATGCTCCCCTCAGCTGTCTGGGC
         [A,G]
         TGTAGAGTGGGTGCGTATCTGCGGTCCAGGCATTTTTGAGAGGGCTCAGATCCTTGGCAT
         CAGCTGCCCTTTCAACATCCTCCTTCCAACCACTTCAGACTCAGTAAGGCCTTTGGAAAA
         AATACCAAAAAAAAAGCAATTAAAAGTGAATATTCAAATCCAATTATCCCAGAGCTCAGT
         GGAGATGGGGAGGTGAGTGCCTGCTGGTAGACAGGGGCTGAAGATTCCAGGAGGAGGGCC
         AGGGGATGAGAAGGCAAGAGAGTGAGGACAGCAAGGACCTCCCAGGGGACATACCCATCA
```

FIGURE 3-79

78774   GAACTTTGCTTCATATAAGCTCCACTCCTCCAGGAAGGCTCCTCGGAGCAGCCTGGGAGG
CCTTCCTGGGAGGGATGCAGGAAAACAGGCTCAGGAGGCAGCGGGGAGCAGCCTGCAGGT
TTGCTTCACTCCCTAGGACCCACACATGCTCCCCTCAGCTGTCTGGGCATGTAGAGTGGG
TGCGTATCTGCGGTCCAGGCATTTTTGAGAGGGCTCAGATCCTTGGCATCAGCTGCCCTT
TCAACATCCTCCTTCCAACCACTTCAGACTCAGTAAGGCCTTTGGAAAAAATACCAAAAA
[A,-]
AAAGCAATTAAAAGTGAATATTCAAATCCAATTATCCCAGAGCTCAGTGGAGATGGGGAG
GTGAGTGCCTGCTGGTAGACAGGGGCTGAAGATTCCAGGAGGAGGGCCAGGGGATGAGAA
GGCAAGAGAGTGAGGACAGCAAGGACCTCCCAGGGGACATACCCATCATCAGGACACACC
CGTCATCATCCCCAAACAGGAATTCTTTTCCATGGCCCCTGTGAAAGGTGAGTGGCTTGCC
AGGCTCAGCTGCTACCTGAAAAAGGATTGGGGGAAGGCCCAGGCCCAGTGCTCTCTCTGG

79135   GTGAGTGCCTGCTGGTAGACAGGGGCTGAAGATTCCAGGAGGAGGGCCAGGGGATGAGAA
GGCAAGAGAGTGAGGACAGCAAGGACCTCCCAGGGGACATACCCATCATCAGGACACACC
CGTCATCATCCCCAAACAGGAATTCTTTTCCATGGCCCCTGTGAAAGGTGAGTGGCTTGCC
AGGCTCAGCTGCTACCTGAAAAAGGATTGGGGGAAGGCCCAGGCCCAGTGCTCTCTCTGG
TATCTGAGCTCTGCTTGCCCACCTTTGTGCCTGGTGTCTGGTGGTGAGCCCATCTCCACA
[A,G]
TTAGGGCGGAGAGGCCCCAGGGTTGGCTGGGCCCTGCTCTCAGGAGCTCCCAGCAGGATG
GGGACTTGAGACCCAGGTGTATGGACGAGGGAAGAGCACTGGAATGGGATTCAGACAGGT
CTGGATTCTAGCTCAGCCCCCTCCCTGTCTCTCTGCTTTCCTACCTGAGGCCCGGTCTAT
TGGCTTAATGGGGTAACAGGGGCCAAGTGCTTGGCACAGTGCCCAGCACACAGTAGGAGC
TCAGTGATTGCTACTTGCACTCCCAAGTCCCAACCAATGATTAGCCTTGAGTGACCTTGA

79648   GGCACAGTGCCCAGCACACAGTAGGAGCTCAGTGATTGCTACTTGCACTCCCAAGTCCCA
ACCAATGATTAGCCTTGAGTGACCTTGAGAAAACGACTTCTCTTCTGGCCTTTTTTCTGT
GAAATGGGTGGGGTTGGGTACAGGGTCCTTCCGATGGTGACCTTTGTGGCTCTGGTCCCC
CCAGGAGGGAGAGGGACTGACCTACAGGCTGCCGTGGAGCCTGAGGCTCTAGCAGTGCCC
GAGGAGGTGGGGGTGTGGGGAGGGTGCTACTCCAGGAAACCCTGGACTGTGGGCAAACAG
[C,T]
AGCAGGTGTGGCGTGGAGGCTGGATCATAGAGACAGATAAGGAGGCCCGAGGCAATGGGC
AGGGAATGGGATCAGGGCAGTGTGGGGAGAGACAGGGTGGAAAAGGGTCAAGGCGGGAGT
GAGGAGGCCCCCGCCAGCTCCCAGCCCCACCTGTCCCTGTTCCTGCCGCTGTTTGGGCTC
TCAGATGCCCAGCTGCATCCCCCCAGTGTGTTTGGCTTTCCTGTCTTCTTGTGCTTGTAA
GGGCTGCTTGCTCCCTTGCAAAGACCGTCCCTGCTCCACTTTCATCTCAGCCAATCCCAT

80969   GGGGGAAGGAGGGCAAGAAGAGGGTCCAGGTCCTGGGGGCTCAGTGAGAGTGGGGGGCTT
AGTGAGGGGATGGGGGCCCAGTGACAGTGGGCAGCCTCAGTGAGGTGATGGGGGCCCAGT
GAGGATATGAGGGCTCAGTGAGAGTGGGGTGGCCCAGTGAGGGGATTGGGGCACAGTGAG
AGTGAGGGGCTCTGTGAGGGGGTAGGGACTTAAGTGAGGGGATGGAGGCTGAGTGAGTGT
GTGGGGGCTCATTGAGAGGGTGGGGGCTAAGTGGGGAATGGGGGCTCAGTGAGGGGATGG
[C,T,A]
GGCTCAGTGAGAGGATGAGGGCTCAGTGAGGGGATGGGGGCTCGGTGAGGGGATGGGGGT
TCAATGAGGGGATGGGGGCTGAGTGAGGGGATGGGGGCTGAGTGAGGGGATGGGGGCTGA
GTGAGAGGATGGGGGCTGAGTGAGGGGATGGGGCTCAATGAGAGGATGAGGGCTAGGTGA
GAGGATGAGGGTTCAGTGAGGGGATGGGGCTCAGTGAGGGGATAGGGGCTCAGTGAGAGG
TTGGGGGCTCAGAGAGGGGATGGGGACTCAGTGGGGGATGAGGGCTCAATAAGGGGATGG

82103   AGTGAGGGGATGAGGCCGAGTGAGAGGTTGCGGCTCAGTGAGGGGATGGGGACTTAGTGA
GAGGATAGGGGCTCAGTGAGGGAATGGGGCTCAGTGAGAAGGTGGGGGCTCAGTGCGGG
ATTGGGTCTCAGTGAGAAGGTGGGGGCTCAGTGAGAGGGTGAGGGCTTAGTGAGGGTATT
CGGGCTCAGTGAGGGGATGGGGCTCAGTGAGAGGATGGGGCTTGGTGAGGAGATGGGG
GCTCAGTGGGGGATGGGGGCTGAGTGAGGGGATGGGGGCTCAGTGAGAGGATGAGACCTC
[G,A]
GTGAGGGGATGGGGGCTCAGTGGGGGATGAGGGCTAAGTGGTAGATGGGGGCTGAGTGGG
GGGATGGGGGCTCAGTGACAGGGTGGGGCTCAGTGAGAGGATGGGGGCTCAGTGAGGTGA
TGGGGCTCAGTGAGAGGGTGAGGGCTTAGTGAGGGGATTGGGTCTCAGTGAGGGGATGGG

FIGURE 3-80

```
        GGCTCAGTGGGGGATGGGGGCTCAGTGGTAGATAGGGGCTGAGTGGGGGGATGGGGGCTC
        AGTGAGAGGGTGAGGGCCTGGCGAAGGGATTGGGGCTCAGTGAGGGGGTGGGGAGTCAGC

83833   CTTATGTGGAGAGTTTTACCCAGGCAGCATGATCGTTCTGAAATCATACCTGACCATTAC
        CGTCCCTGCTCAAATCCCTCCCAGGGCACCCCCTGCCCTCAGGCTCAAGCCCAGCTCCAT
        AGGGCCCTGGCCCCTGTCTAGCCTTGCTCTCGGCTGTCCAGTCACACCAACCTCCTTGTG
        GCCATACCTTTCAGCAGGCACACAATCTTCTCGCCTCCAAGCCTTCACAATTGCAATTCC
        CTGGACATCCTTTCCTGTCTGCCTCGATAACCTCTGCCTGTCCTTTAGGACTCAACTCAG
        [G,A]
        TGTCTCCCTCTACAGGAAGCCTTCTCTGACTCCATCACACCCTGCACCTGAGTGGGCTGG
        GGCCTGCTCTTCCTGCCTTTGGCAGAGCTCTCATCTCCCGACTGAAGCGTGGGTCTGTAC
        GTTGATCTCTGCGTGTTCTTGGCCTCCTCAAGTGAGGCATATGTCTGACCCCTCTGCTCA
        TCTCAGCCCTCAGCACTGAACCTGACCCAGAAGGACCCAGTGAAATGAGAGACTTTAAGT
        AGAATGCTCCCCGAGGTTTTTCATCTAGAACACTTATTCTTGCTCTGCCATGGAGAATGG

84945   CTGCAGTGCGCACTGACCAGCAACGCAAGGACCAGTGCCACCTTGTGGCCTCCGGTTAAC
        CAGATTGTCTGAGGCCAAGGAGCTGGGCAGGGTTTGGCCAGGGGTCACCCCCTGCCTCCG
        TGAAGCCTCAGCCTTCATCAGTTTAATCATCAGGAAACGTGGCTCCCGTTGCCCTCCTGC
        CACCCTACGTCCCTCTCCTTCCCGGGGTGACTGGCAATGTGGACAGCCGGGAACTGGAGC
        CCAGCACTTCAGGAACCTTAAAGGTCCTGGGTGTAGGGGCTGGAAGGTGGGAGACACCAC
        [T,C]
        GGTTCCTGTAGATCCTGGATTACTTAAAGTGGCCAGGAAGGAATGGGTTTGGTTCAGAAT
        GCTGCGTGAGCTTGAACGAGATGCTCAACCTCTTTGGTCCTCGATTTGTCTAGAGTCTCT
        GACCTAGTGATCTCGTGACTTGCAGGCCACCCCCTCCTTTTCCTCATGTGACCTTTGCTG
        GGCTTCCCTTAGTGACCCTGTATGCACACAGTTCCCCAAGTTTCTCTTCTGTCCAGGCCA
        GGCAGTTCCTACAAGCACAATTAAGTGGAGGCAGCATGAGGGATGAAGAACCCAGGACAA

84985   CCTTGTGGCCTCCGGTTAACCAGATTGTCTGAGGCCAAGGAGCTGGGCAGGGTTTGGCCA
        GGGGTCACCCCCTGCCTCCGTGAAGCCTCAGCCTTCATCAGTTTAATCATCAGGAAACGT
        GGCTCCCGTTGCCCTCCTGCCACCCTACGTCCCTCTCCTTCCCGGGGTGACTGGCAATGT
        GGACAGCCGGGAACTGGAGCCCAGCACTTCAGGAACCTTAAAGGTCCTGGGTGTAGGGGC
        TGGAAGGTGGGAGACACCACCGGTTCCTGTAGATCCTGGATTACTTAAAGTGGCCAGGAA
        [A,G]
        GAATGGGTTTGGTTCAGAATGCTGCGTGAGCTTGAACGAGATGCTCAACCTCTTTGGTCC
        TCGATTTGTCTAGAGTCTCTGACCTAGTGATCTCGTGACTTGCAGGCCACCCCCTCCTTT
        TCCTCATGTGACCTTTGCTGGGCTTCCCTTAGTGACCCTGTATGCACACAGTTCCCCAAG
        TTTCTCTTCTGTCCAGGCCAGGCAGTTCCTACAAGCACAATTAAGTGGAGGCAGCATGAG
        GGATGAAGAACCCAGGACAATTAATCATCAAGGAGTGACATTTGGTGCAAACNTCAGGTG

85295   TGGTTCAGAATGCTGCGTGAGCTTGAACGAGATGCTCAACCTCTTTGGTCCTCGATTTGT
        CTAGAGTCTCTGACCTAGTGATCTCGTGACTTGCAGGCCACCCCCTCCTTTTCCTCATGT
        GACCTTTGCTGGGCTTCCCTTAGTGACCCTGTATGCACACAGTTCCCCAAGTTTCTCTTC
        TGTCCAGGCCAGGCAGTTCCTACAAGCACAATTAAGTGGAGGCAGCATGAGGGATGAAGA
        ACCCAGGACAATTAATCATCAAGGAGTGACATTTGGTGCAAACNTCAGGTGCTTAATTAA
        [G,A]
        CGGGATGAGCCAGAGGCTGGGGGGTAGAGGAGGTGGGTTGTGTGGTGGACAGAGAGAAA
        CTCATTCTTCCCATACCAACCTCCCCTGCCTTGGTTCCCACCACCCCTCTGCCACTGTCA
        TACCCTGCCACTCACACCTGCCCCCTGTTCAAAGCTCACACCTCCACAGGTATTTGGGAA
        GGTTCCAGCATAGTGGTTAGACCTAGCCCTGGTGCCACCTACCTGGGTTCAAATCCTGGC
        TCTACCGCTTATTCACTGTGTAACCCTGGGCAAGTGAATTAGCCTCTTGGTGCCATAGCT

89241   GTCAGCTTTGAGGGGCACTGAGGTGAGGGCTGTGTGCAGAGGTGGGGATTGGGAGGTGG
        TGGCTGGGTCACGCACCTCCTTCTCTGCTGAGGGCAAAGGGCCTGGGGTGCCAGGTGCCT
        GAGAAGGACTTCCTTAGATTGAGGCTATGAGGACTGGGTCAGGAGGGAAGTAAGGGGAAG
        ACATTTGGAAGGTTGCTTCCCTTGTGGGCGGAATGCTTGCCATGGCCGCTGCTCACCTTG
        GCTCAGGCTGGGCCAGAGGCCAATGTGTGTGTGTGTGTGTGTGTGTGTGTGTCTCAGGGA
        [C,T]
        GCTGGTGGGATCAGATCACTTACACTTAACTCACCCAGTAGAACTCTGGTCTGGTCCTGC
```

FIGURE 3-81

```
         GGCAGGCTGGGTGCTGGAGCCGACTCTGCCTTCAGGGAGCTCTCAGTCTGGGGGAAGGCA
         GGGACACCCTCCCCACCACAGGCCAGATGAAATACTGTTGCCAGCAGGTGTTCTGGTGGC
         AAAGCCTGGAGCAGCAAGTGGTACCTCATCACAGAGAAAGCATTTGTGTGGGGCCTTGGG
         GCACAGGTAGGAGGTCCACAGGCAGGGAAGAAGGGAAAGGGGATTCTAGGCAGAGGAGGA

91827    AGTGGCCCTCAGATGCTAAAGTCTGCCATGGCTCCCCAGTACTCTCAGGCTAAAGTCTAA
         CTTCTTAGCCTGGCACTCAAGGCCCTTCCTTCTGTGGTACCATGGACCACACCCCTACCT
         GGATCCTCATCTCCCCGCACCACCTACCGCCAGTGTCCTGGTCTCTTCAAGGTCTACTTG
         TCCTCCCCATGCCAATTCAGGAAGCCTTCCAAATGTCCTCCCCTCTGAGCTACCCACCTA
         GTTTTCTCTCTCCTTCCTCAGGTATGAGGCTCCACACCTCCTCCCAGTCATGTCTCCCCA
         [A,G,C]
         TCGTCCCACCCCAGACAGACTGTGAGCTTCCCGAGAACCTGCTGGTCTCCTCCTCCCCAT
         CTGCTCCTGGCAGGAGACCCAGAGCTGAGGCAGGCATTGGCTGCTGACTGGGGAGGGAGG
         AGGAAGGAGGAGCCCCCAGTGCAGGCGCTGTGGGGAGCTCTGCAGGTGGTGAGCAGCTTT
         GAGTAAGCTCCGGAAGCTAGTGACGCAGGTGGGGAGCCTTGCTGGCAGGGCCTGTAGTGG
         GTCCCTAGGCTGCCACCCTCCCTCCCCACCGTCTCTCATTTTCCTCGACAAGCACCCAAG

93127    GGACCAGTGTGTGCTGCGCATGGGGAGGGCACTCTGGCAGAGACAGACACTGAGAGAGGT
         CACAGCTAGTTCCCTTCTCCCATCCCTCCAGGTGCACTGTGGCCAGCTGAGTGATAATGA
         GGAATGGAGCCTGCAGGCGGTGGAGAAGCATGTGAGTGGGAGTGGGGCCATGTGCAATGA
         GGCTGAAGACCCTTATCACAGCTGGTGGGAAGATGGCCTGGCCAGGGAGCTGGACAGACC
         TGGGTTTCAGCTTCGGCTTTGCTGCTTTTGAGCTGTGTGACCTTGAGCAAGTCACTAAAC
         [C,G]
         TCTCTGGGCCTCAGTTTCACACCTGAAAATGGGGATAATGATAGCACCGACTGACCTAGG
         GCAGTGGTGAAACAAAACTGGTCAAATATCTTGTAAATACACACGGTTGCCAACTTACAA
         TTTTCGACTTTTTGATGGATTTATGGGGAAGCAACCCTATCCTAAGTCCAGGAGCATCTG
         TACTTAGAAAGAACCCTCCACATAATGATACTGAGGCTCTTTCATGCCTGAGACTTTATG
         ATTTTGTGACTTTAACAAG

93815    TGGGAGCCCCCGGGGGAGCCCTCAGGAAGGTAGAGTCCAGGGATGAGGTGTTTGGGACGG
         CGGCGGGGTCCCTGGGCCCGGCAGGCAGAGGGAACGGCGGGAGCAAAGGCAGGAATCCCG
         CTGCAGCAAGCGCAGCGAGCTTGGGGCGAGCGGCGCGCTAACCGCTCGGCCTGCCCCAGA
         CCCTGGTCGCCCTGCGGAGGGTGCAGGTCCTGCAGCAGCGCGGGCCCAGGGAGGCTCCCC
         GAGCCGTCCAGAACCCCCCGGAGGGGACGGCGGAAGACCAGAAGGGCGGGGCGGCGTACA
         [C,T]
         CGACCGCGACCGCAAGATCCTCCAACTGTGCGGTGAGGGCCCGGCCTGGACAGGTCACGA
         GGGCGGGGCCGGGCAGAACTTGGAGGGGAGGTGGGCGGGTTAGGCGATCCCGGGAGCCGG
         CGGCGGGCCCGGCGCGGAGCTGAGCGGCGCCTGAGGGACCCGGACACGGAGGTGCGGAGG
         GGCCCTCTCTCTGACCGGCGCCTGGCCCTTGCAGGGGAACTCTACGACCTGGATGCCTCT
         TCCCTGCAGCTCAAAGTGCTCCAATACGTGAGTCCCTGCGCCCCTGCCGGCCACCTCCCC

96136    TGGACAGTGGCTAAAGGGAATATGCTTGGGGACTGGGAAAAGCTGTGGATCTTTTGAGCC
         CCTGACAGGGCAGCTATAAAAATGATACACAAAAATCTCTTTTTTTGTGGGCAGGGCACA
         GTGGACAGGAAAGCAGGCTTGGAGGCTTAGTTGGAAAGGATATCTCGAGAACTGAGGACA
         AACCTGGGGTCTAGAAATGGTGTCATAAATAAATTTCATATCCTACACCAACTCATAAAC
         AGGCAGTAGGTGCCTGAATTTTATTGCAAATGGATCTTAGTTCAGGGAGAAACAGTGCTG
         [C,T]
         GTCTGATGAGCCATTTCTGTCCTGGGTGCAGGTTCACACTTGGGCTGGCAGGATGAGCAG
         TTTGTGCTGTGTCACATAGGTGGGGAGAAGTAGACAGATGAGGGGCTGAGTCCTGATGCA
         AAGAGATGCTGATAGGATGCTGGTCTCTGGAGTCCAAGCAAACAGGCTGGGTTTCAGGGC
         CTGGAGCTCCTGCAGGAGGTGGACACTAGAGAGCCTGGGACTAGGTAGGTGTCAGAGCCC
         GGGCCTGAGGTCTGCTGGGGTAGGGTGGAGATCCAGGAGTCCTAGGTCTGAGCTGCAGAA

96831    TTGGTGGCATTTGGAACTTGTGGGCATCCTAATGGTGGGAGAATTTATGCCATTCAGCAA
         ACAAATATTGAGCACTTAATGTTGCCATCCCAGTGCTGACCAGATGGCCTTGGGAAGGCC
         TTTGGGGAAGGGAAGGTAGAGTGAATGGGGGTCCAGCAGGGGCCATGACTTCTTGCTGCT
         GGCTGTGAGATTGGGTTCTAGGATGGCCCCAGAGCTGGAGAAGAGGTGGTATCAGCAGGA
         AATAAGGATGGGGCCTTGGTGGCAGCTTTGAGGCCCAGGGCAGGGCAGGGCTATCTCTG
```

FIGURE 3-82

```
         [T,G]
         GTCCCACGCATTTCAGGGAGTGAGTGTTGAATGACTGCATGAGCCAGGGTGGGGCTCAGC
         TCAGTGCAGTGACTACAGAGAAGCTTCCTGAAACACAGCTAAGTAGCCAGAGAACAGGGG
         CTCCAGAAGCCCTTCAGCTGTGAGTGGGATGGGGCTGGTGGCAAGGCCAGGGATAGGATA
         CACTGACGACATTAGCAAAGACCTCCGAAGTGTTTCCTCTGTACCAGGCTCTGCACTGGG
         CATGGGTGATATAGTCATGGCCCCATTTCATAAGACTCAAAGCTCATTTTCAGGGCATAG

97038    CCCAGAGCTGGAGAAGAGGTGGTATCAGCAGGAAATAAGGATGGGGCCTTGGTGGCAGCT
         TTGAGGCCCAGGGCAGGGGCAGGGCTATCTCTGGGTCCCACGCATTTCAGGGAGTGAGTG
         TTGAATGACTGCATGAGCCAGGGTGGGGCTCAGCTCAGTGCAGTGACTACAGAGAAGCTT
         CCTGAAACACAGCTAAGTAGCCAGAGAACAGGGGCTCCAGAAGCCCTTCAGCTGTGAGTG
         GGATGGGGCTGGTGGCAAGGCCAGGGATAGGATACACTGACGACATTAGCAAAGACCTCC
         [G,A,T,C]
         AAGTGTTTCCTCTGTACCAGGCTCTGCACTGGGCATGGGTGATATAGTCATGGCCCCATT
         TCATAAGACTCAAAGCTCATTTTCAGGGCATAGAGGGAAGAGAGTGAGAAGGGTATTCTA
         GGCCGAGGGAACAGTGTAGAAAAAAAAGCATGAAGGTGTGAAAGAGCCCAAGGTTTTCTC
         AGAATGATGAGGATCTTTGTGTGGCTGAAGCTGAGAGATGTTCTGGGTTGAGGGGTGACA
         GGTGGGTGGGGCTAGCTGAGGGACCACAAATGTAAGAAAGGTGTGCAGACAGACCCAGGA

97110    GCAGGGGCAGGGCTATCTCTGGGTCCCACGCATTTCAGGGAGTGAGTGTTGAATGACTGC
         ATGAGCCAGGGTGGGGCTCAGCTCAGTGCAGTGACTACAGAGAAGCTTCCTGAAACACAG
         CTAAGTAGCCAGAGAACAGGGGCTCCAGAAGCCCTTCAGCTGTGAGTGGGATGGGGCTGG
         TGGCAAGGCCAGGGATAGGATACACTGACGACATTAGCAAAGACCTCCGAAGTGTTTCCT
         CTGTACCAGGCTCTGCACTGGGCATGGGTGATATAGTCATGGCCCCATTTCATAAGACTC
         [G,A,T,C]
         AAGCTCATTTTCAGGGCATAGAGGGAAGAGAGTGAGAAGGGTATTCTAGGCCGAGGGAAC
         AGTGTAGAAAAAAAAGCATGAAGGTGTGAAAGAGCCCAAGGTTTTCTCAGAATGATGAGG
         ATCTTTGTGTGGCTGAAGCTGAGAGATGTTCTGGGTTGAGGGGTGACAGGTGGGTGGGGC
         TAGCTGAGGGACCACAAATGTAAGAAAGGTGTGCAGACAGACCCAGGATGGTGGGGATGG
         GATCTAGATCCGAATCACTGGATGGCAAGCATGAATGGGGGATGCCCCACCAGGGTGGAG

98446    CCGTGCTCACCAGCACCCTGGCCTTCCAGAAGGAACAGAAACTCAAGTGTGAGTGCCAGG
         TGAGTGACCTGCCTTCAGCCTCTCTCGGGCACCGACTCGCTCAGTTTTCAGCCCCGAGAG
         CCATTCAGAAGGGAAATGCCCATGTCTTTCTGGACTGGTGGCAGCCCTTCCCCAGGTGGC
         TCCATAACCTCATAACTTGAAGGCTTGCAGTTGTTCAGGACCCGCGCCACTGCCCGCAGG
         CACTGTATGTGATCGCCCTCTAGTGTTCAATATGTGCACTACAGCAACACCTAGGCAGCT
         [A,G]
         GAGCTGGCGTGAAGGCGGCTGAGACACTCAGGAGACTCCTCACCTGCACCGGGGCTATTC
         CCTCACTCCTTCACTTAGTAGCCAAATGATATAATTAGACACTGACAGTTTCTGGCTTGT
         CCAGTGAGCCCTAGGGAAGGAAGGAGAAGACCCGGGTGCTGTTGGAGGCAGAAGGTTGGA
         TAGGGTGACCCCTACACCCCGACCCCCCTATGATCTCCATTTCCTTCATTCCAGGCTCTT
         CTCCAAGTGGCAAAGAACCTCTTCACCCACCTGGGTGAGTGCACTGTTCTCTCTGCCTGG

98618    CAGGTGGCTCCATAACCTCATAACTTGAAGGCTTGCAGTTGTTCAGGACCCGCGCCACTG
         CCCGCAGGCACTGTATGTGATCGCCCTCTAGTGTTCAATATGTGCACTACAGCAACACCT
         AGGCAGCTAGAGCTGGCGTGAAGGCGGCTGAGACACTCAGGAGACTCCTCACCTGCACCG
         GGGCTATTCCCTCACTCCTTCACTTAGTAGCCAAATGATATAATTAGACACTGACAGTTT
         CTGGCTTGTCCAGTGAGCCCTAGGGAAGGAAGGAGAAGACCCGGGTGCTGTTGGAGGCAG
         [G,A]
         AGGTTGGATAGGGTGACCCCTACACCCCGACCCCCCTATGATCTCCATTTCCTTCATTCC
         AGGCTCTTCTCCAAGTGGCAAAGAACCTCTTCACCCACCTGGGTGAGTGCACTGTTCTCT
         CTGCCTGGCTGTGTGTGGGCATGGGGGCTGGCATTTGCAGAGGAGAGGCGGGAGGTCTTG
         GCAGCCTGGTCTCACCCTGCCTGGTCTTCTCCCTTCCCCAGATGACGTCTCTGTCCTGCT
         CCAGGAGATCATCACGGAGGCCAGAAACCTCAGCAACGCAGAGATGTGAGTGACTCTACC

99145    GTCTCTGTCCTGCTCCAGGAGATCATCACGGAGGCCAGAAACCTCAGCAACGCAGAGATG
         TGAGTGACTCTACCCAGGGGACAGGGCGAGAGAGGCTGTGGCCTTCAGTCCCCATCATCT
         CCTTTCCTGCCCCACCCACTTCCCTTTCTCTGCCTTCTGCGGGACTTCATCACCTTTTGA
```

FIGURE 3-83

```
         GGGATCCTTTATTTCATGCCTGTCTCCCTCGCTAGACTGTAGGCTCCAATACAGCAGGGA
         CAGGGCTGGCTTTGGATCCTCAGCTCCTATCACAGTGCCTGGCACATAGTAGGTGCTTCC
         [-,A]
         AAAAAAAAAAAAAACAAAACACTTGAATGGACACGTTTCTGGAGCCAGCCAGCCCTGAGCA
         GAGTGTCTTACCTTGGAGCACTCCTCCCAGGCCTCGGAAATCCGGCCTTTGCCTCCTTAT
         GGGACGTGAGGGCGATCAGAGGGGGTTGTCAGGCCCCAGAGGACCAAACCCCTCCCTCCA
         CAGCTGCTCTGTGTTCCTGCTGGATCAGAATGAGCTGGTGGCCAAGGTGTTCGACGGGGG
         CGTGGTGGATGATGAGGTGAGAGGGCGTGGAGGGAGTATGTGGCCCTAGGGGTGTCCGGG

99158    TCCAGGAGATCATCACGGAGGCCAGAAACCTCAGCAACGCAGAGATGTGAGTGACTCTAC
         CCAGGGGACAGGGCGAGAGAGGCTGTGGCCTTCAGTCCCCATCATCTCCTTTCCTGCCCC
         ACCCACTTCCCTTTCTCTGCCTTCTGCGGGACTTCATCACCTTTTGAGGGATCCTTTATT
         TCATGCCTGTCTCCCTCGCTAGACTGTAGGCTCCAATACAGCAGGGACAGGGCTGGCTTT
         GGATCCTCAGCTCCTATCACAGTGCCTGGCACATAGTAGGTGCTTCCAAAAAAAAAAAAA
         [A,-]
         CAAAACACTTGAATGGACACGTTTCTGGAGCCAGCCAGCCCTGAGCAGAGTGTCTTACCT
         TGGAGCACTCCTCCCAGGCCTCGGAAATCCGGCCTTTGCCTCCTTATGGGACGTGAGGGC
         GATCAGAGGGGGTTGTCAGGCCCCAGAGGACCAAACCCCTCCCTCCACAGCTGCTCTGTG
         TTCCTGCTGGATCAGAATGAGCTGGTGGCCAAGGTGTTCGACGGGGGCGTGGTGGATGAT
         GAGGTGAGAGGGCGTGGAGGGAGTATGTGGCCCTAGGGGTGTCCGGGAGTCCGCCGGCGG

99278    ACCCACTTCCCTTTCTCTGCCTTCTGCGGGACTTCATCACCTTTTGAGGGATCCTTTATT
         TCATGCCTGTCTCCCTCGCTAGACTGTAGGCTCCAATACAGCAGGGACAGGGCTGGCTTT
         GGATCCTCAGCTCCTATCACAGTGCCTGGCACATAGTAGGTGCTTCCAAAAAAAAAAAAA
         ACAAAACACTTGAATGGACACGTTTCTGGAGCCAGCCAGCCCTGAGCAGAGTGTCTTACC
         TTGGAGCACTCCTCCCAGGCCTCGGAAATCCGGCCTTTGCCTCCTTATGGGACGTGAGGG
         [C,A]
         GATCAGAGGGGGTTGTCAGGCCCCAGAGGACCAAACCCCTCCCTCCACAGCTGCTCTGTG
         TTCCTGCTGGATCAGAATGAGCTGGTGGCCAAGGTGTTCGACGGGGGCGTGGTGGATGAT
         GAGGTGAGAGGGCGTGGAGGGAGTATGTGGCCCTAGGGGTGTCCGGGAGTCCGCCGGCGG
         CGCTGGGGAGCGGCCCGAGGTTTAACAGTCCCCTCTGTGGCCGGGTCACTAACTTCTTCC
         TCTCGACTCCATCTCTGCTCCGGCAGAGCTATGAGATCCGCATCCCGGCCGATCAGGGCA

99411    CTATCACAGTGCCTGGCACATAGTAGGTGCTTCCAAAAAAAAAAAAAACAAAACACTTGA
         ATGGACACGTTTCTGGAGCCAGCCAGCCCTGAGCAGAGTGTCTTACCTTGGAGCACTCCT
         CCCAGGCCTCGGAAATCCGGCCTTTGCCTCCTTATGGGACGTGAGGGCGATCAGAGGGGG
         TTGTCAGGCCCCAGAGGACCAAACCCCTCCCTCCACAGCTGCTCTGTGTTCCTGCTGGAT
         CAGAATGAGCTGGTGGCCAAGGTGTTCGACGGGGGCGTGGTGGATGATGAGGTGAGAGGG
         [G,A,C]
         GTGGAGGGAGTATGTGGCCCTAGGGGTGTCCGGGAGTCCGCCGGCGGCGCTGGGGAGCGG
         CCCGAGGTTTAACAGTCCCCTCTGTGGCCGGGTCACTAACTTCTTCCTCTCGACTCCATC
         TCTGCTCCGGCAGAGCTATGAGATCCGCATCCCGGCCGATCAGGGCATCGCGGGACACGT
         GGCCGACCACGGGCCAGATCCTGAACATCCCTGACGCATATGCCCATCCGCTTTTCTACCG
         CGGCGTGGACGACAGCACCGGCTTCCGCACGCGCAACATCCTCTGCTTCCCCATCAAGAA

99744    GGAGTCCGCCGGCGGCGCTGGGGAGCGGCCCGAGGTTTAACAGTCCCCTCTGTGGCCGGG
         TCACTAACTTCTTCCTCTCGACTCCATCTCTGCTCCGGCAGAGCTATGAGATCCGCATCC
         CGGCCGATCAGGGCATCGCGGGACACGTGGCGACCACGGGCCAGATCCTGAACATCCCTG
         ACGCATATGCCCATCCGCTTTTCTACCGCGGCGTGGACGACAGCACCGGCTTCCGCACGC
         GCAACATCCTCTGCTTCCCCATCAAGAACGAGAACCAGGGTGCGCGTGGCGGCCCGGGCG
         [G,C]
         AGGGGCGGGGCCTGCGCCGGGCGGGGCGGGTCCGAGCGAGCGGGGGTGGCAACACTTCCC
         CACCGCCTCCGGCGTCCCGGAGCATAAGGGAGTCGGGTTCCATGCCTGGGACGTACGTAA
         CCTGCGGAAACTGCGAGGGCAGGTCCCGGCCGGATCCCTCCCTCCAACCGATCCCTCCCT
         CCACCGGTGGTTCCTTGCCCCTCTCCCTTCCCCAGAGGTCATCGGTGTGGCCGAGCTGGT
         GAACAAGATCAATGGGCCATGGTTCAGCAAGTTCGACGAGGACCTGGCGACGGCCTTCTC

99815    TTCCTCTCGACTCCATCTCTGCTCCGGCAGAGCTATGAGATCCGCATCCCGGCCGATCAG
```

FIGURE 3-84

```
         GGCATCGCGGGACACGTGGCGACCACGGGCCAGATCCTGAACATCCCTGACGCATATGCC
         CATCCGCTTTTCTACCGCGGCGTGGACGACAGCACCGGCTTCCGCACGCGCAACATCCTC
         TGCTTCCCCATCAAGAACGAGAACCAGGGTGCGCGTGGCGGCCCGGGCGGAGGGGCGGGG
         CCTGCGCCGGGCGGGGCGGGTCCGAGCGAGCGGGGGTGGCAACACTTCCCCACCGCCTCC
         [A,G]
         GCGTCCCGGAGCATAAGGGAGTCGGGTTCCATGCCTGGGACGTACGTAACCTGCGGAAAC
         TGCGAGGGCAGGTCCCGGCCGGATCCCTCCCTCCAACCGATCCCTCCCTCCACCGGTGGT
         TCCTTGCCCCTCTCCCTTCCCCAGAGGTCATCGGTGTGGCCGAGCTGGTGAACAAGATCA
         ATGGGCCATGGTTCAGCAAGTTCGACGAGGACCTGGCGACGGCCTTCTCCATCTACTGCG
         GCATCAGCATCGCCCATGTGAGGGCGGGGTTGGGAGTGGGGTGTGGGGTGATAGGGGGCG

100604   CCATGAGAAACTCCCGTTGTCAAAACCTCCTCTCTTCCCTGGAAGCAGTCTCAACCCAAG
         CCGAGTGCTTTTTTGGAAGTGCTGGGTCTCGGTGTCCAGGCCTACTGGCGCTCTGGCCTG
         GGAATCCAGCCCCAAGGTCCCTGACATGATCCCCTCCTTGCTTCTCCTTCCCTGCCATGG
         GCCTTGGGCTCCATCACTGAAGCCTGGATCAGGTGTGGGGGAGTGCAAAGGGCCAGACCA
         AATGCTGGGAGAACTTGATGAGGAGGAACCGGCGCGGGGGTCTGGATGAAAGTGGGGGTG
         [G,A]
         GGTCTTTACTGTGGACTGGAGCTTGAAGGTTTTGACTGGGGCCAGAATGGGACAGGAAGT
         GGGGTGTCTTTTTGACCCCTTCATCCCAGTCCTGGGCATTGCTAAATTTTCACAGCCACC
         TTCCTTGAGCCCCATCTTTCCCTCTTTCCCCTAGTCTCTCCTATACAAAAAAGTGAATGA
         GGCTCAGTATCGCAGCCACCTGGCCAATGAGATGATGATGTACCACATGAAGGTGAGGCT
         TGCAGAGACCTCTGGTCCTCCTCCCAGATTCCCCGGGGACCCAGGGCCAGGCAGGGCTTC

100878   CGGGGGTCTGGATGAAAGTGGGGGTGAGGTCTTTACTGTGGACTGGAGCTTGAAGGTTTT
         GACTGGGGCCAGAATGGGACAGGAAGTGGGGTGTCTTTTTGACCCCTTCATCCCAGTCCT
         GGGCATTGCTAAATTTTCACAGCCACCTTCCTTGAGCCCCATCTTTCCCTCTTTCCCCTA
         GTCTCTCCTATACAAAAAAGTGAATGAGGCTCAGTATCGCAGCCACCTGGCCAATGAGAT
         GATGATGTACCACATGAAGGTGAGGCTTGCAGAGACCTCTGGTCCTCCTCCCAGATTCCC
         [C,A,G,T]
         GGGGACCCAGGGCCAGGCAGGGCTTCCTGATCAATCTCTACTGAGGATGAGAGGATAGGC
         CCAGAGCCACAGCAGGCCTCCTGCCCTCCTTAGGGGCAGCTCCCACCCCTGCTTAGAGAC
         CTCTCCTCCAAGCTGCTTCTGAGCTCAGTCCCAAGGCTGGAAGTAGCCAGAGGAACCAGC
         CCAGGGAGTAATTGGTTCAGCCAGGTATTCCCCATGTTCAGGGAATAATTCCCATCTTGG
         GAATTACTGAGGGCTAGGAAGCTCACCCAGGACCCGTCCCCATGGCTTCCCTAGGTACAA

101440   CTCACCCAGGACCCGTCCCCATGGCTTCCCTAGGTACAATGCCCATGCAGCCCTGGGCAG
         TCTTAATTGCTGATAATCTATCCCATTCCCTACCCTGGGTCACAAAAGCTGGCTTAGTTC
         CATGTATATGGTAGTCGCTGTTCATTTGGACATTTCCTCTCACCTGTGTCCAAACCAGAG
         AGGCCCAGACCTTGTGAGTTGGATCAAAACTGTAGTAGGAAGAGTTAAGGTTAGAGAGTA
         GAAAGGTCTCCACAAAAGGAGGACTGCTACAGTTACTGTGTATGAAATGCTGCCATGGTT
         [A,T]
         GGGGGTGTCATGAAGGGGTGTTGTCGATCTTTGCCAAGGTTATGCTGTTACAGATAAAGG
         GTGGTCACCTGCAGGAAGGCGCGCGGGGTGGGCTGCAGGGCTGTGAGGGGAGGGTGGTGA
         TTTCCTGCCCAGTTACAGTCCACAGCGTGGTGGCCCAACTGTGGTACATTCTGGGTGACG
         GATCCCCCACCTGCCATGGGAATTTGAGGGTGAAGACACCAGATGGGGTGAAGGCTGTCT
         TCTAATGCTCTGGCTGGTCTCCTCTAGGTCTCCGACGATGAGTATACCAAACTTCTCCAT

101516   TCTATCCCATTCCCTACCCTGGGTCACAAAAGCTGGCTTAGTTCCATGTATATGGTAGTC
         GCTGTTCATTTGGACATTTCCTCTCACCTGTGTCCAAACCAGAGAGGCCCAGACCTTGTG
         AGTTGGATCAAAACTGTAGTAGGAAGAGTTAAGGTTAGAGAGTAGAAAGGTCTCCACAAA
         AGGAGGACTGCTACAGTTACTGTGTATGAAATGCTGCCATGGTTTGGGGTGTCATGAAG
         GGGTGTTGTCGATCTTTGCCAAGGTTATGCTGTTACAGATAAAGGGTGGTCACCTGCAGG
         [A,T,C,G]
         AGGCGCGCGGGGTGGGCTGCAGGGCTGTGAGGGGAGGGTGGTGATTTCCTGCCCAGTTAC
         AGTCCACAGCGTGGTGGCCCAACTGTGGTACATTCTGGGTGACGGATCCCCCACCTGCCA
         TGGGAATTTGAGGGTGAAGACACCAGATGGGGTGAAGGCTGTCTTCTAATGCTCTGGCTG
         GTCTCCTCTAGGTCTCCGACGATGAGTATACCAAACTTCTCCATGATGGGATCCAGCCTG
         TGGCTGCCATTGACTCCAATTTTGCAAGTTTCACCTATACCCCTCGTTCCCTGCCCGAGG
```

FIGURE 3-85

101994   CTGGTCTCCTCTAGGTCTCCGACGATGAGTATACCAAACTTCTCCATGATGGGATCCAGC
CTGTGGCTGCCATTGACTCCAATTTTGCAAGTTTCACCTATACCCCTCGTTCCCTGCCCG
AGGATGACACGTCCATGGTGAGTTGCTCTCCTCCACTTGACTGGCCAGGCCGAAGGTATG
TAGCCAGAGGCTTAAGTTAAATGCGCATCAAGAACTTCCTGGGAAGACAGAGTCATCAAG
GAAGGCTGTGGAGGGTCCCTCAGAGATGGAGGGGCTTGTAGTCTGCCATCAGGAAGCCAT
[A,G]
GGGCCTGCCCAGGGGCTAGAGGCTGGACTGGATGATCCCAAGGGCTGCTCTTGGACCAAC
CATGCCCAGGGCATGTGACCTCAGGGTTTGCATCCCTCCCAACCCTGTTTTTCTAACATT
TTGTGTGGGCTTGGTTTCAAGAGTTCTTAGTTCTTAGATCTCTAAAAATGCATAGCTCTG
AGAACGGTTGCTTCAACTATTTTGTGGTTCTCTAGTTTAGATGTAAGTTTCTAAGACTCC
AGATCTTGAGTGTGGAGCTTGAAGAAGGACCCAGGCAAGGGCCCTGTCTTGATACTGGCA

102173   GTAGCCAGAGGCTTAAGTTAAATGCGCATCAAGAACTTCCTGGGAAGACAGAGTCATCAA
GGAAGGCTGTGGAGGGTCCCTCAGAGATGGAGGGGCTTGTAGTCTGCCATCAGGAAGCCA
TGGGGCCTGCCCAGGGGCTAGAGGCTGGACTGGATGATCCCAAGGGCTGCTCTTGGACCA
ACCATGCCCAGGGCATGTGACCTCAGGGTTTGCATCCCTCCCAACCCTGTTTTTCTAACA
TTTTGTGTGGGCTTGGTTTCAAGAGTTCTTAGTTCTTAGATCTCTAAAAATGCATAGCTC
[T,C]
GAGAACGGTTGCTTCAACTATTTTGTGGTTCTCTAGTTTAGATGTAAGTTTCTAAGACTC
CAGATCTTGAGTGTGGAGCTTGAAGAAGGACCCAGGCAAGGGCCCTGTCTTGATACTGGC
AGCCCCTCTGATACCTCCCTCTGCCCTCTCCAGGCCATCCTGAGCATGCTGCAGGACATG
AATTTCATCAACAACTACAAAATTGACTGCCCGACCCTGGCCCGGTTCGTGCGCCCACAG
ACAGCCCCAGTCTTCGCCTCCCTCTTTCCTCTACTGTCACATCCATTGCCCCCGGCATTC

102239   CTGTGGAGGGTCCCTCAGAGATGGAGGGGCTTGTAGTCTGCCATCAGGAAGCCATGGGGC
CTGCCCAGGGGCTAGAGGCTGGACTGGATGATCCCAAGGGCTGCTCTTGGACCAACCATG
CCCAGGGCATGTGACCTCAGGGTTTGCATCCCTCCCAACCCTGTTTTTCTAACATTTTGT
GTGGGCTTGGTTTCAAGAGTTCTTAGTTCTTAGATCTCTAAAAATGCATAGCTCTGAGAA
CGGTTGCTTCAACTATTTTGTGGTTCTCTAGTTTAGATGTAAGTTTCTAAGACTCCAGAT
[G,A,C]
TTGAGTGTGGAGCTTGAAGAAGGACCCAGGCAAGGGCCCTGTCTTGATACTGGCAGCCCC
TCTGATACCTCCCTCTGCCCTCTCCAGGCCATCCTGAGCATGCTGCAGGACATGAATTTC
ATCAACAACTACAAAATTGACTGCCCGACCCTGGCCCGGTTCGTGCGCCCACAGACAGCC
CCAGTCTTCGCCTCCCTCTTTCCTCTACTGTCACATCCATTGCCCCCGGCATTCTGGAGA
GGATCTCTCTAAGGATGACTGGGGAGACCCAGTCTTATGGGGGTGGGGAGGATCCATGAA

102279   CCATCAGGAAGCCATGGGGCCTGCCCAGGGGCTAGAGGCTGGACTGGATGATCCCAAGGG
CTGCTCTTGGACCAACCATGCCCAGGGCATGTGACCTCAGGGTTTGCATCCCTCCCAACC
CTGTTTTTCTAACATTTTGTGTGGGCTTGGTTTCAAGAGTTCTTAGTTCTTAGATCTCTA
AAAATGCATAGCTCTGAGAACGGTTGCTTCAACTATTTTGTGGTTCTCTAGTTTAGATGT
AAGTTTCTAAGACTCCAGATCTTGAGTGTGGAGCTTGAAGAAGGACCCAGGCAAGGGCCC
[A,G,T]
GTCTTGATACTGGCAGCCCCTCTGATACCTCCCTCTGCCCTCTCCAGGCCATCCTGAGCA
TGCTGCAGGACATGAATTTCATCAACAACTACAAAATTGACTGCCCGACCCTGGCCCGGT
TCGTGCGCCCACAGACAGCCCCAGTCTTCGCCTCCCTCTTTCCTCTACTGTCACATCCAT
TGCCCCCGGCATTCTGGAGAGGATCTCTCTAAGGATGACTGGGGAGACCCAGTCTTATGG
GGGTGGGGAGGATCCATGAATGAGAAGCAATTCCTAGACACTGAACTGTCAATAAAGGCA

102458   AAAAATGCATAGCTCTGAGAACGGTTGCTTCAACTATTTTGTGGTTCTCTAGTTTAGATG
TAAGTTTCTAAGACTCCAGATCTTGAGTGTGGAGCTTGAAGAAGGACCCAGGCAAGGGCC
CTGTCTTGATACTGGCAGCCCCTCTGATACCTCCCTCTGCCCTCTCCAGGCCATCCTGAG
CATGCTGCAGGACATGAATTTCATCAACAACTACAAAATTGACTGCCCGACCCTGGCCCG
GTTCGTGCGCCCACAGACAGCCCCAGTCTTCGCCTCCCTCTTTCCTCTACTGTCACATCC
[A,T,CsG]
TTGCCCCCGGCATTCTGGAGAGGATCTCTCTAAGGATGACTGGGGAGACCCAGTCTTATG
GGGGTGGGGAGGATCCATGAATGAGAAGCAATTCCTAGACACTGAACTGTCAATAAAGGC
AAGAAATGAGGCAAGGCAAAGCCTGGAGGCAAGGCCGAGAGTGTGTAGCCAGAGGTTTAA

FIGURE 3-86

```
              GTTAGATGTGCATAGGAACTTCCTGCTAAGACAGAGTCATCAAGGAAGGCTGTGGAGGGT
              CCCTCAGGGATGGAGGGGACATGTAGTTTGCCATCATGGGGCCGTGATGGAGGAGGAGAG

102522    TTTCTAAGACTCCAGATCTTGAGTGTGGAGCTTGAAGAAGGACCCAGGCAAGGGCCCTGT
              CTTGATACTGGCAGCCCCTCTGATACCTCCCTCTGCCCTCTCCAGGCCATCCTGAGCATG
              CTGCAGGACATGAATTTTCATCAACAACTACAAAATTGACTGCCCGACCCTGGCCCGGTTC
              GTGCGCCCACAGACAGCCCCAGTCTTCGCCTCCCTCTTTCCTCTACTGTCACATCCATTG
              CCCCCGGCATTCTGGAGAGGATCTCTCTAAGGATGACTGGGGAGACCCAGTCTTATGGGG
              [G,T,CsA]
              TGGGGAGGATCCATGAATGAGAAGCAATTCCTAGACACTGAACTGTCAATAAAGGCAAGA
              AATGAGGCAAGGCAAAGCCTGGAGGCAAGGCCGAGAGTGTGTAGCCAGAGGTTTAAGTTA
              GATGTGCATAGGAACTTCCTGCTAAGACAGAGTCATCAAGGAAGGCTGTGGAGGGTCCCT
              CAGGGATGGAGGGGACATGTAGTTTGCCATCATGGGGCCGTGATGGAGGAGGAGAGGCTG
              AGGCCCCTCTTCTGCCCTCTTCCCTCCCCAGGTTCTGTTTGATGGTGAAGAAGGGCTAC

102687    ACCCTGGCCCGGTTCGTGCGCCCACAGACAGCCCCAGTCTTCGCCTCCCTCTTTCCTCTA
              CTGTCACATCCATTGCCCCCGGCATTCTGGAGAGGATCTCTCTAAGGATGACTGGGGAGA
              CCCAGTCTTATGGGGGTGGGGAGGATCCATGAATGAGAAGCAATTCCTAGACACTGAACT
              GTCAATAAAGGCAAGAAATGAGGCAAGGCAAAGCCTGGAGGCAAGGCCGAGAGTGTGTAG
              CCAGAGGTTTAAGTTAGATGTGCATAGGAACTTCCTGCTAAGACAGAGTCATCAAGGAAG
              [A,C,G]
              CTGTGGAGGGTCCCTCAGGGATGGAGGGGACATGTAGTTTGCCATCATGGGGCCGTGATG
              GAGGAGGAGAGGCTGAGGCCCCTCTTCTGCCCTCTTCCCTCCCCAGGTTCTGTTTGATG
              GTGAAGAAGGGCTACCGGGATCCCCCCTACCACAACTGGATGCACGCCTTTTCTGTCTCC
              CACTTCTGCTACCTGCTCTACAAGAACCTGGAGCTCACCAACTACCTCGAGTGAGTGGCT
              GCATCTCCCCCACATCTGGCAGCCACTGGGGTCCCCTTCCCTGGGACAGGGAAGCACCCC

103134    CTACCACAACTGGATGCACGCCTTTTCTGTCTCCCACTTCTGCTACCTGCTCTACAAGAA
              CCTGGAGCTCACCAACTACCTCGAGTGAGTGGCTGCATCTCCCCCACATCTGGCAGCCAC
              TGGGGTCCCCTTCCCTGGGACAGGGAAGCACCCCCTGTGTGTCAGGCACTTTACACGCAC
              TGCCTCATGGGATCTTCTTAGCCCCAGGGGACTAGAGGGGAAGGCTGTGAGCCCCATCTT
              CCAGGAGGGGCTTGCTCACAGCCAAGCAGCTAGTGAAGACTGAGCCTGATTTAAACCCGG
              [G,T]
              TCTGCTGGACTCCAAACCAGTGCTTCTTTCCAGGAAGGGAACCCAGGTGTTCCAACCTCC
              TGTCCCAGTGGCTCCTGGGCATGTCATCTCCTGTCTGTCCTCTTGGGGATTTAGGGAGGG
              AACTGTGGGCTGACCTCTTTTTTTTTCTCCTTTCTGCCTCTCAACCAGGGACATCGAGATC
              TTTGCCTTGTTTATTTCCTGCATGTGTCATGACCTGGACCACAGAGGCACAAACAACTCT
              TTCCAGGTGGCCTCGGTGAGACCCTGCCCTGCTCACAGTGGGGACCCTCCATGGGGTGTC

103152    CGCCTTTTCTGTCTCCCACTTCTGCTACCTGCTCTACAAGAACCTGGAGCTCACCAACTA
              CCTCGAGTGAGTGGCTGCATCTCCCCCACATCTGGCAGCCACTGGGGTCCCCTTCCCTGG
              GACAGGGAAGCACCCCCTGTGTGTCAGGCACTTTACACGCACTGCCTCATGGGATCTTCT
              TAGCCCCAGGGGACTAGAGGGGAAGGCTGTGAGCCCCATCTTCCAGGAGGGGCTTGCTCA
              CAGCCAAGCAGCTAGTGAAGACTGAGCCTGATTTAAACCCGGGTCTGCTGGACTCCAAAC
              [C,A]
              AGTGCTTCTTTCCAGGAAGGGAACCCAGGTGTTCCAACCTCCTGTCCCAGTGGCTCCTGG
              GCATGTCATCTCCTGTCTGTCCTCTTGGGGATTTAGGGAGGGAACTGTGGGCTGACCTCT
              TTTTTTTCTCCTTTCTGCCTCTCAACCAGGGACATCGAGATCTTTGCCTTGTTTATTTCC
              TGCATGTGTCATGACCTGGACCACAGAGGCACAAACAACTCTTTCCAGGTGGCCTCGGTG
              AGACCCTGCCCTGCTCACAGTGGGGACCCTCCATGGGGTGTCTTGGATCTCATCCTCTCC

103392    CAGCCAAGCAGCTAGTGAAGACTGAGCCTGATTTAAACCCGGGTCTGCTGGACTCCAAAC
              CAGTGCTTCTTTCCAGGAAGGGAACCCAGGTGTTCCAACCTCCTGTCCCAGTGGCTCCTG
              GGCATGTCATCTCCTGTCTGTCCTCTTGGGGATTTAGGGAGGGAACTGTGGGCTGACCTC
              TTTTTTTTCTCCTTTCTGCCTCTCAACCAGGGACATCGAGATCTTTGCCTTGTTTATTTC
              CTGCATGTGTCATGACCTGGACCACAGAGGCACAAACAACTCTTTCCAGGTGGCCTCGGT
              [G,A]
              AGACCCTGCCCTGCTCACAGTGGGGACCCTCCATGGGGTGTCTTGGATCTCATCCTCTCC
```

FIGURE 3-87

```
         CAGCCTGAATAGGGTGGGAGCGAGTGAGACCAGGAGCCAGGTTTAGACACAGGAGGAGGT
         TCCCCCAGGGTTTGCCCCTGGCTCTGAGATAGGGAGGAGGGGAGAAAGGTGGAAGGGCAG
         GACACTGCTCAGCCTAAAGCAGTGGCACTTGGATCCGGATGTGAGGAGTGACCACAGTTT
         TCCTGGGCTTTTCCAGAAATCTGTGCTGGCTGCGCTCTACAGCTCTGAGGGCTCCGTCAT

103436   CTGCTGGACTCCAAACCAGTGCTTCTTTCCAGGAAGGGAACCCAGGTGTTCCAACCTCCT
         GTCCCAGTGGCTCCTGGGCATGTCATCTCCTGTCTGTCCTCTTGGGGATTTAGGGAGGGA
         ACTGTGGGCTGACCTCTTTTTTTTCTCCTTTCTGCCTCTCAACCAGGGACATCGAGATCT
         TTGCCTTGTTTATTTCCTGCATGTGTCATGACCTGGACCACAGAGGCACAAACAACTCTT
         TCCAGGTGGCCTCGGTGAGACCCTGCCCTGCTCACAGTGGGGACCCTCCATGGGGTGTCT
         [G,T]
         GGATCTCATCCTCTCCCAGCCTGAATAGGGTGGGAGCGAGTGAGACCAGGAGCCAGGTTT
         AGACACAGGAGGAGGTTCCCCCAGGGTTTGCCCCTGGCTCTGAGATAGGGAGGAGGGGAG
         AAAGGTGGAAGGGCAGGACACTGCTCAGCCTAAAGCAGTGGCACTTGGATCCGGATGTGA
         GGAGTGACCACAGTTTTCCTGGGCTTTTCCAGAAATCTGTGCTGGCTGCGCTCTACAGCT
         CTGAGGGCTCCGTCATGGAGGTATCACTCTTCTGTCCCACCCCGTCCTTCTTCCCCTTTA

104138   CTCATTTTCCTGGAGTGGGCTTGGAAGGGTGCAGGTGCGGATGATAGCAAGGATTTGTGT
         TCAGCGTGTTTCCCTTTGGCTGCCTGGGAACACCCCATTCAGCCCCCTCCTGCCAAACTT
         GGGATGGGCTCCACTCCCATCACTTAGCGTCACCTTAGATTGTTTGGTTTGGGTCTGCCT
         ACCTCCTCGTGCACAAGGTCTGAGCCATTTCTGAGTTCCCTGCACTTGGCACAGGGCTTG
         GCACAGAGTAGGAGACACATTTCCAAGGTCACCTTGCCTCATGCTACTTCCCACAACACC
         [T,C]
         CTCCAGAGGCTGCCCCTGCTTGCACACCCCCAGAGACGAGGTTCTCTGTCTCTCTCCCAG
         GAGGCCTGGTGGCAGTGCTGGTTCTGCCCTCTGCCCCCCTGAGATAAGCTGCTCCTTTTC
         TGAGTGACAGCCCTTCAGCATCCGGAAATGGGGGCCTTGCCCTTGCCTCATCACTGCCTC
         TCCTTGTCAGCAAACAAATGTGTTCTGCATGATTTGGTGTCTAGGACTCCAAAGGATCAT
         TTCAAAAATGTTCCAGCTTTCAGGGACCCCAGAGCTTACCTTGTTGGGTCCCTGCATGTG

104175   CGGATGATAGCAAGGATTTGTGTTCAGCGTGTTTCCCTTTGGCTGCCTGGGAACACCCCA
         TTCAGCCCCCTCCTGCCAAACTTGGGATGGGCTCCACTCCCATCACTTAGCGTCACCTTA
         GATTGTTTGGTTTGGGTCTGCCTACCTCCTCGTGCACAAGGTCTGAGCCATTTCTGAGTT
         CCCTGCACTTGGCACAGGGCTTGGCACAGAGTAGGAGACACATTTCCAAGGTCACCTTGC
         CTCATGCTACTTCCCACAACACCTCTCCAGAGGCTGCCCCTGCTTGCACACCCCCAGAGA
         [C,T]
         GAGGTTCTCTGTCTCTCTCCCAGGAGGCCTGGTGGCAGTGCTGGTTCTGCCCTCTGCCCC
         CCTGAGATAAGCTGCTCCTTTTTCTGAGTGACAGCCCTTCAGCATCCGGAAATGGGGGCCT
         TGCCCTTGCCTCATCACTGCCTCTCCTTGTCAGCAAACAAATGTGTTCTGCATGATTTGG
         TGTCTAGGACTCCAAAGGATCATTTCAAAAATGTTCCAGCTTTCAGGGACCCCAGAGCTT
         ACCTTGTTGGGTCCCTGCATGTGACAGCTGAGGAGTCTGAGGCTCAGAGTGGTCTAGGGA

104560   GAGTGACAGCCCTTCAGCATCCGGAAATGGGGGCCTTGCCCTTGCCTCATCACTGCCTCT
         CCTTGTCAGCAAACAAATGTGTTCTGCATGATTTGGTGTCTAGGACTCCAAAGGATCATT
         TCAAAAATGTTCCAGCTTTCAGGGACCCCAGAGCTTACCTTGTTGGGTCCCTGCATGTGA
         CAGCTGAGGAGTCTGAGGCTCAGAGTGGTCTAGGGACTCACCCTGGGTCACACAGAGGGT
         TGAAACAGAGCTCAGAAAGGGAACTGGGGCCCCTGACTCCCCCTTTCTGACTGCTCTGCT
         [T,G]
         ACCTGGGGGCTGGAGCTGGACGAGGCCCCTGCTTCCTCTCTTGGGGTCAATGGTAAGGGA
         GCCCATCTGCCCCAGCTGGGCCCCCATCACTCCTCTCCCCCCAGAGGCACCACTTTGCTC
         AGGCCATCGCCATCCTCAACACCCACGGCTGCAACATCTTTGATCATTTCTCCCGGAAGG
         TGATGGGGTTGGGGGTGGGGTGGGGATTGAGGGGGAGCTGGGAGCTGGCTGGAGGTGGGA
         TAAGGAGCCAAGGAGTGGAGGCTCACTGGGATGGGCAAATGGGTGGGGGTGTCCAGTAGG

104688   GTTCCAGCTTTCAGGGACCCCAGAGCTTACCTTGTTGGGTCCCTGCATGTGACAGCTGAG
         GAGTCTGAGGCTCAGAGTGGTCTAGGGACTCACCCTGGGTCACACAGAGGGTTGAAACAG
         AGCTCAGAAAGGGAACTGGGGCCCCTGACTCCCCCTTTCTGACTGCTCTGCTTACCTGGG
         GGCTGGAGCTGGACGAGGCCCCTGCTTCCTCTCTTGGGGTCAATGGTAAGGGAGCCCATC
         TGCCCCAGCTGGGCCCCCATCACTCCTCTCCCCCCAGAGGCACCACTTTGCTCAGGCCAT
```

FIGURE 3-88

```
        [T,C]
        GCCATCCTCAACACCCACGGCTGCAACATCTTTGATCATTTCTCCCGGAAGGTGATGGGG
        TTGGGGGTGGGGTGGGGATTGAGGGGGAGCTGGGAGCTGGCTGGAGGTGGGATAAGGAGC
        CAAGGAGTGGAGGCTCACTGGGATGGGCAAATGGGTGGGGGTGTCCAGTAGGAGGGCATG
        ACACCCCTGCCCTCGCCTCAGGACTATCAGCGCATGCTGGATCTGATGCGGGACATCATC
        TTGGCCACAGACCTGGCCCACCATCTCCGCATCTTCAAGGACCTCCAGAAGATGGCTGAG

105118  GAGGCTCACTGGGATGGGCAAATGGGTGGGGGTGTCCAGTAGGAGGGCATGACACCCCTG
        CCCTCGCCTCAGGACTATCAGCGCATGCTGGATCTGATGCGGGACATCATCTTGGCCACA
        GACCTGGCCCACCATCTCCGCATCTTCAAGGACCTCCAGAAGATGGCTGAGGGTGACTGC
        TGTTAGCCCCAGTCCTTGGGGCTGGGGAGGAACAACCAGGGGAAGGATTTGCCAGGGGAG
        CATTCCCAGGGTGCAGACCCATCCCCTGCAACATCAACCCTTCTCTGGCTGCACGGCCCC
        [C,T]
        CCCAGGCAGACCCAGCACTGGCCCCTTGGCTCCCATCAAGGGTGCCCAATTCCCTGGACC
        GCTCTGGGTTGGGCCCTGGGAGCCTTGTCCTCAGAAGGGCAAAGAGGCTGGGCCCCGCTC
        CTTGACCCCATCCTCCCCTCAACAGTGGGCTACGACCGAAACAACAAGCAGCACCACAGA
        CTTCTCCTCTGCCTCCTCATGACCTCCTGTGACCTCTCTGACCAGACCAAGGGCTGGAAG
        ACTACGAGAAAGATCGCGGTAGGTGTAGTCCTCCCTGGGAAGGCACAGGCTGCCCACCCT

105179  CCTCGCCTCAGGACTATCAGCGCATGCTGGATCTGATGCGGGACATCATCTTGGCCACAG
        ACCTGGCCCACCATCTCCGCATCTTCAAGGACCTCCAGAAGATGGCTGAGGGTGACTGCT
        GTTAGCCCCAGTCCTTGGGGCTGGGGAGGAACAACCAGGGGAAGGATTTGCCAGGGGAGC
        ATTCCCAGGGTGCAGACCCATCCCCTGCAACATCAACCCTTCTCTGGCTGCACGGCCCCC
        CCCAGGCAGACCCAGCACTGGCCCCTTGGCTCCCATCAAGGGTGCCCAATTCCCTGGACC
        [G,A]
        CTCTGGGTTGGGCCCTGGGAGCCTTGTCCTCAGAAGGGCAAAGAGGCTGGGCCCCGCTCC
        TTGACCCCATCCTCCCCTCAACAGTGGGCTACGACCGAAACAACAAGCAGCACCACAGAC
        TTCTCCTCTGCCTCCTCATGACCTCCTGTGACCTCTCTGACCAGACCAAGGGCTGGAAGA
        CTACGAGAAAGATCGCGGTAGGTGTAGTCCTCCCTGGGAAGGCACAGGCTGCCCACCCTG
        CCCAGCTTTGGGTGCCCCCTGTGCCTGAATACCCTCTCTCTGCTCAGCTCAGCCTGGCTG

106026  ATAGAGGATGTGATGAGAGTGTTGGCCTTTCAGGAGCTGATCTACAAAGAATTCTTCTCC
        CAGGGAGACCTGGTATGTGTGGAGTGACCCCAGGATGTCCAGGATGGGGGAGGGTTCCTG
        GCCTGGGACAGGGAGGGCTTGAACTAGCCTGACCCTGGTACCCGATGGAGGAATGAGAGG
        GACAGGCCTGACGACTCGATGCCTGCAGGAGAAGGCCATGGGCAACAGGCCGATGGAGAT
        GATGGACCGGGAGAAGGCCTATATCCCTGAGCTGCAAATCAGCTTCATGGAGCACATTGC
        [A,G]
        ATGCCCATCTACAAGTGAGTGAGCTCATGGGGACAAGCTGCACCCTGCACAGAGAGGGTA
        GGCTGGAGTGGGGACATCACAGGAAACACAGGTGCTGAGATTGGCCTGGCCCAGCTCCAA
        CTGATTCATCCCCTTGCCTCTGGGCATAACTGTCTCCCGCTGTGCCCCTCAGTGGGTCCT
        TCACTTCATCCTTGGTCCTCAGTGGAAAGAGACCATCATGCTTTCCTAGGTGTCCTCCTC
        TGTCTCACATTCTTGTGGAAGTTCTTGTTTTTTTTGAGATGGAGTCTCACTCTGTTGCCC

106141  TCCTGGCCTGGGACAGGGAGGGCTTGAACTAGCCTGACCCTGGTACCCGATGGAGGAATG
        AGAGGGACAGGCCTGACGACTCGATGCCTGCAGGAGAAGGCCATGGGCAACAGGCCGATG
        GAGATGATGGACCGGGAGAAGGCCTATATCCCTGAGCTGCAAATCAGCTTCATGGAGCAC
        ATTGCAATGCCCATCTACAAGTGAGTGAGCTCATGGGGACAAGCTGCACCCTGCACAGAG
        AGGGTAGGCTGGAGTGGGGACATCACAGGAAACACAGGTGCTGAGATTGGCCTGGCCCAG
        [C,G]
        TCCAACTGATTCATCCCCTTGCCTCTGGGCATAACTGTCTCCCGCTGTGCCCCTCAGTGG
        GTCCTTCACTTCATCCTTGGTCCTCAGTGGAAAGAGACCATCATGCTTTCCTAGGTGTCC
        TCCTCTGTCTCACATTCTTGTGGAAGTTCTTGTTTTTTTTGAGATGGAGTCTCACTCTGT
        TGCCCAGGCTGGAGTGCAATGGCACGATCTTGGCTCACTGCAACCTCCCCCTCCTGGGTT
        CAAGCGATTCTCCTGCCTCAGCCTCCCAAGTAGCTGGGATTACAGGCATGCACCACCACG

106474  AACTGTCTCCCGCTGTGCCCCTCAGTGGGTCCTTCACTTCATCCTTGGTCCTCAGTGGAA
        AGAGACCATCATGCTTTCCTAGGTGTCCTCCTCTGTCTCACATTCTTGTGGAAGTTCTTG
        TTTTTTTTGAGATGGAGTCTCACTCTGTTGCCCAGGCTGGAGTGCAATGGCACGATCTTG
```

FIGURE 3-89

```
          GCTCACTGCAACCTCCCCCTCCTGGGTTCAAGCGATTCTCCTGCCTCAGCCTCCCAAGTA
          GCTGGGATTACAGGCATGCACCACCACGCCCAGCTAATTTTGTATTTTTAGTAGAGATGG
          [G,A]
          GCTTCACCATTTTGGTCAGGCTGGTCTTGAACTCCTGACTTCAGGTGATCCACACACCTC
          GGCATCTCTGAGTGTTGGGATTACAGGCGTGAGCTACCGTACCTGGCCCTTGTGGAAATT
          CTATTTGTTGTGTAGCCCTAGTCTTTCTTGCTGCCCATGGTCTGATTTCTGGCCTCTCAC
          CCTCTGCCCCCATGCACCCGCAGGCTGTTGCAGGACCTGTTCCCCAAAGCGGCAGAGCTG
          TACGAGCGCGTGGCCTCCAACCGTGAGCACTGGACCAAGGTGTCCCACAAGTTCACCATC

106717    GGGATTACAGGCATGCACCACCACGCCCAGCTAATTTTGTATTTTTAGTAGAGATGGGGC
          TTCACCATTTTGGTCAGGCTGGTCTTGAACTCCTGACTTCAGGTGATCCACACACCTCGG
          CATCTCTGAGTGTTGGGATTACAGGCGTGAGCTACCGTACCTGGCCCTTGTGGAAATTCT
          ATTTGTTGTGTAGCCCTAGTCTTTCTTGCTGCCCATGGTCTGATTTCTGGCCTCTCACCC
          TCTGCCCCCATGCACCCGCAGGCTGTTGCAGGACCTGTTCCCCAAAGCGGCAGAGCTGTA
          [T,C]
          GAGCGCGTGGCCTCCAACCGTGAGCACTGGACCAAGGTGTCCCACAAGTTCACCATCCGC
          GGCCTCCCAAGTAACAACTCGCTGGACTTCCTGGATGAGGAGTACGAGGTGCCTGATCTG
          GATGGCACTAGGGCCCCCATCAATGGCTGCTGCAGCCTTGATGCTGAGTGATCCCCTCCA
          GGGACACTTCCCTGCCCAGGCCACCTCCCACAGCCCTCCACTGGTCTGGCCAGATGCACT
          GGGAACAGAGCCACGGGTCCTGGGTCCTAGACCAGGACTTCCTGTGTGACCCTGGACAAG

107099    CTGGACTTCCTGGATGAGGAGTACGAGGTGCCTGATCTGGATGGCACTAGGGCCCCCATC
          AATGGCTGCTGCAGCCTTGATGCTGAGTGATCCCCTCCAGGGACACTTCCCTGCCCAGGC
          CACCTCCCACAGCCCTCCACTGGTCTGGCCAGATGCACTGGGAACAGAGCCACGGGTCCT
          GGGTCCTAGACCAGGACTTCCTGTGTGACCCTGGACAAGTACTACCTTCCTGGGCCTCAG
          CTTTCTCGTCTGTATAATGGAAGCAAGACTTCCAACCTCACGGAGACTTTGTAATTTGTT
          [C,T]
          TCTGAGAGCACAGGGGTGACCAATGAGCAGTGGGCCCTACTCTGCACCTCTGACCACACC
          TTGGCAAGTCTTTCCCAAGCCATTCTTTGTCTGAGCAGCTTGATGGTTTCTCCTTGCCCC
          ATTTCTGCCCCACCAGATCTTTGCTCCTTTCCCTTTGAGGACTCCCACCCTTTGGGGTCT
          CCAGGATCCTCATGGAAGGGGAAGGTGAGACATCTGAGTGAGCAGAGTGTGGCATCTTGG
          AAACAGTCCTTAGTTCTGTGGGAGGACTAGAAACAGCCGCGGGCGAAGGCCCCCTGAGG

107322    ACCTTCCTGGGCCTCAGCTTTCTCGTCTGTATAATGGAAGCAAGACTTCCAACCTCACGG
          AGACTTTGTAATTTGTTCTCTGAGAGCACAGGGGTGACCAATGAGCAGTGGGCCCTACTC
          TGCACCTCTGACCACACCTTGGCAAGTCTTTCCCAAGCCATTCTTTGTCTGAGCAGCTTG
          ATGGTTTCTCCTTGCCCCATTTCTGCCCCACCAGATCTTTGCTCCTTTCCCTTTGAGGAC
          TCCCACCCTTTGGGGTCTCCAGGATCCTCATGGAAGGGGAAGGTGAGACATCTGAGTGAG
          [C,G]
          AGAGTGTGGCATCTTGGAAACAGTCCTTAGTTCTGTGGGAGGACTAGAAACAGCCGCGGG
          GCGAAGGCCCCCTGAGGACCACTACTATACTGATGGTGGGATTGGGACCTGGGGGATACA
          GGGGCCCCAGGAAGAAGCTGCCAGAGGGGCAGCTCAGTGCTCTGCAGAGAGGGGCCCTGG
          GGAGAAGCAGGATGGGATTGATGGGCAGGAGGGATCCCCGCACTGGGAGACAGGCCCAGG
          TATGAATGAGCCAGCCATGCTTCCTCCTGCCTGTGTGACGCTGGGCGAGTCTCTTCCCCT

108611    GTGGAGGCTAAGGGGTGGGTGGCAGATGAGAAGGCCTGGCCATGGAGCAGTGATGGGACA
          TGTTGGCTGGCAGAGATTGTAGAATAGAGGAAAAACAAAGGTTGAGGCAAGCAGGCAGGC
          TGCCTGGAGGAGGTAGCCTGGAGCTTGTCCTAGACCCTCCCAGCGCTGGCCTGCCCTGGT
          CATGAGTGCCCATACGGCGAGGGCCTAGGCCTCTGAACTCTGTTTCTAGCTGCAGTGATG
          CCTGGCTGTGTCCCAGGAAGTCCCACATCCCAGTTACTCTGAGTCCTGCCGAAGGTGCAC
          [G,C]
          CCTGAGTCAGACTCCACACCAGATCCAGCCCCGGGTTGTGTCTGAGGAGTTGCGTCTGTT
          CCTCTGCATGAGAGTGTTTACTTCCGCCCAGTCCAAGATGGGCAGACTGCAGGTTGGGGC
          TACGCGGAGGCTCTGCCTGGCACAGTCTCCAGACCCTGTCCCCGACTTGCCTACCCCCCT
          CTGAGCTCCTCTCCGTGTTCATCTCTTCCTGGTCAGTAAAGGTTGATGTGTTAAGAGGGT
          GGGCACTGGGGTCTCCTTTCTTGGTGGGAGCAGGAAGGAGATGGACAGGGCCATCCTGTG

108664    TGGGACATGTTGGCTGGCAGAGATTGTAGAATAGAGGAAAAACAAAGGTTGAGGCAAGCA
```

FIGURE 3-90

```
          GGCAGGCTGCCTGGAGGAGGTAGCCTGGAGCTTGTCCTAGACCCTCCCAGCGCTGGCCTG
          CCCTGGTCATGAGTGCCCATACGGCGAGGGCCTAGGCCTCTGAACTCTGTTTCTAGCTGC
          AGTGATGCCTGGCTGTGTCCCAGGAAGTCCCACATCCCAGTTACTCTGAGTCCTGCCGAA
          GGTGCACGCCTGAGTCAGACTCCACACCAGATCCAGCCCCGGGTTGTGTCTGAGGAGTTG
          [A,G,C]
          GTCTGTTCCTCTGCATGAGAGTGTTTACTTCCGCCCAGTCCAAGATGGGCAGACTGCAGG
          TTGGGGCTACGCGGAGGCTCTGCCTGGCACAGTCTCCAGACCCTGTCCCCGACTTGCCTA
          CCCCCCTCTGAGCTCCTCTCCGTGTTCATCTCTTCCTGGTCAGTAAAGGTTGATGTGTTA
          AGAGGGTGGGCACTGGGGTCTCCTTTCTTGGTGGGAGCAGGAAGGAGATGGACAGGGCCA
          TCCTGTGACCATCAGCCATTGCCAGCTTTGCCTTTGGGACCACAGAGCCCATCTGCTTCC

109160    GGGTCTCCTTTCTTGGTGGGAGCAGGAAGGAGATGGACAGGGCCATCCTGTGACCATCAG
          CCATTGCCAGCTTTGCCTTTGGGACCACAGAGCCCATCTGCTTCCTCTGCAGCTCCCCCT
          GCCCCACTAGCCTGTCTGGGTTTGGAATCTGCTCCTCTGGCTGAATGGTCTCCAGGTTTC
          CAGCTTCCCTTAGCGTCATGGGGCTCCAGGCTCCTCCCATTCCCAGCTCCTGCTGTGGGC
          TCCCCAAGTCCGTCTCTATCCTCTCACAGCACAGGACCCAGGCTTGGCCAGTGGGTCCCC
          [T,C,G]
          GGTGGGGGTGGGAGTGGTCAGTTTGTGGCCCACGGCCAATAAGAGATGGCTATTCTAATG
          GTGCCTGGCTGACCCCAGGGTCACTGTGGGCTGATGTAGCTGCTCTTCTGCCTGACCCCT
          GACCCTGAGTGTGTGTGCGTGTTCCTCTTCCACAACTCTTCAGGCAAAGAGAACCTTGAC
          CCTGCATCTGTCTGTCCCCAGCCCAGCCCTCCTTTGAGGCTCATGCTGTGACACATCCCT
          GTTTTTCACCAAATGGAGGGAACAACCACAGATATTTCCTTGTGCACGCAGGACCCTGTG

110512    AGAGGACAGATGGGAGGAGGCTCTGCACAGAGCCTGAGGACAGCCCTCACCAGGTTACAG
          AACACAAGGCTTGACCCCATTGGCTTCCTGTAGCTGTCCTGCTCTCCCAACTTAATGGTT
          TCATTTTGCATTTTATTTAAATTTCACAATGATTCTAGCAGATACCATTAGTCTATTCTG
          CAGCCAAGTTGTCTAAGGTTTGGAGAGGTTAAGTAATGCACCAAGGTTAGGATTTTGAGCC
          CTACCTGTCTGATTCCCCTCCGAGAGCTGTCTGATTCCTTTCTCCTCCTCTGGGATAGGG
          [G,A]
          AAGGAGACTCAGAAGGACGGGGTCTCCATCTTCAGTCTTTGCAAGACTATTGTAGGGCAT
          TGGGATGGTGAGCACAAAGTGGGTTGAAGCCCCAGAGAAAGAGCTGAGAGCTGGGATCAA
          CTGTGTGTGTGCATGTGTGTGTCTGTGTGTGTGTGAGTTGGAGTAGGGGGCAGGGAGAAA
          AGAGTGGGGTGGTGGTGGCTTGTAGTGCAGCTCAGGGCCACCAGGTGGTGTCCAGCCCTC
          GCTGTCCTCACCTCCCCAGAGGTCAGAGAAGGATATGGGAGGGGGTGGGGTGGGGTGAGG

110746    TGAGCCCTACCTGTCTGATTCCCCTCCGAGAGCTGTCTGATTCCTTTCTCCTCCTCTGGG
          ATAGGGGAAGGAGACTCAGAAGGACGGGGTCTCCATCTTCAGTCTTTGCAAGACTATTGT
          AGGGCATTGGGATGGTGAGCACAAAGTGGGTTGAAGCCCCAGAGAAAGAGCTGAGAGCTG
          GGATCAACTGTGTGTGTGCATGTGTGTGTCTGTGTGTGTGTGAGTTGGAGTAGGGGGCAG
          GGAGAAAAGAGTGGGGTGGTGGTGGCTTGTAGTGCAGCTCAGGGCCACCAGGTGGTGTCC
          [A,G]
          GCCCTCGCTGTCCTCACCTCCCCAGAGGTCAGAGAAGGATATGGGAGGGGGTGGGGTGGG
          GTGAGGGGGACGCGGCGGGACGGGGGGGACGGTGGTTGGTAGTCTCACTCCTGTCCATT
          CACCCTACAGGTTGAGTATCCCTTATCCAAAATGCTTGGGGCCAGAAGTGTCTCAGATTTA
          AGATTTTTTTCGGATTTTGGAATATTTGCATATACATAATGAGATATCTTGGGAATGAGA
          CCCCAGGCTAAACAGGAAATTCATTTATGTTTTATATACACACAGCCTGAAGCAGTTTTA

110781    TCTGATTCCTTTCTCCTCCTCTGGGATAGGGGAAGGAGACTCAGAAGGACGGGGTCTCCA
          TCTTCAGTCTTTGCAAGACTATTGTAGGGCATTGGGATGGTGAGCACAAAGTGGGTTGAA
          GCCCCAGAGAAAGAGCTGAGAGCTGGGATCAACTGTGTGTGTGCATGTGTGTGTCTGTGT
          GTGTGTGAGTTGGAGTAGGGGGCAGGGAGAAAAGAGTGGGGTGGTGGTGGCTTGTAGTGC
          AGCTCAGGGCCACCAGGTGGTGTCCAGCCCTCGCTGTCCTCACCTCCCCAGAGGTCAGAG
          [A,T]
          AGGATATGGGAGGGGGTGGGGTGGGGTGAGGGGGACGCGGCGGGACGGGGGGGACGGTG
          GTTGGTAGTCTCACTCCTGTCCATTCACCCTACAGGTTGAGTATCCCTTATCCAAAATGCT
          TGGGGCCAGAAGTGTCTCAGATTTAAGATTTTTTTCGGATTTTGGAATATTTGCATATAC
          ATAATGAGATATCTTGGGAATGAGACCCCAGGCTAAACAGGAAATTCATTTATGTTTTAT
          ATACACACAGCCTGAAGCAGTTTTATATAATATTTTGAATAATT
```

FIGURE 3-91

Multiple alignment of isoform1 (110005670832006_pep), human PDE2A3 (gi4505657_pep) and bovine PDE2A1 (gi116569_pep).

```
Name: 110005670832006_pep   Len:  943   Check: 2306   Weight: 1.00
Name: gi4505657_pep         Len:  943   Check:  362   Weight: 1.00
Name: gi116569_pep          Len:  943   Check: 5464   Weight: 1.00

//
                    1                                                      50
110005670832   ~~~~~~~~~~ ~~~~~~~~~~ ~~MRRQPAAS LDPLAKEPGP PGSRDDRLED
gi4505657_pe   MGQACGHSIL CRSQQYPAAR PAEPRGQQVF LKP.DEPPPP PQPCADSLQD
gi116569_pep   ~~~~~~~~~~ ~~~~~~~~~~ ~~MRRQPAAS RDLFAQEPVP PGSGDGALQD 51                                                     100
110005670832   ALLSLGSVID ISGLQRAVKE ALSAVLPRVE TVYTYLLDGE SQLVCEDPPH
gi4505657_pe   ALLSLGSVID ISGLQRAVKE ALSAVLPRVE TVYTYLLDGE SQLVCEDPPH
gi116569_pep   ALLSLGSVID VAGLQQAVKE ALSAVLPKVE TVYTYLLDGE SRLVCEEPPH 101                                                     150
110005670832   ELPQEGKVRE AIISQKRLGC NGLGFSDLPG KPLARLVAPL APDTQVLVMP
gi4505657_pe   ELPQEGKVRE AIISQKRLGC NGLGFSDLPG KPLARLVAPL APDTQVLVMP
gi116569_pep   ELPQEGKVRE AVISRKRLGC NGLGPSDLPG KPLARLVAPL APDTQVLVIP 151                                                     200
110005670832   LADKEAGAVA AVILVHCGQL SDNEEWSLQA VEKHTLVALR RVQVLQQRGP
gi4505657_pe   LADKEAGAVA AVILVHCGQL SDNEEWSLQA VEKHTLVALR RVQVLQQRGP
gi116569_pep   LVDKEAGAVA AVILVHCGQL SDNEEWSLQA VEKHTLVALK RVQALQQRES 201                                                     250
110005670832   REAPRAVQNP PEGTAEDQKG GAAYIDRDRK ILQLCGELYD LDASSLQLKV
gi4505657_pe   REAPRAVQNP PEGTAEDQKG GAAYIDRDRK ILQLCGELYD LDASSLQLKV
gi116569_pep   SVAPEATQNP PEEAAGDQKG GVAYTNQDRK ILQLCGELYD LDASSLQLKV 251                                                     300
110005670832   LQYLQQETRA SRCCLLLVSE DNLQLSCKVI GDKVLGEEVS FPL.TGCLGQ
gi4505657_pe   LQYLQQETRA SRCCLLLVSE DNLQLSCKVI GDKVLGEEVS FPL.TGCLGQ
gi116569_pep   LQYLQQETQA SRCCLLLVSE DNLQLSCKVI GDKVLEEEIS FPLTTGRLGQ 301                                                     350
110005670832   WEDKKSIQL KDLTSEDVQQ LQSMLGCELQ AMLCVPVISR ATDQVVALAC
gi4505657_pe   WEDKKSIQL KDLTSEDVQQ LQSMLGCELQ AMLCVPVISR ATDQVVALAC
gi116569_pep   WEDKKSIQL KDLTSEDMQQ LQSMLGCEVQ AMLCVPVISR ATDQVVALAC 351                                                     400
110005670832   AFNKLEGDLF TDEDEHVIQH CFHYTSTVLT STLAFQKEQK LKCECQALLQ
gi4505657_pe   AFNKLEGDLF TDEDEHVIQH CFHYTSTVLT STLAFQKEQK LKCECQALLQ
gi116569_pep   AFNKLGGDLF TDQDEHVIQH CFHYTSTVLT STLAFQKEQK LKCECQALLQ 401                                                     450
110005670832   VAKNLFTHLD DVSVLLQEII TEARNLSNAE ICSVFLLDQN ELVAKVFDGG
gi4505657_pe   VAKNLFTHLD DVSVLLQEII TEARNLSNAE ICSVFLLDQN ELVAKVFDGG
gi116569_pep   VAKNLFTHLD DVSVLLQEII TEARNLSNAE ICSVFLLDQN ELVAKVFDGG 451                                                     500
110005670832   WDDESYEIR IPADQGIAGH VATTGQILNI PDAYAHPLFY RGVDDSTGFR
gi4505657_pe   WDDESYEIR IPADQGIAGH VATTGQILNI PDAYAHPLFY RGVDDSTGFR
gi116569_pep   WEDESYEIR IPADQGIAGH VATTGQILNI PDAYAHPLFY RGVDDSTGFR
```

FIGURE 3-92

```
                501                                                          550
110005670832    TRNILCFPIK  NENQEVIGVA  ELVNKINGPW  FSKFDEDLAT  AFSIYCGISI
gi4505657_pe    TRNILCFPIK  NENQEVIGVA  ELVNKINGPW  FSKFDEDLAT  AFSIYCGISI
gi116569_pep    TRNILCFPIK  NENQEVIGVA  ELVNKINGPW  FSKFDEDLAT  AFSIYCGISI 551                                                          600
110005670832    AHSLLYKKVN  EAQYRSHLAN  EMMMYHMKVS  DDEYTKLLHD  GIQPVAAIDS
gi4505657_pe    AHSLLYKKVN  EAQYRSHLAN  EMMMYHMKVS  DDEYTKLLHD  GIQPVAAIDS
gi116569_pep    AHSLLYKKVN  EAQYRSHLAN  EMMMYHMKVS  DDEYTKLLHD  GIQPVAAIDS 601                                                          650
110005670832    NFASFTYTPR  SLPEDDTSMA  ILSMLQDMNF  INNYKIDCPT  LARFCLMVKK
gi4505657_pe    NFASFTYTPR  SLPEDDTSMA  ILSMLQDMNF  INNYKIDCPT  LARFCLMVKK
gi116569_pep    NFASFTYTPR  SLPEDDTSMA  ILSMLQDMNF  INNYKIDCPT  LARFCLMVKK 651                                                          700
110005670832    GYRDPPYHNW  MHAFSVSHFC  YLLYKNLELT  NYLEDIEIFA  LFISCMCHDL
gi4505657_pe    GYRDPPYHNW  MHAFSVSHFC  YLLYKNLELT  NYLEDIEIFA  LFISCMCHDL
gi116569_pep    GYRDPPYHNW  MHAFSVSHFC  YLLYKNLELT  NYLEDMEIFA  LFISCMCHDL 701                                                          750
110005670832    DHRGTNNSFQ  VASKSVLAAL  YSSEGSVMER  HHFAQAIAIL  NTHGCNIFDH
gi4505657_pe    DHRGTNNSFQ  VASKSVLAAL  YSSEGSVMER  HHFAQAIAIL  NTHGCNIFDH
gi116569_pep    DHRGTNNSFQ  VASKSVLAAL  YSSEGSVMER  HHFAQAIAIL  NTHGCNIFDH 751                                                          800
110005670832    FSRKDYQRML  DLMRDIILAT  DLAHHLRIFK  DLQKMAEVGY  DRNNKQHHRL
gi4505657_pe    FSRKDYQRML  DLMRDIILAT  DLAHHLRIFK  DLQKMAEVGY  DRNNKQHHRL
gi116569_pep    FSRKDYQRML  DLMRDIILAT  DLAHHLRIFK  DLQKMAEVGY  DRTNKQHHSL 801                                                          850
110005670832    LLCLLMTSCD  LSDQTKGWKT  TRKIAELIYK  EFFSQGDLEK  AMGNRPMEMM
gi4505657_pe    LLCLLMTSCD  LSDQTKGWKT  TRKIAELIYK  EFFSQGDLEK  AMGNRPMEMM
gi116569_pep    LLCLLMTSCD  LSDQTKGWKT  TRKIAELIYK  EFFSQGDLEK  AMGNRPMEMM 851                                                          900
110005670832    DREKAYIPEL  QISFMEHIAM  PIYKLLQDLF  PKAAELYERV  ASNREHWTKV
gi4505657_pe    DREKAYIPEL  QISFMEHIAM  PIYKLLQDLF  PKAAELYERV  ASNREHWTKV
gi116569_pep    DREKAYIPEL  QISFMEHIAM  PIYKLLQDLF  PKAAELYERV  ASNREHWTKV 901                                          943
110005670832    SHKFTIRGLP  SNNSLDFLDE  EYEVPDLDGT  RAPINGCCSL  DAE
gi4505657_pe    SHKFTIRGLP  SNNSLDFLDE  EYEVPDLDGT  RAPINGCCSL  DAE
gi116569_pep    SHKFTIRGLP  SNNSLDFLDE  EYEVPDLDGA  RAPINGCCSL  DAE
```

FIGURE 3-93

ISOLATED HUMAN PHOSPHODIESTERASE PROTEINS, NUCLEIC ACID MOLECULES ENCODING HUMAN PHOSPHODIESTERASE PROTEINS, AND USES THEREOF

RELATED APPLICATIONS

The present application is a divisional of U.S. application Ser. No. 09/754,250, filed on Jan. 5, 2001, and issued on Apr. 23, 2002 as U.S. Pat. No. 6,376,225.

FIELD OF THE INVENTION

The present invention is in the field of phosphodiesterase proteins that are related to cGMP-stimulated 3',5'-cyclic nucleotide phosphodiesterase 2A (PDE2A), recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods. In particular, the phosphodiesterase protein provided by the present invention is a novel alternative splice form of PDE2A.

BACKGROUND OF THE INVENTION

Phosphodiesterases

In general, phosphodiesterases ("PDEs") catalyze the hydrolysis of a phosphodiester bond. Specific classes of phosphodiesterases include those catalyzing the degradation of cyclilc monophosphates.

The signaling pathways regulated by PDEs include the transduction of photon capture in the outer segment of a photoreceptor as well as changes in neurotransmitter release from its inner segment. PDEs also regulate the aldosterone production by atrial natriuretic peptide and platelet aggregation by endothelial relaxation factor.

Experimental data have demonstrated the role of phosphodiesterases in a range of diseases, including inflammatory diseases such as asthma, chronic obstructive pulmonary disease, rheumatoid arthritis and atopy. Drugs that selectively inhibit individual PDE isozymes have a wide variety of different effects on an animals, suggesting specific roles for most of the different PDEs.

Experimental evidence indicates the existence of several related gene families coding for different phosphodiesterases, and that each of these families contain more than one gene. Furthermore, each gene product is differentially spliced in different tissues to yield different isozymes. Isolation of cDNAs for many of the isozymes has allowed a series of structure/function studies to be initiated. Several of these isozymes are regulated by phosphorylation/dephosphorylation mechanisms.

Over 30 phosphodiesterases have been identified. Categories of phosphodiesterases include seven major classes. Class I phosphodiesterases include calmodulin-dependent phosphodiesterases which are expressed in tissues such as the brain, testes, sperm, coronary artery, lung, heart, and pancreas. Class II phosphodiesterases include cGMP-stimulated phosphodiesterases which are expressed in tissues such as the brain, adrenal gland, and the heart. Class III phosphodiesterases include cGMP-inhibited phosphodiesterases expressed in tissues such as T-lymphocytes, macrophages, platelets, smooth muscle, heart, and adipose tissue. Class IV phosphodiesterases include cAMP-specific phosphodiesterases which are expressed in tissues such as monocytes, leukocytes, and the central nervous system. Class V phosphodiesterases include cGMP-specific phosphodiesterases which are expressed in tissues such as lung, smooth muscle, platelets, and the aorta. Class VI phosphodiesterases include photoreceptor-specific phosphodiesterases expressed in the retina. Class VII phosphodiesterases include high affinity cAMP-specific phosphodiesterases.

Cyclic Nucleotide Phosphodiesterases

As is well-known in the art, a myriad of physiological processes are controlling by causing changes in the steady state levels of the second messengers cAMP and cGMP. One of the major mechanisms by which these levels are controlled is via the cyclic nucleotide PDEs that control their degradation by catalyzing the hydrolysis of a phosphodiester bond, yielding 5'-AMP and 5'-GMP, respectively.

Experimental data have demonstrated the role of cyclic nucleotide phosphodiesterases in a range of diseases, including inflammatory diseases such as asthma, chronic obstructive pulmonary disease, rheumatoid arthritis and atopy.

In mammals, four genes are known to code for cAMP-specific PDEs. These genes are known as PDE4A, PDE4B, PDE4C and PDE4D. This was first demonstrated in rats and later in humans and in mice. The four human and four rat genes show a one to one correspondence, in that each of the four human PDE4 genes is more closely related to its homologous rat gene than to any other human gene. The PDE4 genes are located on three different human chromosomes: PDE4B on chromosome 1, PDE4D on chromosome 5; PDE4A on p13.2 of chromosome 19 and PDE4C on p13.1 of chromosome 19. Their four murine homologues are each located in correspondingly conserved regions of the mouse genome. The mammalian PDE4 genes thus comprise a well-conserved multigene family.

The existence of a large number of mRNA transcripts from many of the mammalian PDE4 genes suggests that the genomic structure of these genes is likely to be complex. Partial genomic sequences have been published for the rat PDE4B and PDE4D genes. However, the published data indicate that sequences at the 5' end of the genes, which would include a number of upstream exons and promoter sites, were not included.

cGMP-stimulated 3', 5'-cyclic nucleotide phosphodiesterase 2A (PDE2A)

The novel human protein, and encoding gene, provided by the present invention is an alternative splice form of cGMP-stimulated 3',5'-cyclic nucleotide phosphodiesterase 2A (PDE2A). Specifically, the phosphodiesterase provided by the present invention differs from known phosphodiesterases, particularly bovine PDE2A1 (gi 116569) and human PDE2A3 (gi4505657), in exon 1. These difference are illustrated in the Figures, particularly in the amino acid sequence alignments shown in FIGS. 2 and 3.

For a further review of PDE2A and related proteins, see Rosman et al., *Gene* 1997 May 20;191(1):89–95; Sonnenburg et al., *J Biol Chem* Sep. 15, 1991; 266(26):17655–61; Trong et al., *Biochemistry* Nov. 6, 1990; 29(44):10280–8; and Charbonneau et al., *Proc Natl Acad Sci USA* 1986 December; 83(24):9308–12.

Phosphodiesterase proteins, particularly alternative splice forms of PDE2A, are a major target for drug action and development. Accordingly, it is valuable to the field of pharmaceutical development to identify and characterize previously unknown splice forms of phosphodiesterase proteins. The present invention advances the state of the art by providing a previously unidentified human PDE2A alternative splice form.

SUMMARY OF THE INVENTION

The present invention is based in part on the identification of amino acid sequences of human phosphodiesterase peptides and proteins that are related to PDE2A, as well as allelic variants and other mammalian orthologs thereof. Specifically, the phosphodiesterase protein provided by the present invention is a novel alternative splice form of PDE2A. These unique peptide sequences, and nucleic acid sequences that encode these peptides, can be used as models for the development of human therapeutic targets, aid in the identification of therapeutic proteins, and serve as targets for the development of human therapeutic agents that modulate phosphodiesterase activity in cells and tissues that express the phosphodiesterase. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

DESCRIPTION OF THE FIGURE SHEETS

FIG. 1 provides the nucleotide sequence of a cDNA molecule that encodes the phosphodiesterase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

FIG. 2 provides the predicted amino acid sequence of the phosphodiesterase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phosphodiesterase protein of the present invention (SEQ ID NO:3), allowing one to readily determine specific uses of inventions based on this molecular sequence. As illustrated in FIG. 3, SNPs were identified at 231 different nucleotide positions. FIG. 3 also provides a multiple alignment of isoform1 (11000567083206_pep), human PDE2A3 (gi4505657_pep) and bovine PDE2A1 (gi116569_pep) amino acid sequences, illustrating the differences in exon 1 between the phosphodiesterase of the present invention and known phosphodiesterases.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphodiesterase protein or part of a phosphodiesterase protein and are related to PDE2A. Specifically, the phosphodiesterase protein provided by the present invention is a novel alternative splice form of PDE2A. Utilizing these sequences, additional genomic sequences were assembled and transcript and/or cDNA sequences were isolated and characterized. Based on this analysis, the present invention provides amino acid sequences of human phosphodiesterase peptides and proteins that are related to the PDE2A subfamily, nucleic acid sequences in the form of transcript sequences, cDNA sequences and/or genomic sequences that encode these phosphodiesterase peptides and proteins, nucleic acid variation (allelic information), tissue distribution of expression, and information about the closest art known protein/peptide/domain that has structural or sequence homology to the phosphodiesterase of the present invention.

In addition to being previously unknown, the peptides that are provided in the present invention are selected based on their ability to be used for the development of commercially important products and services. Specifically, the present peptides are selected based on homology and/or structural relatedness to known phosphodiesterase proteins of the PDE2A subfamily and the expression pattern observed. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known PDE2A family or subfamily of phosphodiesterase proteins.

SPECIFIC EMBODIMENTS

Peptide Molecules

The present invention provides nucleic acid sequences that encode protein molecules that have been identified as being members of the phosphodiesterase family of proteins and are related to PDE2A (protein sequences are provided in FIG. 2, transcript/cDNA sequences are provided in FIG. 1 and genomic sequences are provided in FIG. 3). Specifically, the phosphodiesterase protein provided by the present invention is a novel alternative splice form of PDE2A. The peptide sequences provided in FIG. 2, as well as the obvious variants described herein, particularly allelic variants as identified herein and using the information in FIG. 3, will be referred herein as the phosphodiesterase peptides of the present invention, phosphodiesterase peptides, or peptides/proteins of the present invention.

The present invention provides isolated peptide and protein molecules that consist of, consist essentially of, or comprise the amino acid sequences of the phosphodiesterase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphodiesterase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphodiesterase peptide can be purified from cells that naturally express it, purified from cells that have been altered to express it (recombinant), or synthesized using known protein synthesis methods. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. For example, a nucleic acid molecule encoding the phosphodiesterase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphodiesterase peptides of the present invention are the naturally occurring mature proteins. A brief description of how various types of these proteins can be made/isolated is provided below.

The phosphodiesterase peptides of the present invention can be attached to heterologous sequences to form chimeric or fusion proteins. Such chimeric and fusion proteins comprise a phosphodiesterase peptide operatively linked to a heterologous protein having an amino acid sequence not substantially homologous to the phosphodiesterase peptide. "Operatively linked" indicates that the phosphodiesterase peptide and the heterologous protein are fused in-frame. The heterologous protein can be fused to the N-terminus or C-terminus of the phosphodiesterase peptide.

In some uses, the fusion protein does not affect the activity of the phosphodiesterase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphodiesterase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A phosphodiesterase peptide-encoding nucleic acid can be cloned into such an expression vector such that the fusion moiety is linked in-frame to the phosphodiesterase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphodiesterase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphodiesterase peptides of the present invention as well as being encoded by the same genetic locus as the phosphodiesterase peptide provided herein. The gene encoding the novel phosphodiesterase protein of the present invention is located on a genome component that has been mapped to human chromosome 11 (as indicated in FIG. 3), which is supported by multiple lines of evidence, such as STS and BAC map data.

Allelic variants of a phosphodiesterase peptide can readily be identified as being a human protein having a high degree (significant) of sequence homology/identity to at least a portion of the phosphodiesterase peptide as well as being encoded by the same genetic locus as the phosphodiesterase peptide provided herein. Genetic locus can readily be determined based on the genomic information provided in FIG. 3, such as the genomic sequence mapped to the reference human. The gene encoding the novel phosphodiesterase protein of the present invention is located on a genome component that has been mapped to human chromosome 11 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphodiesterase peptide encoding nucleic acid molecule under stringent conditions as more fully described below.

FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Paralogs of a phosphodiesterase peptide can readily be identified as having some degree of significant sequence homology/identity to at least a portion of the phosphodiesterase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphodiesterase peptide encoding nucleic acid molecule under moderate to stringent conditions as more fully described below.

Orthologs of a phosphodiesterase peptide can readily be identified as having some degree of significant sequence homology/identity to at least a portion of the phosphodiesterase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphodiesterase peptide encoding nucleic acid molecule under moderate to stringent conditions, as more fully described below, depending on the degree of relatedness of the two organisms yielding the proteins.

Non-naturally occurring variants of the phosphodiesterase peptides of the present invention can readily be generated using recombinant techniques. Such variants include, but are not limited to deletions, additions and substitutions in the amino acid sequence of the phosphodiesterase peptide. For example, one class of substitutions are conserved amino acid substitution. Such substitutions are those that substitute a given amino acid in a phosphodiesterase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphodiesterase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phosphodiesterase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the phosphodiesterase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphodiesterase peptide. Such fragments can be chosen based on the ability to retain one or more of the biological activities of the phosphodiesterase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphodiesterase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphodiesterase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992).

Accordingly, the phosphodiesterase peptides of the present invention also encompass derivatives or analogs in which a substituted amino acid residue is not one encoded by the genetic code, in which a substituent group is included, in which the mature phosphodiesterase peptide is fused with another compound, such as a compound to increase the half-life of the phosphodiesterase peptide (for example, polyethylene glycol), or in which the additional amino acids are fused to the mature phosphodiesterase peptide, such as a leader or secretory sequence or a sequence for purification of the mature phosphodiesterase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphodiesterase-effector protein interaction or phosphodiesterase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphodiesterases isolated from humans and their human/mammalian orthologs serve as targets for identifying agents for use in mammalian therapeutic applications, e.g. a human drug, particularly in modulating a biological or pathological response in a cell or tissue that expresses the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. A large percentage of pharmaceutical agents are being developed that modulate the activity of phosphodiesterase proteins, particularly members of the PDE2A subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Such uses can readily be determined using the information provided herein, that which is known in the art, and routine experimentation.

The proteins of the present invention (including variants and fragments that may have been disclosed prior to the present invention) are useful for biological assays related to phosphodiesterases that are related to members of the PDE2A subfamily. Such assays involve any of the known phosphodiesterase functions or activities or properties useful for diagnosis and treatment of phosphodiesterase-related conditions that are specific for the subfamily of phosphodiesterases that the one of the present invention belongs to, particularly in cells and tissues that express the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

The proteins of the present invention are also useful in drug screening assays, in cell-based or cell-free systems. Cell-based systems can be native, i.e., cells that normally express the phosphodiesterase, as a biopsy or expanded in cell culture. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. In an alternate embodiment, cell-based assays involve recombinant host cells expressing the phosphodiesterase protein.

The polypeptides can be used to identify compounds that modulate phosphodiesterase activity of the protein in its natural state or an altered form that causes a specific disease or pathology associated with the phosphodiesterase. Both the phosphodiesterases of the present invention and appropriate variants and fragments can be used in high-throughput screens to assay candidate compounds for the ability to bind to the phosphodiesterase. These compounds can be further screened against a functional phosphodiesterase to determine the effect of the compound on the phosphodiesterase activity. Further, these compounds can be tested in animal or invertebrate systems to determine activity/effectiveness. Compounds can be identified that activate (agonist) or inactivate (antagonist) the phosphodiesterase to a desired degree.

Further, the proteins of the present invention can be used to screen a compound for the ability to stimulate or inhibit interaction between the phosphodiesterase protein and a molecule that normally interacts with the phosphodiesterase protein, e.g. a substrate or a component of the signal pathway that the phosphodiesterase protein normally interacts (for example, another phosphodiesterase). Such assays typically include the steps of combining the phosphodiesterase protein with a candidate compound under conditions that allow the phosphodiesterase protein, or fragment, to interact with the target molecule, and to detect the formation of a complex between the protein and the target or to detect the biochemical consequence of the interaction with the phosphodiesterase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, antiidiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphodiesterases or appropriate fragments containing mutations that affect phosphodiesterase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphodiesterase activity. The assays typically involve an assay of events in the signal transduction pathway that indicate phosphodiesterase activity. Thus, the phosphorylation of a substrate, activation of a protein, a change in the expression of genes that are up- or down- regulated in response to the phosphodiesterase protein dependent signal cascade can be assayed.

Any of the biological or biochemical functions mediated by the phosphodiesterase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phosphodiesterase can be assayed. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

Binding and/or activating compounds can also be screened by using chimeric phosphodiesterase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphodiesterase. Accordingly, a different set of signal transduction components is available as an endpoint assay for activation. This allows for assays to be performed in other than the specific host cell from which the phosphodiesterase is derived.

The proteins of the present invention are also useful in competition binding assays in methods designed to discover compounds that interact with the phosphodiesterase (e.g. binding partners and/or ligands). Thus, a compound is exposed to a phosphodiesterase polypeptide under conditions that allow the compound to bind or to otherwise interact with the polypeptide. Soluble phosphodiesterase polypeptide is also added to the mixture. If the test compound interacts with the soluble phosphodiesterase polypeptide, it decreases the amount of complex formed or activity from the phosphodiesterase target. This type of assay is particularly useful in cases in which compounds are sought that interact with specific regions of the phosphodiesterase. Thus, the soluble polypeptide that competes with the target phosphodiesterase region is designed to contain peptide sequences corresponding to the region of interest.

To perform cell free drug screening assays, it is sometimes desirable to immobilize either the phosphodiesterase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphodiesterase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphodiesterase-binding protein and a candidate compound are incubated in the phosphodiesterase protein-presenting wells and the amount of complex trapped in the well can be quantitated. Methods for detecting such complexes, in addition to those described above for the GST-immobilized complexes, include immunodetection of complexes using antibodies reactive with the phosphodiesterase protein target molecule, or which are reactive with phosphodiesterase protein and compete with the target molecule, as well as enzyme-linked assays which rely on detecting an enzymatic activity associated with the target molecule.

Agents that modulate one of the phosphodiesterases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphodiesterase protein activity identified according to these drug screening assays can be used to treat a subject with a disorder mediated by the phosphodiesterase pathway, by treating cells or tissues that express the phosphodiesterase. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. These methods of treatment include the steps of administering a modulator of phosphodiesterase activity in a pharmaceutical composition to a subject in need of such treatment, the modulator being identified as described herein.

In yet another aspect of the invention, the phosphodiesterase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent W094/10300), to identify other proteins, which bind to or interact with the phosphodiesterase and are involved in phosphodiesterase activity. Such phosphodiesterase-binding proteins are also likely to be involved in the propagation of signals by the phosphodiesterase proteins or phosphodiesterase targets as, for example, downstream elements of a phosphodiesterase-mediated signaling pathway. Alternatively, such phosphodiesterase-binding proteins are likely to be phosphodiesterase inhibitors.

The two-hybrid system is based on the modular nature of most transcription factors, which consist of separable DNA-binding and activation domains. Briefly, the assay utilizes two different DNA constructs. In one construct, the gene that codes for a phosphodiesterase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphodiesterase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphodiesterase protein.

This invention further pertains to novel agents identified by the above-described screening assays. Accordingly, it is within the scope of this invention to further use an agent identified as described herein in an appropriate animal model. For example, an agent identified as described herein (e.g., a phosphodiesterase-modulating agent, an antisense phosphodiesterase nucleic acid molecule, a phosphodiesterase-specific antibody, or a phosphodiesterase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphodiesterase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The method involves contacting a biological sample with a compound capable of interacting with the phosphodiesterase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphodiesterase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphodiesterase protein in which one or more of the phosphodiesterase functions in one population is different from those in another population. The peptides thus allow a target to ascertain a genetic predisposition that can affect treatment modality.

Thus, in a ligand-based treatment, polymorphism may give rise to amino terminal extracellular domains and/or other substrate-binding regions that are more or less active in substrate binding, and phosphodiesterase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Accordingly, methods for treatment include the use of the phosphodiesterase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphodiesterase proteins. Antibodies can be prepared from any region of the peptide as described herein. However, preferred regions will include those involved in function/activity and/or phosphodiesterase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitations. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Thus, where a specific protein has been correlated with expression in a specific tissue, antibodies that are specific for this protein can be used to identify a tissue type.

The antibodies are also useful for inhibiting protein function, for example, blocking the binding of the phosphodiesterase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phosphodiesterase peptide or protein of the present invention (cDNA, transcript and genomic sequence). Such nucleic acid molecules will consist of, consist essentially of, or comprise a nucleotide sequence that encodes one of the phosphodiesterase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphodiesterase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the phosphodiesterase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phosphodiesterase protein of the present invention is located on a genome component that has been mapped to human chromosome 11 (as indicated in FIG. 3), which is supported by multiple lines of evidence, such as STS and BAC map data.

FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 231 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phosphodiesterase protein of the present invention is located on a genome component that has been mapped to human chromosome 11 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphodiesterase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phosphodiesterase protein, such as by measuring a level of a phosphodiesterase-encoding nucleic acid in a sample of cells from a subject e.g., mRNA or genomic DNA, or determining if a phosphodiesterase gene has been mutated. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

Nucleic acid expression assays are useful for drug screening to identify compounds that modulate phosphodiesterase nucleic acid expression.

The invention thus provides a method for identifying a compound that can be used to treat a disorder associated with nucleic acid expression of the phosphodiesterase gene, particularly biological and pathological processes that are mediated by the phosphodiesterase in cells and tissues that express it. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The method typically includes assaying the ability of the compound to modulate the expression of the phosphodiesterase nucleic acid and thus identifying a compound that can be used to treat a disorder characterized by undesired phosphodiesterase nucleic acid expression. The assays can be performed in cell-based and cell-free systems. Cell-based assays include cells naturally expressing the phosphodiesterase nucleic acid or recombinant cells genetically engineered to express specific nucleic acid sequences.

The assay for phosphodiesterase nucleic acid expression can involve direct assay of nucleic acid levels, such as mRNA levels, or on collateral compounds involved in the signal pathway. Further, the expression of genes that are up- or down-regulated in response to the phosphodiesterase protein signal pathway can also be assayed. In this embodiment the regulatory regions of these genes can be operably linked to a reporter gene such as luciferase.

Thus, modulators of phosphodiesterase gene expression can be identified in a method wherein a cell is contacted with a candidate compound and the expression of mRNA determined. The level of expression of phosphodiesterase mRNA in the presence of the candidate compound is compared to the level of expression of phosphodiesterase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphodiesterase nucleic acid expression in cells and tissues that express the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Modulation includes both up-regulation (i.e. activation or agonization) or down-regulation (suppression or antagonization) or nucleic acid expression.

Alternatively, a modulator for phosphodiesterase nucleic acid expression can be a small molecule or drug identified using the screening assays described herein as long as the drug or small molecule inhibits the phosphodiesterase nucleic acid expression in the cells and tissues that express the protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

The nucleic acid molecules are also useful for monitoring the effectiveness of modulating compounds on the expression or activity of the phosphodiesterase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphodiesterase nucleic acid expression, and particularly in qualitative changes that lead to pathology. The nucleic acid molecules can be used to detect mutations in phosphodiesterase genes and gene expression products such as mRNA. The nucleic acid molecules can be used as hybridization probes to detect naturally occurring genetic mutations in the phosphodiesterase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphodiesterase gene associated with a dysfunction provides a diagnostic tool for an active disease or susceptibility to disease when the disease results from overexpression, underexpression, or altered expression of a phosphodiesterase protein.

Individuals carrying mutations in the phosphodiesterase gene can be detected at the nucleic acid level by a variety of techniques. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements. The gene encoding the novel phosphodiesterase protein of the present invention is located on a genome component that has been mapped to human chromosome 11 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphodiesterase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphodiesterase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphodiesterase gene in an individual in order to select an appropriate compound or dosage regimen for treatment. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphodiesterase gene expression in cells, tissues, and organisms. A DNA antisense nucleic acid molecule is designed to be complementary to a region of the gene involved in transcription, preventing transcription and hence production of phosphodiesterase protein. An antisense RNA or DNA nucleic acid molecule would hybridize to the mRNA and thus block translation of mRNA into phosphodiesterase protein.

Alternatively, a class of antisense molecules can be used to inactivate mRNA in order to decrease expression of phosphodiesterase nucleic acid. Accordingly, these molecules can treat a disorder characterized by abnormal or undesired phosphodiesterase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphodiesterase protein, such as substrate binding.

The nucleic acid molecules also provide vectors for gene therapy in patients containing cells that are aberrant in phosphodiesterase gene expression. Thus, recombinant cells, which include the patient's cells that have been engineered ex vivo and returned to the patient, are introduced into an individual where the cells produce the desired phosphodiesterase protein to treat the individual.

The invention also encompasses kits for detecting the presence of a phosphodiesterase nucleic acid in a biological sample. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. For example, the kit can comprise reagents such as a labeled or labelable nucleic acid or agent capable of detecting phosphodiesterase nucleic acid in a biological sample; means for determining the amount of phosphodiesterase nucleic acid in the sample; and means for comparing the amount of phosphodiesterase nucleic acid in the sample with a standard. The compound or agent can be packaged in a suitable container. The kit can further comprise instructions for using the kit to detect phosphodiesterase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee at al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphodiesterase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphodiesterase gene of the present invention. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphodiesterase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook at al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al, *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195(1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning. A Laboratory Manual.* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as phosphodiesterases, appropriate secretion signals are incorporated into the vector. The signal sequence can be endogenous to the peptides or heterologous to these peptides.

Where the peptide is not secreted into the medium, which is typically the case with phosphodiesterases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phosphodiesterase protein or peptide that can be further purified to produce desired amounts of phosphodiesterase protein or fragments. Thus, host cells containing expression vectors are useful for peptide production.

Host cells are also useful for conducting cell-based assays involving the phosphodiesterase protein or phosphodiesterase protein fragments, such as those described above as well as other formats known in the art. Thus, a recombinant host cell expressing a native phosphodiesterase protein is useful for assaying compounds that stimulate or inhibit phosphodiesterase protein function.

Host cells are also useful for identifying phosphodiesterase protein mutants in which these functions are affected. If the mutants naturally occur and give rise to a pathology, host cells containing the mutations are useful to assay compounds that have a desired effect on the mutant phosphodiesterase protein (for example, stimulating or inhibiting function) which may not be indicated by their effect on the native phosphodiesterase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphodiesterase protein and identifying and evaluating modulators of phosphodiesterase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphodiesterase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphodiesterase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phosphodiesterase protein activation, and signal transduction, may not be evident from in vitro cell-free or cell-based assays. Accordingly, it is useful to provide non-human transgenic animals to assay in vivo phosphodiesterase protein function, including substrate interaction, the effect of specific mutant phosphodiesterase proteins on phosphodiesterase protein function and substrate interaction, and the effect of chimeric phosphodiesterase proteins. It is also possible to assess the effect of null mutations, that is mutations that substantially or completely eliminate one or more phosphodiesterase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of
   SEQ ID NO:2.
2. An isolated polypeptide having an amino acid sequence comprising
   SEQ ID NO:2.
3. A method for identifying a modulator of a peptide of claim 2, said method comprising contacting said peptide with an agent and determining if said agent has modulated the function or activity of said peptide.
4. The method of claim 3, wherein said agent is administered to a host cell comprising an expression vector that expresses said peptide.
5. A composition comprising the polypeptide of claim 1 and a carrier.
6. A composition comprising the polypeptide of claim 2 and a carrier.

* * * * *

SEQUENCE LISTING

<160> NUMBER OF SEQ ID NOS: 5

<210> SEQ ID NO 1
<211> LENGTH: 4171
<212> TYPE: DNA
<213> ORGANISM: Homo sapien

<400> SEQUENCE: 1
gggccggcgg gcgggcgggc ggctgcgagc atggtcctgg tgctgcacca catcctcatc    60

-continued

| | |
|---|---|
| gctgttgtcc aattcctcag gcggggccag caggtcttcc tcaagccgga cgagccgccg | 120 |
| ccgccgccgc agccatgcgc cgacagcctg cagccagcct ggacccctt gcaaaggagc | 180 |
| caggaccccc agggagtaga gacgaccgac tggaggacgc cttgctgagt ctgggctctg | 240 |
| tcatcgacat ttcaggcctg caacgtgctg tcaaggaggc cctgtcagct gtgctccccc | 300 |
| gagtggaaac tgtctacacc tacctactgg atggtgagtc ccagctggtg tgtgaggacc | 360 |
| ccccacatga gctgccccag gaggggaaag tccgggaggc tatcatctcc cagaagcggc | 420 |
| tgggctgcaa tgggctgggc ttctcagacc tgccagggaa gcccttggcc aggctggtgg | 480 |
| ctccactggc tcctgatacc caagtgctgg tcatgccgct agcggacaag gaggctgggg | 540 |
| ccgtggcagc tgtcatcttg gtgcactgtg ccagctgag tgataatgag gaatggagcc | 600 |
| tgcaggcggt ggagaagcat accctggtcg ccctgcggag ggtgcaggtc ctgcagcagc | 660 |
| gcgggcccag ggaggctccc cgagccgtcc agaaccccc ggaggggacg gcggaagacc | 720 |
| agaagggcgg ggcggcgtac atcgaccgcg accgcaagat cctccaactg tgcggggaac | 780 |
| tctacgacct ggatgcctct tccctgcagc tcaaagtgct ccaatacctg cagcaggaga | 840 |
| cccgggcatc ccgctgctgc ctcctgctgg tgtcggagga caatctccag ctttcttgca | 900 |
| aggtcatcgg agacaaagtg ctcggggaag aggtcagctt tccttgaca ggatgcctgg | 960 |
| gccaggtggt ggaagacaag aagtccatcc agctgaagga cctcacctcc gaggatgtac | 1020 |
| aacagctgca gagcatgttg ggctgtgagc tgcaggccat gctctgtgtc cctgtcatca | 1080 |
| gccgggccac tgaccaggtg gtggccttgg cctgcgcctt caacaagcta gaaggagact | 1140 |
| tgttcaccga cgaggacgag catgtgatcc agcactgctt ccactacacc agcaccgtgc | 1200 |
| tcaccagcac cctggccttc cagaaggaac agaaactcaa gtgtgagtgc caggctcttc | 1260 |
| tccaagtggc aaagaacctc ttcacccacc tggatgacgt ctctgtcctg ctccaggaga | 1320 |
| tcatcacgga ggccagaaac ctcagcaacg cagagatctg ctctgtgttc ctgctggatc | 1380 |
| agaatgagct ggtggccaag gtgttcgacg ggggcgtggt ggatgatgag agctatgaga | 1440 |
| tccgcatccc ggccgatcag ggcatcgcgg gacacgtggc gaccacgggc cagatcctga | 1500 |
| acatccctga cgcatatgcc catccgcttt tctaccgcgg cgtggacgac agcaccggct | 1560 |
| tccgcacgcg caacatcctc tgcttcccca tcaagaacga gaaccaggag gtcatcggtg | 1620 |
| tggccgagct ggtgaacaag atcaatgggc catggttcag caagttcgac gaggacctgg | 1680 |
| cgacggcctt ctccatctac tgcggcatca gcatcgccca ttctctccta tacaaaaaag | 1740 |
| tgaatgaggc tcagtatcgc agccacctgg ccaatgagat gatgatgtac cacatgaagg | 1800 |
| tctccgacga tgagtatacc aaacttctcc atgatgggat ccagcctgtg ctgccattg | 1860 |
| actccaattt tgcaagtttc acctatacc ctcgttccct gcccgaggat gacacgtcca | 1920 |
| tggccatcct gagcatgctg caggacatga atttcatcaa caactacaaa attgactgcc | 1980 |
| cgaccctggc ccgttctgt ttgatggtga agaagggcta ccgggatccc cctaccaca | 2040 |
| actggatgca cgccttttct gtctcccact tctgctacct gctctacaag aacctggagc | 2100 |
| tcaccaacta cctcgaggac atcgagatct ttgccttgtt tatttcctgc atgtgtcatg | 2160 |
| acctggacca cagaggcaca aacaactctt tccaggtggc ctcgaaatct gtgctggctg | 2220 |
| cgctctacag ctctgagggc tccgtcatgg agaggcacca ctttgctcag gccattgcca | 2280 |
| tcctcaacac ccacggctgc aacatctttg atcatttctc ccggaaggac tatcagcgca | 2340 |
| tgctggatct gatgcgggac atcatcttgg ccacagacct ggcccaccat ctccgcatct | 2400 |
| tcaaggacct ccagaagatg gctgaggtgg gctacgaccg aaacaacaag cagcaccaca | 2460 |

-continued

```
gacttctcct ctgcctcctc atgacctcct gtgacctctc tgaccagacc aagggctgga    2520
agactacgag aaagatcgcg gagctgatct acaaagaatt cttctcccag ggagacctgg    2580
agaaggccat gggcaacagg ccgatggaga tgatggaccg ggagaaggcc tatatccctg    2640
agctgcaaat cagcttcatg gagcacattg caatgcccat ctacaagctg ttgcaggacc    2700
tgttccccaa gcggcagag ctgtatgagc gcgtggcctc caaccgtgag cactggacca    2760
aggtgtccca caagttcacc atccgcggcc tcccaagtaa caactcgctg acttcctgg    2820 atgaggagta cgaggtgcct gatctggatg cactagggc ccccatcaat ggctgctgca    2880
gccttgatgc tgagtgatcc cctccaggga cacttccctg cccaggccac ctcccacagc    2940
cctccactgg tctggccaga tgcactggga acagagccac gggtcctggg tcctagacca    3000
ggacttcctg tgtgaccctg acaagtact accttcctgg gcctcagctt tctcgtctgt    3060
ataatggaag caagacttcc aacctcacgg agactttgta atttgttctc tgagagcaca    3120
ggggtgacca atgagcagtg ggccctactc tgcacctctg accacacctt ggcaagtctt    3180
tcccaagcca ttctttgtct gagcagcttg atggtttctc cttgccccat ttctgcccca    3240
ccagatcttt gctcctttcc ctttgaggac tcccacccct tggggtctcc aggatcctca    3300
tggaagggga aggtgagaca tctgagtgag cagagtgtgg catcttggaa acagtcctta    3360
gttctgtggg aggactagaa acagccgcgg ggcgaaggcc ccctgaggac cactactata    3420
ctgatggtgg gattgggacc tgggggatac aggggcccca ggaagaagct gccagagggg    3480
cagctcagtg ctctgcagag aggggccctg gggagaagca ggatgggatt gatgggcagg    3540
agggatcccc gcactgggag acaggcccag gtatgaatga ccagccatg cttcctcctg    3600 cctgtgtgac gctgggcgag tctcttcccc tgtctgggcc aaacaggag cgggtaagac    3660 aatccatgct ctaagatcca ttttagatca atgtctaaaa tagctctatc gctctgcgga    3720
gtcccagcag aggctatgga atgtttctgc aaccctaagg cacagagagc caaccctga    3780 gtgtctcaga ggcccctga gtgttccct tggcctgagc cccttaccca ttcctgcagc    3840
cagtgagaga cctggcctca gccctggcag ggctctctct tcaaggccat atccacctgt    3900 gccctgggc ttgggagacc cataggggcc gggactcttg ggtcagcccg ccactggct    3960 tctctctttt tctccgtttc attctgtgtg cgttgtgggg tggggagggg ggtccacctg    4020
ccttaccttt ctgagttgcc tttagagaga tgcgtttttc taggactctg tgcaactgtc    4080
gtatatggtc ccgtgggctg accgctttgt acatgagaat aaatctattt ctttctacca    4140
gaaaaaaaaa aaaaaaaaa aaaaaaaaaa a                                   4171
```

<210> SEQ ID NO 2
<211> LENGTH: 920
<212> TYPE: PRT
<213> ORGANISM: Homo sapien

<400> SEQUENCE: 2

```
Met Arg Arg Gln Pro Ala Ala Ser Leu Asp Pro Leu Ala Lys Glu Pro
 1               5                  10                  15

Gly Pro Pro Gly Ser Arg Asp Asp Arg Leu Glu Asp Ala Leu Leu Ser
            20                  25                  30

Leu Gly Ser Val Ile Asp Ile Ser Gly Leu Gln Arg Ala Val Lys Glu
        35                  40                  45

Ala Leu Ser Ala Val Leu Pro Arg Val Glu Thr Val Tyr Thr Tyr Leu
    50                  55                  60
```

-continued

```
Leu Asp Gly Glu Ser Gln Leu Val Cys Glu Asp Pro His Glu Leu
 65                  70                  75                  80

Pro Gln Glu Gly Lys Val Arg Glu Ala Ile Ile Ser Gln Lys Arg Leu
                 85                  90                  95

Gly Cys Asn Gly Leu Gly Phe Ser Asp Leu Pro Gly Lys Pro Leu Ala
            100                 105                 110

Arg Leu Val Ala Pro Leu Ala Pro Asp Thr Gln Val Leu Val Met Pro
        115                 120                 125

Leu Ala Asp Lys Glu Ala Gly Ala Val Ala Ala Val Ile Leu Val His
130                 135                 140

Cys Gly Gln Leu Ser Asp Asn Glu Glu Trp Ser Leu Gln Ala Val Glu
145                 150                 155                 160

Lys His Thr Leu Val Ala Leu Arg Arg Val Gln Val Leu Gln Gln Arg
                165                 170                 175

Gly Pro Arg Glu Ala Pro Arg Ala Val Gln Asn Pro Pro Glu Gly Thr
            180                 185                 190

Ala Glu Asp Gln Lys Gly Gly Ala Ala Tyr Ile Asp Arg Asp Arg Lys
        195                 200                 205

Ile Leu Gln Leu Cys Gly Glu Leu Tyr Asp Leu Asp Ala Ser Ser Leu
210                 215                 220

Gln Leu Lys Val Leu Gln Tyr Leu Gln Gln Glu Thr Arg Ala Ser Arg
225                 230                 235                 240

Cys Cys Leu Leu Leu Val Ser Glu Asp Asn Leu Gln Leu Ser Cys Lys
                245                 250                 255

Val Ile Gly Asp Lys Val Leu Gly Glu Glu Val Ser Phe Pro Leu Thr
            260                 265                 270

Gly Cys Leu Gly Gln Val Val Glu Asp Lys Lys Ser Ile Gln Leu Lys
        275                 280                 285

Asp Leu Thr Ser Glu Asp Val Gln Gln Leu Gln Ser Met Leu Gly Cys
290                 295                 300

Glu Leu Gln Ala Met Leu Cys Val Pro Val Ile Ser Arg Ala Thr Asp
305                 310                 315                 320

Gln Val Val Ala Leu Ala Cys Ala Phe Asn Lys Leu Glu Gly Asp Leu
                325                 330                 335

Phe Thr Asp Glu Asp Glu His Val Ile Gln His Cys Phe His Tyr Thr
            340                 345                 350

Ser Thr Val Leu Thr Ser Thr Leu Ala Phe Gln Lys Glu Gln Lys Leu
        355                 360                 365

Lys Cys Glu Cys Gln Ala Leu Leu Gln Val Ala Lys Asn Leu Phe Thr
370                 375                 380

His Leu Asp Asp Val Ser Val Leu Leu Gln Glu Ile Ile Thr Glu Ala
385                 390                 395                 400

Arg Asn Leu Ser Asn Ala Glu Ile Cys Ser Val Phe Leu Leu Asp Gln
                405                 410                 415

Asn Glu Leu Val Ala Lys Val Phe Asp Gly Gly Val Val Asp Asp Glu
            420                 425                 430

Ser Tyr Glu Ile Arg Ile Pro Ala Asp Gln Gly Ile Ala Gly His Val
        435                 440                 445

Ala Thr Thr Gly Gln Ile Leu Asn Ile Pro Asp Ala Tyr Ala His Pro
450                 455                 460

Leu Phe Tyr Arg Gly Val Asp Asp Ser Thr Gly Phe Arg Thr Arg Asn
465                 470                 475                 480

Ile Leu Cys Phe Pro Ile Lys Asn Glu Asn Gln Glu Val Ile Gly Val
```

-continued

```
                485                 490                 495
Ala Glu Leu Val Asn Lys Ile Asn Gly Pro Trp Phe Ser Lys Phe Asp
            500                 505                 510
Glu Asp Leu Ala Thr Ala Phe Ser Ile Tyr Cys Gly Ile Ser Ile Ala
            515                 520                 525
His Ser Leu Leu Tyr Lys Lys Val Asn Glu Ala Gln Tyr Arg Ser His
            530                 535                 540
Leu Ala Asn Glu Met Met Met Tyr His Met Lys Val Ser Asp Asp Glu
545                 550                 555                 560
Tyr Thr Lys Leu Leu His Asp Gly Ile Gln Pro Val Ala Ala Ile Asp
            565                 570                 575
Ser Asn Phe Ala Ser Phe Thr Tyr Thr Pro Arg Ser Leu Pro Glu Asp
            580                 585                 590
Asp Thr Ser Met Ala Ile Leu Ser Met Leu Gln Asp Met Asn Phe Ile
            595                 600                 605
Asn Asn Tyr Lys Ile Asp Cys Pro Thr Leu Ala Arg Phe Cys Leu Met
            610                 615                 620
Val Lys Lys Gly Tyr Arg Asp Pro Pro Tyr His Asn Trp Met His Ala
625                 630                 635                 640
Phe Ser Val Ser His Phe Cys Tyr Leu Leu Tyr Lys Asn Leu Glu Leu
            645                 650                 655
Thr Asn Tyr Leu Glu Asp Ile Glu Ile Phe Ala Leu Phe Ile Ser Cys
            660                 665                 670
Met Cys His Asp Leu Asp His Arg Gly Thr Asn Asn Ser Phe Gln Val
            675                 680                 685
Ala Ser Lys Ser Val Leu Ala Ala Leu Tyr Ser Ser Glu Gly Ser Val
            690                 695                 700
Met Glu Arg His His Phe Ala Gln Ala Ile Ala Ile Leu Asn Thr His
705                 710                 715                 720
Gly Cys Asn Ile Phe Asp His Phe Ser Arg Lys Asp Tyr Gln Arg Met
            725                 730                 735
Leu Asp Leu Met Arg Asp Ile Ile Leu Ala Thr Asp Leu Ala His His
            740                 745                 750
Leu Arg Ile Phe Lys Asp Leu Gln Lys Met Ala Glu Val Gly Tyr Asp
            755                 760                 765
Arg Asn Asn Lys Gln His His Arg Leu Leu Leu Cys Leu Leu Met Thr
            770                 775                 780
Ser Cys Asp Leu Ser Asp Gln Thr Lys Gly Trp Lys Thr Thr Arg Lys
785                 790                 795                 800
Ile Ala Glu Leu Ile Tyr Lys Glu Phe Phe Ser Gln Gly Asp Leu Glu
            805                 810                 815
Lys Ala Met Gly Asn Arg Pro Met Glu Met Met Asp Arg Glu Lys Ala
            820                 825                 830
Tyr Ile Pro Glu Leu Gln Ile Ser Phe Met Glu His Ile Ala Met Pro
            835                 840                 845
Ile Tyr Lys Leu Leu Gln Asp Leu Phe Pro Lys Ala Ala Glu Leu Tyr
            850                 855                 860
Glu Arg Val Ala Ser Asn Arg Glu His Trp Thr Lys Val Ser His Lys
865                 870                 875                 880
Phe Thr Ile Arg Gly Leu Pro Ser Asn Asn Ser Leu Asp Phe Leu Asp
            885                 890                 895
Glu Glu Tyr Glu Val Pro Asp Leu Asp Gly Thr Arg Ala Pro Ile Asn
            900                 905                 910
```

Gly Cys Cys Ser Leu Asp Ala Glu
        915                 920

<210> SEQ ID NO 3
<211> LENGTH: 111282
<212> TYPE: DNA
<213> ORGANISM: Homo sapien
<220> FEATURE:
<221> NAME/KEY: misc_feature
<222> LOCATION: (1)...(111282)
<223> OTHER INFORMATION: n = A,T,C or G

<400> SEQUENCE: 3

| | | | | |
|---|---|---|---|---|
| acgtggatga | acacccaccc | acacacagct | ctctaggaaa | attgctcccc ttccctcctg | 60 |
| ctcctcctcc | accctgtcct | cccaccacca | cccacttcca | aatgctgaga ccaaagagat | 120 |
| gggctggacg | gtgcctctca | ccacttgtca | gcctgggacg | ccctcctccc tttgtgacta | 180 |
| gcatgccctc | ctcccctgc | ccgtctgcct | ccccagctct | ctctgcctcc ctgtcgccct | 240 |
| gccacctccc | tgcgttcctg | tgtatctgcc | ctccacacaa | gtcactctga ggcctctctt | 300 |
| tgttactctt | gactctgaag | tggaaactgc | tcctcccagc | tctcctgaga ggctcaggat | 360 |
| ggggacctga | cctcataggg | ctgatggagg | catagggaca | agtgaaaggg accccaggtc | 420 |
| ccgaatctcc | tcagctcctg | tcaccttcag | tccctcctat | tgggttaggg gagggctgtg | 480 |
| tgcctggcac | catggagacc | agtgtcatgg | caacacagtt | cgggtgggca cagcttcctc | 540 |
| ctcctggggt | gtggggtcca | taagaggagg | tgccgaggag | gtgggccttg tgctggtgcc | 600 |
| caccatggct | gcctccagct | caccattccc | aggacagccc | accccatcc ccccagccaa | 660 |
| ctttgcttgc | cactgcagct | tccagtgcca | caagtcactg | atcccatttg ggaaatcctc | 720 |
| tctcaaacac | cagctccaga | gctgggcgcc | agagagggca | ggggcttgcc cagggtcaca | 780 |
| cagcaagtct | ggccaagctc | ctgactctca | gacctgtttt | ctcctccggt ctcccacctt | 840 |
| ccacccagaa | aggggactgg | gggcagaggg | gtcagtccaa | cctcagttcc caccacgatc | 900 |
| ttcagccagc | ccttagagtt | ggcagtggga | gtgaagatgc | aagtgatagt gccgagaaac | 960 |
| catcatgggg | cgcccaccac | ctgctgtgcc | aaggctttgc | atgtgtcatc ccattttatt | 1020 |
| ccaagaccca | ggaggaagat | gactggtaag | tggagtagct | gggacaggaa cacaggtccc | 1080 |
| tctcagatgg | ggcaggtgag | tcaaggctcg | tgtgtattgc | tgtctccatc aggcgctctt | 1140 |
| ttaaaagaat | ggcaaagctt | ttaatcccat | ctttattacc | ggtaagagtg taggggggagg | 1200 |
| atctggggca | tagcctgggt | ctggccttag | ggtttctaga | aaccagggga tatttttcta | 1260 |
| agaagataga | gaatagagct | ttcctagtgt | ggttagacct | agggaagacc tttcttgcag | 1320 |
| tgcagcaatg | cagaccgact | tccaatccct | aggtcaagct | ggagtctagg gacagagggg | 1380 |
| aggagacccc | tgcctcctgt | gcccagcctc | aacttgtctc | ctgaccttca tggagtcacg | 1440 |
| ttgcagctgc | ctccctcctg | gcttatgtaa | taattcaaat | atagcagctg cctttatccc | 1500 |
| actgagtcac | acccctgca | tcccccctca | ggtgcgggga | gttatggggg aagaggtggt | 1560 |
| tcagggctga | gtgggaggtt | cggggcctcc | tggcaaggaa | gatccctagt gtgctggatt | 1620 |
| ggagggtggt | ggtggtgagg | gggctggtgc | tgaggcccca | agaagagcag agccttcgcc | 1680 |
| agaatatgaa | gccacagggg | ccacttctgc | cctgacccat | ccctgctgga attccacatt | 1740 |
| cctgggggcc | ctccccagag | tcacaagcta | tatgtacagc | cttctcttgt gggctgctgt | 1800 |
| ctcagttgga | ggaggaagga | gagtggaag | agtatgaaga | gggggaagta gtccggtggg | 1860 |
| gcaatggcca | ccgtctttgg | tcctaggctc | agcctcgccc | ttcactcact gggttacctg | 1920 |

```
ggcacccctc tgacctcagt tttcccatct gcacagtgaa ggattagatt aactggctct    1980
agcgtctcat tctctccgat ttataaccct ggagatgatc tcaacctgag gctgaaggca    2040
cttccgagtg tctggcccag ccgcgttcca ggctgacttc cctccctctt ttctctgcca    2100
tccctcctag accaatgcag ccaccccac ccacaagaca aaagaggcag gagagggccc     2160
tggactcagc tggggctggg cggcttctcc cttccctgaa ctcgccatct gttccagccc    2220 cccagcccc tgcctagcag ccatgggtag gtcactgccc tcacctgggg tcaccccttc     2280
ctccccggag agctctgaca gatatcctgg aacctgaagt ggatccttca tgccccatcc    2340
tgaatcccaa agccaccttc ctgaggtgtt aagaagctg ctccaccttg gaactactat     2400
aggggctgtg gtggccttc attcctttat cagcaaaagc ttttgtcact tgtgtggtgg     2460
gggacatgct tagtgtgaga atgcagagac ccatgccagg ccctacccaa ggacatggtg    2520
ctccttcagc cattgtcatc agagccacag aggggagctt cctggcagag gaggagtggg    2580
gagaagctgt ggaatggctc cttgagctcc ccactccacc ccttcCCcat gcctgggctc    2640
ccattgcaaa gacccagatg tgggcttatc ctgtccccca gccagaggga gtcacccagg    2700
ggtgttcagg ccaacccttt gtgaaatcca tgttccacca gttaccagcc tttctccgga    2760
gagctgaggg ctgtctcaca ctgggtagtc tcagcctgcc ctggggttgg ggggtgctc     2820 acagagcagt aagcgtcact gcctgcatcc ccacacacct gcattatctt gtctgcaaga    2880
cacgtgtgcc cctgagctga gctctgttgt gcaccaccg atttccgtcg gcctcctttc     2940 tgactttct ccatcaacat ttcctgcttg ggcctgttgc gggctgccca aaggctgtgg     3000 actgggccg aggtacatag gactttggct tgtcttttga gctaacagga tcctgtagaa     3060
gaaatgagat gagcctgaga gggggtcggg gggtgagaca ttagggaagg gagaggccac    3120
caagggtctc tagcccagaa tccaatgccc cttcctgcct acctgtcctt gtgggtggga    3180
ggcagggtgt gtgctgactg gcccagcaat ggtgggctag gatttgggat aggcagagaa    3240
aaggaagagg agggggaagt cggcctggga ggagaaacac tgtacaaagt cgaggaggag    3300
agaaccagag tgtgcttagg gaccagacct ggccccacct ggagcagagg atggtgaggt    3360
cagtcagggc tggatcacaa gggacctcaa atgccaggct gaggagcttg gcctttatcc    3420
tgagggcact ggggagccct gcaaaggttt tgagagggaa ttccattacc agatagatgt    3480 cttttggaagc cgcctctagg tgcaaggagg aggtggagta gagaggttga cctggggtaa    3540
gggttggagc atgaccaggg gaggggaag gaagcagggg gtggggatgg agggagtgga    3600
tggatctaag agaatctact gtcctttgga acaaacgata caggaagtgt aggagaggga    3660
tggggcaagg cgactttgaa gtgtccagct cagagattgg aggtttgctg atgcctttgg    3720
gaggccaagg caggcagatc acgaggtcag gagttgaaga ccagcctggc caatatggtg    3780 aaacccgtc tctactaaaa atacaaaaat tagccgggcg tggtgcgggt gcctgtagtc    3840
ccagctactt aggaggctga ggcaggagaa ttgcttgaac ccgggaggca gaggttgcag    3900
tgagcccaga tcgcaccact gcactcccca ctccacccct tccccatgcc tgggtgacag    3960
agcgagactc cgtctcaaaa acaaaacaaa acccaaaaa acaaaaaact aagaagtttg    4020
ctgatgcctt taatagtaac aaaaggtgta ttggatgttc aatatttgag ggacctacgg    4080
gttgttccca gaggagatgt ccaagagaca gcctggacac ctggagctcc agggagaggg    4140
atgggcagca ggggacaccc ggagttgttg gtatgctggg agaaggctgc atgctccgtg    4200
ggagtagggt ggagaatgag gagagacagg gccgccgtcc tgcaaggagc atccatattg    4260
```

```
aggggggcgaa gataggggtgc accagtgagg gagacagagg aggggccgtc tggaaggtgg   4320
gagggaaaca gccgcgcagg acgggcggg ggcgggcgct gagaagaagc cgccttcttc    4380
ggcaaagagg tagctgaagc ctgtggagcc tgcagtcctc tcaaggctat gggggcagcg   4440
cggaggccgg attccagaac tgaatcttcc catcgctttg ggcagccacc ctacctccca   4500
ggagcatcct tcctgccatc ccacctccag ttccccagct aacaaaaaac ggtgtttctt   4560
gactcccggc agggcggcgg ggcgggcagg tcttgtgaac acggctcgca gggttcagca   4620
ccctggagag aggcctgtgg ccggggcggg gcctgcggcg ggggtagggg cgcgcagtca   4680
gagcagtcgg gcctttggct ccgtctggga gcggtcttgc aggcaggcaa ttggtggagg   4740
agggaaaaac aatcttggat tttctccagc tctctcccct ttatgcacct cccccatccc   4800
ggcactggcc tacaggagcc cctatcccag catttgggc tattactctc ctgacgactt    4860
caggaaatga gatgggagga gaggggcaac tatttactgg gaacttttca gacattccca   4920
aaacctcaca acctttgag cttggaattc gtgaccccat atttcagatg aggaaactaa     4980
attgaagttc aggaaggtga ataccttgc ctaggcactt ggcagagctg ggatttgaat     5040
tccacctgcc gggctctaag tcctgagtgc ccattagccc ttctgagtcc tgaatcttgc   5100
agtttgttcc tgcagactct ccacttctgg gtggctgtgg agtctggtgt ggcagtggga   5160
tggggaggag accttcctt ccacctgctt gcttgagtgt attcccagga gatttctgaa    5220
gatgaggcca ccaccattgt ttctgaagtg ggagggcaga aaggaggctg agggccaggt   5280
gagacctcgt cacacctgca cccatgcatg cccaggagga accctccttt gaactcttct   5340
gactcagctt cttgctgcca ggttcctccg accagtgagc aggttcccag acatgaagg    5400
ggagctgtga gggagcagga cgccatggtc cagggctgca gcttcctgag cccagagaat   5460
gccttcctag ctgtcaggaa tggagcagcg aggccccagt gataggtgag gtggagaagc   5520
aagacatgag ttctgggctg gctcagctgc tttacaacca gcctgggcct cgttcccttt   5580
gagaaaatgg tttgcccaga gttcagagat ctaaaattct atgatgcctt ctggggccac   5640
agtgggaaac aaagactcct catatttct ttcctgacac ttcccaggcc acaagacaac    5700
tgctttctgc agcacccagc ctgggcaggc catctacaca agctcagtca tttctgacct   5760
tgcccccctcc accgtgcacc cccatgttct tcaacatggg tcaggtttct attcagcctc   5820
agggacttct ctgcttgaag cctgttgtgt ggcggggagg tattctcccc acagctcaga   5880
gagatggggt tgctgtggag ggtttgctgt agctcctcta ccctggaata tacccctcttc   5940
tgccttaaaa gacccaactt ggaccctctc ttccagaaat gcttgctaac cgccccccca   6000
ccacccaaac taggtcaggg gtccctctgg gcttcacaga ccctgtgctt ctttctgtca   6060
cagcctgcaa gtctccctc cccactcccc agcccgagtg cttctctgag acaagggata    6120
gtgtgagcca tgagctcagc cactggtagg ccaatgaata agtaagttaa tggtgaagcc   6180
aggatccaaa tccccatttc ctgcctcaag gtgtggagct gtttctcctg catacaatag   6240
tagctctgct gtgacaactc tctatctgtc ctagggccta aaatgcctct atttcactag   6300
gttatagctt tatcctaggg agtcctcttt ggaagcaggg tggggtgca acaggccttc    6360
ccccatgcct gtagtctgtg agcagcgaag gccatgtggg gcaggctgtg gcctaggtct   6420
ccacagatcc tggtagaagt ccatgctcac gcatcagctc caagtcccag ctaaaccaag   6480
ccaccaagag gtgggccctg tgacaaggct ctgagtccaa aggccatcag taaagccccc   6540
taagtcttcc gtgacccag ctccaggctg ggatgcacgc taggagatga tacacaccgg    6600
gtgagggagc ccagaggaga gggcagctag ctgtgcatgg aggcctgatc tctcagactt   6660
```

-continued

```
gagggcacaa gcgtgtcccc tcatcctgaa ggcttctgcg atggggcagc agagggtctg    6720
ggtctgctgc ccctcaagtc cccagcccca tcctagccca tgaggattgt aaatccctcg    6780
tcctctcccc tctctcctct gtcagccact ccccttccc cctacccac tctctttcta      6840 tttctgcctc tgattttttt tccttttctg cctttgttcc tctgtgtgtg tgtttctcta    6900
tgcctctctg atctctttgt acttccatct tgatctcgct aaggctctga tccctctctc    6960
ctctccctct tcatgtgtta ctgtcccct tcctgtctct gtttatctct cagtctctct     7020
gtctgtgagt cttttttcct ctctcccagt cagactctct ctctaccct cctctctcc      7080 ctctctccct ctctgtctgg gcctctctct gttcctcctc cctcctccct ccccttctg     7140 cattatcaga cctgctccaa cctcctccca gagccagccg agcagcagag gcagtggcag    7200
cgggagaggc gggagcagcg gggcagcaga gctggattgg ggtgttgagt ccaggctgag    7260 taggggcag cccactgctc ttggtccctg tgcctgctgg gggtgccctg ccctgaactc     7320
caggcagcgg ggacagggcg aggtgccacc ttagtctggc tggggaggcg gacgatgagg    7380
agtgatgggg caggcatgcg gccactccat cctctgcagg agccagcagt acccggcagc    7440
gcgaccggct gagccgtgag tatagtgagg ggctggggtg gtgagcggct gtgagaggtg    7500
ccacagacag ggtcctggga gtccctccaa ggagctgggg ctggcatgga gctgagccac    7560
gtggaaggat cgatcctgtt cctgggcacc cctcctcccc gcgttgccag actgcagcct    7620
ggggtggggg caggttacct ctgagcagaa tgagggtgtc taacgtcaac ctagtaggtg    7680
atgaggctgg ggtcccatgg aagggctgc tggttggagg aggggctgat aatgaacctg     7740
aaccgcttct tcaagggctg agggtgtatg tggggagggg gaggtctgcc aagtagttgg    7800
gaggagctct cggggctgca ataggctggt tcaggaccct ggagagggag agtgtcttgg    7860
cccaccaagg ctatgtgtgt gtgaaggagg tggggagggg gaaagatgga gaaaatatga    7920
ataagagtgg ccctggagca agagagggtt agaggtaacc accttccatg gaattgggaa    7980
ttggggttca gggacaccac tttatgaaac tttaccccaa agcgtctgtc ccaggatagg    8040
gttctacgga gccagatgga atatggtgcc agcctcgtgt gtgtccacgt gcagggggggt  8100 gcatgtgcaa gtgagtgggg ggcgccgtgg cgacacccct ctactaaggg ctgccgaggt    8160
ggtaggcagg gtgtgtgtgt gtgtgtgtgt gtgtgtgtgt atacatgtgg aatgtaaggg    8220
acatgttggg tgtagagggg cctgtagagc tctagggtcc ttggtggttg gatgtaaagc    8280
agcctgtcag agtttgtgat catccctgtg tgagtgagag tttattcgca tgtgtctgag    8340
tgtgagtgca ggttggtctg catatgtatg taggtgtgtc tattaggttg agtttgtata    8400
ttatgtgtgt tgtgtctgca aaatagagtg aatcagtgtg catttttat ctgttccatg     8460 tgcatttatg tgtgtgtatt tgttagtgtg tgaataatag cattgctgtg tgtggaggtg    8520
gatgtggctg tgtgcgtata agtattctgg tgtgggtgtg tgatcatggt gctagtgtgt    8580
atatcggtgc ttctgtggct ggtgtgtgtg tgtatctata tgtgtgtatt catctgagtg    8640
tgtgtgggtg gctgtttcct tccctggca attgaggata cagctgggac accatggccc     8700
actgatgcag ggcagggagg ggctgaatgt atgaccgcct ctttgaactc aggacaattc    8760
attctacacc ctgtgggaaa gatgcagaaa agaaataggc aataatgact ctgccctctg    8820
gggcttccta agcttcttag acataaaata gcttgagaat aattaagcag tagagatcaa    8880
cgtcatgcta acaggtgggg gtggggtggg aactgcataa gcaaaggccc tgggctgggc    8940
atgtcctgga gcagtgaaga cactgtatag agtgggggc aggcaggacc cacattcaat     9000
```

```
agaactttaa gatccaggac tcttaggctt tatccagaga gccctgggga gcccagaaag    9060
gttttatata gcggagagac atgatcagat ttgggttcta gaaacctgcc ctgggccagg    9120
catggtggct catgcctgta atcccatcac tttgggaggc agaagcaggt ggatcacttg    9180
aggccaggag tttgagacga gactggccaa catggtgaaa cccagtgtct attagaaata    9240
caataaaatt agctgggtgt ggtggcacac gcctgtagtc ccagctactt agaaggctga    9300
ggcatgagaa tatgagaatc gcttgaactt ggaggtggga ggttgcagtg agctgagatt    9360
gccttactgc actttagcct gggggtgaca aagtgagact ctgtctcaaa aaagaaaaa    9420
aaaagaagaa gaaaaataaa agaaacctgc ctcggtggca ttgtctgggt tgaactggaa    9480
gagagaggtg gggccaggag gctagagtgg aggccaagcc aatacagggg tcagtgagtt    9540
ctggagcttt ttgagaactt gggaaaggct ggatagatga aacagggaa gggaatgtct    9600
aggtggctca ggcttggact ggggtcaggg gtgtagtgca gacatctcag taagtcagga    9660
tctcatgagg gaaaaggctc atggaaggct caggaaagct gggcgtgggt gggctgaggt    9720
agtgggagag atctttgtag tgtttctagc taggatgcag agggtcagag atcatggagc    9780
catctcttgc cagacaggga aactgagact atggcttcat cactatcctt tggctgcaag    9840
gctggggctc aacctcttca tcagacctga ccctcaatat cattctcctt caggccctgc    9900
ccggaacctc ttggttgctg agcttggtca gctcagtgag ggttaattgt ctttatgctc    9960
cctgcacccc caccccccgc agtcattccc cctgcccacc aagcagctcc tgccactctt   10020
cctgcttccc actccagcct cctgtcccca gggactgctg atggcttggc tgggatctag   10080
ccaaatggtg gggggtgggg gcgggggtgg gggaagagc tcccagcagt cctttacccc    10140
ttggtcttaa tggactggga gtctcaccct cagccatgct gctgtcaggc caggcctgcg   10200
ctccccgggc ttctgctgct tgggcctatg aaatctcccg actcagcatg attccattgc   10260
tgcattcatt cattcaacca ctcaacagga acttctcagt agctgcttgg tgcccacttg   10320
gcttgtcacc ggggacacag agcagacact gactgagtcc ctgttctcag ggagtgccca   10380
gtctgatgaa ggagaaagaa atggaaagct gcaaccctac agggtgagca gtgctgtgta   10440
ggaggtgggg ggcccacagc aagcctgggc ttcagaggaa gagacatttg agccggacct   10500
tgaaggatgg gtaggaatca cccaggcagg gaagagcaga gggaacagtt tgtgaaggtg   10560
ggtaggaaag gcacagggct aggcacctga ctcagtgcag cctctgggtg ggagaagaca   10620
gtaagggcgt ttgggtcatt ttctagcagt tgttttagta ctctctacaa cttgccctgc   10680
agatctatcc agcctgctgt ttgcataccc ccggacatag gatgttcatc tcttccctcc   10740
tgggcagccc ttcccttgtg gtggttatat ctgtcctggg tcttctccgc agggcccagc   10800
aactccaggc tacccagcct ggccttatgt cctttctccg tcctgtgtca ctgtcccctg   10860
aagtagggcc aggctggggc acaatgatcc aggagtggca agaacacatc taggcagaga   10920
gtgggagaaa tgcgcagcct ttattaacaa aaatctgaga tgggtgcagg ccctgactcc   10980
tctccaaaaa taatgataaa gaagcaggca tggccaaata agggagtgag acagacagc    11040
aggaagaact tcctaccaat gcagaagggc tgtgagtctc ttggttttat gagagtgggc   11100
tgtacgtgtg aaagggaggg tctcagagga caagaggggg aattggaggc agaggcactg   11160
tcagcctctg actctcccat aggtgagtga gtgaagtcat ccaggagag ggaacagagg    11220
agggagatca ggactcatca ttcattcatt cagcagccgt tcactggccc taccaaacat   11280
gacacccctg ggggcagatg gacagagcca gtgaccacgt ggatgaaagc tccgagtctt   11340
tcctacctgt gttaatgtcg caggaaggta tttaggagga ggggccattg gggctggcct   11400
```

-continued

```
tataaggaag agccacttca ggctgagttg agggacagca ctaggaagat ggaagagcat    11460
ttgcaaaggc ctcaaggtaa gggcaagcag gattttgttc acttagcact ataggagttc    11520
agagtggcct aggcatgaag tgccaggctg ggggaagcc  ctgggccgtg gtggagcagg    11580
agaggagtgg ggaattgagc ctagactgta ggaagcactt tcttccgtga aggtgtctcc    11640
aacaggcttg atgtgtaggc attattgtaa gtttgcaact tcttggtctc tcctggtgct    11700
cgtgaccaga gcttgctgag ggacccagcc ttgcttgaga aagggtgtt  cagtgaacaa    11760
aagagaccct ggaaatgaga gagaagcagt ggctgaagaa tgtgggcccc ttccagaaag    11820
tggcgtgcaa acaaatacaa agcaatatgc aaatcagctg gctagggctt ggcagctttg    11880
gttggaagaa atgagccatc acccttatt  atgccggcct cctacccct  ctgcccagc     11940
ctccaggaca gccggaacag ccttgtctgc tccttggagc gccccagctt ttctgagaca    12000
caggattgtg gcctccaggg tggtggccgt gggctccctg tcagcaccct cgtcctcctg    12060
ggaagtcgat atatttagta acagaaatgt tttcacacat ttatctccta ttgttcagct    12120
gcttgctccc tgggaaaggc caggtcccca gtgatgtgac ccacttcttg aagtccctga    12180
agtcacccct ctcactgccc ccccacccg  aaaaacagga ggcaactggg gcttggtgca    12240
gcagaacaga tttgagtcaa atatctggga ggacttccca acagtgtggt tgctgagatg    12300
tgtggaccct ggatttctgg gctttcattc tttggatggt tgccttgggc gcagaggagg    12360
ctttgaagat agagcagaga aggtggcagg caggcttatg ctcaaatttc agcatactga    12420
aagatgtact gttactctgt agctgtgtgg tcctgggcaa gttacttaac ttctctgaac    12480
cttgtgtgaa tagtggggtg gagataatta tcctttcttg gcaggatgat tctgaagaat    12540
ctggaagtgc agagcttagc ccctggcatg cggcaggtgc tcacaaaggt tagctactgt    12600
cattatgaac cacccacgat cagccacact ttcagaaaga tttagcgggg cctggagagg    12660
gagagaccag agctaggagc tcagggctgt catcgtgtgg gagggaccag gaggcctgaa    12720
acagagctgt ggttgtggct acggtgagaa gcacaaagct ctgtgggagg gaccgaggtt    12780
tctcagagaa gtgtggccac ctcattaagt tgttctgact ggtctgagac caatccccag    12840
ataatacaat ggaagaaagg gcttggtgaa gaaggggtta agtctgtggc cacacccatg    12900
cagtctgtga gccattctgg gagctgtagt ctgttgtgaa tttgcagtaa gcatagtttg    12960
tactgcctct tttgatccaa atccacaccc tgctgccaag gctggccgag ggccggccct    13020
ggtgggtgct gggctgtgtg gagcccaaag gtgaagcagc atcgacctct tccctcaggg    13080
acccctggc  ttgctatgtg ttggggggtg caggtaggag cagggataga agtattaagc    13140
cataattacg acttctcaca tgttcacaca gaagtttaca gcttcctgag cactgttttcc   13200
acacctgtga tctcatttaa tcctcaccac aaacccaaga gactgctgtt ttctggatga    13260
agaaacagag gatccaggag gggaaatcgc ttgcccacag gtattcagcc agtgagcca     13320
gacctgggc  acaaatctgt ctgcttccag agctcctgct cttccatac  attactgttc    13380
cagatggcag acaggcaaga tgtggacaac taaagttgga tgtgagacat ctcggcagag    13440
gaacagctga gcagagagct gctgattcca ggctgagagt ttggactttg tgttgtggcc    13500
caccaggatc cacccaaggg ttttctgatt agagctgagc tttgagagaa ttggtcttgc    13560
agcttaggct gaatggattg aactggagaa accaaagtca gactgaggct tctaaatccc    13620
atccttggtg cacccagcac tttgctgctg tccctcctcc atgcttcttc tcagtttctt    13680
ccttctcctc tccttcatct tcttccctca ccctttttt  tttttttttt aatagagaca    13740
```

-continued

```
gtgtcttgct ggctggagta cagtggtgcc ataatagctc actgcagcct caaattcctg    13800
ggctgaagct atcctcctgc ctgggcctcc caaagtgctg ggattacagg tgtgagccac    13860
tgcacccagc tcatcttcct ctttctctcc tactcctctc tgcctcaggc tgaggagtga    13920 tgactttat accatagagc tgtgctgtaa tatcacatgt ctccagaagg gggtgctgtc     13980
acatacagtc cattccagcc tgaatcttcg ttgtgtttga agggccagta gaagtgttgg    14040
acaagtggca gagatgaagg atggagagaa ggatagccca ttgttctcca cctccattga    14100
gcccaggaca tgagggccct gctgaaatgg cactgggagg aatgaaggct gaggagaggt    14160
tggaccccaa ccagaaggga cagacatact gagttaagcc agaggaaatt ttctcctcat    14220
ggttctggga caggctaaga tttggaaatg catctagaat gacattgcag ttggggtctg    14280
ggtttctttt gggtcatgac ttgcttgata ctgaggtgct ggggatattg cttgtgtctc    14340
agtgtgtgta tgtgtacctg aatgtgagct tccagttgtg catatgtgta tgctgatctg    14400
agagggtgag aatgtgtggg tcagtgttcg tataaaagtg tgaacatact cacatgtgtg    14460
agcatgtgag tgtcctttt tttagtttag ttttgagaca gggtctcaca ctctcaccca     14520
gactggagtg cagtggcgtg atctcggctc accgcaacct ccgcatccca ggctcaagct    14580
attctcctgc ctcagcctcc tgagtagctg ggactacagg catgcaccac cacacctgca    14640 taattttgt attttagta gagatggggt ttcaccatgt tggccaggct ggtcttgaac       14700
tcctgacctc aaatgatcca cccaccttgg cctcccaaag tactgggatt acaggcatga    14760
gccactgcac ccggctgtga ctgtccatct ttatgtctga ttttggtaaa cagttatatg    14820
catgtgactg tggcttgtgt gtgtgtacat gtatgtagag tgccatatac atatgttcta    14880
gtgaaaccgt atgtgtgttc cctgtgtata cagatgcctg tgtctcaatg tgagcacagg    14940
gatgagggga tatgtgtgtg tgaaggccca gacacctgct gtgctaacct ttaaggccgc    15000
gcctaatgtc tggctattca atactttttc tcctgggtcg cgctttcctg taggtagaga    15060
cccttgaagg gctgggcttc cttcagggga ctctgggcca gagtcaggct ttgtgttcag    15120
tctcaggttg ggccagccag ggtcctagtc tatcggattg ggcagctaga catggctggg    15180
aagtgtctag gttccattct ccccaggaac tcttaatggt cacacttaaa gagtttcagg    15240
gactcccagc acggtcctct tgtactgatg caactactga agttcagaga ggtgcagtga    15300
ttaacccaag gtcacccagc aggacccagg atgagatgat agggcttgca gcagagaggg    15360
gagtgtctga cctggaaggc tgccctccct ccagccccta gagcaggtgg ggagctcaga    15420
ggagagccaa gtctgtggtg tgaagccacc tcctgcacct ggctatttcc atgcctcctg    15480
ggcctcagag gctgcctttg aagttttac cagagcttct gcatgctgtg agattcctcc      15540
tggggacgtg tgaagtcgac tgttccatgg agcatggaga ctcgatggag aggagcccag    15600
tggtgaagtg aggccagagg aggggcttcc tctggaagcc tcaatttctt ctttgcagta    15660
gttgcttttt ttttcgtgtt ttttttgtt gttgttttt aggttttcac cgttctaaca       15720
ttcaaggctt tctctgttat ctctctttga gctcttagta ctgagacagt gctgggttt      15780 ggggcagtcc tggaggccta tctgggctca agtgagggt ggcagggcag tcccttaggg     15840
aaagggctgc gtgggagaca gggatgagct tcctgcccat agtgggagg catgagcagg     15900 ggctggacag cctggttagc aaggctgtat acaaggtacc taccctagtg aggaagttgg    15960
ttgcagatta tcttgagtcc cttcaagctg tagctgccat gggggccag agaagaacgt      16020 gcctcagctc tcttgggcct ggggaggatt gagtccacag agtgctcctg gtgtcctggg    16080
cagtggaagg tgcaaggtta gactgtgcac ctggaagcag agagatccca ttccctggag    16140
```

-continued

```
aactgaaggg aaatttgtct tcctggaggt ttggggctgg aggcaggggc tggatgggag    16200
gacactctgg ggtggagtgg gggtgggatg gggaggactg ggcaagtccg aggcggctct    16260
gctgttcagc acccgcagga aggagcaggg aggcatatcc tgaatcatgc agggctctag    16320
ggtgggaggc ccatggttgt ggggctcaaa catgggctct ggttgggcca gaggagaggc    16380
ttcctggggt tggggtctgg gcaggaattg ggtagaaaa ggagagaagc agcaattggg     16440
taccacctcc ttcccaggtc aggtaattcg gagttgtctt aaaactctca gtgggccagg    16500
catagtggct cgcgcctgta acccaagcac tttgggaggc tgaggtgggt ggatcacctg    16560
aggttgggag ttcaagacca gcctggccaa cctggagaaa ctctgtcttt actaaaaata    16620
cagaattagc tgggcgtggt ggtggatgcc tgtaatccca gctactcggg gggctgaggc    16680
aggagaattg cttgaaccca ggaggcggag gttgcagtga gcctagattg tgccattgca    16740
ttccagccta ggcaacaaga gcaaaactct gcctcaaaca agaaacaaa caaaacctct     16800
cagtgagggg ggatctgggg tccagatgga gagaactaat gtttacagag tgacctttaa    16860
gttttaaaaa tgattattta aggaggcgat taaacaaatc gcctccttaa ataatccttc    16920
cagggaggcc gggcacggtg gctcacacct gtaatcccag tactttggga ggctgaggtg    16980
ggcggatcac gaggtcnnnn nnnnnnnnnn nnnnnnnnnn nnnnnnnnnn nnnnnnnnnn    17040
nnnnnnggaa aagagatatt agntggagta ttagtaagag ataaaagaga aaacaacga     17100
aaaaaaagca gagtgataga agggaaatag aataaggaag aatagattga tagtagcggc    17160
ggacgaagaa aaagacgaaa aacagcgagt acggaggcgg gggcggtata atgagaaaat    17220
agaagatgaa cgcgatacga aggatgaggg cggaggaaa gtacaatggt ggtgggtat     17280
ggaggcgaga gtgaaaggga ggtaaatgac gcacaaaaac aaaagacgga aggggaacag    17340
gaggagggg tggtaggggg gnatcgcctc cttaaataat ccttccaggg aggccgggca    17400
cggtggctca cacctgtaat cccagtactt tgggaggctg aggtgggcgg atcacgaggt    17460
caggagatcg agaccatcct ggctaacacg gtgaaacccc gtctctacta aaaatacaaa    17520
aaattaaccg ggcgtggtgg ggggcgcctg tagtcccagc tactcgggag gctgaggcag    17580
gataatggca tgaactcagg aggcggagct tgcagtgagc cgagattgtg ccactgcact    17640
ccaagcctga gggacagagc aagactccgt ctcaaaaaaa aaaaaaaaa aaaaaaaat     17700
ccttcaaggg gctagcccta ttttgtagag gggaaacaga tgacaaactt aaatggttta    17760
actgaagaca gttagtgaag caagtattat ggagatgggg aaggcttaag ggaaccagca    17820
ggacatgtca agttactcag gactggcatc caaggggcca ggggcgttgg cagagggggg    17880
ccgaggagag tgccccagct ccatgagcca gagccctgga gatggggctg ccctgcagga    17940
gctgtggctg cagccactgc ttgtcgaagg aggcaggtgg gtgagggggt gaatacccac    18000
catgagcctg catgcttctc acccttttgct ctcctgccag taccctgacc ctcactggca    18060
gaatttctct ggatgccagg gggcaaggga gccctggatg aagctgccac ttagaagtcg    18120
gcctctgggg cacacaaccc agcagcaaaa gttagagatt ggatgtggag ggacaaagag    18180
atgatgggaa accgaagaac agagagggca tggacttgcc caaggtcaca cagcctgttg    18240
atatcagaat tggagtcaga agccaggctc tgcctctgaa cactcacttt tttgtttgtt    18300
tggttttctt tttttctttt cttttttttt tttttgaga cagtcttgct ctgtcgccca    18360
ggctggagtg cagtggtgcg atcttgtctc actgcaacct ccacctcctg ggttcaagtg    18420
attgtcctgc ctcagcctcc caagtagctg ggatcacagg cacctgccag catgcccggc    18480
```

```
taatttttgt acttttggta gagacggggt ttcaccatat tggccaggct ggtctcgaac    18540
tcctgccctc aggtgatctg cccgccttga cctcccaaag tgctgggatt acaggcgtga    18600
gccactgcac ctggcctgaa cactcacttt gtcacattca ctgaggtctc ctgagtggac    18660
tcatatgcgc attatctact ctctggctga gagctgcttc ctgccgtgat caccgcgctc    18720
tgtatctggg cagcacaggg gctgctgaag aatgtcattc tcagaacgca gtgtgccctg    18780
gagcccccca agccacctgt tcattcatcc caactggcct tgaggtgcc ctggtgtgcc    18840
ctgcctgtgc ttgtcaccct ggccatggag atggacccaa aagcccttgc tctccgcttc    18900
attagagaca ggcacaccca gacgcaggca atcaattttg tcgggtgagt gctgggaccg    18960
ctgatgagga cccttcctga ggaggcgatg ctgggtctta gccttaaaga caactgaga    19020
gttttccagg tggaggagaa aaggaagggt attccaggca aaaatcccca taagagcaaa    19080
ggtgtgagca gcaagaaatc aagggtggca ggttcagggc tcctgggctg gaggaagggc    19140
ctggcggtgg agaggaaggg agtgaaggcc cagctcacaa aggaagcag aggaaagttt    19200
aagcagggtc aggccatggt tagctttggg gttaggaagc tccaaatgat gggtgaagta    19260
gggggggctag acccaggtga gaggcagtat tgcggttggc caaggacacg tgagttgcat    19320
aaatgggcca gaggagggt gacagccgct acttcccggc tcacctgcct gagctaaggc    19380
cctagttcct cagtgtctgc ccaccaatgc aggtgtgtgg cagctctaga ccctcctcta    19440
gggacatccc tccctgcctc atgctgccta tggctttcac tctctggagc actcatccat    19500
ggcacccata agccaccccc tcagacaatg gcccctaaag caaaactgtg tcaccgttgc    19560
atatctcttg ataacactct gaccctcca ctgccaaatc tgataaaaga cctcccttg    19620
aagaccttcc tcctggagtc ggatctcagt ccttcttgct gtccagagcc tgggccttgg    19680
gcctccctgg gaggcgagtc agtgagggca gccccttat ggtgctggga gttgagggac    19740
cttggcccag ccaactcatc cctgttgtgt cagcctctct gggcctgggc agccaactca    19800
ttttcagtgc taattagcat ctcccctgca gctttctgcc ccactctaag tgcttgacaa    19860
tcattaggtg ttactgtgtg caactggatc ccagctccgg cacctccctg ccccagcttc    19920
tcctccagac cccagctgcc tgagataagg gacctggcca caaacataca acacaccgaa    19980
acccggacac aatctaggca tagggacttg aacaccaaca taaatataca aagaggaaaa    20040
acccaataac acagaagaac tccccatacc aggaagcaga ccatagcaca gacagagacc    20100
cacagtacac acacaacaca gacaccaaca gatgctgaaa agcagacaca ggatcattcc    20160
aaaaagtgac ccagaaacga aaacagaaca aatgggaaca tcaatgcaca tgacacaggt    20220
atacacatct agatatgcaa cacagtacg attcagcaca tgtgtggcgc atcgcaggga    20280
agcacttgca cttgaagtat acacagatgc caagatagtc agagggagcc gcctgtggtt    20340
ccccacctgt gcagcgtctc tcgcctctgg gctgccgcac atgctgttgc ccggaattcc    20400
cttccccaag gccctcctct ttttacctgg ctaattcctg tcattcttca gatcttctag    20460
gaagacttct gcctccttga taggggcctt tccatactcc ccagccttgg agtgcttcct    20520
gccacatggc atcactgact gttttccaat gagtttctgt caagttttgg gatgaaggat    20580
tttgcctgtg ctcgttgagg tggtgactgt gggtgtgagt gggtgattag ggccaaaaaa    20640
accccccaaa aaactggaca gaggcaaatt tgggggaaa tgagttagga atagctgtga    20700
ggagccccag ctactcaggg cctcagaaga tatttatttc tgtatttatt tatttattga    20760
gacagagtct tgctctgtca cccaggctgg agggcagtgg cgctatcctg cccactgca    20820
acctccacct cccaggttca ggcgattctc cttcctcagc ctcccgagta gctgggatta    20880
```

```
caggtgcgca ccaccatgcc tggctaattt ttctattttt agcagagacg gggtttcacc   20940
atgttggcca ggctggtctt caacttctga gctcaggtga tcctcctgcc tcggcctccc   21000
aaagtgctga gattacaggt gtgagccact gcacccgacc tcagaagaca ttgaaaccca   21060
cagagaggac acagccagat gccctctgcc tcattttctc agaccctgcc tgatttctct   21120
tatgtttctt ctaggcttgc tccctgaccc agttccctcc ttcccagagc tggccttgcc   21180
ccttgccacc tctcggagct cacacatact cactcacctt ctctgcttgg ctgtgcccta   21240
cccctacttc tacgtgcagt gaaatccttg ttattcaagg cctgaggtca gtgggcacat   21300
catccatgcc tggcgtccta acccgtgcca ctgagtatcg tgaagggagg tagtggaggg   21360
acgtgcttgg gagcacaagc cttgaggact gtctcttggt tcagatctct gctcctctac   21420
ttcttagctg caggattgtg caagttctgc cacctttgtt ccctcatctg tagaaaggag   21480
aggataatag agcccacctc attagggcag ccatgaggat taaatgagac acagtgtgta   21540
atgtacctgg ctccctctcc aggttgcgtg agagcaggga gaaagctaat gagatcaagg   21600
atgtgcaaat gcactcagaa ggtgcctagt gagtccttgc taactggcac ttagtgaaac   21660
aaacacctcc tgtgtgagca cctaatatgt gcctctgtag tgggctctgt gacccgcccc   21720
tccttagttt ctgcatggct gccagttctg cacagctgtt actgctgtgg gggcttagaa   21780
ggtgggggta tgactacttt ttctgaattt attttttaatt ttttacatct gttttatgga   21840
ggcataattt acatacagta aaatcaccaa tttaaagtgt ataatgagtt ttgataaata   21900
tatatggtca taaccaccat gacaattaag aaaagaatat tttatcctg gcaaacttcc   21960 cttgtgccct ttgtagtcag tcccttgag ggggacttct tataggagtg tgagaagtac   22020
tgggttttcc ttgggctgca aacctgggca catggagtgg gggtgcctcc aacatgctgg   22080
aagttgccag ggaactgctg accctctctg ggccttggtt cctggcagag gcagtgcagc   22140
caggcagggg aagggatgct taggccttgg tctcctgagg gcaagccttg gatgtgaggg   22200
ttggatcagc tggaagtggt ggcttcagaa acccatagag tgggtgacag ggtagggact   22260 tggtgttttcc acaaacccgc ccctccttg accaggtgtg ccctgtggtc ctggtggaaa   22320
tggctatata ttgtccagac tgtagcaggg gctggccaag atggtccact cctctcccca   22380
tcctcctcca accagaggcc ataaacccca ctctatagat taacaattcc ctgaaaagaa   22440
gggggtcact tttgttcccc agttctagaa ctaaatatta aagcaattat gtaactagca   22500
ataaattact taaagtagtg actcactcag cttaattaga gcgcaagcaa ggagggatta   22560
aggtattttt agagcacaca cctcactctc tcctgtgggg gaggcctctg tgcaaggtgg   22620
gggtggaaaa aaggctggga actcatggga gcacccagg tgtctgcaag gagatgaaag   22680
ctgatcctcc gccccactga ggtcctaagg aagaaaggcc gagtcagagc tgcagcagga   22740
gggattcgga tcagactcaa gaacacttcc cagtggtgct tatttgagaa ctgggacggc   22800
aacactagat tgtaaactct gtgagggcag ggattaggtc tgtgaccgcc tcctcaccca   22860
gcgggagacc aagaatgaga cttgggagtc agacacaact gggtgtgact cctgcctttg   22920
cgggttgcca gcacgtgggc ttgggcaggt tcctttatca ccagaagctt tgccgtctcc   22980
tccactataa agtgggcaca ataacatcca cctgcatgca tattataagg attgagtggg   23040
ttaaaatgtg caaagcaaga ctttgtgctc agctgggcac agcggctcac acctgtaatc   23100
ccagtacttt gggaggctga gacagagtgc ttcagcccag tagttttgag accagcctgg   23160
gaaacatagg gagaccctgt ctcttaaaag aaaaaaaaaa ttagaagact cggtgctgac   23220
```

```
tctgctagac caaaagccca caaaggcagg gattaggttt ggtttgtgtt gttcattgtt   23280
gtatctcaag cttcattcat aggactgcac aaagtaggtg ttcagtaaat gctttgttgt   23340
gtgactgcgt gttaattttg ttcccattct cctgctccaa aaaaaagttc attttcctga   23400
ggttgtgagt gaagaaaata ggcagtgtgg gctggtgtg gtgtctcatg cctgtaatcc    23460
ccagcacttt gggaagctga ggcgggagga tcacttgagg ccaggagttc aagaccagcc   23520
tgggtaactt agcgagatcc catctctact tcaaaaaaat ttaaaacaga aaaaatctag   23580
ggtgtgtggg ggggcaggtg gggaggttgc agggtgcct cacaggtggg agtctggcat    23640
ttctcctcca ggctgaggag gtggtgactt ccagggaaag tcctgggagg atcagaacc    23700 acagctccag cctgcttgga taagggtggt cttctggctg ccaggagggt agctaggtgg   23760
gaagatctgc ccttgtttcc tccataacct ggggtgggag gaggaggagc tcccagccca   23820
atctgatggg ggagaccaga accctcaccc accattgctg gcagttcaga aaggcagcg    23880 ataagtcggg gtggggcatc ctgaaaggct tcccagagga ttggatggga ggattagctg   23940
agaagacatc cggcatccgt aaaatggagt aatgattctg accctgcagg ttttctggga   24000
ggattaaatg agttacattt taaagatgcc tggtacatgc ctgccaggag aaggcacaac   24060
atatgaactc cctccctctt ccctccaccc ctcctcagct cctgtgacat caggagggac   24120
atgccctgcc ctgctcacag aggctgggtg ggaggctccc atcatggcct tcactgaggc   24180
tgcctctgca gttggaccaa gctggacaca cagtaggtgc acataacaga tggggcagg    24240 tctgtgcttg ttttaccagg gtgttgggag gctgagggaa gggcacagct ggattggggt   24300
gatggagttc aatccctgct cctcccccag atccaagatc ctaagacgcc tatgtccagt   24360
ggctgctctg atcagctctg accagctctc ctcacacctc ataggccttc cagggttcag   24420
gtgatgaatt agtgatgaca gcatccagca tcgctatgac aaccacatgg cactcttagc   24480
ctccagtcag ggctcagccg cagaggccag agacccottt ggctctgggc ctttgtactg   24540
gcgtgtgtga gcggggctgg ggcctgaggg agatggagga gtgggagggg caggggccgg   24600
ggcatggggc tgcatctggc atggactgga gttcattcag attgttccat ccagagggac   24660
cttggggaca gttgtttctc tccttccttc ccctttctt ttcattcctc catccctcct    24720
cttttccctc ctcccactc ttctgagcct tgttcctgtt tgaggccctg ggctgccaac    24780 cctttccc tcctctggga ataaagccag gctcagccct caccccgggg agctgagtga     24840
ggtgggggac agccaccttc tggtctaggc ctcaggaaag gtgtgtgggg accactgatg   24900
gcttggtgag agggcctgac ccagctggc caggggctgt gcaagtggct gctgaccctg    24960
atgagtgggg aggaggtttt cagtagagag gcagggtcag agatgaagca gcgtgggatg   25020
ggggagcgac agatgttcag agtggcctaa gtgtgagatg cggagcagag aacgtgggag   25080
gaatcgaggc tcgagaagga ctgggagaga gtggatgcag tgaggagttt gaagtttgtc   25140
cctgggggaa gaggagccct gaagattttt gttgttgctt ctttgatttt taaatggag    25200 ggttcatttt agagatgggg aaacaggccc agggtgggaa agtgacttgc tcaagcttaa   25260
gtcactagag acagactgag agtacaggct ctgcttgggt cctgctggac tctagctggg   25320
acctcttgcc ccagacttgc tggccaggat tttcccaggt aatcactacc tccgagaaag   25380
gcgaggagag cccatgggtg actttgccct cagtttgaat gaaatttgca tcagcaaggg   25440
ctatgccgat agtcctttct gctcgtgtct ggcctgtttg ggggtgggag tggggtggag   25500
gtgagcatcc agggaaggat ctgggaagtc aggggcttgc cagggccagc aaggcattag   25560
ggtcagagat ggattcaaac ttgggtcttt ggagacccag cccagactct gtgctccatc   25620
```

```
tccttcctcc gtctctcagg agcctttggc tgagttaggc acctacagga ggcaagggcc      25680
cccccgagcc cctcacattc tcctcagggc tccttctggc cctggggcct gatattgggc      25740
ctgctgtgct ggaacttatc caggcagaat aaacctttag ccccattgtc ctgatgaaga      25800
aactgaggtc ccgaggtaac agtgactcat tcaggttac aacaggtcag tggctgggct       25860
gggcctagcg tctggccctc agcttgtcta catggccccc ctcgtggctc tccccttgcc      25920
tctcgcaccc cactgtgcag catggttggg cctgccagcc ttgatggatg ctctgcagc       25980
tcaacctccc tcccattcct ctccagatgc cgggccgtga gcctcctaat caccagtcct      26040
gcctggtggc cgccaagcca tccatctccc cacacagcct tgcccagcac aggtgatttt      26100
gtttggggag aaggggggca cagcaggtct tcctctgagg ctgagccaag agtttggctg      26160
cagcccccac tctggggtgc ccgagggtta gggaatagcc tgcactccct tgctggagtg      26220
tcagaaatcc ctcctgaatc tccctagggc acgtgcacat gcacacacag gcacacacac      26280
tcacagtaac actaataaaa gctctcgtgt agcaaaagaa tattgtatgg caagtattgt      26340
tgcagagcca tatgtatcat ctcattcatc actccactgt agagatacag aaactcaggc      26400
tcagagaggt taagtgactt gcataggctc catatccagg aaatggagga gctgggattt      26460
gaacccacat cctttatggct cacatcttgc attcacaact cctgctctac tgactcacct      26520
gtgcacacac acacacatgc acacacacac acgtgcgtgc acacacacac acaggcactc      26580
acttgcatgc atgagcacga gccaccattt tggctcttgt accatccatc tacctgggcc      26640
aggttcttga ggagtgagga gaatgctggg ctgcagaggg catgagggt cactgctcat        26700
tgtccccagg ctgccccaag ctggctgtgg cactggctgg ctgggagct gcagggaggc        26760
agcagcctcc aggcagtgga aaggggaggc tgggagacag tcgatcgatc atccctgcag      26820
tgcctccttc caggaactgg ggcccagggg agtgtggcgc cacgggtcga tgttctgggc      26880
agcagcacag tctctgagtg cgtacagggt gtgtgtgggg cgaggctggt gtgcagctgc      26940
ccgccttccc ctggctccct tcccctgctc ctgccttcct cctgccattc acctgccagc      27000
cccacacctt cccctgattc ccccactgtc cccaacctgg gcactacaga ggctgagaat      27060
caaactccca gttcccaggc acctgtgtgc ctgctgctac catcccgccc tgccctagag      27120
gcaggtctcg ggtgggtgct gcaagagtca ccctatggtg gttggggatg ggtgggtagg      27180
gggaccgggg gctggagctg tggggatgtg aggcaagccc acctcagagc ctttggagac      27240
ctcgacagac aatacgatga gttaagaaat gtaaagggc acatagtggg tgctgaattc       27300
atcttgtctc gttcctccag taagagtctg gagaaaccaa gagcagctgg gtgcctctga      27360
gggcacagga gctcccaggg ctggctggca ggtgcagcta acagtgttag caatcccaag      27420
gacaggtagc ttgggcgga ggacagcatg ctgtcaccca tcctgatgag gggagagatg        27480
tctggtgcta ggagcagtgg tggccggagg agggctgggg accctcccca ggccacccca      27540
cactctccct ctgggagggg ctcctgagca ggcctggtca ccttgcttct tggctgcttc      27600
ttccccggcg gaggagcctc ccccaggctc tcccacctgc actggcctca agagagctgg      27660
gattgagccc cagttcaggc acctgctggc tggcggaggt tagggcaaat cactttcctc      27720
agccctctca tccgtgacag gctctggtga gggttaaatg agatgttgcc cgtcaagtgc      27780
ctgccacttc cctgacgccg agcagctagg ctgctctggg ttctctagca cctgcctccc      27840
ctggtcccag cactgggtgg gcggctgtgt tctaccggtc actggtgggt cctcagggcc      27900
ccgacacagg gcctgctatt gggaaagagg gaagtaaaca tccagggct ggagctctgc       27960
```

| | |
|---|---|
| ccactatgga ggtgttccat cttaggctct gtaatctcct cattcactct ggtatgggga | 28020 |
| caaatgtgcc tctctgcact aactgagccc ccatgggcaa ctaggagtgg tgtcacttgg | 28080 |
| ggtggaggtg ggcaaggatc tctggactgg gatttccaag ccctgacttc ctgttatttc | 28140 |
| aggcactacc tcattgttcc atcttgggca agacctgtcc ccttgagggt aagagacaca | 28200 |
| tgtgacctct gacctccaga gtctctcttc tgagcttctg tgcccagatg attctgtgtt | 28260 |
| ctagggggaca ggcgaggctg gggggtgacc cccatgccac tgatgggcag actaaggagc | 28320 |
| aggggcccag gactgggggcc agctcaggac tctggtggcc tcggtgccct tgacctggta | 28380 |
| ttgctgccgt tttgccccac tgctgtctgt ctccgcgtcc gagtcaccac ctgtccctct | 28440 |
| ccagtcctct cctctcttcc tttattacta tctctatatt gcctcctgcc tcaggcttat | 28500 |
| ctcctcctgt catgcctcta tccacctctg tcactcccct gcgactctgc ctcactccct | 28560 |
| ggcacaccct ctccctccct gggagtcggg agtggagcct cgctgggaat caggacccccc | 28620 |
| ctgcctctgg tctctgtcta agcagtctct gcgattctgg ccagctctta tctttttcca | 28680 |
| ccttcccgaa tctctcttgc tgtctgatgg tgtctctgcc tttcactgtc tctgaactcc | 28740 |
| ctttgttttt ctctatatgc ttctctctgc tcttatctct gggcctctgt ctctcagggc | 28800 |
| ctgactggtc ttgacctctt tgcctccttc ttcccctcga gagcccagcc aggcagcagg | 28860 |
| tccagccctc cagcccagag aacagatgga gtccaccctc cctctctctt gctggctgcc | 28920 |
| tcggaagccc caaacaatgg cctccgccct gcaccgtgcc ttgttgctag gccttgggct | 28980 |
| ggcagcacct ggcttccata gcgacgggtg cttagaaaca gaatgccaca tctcccagtc | 29040 |
| ccaccacagg agcctttgcc gattgagcga gtgccttttg atcaatcagg aagtgtggcc | 29100 |
| aggctctagg ttgcctccaa cttgaggagg caagagagga ggggactgtg gtctctgcct | 29160 |
| tctggagctg ggggggactgc tgggctggga ggagttgctc aagtacagcc ctgaagccaa | 29220 |
| ggaaggactg ggggagcccc tgggctctt tccccaagtc agcctgctgc aagaggcaca | 29280 |
| agcttgggag ctggaagggg ctgtgttgaa attgctgttc catcatttct agctgcatga | 29340 |
| ctttggatga atgacctcag gtcccagggc ctcagtttca tcaactgtaa aattgggcta | 29400 |
| ataatatcat gaagattaaa tgagagaata gatctggcac ttagtaggtg gtcatcaatg | 29460 |
| gccattcccc tcccttcccc tttaaagttg tttaaaattt aattgacaga gaggagaagg | 29520 |
| agggttcttc aggcctgtgg aatggtgtaa gcaaaggggt ggaggctggc atgcacctca | 29580 |
| catatgctgg agtatttagg gaggaccagg ggccatatct ggaaatggtt ctgccagaag | 29640 |
| cagccaggcc aagctgggtg ccatgtcatg cacctgtaat tccagctact agggaggctg | 29700 |
| aggcaggagg atcacttgag ccctggagtt ccagatcagc ctgggcaaca tagtgagacc | 29760 |
| ccatctcaaa aaacaaaac acaacaggca ggctgatggg cccatggaga agggactctg | 29820 |
| tctcctggga ggtatattct tgccaggtgc aaagggatgg gcttgactaa tttctcctct | 29880 |
| agcatttggg gctgctgggt agggagctac attggggtcc ccttgcttat tctcatgctg | 29940 |
| ctccctactt ctgccctgtc acttggtccc aggagagggg ctcccactgg ttccttttcc | 30000 |
| ctgccaggcc tgcccaccaa ggccaccatg gccacacagc ctgaatcctg ggggccagcaa | 30060 |
| gtgtccatgg aagccccac tctgtcatcg tagagatcag gaaacaggct cagaagtagg | 30120 |
| agggcttcct ggtcctaggg cccagctctt ccctctttc aggcctgtct tctgcactaa | 30180 |
| ggacttcagg ccaccaggga aggtggggag ggaggaaagg agatgagata gacttgggcg | 30240 |
| ggggcctgag gacagagttt catgtcactt gggcagccag gaaagggtta aagatcccctt | 30300 |
| atcccaagcc atgggcactg gcactgccag aggatgctga ggcctgctgg ggcataagga | 30360 |

-continued

```
caacaagcaa catcctttc tgagctgttg ggagtgccaa gctctctgtt aaatacttt     30420
gagcctcttc tcatgtattc acagccacct ttcaaggaag gccagttgat ccccagttta   30480
gaagtgagaa acggggtct ccaggaggca cttgtctaag gtgacacagc tggagagttg    30540
gagatggtgg ttagaccgag tcaccccccc agaccctggc ctctccctgc gtgcccttc    30600
caggacaccc atcactccct tgacacccct tgggagtggg tgttcatttc cttgggctct   30660
cccaatccca gtccttggta tccccaactg caggcagaca caggtgcttg ctgctgtgcc   30720
ctccccttta cctggcatca cagagactca agcccactga ccattaggct ctcaggggca   30780
tagaaaccag gtgctggagt cttagagtcc tgcaatcagg catctcaggc agtcaggaca   30840
ttagaatgtt agaatcttgg gcttctacat tctcaagacc ccaggttctc gcattcacag   30900
aatgtaagaa aaacagactt tttgaatgat ggggtgttat aacagaagct tgatttct    30960
aagaacatga agctctggga gttcttggag ccttgaagcc atagactggg gcctccctgt   31020
gtgatggttt ctgagttagc agggagtgtt cagagtatgg ggccttggtc cctgttgctt   31080
agaccttctt gccttggtat ctctgatggg ctcagctctt agtagccttt gtgtatgtgt   31140
gtgtgtatgt gtgtgtgtgt gtgtgtgtgt gtgtgtgtgt gtgtgtgtgt agtggggact   31200
ggggtcaggg gtcagggact gactctaacc tgaggcaccc ctggagtggg gccagcccag   31260
gaatagcagg tggaggaaag ccgggcagcc tcagggctgc agctgtctgg tggtacaggg   31320
cagggctctg ggtggctgcc tttggcagag gaccagcctg cctccttcgt cccctaccca   31380
gcctgctacc aggatcagga ggaggcatct ccatgggact cctagggctg gagtcagagc   31440
agcccctcca ggttctgcag cctggacggt aggaggtgcc actaagggga ggagattggg   31500
gaaggattgg gacctttatc tgcggtgagg tggggcacgg ggggatgaga gatatagtgg   31560
gagtctttga agggtgtggg atcagtgaag gggctgggga tttagtgatg ggctggggct   31620
taggatggag ccaaggggctc tgtgggtggg agacctttg agagggtgga gactcagaga   31680
gaaggatggg ggctcagcaa ggggatgtgg ctcagtggag gttgctgaag agtttcttgg   31740
ggttggctac acgcggtggc tcacgcctgt aatcccagca cttgggagg ccaaggcgga   31800
tggatcactt gaggtcagga cttcaagacc agcctggcca acatggtgaa accctgcctc   31860
taccaaaaaa tacaaatatt agccgggcgt aatggcaggc gcctgtaatc tcagctactc   31920
gggaggctga ggcaggagaa ttgcttgaac ctgagaggcg gaggttgcag tgagtcgaga   31980
ttgtaccact gcattccagc cctgggcgac agagcaagac tccatctaaa aaaaaaaaa   32040
aaaaaagtc tcagggctgt ctctgcactg ctccaggttc ctgaggacgg cggttgggc    32100
tgggggagtc ttctgtccct gggggtaggct gagaagcaag agctccttt cccaactctg   32160
cccaaagctg gaaaggttgt tagagctgct aagaaagctg gcatctgcct ctccttttgc   32220
tcatcttcct ttctggttc catgggaatc tgtggctcag gatgatcagg ggttgacagg   32280
atggcgctgt ggaaggagtc tgtgtcaggc acagccatcc cacatgggaa ggagccggct   32340
ggtaagaaag tgagttccct gtccctggga gtgtgcaagc agggtagggg ctgaatggct   32400
agagtgactc cagaaagggg ttcagatggg gcagaggaag cagtctggag gccacttccc   32460
tgagacaatc atgttttgtg tgattggctc tgggggcccc accagcccca ccttccagac   32520
gtccctgggc ctcacaaagg gggttgctgc accctaggca ctgcctctga tccagcccca   32580
actcctgtgc tctgtgcctg gcctatgctg aacacggaca tgtgcagctg aatcagattc   32640
agtctctgcc tagaggagcc ccagtctgat gggggaggca cacagggaca caaatatagc   32700
```

```
tgggtaagtc ctacaaaagg gggcatacct ggctgggagg cagttccatc actgattcct    32760
gtagtctgta gatgtctttt tgagcaattc ttctgggtca agacttgttc ttatttgctg    32820
ggataaaaca gcagtgagca aaacagagct gacagcatgg tgggaaggtt gagctcttcc    32880
agaccgtgat gagaagtatt ggtgagtggt ggggagagtg gccagaaggc agagtgtggg    32940
cgcagcatga gaggaggctt tgtccagact taaggacctg gaaggccttg aaggccagga    33000
ccagggctcc aattgtcctg ctggcaatag gaagccatat gggtgggggt gaggcagaat    33060
cagatttagg tgtggaaaag atgactccag ccagtgtggg catcgaagag gaggcacaga    33120
agcaggcgtg gccacctgtg cctctgtgta ggagctgtgt gagcatgtgc ttgaggatgt    33180
gtgtctgtgt agaggactgg ggtgtaggcg tgataggaac atggacgtgt atctatggaa    33240
agactccaat tgtgcatagg ggtgtatgtg tgtaagattc tgtggcccag ggcagcctgt    33300
gaaaaggaag gatcttgggg tctctggatg atggggagca gagactaagg cctaaggtat    33360 gctgggctc gagcccctg gactttatc cctgtgagct ggcaggtctt agactagtcc    33420
tggactagaa tcctatgggt tcccttcccc cagagggtca tggggccagc catctgctgc    33480
agacaagaca aacatgcatg caaatcacat gaaaatggat gaggcctgtg gctgacccac    33540
cctacagccc ccatcccctg ggcctgagtt cactcagcct gtaccctcc tgacccagag    33600 ctgctgccag ggctctggga acaggccttg cccactagga gctgaaattc acattgtccc    33660
cagcacctgc ccgtggccac atcctctctc tgtgagggct accccacat ctggagccat    33720 agccagcgga cacagagctg gatctggact ggtggccatg ggcagcacct ctggcaggtg    33780
ctgaggtgga ggaggcagta tccaggcagg catccctggg cagaaggtac ctctcctgag    33840
cagacaggcc tacccaggca ccaggcccaa agatagggc aagggctaga tcctggtatt    33900
ggaggaccct caggagaggc tgtgtgtgac ttgctctctc tctgacctgg gctagagcat    33960
aaacacgtgt cacatacttg cacacacatt cacacgtgaa agcacgcaca tgctattcct    34020
ggacacttgt gtacacacac cactgcacac atataccgc atgtgtgaat atacactcac    34080
ttctgcacac agacacatgc ctatctgcat agacacaccc gtgccaaccc ctatagatac    34140
acagacatat ctgtgtatac acatataagt tcagctatac cactgcagta tcacacaccc    34200
tcacaaggat acaaacctgt gctcacactc tcttccaccc tcacacacat catgcttaca    34260
agcctgtgtg cagccttaca cacatgcaca cacgtacaga gcagcctaag ggtggctcac    34320
ccctgcccag gtgaacacct gtgcccactc cagggctgga gtgttgagga aagggtctgg    34380
atggaggcag aacctgcaga gatgtcagtt tcttccagga agcatcttgg attgtccctt    34440
cacagagccc ttggaagtgg ggccctcttt tagtccatgg gctctagccc aggtcacaga    34500
gagagcaagt cacacacagc ctctcctgag ggtcctccaa taccaggatc cagcccttgt    34560
ccatatcttt gggcctggtg cctgcgtagg accatctgct caggagaggt accttctgcc    34620
cagggaggcc tgcctggata ctgcctcctc cacctcagct tcctgagcac tcaaagagaa    34680
gcaggccaag cttcacggct gctgagaagt ctgagaccag ggagggccaa agccttgcct    34740
gaggtcaccc agcatgtcag ggaagggcta gggtttgaac ctgggcttcc aggtgggggt    34800
gtaaccatgg tccatggcaa caggatagat gcatgtcagg cagcagacag gcccttggaa    34860
gcaagacatg tggtcatggg ggataggaaa agacttacag tctatggaga tctgccagga    34920
ccaagtgtgt gagatggaga gatggtgctt cttcaccaga gctcactggg caccacaggg    34980
ctcccagctt ggctggacca tggggactca gggaagaatc agacaggccc tgctcttgag    35040
ggagggctgg ggataggtga agaaggaaga gggcattata gactggggag atggtggggg    35100
```

```
ctacttctcg ttggatggca gttttcttcc tgcatcttga aagatctaac tttcaaattt    35160
ctttaccctc aaaactcggc atggagtaca ttctcagtaa atatttatgg catgaatgaa    35220
ttaatgaaag tatgatattg gcaggcagat atgcctttgg aagggtattc aaaatgggag    35280
ggcaacaggt tgggcaaagg caaagaggtg aagaaaagc  cagaggttca gggtacagct    35340
gagtcaggca tggctggacg ggaagtggta ggagaagcag caggaaaaag tcacgtgggg    35400
atgagccttg catcttatac tgagtttgga tgttgccttg gaggccatgg ggagcccagt    35460
gaagattatg agcagagggt gaacatggtc agagtgaacc tgccctggct ttgggggtc    35520 ctgggctaca tagtagctgc ttatccttgg tgcaaagagc actgggtttg gagtctatag    35580
gccagggttc acattcctat agtaaccagc tgtgccatct caggtaagca tctacatttc    35640
tctgagcctc actttcctta tttgtaaaat ggggctaatg ccgtgcctcc tgaggctgtt    35700
ggatctggcc tgggtgagga aatgctttgc cagcacaagg ccctaccaat gagaggtgtc    35760 attttatta  ggaacaaggc agggctggtt cctagacagg gcctgaggtt gagtgggccc    35820
aggacccagg ctgacagctg agtcaccttt tccaggccaa gtggcctcta aggtgggaag    35880
acaaaaagag ttggctagag gggctgggct atgcattcct aagctggagc tgggaggaaa    35940 gctgggctg  ggactgggct tcctggtgtc cgagatgggc agagggtgca gacaccggga    36000
tagtaggacc ctcagccact gcattcttgg ggacaaaaga ggagctggga aatctgattt    36060
ccttacctgg ctttgctcaa gaagcaagga atgtatttaa ggcacagact ggagtgagat    36120
ggcctgggtt tgaattttga ctacttacaa gctatgtgac tgtgggcagt ttactttgtg    36180
cctgagtttt ccttatctgt gaagtgtgac taataataga tcccacccta taacattgtt    36240
gagaagatga aatgtgaggc acacagtatg tgctcaataa atgcgaaagc ctcccagccc    36300
cagatgtata cactcggcca gtaggggcca gccctggccc tcacctccat gggacagagg    36360
tcagccaggg aggagatgca tctactccag ggttctctga cctggcagca aattagaatc    36420
accgggggac attcacaaac atctgggatg ggggttccag atatcagtat ttaaaatgct    36480
cccaggcaat tctaacatga gtcagggtga gaacccagaa caggatcaca gattgtgcag    36540
ttggagtgag gtagggatct gcgtgtgagt ggaggagtcc ttggagtggg gtcactccta    36600
gctataagag ctcggcaagg cctttaaatg tgccaactca aggagccttg gttgcccct    36660 caggaagggt gctggttggg gaatttcaag gattgtgtga gagggttttt ctgaaagggc    36720
tctgcactct accaagcact ggaagaaagc agtgcacttg tttattgagt ctagtgtaat    36780
aacatttcac agatggggaa atagaggcct agagaggtgc tgtggcctgc tcagaatccc    36840
acagcaagtc tatggcacag ttaggactca aaccctctga ggaatgcttg gatctgaaag    36900
gttgacacag aaagactctt tgagctgagg gacacataga gcacacacca gggacccag    36960 tcattgagct gtagtttgag agattcaagt aagactgaag aaataacttc ttggctgggt    37020
gcagtggctc acacctgtaa tcccaacact ttgggaggct gaggtgggtg gatcatgagg    37080
tcaagagatc gagaccatcc tggccaacat ggcgaaatcc catctgtact aaaaatataa    37140
aaattagctg ggcatggtgg tgcatgcctg tagtcccatc tactcgggag ctgaggcag    37200 gagaattgct tgaacccggg aggcggaggt tgcagtgagc tgagatcgcg ccactgcgct    37260
ccagcctggt gacagagcga gactccgtct caaaaaaata aataaaata  aataaaaata    37320 aaataaaata aaataaaata aataaataa  aataacttct caagaggtga gtgccatgga    37380
ggtggtgcct ggagttggga gcccaagaga tggtggcggt gccaggccag ggtcggctgt    37440
```

```
tgaccatggt ctgaggtggc ctcccctgaa gaacaagtaa ctctggccag tggctgtaac    37500
agatacctcc cgggcacctg tatctcaccc agccttgtcc agagcccagg actgagccag    37560
tgacacatgc tcagaattta ccaagagact tgtgcactga gctcagactc agacctagtc    37620
cttccaacag cccttacatg ggtcatcccc ttttacggaa gagaaaactg aggccaaaaa    37680
taggaaggga ggccctgtgg gggccagaac ctttacacat cttagcccag gtaattttt    37740 ctacagtgtt aataagtagg atgaattgcc cctgtttgga agattcagta aaatacattg    37800
acttggccca gatcacttac tctacacctc tcctaagtcc ccagatgtga ctcccaggaa    37860
agacacaaaa aagggctacc cagagggata agatagtaac cagggaagcc ctcccagagg    37920
aggtgggcct tcaaatggcc cctaaatgac aggcaggagg gaaggatctg ggagggtatt    37980
gggggtgggg tggcatgggc aaaggcctgg aggtgagagt cagtcagtca ttgatgtgag    38040
aagagcaaga agtagaaatg taaggaatgg tggggagggg agtcagagct ggatgaccaa    38100
gcaagggttc agctgtagag ggtctggccc gccaggctca gggctcgggc tttattgtgc    38160
tggtggtagg gagccactga gggtgagtgg gggagagcat gccagagcat gcctcagaaa    38220
gaaaggtggg agaaacgctg gcatggaggg ccgcccctg agttggtggg gtggccgggc    38280
tctgccaagg ctatgtgcca gctgcctgga ctgtgtccag gaatgggcac aatgactcaa    38340
cattgagaaa atcactcccc agggagaaag ggccctgatg aatcacccag ctgaggtggg    38400
gaggctggga ggctgggagg ctgggaggct gggagctcac tgagtcaccg tccaagagtt    38460
ggtgaggagg ggagctgcag agagaggggc cggcagtgca gttgacgggg ggattcaggt    38520
cagaccacat tgagggctgt cggggactc taccttcccg ccattcccgg gtttggtcct    38580
cctggccgtc ctgtgaggga gatgagaaaa ctgaggccca ggaagtgggg ggagggatc    38640 cgagcaaggt catgcggcaa gtcgctggca aaggcctagc gagacccaag cgcaccctcc    38700
agtccagaca cgtcctgccg ccccagccgc tttcatgcca agcagaggcc taagaaccgg    38760
gtcggtccgg gcaggagct gaccccggtg acccgctgaa tccccggacg cggcccctcc    38820
gggcagccgg caactgaggc cggattgcgc cgccgcgatg ggacggcagg gggcgcagga    38880
gcgtcgcggc tgccgcaggc tcctgaaccc agaagccgct ctgcggagaa acgcgctccc    38940
ggagcgcggg tcccaccgcg gaactgcgga ccgtgtggcc ctggggcctg caccctctcc    39000
ggctccgggg acgcgacag agacctgccc acccaggcct gggggcccca gtcagtggcg    39060
gccgccgtgt gtgcgctcgg tgtctgttcg cacgtgtctc cctcgcagat gggcgactgc    39120
tccagggcct gtccgtctca cagcgacctc caacattctc ccgacttccc cctgcctcct    39180
aggctgaggg agaggagcaa gcccgaggct cctgcggtgt ccgcggcccc tgccccctt    39240 ccccttccct ccccacccca ccccactgcg ccggtctctg cctggggctc tggccgggcc    39300 ccggaccca gagtggtggc ggggaaacag ggtgcgatca gacagggtgg aggctctgag    39360 agcggccct gcgagatgcg agagaagtgg cgacggggcg aggggcagcg agcgcaggct    39420
gacagcaggc cagctggaag ggccgaggga acccagggcg agacagaagc ggggtgacag    39480
cggccgggtg tccggtgggg tcggaggatc cgacgggccg agaggtgcgg tccgcggtgg    39540
cggggacata ggcggggccg gggcgggccg gggcgggcg ggggcgggc cggggcgggg    39600 ccggggcgga cactcgggcg gaccaggcga agctgtcgcg gacgcgctga ccgagcgcag    39660
cggccgggcc ggcgggcggg cgggcggctg cgagcatggt cctggtgctg caccacatcc    39720
tcatcgctgt tgtccaattc ctcaggcggg gccagcaggc cttcctcaag ccggacgagc    39780
cgccgccgcc gccgcagcca tgcgccgaca gcctgcaggt agggggccc ccgcgctggg    39840
```

```
caccaggaga acggggtgtc cggcgagcgc cgggccgggt ctgcccgccc ccgtaaccct    39900
tctcagggta ggagacccct cctctagttc tgaattctac tcctgtgctg ggacggcagc    39960
gcagaccaag agcccttgaa gcccagctc tcagtccaca cgtcacccca gactctgaac     40020
tcctttcgga tccggggctc caccccaagc actgagcttc cagtccacgg tgggaccgca    40080
gtgcacactg agagctgtgc ccaagcctcg aattcccttt ccttagatta gtggggaccc    40140
tgcccacgcc tcggaacctt caccatatat gtggggctcc cggcacacct ggagcacctg    40200 aaccccagc tgtcatccag gactccacct cagagccggc ctcacccaaa gccccaaacc     40260
tccattccaa gcctcaactg gacacccgct cagattccca cccaaacatc tggacttcag    40320
tcctcagcct ggaacctacc ccagagtcca aatctctcct tccatcaggg cttcactggc    40380
tttctctgtg ggacccactc cccgatccct tccctccctc ctgtgttgga gatctccgag    40440
tctttcctcg tgggggcccc ctcctctctgt tcctctccag gtacagtggt cccactttat    40500
tctctgggct tctcctctgg tttctcttca agtatttctg ggctctctaa tttggtctgt    40560
tgccccatgt gcccacctct cttggtctat cttggtctct ctcctgttc tctaggtctc      40620 catcttcgtt ttgggggtctc tttctgcagc caccccttcc tcttgtatct acctctgctt    40680
tgtggtgagg aggggggcagg ctcagagagc agggctagtg tccctgggac accccccgccc   40740 cccatgttct caggcatggc atggtgtggg ctcaggtgga agggcctaaa tgtggagtgt    40800
gctgccctca ggcgatgccc agggatctga ggtggtgggg ggatgatgtg gtgggcactg   40860
gcttttgtaa cttataaagc ccctcatccc agctgccctg gtcttgacgg gggcggctag    40920
ggcttgagat agggaagagt aaactgcaat ctggtgtcaa cctgcggtgg gatgtgtcca    40980
ggctgggtgg gtctatagtg tatgtgtttg tgtgagtgtt cctgtctgtg tgtagcacgg    41040
gctgggttgc atgtgttggg tgtgtcttgt gtgtaatcat gtgtgttgtg ccgtgtatga    41100
atgtgtcatc gagagtggga ttatttgtgg ggagattatg ggaattatgg gtctatggca    41160
ttgtgtgcta tgtgtggctg gggaggcagt gttgtggctg tggagtggta gctgggtgtg    41220
tggctgttgt gtgtgtagag aacttgtgtg tatgtggctg tatgtctgtt attgtacagt    41280
ggagttgttg tagggacagc ttgcatacag gattctatat gtagttgtgt gtgttactgg    41340
ctgttgtgtg tggccaggaa gggccactgc aggggcctga tggtttccac tgggtgtctt    41400
gtcagagagg agttggggca gggggtgccg tgtgtgccaa tgtgtttgca gcctaggtgg    41460
ctggcttaga gtcactatgg cacatcctgg gattgcttgg gtaatatatc tattaggacc    41520
tgagtgctgg tgtttgaatg tcatgtgtct gtgtggtggc tgctcccgcg attctggaca    41580
ggaaagggtt gcagccaggg ctgaggggtc tgaggtgagg agccagttga caagtgtgtg    41640
agtgtgtgag tgtgtgtgtg tgcgtgcatg tacacgtgca tatgggaatg gggtggggtg    41700
ggaggaggca gtgggccagc agcgctgtct atgctgaggg gctgtgtgtg cccacaaacg    41760
tgtgacatta ggtgtgcaca ttatctatgc aggttgtgtc tgcatgtgtc tctgtgtcta    41820
ggtggcgtgc gtattgaatt taattggatg catacacctg tggctgggga ggtgagaggt    41880
gtgtgaggtg cgtggtggga gacggtgtga gtgtggtgtg aagtgagggt gtgtgagctg    41940
ggtgactttt tggtgtgacg tgtgaattat gtgatctttt ctccccatga gctgtgtgtg    42000
cctgtggtga ggagtgagtg gaggatggcc agtgagctgg cggtgtgtgt gttggggggtg    42060 ttgaggactg tagaatgtgc tgcggtggca gtgtgtgcat gaggtgtgtg tgaggaatga    42120
ggtctgtaac atttggggcg tgtggaatat agtgggtgtc cccataaatg tctgtggagt    42180
```

```
gacgcatgtg tgcaaaaggg cttggctgcc atcctgttct tgctcccctc ctgatcaggt      42240
ccctagagat gccctggaat gttctccatg cccccccaac cccagctgcc cctacccttt      42300
gcccttcatc ctccttgcct tgaccaagcc ctttgttttg ggtttccggc ggagcaggcg      42360
ctggacaggc gggcggcagg caatgtcgtg gtctgagaac ctttgttctc ttagtttgac      42420
tggtgtttgg ggccttggtt tggaggaggg tgtggagagg atgcacgtgg cagcaaggtc      42480
actgtgttta ctacaccact tcgtgctccg cagaggggag gcgtacgcg caggcagtga       42540
ggcctgggtg gtgtctttgg tggcgcctgt tggtgtaaga acagcttagg ctgggcttgg      42600
agtttgccag ccatgcagtc ttagtccata gtggcccagc gcccttcctg gctcatgtca      42660
gcggggctga gcagccgagc agccaagcac tcacttctcc aagttcacct gccctcgccc      42720
cttctctgtg tggctgcagc ccctgggaga aaccaggaag acctcgattt agttctattt      42780
gtgttcactc caggtcagat ggaggagaaa gagtccccat cctcacagag acacttatct      42840
gaaaggagag agctggtcac acctttgggg accctctaga ctgacgcagt ctgtaggggg      42900
atcgaggtca taccttccag agagagctgt gggaaaaccc tactgggctg cctcccagca      42960
ggtgcttgag agaagaaaca tccaaggttc cttgagattg gaaggcttag agaagtctga      43020
gtcagtcagg gaaggggctg gggtcgatgc cgcagtgtca cataccagaa ggttctctga      43080
aatgaatagg cttgaactgg accttgaagg gggtgttggg gtgggcagag aaatgcagcc      43140
tggggctgag gaaggttctg gcctgactgg caaaagggat cttgctggcc attccccagg      43200
caacactgtc tggctttggg tagccatccc tgggcctcca gccttctcaa gctttcacgg      43260
tacctttttt atcccattgt ctctggctgg aattatcttc attgtcgttg acattgtcat      43320
cttcatcatc ttttaggcag ttatttccaa attccagggt cctttcacaa atgtctcatt      43380
tagcaggtta actcatgcaa ttgtccaaaa gtctttatgg aacactgctg tgtaccaggc      43440
aggcacagtt ttaagtgccg gggtcatggt ggtggccaaa ctggcctcat ggagctccta      43500
ccttctgtgt ccagccatgc tgtcagttgc ccacccttct gtgtttcccc cagtctgggg      43560
cgcctggttc tgtggggctc cgcatgtgca ccctctggtg ctggggtctg gctcctacca      43620
gaatgtgagc tctgcagagg ctgggcccgg gtctctcctc tacccaccgt gtgtgtcctg      43680
agctgggtct ggcagagtcc agatgctcac acctatcatc aagtgactgg aactgccatg      43740
tagggttggc agtccagctc tgtctaggga aactggggtc catcggatga ggggactctc      43800
atctcatcag gcagcatctc atcaggccct tcttttacca gtagctccag agaccaagaa      43860
gggtcaggtg actggtgcag gtctcacagc agggtggcgc ggctggtgtc agaagacagc      43920
acttcttgct gccaggttgg gctctggtcc tagcaccatg ctgctctctg gctggcctct      43980
gtgctgcctg cggcgggtaa acgattatta atgaccccc tggcaaggag acaggaaatg       44040
tttcccagcc acagctgggg acctgctccc tgccagcccc agctatccat acccgtcctg      44100
accatggcat cggtgctgat gttatcttca ttctgcctca gtcttcttta ctccttctgc      44160
ccatcccccg acctccctga tcttgacatc ctaagggtaa atgacgagaa gctacagagc      44220
tttcttttcc atatccctgt ccctcaccac tttctccaac ctgactcatc tctaccttct      44280
tccttgtccc atgccagcca gaagtagctc ttcctccaag aaggcttctc tgaatgcaca      44340
gccagctcct ccagtgtcca ctaccctgag cccgaggcac tgagtccccc tcattgcaga      44400
ctctagtcct ccactgatgg tttgctctga cagccctagg gctggcctgg gcacttcccg      44460
cagactgtcc ctaattgctg ccttaggact gacatatgaa gggtcctccc agatgctacc      44520
tccaggaagt ctccagttcc actcagccca gggattctta cctcctttga gcacagtgcc      44580
```

-continued

```
cttcctgtct gagtcacaca tgtgtacttc caggacttcc taggtggaca ttagtgaaca    44640
cctgctatgt gcccagcaca gagggtggga agagatgagc aggatgcagg ccttaaaatc    44700
cccacacctt cctccaagcc tgagcaatgt tgcatcagcc ccttggcagg tggcacagac    44760
ctaggtacta gggctggggg aggggaggcg gagaaacagg gagtgatgtt ggtagagtgt    44820
gtggggaggg caacgaggga gataaactca ggggccatgg tgatataaag cagggacccc    44880
tatttcagcc cagagtggga gggagggca tgttgggag cttccaggag gaaacaaatc    44940
tgaactgaga gctaaggtca agccaggaga aagttctgga cagaggggag agaatggtta    45000
ctgtgaaggt tcgctggtgg cagacagagg gaggagagcc tgtggcagca ccactccatg    45060
gagcaggccc ctgggtgcca gccggctggg tccgggggga tggggactgg taaagctggc    45120
ccagccagat ggtgcaggac ttgtaagcca tgttaaggac tgcggactta ttctggaggg    45180
aaattgaccc tggggaagag ttgagagaac ggatatgaca gatcagatct gcatgttcaa    45240
tagctccctg gaccatggtg tggagactga agggaggct ggtgtggtcc aggtaagcgg    45300
gggtgatgag gcctggacag ggaaatggct gaagaatgga ggggaggga cggagtggcc    45360 agggctggtg gagggagctg gacagctgta gacgtgaagg gcaagggagg agaatgctgc    45420
cccacccagg tgtctggatg ggttttgtgc agtctctgag atgtatagga gggaagacag    45480
gggttagtgg cagatgcctg ggcctgtgtc agggcccttt aaggaccaaa aggtcttgga    45540
aaagcctcag aggagatcat gagctttgag attaaaggga gacctgaagc cggcccaggg    45600
ctgctacagc ctcacctgta acatgggaac ttgagatctg ccctgggcaa agggtgttca    45660
gaattcaata atcaaaacaa tctgtgaaat gtaatactta ataaaattca aatccaaaaa    45720
tgtctgagta cattccaaaa tgagtaaaaa tgtaaattta tgaaaatgct aaacatgcgt    45780
gattgttcta atgtaaattg taagcctcag ctgcttccca gaactttgga tctggctccc    45840
ttgaagctgc tgcctctgat gtggctgccc cctgcagctc caggaccttc ctgttcagct    45900
cccttgagag tagccggcag ggcccctcct ctgcagagcc tgtactctgg ctggtggctt    45960 caggggcag gcattctgcc tttcctgtct cccaccctaa gggagttggc cttgcatgcc    46020
tcccatccac ggttgcctct actgggggct gccactggga gacaggaagg gcatgggagt    46080
ttcgggagct cagggtaaga gggctgaga tctcgtggtg tggagggga gcggaaggt    46140 cgggtggccg aaagaatgga gagggccggg agtgagagca aagggagaca ggcagagctg    46200
aagagcagta tcgccccaac atcaatactg gtatttcaga atgggaaagc tgttccattt    46260
cccgaaatat cagaatgctg aggtccgatc ttgcagtctc tgagctgggc attccttggc    46320
ccccactctc gggtattctt gcacaagacc attttctgg gctgcatttt ctcacttgta    46380
aaaggaggaa gttgggggtc aatatctcca agcgatatat gagctctagc tctaggagta    46440
taggattttg agaatctgga attgttagtc tgtggggttc taactgggac aattctagca    46500
ttccttgact ctcagctccc agccagggct gtgtggatgc gtggttgtgt gattccgaca    46560
ttctgagact ttaagatgct gaggctctag gagctagaga tacggacatt ctgtgaatct    46620
aggattctag gatttgatgg tttgatgatt caatgattct aaatgggct gctgggaaga    46680 gctgcaacca cctgccttgt taatgtcaat gttcagttat taaaaacata acaagaagca    46740
atggagacag atagctcaga atggtgggcg ctccctccac tcccagtgag ggaggacaga    46800
agaggctggg ctggccttag agaatagaga cctttcaac ctgggtcaca caggttgttt    46860
ctcctgtcac aacagaactg gtgtgtgtac attcgagaga gcttccactc ccaaagcttg    46920
```

```
cagggtaagg ggctcatttc cttcagcact ggcctctatt ccttaaccat ttcagactgg    46980
gcagagagag gggtaactac cctttcctcc cagccctcga agtctctggg cagaaatggc    47040
agcagtggag gaaggagagg tctgctcacc cccgcccctt ccctgacagc ctgaggggga    47100
aaacaggaca tgaatacttc ctggacacag acatggaaat gcatgaaccc ctgccttcga    47160
gggccccgcg tccaaaggct cagacaaggg cagaggccag acagccagt ggggtcccat     47220 cagcaccctc tcagtatagg ctgaggaggg aagaccctgt tcttgcccca agggtgacag    47280
tgagaagggg tcaaggaaag gagtcccagg tcagggactg gaagtgctga caggtcctcc    47340
cctgtgtgca aggccacagt ccagcctggc agaaggccac cccaattgtc cagtgtttca    47400
ctgcctcctg agtccttctt atgccttggc acccaggcca gagttgggga ggggtccagg    47460
ctgcagggga gggtttcctt ccagagtgcc catccctgat ggatccttag aagcccagta    47520
cagctgcaca gttccaaggg cttccgctgc ctggtaggtt cacagaccaa agctggccct    47580
ggtcacacag cacaacgggg cctgaaatca ggcttcctga ttcccagtcc tgggtgttcc    47640
tttttgccca cagcctcccc cacttcccct gggacacctg aggggcagga gtggaggtgg    47700
ggctcaggtt agggagcaga gcctctgtcc atcatccctc cgtcttcctc ttcccacagg    47760
ccagaagcag gtgtggtggt gacagctgcc cccagtcctc cacaaggctc cattgtcccc    47820
ggcagggagc ccctccccag ctgcaggcca gaagtgtgcc tccccgggcc ctcctgtcgt    47880
gactctgcca cccgcttcct cctgctgccc cttccctctt ctcatctccg cttgccctca    47940
ggcccctccc atcccgtga ggtctcgtct ctggcgctct ctgggtttaa gcctctctcc     48000
agtgaaagtt agatttggaa gggccctggg agatcaccaa gtccaaccct tttattcttc    48060
ggataaggag gccaggtcag agaggggaag gtcctgtcca aagctgcaca gtaggctgag    48120
gcagagccca gtgctgtgct cccttcagcg ctgggtcatg ggtgcacact gcccttggca    48180
tcaggcgtcc agggtttgag aactgactgt gatgatcagc gctaagcaca caggcaccta    48240
cagaaatgcg gtagggggct tctctcctca gcccttcttc acagccctga gctgccctcc    48300
cttcctcttc tttgcccagc tcctctctcc ttcactatcc ctgctgtctg ctgactcctg    48360
cctctggcag acactgtcct tgggacacag actagagctc aggcctccag gactgggatg    48420
cacacccatg cacccagaca cagacacata aacatgtgca agcgtgtcac ggggtccata    48480
aatcccagct gaaaactggt cagaccatca ggaggccacc ctggaaccca gtgtcctcct    48540
cttcctgtca ggcctcacac acctcctcca ggaagcccct taggacccct gaagaccatc    48600
ttcatccaac tagccccttt gtgacaactg aactctgtga gcctaggttc ctcctgtgac    48660
tcgaagggca aggctgagtc ccccttcag tcctggggcc actccttcag tgtcttcagg     48720
aggggctcag cttcctgttg ctgggtgggg agagccctga ggtccccaca ggacgtggga    48780
caatggggag gcggtgacag atgagaggct gagtcttccc taaagcagac tccaccctcc    48840
cctgacctcc ctggctggtg gcttggacac agccctggcc tggactaggg tcctggtctg    48900
accccacaat gcagaggtct gggaatcaga agccctggtt ctccagcagc agttctctaa    48960
ctggcggcta tggagtccag gcctccaggg cactggtagg ttattggcgg gttggtgcag    49020
attccagtgt ccaggagggg tgagctggcc tgggggggcct atgtacagga gataggaggg   49080
tgataaacac aggctaggtg ggattacagg gagctgggaa tacctagcta agaatcccct    49140
catcctaggc actttcccca cacttgaaat tggctggagg gggaaccaga agttaggtgg    49200
ggttggggag ggacaggagc cagcaccctg cctccacctc cggcagtgc ctctgctggg     49260 gggagggaac ctgtcctggg ggtggtggga ggtgtgaggg gggagctgga ttctccagtg    49320
```

-continued

```
aaactggccc tccctcctct caggggaggg gaggggggctg tccctggctg ctcagcaggt   49380
agcccatctg gctgtgggtg gaaaagaaga ctcaggcttt gtggataaaa gggacagccc   49440
tgggtcaggc acttatctca accctcgtca tttcctctgc cggacatgac tgggtgagtg   49500
gggtcattgc acagagggaa ggaacaggcc agggccagtg cataccaggc cctacaggag   49560
agtcaggcac atgggtgacc ctgccacacc ctgggctgca gtcagcccct catagaggcc   49620
cagacacaca ccacagtcac tgccggagat ggccacacct agaccatcac accacacaca   49680
gacccagtct ctccaggtga cactcaggcc cagctgcagg cgcagctaag agggaagacc   49740
ctgcagggca cagggacacg tgggacaacc agacgccctg cttcggccac accacaagcc   49800
tccacacacc aggtgcagct cctgtcaccc ctacggtcaa cccaaggaga gccagagatt   49860
ccagtagtcg tgggcaggta tccagtgccc aggcgagaag aggggacac cagcagggaa   49920 cccagaacct cctccatgcc agactgtgcc ctcccccag ctcacagaag gagtgcctca   49980
ggctgtttat ttcctagcag ggactagcag ggatgggtgt ctcatccccc tcccctccc   50040 agtccccacc acacgattct gaagctgcca aatcaaatca gccctgcac ccgcgccagg   50100 ctggcatggc ggccagcagc tgacgggaac gaagccaggc tcagaatatc ccaccgcctg   50160
tccgatgcct gagtaggctt gttgggtggg gtgggggagg ggcaggagcc tggcagccag   50220
gccctgggca gtgcccctca gagaggctgg gggtttggaa tgctgcaggg tggtgggctt   50280
ctggagaatg agtgagcagg tctctgttgt gtctccaggc tgctgtggca gtgtctccac   50340
cgctagcatt ccgggaactg tggaagtggt gctggtagga tacaggtcgg gggtctgatc   50400
ccagtccaga tgactgggcg ccaggctggg gtagggggc tcccacatgg tctcacattc   50460
atttgagact cacagcaccc aggttggaag cccttggtt gtctgtcagt aaaggcccaa   50520
ctcactgtgg aggccagtg actgtgtgag gtggacatta cggatcccat tttacagaca   50580
gagaaactga ggcttagaga gggctagtag agctccctgg agagaagcag aagtggagga   50640
ggcctcagaa agagtaaaga ggtggtcatt tccactcctt aggagcccta ggtggaaaga   50700
aggaatatgg ctctgttctc agagtcaagg aacagagaat atggcagagc cagaggtgcc   50760
catgggaagc agagaacaag gagggagtct tgggagagag cagggtgcaa gcaggcaagg   50820
ctccctggag gaggggcca tccgtgggct tgctggggc taatgggagg acagtctggg   50880
gagaagggga gaaggcctgg ccggcctcag cccctgacct tcttgtctct gcagccagcc   50940
tggaccccct tgcaaaggag ccaggacccc caggagtag agacgaccga ctggaggtga   51000
gagctcagtg gagggagaag tgggtgggct tgaggggggtg gggcgcagac tgaagatcag   51060
tctgagtggt gccctccccc ttgggaggac ggggaggctg gagtcacatc ccagcccag   51120 ccctccagac taggaccacc cctatatcaa gaccatctcc cctcaccta tatatcccca   51180 gcctggaagt cctcccatga ggattcctcc tcccaactca cctggggagt cactacagac   51240
tcctcccttg tcctccccac cctcacccaa caattcccgt tgattctctg ccctgagtat   51300
ttcccgagtt cctctcctct ccattctgcc gcctgcttgg gtccaggctc cctcaactct   51360
cccctgggcc actcactggc tgcttgcttt cagtttcccc catcatccac gtggccacca   51420
ggaggatctt tctaatgcac agacctgaac ttgtcactct cttgccccag aatcctccat   51480
gctccccacc cccatgcccc ctccacaacc ccagcctggc aatcgttccc cttcatccat   51540
tcctgcctcc cccaaactgc tcctgctggc ctcttcccca ctcagcttcc taaatccttc   51600
ggggatcagc tctagcctcc tttcctctgg gaagtcctct ctacccctg accatgggac   51660
```

-continued

```
caagctcact cctgctccct cctctgagct ctcctgccct ggcagtcaga tgccagggcg    51720
ctctgctgtc tgtcgcccac tgtgctgtgc cacgagcacc ctgttttctc catcatgtga    51780
ctctgtatgt gtgtctgcct tgtcttctct gcactgtgag ctctttgagc ctcgggactg    51840
tgctttcttc attcctgaac cttctaccac ccttggatgg gtaccggtgc agggctcagc    51900
cagcgcattt cctgccctgc gagggtgcc atccccaccc cccgaccatg ccttccttcc    51960
ctgtgagggg tgcctcatag gactcttcag tgctcaaagg ggccttgacg agcaaacaag    52020
gtgggctgct gatgttgaag atcggcacag aggagggtgt gtgtgtgtgt gagagagaga    52080
gagagaactg gacccacagc cagaacagag tctgcccagg cctggctgag agggagagga    52140
agatgatgct tgtatcagcc ctcctgtgtg ccaggagcct ttgacaccca ccttgtttaa    52200
ttattacagc accccatga ggtaggggct gctattattc ctatttcaca tttggggaag    52260
ctgaggccca gagggatcat tcagcaagtg agttgggaca gagctaagat tggagcctag    52320
atgtgtctca ggctcgaggc tcactctttc ccggcccctg agtaagatgg gaaagaaggt    52380
gcccacacag ggcctggtgc acaggagggg ctcagcacag gttccctgct gggacacagg    52440
gccaagacct gagaatgtgc ctccaagtgg ggctgggccc tgctgctggg agctggcaaa    52500
gggagctggg aggggagggc ctggaaagcc acattattaa tttatttact gccatggcat    52560
tccccatggg gcggggctcc ccccagagct gggacagatg tgttcctggg gagcctgcag    52620
tgtctcagca gcctcggcca cccgccagga aagactggat ttgtcatcca cccagggagc    52680
cacaagaaga gggggctttg gcaaagctga gaccctcctg ggcaacgggg actgtgccct    52740
gagggaagga gtatggctcc aggcaccctg ctatgcctct ggggcagccc ccgctgccta    52800
ggccatctgc ctgccctctg caggttcaag ttctgctctt tgtccagctc caccggcctc    52860
gtccttccca tgaggcttcc ctgggtcggc cccacctgct cctatccctg tattttctct    52920
gcctttcctt gagctgggtc ctgctgcctc ttccctctga ccgaggatct ggagccatga    52980
gctcctcagc cctcagctct gtcctgaccc catccccaca ctcatcccca aaacagttag    53040
tgtctgcctg gactcttggc agggcctgct ggatttctgg gtcctgccag cacccacccc    53100
gagtgcccag gcctatactc agcactgctg ggaagagatg ggctgcctga ggggacgctg    53160
ccaacatgga gagggcaaga ctggagagag tggggacccg agggcattgc tcagaccaca    53220
ggggcagctg gagggaaaag ggactgggag cctgaggggc cctcctgtca gggtggatct    53280
gggaagccaa gatggcctca tatagtggac aagccacagg gtcagatgag cacgggttca    53340
agtcccaact cccttgcttc ctaggtgtgt ggccttgtgc ctgtcactta accagcctga    53400
gcatcagtct cctcacctgc caggcggat aagaacgtct atcactgccg ggagcggtgg    53460
ctcacgcttg taatctcagc actttgggag gccaaggcag gtggatcaca aggtcaggag    53520
atcgagacca ttctggttaa cagggtgaaa cctgtctcta ctaaaaatac aaaaaattag    53580
ccggttgtgg tggtgggcgc ctgtagtccc agctacttgg gaggctgagg caggagaatg    53640
gtgtgaaccc gggaggcaga gcttgcagtg agccgagatc gcgccactgc acttcagcct    53700
gggtgacaga gtgagactcc atctcaaaaa aaaaaaaaa gaacctctat cattcttgga    53760
tgtaatcact gttattcaac attaccacaa tagagctgtt gggagaagtt acaaagactg    53820
tatgtgtggg gtgcccggcg caggcctggc acatggcaga tccttgggga gagttagcct    53880
cctctctgtt tccctcaagg atgacatcct tagagccagg actaggctgt acccctgtga    53940
gacaggatgc tctgcagagc tgggctgagg cttatgaagg ttctatgggc atggcacact    54000
ctcctggcac tggctgggca gcagccaaga aagcagagct gccagcaccc atccccaccc    54060
```

```
agcaggcgtg tgttcagcac accctcctgg gatggttacc tagccsctgt gccagcagct    54120
gacttggagg aggggctctt ccagctcagc ctggcatcct ccttcagggc caggcctctg    54180
catcattact gtctctctga aagtcaggtc tggggcagtt caagttggtg aattgagcat    54240
gctgagtcaa tgccctcttt gtgatggctc tcagggccca gatggcggct gggagcctt     54300
agctgggatg ggggcatggg gagaggcgga cgtggatgag ggcactgaca tccacaataa    54360
gtactgaaat gcactgccca acaccggctc ctctattgct gcccttggga caaagaccac    54420
accccttggc agggcattgc tggccttgcc tgctgggtcc cctcatgtcc ccttgtgtcc    54480
ccttatgccc tgagacagcc agcgctacag ccacattgtt gtgttcactc ccagcacaca    54540
gcagctcccc ctgcctccct gcctttgctc acactgacca cctgtctgga atacctttcc    54600
tttctttctc cacctactct cttttcaagg cccagatgaa atgtcacctc ctttgtgacg    54660
ttcctcagac tggtccctct acctcaggcc gagccagtct cctcccttcc ctgggcactc    54720
acagtcccca tttccctgag cccacagttg ggaaacctgt taccccacgg ggtgctgtgg    54780
gtagtgtatc cttccccatg gggttgtaaa cacccaggag gcagaggctg agactgagtc    54840
tcctttgtct ctcttgggcc catgtggtgc ttggtatagg cctggtatat ggtaggtgct    54900
caataaatac ttcttgaatg aacaagagtg gctgtgagta gggctggagt agttccaaga    54960
aggggcacag ttgggttggg cggtcttgga gacttggagg aggcaacctt agaactttga    55020
aggatggaga gggtcaaggg caccaaccga agaagccagg gaccagctag gcagtcagag    55080
aggtccatga ggtcagcttc tgacagcagc agctaaggac aaccaggacc agaacaggac    55140
tgggaaaaag cagatagagg aggctggagc aaggactcag ccccagagga ggctgcagga    55200
ggttggctca tgctcagaac ccggctccaa aacactctgc ccatgagtgc tgggctgagg    55260
aaggcttggt gccagagtca gggtgaggct gaggccacca gtgaatatgt gggcccagct    55320
gcgggggtag cactaggcag gggcgggagc caggttggag ggggtattgc cattgccgct    55380
gcaggtggag tagggcttcg ctggggaagg agcagcttgt gcgagagtgt gggcaggagt    55440
gggaggggag aaggctccga gtatacgagc atagcttacc agcaagtcct ggggtgaggc    55500
tggaggggcc gcgctgtagg cagcactttt caggccctta tctaacattc tcaagtgagt    55560
gctcctagct gccagatgtg ctacttcctc ctggattctg cacatcagga gccagtggcc    55620
tctacaatgc cccatggccc caagggagtg gctgccaaca agttggcctt agcatctggc    55680
atccatgggg gtcctgaggc cctgccatct gtctgtgccc ctgttgggct gcacaggccc    55740
ggggcgtgca gggacctggg accagggagg cggtctcagc tgccactcta gcctgtctct    55800
ctgcctgccc atccactgtc cacacccctg gctgactgag taaagagaga gatgggcatc    55860
gcaggtcctg ccatcaaaga agcctagtct aaaggaggag gcataaagca ccggggactt    55920
atacccagag aagacacatg ctgagaccac gccaggctcg cgggcaaggc ctaggcccag    55980
ggagggccag cctcgtcaag ggcctggagt tgagactcag ggaaaggcag gagctggctt    56040
agaggcgcag gcaggtccaa ggcagtgccc aggccagatg cggcggcccc gggctgaggt    56100
tgctccagcc ggccccaccc cccaccgtcc tgcctggcct ttggctgtaa acactgagag    56160
aacaagttcc gtttcccggg aaatatttat ctcaggctgt gtgaagagcg tgtgcactgg    56220
cctccgtgtg tccttcctgc agaccggctg ggcaggagg agagggagct tggcagcgcc    56280
cttgctgggg ggagtctgtg gggctaggag ggaagggtgt gccagaggcc cctgcctaga    56340
gcctgaattt gagtgctggc tgagggagag gtgggagcag atgggagaga agcctgtttt    56400
```

```
ctccaaaccc cacaaatgcc ctccgcctct ctcatgttcc tttcttcttc ctggtccatc    56460
ctgtctcctc caggttccgg cctccagcct ggtgtccect cctcaggctg ccttttcctc    56520
ctcctcctcc ctgtttcctg gctcttagcc gctccatctg ggaagtcttc ctcaacttta    56580
aaccctcgaa cccttgtcct ctgccctcca tctcccactc ctcaggcttt cagcagcttc    56640
acgtggagca ttgggctggt cctgtccaca gttgttcagt tgctgtaaca gcttgtgcag    56700
gctgccctgg agccctgttc tgggaagcac aggtctgggc accctgggge tggggcgagg    56760 cccggagctg atctcctctg tccatcccag tagagccagc accagtgcag acacatgggg    56820
gatccaggtt ggtggaccag gggaggatgg aaagtcccat ggatccagcc ggaatgttgg    56880
agtggggagg cagagggccc agggttcctg ctggccagcc tctgggctta ggggtgtgta    56940
tcccagacag gccaggcctg ccaggggccc tgacaacagg aaatccttga aggaacaagc    57000
agaggctgag gactctgagc acaacaacag gaaacagccg tgacatgggg caacagccct    57060
ggcgactgtg cccagttggg gtggggacga ggggccaagc ttgtgggacc cagggtgatg    57120
ccaagaggga cactgagaca ctgtgggaca gggggcgttc tgcacatgtg acacggagct    57180
tatgacgtgt aatatcaagt acgtgaccat gatcataggg tactgtgtgg agtgtgggtg    57240
agtcactgag tatgtgacac tggctgtgag gcactccatg atagcagatg tgtacagtgg    57300
ctgtgccacc aagtgtgtaa cactgtgtga tattgattgt gtgatgctga caccgagtgt    57360
gtgacattgc acattgcatg ctaccacgtg tgtgacactg aaagtgacag tgagcacatg    57420
gagggtgtgt ctccatgaga atcaaataca gaaacgtgag caaatgacgc tgcagtagca    57480
ggtatggtcc tgagtctgtg gctcgagtgt ctgacactga attgtgacat tgagtgtgtc    57540
ccaagcatat gatctagtga ggctgagtgt gtaaacaaag gcatgacatg gagtgatagc    57600
aagtgtgtgg aagtgggtgt gtgatgctgt gtgatcttgg gcctgacatt acatgtgtga    57660
tgctctgtaa tggttgtaac agtatgcaat gtgcacatac agtgctgtgt aggacactgt    57720
catgggaagg caccgatggg ttcaggcggg aaagtaacac cgtccaaagg atggttttaa    57780
aagattgctc tggccggatg cagtggctca cacctataat cccagcactt tgggaggctg    57840
agctgggtgg atcacctgag gtcaggagtt caagaccagt ctggtgaaac cccatctcta    57900
ctaaaaatac aaaaattagc caggcatggt gacaggcgcc tgtaatctca gctgctcggg    57960
aggttgagac aggagaatca cttgaaccca gggggcagag gttgcagtga gccaagattg    58020
agccattgca ctccagcctg ggtgacgagt gaaataccat ctcaaaaaaa aaaaaagaa    58080 aaagattgct caggttgcag aatatgtatg tgtgcgagtg tgcatggtgc gtggcagggg    58140 agggagata agttaggggg aggcagagag aaggtgggta gagcaactgg aggctcctgc    58200
agctgcccag gcaggagatg gtggtgcctg tgttaatgga atggcagaag agttagagat    58260
atggagcaac tttggagata tttgaaaaca gaaatgacag aacttgctga taaatgagaa    58320
gatgagcaag agggaaaacc agagaacaat ttccagggtt ctggcttgaa gaaccaagcg    58380
atggatggtg aagatgtttc tgagatgggc aaaggcaagg gggagggtca gcactagtgg    58440
ggtgggagga caaggaggca gaaaccgagt gagctgtttt ggatgtgtta agggaagcat    58500
ccaggtgaag gtgtgcagtg ggcagcgggg ccaggctagg gatacatctg ggagtcgaca    58560
ggcatggggg gtttgttaag gtcgtggacc tggctgggat aatggagaga gggagcttgg    58620
caacagaaga ggtgggggact gaggaccgag ccttaaactc tgaatattcc attgtctaga    58680
ggccggggga gtgagaagga gcagcaacga gacagaggag gagggccagg gaggcagagg    58740
agaccaggag tgtgaagcca gaagccaagg gaggaaagag gctcaagtgg gagggagggt    58800
```

```
cggtgtgtgg atggtgctgg cccacaggta agatgggaac cggaagattg tgctgtgctg    58860
ggcactgtgg gtgagtcagg ctaatgggag ccatttcagt gatgggctgg agccagaagt    58920
cagactggcc tgtgtaggat ggtgagggag gtgaagacgt tagcctggag agcccttggg    58980
agacgttggg ctgtgagggc tgcagagaag gacatgatcg ctggaaaggg agattacatt    59040
tttttattat gggtgattct aagcagacac aataccagag agaagcatat aagaaactgc    59100
catatactca tcaccccagt tcaacagttg ctgggatttg gcctcatttc ttcctctctt    59160 gcccoctatc tgttctttca ttttcctttg cttaagctta aaatttttta aattgtggta    59220
aaatatacat aacttaaact ttaccatcat aaccatttct aagtgtacag ttcagttgtg    59280
gtaggtacat tcacactgtt ttgcaaccaa tctctggaac tctttcatct tctcaaactg    59340
aaactctgca cctattaaac gacagccccc atcctcctct gtctccagct cctggcaccc    59400
accattctac tttctgtctc tatgacttgg actactctag atacctcaag taattggaat    59460
aatgtagtat ctgtcttttt gtgactggtt tttaagttta cttagcataa cgtcttcaag    59520
ttttacccat gttgtagcat gtgacaggat ttccttcctt tttatggcca cataatattc    59580
cagtgtatgg acagaccaca tccatccaac accagacact tgggttgctt tcacatttta    59640
gctattgtga gtaatgctgc tatgaacata agtgtacaaa tatctcttca agatcctgct    59700
tccaattctt tcagatgtat acctagaagt acgcttgctg gatcacacag tcattctatt    59760
ttttggtttt tgaggaactg ccatactgtt ttctgtatct ttttacattc ccacggacag    59820
tgtacagggg tttcagtttc tccacatcct tgccaacatg tgttattttc tgttcttttt    59880 tttctttat tttttaatg gtagccatcc taatgggtgt ggggtgacat tcattgtgg    59940 ttttgatttg catttcccta atgattagtg aagttgagca tcttttcatg tgctggttgg    60000
ccacttgtat atcttctttg ggaaaatgtt gattcaagtc ctttgcccat ttaaaacatt    60060
gggttgtttg ctttttttgtt gttattgaat tgcaggggtt ctttatatat tccagatatt    60120
acctctttat cagataaaag ctttgcaaat attttctcc catttcatag gttgcttcgc    60180
tgaaatattt taaagcaaat cccagacatg atgtcatttc accaaaggta gactttttt    60240 ttggtggggg gagctttccg gtgaagactg aaaaacctgc tagacaaatt ctaaaataga    60300
tgtgactttg gattttttgtt ttttaaggct aggaggtcct ggatgatgct gaaatgtaac    60360
agtgacacag agccagtgtg gaactgtgtc tgatgctgtg tgagggtgac atggtggctt    60420
tgggaacatg ggtgcaacac tgaagatatg ggagactcca agtgagggtg acagtgagag    60480
atcactgtgt gtgtggccct gtgacaccca gtgacatggg acagtgggac gctgtggacc    60540
ctgaaatgac tgtgtgtcac cgagcaggtg ggacctgctg tgtgaaggcc acaggtgtca    60600
tgtcttcttg tgtcatcctg gttgatgagt gtgacacagt gcaggactct gcatgggagt    60660
aagagggact gaagctgtgc tataggtgac cgggctgcat gtgattcaag tgggctcagc    60720
cccagcttca gctgctgagt atgggaggga gcatggacat tgtagggtag atgaggagaa    60780
acactgaatg ggaacagaaa tggtgtctgt gcccagatgc gagctcctcc cttctctgaa    60840
tacccaggaa ggcttcctgg aggcaggatg tgggcacttc agcaggatgt tgtaggtgct    60900
gattaagagc agggcctgtg gtgtcagaca gccctgtcta ggctctgaca ttcagcaggt    60960 catttttatct cttgagcctc aatttcctca agtataaaat gggagctctt aggaggattg    61020
catgaagcag tgctccaatg catgcagtct ctggcacttg gtaaatactc tatggtctct    61080
tggggagcag caacctcaac acctgcaccc caggtcccca aataacagga gcaccagtag    61140
```

-continued

```
gagcacagtg aaggtgcgct gagtgaggtg tcctcttaca cccacagccc tcctctctcc   61200
ctctccccca acttctgtcc cctgcttggt gttgtcagcg ataccccctc ctgcccactc   61260
actcctgccc cctcctctcc cctgccgtcc ttaccactgt cagcctccag cccaggctcc   61320
tgcagcctca tccaattagg ccaatgcaat ttgctcaaga aaaagcccca taatttggtt   61380
aatcacacca gtaggggatc tggtcccggt cgggagggtg gggtggata ggagtccata    61440 cccgcagctg aggcacaggt gtcaaagtgc ctgtcttttg ggacctttac ccacttcctt   61500
gggctccttt caggagccaa cagagtccca aagcttgggt cttctcaaac cccaactaca   61560
gaggccttga aacaggagtc tggacttcct gggttcgctt gtgttcctgg gagggtccct   61620
gctactctct gggcctcagt ctccctttcc aaaaatggga gtggaactgg ggagtctcag   61680 aggcccccagt tggcctagct ctgcatccca gctctggtca gtccccttg tggcttctga    61740 ggggccttct cctgggcctt ggggagggag cactgagggg taggtggaga gcacagggcc   61800
ccagggaagt gaggagggt aagtgtcctc tgagtctcat ctggaatgtg tctaccccag    61860
tcctataatc agagaccctc tagttccagg ctgcacacct gaaggtgggg caggaagaaa   61920
ggaagctgcc ctttcttggt cacctgcaag gccaaagtct cttaaccgtg caggctatac   61980
cttgcacagg agctccagca gaggtggggt ggtgctgaaa ctgagcccac tctccctcac   62040
caagcctttc ccctcaggcc cgcatctgcc cagagaattg gggtccctcc tttctaatgt   62100
gcacacaggt ggccccagcc ccctgctggg agtcagctta ggcaaggttt gatggctcag   62160
cttaatcttc tcagcagctc tgggggaaga gaccattta cggatgagga actgagccca    62220
ggaaggtcca aagacttgtc cagtacatgt ggtgtgtggc agggcaggca gatgagcccg   62280
catctgaggg aggcgatggg agaagtgaca ggggtgcgca gaggaggaga attagaccct   62340
ctcagattcc accactctca gccacacgtt cactcactca tttggagaca agactaacca   62400
ccagcgcatt cacagccccc cagacagcca catactgact ataccactgt cacatggaca   62460
tcaatgacct gaatcacata tgcatagatg caggcccaca tggtcactcc cacgtgcaga   62520
tggccagtgc acacacatag acacagggta ctcacacatg tttacactct cacgacccat   62580
gtgggttaca gattcctaca gagacacaga cctacatact ttcacaagga aattctccca   62640
gtgacccagg gaacatagtc tgccatgatg atgtgatggt ccgtaggggc tcgccactat   62700
ggaccattaa tgggcaggct gcacacatgc ttaggtcccc agcaaagcgg gagttctgca   62760
cagagtgaga ggagaggtca gttctgatga gtgtatccag aattttgcaa tcagaaaaac   62820
cacacaaaaa ctattttaat tttcatttcc aagataaaat ttagtttgaa ttgtatagag   62880
ggtccgaggg tctggtggga gggcatcatc atcttttcaa ggctttgggg ttctaaggca   62940
cccacagatt cacaacagtc ccacaagata tcccaggctg acatatttac ccagcccagt   63000
gtgtgcgtgt gtgtgtgtgt gtgtgcgcac gctgtgtgca tgctcatgct ggctcccaga   63060
tcctcgggat gtgaggaagg aaagtaggag agattccaga gactccggat gtttgttctc   63120
tggcttcctg ggcccttcaa aggaaaataa ctctggatgt cagcctgcct gcctggcggg   63180
ctgggtggag aggtgggctg tttgggagg tgggctgtat gacagcctgc ctcagcccct    63240
gtggccccac tgaccgggac cctgtgtaat gaggcagagt gaccaaggcc catggccagc   63300
gtcccatggg ctcgtaggcc catcgcctcc cctctctggg gcttggctct tcatctgaa    63360 aaatggaggt gggaaggaga tgagactgga tgggctttct cctggagact gattagagag   63420
acagagactc aggcccgggg tccagaaaag acaaccaaag ctggggaggg cacatgaagg   63480
ggggcaaaga aggtctgggt tcaggggagt gcgtggggcc ccagagcctg ccatgtctcc   63540
```

```
gccaactctc tccctcactg gaggagggct ctgtgccttg gtgccccacc tgcccagggc    63600
cctgtggctc agcccttgc ttgctctgtg aggggacgg gagaaggatg agagtcccag    63660 tgatagggg aggacaagac caggggagag ggctgggggt ttctggaggg ccagagcagg    63720
aagagcagga gagaagagag gacaccacag tgcaggaaac ggaggagcaa aggctgggag    63780
tggggaggct ggaggggtgc agggaatcag actgggcgc tgcgaagagg cctgaggcca    63840
gagcaggcag tgcctggatg gagggagcga gcagctcctc accctcagct ccttgatgag    63900
gtaaggtgac cacgagccct gctccaggct gtgtgctgag cactttgctc ggagcctgtc    63960
actctggagg aggggagggg gtgttcccag gagctatgac agtcttgtgc aagggaggga    64020
cagggtcaca tttatgttta acaaagcact gcgctgggag agaggagctg agagaccccg    64080
gccctgggga gcatggtggc tgggaccccg gagggcaggc gtgccccaga cggacccac    64140 tcagaagatt gcttatccca accccccaaa gagaaaggct attttagga acaataaaag    64200 tgctcacaca ttcctgcagg ggcagagaga gggaaagggg gcaggagtca gtgcagagga    64260
agagggtgga ccccgctctt ctcccaactc tgccttggtc ttcagggact tctcctcagg    64320
ggcttcccca gccagccctg cctctccagc ctccgcctgt ccctgggtt ccctaccggc    64380 tcttatgtct atccctctgc ttctgaattg gtacttgttc tgtccctgtc tctctttctc    64440
atacttccac tttcccctc ccctgggg ttggggaaca gctggatgg gccaagctct    64500 gttgagagag ccaaatacag tcataggaca aagcagcggg aggctgtggg atacacacat    64560
gccgcagagc acagacagag agaggtggcc aggcacagag agagcgccca gggaggctga    64620
gaggcaggga gaaaacacgc tgggacagtc agggagagcc ccagggcagg catcaccggg    64680
cagccagcct ctgtgccctg ctctctatct tgtccctaag aagaccagca tggctgggct    64740
tgcctcccgc catccacccc accagcccta ccccaggctg gccttcctc cccgccctct    64800 gcaggcccac actaacccta ggccaggccg cctccttcag catttacctc ccacacacaa    64860
tgggcacagt gaggacataa gagacccagt ctctggcctg gaggcagata ctcagcctta    64920
cccgacatct gagagggctc agcccatccc ctggccaagg caggtattag aggggcccca    64980
aagacaagca ggactctggg acaaggtgtc ctagtgtggc ccaaagggct gggctgaagc    65040
atgggtctcc tggctccaga tgagagcctg ggtgaatcct tccctgcctc ctctggcctt    65100
agtctacccc atcaagcttg ggattggact acatgaggcc tgaggccctg tagcccctgg    65160
tccctgggaa ttctcagaag gcctgggagg gggacaggtg accacgcagg aaggcttcct    65220
ggaggaggtg tcctcactca tgaaagaagg tgatagtgac agtgctcctc ttggggaaga    65280
gccctccatc ctgacctgct gcccccaccc ggtctgcacg tggagatgat cctgaagcac    65340
aaagggcctc ccggcctgca gaggtgcctg ggagaggttg ccaaaggctc tcagtaggag    65400 acacccatt cctcaggctc cttctctgag actgtaactg tgccagactg gggaggcttt    65460
gagaggtctc agctatctcc cctgcctaga tccttcctcc acacccctct tctccctgat    65520
ggcatgtagc cctcacagta cagtagtcct gggcacacag gagtttaccc agtcatttac    65580
agctcagcaa acacctacca acacctatga ggggctgggt aatgctggag acccggagag    65640
gggcaggaca caatctctgc cctccaaaag ctcccagtct gttgtgggag ccagacggga    65700
aagggtggca ctgcattgat gcacacagtg catgccatgg tgggggaaag gggggcagtg    65760
ggagccccag gtgggagggt cagacttgcc tggagagaga acaacaacag actctccctg    65820
gaggggatcc agagaaggga gatcacttca ttcattcatt cgtcattcat ccatccaccc    65880
```

```
attcaattat tcctttggcc atcatttcct gagggatgta aactctcttc tgacactgac    65940
ccagcgggac actcagcgtc ctcctcctct cctgcttgag ccaccatgcc tgcctcttgg    66000
aggctcctgg acttgctttg ctcagctccc aacccaccct gaggggggtga ggctgaggag    66060
ggtgtacaga cattcagggt caccaaactc agagctggag gcctgccacc tcaccagggg    66120
cctttctcag ggcacaggct ccctggtggc agggccttgg cccttgcttg cacacccttg    66180
gggactagga gcccctcat ccatcctgct caggctctct tttgtggcgc gactctgatt    66240
cacagtgtgc ccaaatctgc ctccttgtga ctgccgcgag ctgcctcgtg gccccaggc    66300
cagaggacaa ggatagctag aatgccaggt gaccaggatg actgtgatgg catggagagg    66360
gggatgctgt gatgtgtttg ggaggaagtt tgtggtgtcc aggagaatgt gggcagcaga    66420
aatgggacca ctctcggttc ttccctgtag atgaagcagc tgaaggtggg aggggtggg    66480
aggagacctg agctggctct gccccgcttg atctgatgtc tgccttgcag ggccatcctc    66540
cccctcccca cactcagctc ctgcctccct ccctctaccc actctgactg ttccctcctt    66600
tcctgactcc agactctggg tgagggactg aggtgattcc agtgagtcag gccctcaggg    66660
aactgatcgt gcaggcaact cttgcctgcc ttctcctgct cttccctct tcccattcct    66720
tcatccaccc ccaaacctag ctcctgatgg atccaagggt gcgggggaca accgggaggt    66780
cattttggag gaggcaggag ctggaataga agctgggact ggcttgggaa gggcgagagg    66840
ccggggcgga gctggttgtg ggcgctggaa gggaggagcc aacagtgtgg ggtcaggctc    66900
ctgtggacgg ggacacccct gggaggcact gggactggct caggtgtatt ctacagtgca    66960
cgtgtctcca gtgtggctcg gaggctggag acgcggccct gttggagtaa caactgaagc    67020
cggagtctgc gaagggtggg caggagggtg gagggatggg ggcatggagc gggaggggt    67080
aagtagagga gggaggggag gaagagaaag agggaggagg aaaggtctct ggcaggtccc    67140
tcctttaaga ctgggctcct gcgctgcgag tggccccgtc catactgcct tgttatccat    67200
atctccccac cactagtctc cctctgtcct tccaccccca gcctctcccc tccattggga    67260
ccttccctgg ggcgtcccct cattggctgt tctcacctga gcaaggcccc tcccctccag    67320
tccttagcct cttcacctgt acaatgggat gacccaaaca ggcacctctt gggcttgtag    67380
gaggatccaa gatagtgtca gtgggtctcg aggtgtggtc ccccgaccag cagcatcagt    67440
gtcatctagg aatgtttgga aacgcaagtt cttggacctc gtcccagacc tactgtatca    67500
gaaaccctgg gggtgggggcc agcaatctgc acttttaacaa gcactctggg tgggttctgg    67560
tgcacatgaa aattggggaa cggctggtgg aaacctctag ccacaggagg tgcttgggaa    67620
aggtaccttc ccctccccaa agcctgatgc ctcactcaag catgacactg acagttgggc    67680
tagttcagct gcgttctggg tctctgtctt gcctcctcct tcagactaag cctcccaagg    67740
gttgccaagc ctcttttcctc tattctcctc accctgatcc agctcagcct cattgagaga    67800
agtctggggc tgcaagatct tcgcactcac aggcagttcc tctttgcaca tccaaggcac    67860
cagtgtcttt gagaggcgtc tccttggcca ggtggcaggc gtgggtgtgt ggggaggaag    67920
gaggaggaac cgccttgttc tgctttcttg tctctgactc tgcaggctgg gggtgctgta    67980
aggctgcgag gaggcataga gtcagcttgg gtgctgggct gaggccaggg gccgaggctc    68040
agctgaagcg ggcttctctg gtctgagcct acaggatgcc tcctttgggg cagttctgcc    68100
agtcaccctg actgggcggc tgtgcttgct agtgccagac ccatgctagg cacagaggtc    68160
gatacgttct cctgtgctct tgaagggccc tgtcctctgg gaagataaga ggctgtgtat    68220
attgcccacc ggaacaggag gcaggaagca aaagaggcgt agatgacact tgcctggcac    68280
```

-continued

```
cccctgtttc ccctctagct gccttcctgg gtttcccatt ctgtgggcgc ttctcttgag   68340
ttaggtgctt tctcccagtg ttctcaaggt gactatttgg aggtttgtgg gaggagtggg   68400
ctggagacac aggagtaggt gggggcagga agtatgcagg agagagatgg agagtgggag   68460
gagaagctat gagaggaaga gaggacgcgg aagtgggaaa agacgtcaag actcctggag   68520
aggaacagga gtgcagcctg ggacagaggt ggacgtcggc cggggaggc agggaggaag    68580 gcagggaggt ccacccgaaa ggaagggaag ggatgatgga cagagaatga gagggctccg   68640
aggtcctggg ggatctagaa ggacccttcc ctttacagaa ggggacacca aggcccagag   68700
agagaggagg gcctcacaga ggacctaaca caagcagagt tgcatgaatc agtgtgaacg   68760
gacagtccca agagcacagc cggaccttgg gaggtacttg actcttgagt ttgatgttat   68820
tgccttcctg taggccagtg tgagggcac tgtgaggctt ccttccagag aaggaggcat    68880
ggagccagtg ccaggcagtg gggtgagcca taggaggacc tgtggagatg gggaaaggca   68940
tagagactca tgaagatgaa acaggaaaga tcttatggca gcgaccccaa ccctcaggaa   69000
gggcgttggt cttgtgcttg tggctccaaa ggggataaga ccaaggtctc tggtttcata   69060
gaatcttagg ctttaagaac gagttagaag taatttagtc cagaccctct cctctcccca   69120
gataagtgca gaaatgcaga tctagcccac ggctgagccc caaccctggc ttcagaggag   69180
gcctgactca gaacaggctc cccttttcttg gtacctgggg tgaatgaaag ataagtctgt   69240
ggtaatggtg ctgtctgtgg tgctgactgg ccttaccttg gactacagag ctgcaggtgg   69300
agctggagag agcagaaagg ctccatctat ccatctaccc acccacccag ccacccatct   69360
acctatccac ccaccatcca cccacccatc catccaccat ccctccccca acccatcctg   69420
cacccattca tctatccacc tacccactca tccatccagc tcattgaat taaaccatag    69480 aactatatgc tgcagagcta gaaagatcca ttttttagta atgacaaaac tgaggctcag   69540
aagaggaaag gtgttgcgta aggccacaca gaacttctgt agtcagtctg gtacaggatt   69600
ggaaattgcg gctctttttct acacaccaca agttctcctc tgtggtctgg gaaattgcct   69660 ggttttatg ctgatatcta tactgatatt tgttccaaaa agctgtgaag gcaggaaatg    69720
tgacctcctt cacccccatcc cgagcctgag ttctgtgtgt gtgtgtgtgt gtgtgtgtgt   69780
gtgtgtgtgt gtatgtgatg tgcatgtcta agtgcaacct tgtatatgca ttgaatatat   69840
gattgccttt tgatctgtct gtgtgcgtgt ttgtgtgaga gcctgtgcat atacgtatga   69900
gtagaggagt gcgtagcaat atgtatttgt gtggcatgtg tagatgggca tgtgagcagg   69960
taaagctgtg tctgtatttt tccttttcctc ttccttttaa gatcgaagcc ccctgacttg   70020
agccttgctc cccatctgtg cctccaattc aggaatctcc ctgcttccca ttagcagctg   70080
ctccccactg attctctcct tccttcactg aagcagcaac tcttccctct gagcccacac   70140
ctcatgggct ttgcaatttg agctatttcc tcccctgagt tggtgcaatg ggggtgaagt   70200
tgctttgaga tctgaggaag attcatggag gagatggcat ttgagcaagc cttgaaggcc   70260
cctttgagtg ccagatctga agtggcccctt cccagctgca gttcctgcac ccaacaccct   70320
ccattcctgg ggcatgctgg gcaggaccag gaggtggatt gacagaagga tgcccacaaa   70380
gagccctggg cttcatcagt cacattacca tccagtccgc tctagcacag atgggaagcc   70440
cttccctgct gctgccccaa ctctccccaa cttttccttc ctgctctcct tattgctact   70500
atcctgcact tggcctgaaa agtcacagaa aactgaacaa tcagagcaaa ggtcaggcag   70560
gcacccacca attccagtaa aggacagttg agggcattcc ccaattgaag caaagggcag   70620
```

-continued

```
gttgaggagt ccaccaatca gaataaagga cagactgttc tttctgagca ccctagggtg    70680
ggagctgggg atcgggtgct gagcaggaac cagacagggc tagagatcca gaggtttggg    70740
ttctggacct ggctctgctc tgactggctg tctgaccaca ggttgatcat tgcttctcat    70800
tgaacctcag cttcctcatc ggtcaaatgg ggagacttag ctctctgaag gctgtggctt    70860
tgaagaattt ctcccctgt atcaggctca ctccgtcacc tgggtctctc ttccccaagt    70920
ccacatcaca tacatcagac tccaccaagg gcagggcctc tcaggagtca gcttgtgggc    70980
tcctctgcct ccaagaagga atagacacaa accaacacca ccttctgtgc tgtctttaga    71040
gcccccgtct ggggagcgtg catctggaag actttatctt gggagtactg ggggcatcag    71100
ctcttcctcc cctttttagt cttcagaatt gaccttggaa ggccataata gcctgcgtgt    71160
attgtgcaca ggtatcactc gagctcttgc cctgtgaatc tttaaggaac tgtaccagtg    71220
agaacgtgtg tgtgtgtgcg cacatggatg gtgtctgaag gcctgctggg atgtctgcga    71280
ggacgtggga tctgtggctg tgtggtgctg aagttgtctg tgctgtgatg aggagtgcct    71340
aagggtcaaa agacaagtga tccaatttgg gtattgtgtt gtctggaatc agtagcttct    71400
gatgtctgag ggtagacatc ttcccatgac caagatatgt gtcttcatcc ttgagcagtg    71460
ggagggacca aggaagcctg ggggttgggg aaagcgatgc tgagtaagca tctggggaga    71520
aggcccacta ctgccctcct cctgggaaca ctggattggg tggggaagg ggaggaaact    71580 gcagccaaga agacccagga gtgaaatttg gagctgaagc ctggatgcaa gtcttcattg    71640
agagcccagc gtggaacttt ctggcaaata ggcattcagc ccactcttgt gcacccttga    71700
ggatgggaag ctcacttcct ccctctctcc tggtgacctg tggcatgcct ttgtagcatg    71760
gccctacctg gaagaaggtc cttcagccca ctagaccaag gccagcctcc tgtgaaatcc    71820
tatgggtccc caggctgtcc atggggccac agagttcaga tcccccatct aggagggtct    71880
gagagattgg agttggagac tgataaccct gggtctcctc tgctttagat gaggcatccc    71940
tgggttatcc agtcttagtc acatgcaaaa cttggtttcc aattccctcg tttcataggt    72000
cgcctcctct ggatgagtgt catcttgtca gcccctggga cacaatgaac aggggatggt    72060
ctaactagac tataaaagtg ggggaactgt catcttccca attgggttaa cagacctcta    72120
ttaatatggc ctgcagtttg agcattttta tttcttgcca gtcatgctta cactgtgggc    72180
tcatgctgaa ctgtggtctt ttaagaccct caacctcata tcatgttcac atgaatgggg    72240
acccagccat gtctccttca tcttgcagtt aatcactttg cttctgaac acagacccaa    72300 ccttccactg ggaagacatc tgaaaggact tccaagggct tgcgggaggg catggctggt    72360
ggctggtatg agtcacgatc ttgccttggc cctcgtttcc tttgttctgt tacctttctc    72420
tttgatcccc atggctctgg ccaagttaat agagcgagaa gcaggactt ttgtctccgt    72480 tccggctctg caaggacgag ttctgttcct gggatgggaa ggctgtgaga cagtcaaggc    72540
tgacgtctcc ttctcctcct atagttgcca ggggtggccc agctgttctc ccaccttatg    72600
ggttatgcac cccataggct cttgctactc tcaacccagc ccctcactag gctggaaaat    72660
gagactaggt gagaccacct tccttctggg gaaagtgagc gggacccagc ttcagcgaat    72720
attcagctga gcatctactc tgtgttgggc attctgtgag gcacttttag gactctgatt    72780
tttattttca tttttaaggg ctcaattcca ttttatcttc atgtcagcct gtagggggca    72840
atagccccag ctgcttccaa cttacagata ggagactgag gctcagtgac tgaaccaaga    72900
cactcactgc tcatacacag cggagctagg attcaaattt gggtgttttt ttgtttgctt    72960
gttttgtttt aatttggagc cttgtggttt ccctactgtg ccagaattgt cctcgactag    73020
```

-continued

```
agaacaagag acctggggtc taggccaggc ttgacctgtt gactcactat gaggcctttg    73080
ctaagtccct ggcccttctc tgcgcctcag tttccccacc tgtaagatga gggtacttgg    73140
acattctgtg gccttaagac tgtttgattt tgagatccta agatcctggg attcctgtgc    73200
ctgaaagact cgggctctgg actaagctgg ggggttttgc tcacagtcct ttgggcagat    73260
ggggctgccc tggcctgcct ggcaaagcct ctcactgccc tctcctctct tccaggacgc    73320
cttgctgagt ctgggctctg tcatcgacat tcaggcctg caacgtgctg tcaaggaggc     73380
cctgtcagct gtgctccccc gagtggtagg tgcccgccct tgcccacgc ttcccacccc     73440 accccaaat cctttgacca gctctatgct gtacctcact cagggccaag gaggaaggaa     73500
gaggcagggt ccctgcccag aggactttca tggggaagtg aagggtctgg atgggtgttc    73560
tgagacagct ttctggagga ggaagcctta ggctaagcat caaggaatga acttgcatag    73620
gaatcctgca atggctgagc cagaaggggc cttagaggtt aagtggaaaa gctgtgtctc    73680
agataatgaa agggattcac ctaggataac aggacgtggt ggagccagct gagttttgga    73740
atacatgcag caggagaagt tgagggtaga catgtagaag aacttcctgg aagccaggtc    73800
tgggaggtac tagaataggg ctcagctttg atgaatagac atgcattggg ttaaagtgcc    73860
ctgcctggag atgggaggct ggaaaaatgg cctctagcag ccttttagca gctttctttc    73920
tgtcccatcc caataccatg gatgagttgc aggtttgggg caggtttggg gtgatcatgg    73980
ttgcctgagc ccagagtgcc ttactgggga gattgtgccc ctcatcatct gttccaggcc    74040
actcccctac ctggcttcaa tggccactgt tcatccctta gcaggagga tgggtaaacc     74100 agcccttgag gcccaaagta gcaggtgtt agttgcacca gaaagaggga agcaggggac     74160
gtttgaagcc tggagaaggg agtctgatcc agcctaaggg gcatgaagac cttcctggag    74220
gaggagattc cctaactgag tcctgatagc cttgaatgtc ctcttcccta ctctaaaccc    74280
ggccaagggc agcctctgct ccaggaaata tggccaactc agaatgtgac cttcccatcc    74340
ctccagagcc cattgtccct gaatctgctt gatggatgaa ccaccggagg cccagagaga    74400
gagggcactt gtcccaaggt cacacagcat gacaggata aatgggactt ggtatctaag     74460
cagccccatt ccctctcttc agctctgcct tccccaaacc tcctagaagt tcagagccca    74520
ggaggagggc taatgagtga gctttattga gtgtgaaatt ggtaggaagt gggtggtgtg    74580
ttggcgccca aaaataaatc ctcctggaga aggacgggac taaggcaaca tctggcctgg    74640
ggtgaaggca catctgggaaa gggagggtgg tggaaactgg caggtcggtt tctgtagggc   74700
tgccccgaga gcctctgtgg ccactgaggc tgccgtaggg tgggaggagg aagtgactgg    74760
ctctgtttca caggcagggt gccctggcgg ctgtgccagc ctagatgctc tgcaacagat    74820
taattgtctc cccaaagctg ggggctggga tgacagctgt ggtccaggtt cctgggacag    74880
tgggaaatgt cagccctggc ccacccaaga gccctatagg agctagggaa gccctgactt    74940
tcgggagtcc tggcttgatt gcacggaggg gctcagcccc cagtgaggta agggagctga    75000
ggtctgctct gctgcccca gggagggaag cagagatggg gaggggaccc ccgcccaggg    75060
aggagagctg ctggcacctg gcttcctcat cagcacccat tgtggcaggc agccccgaat    75120
gcagatggtg ctgatgtgtc tgaaatggtt ccctccttct ctccaataga ctcagctaat    75180
tttaacccag agggctgaga gtaagggggt gggagacata cggacatgcg gaagtgaagc    75240
gagaatctgt ccccctctgc ccccatggac tacccacccc tccctctgcc tgggcaggac    75300
tttctgtata accccggctg gtctcttaac ctctttgggc caaataactc aggcccctcc    75360
```

```
caggctgctg gaagagatgg atgacaagga ggctagatat agccgaagag tgggcggcct    75420
ccttcccact gaattcttta tccctgaaca tcccacttag gtttccttcc agccaaacaa    75480
gagggtgtct gcccctctca ctcccttcag gccttatcat tcccacccca tgccacaccc    75540
accacggaac ctggctcagt gtctctggaa gtagtggcca ggcatctcct gtggtggggg    75600
ctggctggcg acagctgatg acaagaagag tggctggcag gattgtggac gctctcagag    75660
tcatggaagg caactgcttc ttctgggaag gattccacac ttactgaggg tgggccttca    75720
acacgtagct ccactgtcag ctcctcccaa agccctccag gatacccyca gctgggaggc    75780
aagcccttct ccatcctcct gcggagaaaa cagcagagtt gtggacaagg ctgcgttgca    75840
tgggggttgg tcagggatcc cgaagggttg ccagttctgc ttggaaggaa tgtggatttt    75900
tgcctgtagg tcagtgaggg caactacttc tgccaagaca tggcctggaa ctgaggccag    75960
agctgctctg ggcccttggg gagggaggat taaagagcaa gagctttgat ctccctctga    76020
ggagtaatcg gtccaaaata caaatctgct cacgtctccc tgtgcacgtc ctgccctgcc    76080
ccagttctgt tcgtaagccc atcccactca gccctactga ccttgggccc agcccctgtg    76140
ccccttccct cactgtctgt tcctaaatgc tccatgcttt atacgcctct ggacctacct    76200
gtgtacctgc tataaggcct gggagcccat tctgcaccct gcccactccc tgaatgtgtc    76260
taattcccac tcagtgacag ctgaaaggtc acttcctcca ggaagccctc tccagcccca    76320
ccggaggatg gcgcagtgcc ctgctctgtg ttcctcccct ggctggggtt atgggtgtgt    76380
ggtttcttgt agaggtgaag gagggatgct tcctagaaca ttctgagccc catccctggt    76440
acagctcaga gtggatgctc agttattgtt tgctgaatgc ctgaggctgg agtcaggcag    76500
ggaaatatcc caggtgggag gtgatttgtc tgcaccctca gtccttgaaa ctctttacct    76560
ggcacattgg gttttgggtg gtaaaaaagg tcataggttc atgaatcatt gcctgcttag    76620
aattccttcc aagaggagag gacgaggtgc ttagttcacc gggtgttttg ctgccctggc    76680
tgcatcttag aatcacctgg agagaaaaac aaacagatca ttgccagagc tccactccca    76740
caggttccat gaccttgccc cacagacccc tgtgtacagg ctgggactgg gcagctggga    76800
gggcctctcc acagggtctc ataagtgcct tctgtcctag gaaactgtct acacctacct    76860
actggatggt gagtcccagc tggtgtgtga ggaccccca catgagctgc cccaggaggg    76920
gaaagtccgg tgagccattc tctgcacccc cattgccctc ttgcatggcc aaggattctc    76980
agggctgagg caccatccaa ggtcatctgg tctgaccctc cccttccaac attgatcccc    77040
gcctccctgc caggtgggat tccttggcca ggttgctgac tccagcacag aagggcagaa    77100
gcaatgtctt ctcttccttg gggaaatgga taggcacaga gaaaatacca attgatggta    77160
aatttctcc ttctaattgc ttctaaatgg ctgcagcctc ctcagagcag agtctcagaa    77220
cattggggct atgggtgta tcagttagaa caccggcatg ctgtgagaac tactgcgagg    77280
ctggacctgg aatcccagca tgctgggcct gcaggagctc acagtgccaa ctccttgcat    77340
ctgagaacag ggagatcaca ggcagcgtcc tgctgagggt tctggagccc cactgcctgg    77400
gttcaaatct cagctccctg tttactagct gtgtaacctt gggcaaatga cacaacctct    77460
ctgtgcctca gttttgttta tgaaatggtg ataataatgg tgcttatagg attgtgggga    77520
ggattaaatg tgtcacacat gtaaagcatt taaatcaggc ctgatccatg gtgagggctg    77580
tctgttgggg attaccattg tgagagaatg ctggaatcac tgacttcagg atcatgggat    77640
cagggcactt ggcccctga taccttgatg cccatttaat tcagcctcct catcttccag    77700
atgggtggat atcatgagac atgaccaagg ccacatgcca ggtatgaggc agagccaggc    77760
```

```
ctaggactcg ggtcttctga ctcctggctg tttaggggaa agtgagagga agtggaactc    77820
atcagatgag aaaaccttgg gggcaggcat gctgctggga ggaggcaggc tctgaaggat    77880
gtggccattg cctgctaagc actgaatgca gggccattgt ggggcccagg gagcactggg    77940
caggagctga gggcagagtg ggcaccagtg gggatgtccc aagaaggcag ctctctaccc    78000
ctgtgaggag ggcttttcca gcaggccagg tggtccaggg atgtggcttt ttcaggtagc    78060
agctgagcct ggcaagccac tcacctttca cagggaccat ggaaagaatt cctgtttgag    78120
gatgctggac tcatggtcct gaggcccctc cttgtgctgg aaaccctggt ttctaggatg    78180
ctggtctctc ctcagccctt tcccgtggaa ggagttggtt ctgctctgat agccaccttc    78240
ccatttccta ttctcccact gagctccttt caccttcccc taacaacttc tccgtcaagg    78300
agcatgggaa caaagccatt accacctctc tctagccttt gtgtcccgtc tgtaagagga    78360
tggtctgaaa ggtctttaga accttaaggg gaaaaatgtg gtcatgtccc cctttctcct    78420
ctaattccaa agaacttcgc tctcctccag catcccccac ctctaattct aaagaacttt    78480
gcttcatata agctccactc ctccaggaag gctcctcgga gcagcctggg aggccttcct    78540
gggagggatg caggaaaaca ggctcaggag gcagcgggga gcagcctgca ggtttgcttc    78600
actccctagg acccacacat gctcccctca gctgtctggg catgtagagt gggtgcgtat    78660
ctgcggtcca ggcattttg agagggctca gatccttggc atcagctgcc ctttcaacat    78720
cctccttcca accacttcag actcagtaag gcctttggaa aaaataccaa aaaaaaagca    78780
attaaaagtg aatattcaaa tccaattatc ccagagctca gtggagatgg ggaggtgagt    78840
gcctgctggt agacagggc tgaagattcc aggaggaggg ccaggggatg agaaggcaag    78900
agagtgagga cagcaaggac ctcccagggg acatacccat catcaggaca cacccgtcat    78960
catccccaaa caggaattct ttccatggcc cctgtgaaag gtgagtggct gccaggctc    79020 agctgctacc tgaaaaagga ttgggggaag gcccaggccc agtgctctct ctggtatctg    79080
agctctgctt gcccaccttt gtgcctggtg tctggtggtg agcccatctc cacaattagg    79140
gcggagaggc cccaggggttg gctgggccct gctctcagga gctcccagca ggatggggac    79200
ttgagaccca ggtgtatgga cgagggaaga gcactggaat gggattcaga caggtctgga    79260
ttctagctca gcccctccc tgtctctctg ctttcctacc tgaggcccgg tctattggct    79320
taatggggta acaggggcca agtgcttggc acagtgccca gcacacagta ggagctcagt    79380
gattgctact tgcactccca agtcccaacc aatgattagc cttgagtgac cttgagaaaa    79440
cgacttctct tctggccttt tttctgtgaa atgggtgggg ttgggtacag ggtccttccg    79500
atggtgacct ttgtggctct ggtccccca ggagggagag ggactgacct acaggctgcc    79560
gtggagcctg aggctctagc agtgcccgag gaggtggggg tgtggggagg gtgctactcc    79620
aggaaaccct ggactgtggg caaacagcag caggtgtggc gtggaggctg gatcatagag    79680
acagataagg aggcccgagg caatgggcag ggaatgggat cagggcagtg tggggagaga    79740
cagggtggaa aagggtcaag gcgggagtga ggaggccccc gccagctccc agccccacct    79800
gtccctgttc ctgccgctgt ttgggctctc agatgcccag ctgcatcccc ccagtgtgtt    79860
tggctttcct gtcttcttgt gcttgtaagg gctgcttgct cccttgcaaa gaccgtccct    79920
gctccacttt catctcagcc aatcccattg taattatctt tcatggcctg accagaagct    79980
gtcttgggga agcctgctcc acagttccct gacactgaga aggaaccaag tttcagaaaa    80040
ggggtctggg ccatattggc ctcccttagg gttcttccac aggaagaacc ttgggctggg    80100
```

-continued

```
agtcagagac ctgggatcca ggacaacatg gctgcaatca caatccgatg ccctcttcct    80160
gggcctccat atgcccttct gtaaaatgat acgctgaaca ttctgatatt gagggctggt    80220
gaggctctga attgtaaggg ctgcaaacga ccttggggct ggagaggaga gaatcctgga    80280
aggctgcctg ggccagggtc ttcctgaaag gaggcttcac ttccctcttg ttggtgcccc    80340
acctccatct cccagactgt ttcaggcccc agctctgccg ccttcctctt cttgtgtctc    80400
ctgctatctt aaagcctctg attacctgat gctgagtgca gcaaaatct caggccttc     80460
agctgcaact gaagcaccca ccgcccacct cggcccaggc tggctgtctc cctctgctac    80520
cattttgggg tccccagggc ccatccctaa gaaatttctt cccctaagct gaccaggtct    80580
tctttcattg cagaatctga ccatccctag gggttgtctc agaggacacc gggaacggtc    80640
tgctcccatc tcgggatcct cacatgctgg ggaaggagg gcaagaagag ggtccaggtc     80700
ctgggggctc agtgagagtg ggggcttag tgagggatg gggcccagt gacagtgggc       80760
agcctcagtg aggtgatggg ggcccagtga ggatatgagg gctcagtgag agtggggtgg    80820
cccagtgagg ggattggggc acagtgagag tgagggctc tgtgagggg tagggactta      80880
agtgagggga tggaggctga gtgagtgtgt ggggctcat tgagagggtg ggggctaagt    80940
ggggaatggg ggctcagtga ggggatggag gctcagtgag aggatgaggg ctcagtgagg    81000
ggatgggggc tcgtgagggg atgggggtt caatgagggg atggggctg agtgagggga     81060
tgggggctga gtgagggat gggggctgag tgagaggatg gggctgagt gagggatgg      81120
ggctcaatga gaggatgagg gctaggtgag aggatgaggg ttcagtgagg ggatgggct    81180
cagtgagggg ataggggctc agtgagaggt tgggggctca gagagggat ggggactcag    81240
tgggggatga gggctcaata aggggatggg ggctgagtga gaggatgggg gctgagtgag    81300
gggatggggg ctgagtgaga agatggggggc tgagtgagag gatgggggct gagtgagggg   81360
atggggctc agtgggggat gagggttcag tgagaggatg ggggctcact cgaggggatg    81420
ggggctcagt gagggatgg gggctcagtg agaagttggg ggctcagtga ggggatgggg    81480
gctcagtgag aggaagaggg ctaagtaaga ggatgagggc tcaatgaggg gatgggggct    81540
gagtgagggg atgggctca gtgagaggat gagggctagg tgagaggatg aggtttggt     81600
gatgggatgg gggttagtga ggggataggg gttcagtgag aggatggggg ctcagtgagg    81660
tgatggggc tcagtgggg attagggctc agtgagagga tggggctca gtgagaggat      81720
gagggttagt gaggggatgg ggctcagtga gaggatgggg gcttagtgaa atgatgggag    81780
ctcagtgaga ggatgggggc tcagtgaggg gatgaggccg agtgagaggt tgcggctcag    81840
tgagggatg gggacttagt gagaggatag ggctcagtg agggaatggg ggctcagtga     81900
gaaggtgggg gctcagtgcg ggattgggtc tcagtgagaa ggtggggct cagtgagagg    81960
gtgagggctt agtgagggta ttcgggctca gtgaggggat gggggctcag tgagaggatg    82020
ggggcttggt gaggagatgg gggctcagtg gggatgggg gctgagtgag gggatggggg    82080
ctcagtgaga ggatgagacc tcggtgaggg gatgggggct cagtggggga tgagggctaa    82140
gtggtagatg gggctgagt ggggggatgg gggctcagtg acagggtggg gctcagtgag    82200
aggatggggg ctcagtgagg tgatgggct cagtgagagg gtgagggctt agtgagggga    82260
ttgggtctca gtgaggggat gggggctcag tgggggatgg gggctcagtg gtagataggg    82320
gctgagtggg gggatggggg ctcagtgaga gggtgagggc ctggcgaagg gattgggggct   82380
cagtgagggg gtggggagtc agcggggat aggagctcag tggggatgg agggtcagtg     82440
ggggatgggg gctgagtggt agatggggc tgagtggggg gatggaggct cagtgagagg    82500
```

-continued

```
atggggctc agtgagggga tggggctcag tgaaagggtg agggcttagt gaggggattg   82560
gggctcagtg gtagatgggg gctcaattgg gggatggggg ctcagtgagg gggtggagac   82620
ttagtgagag tcgggggggct cagtgagggt ggggggttccc ctgggggggat ggggttccgt   82680 gggaggatgg gctcagcaac aggcttggct gcttaatgat gcctgggacc tagtgggtgt   82740 tggaggggggg cttctccaaa gtagagaacg cgagaaggac acacacaggg gctcagagaa   82800 gtgcaggggga cccagctctt tccaggctgt tggccctacc agcagagaac ctttccctcg   82860 attcttttttc cattaaacaa atagttgtta aagggacgga actgccataa agtccacgcc   82920
tgttcctctc tccactctgt gcccatctgt ccttatcttc agtggggcag gccatgacca   82980
cccaggcacc cagtgctgtc attagccttc gcctgggcag ctggccctgg gttgtggagt   83040
tccccacaac ccccagcatg agcctggaag gcagggtggg ggtgggggtag tagtaaggga   83100 ggaactggag aggagcaggg agcggctctg agttgagcaa ggagctatcg ggggtctgag   83160
cagtggacga agctcccgct cccatgtggg tgggggagac tcagccttgg cacattcccc   83220
ctcgcagtct gtgggcatct ttggagactt caggaggaca gcagttctgg gagggctatg   83280
gcagaggaaa ggggctccca tgggggtagg ttgaggtgag tgtgggctat ggggtcccgc   83340
aaagccgggg gagggcaggc tgcagagcaa ggtgccgagg ctgcctaaga attgagggtc   83400
cttggaagcc ccagtgcttg ggggcatctc ggcttatcaa gattggtcta tcccagctca   83460
gcctctgtct tgtccagggc cactaagatg ataggaccct cactgagacc aggtttccag   83520
tgtcacagtc tccttatgtg gagagtttta cccaggcagc atgatcgttc tgaaatcata   83580
cctgaccatt accgtccctg ctcaaatccc tcccagggca ccccctgccc tcaggctcaa   83640
gcccagctcc atagggccct ggcccctgtc tagccttgct ctcggctgtc cagtcacacc   83700
aacctccttg tggccatacc tttcagcagg cacacaatct tctcgcctcc aagccttcac   83760
aattgcaatt ccctggacat cctttcctgt ctgcctcgat aacctctgcc tgtcctttag   83820
gactcaactc aggtgtctcc ctctacagga agccttctct gactccatca cccctgcac   83880 ctgagtgggc tggggcctgc tcttcctgcc tttggcagag ctctcatctc ccgactgaag   83940
cgtgggtctg tacgttgatc tctgcgtgtt cttggcctcc tcaagtgagg catatgtctg   84000 accccctctgc tcatctcagc cctcagcact gaacctgacc cagaaggacc cagtgaaatg   84060
agagacttta agtagaatgc tccccgaggt ttttcatcta gaacacttat tcttgctctg   84120
ccatggagaa tggattgaag agacccagct aggaggctag aggcttgggg agaggctgct   84180
tcagggttca gggaaaaggt gtctccatgt gagctgggca gtggcttggg catagagagc   84240
agaggacagt tgtgagagac aactgggagg tgactcactg atcggatggg ggaggtgagg   84300
aaagaaggca ggtttttgga caagccgtga aggacctggt ggatggttgt gctgctttgt   84360
tgtgaggtgg agggagtgga gataataatt cagatggtat gggggtccct gggccacctc   84420
agggacgtgg tggggaggct ccaggtggcc tttgggtatc tggggtctgg agctcatgag   84480
tgagggctgg agagtcatga ggccgtgagc acagaggagg ggttttgtgc aaaagagaag   84540
aaaggctgag gacagattcc ttcatcaggg tcctgggaaa gagaggccaa gcagctccag   84600
tccaggggtg ggaggggaaa tagttgggag tcggcaggat gaggctgcag tgcgcactga   84660
ccagcaacgc aaggaccagt gccaccttgt ggcctccggt taaccagatt gtctgaggcc   84720
aaggagctgg gcaggttttg gccagggggtc acccccctgcc tcgtgaagc ctcagccttc   84780 atcagtttaa tcatcaggaa acgtggctcc cgttgccctc ctgccaccct acgtccctct   84840
```

```
ccttcccggg gtgactggca atgtggacag ccgggaactg gagcccagca cttcaggaac   84900
cttaaaggtc ctgggtgtag gggctggaag gtgggagaca ccaccggttc ctgtagatcc   84960
tggattactt aaagtggcca ggaaggaatg ggtttggttc agaatgctgc gtgagcttga   85020
acgagatgct caacctcttt ggtcctcgat ttgtctagag tctctgacct agtgatctcg   85080
tgacttgcag gccaccccct ccttttcctc atgtgacctt tgctgggctt cccttagtga   85140
ccctgtatgc acacagttcc ccaagtttct cttctgtcca ggccaggcag ttcctacaag   85200
cacaattaag tggaggcagc atgagggatg aagaacccag acaattaat catcaaggag    85260
tgacatttgg tgcaaacntc aggtgcttaa ttaagcggga tgagccagag gctgggggt    85320
agaggaggtg ggttgtgtgg tgggacagag agaaactcat tcttcccata ccaacctccc   85380
ctgccttggt tcccaccacc cctctgccac tgtcataccc tgccactcac acctgccccc   85440
tgttcaaagc tcacacctcc acaggtattt gggaaggttc cagcatagtg gttagaccta   85500
gccctggtgc cacctacctg ggttcaaatc ctggctctac cgcttattca ctgtgtaacc   85560
ctgggcaagt gaattagcct cttggtgcca tagcttctcc atctgaaaat gaagatatct   85620
aattcataga attgctggga attctgagtt catctatgtg agttgcttgg gctgtgcacg   85680
ggacatagga aatggccaat aaactttagt tatgatgatt acctcctgtg cttagcacta   85740
aaagctgatc aacaattgtt ttctgaggat ggtgacaggg agggttcttc tctctccacc   85800
ctagttctcc ttgggaagat cagagaggtc aggtcatgtg cctaaggtca gattgtagca   85860
ggcagcctag ctttgagccc ctgcattcac ttcctctgct ctcccactgc ctggaagatc   85920
tgcactgggc cccacccgag cctttaccag caaggggcac cagaggccaa actgtggctg   85980
cctgtttctc cacatagggt ccagggtccc ctacttttt acttgtgctg tcatcgtgtc    86040
caacctgagg caggtcagct tgcccagatc cttgcacatg tgcagggtcc aaactgtcct   86100
gtgttcccag gccaggcctc gttcctccct gagtcggggg ctctcaaggt ggcatcatgt   86160
cctcttttca gggaggctat catctcccag aagcggctgg gctgcaatgg gctgggcttc   86220
tcagacctgc caggggaagc ccttggccag gctggtggct ccactggctc ctgatacccca  86280
aggtaagggc taggggctgg gcaggggcag gggcagggag ggactgtggc ccctgcactc   86340
caggtcatgt gtgtcttcta ttcctcttca tctctggctc cttnnnnnnn nnnnnnnnn    86400
nnnnnnnnnn nnnnnnnnnn nnnnnnnnnn nnnnnnnnnn nnnnnnnnnn nnnnnnnnnn   86460
nnnnnnnnnn nnnnnnnnnn nnnnnnnnnn nnnnnnnnnn nnnnnnnnnn nnnnnnnnnn   86520
nnnnnnnnnn nnnnnnnnnn nnnnnnnnnn nnnnnnnnnn nnnnnnnnnn nnnnnnnnnn   86580
nnnnnnnnnn nnnnnnnnnn nnnnnnnnnn nnnnnnnnnn nnnnnnnnnn nnnnnnnnnn   86640
nnnnnnnnnn nnnnnnnnnn nnnnnnnnnn nnnnnnnnnn nnnnnnnnnn nnnnnnnnnn   86700
nnnnnnnnnn nnnnnnnnnn nnnnnnnnnn nnnnnnnnnn nnnnnnnnnn nnnnnnnnnn   86760
nnnnnnnnnn nnnnnnnnnn nnnnnnnnnn nnnnnnnnnn nnnnnnnnnn nnnnnnnnnn   86820
nnnnnnnnnn nnnnnnnnnn nnnnnnnnnn nnnnnnnnnn nnnnnnnnnn nnnnnnnnnn   86880
nnnnnnnnnn nnnnnnnnnn nnnnnnnnnn nnnnnnnnnn nnnnnnnnnn nnnnnnnnnn   86940
nnnnnnnnnn nnnnnnnnnn nnnnnnnnnn nnnnnnnnnn nnnnnnnnnn nnnnnnnnnn   87000
nnnnnnnnnn nnnnnnnnnn nnnnnnnnnn nnnnnnnnnn nnnnnnnnnn nnnnnnnnnn   87060
nnnnnnnnnn nnnnnnnnnn nnnnnnnnnn nnnnnnnnnn nnnnnnnnnn nnnnnnnnnn   87120
nnnnnnnnnn nnnnnnnnnn nnnnnnnnnn nnnnnnnnnn nnnnnnnnnn nnnnnnnnnn   87180
nnnnnnnnnn nnnnnnnnnn nnnnnnnnnn nnnnnnnnnn nnnnnnnnnn nnnnnnnnnn   87240
```

```
nnnnnnnnnn nnnnnnnnnn nnnnnnnnnn nnnnnnnnnn nnnnnnnnnn nnnnnnnnnn    87300
nnnnnnnnnn nnnnnnnnnn nnnnnnnnnn nnnnnnnnnn nnnnnnnnnn nnnnnnnnnn    87360
nnnnnnnnnn nnnnnnnnnn nnnnnnnnnn nnnnnnnnnn nnnnnnnnnn nnnnnnnnnn    87420
nnnnnnnnnn nnnnnnnnnn nnnnnnnnnn nnnnnnnnnn nnnnnnnnnn nnnnnnnnnn    87480
nnnnnnnnnn nnnnnnnnnn nnnnnnnnnn nnnnnnnnnn nnnnnnnnnn nnnnnnnnnn    87540
nnnnnnnnnn nnnnnnnnnn nnnnnnnnnn nnnnnnnnnn nnnnnnnnnn nnnnnnnnnn    87600
nnnnnnnnnn nnnnnnnnnn nnnnnnnnnn nnnnnnnnnn nnnnnnnnnn nnnnnnnnnn    87660
nnnnnnnnnn nnnnnnnnnn nnnnnnnnnn nnnnnnnnnn nnnnnnnnnn nnnnnnnnnn    87720
nnnnnnnnnn nnnnnnnnnn nnnnnnnnnn nnnnnnnnnn nnnnnnnnnn nnnnnnnnnn    87780
nnnnnnnnnn nnnnnnnnnn nnnnnnnnnn nnnnnnnnnn nnnnnnnnnn nnnnnnnnnn    87840
nnnnnnnnnn nnnnnnnnnn nnnnnnnnnn nnnnnnnnnn nnnnnnnnnn nnnnnntctg    87900
ccccacctcg aataggtagg atgaagccat tgcccagtc agcagctttc tgaggggtgt      87960
gcaagcccct gctggactct cagcccccat aaggttagaa ggcccagcct ttggcgtacg     88020
cagcactaac cttggtttct ctttgggatc ctccagatgg ggtggggata atgtccagga    88080
gggcatgaac caagtgaggt gtgaagagag atgctgcgga gggacagatg gacataaggg    88140
cctgaccaat agagatagtg tggaaaacta gccagagatt tggagtggct ggagctgggg    88200
gccttgagga gagaaaggcc atggtcaggc cagccagacc cagggctgag gctgggcgga    88260
agacaggcag ctagggggc tttctggagt ggctgaggaa ggagtgttag tgggaagtgg     88320
tggatgctct gccagagccc cagaacccag acaagcctcc ctctgcagcc cctcgaggag    88380
ttcccagggt ttctgctccg tggagggat tgtggaagtg cagagcctgt ggggacggga    88440
ttctgccgct ctttccgttt cttctcctgt atggaggtgg gggttcaaac tcgttctatc    88500
ctagtaacca aaggatgagt tccccaaatt gctattattg ggggtctgct tctgtcgagg    88560
gggctgccat tccagtaaag ggcaggcttg ggggcatgga cagataaatg agcaggtgtt    88620
ggttccccgg ggactcctct ccagctcatt aaaatggaat taaacgcttc ccaggcgcct    88680 gaccttctg agctgctggc aggagagggc agtgggagtc agggatggct gagaggggag     88740 gagaggggg aggggaggga ggggtacttg gctgggtctc ctctgcaccc atcttcctga    88800
ctgagggagc caaggccgct gcttggtttc tccgcaagct gctccccca ccccggttt      88860 ctggaacgga gctgctgttg cacggagttc tcaggggtc gcctcccct attctttgct     88920 cttggtctgc cccagggctg gtcagctttg aggggcactg aggtgagggg ctgtgtgcag    88980
aggtggggat tggaggtgg tggctgggtc acgcacctcc ttctctgctg agggcaaagg    89040
gcctggggtg ccaggtgcct gagaaggact tccttagatt gaggctatga ggactgggtc    89100
aggagggaag taaggggaag acatttggaa ggttgcttcc cttgtgggcg gaatgcttgc    89160
catggccgct gctcaccttg gctcaggctg ggccagaggc caatgtgtgt gtgtgtgtgt    89220
gtgtgtgtgt gtctcaggga cgctggtggg atcagatcac ttacacttaa ctcacccagt    89280
agaactctgg tctggtcctg cggcaggctg ggtgctggag ccgactctgc cttcagggag    89340
ctctcagtct gggggaaggc aggacaccc tccccaccac aggccagatg aaatactgtt     89400
gccagcaggt gttctggtgg caaagcctgg agcagcaagt ggtacctcat cacagagaaa    89460
gcatttgtgt gggccttgg ggcacaggta ggaggtccac aggcagggaa gaagggaaag     89520
gggattctag gcagaggagg aatgtgagca aggcaggaag gaggccgggg gaaggggtgg    89580
```

```
tgtgctgagg ggagagtgtg gtcctgggga agctgaagta ggggtgcatg ctgttgagca    89640
ggatgctagc cagctgggct ctggctgcca ggagttttca acaaccgtcc cttcacctcc    89700
tcaaataccc tgggcaggga agaactcttg aaaggtgttt agattattca catctgcctc    89760
tcctctaagc ctgcaccttc ccactcatgt gtaaatgcac ttccctagga tgcccctcc     89820 ccaaggcata catgtctgac agatgcaccc tggctcacag gatctcactg cctcccagag    89880
gtagcacagg cagccccaga cttcccagct gctgccagat cctgagggca gagggtgcag    89940
aaggaagatg gagagccaca gggtcggttg atcttttggg aaggccgagt caccagctcc    90000
ttcctggaca agccccattc ccctctctca gtctctgctc ttagtattca tccactgatc    90060
cacctaccca tccacccct  catccatcag ttgaacaact atttcttgag tacccactgt    90120
atgtcaggca tggagtgcta ggtgctggga acacagaagt gaccaagaca gattagacag    90180
gccctgcctt cacagaccat atggtctgga gggttggtgg tgagaagcac taaagtgagc    90240 ataccccag  ctacttggga gtattccttg agctcaggga tttgaatctg gcctggagaa    90300
tagagtgcga ctccatctct aaagacaata aaaataacaa aaatactgca aaacaagtga    90360
gcaaaataag gataggatca cacgtgatgg caagtgctag caaggaaacc cctcgaggga    90420
gtcctgcaaa ggaatgctgg ggtccagtgg cgacgccatc agcgagggct ctctgaggaa    90480
tatgctggcc aggtgcaggg ctgtgtggct gacttctggg cctttacagc tcactgctca    90540
aagcaccttg attgcaaatt ttttgtgtgg aaagtctttg gctctgttcc ttaatcctgg    90600
gataataagt cccttttgagg agtggcagcc cttggtctct ggcatttgat gcctgatttg    90660
tgcccactct tcccccagct gcaccagcca caccagctcc ctgcacgggg atgggtgtt    90720 catgccatta accattttga acttggttag ggtgggggacc tggggggctgt gctgggtttt   90780 aaccctctct tacagccaca gtcccaatg  ttgagtgttc ccactgggtc ccagacactt    90840
gccctgatta gcaagagcag gtgtaagtgt gtgttcctgt tggcgaacaa aaagccatga    90900
gtgtgtgggg gtgattgtgt gtgtttgtgt atggggcgc  caggtgcatg tgcatggctt    90960
ttgggtaagt gaactatttc ctgtgtacag gcatgaatgt gcctgtgggg atgctgtgga    91020
cactgtaagg gtgggtgtgt ggatgtcttt gtgtctgtga ctgcaccgtg tgtgtgtgtg    91080
tgtgtgtgtg tgtaccacct ccatgggaga ttgagtgtaa gtgcatgtgt gtgagggcct    91140
gacgttcttc atgagagtgt aggtgtgtgt gtttgtgcac atgctgggtg caagtaggcc    91200
aaggcagccc gagaactggt tgcccccaca gccttagagg ggtcccagcc ttctctattc    91260
ttgagagatg ggaccaggtg gaaggaacaa gaaccacgtc ctcctccatg tgctaacagt    91320
aaaatgccaa catatttata taagccatat gcaaatgaac catagcccca gcttctcctc    91380
cctcccgccc ccgctgtcct gtaggagtca cagattgagc ctcatccaga gcttaagttt    91440
aaacaccatc cttgacagcc caggtctctt ccaggtcttc ctgcctccaa tctccctccc    91500
tcaaattcac cctacacccc acagacagtg gccctcagat gctaaagtct gccatggctc    91560
cccagtactc tcaggctaaa gtctaacttc ttagcctggc actcaaggcc cttccttctg    91620
tggtaccatg gaccacaccc ctacctggat cctcatctcc ccgcaccacc taccgccagt    91680
gtcctggtct cttcaaggtc tacttgtcct ccccatgcca attcaggaag ccttccaaat    91740
gtcctccccc ctgagctacc cacctagttt tctctctcct tcctcaggta tgaggctcca    91800
cacctcctcc cagtcatgtc tccccactcg tcccacccca gacagactgt gagcttcccg    91860
agaacctgct ggtctcctcc tccccatctg ctcctggcag gagacccaga gctgaggcag    91920
gcattggctg ctgactgggg agggaggagg aaggaggagc ccccagtgca ggcgctgtgg    91980
```

```
ggagctctgc aggtggtgag cagctttgag taagctccgg aagctagtga cgcaggtggg    92040
gagccttgct ggcagggcct gtagtgggtc cctaggctgc caccctccct ccccaccgtc    92100
tctcattttc ctcgacaagc acccaagtag gagtggggga agggacttca cagagtatga    92160
aagatgggct gagttccctg gtgactggca cagggagctt ggagagggac aggatgatgg    92220
gggtggtgga gagagtggat ctagaggggg aaggtgtgg gcagagaacg ggagggagtg    92280
ggtggtgctg tcttcactct gccactttct gctatgtgat tttgggcaag tcactccact    92340
tttctggcca tggcttgcct gccaggtgga ggcttgcatc acagtggtga gaatcacatg    92400
taaggcaaag cacttcacga acccatttat ccatttattc attcacccgt ccatcctcac    92460
catggcaggt gcatcatact gagcccattc ctttatccaa gacttagggg cagctcaaac    92520
cctaactcag acaggataga gccgggaggc tgaggctaat accaccaatt ctaaaatcag    92580
gacctgcagc gctccataat ctgtgagcta aaaaggggtc taaggtccct ccatcccctg    92640
aaccatacac ccggactgtg ctcttgatga gacagtgatt gaaaaggcag agacaaaaaa    92700
gtttcacgtc cttaggttag tcctaggaga cttcctacag gagggatttt cctggagctg    92760
tctgagtggt cagaaagatg gggttatcac tgaggcccac agactggagt gtgtatgtgt    92820
tggtggggac cagtgtgtgc tgcgcatggg gagggcactc tggcagagac agacactgag    92880
agaggtcaca gctagttccc ttctcccatc cctccaggtg cactgtggcc agctgagtga    92940
taatgaggaa tggagcctgc aggcggtgga gaagcatgtg agtgggagtg gggccatgtg    93000
caatgaggct gaagacccctt atcacagctg gtgggaagat ggcctggcca gggagctgga    93060
cagacctggg tttcagcttc ggcttttgctg cttttgagct gtgtgacctt gagcaagtca    93120
ctaaacctct ctgggcctca gtttcacacc tgaaaatggg gataatgata gcaccgactg    93180
acctagggca gtggtgaaac aaaactggtc aaatatcttg taaatacaca cggttgccaa    93240
cttacaattt tcgactttt gatggattta tggggaagca accctatcct aagtccagga    93300
gcatctgtac ttagaaagaa ccctccacat aatgatactg aggctctttc atgcctgaga    93360 cttttatgatt ttgtgacttt aacaaggact tacgacttcc tgagggggct ggagacaaa    93420 atctgacatc ttgtcttgga agaatctagg ggctagggat ggagatagac cctgtaccct    93480
cctgttcctg gaccgccgga cgctccaggg gctgtgggag ccccgggggg agccctcagg    93540
aaggtagagt ccagggatga ggtgtttggg acggcggcgg ggtccctggg cccggcaggc    93600
agagggaacg gcgggagcaa aggcaggaat cccgctgcag caagcgcagc gagcttggg    93660 cgagcggcgc gctaaccgct cggcctgccc cagaccctgg tcgccctgcg gagggtgcag    93720
gtcctgcagc agcgcgggcc cagggaggct ccccgagccg tccagaaccc cccggagggg    93780
acggcggaag accagaaggg cggggcggcg tacaccgacc gcgaccgcaa gatcctccaa    93840
ctgtgcggtg agggcccggc ctggacaggt cacgagggcg gggccgggca gaacttggag    93900
gggaggtggg cgggttaggc gatcccggga gccggcggcg ggcccggcgc ggagctgagc    93960
ggcgcctgag ggacccggac acggaggtgc ggaggggccc tctctctgac cggcgcctgg    94020 ccccttgcagg ggaactctac gacctggatg cctcttccct gcagctcaaa gtgctccaat    94080
acgtgagtcc ctgcgcccct gccggccacc tcccgtcct gtctccctcc gggaccaac    94140 ttccccttga gccctccatc tcagttccaa ttacgatgtc cttccttcct ctctcctcca    94200
cccgcctgaa gagccccgga gagggagca gtgggaagt gggtgaccc ggatccgcgg    94260 tcaccccctc gccctgcctg tccctctctc agctgcagca ggagacccgg gcatcccgct    94320
```

```
gctgcctcct gctggtgtcg gaggacaatc tccagctttc ttgcaaggtg agggcccagg    94380
tccactgtag agcgggggcg gggctgggcg aggaactcgg gtctccgagg gggaaatcca    94440
ttgcctttcc tttaaccagc cccctgcact ccgttcctca ggtcatcgga gacaaagtgc    94500
tcggggaaga ggtcagcttt cccgtgagtc ccgcgtctgt cttctcgttg gagtctgcag    94560
gggcggttga ggccgggtag acactcctgg gatctgcctg gagtatttgg atcttctaga    94620
ctcttggaat ccgatggaat tatctggatc ttggactac ttagaaatgc tgcagggatc    94680
acaacctgtg atcagcaggc tctattagga agaatctctt agcatctaca gaaaggctta    94740
cctgggacct gttcacttct gttggagtat ttctggatat ggatctgcta gaatctgttg    94800
acgagaatcc ttggagtctg cttatctctc tcgtagttag ggaagactct agagtccttt    94860
atagcgaatt ctgccagact cccctccatc tctgctcatc aatgctgacc ctgtccacca    94920
tttggactga ctgaagggtt cttttgaaact ccagatttg agggtgggga caggttgaga    94980 tccctgacc tggggagtac tgggcccga ctcagtctct cctcaccccc tagttgacag    95040
gatgcctggg ccaggtggtg gaagacaaga agtccatcca gctgaaggac ctcacctccg    95100
taagtcatgg cctggctgac ccagagggga aagaggagac cccactgcca gccctagag    95160 ccagggtctc tgttacagag cagcctagga atggggcaga taagacctgg ggactttcta    95220
ctgtcccatc tccatgacac agagcttcca gccttgcatg agtcccttag aactgcctgt    95280
tgcaaaatgt gatggagggc tggaggaggg aagcatactg cgccctgctt ccctgccctg    95340
acttgcctcg cctttgcagg aggatgtaca acagctgcag agcatgttgg gctgtgagct    95400
gcaggccatg ctctgtgtcc ctgtcatcag ccgggccact gaccaggtgg tggccttggc    95460
ctgcgccttc aacaagctag aaggagactt gtgagtcttt gtgggatgat gcagatcagg    95520
agatgtcact gagaggctgg ctagggctcc acgagggtaa caatgtggga tgggtactgg    95580
gcaggggcta ctgtctcagc agcagtgggt tgaacagtgt gttagtcaa gagaatgaaa    95640 gtcatgttga ggtccaagct agttcctctt ctcttctcct gcttcctgaa gtttgggtaa    95700
tctgctcttg gggtattggg ttccctccct tgccatccct gtttttgcat tactgctata    95760
aactgctaga tggaggggtg ggtgtgctct gggttggatg aaccctctgg gacccacaaa    95820
gcatcatcaa cacagtggac agtggctaaa gggaatatgc ttggggactg ggaaaagctg    95880
tggatctttt gagcccctga cagggcagct ataaaaatga tacacaaaaa tctcttttt    95940 tgtgggcagg gcacagtgga caggaaagca ggcttggagg cttagttgga aaggatatct    96000
cgagaactga ggacaaacct ggggtctaga aatggtgtca taaataaatt tcatatccta    96060
caccaactca taaacaggca gtaggtgcct gaattttatt gcaaatggat cttagttcag    96120
ggagaaacag tgctgcgtct gatgagccat ttctgtcctg ggtgcaggtt cacacttggg    96180
ctggcaggat gagcagtttg tgctgtgtca cataggtggg gagaagtaga cagatgaggg    96240
gctgagtcct gatgcaaaga gatgctgata ggatgctggt ctctggagtc caagcaaaca    96300
ggctgggttt cagggcctgg agctcctgca ggaggtggac actagagagc ctgggactag    96360
gtaggtgtca gagcccgggc ctgaggtctg ctggggtagg gtggagatcc aggagtccta    96420
ggtctgagct gcagaaccta ccagcatgga actgtgttga cagttgggtg ggcctggaga    96480
aacaaagata ggggcaaggc agaatcagct gaggcaggga gaatgtggga ttggtggcat    96540
ttggaacttg tgggcatcct aatggtggga gaatttatgc cattcagcaa acaaatattg    96600
agcacttaat gttgccatcc cagtgctgac cagatggcct tggaaggcc tttggggaag    96660 ggaaggtaga gtgaatgggg gtccagcagg ggccatgact tcttgctgct ggctgtgaga    96720
```

```
ttgggttcta ggatggcccc agagctggag aagaggtggt atcagcagga aataaggatg   96780
gggccttggt ggcagctttg aggcccaggg caggggcagg gctatctctg ggtcccacgc   96840
atttcaggga gtgagtgttg aatgactgca tgagccaggg tggggctcag ctcagtgcag   96900
tgactacaga gaagcttcct gaaacacagc taagtagcca gagaacaggg gctccagaag   96960
cccttcagct gtgagtggga tggggctggt ggcaaggcca gggataggat acactgacga   97020
cattagcaaa gacctccgaa gtgtttcctc tgtaccaggc tctgcactgg gcatgggtga   97080
tatagtcatg gccccatttc ataagactca aagctcattt tcagggcata gagggaagag   97140
agtgagaagg gtattctagg ccgagggaac agtgtagaaa aaaaagcatg aaggtgtgaa   97200
agagcccaag gttttctcag aatgatgagg atctttgtgt ggctgaagct gagagatgtt   97260
ctgggttgag gggtgacagg tgggtggggc tagctgaggg accacaaatg taagaaaggt   97320
gtgcagacag acccaggatg gtggggatgg gatctagatc cgaatcactg gatggcaagc   97380
atgaatgggg gatgccccac cagggtggag caccaaggcc agccaaaaag tggggaaggg   97440
cttaggcagg gacacctcag ggcagcgtga tgtgggctaa ggcaggctct tcccatgacc   97500
cacaccattg gtccacccag ccccatgcag ctccccagtg acaaatcatt tggtggccag   97560
attgaatgac gtgagcagga tttgggcttt atcttgtctc accagagcta gctccatgag   97620
cagggcaagc agtcctctcc acaccaccac cctaagattt ctggaggcac cgaatcaggg   97680
ccagcggagt ccaggagag tggggtagtg acaggagctg cacaagatag ggcagtgcca   97740
ccgcccctcc ccaaggctgg aggtgtgcct ggggaagagc agaacaccag cttgagccca   97800
ggcaatctct agtctgaggg aggagaccca gctttgggct gggtaaatcc caaatcagag   97860
acgggaggta tggctctggt ttcaagcatc taaggaggac tggagccctc cccttgggca   97920
gcccccagtc tgcagggtca tggggggtggg aagctgttcc aagggcctgt gcagtggtta   97980
tatagttggc aggtgggtac ccctgtgggc ttctgatgga acagaagtaa ggagagtggg   98040
gagagaagcc agtcttccct tccctcctga gtgagcccac cccctcctcc aggttcaccg   98100
acgaggacga gcatgtgatc cagcactgct tccactacac cagcaccgtg ctcaccagca   98160
ccctggcctt ccagaaggaa cagaaactca agtgtgagtg ccaggtgagt gacctgcctt   98220
cagcctctct cgggcaccga ctcgctcagt tttcagcccc gagagccatt cagaagggaa   98280
atgcccatgt ctttctggac tggtggcagc ccttccccag gtggctccat aacctcataa   98340
cttgaaggct tgcagttgtt caggacccgc gccactgccc gcaggcactg tatgtgatcg   98400
ccctctagtg ttcaatatgt gcactacagc aacacctagg cagctagagc tggcgtgaag   98460
gcggctgaga cactcaggag actcctcacc tgcaccgggg ctattccctc actccttcac   98520
ttagtagcca aatgatataa ttagacactg acagtttctg gcttgtccag tgagccctag   98580
ggaaggaagg agaagacccg ggtgctgttg gaggcagaag gttggatagg gtgaccccta   98640
caccccgacc cccctatgat ctccatttcc ttcattccag gctcttctcc aagtggcaaa   98700
gaacctcttc acccacctgg gtgagtgcac tgttctctct gcctggctgt gtgtgggcat   98760
gggggctggc atttgcagag gagaggcggg aggtcttggc agcctggtct caccctgcct   98820
ggtcttctcc cttccccaga tgacgtctct gtcctgctcc aggagatcat cacgaggcc   98880 agaaacctca gcaacgcaga gatgtgagtg actctaccca ggggacaggg cgagagaggc   98940
tgtggccttc agtccccatc atctcctttc ctgccccacc cacttccctt tctctgcctt   99000
ctgcgggact tcatcacctt ttgagggatc ctttatttca tgcctgtctc cctcgctaga   99060
```

-continued

```
ctgtaggctc aatacagca gggacagggc tggctttgga tcctcagctc ctatcacagt    99120
gcctggcaca tagtaggtgc ttccaaaaaa aaaaaaaaca aaacacttga atggacacgt    99180
ttctggagcc agccagccct gagcagagtg tcttaccttg gagcactcct cccaggcctc    99240
ggaaatccgg cctttgcctc cttatgggac gtgagggcga tcagagggg ttgtcaggcc     99300 ccagaggacc aaaccctcc ctccacagct gctctgtgtt cctgctggat cagaatgagc     99360
tggtggccaa ggtgttcgac ggggcgtgg tggatgatga ggtgagaggg cgtggaggga     99420
gtatgtggcc ctaggggtgt ccgggagtcc gccggcggcg ctgggagcg gcccgaggtt     99480 taacagtccc ctctgtggcc gggtcactaa cttcttcctc tcgactccat ctctgctccg     99540
gcagagctat gagatccgca tcccggccga tcagggcatc gcgggacacg tggcgaccac     99600
gggccagatc ctgaacatcc ctgacgcata tgcccatccg cttttctacc gcggcgtgga     99660
cgacagcacc ggcttccgca cgcgcaacat cctctgcttc cccatcaaga acgagaacca     99720
gggtgcgcgt ggcggcccgg gcggagggc ggggcctgcg ccgggcgggg cgggtccgag     99780
cgagcggggg tggcaacact tccccaccgc ctccggcgtc ccggagcata agggagtcgg     99840
gttccatgcc tgggacgtac gtaacctgcg gaaactgcga gggcaggtcc cggccggatc     99900
cctccctcca accgatccct ccctccaccg gtggttcctt gcccctctcc cttccccaga     99960
ggtcatcggt gtgccgagc tggtgaacaa gatcaatggg ccatggttca gcaagttcga    100020
cgaggacctg gcgacggcct tctccatcta ctgcggcatc agcatcgccc atgtgagggc    100080
ggggttggga gtggggtgtg gggtgatagg gggcggggcc cacgaaggac cctcggttct    100140
cctcctccga ctgactctcc ttgtggattg atcccttggt ctggcactca gagtcccgcc    100200 gctgggtgc agccttcagg acacgctggc cacctctggg ctcagtttcc catctaaaaa    100260
ttgggcatac gatttcctgc cctgtccact cagcctcctg ggaccatgag aaactcccgt    100320
tgtcaaaacc tcctctcttc cctggaagca gtctcaaccc aagccgagtg cttttttgga    100380
agtgctgggt ctcggtgtcc aggcctactg gcgctctggc ctgggaatcc agccccaagg    100440
tccctgacat gatcccctcc ttgcttctcc ttccctgcca tgggccttgg gctccatcac    100500
tgaagcctgg atcaggtgtg ggggagtgca aagggccaga ccaaatgctg ggagaacttg    100560
atgaggagga accggcgcgg gggtctggat gaaagtgggg gtgaggtctt tactgtggac    100620
tggagcttga aggttttgac tggggccaga atgggacagg aagtggggtg tctttttgac    100680
cccttcatcc cagtcctggg cattgctaaa ttttcacagc caccttcctt gagcccatc     100740 tttccctctt tccctagtc tctcctatac aaaaagtga atgaggctca gtatcgcagc      100800
cacctggcca atgagatgat gatgtaccac atgaaggtga ggcttgcaga gacctctggt   100860
cctcctccca gattccccgg ggacccaggg ccagcaggg cttcctgatc aatctctact     100920
gaggatgaga ggataggccc agagccacag caggcctcct gccctcctta ggggcagctc   100980 ccaccccctgc ttagagacct ctcctccaag ctgcttctga gctcagtccc aaggctgaa   101040 gtagccagag gaaccagccc agggagtaat tggttcagcc aggtattccc catgttcagg   101100
gaataattcc catcttggga attactgagg ctaggaagc tcacccagga cccgtcccca     101160
tggcttccct aggtacaatg cccatgcagc cctgggcagt cttaattgct gataatctat    101220
cccattccct accctgggtc acaaaagctg gcttagttcc atgtatatgg tagtcgcgt    101280 tcatttggac atttcctctc acctgtgtcc aaaccagaga ggcccagacc ttgtgagttg    101340
gatcaaaact gtagtaggaa gagttaaggt tagagagtag aaaggtctcc acaaaaggag   101400
gactgctaca gttactgtgt atgaaatgct gccatggttt gggggtgtca tgaagggtg    101460
```

-continued

```
ttgtcgatct tgccaaggt tatgctgtta cagataaagg gtggtcacct gcaggaaggc   101520
gcgcggggtg ggctgcaggg ctgtgagggg agggtggtga tttcctgccc agttacagtc   101580
cacagcgtgg tggcccaact gtggtacatt ctgggtgacg gatcccccac ctgccatggg   101640
aatttgaggg tgaagacacc agatgggtgg aaggctgtct tctaatgctc tggctggtct   101700
cctctaggtc tccgacgatg agtataccaa acttctccat gatgggatcc agcctgtggc   101760
tgccattgac tccaattttg caagtttcac ctataccccct cgttccctgc ccgaggatga   101820
cacgtccatg gtgagttgct ctcctccact tgactggcca ggccgaaggt atgtagccag   101880
aggcttaagt taaatgcgca tcaagaactt cctgggaaga cagagtcatc aaggaaggct   101940
gtggagggtc cctcagagat ggagggggctt gtagtctgcc atcaggaagc catgggggcct   102000
gcccagggc tagaggctgg actggatgat cccaagggct gctcttggac caaccatgcc    102060
cagggcatgt gacctcaggg tttgcatccc tcccaaccct gttttttctaa catttttgtgt  102120
gggcttggtt tcaagagttc ttagttctta gatctctaaa aatgcatagc tctgagaacg   102180
gttgcttcaa ctatttttgtg gttctctagt ttagatgtaa gttttctaaga ctccagatct   102240
tgagtgtgga gcttgaagaa ggacccaggc aagggccctg tcttgatact ggcagccccct  102300
ctgatacctc cctctgccct ctccaggcca tcctgagcat gctgcaggac atgaatttca   102360
tcaacaacta caaaattgac tgccccgaccc tggcccggtt cgtgcgccca cagacagccc    102420
cagtcttcgc ctcccctcttt cctctactgt cacatccatt gccccccggca ttctggagag   102480
gatctctcta aggatgactg gggagaccca gtccttatggg gtggggggagg atccatgaat   102540
gagaagcaat tcctagacac tgaactgtca ataaaggcaa gaaatgaggc aaggcaaagc    102600
ctggaggcaa ggccgagagt gtgtagccag aggtttaagt tagatgtgca taggaacttc   102660
ctgctaagac agagtcatca aggaaggctg tggagggtcc ctcagggatg gaggggacat    102720
gtagtttgcc atcatgggggc cgtgatggag gaggagaggc tgaggccccct cttctgccct    102780
cttccctccc ccaggttctg tttgatggtg aagaagggct accgggatcc cccctaccac    102840
aactggatgc acgccttttc tgtctcccac ttctgctacc tgctctacaa gaacctggag   102900
ctcaccaact acctcgagtg agtggctgca tctcccccac atctggcagc cactgggggtc    102960
ccccttccctg ggacagggaa gcaccccctg tgtgtcaggc actttacacg cactgcctca    103020
tgggatcttc ttagccccag gggactagag gggaaggctg tgagccccat cttccaggag   103080
gggcttgctc acagccaagc agctagtgaa gactgagcct gatttaaacc cgggtctgct     103140
ggactccaaa ccagtgcttc tttccaggaa gggaacccag gtgttccaac ctcctgtccc    103200
agtggctcct gggcatgtca tctcctgtct gtcctcttgg ggatttaggg agggaactgt   103260
gggctgacct cttttttttttc tcctttctgc ctctcaacca gggacatcga gatctttgcc    103320
ttgttttattt cctgcatgtg tcatgacctg gaccacagag gcacaaacaa ctcttttccag   103380
gtggcctcgg tgagaccctg ccctgctcac agtggggacc ctccatggggg tgtcttggat     103440
ctcatcctct cccagcctga ataggtgggg agcgagtgag accaggagcc aggtttagac    103500
acaggaggag gttcccccag ggtttgcccc tggctctgag atagggagga ggggagaaag    103560
gtggaagggc aggacactgc tcagcctaaa gcagtggcac ttggatccgg atgtgaggag   103620
tgaccacagt tttcctgggc ttttccagaa atctgtgctg gctgcgctct acagctctga    103680
gggctccgtc atggaggtat cactcttctg tcccaccccg tccttcttcc cctttaaggc     103740
cagtgacttg caaagttatg acccagctcc tcctattccc aaaccatgct ctccagacag    103800
```

```
gctgcgagag ctgcagccac acctaggaca tgtctggctc attttcctgg agtgggcttg 103860
gaagggtgca ggtgcggatg atagcaagga tttgtgttca gcgtgtttcc ctttggctgc 103920
ctgggaacac cccattcagc cccctcctgc caaacttggg atgggctcca ctcccatcac 103980
ttagcgtcac cttagattgt ttggtttggg tctgcctacc tcctcgtgca caaggtctga 104040
gccatttctg agttcccctgc acttggcaca gggcttggca cagagtagga gacacatttc 104100
caaggtcacc ttgcctcatg ctacttccca caacacctct ccagaggctg cccctgcttg 104160
cacaccccca gagacgaggt tctctgtctc tctcccagga ggcctggtgg cagtgctggt 104220
tctgccctct gcccccctga gataagctgc tccttttctg agtgacagcc cttcagcatc 104280
cggaaatggg ggccttgccc ttgcctcatc actgcctctc cttgtcagca aacaaatgtg 104340
ttctgcatga tttggtgtct aggactccaa aggatcattt caaaaatgtt ccagcttttca 104400 gggaccccag agcttacctt gttgggtccc tgcatgtgac agctgaggag tctgaggctc 104460
agagtggtct agggactcac cctggtcac acagagggtt gaaacagagc tcagaaaggg 104520
aactggggcc cctgactccc cctttctgac tgctctgctt acctggggc tggagctgga 104580 cgaggccccc gcttcctctc ttggggtcaa tggtaaggga gcccatctgc ccagctggg 104640 cccccatcac tcctctcccc ccagaggcac cactttgctc aggccatcgc catcctcaac 104700
acccacggct gcaacatctt tgatcatttc tcccggaagg tgatgggtt ggggtgggg 104760 tggggattga gggggagctg ggagctggct ggaggtggga taaggagcca aggagtggag 104820
gctcactggg atgggcaaat gggtggggt gtccagtagg agggcatgac accoctgccc 104880 tcgcctcagg actatcagcg catgctggat ctgatgcggg acatcatctt ggccacagac 104940
ctggcccacc atctccgcat cttcaaggac ctccagaaga tggctgaggg tgactgctgt 105000
tagccccagt ccttggggct ggggaggaac aaccagggga aggatttgcc aggggagcat 105060
tcccagggtg cagacccatc ccctgcaaca tcaaccctc tctggctgca cggcccccc 105120 caggcagacc cagcactggc cccttggctc ccatcaaggg tgcccaattc cctggaccgc 105180
tctgggttgg gccctgggag ccttgtcctc agaagggcaa agaggctggg ccccgctcct 105240
tgaccccatc ctcccctcaa cagtgggcta cgaccgaaac aacaagcagc accacagact 105300
tctcctctgc ctcctcatga cctcctgtga cctctctgac cagaccaagg ctggaagac 105360 tacgagaaag atcgcggtag gtgtagtcct ccctgggaag gcacaggctg cccaccctgc 105420
ccagctttgg gtgcccctg tgcctgaata ccctctctct gctcagctca gcctggctgt 105480
gttctgggga gacagaaacc tagaccatct caggggtgaca aatggagact cagagagggg 105540
aacagaccta gcaagtcagt ggctggtgga aggtgggccc caaccagcc actccctgcc 105600 tcaggccatc ccactgccaa gctggggctg gtggggacgg ctcctgagct gggactgaat 105660
ccctgggcct cagttttctc tcctgggaac gggctgtcag aggagcttgg gtggatgtat 105720
cctacataga ggatgtgatg agagtgttgg cctttcagga gctgatctac aaagaattct 105780
tctcccaggg agacctggta tgtgtggagt gaccccagga tgtccaggat ggggagggt 105840 tcctggcctg ggacagggag ggcttgaact agcctgaccc tggtacccga tggaggaatg 105900
agagggacag gcctgacgac tcgatgcctg caggagaagg ccatgggcaa caggccgatg 105960
gagatgatgg accgggagaa ggcctatatc cctgagctgc aaatcagctt catggagcac 106020
attgcaatgc ccatctacaa gtgagtgagc tcatgggac aagctgcacc ctgcacagag 106080
agggtaggct ggagtgggga catcacagga aacacaggtg ctgagattgg cctggcccag 106140
ctccaactga ttcatcccct tgcctctggg cataactgtc tcccgctgtg cccctcagtg 106200
```

```
ggtccttcac ttcatccttg gtcctcagtg gaaagagacc atcatgcttt cctaggtgtc 106260
ctcctctgtc tcacattctt gtggaagttc ttgttttttt tgagatggag tctcactctg 106320
ttgcccaggc tggagtgcaa tggcacgatc ttggctcact gcaacctccc cctcctgggt 106380
tcaagcgatt ctcctgcctc agcctcccaa gtagctggga ttacaggcat gcaccaccac 106440
gcccagctaa ttttgtattt ttagtagaga tggggcttca ccattttggt caggctggtc 106500
ttgaactcct gacttcaggt gatccacaca cctcggcatc tctgagtgtt gggattacag 106560
gcgtgagcta ccgtacctgg cccttgtgga aattctattt gttgtgtagc cctagtcttt 106620
cttgctgccc atggtctgat ttctggcctc tcaccctctg ccccatgca cccgcaggct 106680
gttgcaggac ctgttcccca aagcggcaga gctgtacgag cgcgtggcct ccaaccgtga 106740
gcactggacc aaggtgtccc acaagttcac catccgcggc ctcccaagta caactcgct 106800
ggacttcctg gatgaggagt acgaggtgcc tgatctggat ggcactaggg cccccatcaa 106860
tggctgctgc agccttgatg ctgagtgatc ccctccaggg acacttccct gcccaggcca 106920
cctcccacag ccctccactg gtctggccag atgcactggg aacagagcca cgggtcctgg 106980
gtcctagacc aggacttcct gtgtgaccct ggacaagtac taccttcctg ggcctcagct 107040
ttctcgtctg tataatggaa gcaagacttc caacctcacg gagactttgt aatttgttct 107100
ctgagagcac agggggtgacc aatgagcagt gggcccctact ctgcacctct gaccacacct 107160
tggcaagtct ttcccaagcc attctttgtc tgagcagctt gatggtttct ccttgcccca 107220
tttctgcccc accagatctt tgctcctttc cctttgagga ctcccaccct tggggtctc 107280
caggatcctc atggaagggg aaggtgagac atctgagtga gcagagtgtg gcatcttgga 107340
aacagtcctt agttctgtgg gaggactaga acagccgcg gggcgaaggc cccctgagga 107400
ccactactat actgatggtg ggattgggac ctgggggata caggggcccc aggaagaagc 107460
tgccagaggg gcagctcagt gctctgcaga gaggggccct ggggagaagc aggatgggat 107520
tgatgggcag gagggatccc cgcactggga gacaggccca ggtatgaatg agccagccat 107580
gcttcctcct gcctgtgtga cgctgggcga gtctcttccc ctgtctgggc caaacaggga 107640
gcgggtaaga caatccatgc tctaagatcc attttagatc aatgtctaaa atagctctat 107700
cgctctgcgg agtcccagca gaggctatgg aatgtttctg caaccctaag gcacagagag 107760
cccaaccctg agtgtctcag aggccccctg agtgttcccc ttggcctgag cccccttaccc 107820
attcctgcag ccagtgagag acctggcctc agccctggca gggctctctc ttcaaggcca 107880
tatccacctg tgccctgggg cttgggagac cccatagggc cgggactctt gggtcagccc 107940
ggccactggc ttctctcttt ttctccgttt cattctgtgt gcgttgtggg gtgggggagg 108000
gggtccacct gccttacctt tctgagttgc ctttagagag atgcgttttt ctaggactct 108060
gtgcaactgt cgtatatggt cccgtgggct gaccgctttg tacatgagaa taaatctatt 108120
tctttctacc agtcctcccc catggggctg tttgcagact ttgtgcttgg ggtgggtgga 108180
gggggggaat agaactggga gaggcaaacg ccctttggaa ctccatggct tccagggtcc 108240
tccaccctgg gtgcctagcc cccttctgg ggaagtcata gacctgttgg ggtactccct 108300
aggccagatc gtggaggcta aggggtgggt ggcagatgag aaggcctggc catggagcag 108360
tgatgggaca tgttggctgg cagagattgt agaatagagg aaaaacaaag gttgaggcaa 108420
gcaggcaggc tgcctggagg aggtagcctg gagcttgtcc tagaccctcc cagcgctggc 108480
ctgccctggt catgagtgcc catacggcga gggcctaggc ctctgaactc tgtttctagc 108540
```

-continued

```
tgcagtgatg cctggctgtg tcccaggaag tcccacatcc cagttactct gagtcctgcc    108600
gaaggtgcac gcctgagtca gactccacac cagatccagc cccggttgt gtctgaggag     108660
ttgcgtctgt tcctctgcat gagagtgttt acttccgccc agtccaagat gggcagactg    108720
caggttgggg ctacgcggag gctctgcctg gcacagtctc cagaccctgt ccccgacttg    108780
cctaccccccc tctgagctcc tctccgtgtt catctcttcc tggtcagtaa aggttgatgt   108840
gttaagaggg tgggcactgg ggtctccttt cttggtggga gcaggaagga gatggacagg    108900
gccatcctgt gaccatcagc cattgccagc tttgcctttg ggaccacaga gcccatctgc    108960
ttcctctgca gctcccccctg ccccactagc ctgtctgggt ttggaatctg ctcctctggc   109020
tgaatggtct ccaggtttcc agcttcccctt agcgtcatgg ggctccaggc tcctcccatt   109080
cccagctcct gctgtgggct ccccaagtcc gtctctatcc tctcacagca caggacccag   109140
gcttggccag tgggtccccg ggtgggggtg ggagtggtca gtttgtggcc cacggccaat   109200
aagagatggc tattctaatg gtgcctggct gaccccaggg tcactgtggg ctgatgtagc    109260
tgctcttctg cctgaccccct gaccctgagt gtgtgtgcgt gttcctcttc cacaactctt   109320
caggcaaaga gaaccttgac cctgcatctg tctgtcccca gcccagccct cctttgaggc    109380
tcatgctgtg acacatccct gtttttcacc aaatggaggg aacaaccaca gatatttcct   109440
tgtgcacgca ggaccctgtg ctagggctga gggctttgtc tttgtcctgc tctgaaagt    109500
ctcacagttt gattggagag ctagatctaa actcagatgc aggccatgac aacgctgtgg    109560
ggtgcccggc catgggctc caggcaggat cataaccctg agaacaacaa tgaggtttga    109620
aagatgagca gatgttgttt ataggcaaaa ggggacaggc actcctggta gaagaaactg    109680
cttttgcaaa ggcctcgaga acagaaggga ctggcaggtg gaggagccga gagatggagg    109740
aggaggcaag gccagatcct gaagggcctt aaatgccagg ttgtggagtt tggctttatt    109800
ctgtgggcag tggagaacca gagaaaggtt ttcagtagga gagtgactca gaagtgcatt   109860
ttagaaagat cccccctggag agcagggaag tgactgcaag gggagagggt gggcagggat   109920
tattctatgg gtgatgtgct gtgccctggg ctgggcgagg agaggaattc ggagatgcta    109980
ggttggcaga acatggtgac cagtgggtcg ggggatgcag agggaggact tggaggggcc    110040
ctggaggtg gggtctatgc cactccatga agagctgtgg gggctctgtt cagcatcacc     110100
ctcacccaca acaggtattg ggtggagcct ctggcagggg tgagctccct gcaaaggtga    110160
gcaaaacagc tatctgagga tgcccaggga ggagaggtgg gaggaaggga gagaggacag    110220
atgggaggag gctctgcaca gagcctgagg acagccctca ccaggttaca gaacacaagg    110280
cttgaccccca ttggcttcct gtagctgtcc tgctctccca acttaatggt ttcattttgc   110340
attttattta aatttcacaa tgattctagc agataccatt agtctattct gcagccaagt   110400
tgtctaaggt ttggagaggt taagtaatgc accaaggtta ggatttgagc cctacctgtc    110460
tgattccccct ccgagagctg tctgattcct ttctcctcct ctgggatagg ggaaggagac   110520
tcagaaggac ggggtctcca tcttcagtct ttgcaagact attgtagggc attgggatgg    110580
tgagcacaaa gtgggttgaa gccccagaga aagagctgag agctgggatc aactgtgtgt    110640
gtgcatgtgt gtgtctgtgt gtgtgtgagt tggagtaggg ggcagggaga aaagagtggg    110700
gtggtggtgg cttgtagtgc agctcaggc caccaggtg tgtccagccc tcgctgtcct     110760
cacctccccca gaggtcagag aaggatatgg gaggggtgg ggtggggtga gggggacgcg    110820
gcggggacgg gggggacggt ggttggtagt ctcactcctg tccattcacc tacaggttga    110880
gtatccccta tccaaaatgc ttggggccag aagtgtctca gatttaagat ttttttcgga   110940
```

-continued

```
ttttggaata tttgcatata cataatgaga tatcttggga atgagacccc aggctaaaca    111000
ggaaattcat ttatgtttta tatacacaca gcctgaagca gttttatata atattttgaa    111060
taattttatg catgaaacaa agtttgtgca cattgaagca agtgtggaat tttccacttg    111120
tggcattatg tcggtgctaa aaaatgtttt agattttgga gcattttgga tctcagaact    111180
ttgcattagg aattgaggac taagtctgat attctgtctt acccagattc ctacctaaga    111240
ggtctaggaa gtcatgccct acaaaccata cattctcatc ag                      111282
```

<210> SEQ ID NO 4
<211> LENGTH: 905
<212> TYPE: PRT
<213> ORGANISM: Homo sapien

<400> SEQUENCE: 4

| | | | | | | | | | | | | | | |
|---|---|---|---|---|---|---|---|---|---|---|---|---|---|---|
| Pro | Pro | Pro | Pro | Gln | Pro | Cys | Ala | Asp | Ser | Leu | Gln | Asp | Ala | Leu | Leu |
| 1 | | | | 5 | | | | | 10 | | | | | 15 | |
| Ser | Leu | Gly | Ser | Val | Ile | Asp | Ile | Ser | Gly | Leu | Gln | Arg | Ala | Val | Lys |
| | | | 20 | | | | | 25 | | | | | 30 | | |
| Glu | Ala | Leu | Ser | Ala | Val | Leu | Pro | Arg | Val | Glu | Thr | Val | Tyr | Thr | Tyr |
| | | 35 | | | | | 40 | | | | | 45 | | | |
| Leu | Leu | Asp | Gly | Glu | Ser | Gln | Leu | Val | Cys | Glu | Asp | Pro | Pro | His | Glu |
| | 50 | | | | | 55 | | | | | 60 | | | | |
| Leu | Pro | Gln | Glu | Gly | Lys | Val | Arg | Glu | Ala | Ile | Ile | Ser | Gln | Lys | Arg |
| 65 | | | | | 70 | | | | | 75 | | | | | 80 |
| Leu | Gly | Cys | Asn | Gly | Leu | Gly | Phe | Ser | Asp | Leu | Pro | Gly | Lys | Pro | Leu |
| | | | | 85 | | | | | 90 | | | | | 95 | |
| Ala | Arg | Leu | Val | Ala | Pro | Leu | Ala | Pro | Asp | Thr | Gln | Val | Leu | Val | Met |
| | | | 100 | | | | | 105 | | | | | 110 | | |
| Pro | Leu | Ala | Asp | Lys | Glu | Ala | Gly | Ala | Val | Ala | Ala | Val | Ile | Leu | Val |
| | | 115 | | | | | 120 | | | | | 125 | | | |
| His | Cys | Gly | Gln | Leu | Ser | Asp | Asn | Glu | Glu | Trp | Ser | Leu | Gln | Ala | Val |
| | 130 | | | | | 135 | | | | | 140 | | | | |
| Glu | Lys | His | Thr | Leu | Val | Ala | Leu | Arg | Arg | Val | Gln | Val | Leu | Gln | Gln |
| 145 | | | | | 150 | | | | | 155 | | | | | 160 |
| Arg | Gly | Pro | Arg | Glu | Ala | Pro | Arg | Ala | Val | Gln | Asn | Pro | Glu | Gly |
| | | | | 165 | | | | | 170 | | | | | 175 |
| Thr | Ala | Glu | Asp | Gln | Lys | Gly | Gly | Ala | Ala | Tyr | Thr | Asp | Arg | Asp | Arg |
| | | | 180 | | | | | 185 | | | | | 190 | | |
| Lys | Ile | Leu | Gln | Leu | Cys | Gly | Glu | Leu | Tyr | Asp | Leu | Asp | Ala | Ser | Ser |
| | | 195 | | | | | 200 | | | | | 205 | | | |
| Leu | Gln | Leu | Lys | Val | Leu | Gln | Tyr | Leu | Gln | Gln | Glu | Thr | Arg | Ala | Ser |
| | 210 | | | | | 215 | | | | | 220 | | | | |
| Arg | Cys | Cys | Leu | Leu | Leu | Val | Ser | Glu | Asp | Asn | Leu | Gln | Leu | Ser | Cys |
| 225 | | | | | 230 | | | | | 235 | | | | | 240 |
| Lys | Val | Ile | Gly | Asp | Lys | Val | Leu | Gly | Glu | Glu | Val | Ser | Phe | Pro | Leu |
| | | | | 245 | | | | | 250 | | | | | 255 | |
| Thr | Gly | Cys | Leu | Gly | Gln | Val | Val | Asp | Lys | Lys | Ser | Ile | Gln | Leu |
| | | | 260 | | | | | 265 | | | | | 270 | | |
| Lys | Asp | Leu | Thr | Ser | Glu | Asp | Val | Gln | Gln | Leu | Gln | Ser | Met | Leu | Gly |
| | | 275 | | | | | 280 | | | | | 285 | | | |
| Cys | Glu | Leu | Gln | Ala | Met | Leu | Cys | Val | Pro | Val | Ile | Ser | Arg | Ala | Thr |
| | 290 | | | | | 295 | | | | | 300 | | | | |
| Asp | Gln | Val | Val | Ala | Leu | Ala | Cys | Ala | Phe | Asn | Lys | Leu | Glu | Gly | Asp |

```
                305                 310                 315                 320
Leu Phe Thr Asp Glu Asp Glu His Val Ile Gln His Cys Phe His Tyr
                325                 330                 335
Thr Ser Thr Val Leu Thr Ser Thr Leu Ala Phe Gln Lys Glu Gln Lys
                340                 345                 350
Leu Lys Cys Glu Cys Gln Ala Leu Leu Gln Val Ala Lys Asn Leu Phe
                355                 360                 365
Thr His Leu Asp Asp Val Ser Val Leu Leu Gln Glu Ile Ile Thr Glu
                370                 375                 380
Ala Arg Asn Leu Ser Asn Ala Glu Ile Cys Ser Val Phe Leu Leu Asp
385                 390                 395                 400
Gln Asn Glu Leu Val Ala Lys Val Phe Asp Gly Gly Val Val Asp Asp
                405                 410                 415
Glu Ser Tyr Glu Ile Arg Ile Pro Ala Asp Gln Gly Ile Ala Gly His
                420                 425                 430
Val Ala Thr Thr Gly Gln Ile Leu Asn Ile Pro Asp Ala Tyr Ala His
                435                 440                 445
Pro Leu Phe Tyr Arg Gly Val Asp Asp Ser Thr Gly Phe Arg Thr Arg
450                 455                 460
Asn Ile Leu Cys Phe Pro Ile Lys Asn Glu Asn Gln Glu Val Ile Gly
465                 470                 475                 480
Val Ala Glu Leu Val Asn Lys Ile Asn Gly Pro Trp Phe Ser Lys Phe
                485                 490                 495
Asp Glu Asp Leu Ala Thr Ala Phe Ser Ile Tyr Cys Gly Ile Ser Ile
                500                 505                 510
Ala His Ser Leu Leu Tyr Lys Lys Val Asn Glu Ala Gln Tyr Arg Ser
                515                 520                 525
His Leu Ala Asn Glu Met Met Met Tyr His Met Lys Val Ser Asp Asp
                530                 535                 540
Glu Tyr Thr Lys Leu Leu His Asp Gly Ile Gln Pro Val Ala Ala Ile
545                 550                 555                 560
Asp Ser Asn Phe Ala Ser Phe Thr Tyr Thr Pro Arg Ser Leu Pro Glu
                565                 570                 575
Asp Asp Thr Ser Met Ala Ile Leu Ser Met Leu Gln Asp Met Asn Phe
                580                 585                 590
Ile Asn Asn Tyr Lys Ile Asp Cys Pro Thr Leu Ala Arg Phe Cys Leu
                595                 600                 605
Met Val Lys Lys Gly Tyr Arg Asp Pro Tyr His Asn Trp Met His
                610                 615                 620
Ala Phe Ser Val Ser His Phe Cys Tyr Leu Leu Tyr Lys Asn Leu Glu
625                 630                 635                 640
Leu Thr Asn Tyr Leu Glu Asp Ile Glu Ile Phe Ala Leu Phe Ile Ser
                645                 650                 655
Cys Met Cys His Asp Leu Asp His Arg Gly Thr Asn Asn Ser Phe Gln
                660                 665                 670
Val Ala Ser Lys Ser Val Leu Ala Ala Leu Tyr Ser Ser Glu Gly Ser
                675                 680                 685
Val Met Glu Arg His His Phe Ala Gln Ala Ile Ala Ile Leu Asn Thr
                690                 695                 700
His Gly Cys Asn Ile Phe Asp His Phe Ser Arg Lys Asp Tyr Gln Arg
705                 710                 715                 720
Met Leu Asp Leu Met Arg Asp Ile Ile Leu Ala Thr Asp Leu Ala His
                725                 730                 735
```

-continued

```
His Leu Arg Ile Phe Lys Asp Leu Gln Lys Met Ala Glu Val Gly Tyr
            740                 745                 750

Asp Arg Asn Asn Lys Gln His His Arg Leu Leu Cys Leu Leu Met
        755                 760                 765

Thr Ser Cys Asp Leu Ser Asp Gln Thr Lys Gly Trp Lys Thr Thr Arg
        770                 775                 780

Lys Ile Ala Glu Leu Ile Tyr Lys Glu Phe Phe Ser Gln Gly Asp Leu
785                 790                 795                 800

Glu Lys Ala Met Gly Asn Arg Pro Met Glu Met Met Asp Arg Glu Lys
                805                 810                 815

Ala Tyr Ile Pro Glu Leu Gln Ile Ser Phe Met Glu His Ile Ala Met
            820                 825                 830

Pro Ile Tyr Lys Leu Leu Gln Asp Leu Phe Pro Lys Ala Ala Glu Leu
        835                 840                 845

Tyr Glu Arg Val Ala Ser Asn Arg Glu His Trp Thr Lys Val Ser His
    850                 855                 860

Lys Phe Thr Ile Arg Gly Leu Pro Ser Asn Asn Ser Leu Asp Phe Leu
865                 870                 875                 880

Asp Glu Glu Tyr Glu Val Pro Asp Leu Asp Gly Thr Arg Ala Pro Ile
                885                 890                 895

Asn Gly Cys Cys Ser Leu Asp Ala Glu
            900                 905

<210> SEQ ID NO 5
<211> LENGTH: 921
<212> TYPE: PRT
<213> ORGANISM: Bos taurus

<400> SEQUENCE: 5

Met Arg Arg Gln Pro Ala Ala Ser Arg Asp Leu Phe Ala Gln Glu Pro
1               5                   10                  15

Val Pro Pro Gly Ser Gly Asp Gly Ala Leu Gln Asp Ala Leu Leu Ser
            20                  25                  30

Leu Gly Ser Val Ile Asp Val Ala Gly Leu Gln Gln Ala Val Lys Glu
        35                  40                  45

Ala Leu Ser Ala Val Leu Pro Lys Val Glu Thr Val Tyr Thr Tyr Leu
    50                  55                  60

Leu Asp Gly Glu Ser Arg Leu Val Cys Glu Glu Pro Pro His Glu Leu
65                  70                  75                  80

Pro Gln Glu Gly Lys Val Arg Glu Ala Val Ile Ser Arg Lys Arg Leu
                85                  90                  95

Gly Cys Asn Gly Leu Gly Pro Ser Asp Leu Pro Gly Lys Pro Leu Ala
            100                 105                 110

Arg Leu Val Ala Pro Leu Ala Pro Asp Thr Gln Val Leu Val Ile Pro
        115                 120                 125

Leu Val Asp Lys Glu Ala Gly Ala Val Ala Ala Val Ile Leu Val His
    130                 135                 140

Cys Gly Gln Leu Ser Asp Asn Glu Glu Trp Ser Leu Gln Ala Val Glu
145                 150                 155                 160

Lys His Thr Leu Val Ala Leu Lys Arg Val Gln Ala Leu Gln Gln Arg
                165                 170                 175

Glu Ser Ser Val Ala Pro Glu Ala Thr Gln Asn Pro Pro Glu Glu Ala
            180                 185                 190

Ala Gly Asp Gln Lys Gly Gly Val Ala Tyr Thr Asn Gln Asp Arg Lys
```

-continued

```
            195                 200                 205
Ile Leu Gln Leu Cys Gly Glu Leu Tyr Asp Leu Asp Ala Ser Ser Leu
    210                 215                 220

Gln Leu Lys Val Leu Gln Tyr Leu Gln Gln Glu Thr Gln Ala Ser Arg
225                 230                 235                 240

Cys Cys Leu Leu Leu Val Ser Glu Asp Asn Leu Gln Leu Ser Cys Lys
                245                 250                 255

Val Ile Gly Asp Lys Val Leu Glu Glu Ile Ser Phe Pro Leu Thr
            260                 265                 270

Thr Gly Arg Leu Gly Gln Val Val Glu Asp Lys Ser Ile Gln Leu
            275                 280                 285

Lys Asp Leu Thr Ser Glu Asp Met Gln Gln Leu Gln Ser Met Leu Gly
    290                 295                 300

Cys Glu Val Gln Ala Met Leu Cys Val Pro Val Ile Ser Arg Ala Thr
305                 310                 315                 320

Asp Gln Val Val Ala Leu Ala Cys Ala Phe Asn Lys Leu Gly Gly Asp
                325                 330                 335

Leu Phe Thr Asp Gln Asp Glu His Val Ile Gln His Cys Phe His Tyr
            340                 345                 350

Thr Ser Thr Val Leu Thr Ser Thr Leu Ala Phe Gln Lys Glu Gln Lys
            355                 360                 365

Leu Lys Cys Glu Cys Gln Ala Leu Leu Gln Val Ala Lys Asn Leu Phe
    370                 375                 380

Thr His Leu Asp Asp Val Ser Val Leu Gln Glu Ile Ile Thr Glu
385                 390                 395                 400

Ala Arg Asn Leu Ser Asn Ala Glu Ile Cys Ser Val Phe Leu Leu Asp
                405                 410                 415

Gln Asn Glu Leu Val Ala Lys Val Phe Asp Gly Gly Val Val Glu Asp
            420                 425                 430

Glu Ser Tyr Glu Ile Arg Ile Pro Ala Asp Gln Gly Ile Ala Gly His
            435                 440                 445

Val Ala Thr Thr Gly Gln Ile Leu Asn Ile Pro Asp Ala Tyr Ala His
    450                 455                 460

Pro Leu Phe Tyr Arg Gly Val Asp Asp Ser Thr Gly Phe Arg Thr Arg
465                 470                 475                 480

Asn Ile Leu Cys Phe Pro Ile Lys Asn Glu Asn Gln Glu Val Ile Gly
                485                 490                 495

Val Ala Glu Leu Val Asn Lys Ile Asn Gly Pro Trp Phe Ser Lys Phe
            500                 505                 510

Asp Glu Asp Leu Ala Thr Ala Phe Ser Ile Tyr Cys Gly Ile Ser Ile
            515                 520                 525

Ala His Ser Leu Leu Tyr Lys Lys Val Asn Glu Ala Gln Tyr Arg Ser
    530                 535                 540

His Leu Ala Asn Glu Met Met Met Tyr His Met Lys Val Ser Asp Asp
545                 550                 555                 560

Glu Tyr Thr Lys Leu Leu His Asp Gly Ile Gln Pro Val Ala Ala Ile
                565                 570                 575

Asp Ser Asn Phe Ala Ser Phe Thr Tyr Thr Pro Arg Ser Leu Pro Glu
            580                 585                 590

Asp Asp Thr Ser Met Ala Ile Leu Ser Met Leu Gln Asp Met Asn Phe
            595                 600                 605

Ile Asn Asn Tyr Lys Ile Asp Cys Pro Thr Leu Ala Arg Phe Cys Leu
    610                 615                 620
```

-continued

```
Met Val Lys Lys Gly Tyr Arg Asp Pro Pro Tyr His Asn Trp Met His
625                 630                 635                 640

Ala Phe Ser Val Ser His Phe Cys Tyr Leu Leu Tyr Lys Asn Leu Glu
                645                 650                 655

Leu Thr Asn Tyr Leu Glu Asp Met Glu Ile Phe Ala Leu Phe Ile Ser
                660                 665                 670

Cys Met Cys His Asp Leu Asp His Arg Gly Thr Asn Asn Ser Phe Gln
                675                 680                 685

Val Ala Ser Lys Ser Val Leu Ala Ala Leu Tyr Ser Ser Glu Gly Ser
                690                 695                 700

Val Met Glu Arg His His Phe Ala Gln Ala Ile Ala Ile Leu Asn Thr
705                 710                 715                 720

His Gly Cys Asn Ile Phe Asp His Phe Ser Arg Lys Asp Tyr Gln Arg
                725                 730                 735

Met Leu Asp Leu Met Arg Asp Ile Ile Leu Ala Thr Asp Leu Ala His
                740                 745                 750

His Leu Arg Ile Phe Lys Asp Leu Gln Lys Met Ala Glu Val Gly Tyr
                755                 760                 765

Asp Arg Thr Asn Lys Gln His His Ser Leu Leu Leu Cys Leu Leu Met
                770                 775                 780

Thr Ser Cys Asp Leu Ser Asp Gln Thr Lys Gly Trp Lys Thr Thr Arg
785                 790                 795                 800

Lys Ile Ala Glu Leu Ile Tyr Lys Glu Phe Phe Ser Gln Gly Asp Leu
                805                 810                 815

Glu Lys Ala Met Gly Asn Arg Pro Met Glu Met Met Asp Arg Glu Lys
                820                 825                 830

Ala Tyr Ile Pro Glu Leu Gln Ile Ser Phe Met Glu His Ile Ala Met
                835                 840                 845

Pro Ile Tyr Lys Leu Leu Gln Asp Leu Phe Pro Lys Ala Ala Glu Leu
                850                 855                 860

Tyr Glu Arg Val Ala Ser Asn Arg Glu His Trp Thr Lys Val Ser His
865                 870                 875                 880

Lys Phe Thr Ile Arg Gly Leu Pro Ser Asn Asn Ser Leu Asp Phe Leu
                885                 890                 895

Asp Glu Glu Tyr Glu Val Pro Asp Leu Asp Gly Ala Arg Ala Pro Ile
                900                 905                 910

Asn Gly Cys Cys Ser Leu Asp Ala Glu
                915                 920
```